(12) United States Patent
Horne et al.

(10) Patent No.: US 11,766,442 B2
(45) Date of Patent: Sep. 26, 2023

(54) T-CELL LYMPHOMA TREATMENTS

(71) Applicant: City of Hope, Duarte, CA (US)

(72) Inventors: David Horne, Altadena, CA (US);
Sangkil Nam, Tujunaga, CA (US)

(73) Assignee: CITY OF HOPE, Duarte, CA (US)

( * ) Notice: Subject to any disclaimer, the term of this patent is extended or adjusted under 35 U.S.C. 154(b) by 461 days.

(21) Appl. No.: 16/622,581

(22) PCT Filed: Jun. 15, 2018

(86) PCT No.: PCT/US2018/037801
§ 371 (c)(1),
(2) Date: Dec. 13, 2019

(87) PCT Pub. No.: WO2018/232274
PCT Pub. Date: Dec. 20, 2018

(65) Prior Publication Data
US 2021/0145840 A1    May 20, 2021

Related U.S. Application Data

(60) Provisional application No. 62/520,946, filed on Jun. 16, 2017, provisional application No. 62/520,921, filed on Jun. 16, 2017.

(51) Int. Cl.
*A61K 31/548* (2006.01)
*A61P 35/00* (2006.01)
*A61K 31/4985* (2006.01)
*A61K 31/5377* (2006.01)
*A61K 31/554* (2006.01)
*A61K 45/06* (2006.01)

(52) U.S. Cl.
CPC ........ *A61K 31/548* (2013.01); *A61K 31/4985* (2013.01); *A61K 31/5377* (2013.01); *A61K 31/554* (2013.01); *A61K 45/06* (2013.01); *A61P 35/00* (2018.01)

(58) Field of Classification Search
CPC .................................................. A61K 31/548
See application file for complete search history.

(56) References Cited

U.S. PATENT DOCUMENTS

| 9,353,150 | B2 | 5/2016 | Movassaghi et al. |
| 2009/0264421 | A1* | 10/2009 | Bible ..................... A61P 35/00 544/5 |
| 2015/0283178 | A1 | 10/2015 | June et al. |
| 2015/0291622 | A1 | 10/2015 | Overman et al. |

OTHER PUBLICATIONS

Baumann et al, Chem. Sci., 2015,6, 4451-4457. (Year: 2015).*

(Continued)

*Primary Examiner* — Benjamin J Packard
(74) *Attorney, Agent, or Firm* — Irina E. Britva; Mintz, Levin, Cohn, Ferris, Glovsky and Popeo, P.C.

(57) ABSTRACT

Described herein are methods for treating T-cell lymphoma in a subject in need thereof, comprising administering to the subject in need thereof, an ETP compound. Also described herein are pharmaceutical compositions and compositions for use that include such ETP compound.

5 Claims, 11 Drawing Sheets

(56) References Cited

OTHER PUBLICATIONS

Borthwick, A.D. (Jul. 11, 2012, e-published May 11, 2012). "2,5-Diketopiperazines: synthesis, reactions, medicinal chemistry, and bioactive natural products," *Chem Rev* 112(7):3641-3716.

Carmack, M. et al. (1967). *J. Am. Chem. Soc.* 89(26):7134-7136.

Hauser, D. et al. (1970). "[Isolation and configuration of Chaetocin]," *Helv. Chim. Acta* 53(5):1061-1073.

Iwasa, E et al. (Apr. 6, 2011), "Epipolythiodiketopiperazine Alkaloids: Total Syntheses and Biological Activities," *Israel J. Chem* 51:420-433.

Martins, M.M. et al. (2007). "Diketopiperazines: biological activity and synthesis," *Tetrahedron* 63:9923-9932.

Minato, H. et al. (1971). "Verticillin A, a new antibiotic from *Verticillium* sp," Journal of the Chemical Society D;Chemical Communications 44-45.

Nagarajan, R. et al. (Oct. 31, 1973). "The circular dichroism of gliotoxin and related epidithiapiperazinediones," *J Am Chem Soc* 95(22):7212-7222.

Nicolaou, K. C. et al. (Jun. 1, 2011, e-published May 11, 2011). "Total synthesis of epicoccin G," *J Am Chem Soc* 133(21):8150-8153.

Nicolaou, K. C. et al. (Oct. 17, 2012, e-published Oct. 4, 2012). "Synthesis and biological evaluation of epidithio-, epitetrathio-, and bis-(methylthio)diketopiperazines: synthetic methodology, enantioselective total synthesis of epicoccin G, 8,8'-epi-ent-rostratin B, gliotoxin, gliotoxin G, emethallicin E, and haematocin and discovery of new antiviral and antimalarial agents," *J Am Chem Soc* 134(41):17320-17332.

International Search Report dated Oct. 11, 2018, for PCT Application No. PCT/US2018/037801, dated Jun. 15, 2018, 5 pages.

Written Opinion dated Oct. 11, 2018, for PCT Application No. PCT/US2018/037801, dated Jun. 15, 2018, 8 pages.

\* cited by examiner

A: Compound (1)

B: Romidepsin (FK-228)

C: Vehicle

Compound (2)

LEO-16-1839

T-CELL LYMPHOMA TREATMENTS

CROSS REFERENCES TO RELATED APPLICATIONS

This application is a U.S. national phase application, pursuant to 35 U.S.C. § 371, of PCT/US2018/037801 filed Jun. 15, 2018, which claims the benefit of priority of U.S. Provisional Application No. filed 62/520,921 on Jun. 16, 2017 and U.S. Provisional Application No. 62/520,946 filed on Jun. 16, 2017, which are incorporated herein by reference in their entirety and for all purposes.

BACKGROUND

Malignant cancerous growths, due to their unique characteristics, pose serious challenges for modern medicine. Their characteristics include uncontrollable cell proliferation resulting in unregulated growth of malignant tissue, an ability to invade local and even remote tissues, lack of differentiation, lack of detectable symptoms and, most significantly, lack of effective therapies. There is a need in the art for treating T-cell lymphomas. Provided here are solutions for these and other needs in the art.

BRIEF SUMMARY

Described herein, inter alia, are methods for treating T-cell lymphoma in a subject in need thereof, comprising administering to the subject in need thereof, an ETP compound. Further provided herein are methods for treating T-cell lymphoma in a subject in need thereof, comprising administering to the subject in need thereof, a bridged ETP compound or a non-bridged ETP compound. Also described herein are pharmaceutical compositions and compositions for use that include such ETP compound.

In an aspect, the compound (ETP compound) has the structure of formula (1):

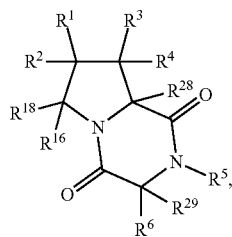

(1)

or a pharmaceutically acceptable salt thereof.

$R^1$ is hydrogen, halogen, $-N_3$, $-CF_3$, $-CCl_3$, $-CBr_3$, $-CI_3$, $-CN$, $-CHO$, $-OR^{1A}$, $-NR^{1B}R^{1C}$, $-COOR^{1A}$, $-CONR^{1B}R^{1C}$, $-NO_2$, $-SR^{1D}$, $-SO_{n1}R^{1B}$, $-SO_{n1}OR^{1B}$, $-SO_{v1}NR^{1B}R^{1C}$, $-NHNR^{1B}R^{1C}$, $-ONR^{1B}R^{1C}$, $-NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, $-N_3$, $-CF_3$, $-CCl_3$, $-CBr_3$, $-CI_3$, $-CN$, $-CHO$, $-OR^{2A}$, $-NR^{2B}R^{2C}$, $-COOR^{2A}$, $-CONR^{2B}R^{2C}$, $-NO_2$, $-SR^{2D}$, $-SO_{n2}R^{2B}$, $-SO_{n2}OR^{2B}$, $-SO_{v2}NR^{2B}R^{2C}$, $-NHNR^{2B}R^{2C}$, $-ONR^{2B}R^{2C}$, $-NHC(O)NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, $-N_3$, $-CF_3$, $-CCl_3$, $-CBr_3$, $-CI_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{n3}OR^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, $-N_3$, $-CF_3$, $-CCl_3$, $-CBr_3$, $-CI_3$, $-CN$, $-CHO$, $-OR^{4A}$, $-NR^{4B}R^{4C}$, $-COOR^{4A}$, $-CONR^{4B}R^{4C}$, $-NO_2$, $-SR^{4D}$, $-SO_{n4}R^{4B}$, $-SO_{n4}OR^{4B}$, $-SO_{v4}NR^{4B}R^{4C}$, $-NHNR^{4B}R^{4C}$, $-ONR^{4B}R^{4C}$, $-NHC(O)NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, $-N_3$, $-CF_3$, $-CCl_3$, $-CBr_3$, $-CI_3$, $-CN$, $-CHO$, $-OR^{5A}$, $-NR^{5B}R^{5C}$, $-COOR^{5A}$, $-CONR^{5B}R^{5C}$, $-NO_2$, $-SR^{5D}$, $-SO_{n5}R^{5B}$, $-SO_{n5}OR^{5B}$, $-SO_{v5}NR^{5B}R^{5C}$, $-NHNR^{5B}R^{5C}$, $-ONR^{5B}R^{5C}$, $-NHC(O)NHNR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, $-N_3$, $-CF_3$, $-CCl_3$, $-CBr_3$, $-CI_3$, $-CN$, $-CHO$, $-OR^{6A}$, $-NR^{6B}R^{6C}$, $-COOR^{6A}$, $-CONR^{6B}R^{6C}$, $-NO_2$, $-SR^{6D}$, $-SO_{n6}R^{6B}$, $-SO_{n6}OR^{6B}$, $-SO_{v6}NR^{6B}R^{6C}$, $-NHNR^{6B}R^{6C}$, $-ONR^{6B}R^{6C}$, $-NHC(O)NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{16}$ is hydrogen, halogen, $-N_3$, $-CF_3$, $-CCl_3$, $-CBr_3$, $-CI_3$, $-CN$, $-CHO$, $-OR^{16A}$, $-NR^{6B}R^{16C}$, $-COOR^{16A}$, $-CONR^{6B}R^{16C}$, $-NO_2$, $-SR^{16D}$, $-SO_{n16}R^{16B}$, $-SO_{n16}OR^{16B}$, $-SO_{v16}NR^{16B}R^{16C}$, $-NR^{16B}R^{16C}$, $-ONR^{16B}R^{16C}$, $-NHC(O)NHNR^{16B}R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{18}$ is hydrogen, halogen, $-N_3$, $-CF_3$, $-CCl_3$, $-CBr_3$, $-CI_3$, $-CN$, $-CHO$, $-OR^{18A}$, $-NR^{18B}R^{18C}$, $-COOR^{18A}$, $-CONR^{18B}R^{18C}$, $-NO_2$, $-SR^{18D}$, $-SO_{n18}R^{18B}$, $-SO_{n18}OR^{18B}$, $-SO_{v18}NR^{18B}R^{18C}$, $-NHNR^{18B}R^{18C}$, $-ONR^{18B}R^{18C}$, $-NHC(O)NHNR^{18B}R^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{28}$ is $-SR^{25}$ and $R^{29}$ is $-SR^{26}$, wherein $R^{28}$ and $R^{29}$ are optionally joined to form *$-S_p-$* wherein p is an integer from 2 to 4 and each * represents the point of attachment to the remainder of the compound.

$R^{25}$ is hydrogen, $-C(O)-L^1-R^{32}$, $-C(S)-L^1-R^{32}$, substituted or unsubstituted alkyl, substituted or unsubstituted heteroalkyl, substituted or unsubstituted aryl, or substituted or unsubstituted heteroaryl. $R^{26}$ is hydrogen, $-C(O)-L^2-R^{33}$, $-C(S)-L^2-R^{33}$, substituted or unsubstituted alkyl, substituted or unsubstituted heteroalkyl, substituted or unsubstituted aryl, or substituted or unsubstituted heteroaryl. $R^{25}$ and $R^{26}$ may optionally be joined to form

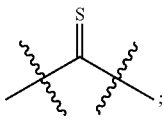 [SMILES: *C(*)=S ; ";"]

;

$L^1$ is a bond, —O—, —NH—, substituted or unsubstituted alkylene, substituted or unsubstituted heteroalkylene. $L^2$ is a bond, —O—, —NH—, substituted or unsubstituted alkylene, substituted or unsubstituted heteroalkylene.

$R^{32}$ and $R^{33}$ are independently halogen, substituted or unsubstituted $C_1$-$C_3$ alkyl, substituted or unsubstituted aryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{16A}$, $R^{16B}$, $R^{16C}$, $R^{16D}$, $R^{18A}$, $R^{18B}$, $R^{18C}$, and $R^{18D}$ are independently hydrogen, halogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

X is independently —F, —Cl, —Br, or —I. n1, n2, n3, n4, n5, n6, n16, and n18 are independently an integer from 1 to 4. v1, v2, v3, v4, v5, v6, v16, and v18 are independently 1 or 2.

In an aspect, the compound has the structure of formula (I):

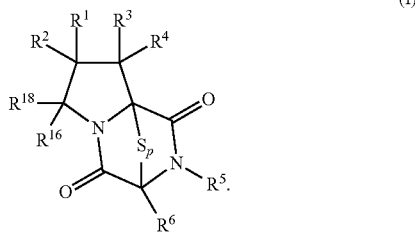

(I)

In an aspect, the compound has the structure of formula (XXI):

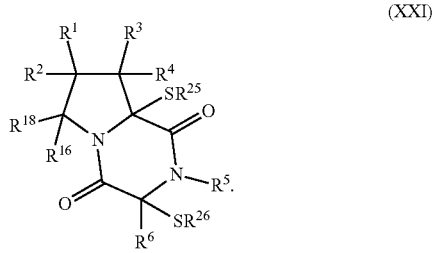

(XXI)

BRIEF DESCRIPTION OF THE DRAWINGS

FIG. 2A shows the cell proliferation assay result at a concentration of 0 nM of compound (1);
FIG. 2B shows the cell proliferation assay result at a concentration of 1 nM of compound (1);
FIG. 2C shows the cell proliferation assay result at a concentration of 10 nM of compound (1);
and FIG. 2D shows the cell proliferation assay result at a concentration of 100 nM of compound (1).

DETAILED DESCRIPTION

Figure 1A:
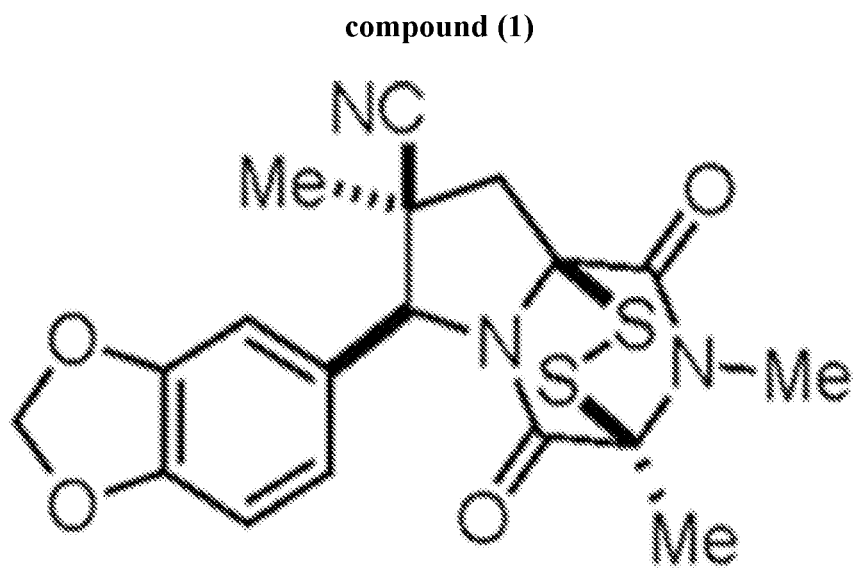
FIG. 1A illustrates compound (1).

T-cell lymphoma represents a subset of non-Hodgkin's lymphoma (NHL). In Europe and North America, T-cell lymphoma accounts for 5-10% of all cases of NHL while in Asia, this percentage is as high as 24%. T-cell lymphomas, as a group, carry a poorer prognosis compared to their B cell counterpart. In the subgroup of patients with a low international prognostic index (IPI) score of 1-2, 5-year overall survival (OS) was 55% in those with T-cell lymphomas and 71% in those with B-cell lymphomas, and this difference in survival was also reflected in patients with higher IPI scores. T-cell lymphomas, however, represent a heterogeneous group of diseases with variations in clinical characteristics, prognosis, and response to treatment.

Peripheral T-cell lymphoma not otherwise specified (PTCL-NOS), angioimmunoblastic T-cell lymphoma (AITL), and anaplastic large-cell lymphoma (ALCL) are the most common subtypes and account for up to 74% of all T-cell lymphomas. AITL tends to occur in elderly patients, and patients often present with disseminated lymphadenopathy, hepatosplenomegaly, and autoimmune phenomena. ALCL ALK+ typically occurs in young men and presentation can be nodal or extranodal, involving the skin, bone, soft tissues, lung, and liver. On the other hand, ALCL ALK– tends to occur in an older population of patients, the presentation is usually nodal, and the disease runs a more aggressive clinical course. PTCL-NOS, represents a heterogeneous category of nodal and extranodal T cell lymphomas that cannot be grouped into defined entities. Most present with peripheral lymph-node enlargement, B symptoms and, at diagnosis, the disease is advanced.

Other uncommon T-cell lymphomas include enteropathy-associated T-cell lymphoma (EATL), adult T-cell leukemia/lymphoma (ATLL), hepatosplenic T-cell lymphoma (HSTL), and subcutaneous panniculitis-like T-cell lymphoma (SPTCL). It is recognized that EATL lymphoma consists of two distinct forms: classical or type I EATL and type II EATL. Type I EATL is associated with coeliac disease while type II EATL occurs in Asia and is not associated with coeliac disease. ATLL is caused by infection with the human T-cell-lymphotropic virus type 1 (HTLV-1), and is rare outside HTLV-I-endemic areas such as the Caribbean, Japan, and parts of central Africa. HSTL is rare; patients present with hepatosplenomegaly and systemic symptoms, and in 20% of cases it occurs in the context of chronic immune suppression. SPTCL occurs more commonly in women, and is associated with autoimmune conditions such as systemic lupus erythematosus.

Cutaneous T-cell lymphoma (CTCL) is caused by an expansion of malignant T-cell lymphocytes (involved in cell-mediated immunity) normally programmed to migrate to the skin. These skin-trafficking malignant T-cells migrate to the skin, causing various lesions to appear that may change shape as the disease progresses, typically beginning as a rash and eventually forming plaques and tumors. The disease generally presents with skin involvement only, manifested as scaly, erythematous patches. However, in advanced stages the disease is diffused to the lymph nodes and visceral organs.

CTCL constitutes a rare group of NHLs, occurring in about 4% of the approximate 500,000 individuals living with the disease. It is estimated, that CTCL affects about 40,000 individuals in the US, with approximately 2,800 new cases seen annually. CTCL mortality is related to the stage of the disease and median survival generally ranging from about 12 years in the early stages to only 2.5 years when the disease has advanced.

CTCL describes many different disorders with various symptoms and outcomes. The two most common types are mycosis fungoides (MF) and Sezary syndrome.

Mycosis fungoides is the most common type of CTCL, with approximately 16,000 to 20,000 cases across the United States, accounting for half of all CTCLs. The disease looks different in each patient, with skin symptoms that can appear as patches, plaques, or tumors. Patches are usually flat, possibly scaly, and look like a rash; plaques are thicker, raised, usually itchy lesions that are often mistaken for eczema, psoriasis, or dermatitis; and tumors are raised bumps, which may or may not ulcerate. It is possible to have more than one type of lesion.

A medical history, physical exam, and skin biopsy may be necessary for diagnosis. A physician may examine lymph nodes, order various blood tests, and may conduct other screening tests, such as a chest x-ray or a computed axial tomography (CAT) scan. Scans are usually not needed for those with the earliest stages of the disease. Mycosis fungoides is difficult to diagnose in its early stages because the symptoms and skin biopsy findings are similar to those of other skin conditions.

Sezary syndrome is an advanced, variant form of mycosis fungoides, which is characterized by the presence of lymphoma cells in the blood. Extensive thin, red, itchy rashes usually cover over 80 percent of the body. In certain patients, patches and tumors appear. Patients may also experience changes in the nails, hair, or eyelids, or have enlarged lymph nodes.

Many of the same procedures used to diagnose and stage other types of cutaneous T-cell lymphomas are used in Sezary syndrome. In addition, a series of imaging tests may be needed to determine if the cancer has spread to the lymph nodes or other organs (although that uncommonly occurs). These tests may include a CAT scan, a positron emission tomography (PET) scan, and/or a magnetic resonance imaging (MRI) scan. A bone marrow biopsy may also be done, but is usually not necessary.

Certain Terminology

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group may have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The term "ETP compound or derivative" or "ETP compound" as used herein, means a compound having the structure of formula (1), (I), (I(S)), (I(R)), (II), (II(S)), (II(R)), (II1), (II1(S)), (II1(R)), (II2), (II2(S)), (II2(R)), (II3), (II3(S)), (II3(R)), (II4), (II5), (III), (III(S)), (III(R)), (III1), (III1(S)), (III1(R)), (IV), (IV(S)), (IV(R)), (IV1), (IV1(S)), (IV1(R)), (IV2), (IV2(S)), (V2(R)), (V), (V(S)), (V(R)), (V1), (V1(S)), (V1(R)), (V2), (V2(S)), (V2(R)), (V3), (V3(S)), (V3(R)), (V4), (V4(S)), (V4(R)), (VI), (VI(S)), (VI (R)), (VI1), (VI1(S)), (VI1(R))), (XXI), (XXIa), (XXII), (XXII(S)), (XXII(R)), (XXIII), (XXIII(S)), (XXIII(R)), (XXIV), (XXIV(S)), (XXIV(R)), (XXV), (XXV(S)), (XXV (R)), (XXVI), (XXVI(S)), (XXVI(R)), (XXVII), (XXVII (S)), (XXVII (R)), (XXVIII), (XXVIII(S)), (XXVIII(R)), (XXIX), (XXIX (S)), (XXIX (R)), (XXX), (XXXI), (XXI'), (XXII'), (XXIII'), (XXIII'(S)), (XXIII'(R)), (XXIV'), (XXIV' (S)), (XXIV'(R)), (XXV'), (XXV'(S)), (XXV'(R)), (XXVI'), (XXVI'(S)), or (XXVI'(R)), including embodiments thereof described herein. The term "ETP" is derived from the term epidithiodiketopiperazine. However, ETP compounds provided herein are not strictly limited to epidithiodiketopiperazine scaffolds as is readily seen from the formulae provided herein. Therefore, the "ETP" term provided herein is merely a term of convenience to refer to the compounds disclosed herein and is not intended to limit the scope of the formulae disclosed herein.

The term "bridged" ETP compound or derivative as used herein, means a compound having a sulfide bridge having p sulfurs, i.e. "$S_p$" in a core structure, (e.g. $S_2$ is —S—S—, $S_3$ is —S—S—S—, $S_4$ is —S—S—S—S—). In contrast, the term "non-bridged" ETP compound or derivative as used herein, means a compound not having sulfide bridge ("$S_p$") anywhere in its formula.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si ($CH_3$)$_3$, —$CH_2$—CH=N—$OCH_3$, —CH=CH—N ($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si ($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single bonded to carbon or to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$R', —NR—C(NR'R"R'")=NR"", —NR—C(NR'R")=NR', —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the disclosure includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —CF$_3$, —CCl$_3$, —CBr$_3$, —CI$_3$, —CHF$_2$, —CHCl$_2$, —CHBr$_2$, —CH$_2$, —CH$_2$F, —CH$_2$Cl, —CH$_2$Br, —CH$_2$I, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$, —CN, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

Certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

The symbol "~~~" denotes the point of attachment of a chemical moiety to the remainder of a molecule or chemical formula.

"$S_p$", "$S_t$", or "$S_n$" refers to a sulfide bridge having p, t, or n sulfurs (e.g. $S_2$ is —S—S—, $S_3$ is —S—S—S—, $S_4$ is —S—S—S—S—).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present disclosure is limited by principles of chemical bonding.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form. Prodrugs of the compounds described herein include those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts.

The terms "treating" or "treatment" refers to any indicia of success in the treatment or amelioration of a disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In particular, "disease" or "condition" refer to T-cell lymphoma.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies, for example alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof. The compound of the disclosure can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

The term "T-cell lymphoma" as used herein, means a disease that affects T-lymphocytes (T-cells). T-cell lymphoma occurs when cells of the immune system called T-lymphocytes, a type of white blood cell, grow and multiply uncontrollably. Cancerous T-cell lymphocytes travel to many parts of the body, including the lymph nodes, spleen, bone marrow, blood, or other organs, and form a mass called a tumor.

The term "cancer" as used herein, refers to T-cell lymphoma.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are understood as cells exhibiting phenotypes or genotypes similar to in vivo cancers. Cancer cell lines, as used herein, include cell lines from animals (e.g. mice) and from humans, such as HUT78.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In some embodiments, anticancer agents herein may include alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

The terms "synergy", "synergism," "synergistic," and "synergistic therapeutic effect" are used herein interchangeably and refer to a measured effect of compounds administered in combination where the measured effect is greater than the sum of the individual effects of each of the compounds administered alone as a single agent.

Compounds

Described herein are compounds (ETP compounds) for use in the methods provided herein having the structure of formula (1):

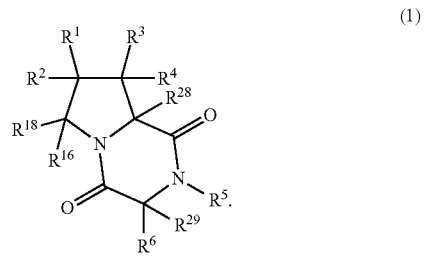

(1)

or a pharmaceutically acceptable salt thereof.

$R^1$ is hydrogen, halogen, $-N_3$, $-CF_3$, $-CCl_3$, $-CBr_3$, $-Cl_3$, $-CN$, $-CHO$, $-OR^{1A}$, $-NR^{1B}R^{1C}$, $-COOR^{1A}$, $-CONR^{1B}R^{1C}$, $-NO_2$, $-SR^{1D}$, $-SO_{n1}R^{1B}$, $-SO_{n1}OR^{1B}$, $-SO_{v1}NR^{1B}R^{1C}$, $-NHNR^{1B}R^{1C}$, $-ONR^{1B}R^{1C}$, $-NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, $-N_3$, $-CF_3$, $-CCl_3$, $-CBr_3$, $-Cl_3$, $-CN$, $-CHO$, $-OR^{2A}$, $-NR^{2B}R^{2C}$, $-COOR^{2A}$, $-CONR^{2B}R^{2C}$, $-NO_2$, $-SR^{2D}$, $-SO_{n2}R^{2B}$, $-SO_{n2}OR^{2B}$, $-SO_{v2}NR^{2B}R^{2C}$, $-NHNR^{2B}R^{2C}$, $-ONR^{2B}R^{2C}$, $-NHC(O)NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, $-N_3$, $-CF_3$, $-CCl_3$, $-CBr_3$, $-Cl_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{n3}OR^{3B}$, $-SO_{v3}NR^{3B}R^{3C}$, $-NHNR^{3B}R^{3C}$, $-ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, $-N_3$, $-CF_3$, $-CCl_3$, $-CBr_3$, $-Cl_3$, $-CN$, $-CHO$, $-OR^{4A}$, $-NR^{4B}R^{4C}$, $-COOR^{4A}$, $-CONR^{4B}R^{4C}$, $-NO_2$, $-SR^{4D}$, $-SO_{n4}R^{4B}$, $-SO_{n4}OR^{4B}$, $-SO_{v4}NR^{4B}R^{4C}$, $-NHNR^{4B}R^{4C}$, $-ONR^{4B}R^{4C}$, $-NHC(O)NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, $-N_3$, $-CF_3$, $-CCl_3$, $-CBr_3$, $-Cl_3$, $-CN$, $-CHO$, $-OR^{5A}$, $-NR^{5B}R^{5C}$, $-COOR^{5A}$, $-CONR^{5B}R^{5C}$, $-NO_2$, $-SR^{5D}$, $-SO_{n5}R^{5B}$, $-SO_{n5}OR^{5B}$, $-SO_{v5}NR^{5B}R^{5C}$, $-NHNR^{5B}R^{5C}$, $-ONR^{5B}R^{5C}$, $-NHC(O)NHNR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{v6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{16}$ is hydrogen, halogen, —$N_3$, —$CF_3$, —$CCl_3$, —$CBr_3$, —$CI_3$, —CN, —CHO, —$OR^{6A}$, —$NR^{16B}R^{6C}$, —$COOR^{16A}$, —$CONR^{16B}R^{16C}$, —$NO_2$, —$SR^{16D}$, —$SO_{n16}R^{16B}$, —$SO_{n16}OR^{16B}$, —$SO_{v16}NR^{16B}R^{16C}$, —N—$R^{16B}R^{16C}$, —$ONR^{16B}R^{16C}$, —NHC(O)$NHNR^{16B}R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{18}$ is hydrogen, halogen, —$N_3$, —$CF_3$, —$CCl_3$, —$CBr_3$, —$CI_3$, —CN, —CHO, —$OR^{18A}$, —$NR^{18B}R^{18C}$, —$COOR^{18A}$, —$CONR^{18B}R^{18C}$, —$NO_2$, —$SR^{18D}$, —$SO_{n18}R^{18B}$, —$SO_{n18}OR^{18B}$, —$SO_{v18}NR^{18B}R^{18C}$, —$NR^{18B}R^{18C}$, —$ONR^{18B}R^{18C}$, —NHC(O)$NHNR^{18B}R^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{28}$ and $R^{29}$ are joined to form —$S_p$— wherein p is an integer from 2 to 4, or $R^{28}$ is —$SR^{25}$ and $R^{29}$ is —$SR^{26}$. $R^{25}$ is hydrogen, —C(O)-$L^1$-$R^{32}$, —C(S)-$L^1$-$R^{32}$, substituted or unsubstituted alkyl, substituted or unsubstituted heteroalkyl, substituted or unsubstituted aryl, or substituted or unsubstituted heteroaryl. $R^{26}$ is hydrogen, —C(O)-$L^2$-$R^{33}$, —C(S)-$L^2$-$R^{33}$ substituted or unsubstituted alkyl, substituted or unsubstituted heteroalkyl, substituted or unsubstituted aryl, or substituted or unsubstituted heteroaryl. $R^{25}$ and $R^{26}$ may optionally be joined to form

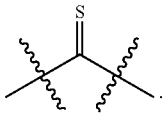

$L^1$ is a bond, —O—, —NH—, substituted or unsubstituted alkylene, substituted or unsubstituted heteroalkylene.

$L^2$ is a bond, —O—, —NH—, substituted or unsubstituted alkylene, substituted or unsubstituted heteroalkylene.

$R^{32}$ and $R^{33}$ are independently hydrogen, halogen, substituted or unsubstituted $C_1$-$C_3$ alkyl, substituted or unsubstituted aryl.

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{16A}$, $R^{16B}$, $R^{16C}$, $R^{16D}$, $R^{18A}$, $R^{18B}$, $R^{18C}$, and $R^{18D}$ are independently hydrogen, halogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

X is independently —F, —Cl, —Br, or —I. n1, n2, n3, n4, n5, n6, n16, and n18 are independently an integer from 1 to 4. v1, v2, v3, v4, v5, v6, v16, and v18 are independently 1 or 2.

In embodiments, $R^{28}$ and $R^{29}$ are joined to form —$S_p$— and the compound has the formula:

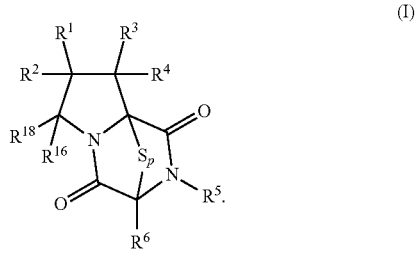

(I)

In embodiments, $R^{28}$ and $R^{29}$ are joined to form —$S_2$— and the compound has the

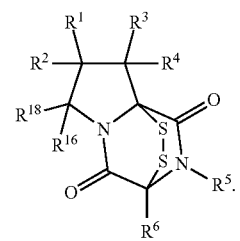

In embodiments, $R^{28}$ and $R^{29}$ are joined to form —$S_3$— and the compound has the formula:

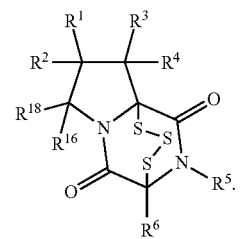

In embodiments, $R^{28}$ and $R^{29}$ are joined to form —$S_4$— and the compound has the formula:

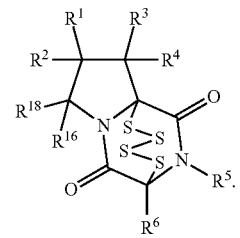

In embodiments, $R^{28}$ is —$SR^{25}$ and $R^{29}$ is —$SR^{26}$ and the compound has the formula

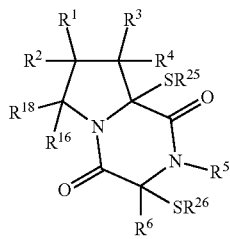

(XXI)

In embodiments, $R^{25}$ is hydrogen. In embodiments, $R^{25}$ is —C(O)-$L^1$-$R^{32}$. In embodiments, $R^{25}$ is —C(S)-$L^1$-$R^{32}$. In embodiments, $R^{25}$ is substituted or unsubstituted alkyl. In embodiments, $R^{25}$ is substituted or unsubstituted heteroalkyl. In embodiments, $R^{25}$ is substituted or unsubstituted aryl. In embodiments, $R^{25}$ is substituted or unsubstituted heteroaryl. In embodiments, $R^{26}$ is hydrogen. In embodiments, $R^{26}$ is —C(O)-$L^2$-$R^{33}$. In embodiments, $R^{26}$ is —C(S)-$L^2$-$R^{33}$. In embodiments, $R^{26}$ is substituted or unsubstituted alkyl. In embodiments, $R^{26}$ is substituted or unsubstituted heteroalkyl. In embodiments, $R^{26}$ is substituted or unsubstituted aryl. In embodiments, $R^{26}$ is substituted or unsubstituted heteroaryl. In embodiments, $R^{25}$ and $R^{26}$ are joined to form.

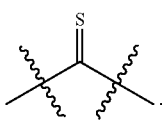

Bridged Forms of Compounds

Described herein are compounds (ETP compounds) for use in the methods provided herein having the structure of formula (I):

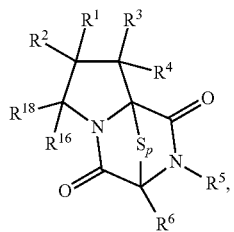

(I)

or a pharmaceutically acceptable salt thereof. $R^1$, $R^2$, $R^3$, $R^4$, $R^5$, $R^6$, $R^{16}$ and $R^{18}$, and p are as described above.

In embodiments, p is 2. In embodiments, p is 3. In embodiments, p is 4.

In some embodiments of a compound of formula (I), $R^{18}$ is substituted or unsubstituted heterocycloalkyl, substituted or unsubstituted aryl, or substituted or unsubstituted heteroaryl. In some embodiments of a compound of formula (I), $R^{16}$ is hydrogen. In some embodiments of a compound of formula (I), $R^3$ and $R^4$ are independently hydrogen. In some embodiments of a compound of formula (I), $R^1$ is —CN, —$COOR^{14}$, —$CONR^{1B}R^{1C}$, or substituted or unsubstituted heteroalkyl. In some embodiments of a compound of formula (I), $R^1$ is —CN. In some embodiments of a compound of formula (I), $R^2$ is —$CF_3$, substituted or unsubstituted alkyl, substituted or unsubstituted heteroalkyl, substituted or unsubstituted cycloalkyl, or substituted or unsubstituted heterocycloalkyl. In some embodiments of a compound of formula (I), $R^2$ is substituted or unsubstituted alkyl or substituted or unsubstituted heteroalkyl. In some embodiments of a compound of formula (I), $R^2$ is methyl or methoxy. In some embodiments of a compound of formula (I), $R^5$ and $R^6$ are independently hydrogen, halogen, substituted or unsubstituted alkyl, or substituted or unsubstituted cycloalkyl. In some embodiments of a compound of formula (I), $R^5$ and $R^6$ are independently hydrogen, methyl, ethyl, allyl, or cyclopropyl. In some embodiments of a compound of formula (I), $R^5$ and $R^6$ are independently hydrogen or unsubstituted methyl. In some embodiments of a compound of formula (I), p is 2.

In some embodiments, the compound of formula (I) has the structure of formula (I(S)):

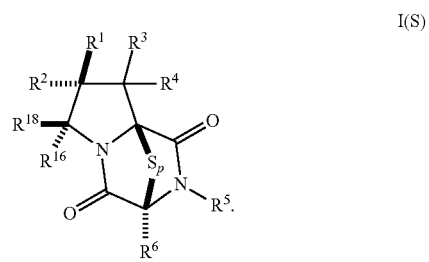

I(S)

In some embodiments, the compound of formula (I) has the structure of formula (I(R)):

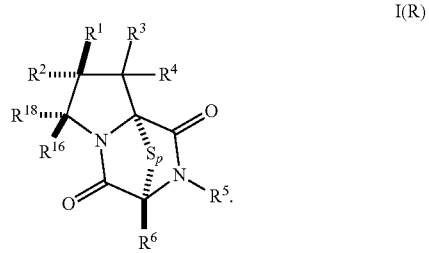

I(R)

$R^1$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). Rr may be halogen, —$CF_3$, —$CCl_3$, —$CBr_3$, —$CI_3$, —CN, substituted or unsubstituted alkyl, or substituted or unsubstituted heteroalkyl. $R^1$ may be —CN, substituted or unsubstituted alkyl, or substituted or unsubstituted heteroalkyl. $R^1$ may be —CN or substituted or unsubstituted alkyl. $R^1$ may be —CN or unsubstituted alkyl. $R^1$ may be —CN, or unsubstituted heteroalkyl. $R^1$ may be hydrogen.

$R^1$ may be hydrogen, $R^{1E}$-substituted or unsubstituted alkyl (e.g., $C_1$-$C_8$, $C_1$-$C_6$, or $C_1$-$C_4$ alkyl), $R^{1E}$-substituted or unsubstituted heteroalkyl (e.g., 2 to 8 membered, 2 to 6 membered, or 2 to 4 membered heteroalkyl), $R^{1E}$-substituted or unsubstituted cycloalkyl (e.g., $C_3$-$C_8$, $C_3$-$C_6$, or $C_5$-$C_6$ cycloalkyl), $R^{1E}$-substituted or unsubstituted heterocycloalkyl (e.g., 3 to 8 membered, 3 to 6 membered, or 5 to 6 membered heterocycloalkyl), $R^{1E}$-substituted or unsubstituted aryl (e.g., $C_6$-$C_{10}$, $C_{10}$ aryl, or phenyl), or $R^{1E}$-substituted or unsubstituted heteroaryl (e.g., 5 to 10 membered, 5 to 9 membered, or 5 to 6 membered heteroaryl). $R^1$ may be $R^{1E}$-substituted or unsubstituted alkyl (e.g., $C_1$-$C_8$, $C_1$-$C_6$, or $C_1$-$C_4$ alkyl), $R^{1E}$-substituted or unsubstituted heteroalkyl (e.g., 2 to 8 membered, 2 to 6 membered, or 2 to 4 membered heteroalkyl), $R^{1E}$-substituted or unsubstituted cycloalkyl (e.g., $C_3$-$C_8$, $C_3$-$C_6$, or $C_5$-$C_6$ cycloalkyl), $R^{1E}$-substituted or unsubstituted heterocycloalkyl (e.g., 3 to 8 membered, 3 to 6 membered, or 5 to 6 membered heterocycloalkyl), $R^{1E}$-substituted or unsubstituted aryl (e.g., $C_6$-$C_{10}$, $C_{10}$ aryl, or phenyl), or $R^{1E}$-substituted or unsubstituted heteroaryl (e.g., 5 to 10 membered, 5 to 9 membered, or 5 to 6 membered heteroaryl).

In embodiments, $R^1$ is $R^{1E}$-substituted or unsubstituted alkyl (e.g., $C_1$-$C_8$, $C_1$-$C_6$, or $C_1$-$C_4$ alkyl). In embodiments, $R^1$ is $R^{1E}$-substituted alkyl (e.g., $C_1$-$C_8$, $C_1$-$C_6$, or $C_1$-$C_4$ alkyl). In embodiments, $R^1$ is an unsubstituted alkyl (e.g., $C_1$-$C_8$, $C_1$-$C_6$, or $C_1$-$C_4$ alkyl).

In embodiments, $R^1$ is $R^{1E}$-substituted or unsubstituted heteroalkyl (e.g., 2 to 8 membered, 2 to 6 membered, or 2 to 4 membered heteroalkyl). In embodiments, $R^1$ is $R^{1E}$-substituted heteroalkyl (e.g., 2 to 8 membered, 2 to 6 membered, or 2 to 4 membered heteroalkyl). In embodiments, $R^1$ is an unsubstituted heteroalkyl (e.g., 2 to 8 membered, 2 to 6 membered, or 2 to 4 membered heteroalkyl).

In embodiments, $R^1$ is $R^{1E}$-substituted or unsubstituted cycloalkyl (e.g., $C_3$-$C_8$, $C_3$-$C_6$, or $C_5$-$C_6$ cycloalkyl). In embodiments, $R^1$ is $R^{1E}$-substituted cycloalkyl (e.g., $C_3$-$C_8$, $C_3$-$C_6$, or $C_5$-$C_6$ cycloalkyl). In embodiments, $R^1$ is an unsubstituted cycloalkyl (e.g., $C_3$-$C_8$, $C_3$-$C_6$, or $C_5$-$C_6$ cycloalkyl).

In embodiments, $R^1$ is $R^{1E}$-substituted or unsubstituted heterocycloalkyl (e.g., 3 to 8 membered, 3 to 6 membered, or 5 to 6 membered heterocycloalkyl). In embodiments, $R^1$ is $R^{1E}$-substituted heterocycloalkyl (e.g., 3 to 8 membered, 3 to 6 membered, or 5 to 6 membered heterocycloalkyl). In embodiments, $R^1$ is an unsubstituted heterocycloalkyl (e.g., 3 to 8 membered, 3 to 6 membered, or 5 to 6 membered heterocycloalkyl).

In embodiments, $R^1$ is $R^{1E}$-substituted or unsubstituted aryl (e.g., $C_6$-$C_{10}$, $C_{10}$, or phenyl). In embodiments, $R^1$ is $R^{1E}$-substituted aryl (e.g., $C_6$-$C_{10}$, $C_{10}$, or phenyl). In embodiments, $R^1$ is an unsubstituted aryl (e.g., $C_6$-$C_{10}$, $C_{10}$, or phenyl).

In embodiments, $R^1$ is $R^{1E}$-substituted or unsubstituted heteroaryl (e.g., 5 to 10 membered, 5 to 9 membered, or 5 to 6 membered heteroaryl). In embodiments, $R^1$ is $R^{1E}$-substituted heteroaryl (e.g., 5 to 10 membered, 5 to 9 membered, or 5 to 6 membered heteroaryl). In embodiments, $R^1$ is an unsubstituted heteroaryl (e.g., 5 to 10 membered, 5 to 9 membered, or 5 to 6 membered heteroaryl).

$R^1$ may be $R^{1E}$-substituted or unsubstituted methyl, $R^{1E}$-substituted or unsubstituted ethyl, or $R^{1E}$-substituted or unsubstituted propyl. $R^1$ may be unsubstituted methyl, unsubstituted ethyl, or unsubstituted propyl.

$R^1$ may be halogen, —$CF_3$, —$CCl_3$, —$CBr_3$, —$CI_3$, —CN, —CHO, —OH, —$NH_2$, —$NO_2$, or —$COOR^{1A}$. $R^{1A}$ may be hydrogen, $C_1$-$C_3$ unsubstituted alkyl, 2 to 5 membered unsubstituted heteroalkyl, or 5 or 6 membered unsubstituted aryl. In embodiments, $R^1$ is —$COOR^{1A}$, wherein $R^{1A}$ is $C_1$-$C_3$ unsubstituted alkyl. RIA may be unsubstituted methyl, unsubstituted ethyl, or unsubstituted propyl. $R^1$ may be —$COOCH_3$. $R^1$ may be halogen, —$CF_3$, —$CCl_3$, —$CBr_3$, —$CI_3$, —CN, —$NH_2$, or $NO_2$. $R^1$ may be —CN. $R^1$ may be unsubstituted 2 to 5 membered heteroalkyl.

$R^{1E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1F}$-substituted or unsubstituted alkyl (e.g., $C_1$-$C_8$, $C_1$-$C_6$, or $C_1$-$C_4$ alkyl), $R^{1F}$-substituted or unsubstituted heteroalkyl (e.g., 2 to 8 membered, 2 to 6 membered, or 2 to 4 membered heteroalkyl), $R^{1F}$-substituted or unsubstituted cycloalkyl (e.g., $C_3$-$C_8$, $C_3$-$C_6$, or $C_5$-$C_6$ cycloalkyl), $R^{1F}$-substituted or unsubstituted heterocycloalkyl (e.g., 3 to 8 membered, 3 to 6 membered, or 5 to 6 membered heterocycloalkyl), $R^{1F}$-substituted or unsubstituted aryl (e.g., $C_6$-$C_{10}$, $C_{10}$ aryl, or phenyl), or $R^{1F}$-substituted or unsubstituted heteroaryl (e.g., 5 to 10 membered, 5 to 9 membered, or 5 to 6 membered heteroaryl).

$R^{1F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^1$ may be an electron withdrawing group (EWG) (e.g. halogen, —$N_3$, —$NO_2$, —$CF_3$, —$CCl_3$, —$CBr_3$, —$CI_3$, —CN, —CHO, —$CONH_2$, or substituted or unsubstituted 2 to 8 membered heteroalkyl). An "electron withdrawing group" is used herein according to its common meaning in the art and refers to a chemical moiety that tends to remove electrons (electron density) from a portion of the compound to which it is attached (e.g. a deactivating group). $R^1$ may be —CN. $R^1$ may be —$NO_2$. $R^1$ may be —$CF_3$, —$CCl_3$, —$CBr_3$, or —$CI_3$. $R^1$ may be substituted or unsubstituted 2 to 8 membered heteroalkyl. $R^1$ may be —$COOCH_3$.

$R^2$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_5$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^7$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^2$ may be halogen, —$CF_3$, —$CCl_3$, —$CBr_3$, —$CI_3$, —CN, substituted or unsubstituted alkyl, or substituted or unsubstituted heteroalkyl. $R^2$ may be —CN, substituted or unsubstituted alkyl, or substituted or unsubstituted heteroalkyl. $R^2$ may be —CN or substituted or unsubstituted alkyl. $R^2$ may be —CN or unsubstituted methyl. $R^2$ may be —CN, or unsubstituted heteroalkyl. $R^2$ may be substituted alkyl or substituted heteroalkyl. $R^2$ may be hydrogen.

$R^2$ may be hydrogen, $R^{2E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{2E}$-substituted or unsubstituted cycloalkyl (e.g., $C_3$-$C_8$, $C_3$-$C_6$, or $C_5$-$C_6$ cycloalkyl), $R^{2E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{2E}$-substituted or unsubstituted heteroaryl (e.g., 5 to 10 membered, 5 to 9 membered, or 5 to 6 membered heteroaryl). $R^2$ may be $R^{2E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{2E}$-substituted or unsubstituted cycloalkyl (e.g., $C_3$-$C_8$, $C_3$-$C_6$, or $C_5$-$C_6$ cycloalkyl), $R^{2E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{2E}$-substituted or unsubstituted heteroaryl (e.g., 5 to 10 membered, 5 to 9 membered, or 5 to 6 membered heteroaryl).

In embodiments, $R^2$ is $R^{2E}$-substituted or unsubstituted alkyl (e.g., $C_1$-$C_8$, $C_1$-$C_6$, or $C_1$-$C_4$ alkyl). In embodiments, $R^2$ is $R^{2E}$-substituted alkyl (e.g., $C_1$-$C_8$, $C_1$-$C_6$, or $C_1$-$C_4$ alkyl). In embodiments, $R^2$ is an unsubstituted alkyl (e.g., $C_1$-$C_8$, $C_1$-$C_6$, or $C_1$-$C_4$ alkyl).

In embodiments, $R^2$ is $R^{2E}$-substituted or unsubstituted heteroalkyl (e.g., 2 to 8 membered, 2 to 6 membered, or 2 to 4 membered heteroalkyl). In embodiments, $R^2$ is $R^{2E}$-substituted heteroalkyl (e.g., 2 to 8 membered, 2 to 6 membered, or 2 to 4 membered heteroalkyl). In embodiments, $R^2$ is an unsubstituted heteroalkyl (e.g., 2 to 8 membered, 2 to 6 membered, or 2 to 4 membered heteroalkyl).

In embodiments, $R^2$ is $R^{2E}$-substituted or unsubstituted cycloalkyl (e.g., $C_3$-$C_8$, $C_3$-$C_6$, or $C_5$-$C_6$ cycloalkyl). In embodiments, $R^2$ is $R^{2E}$-substituted cycloalkyl (e.g., $C_3$-$C_8$, $C_3$-$C_6$, or $C_5$-$C_6$ cycloalkyl). In embodiments, $R^2$ is an unsubstituted cycloalkyl (e.g., $C_3$-$C_8$, $C_3$-$C_6$, or $C_5$-$C_6$ cycloalkyl).

In embodiments, $R^2$ is $R^{2E}$-substituted or unsubstituted heterocycloalkyl (e.g., 3 to 8 membered, 3 to 6 membered, or 5 to 6 membered heterocycloalkyl). In embodiments, $R^2$ is $R^{2E}$-substituted heterocycloalkyl (e.g., 3 to 8 membered, 3 to 6 membered, or 5 to 6 membered heterocycloalkyl). In embodiments, $R^2$ is an unsubstituted heterocycloalkyl (e.g., 3 to 8 membered, 3 to 6 membered, or 5 to 6 membered heterocycloalkyl).

In embodiments, $R^2$ is $R^{2E}$-substituted or unsubstituted aryl (e.g., $C_6$-$C_{10}$, $C_{10}$, or phenyl). In embodiments, $R^2$ is $R^{2E}$-substituted aryl (e.g., $C_6$-$C_{10}$, $C_{10}$, or phenyl). In embodiments, $R^2$ is an unsubstituted aryl (e.g., $C_6$-$C_{10}$, $C_{10}$, or phenyl).

In embodiments, $R^2$ is $R^{2E}$-substituted or unsubstituted heteroaryl (e.g., 5 to 10 membered, 5 to 9 membered, or 5 to 6 membered heteroaryl). In embodiments, $R^2$ is $R^{2E}$-substituted heteroaryl (e.g., 5 to 10 membered, 5 to 9 membered, or 5 to 6 membered heteroaryl). In embodiments, $R^2$ is an unsubstituted heteroaryl (e.g., 5 to 10 membered, 5 to 9 membered, or 5 to 6 membered heteroaryl).

$R^{2E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{2F}$-substituted or unsubstituted alkyl (e.g., $C_1$-$C_8$, $C_1$-$C_6$, or $C_1$-$C_4$ alkyl), $R^{2F}$-substituted or unsubstituted heteroalkyl (e.g., 2 to 8 membered, 2 to 6 membered, or 2 to 4 membered heteroalkyl), $R^{2F}$-substituted or unsubstituted cycloalkyl (e.g., $C_3$-$C_8$, $C_3$-$C_6$, or $C_5$-$C_6$ cycloalkyl), $R^{2F}$-substituted or unsubstituted heterocycloalkyl (e.g., 3 to 8 membered, 3 to 6 membered, or 5 to 6 membered heterocycloalkyl), $R^{2F}$-substituted or unsubstituted aryl (e.g., $C_6$-$C_{10}$, $C_{10}$ aryl, or phenyl), or $R^{2F}$-substituted or unsubstituted heteroaryl (e.g., 5 to 10 membered, 5 to 9 membered, or 5 to 6 membered heteroaryl). $R^{2E}$ may be unsubstituted pyridine. $R^{2E}$ may be unsubstituted morpholino. $R^{2E}$ may be unsubstituted methyl.

$R^{2F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH$—$_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, $R^2$ may be —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2Ph$, —$SO_2NH_2$, —$NHNH_2$, —$ONH_2$, $R^{2E}$-substituted or unsubstituted $C_1$-$C_3$ alkyl, or 2 to 3 membered $R^{2E}$-substituted or unsubstituted heteroalkyl. In embodiments $R^2$ is unsubstituted $C_1$-$C_5$ alkyl or unsubstituted 2 to 5 membered heteroalkyl. In embodiments $R^2$ is unsubstituted methyl. In embodiments $R^2$ is unsubstituted methoxy (e.g. —$OCH_3$).

$R^2$ may be $R^{2E}$-substituted or unsubstituted $C_1$-$C_5$ alkyl (e.g. $R^{2E}$-substituted or unsubstituted methyl). $R^2$ may be $R^{2E}$-substituted $C_1$-$C_5$ alkyl. When $R^2$ is substituted or unsubstituted $C_1$-$C_5$ alkyl, $R^{2E}$ may be unsubstituted heterocycloalkyl, unsubstituted aryl, or unsubstituted heteroaryl. $R^{2E}$ may be substituted or unsubstituted morpholino (e.g. $R^{2F}$-substituted or unsubstituted morpholino). $R^2$ may be $R^{2E}$-substituted or unsubstituted 2 to 5 membered heteroalkyl. When $R^2$ is substituted or unsubstituted 2 to 5 membered heteroalkyl, $R^{2E}$ may be unsubstituted $C_1$-$C_5$ alkyl, unsubstituted heterocycloalkyl, unsubstituted aryl, or unsubstituted heteroaryl. $R^2$ may be —$OCH_3$. $R^2$ may be unsubstituted methyl. $R^2$ may be —CN.

In embodiments, $R^1$ is halogen, —$N_3$, —$NO_2$, —$CF_3$, $CCl_3$, $CBr_3$, $CI_3$, —CN, —CHO, —$CONH_2$, or substituted or unsubstituted 2 to 8 membered heteroalkyl and $R^2$ is hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{2E}$-substituted or unsubstituted $C_1$-$C_8$ alkyl, $R^{2E}$-substituted or unsubstituted 2 to 8 membered heteroalkyl, $R^{2E}$-substituted or unsubstituted $C_3$-$C_8$ cycloalkyl, $R^{2E}$-substituted or unsubstituted 3 to 6 membered heterocycloalkyl, $R^{2E}$-substituted or unsubstituted phenyl or $R^{2E}$-substituted or unsubstituted 5 or 6 membered heteroaryl. In embodiments, at least one of $R^1$ and $R^2$ is an electron withdrawing group (EWG) (e.g. halogen, —$N_3$, —$NO_2$, —$CF_3$, $CCl_3$, $CBr_3$, $CI_3$, —CN, —CHO, —$CONH_2$, or substituted or unsubstituted 3 to 8 membered heteroalkyl. When $R^1$ is CN, $R^2$ may be —CN. When $R^1$ is halogen, $R^2$ may be halogen. When $R^1$ is —CN, $R^2$ may be unsubstituted $C_1$-$C_5$ alkyl. When $R^1$ is —CN, $R^2$ may be unsubstituted methyl. When $R^1$ is unsubstituted 2 to 8 membered heteroalkyl (e.g. —$COOCH_3$), $R^2$ may be may be unsubstituted $C_1$-$C_5$ alkyl. When $R^1$ is —CN, $R^2$ may be $R^{2E}$-substituted or unsubstituted $C_1$-$C_5$ alkyl. When $R^1$ is —CN, $R^2$ may be $R^{2E}$-substituted or unsubstituted 2 to 5 membered heteroalkyl. $R^{2E}$ may be unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is a polar substituent and provides polarity to the compounds provided herein (e.g. where $R^2$ is a substituted or unsubstituted 2 to 8 membered heteroalkyl). A "polar substituent" is understood by one skilled in the art to be a moiety that creates a dipole moment, thereby forming a positive or negative charge on a molecule. $R^2$ may be an aqueous solubility enhancing substituent (e.g. a moiety that increases the water solubility of the compound), where germinal substitution at $R^2$ with a substituent other than methyl improves the solubility of the compound in an aqueous medium. Solubility enhancing substituents may include basic substituents or groups that add polarity.

$R^3$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^3$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^3$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^3$ may be halogen, or substituted or unsubstituted alkyl (e.g., $C_1$-$C_8$, $C_1$-$C_6$, or $C_1$-$C_4$ alkyl). $R^3$ may be halogen, or alkyl (e.g., $C_1$-$C_8$, $C_1$-$C_6$, or $C_1$-$C_4$ alkyl). $R^3$ may be halogen, or substituted or unsubstituted heteroalkyl (e.g., 2 to 8 membered, 2 to 6 membered, or 2 to 4 membered heteroalkyl). $R^3$ may be halogen, unsubstituted heteroalkyl (e.g., 2 to 8 membered, 2 to 6 membered, or 2 to 4 membered heteroalkyl. $R^3$ may be halogen, —$CF_3$, —$CCl_3$, —$CBr_3$, or —$CI_3$. $R^3$ may be hydrogen.

$R^3$ may be hydrogen, $R^{3E}$-substituted or unsubstituted alkyl (e.g., $C_1$-$C_8$, $C_1$-$C_6$, or $C_1$-$C_4$ alkyl), $R^{3E}$-substituted or unsubstituted heteroalkyl (e.g., 2 to 8 membered, 2 to 6 membered, or 2 to 4 membered heteroalkyl), $R^{3E}$-substituted or unsubstituted cycloalkyl (e.g., $C_3$-$C_8$, $C_3$-$C_6$, or $C_5$-$C_6$ cycloalkyl), $R^{3E}$-substituted or unsubstituted heterocycloalkyl (e.g., 3 to 8 membered, 3 to 6 membered, or 5 to 6 membered heterocycloalkyl), $R^{3E}$-substituted or unsubstituted aryl (e.g., $C_6$-$C_{10}$, $C_{10}$ aryl, or phenyl), or $R^{3E}$-substituted or unsubstituted heteroaryl (e.g., 5 to 10 membered, 5 to 9 membered, or 5 to 6 membered heteroaryl). $R^3$ may be $R^{3E}$-substituted or unsubstituted alkyl (e.g., $C_1$-$C_8$, $C_1$-$C_6$, or $C_1$-$C_4$ alkyl), $R^{3E}$-substituted or unsubstituted heteroalkyl (e.g., 2 to 8 membered, 2 to 6 membered, or 2 to 4 membered heteroalkyl), $R^{3E}$-substituted or unsubstituted cycloalkyl (e.g., $C_3$-$C_8$, $C_3$-$C_6$, or $C_5$-$C_6$ cycloalkyl), $R^{3E}$-substituted or unsubstituted heterocycloalkyl (e.g., 3 to 8 membered, 3 to 6 membered, or 5 to 6 membered heterocycloalkyl), $R^{3E}$-substituted or unsubstituted aryl (e.g., $C_6$-$C_{10}$, $C_{10}$ aryl, or phenyl), or $R^{3E}$-substituted or unsubstituted heteroaryl (e.g., 5 to 10 membered, 5 to 9 membered, or 5 to 6 membered heteroaryl).

In embodiments, $R^3$ is $R^{3E}$-substituted or unsubstituted alkyl (e.g., $C_1$-$C_8$, $C_1$-$C_6$, or $C_1$-$C_4$ alkyl). In embodiments, $R^3$ is $R^{3E}$-substituted alkyl (e.g., $C_1$-$C_8$, $C_1$-$C_6$, or $C_1$-$C_4$ alkyl). In embodiments, $R^3$ is an unsubstituted alkyl (e.g., $C_1$-$C_8$, $C_1$-$C_6$, or $C_1$-$C_4$ alkyl).

In embodiments, $R^3$ is $R^{3E}$-substituted or unsubstituted heteroalkyl (e.g., 2 to 8 membered, 2 to 6 membered, or 2 to 4 membered heteroalkyl). In embodiments, $R^3$ is $R^{3E}$-substituted heteroalkyl (e.g., 2 to 8 membered, 2 to 6 membered, or 2 to 4 membered heteroalkyl). In embodiments, $R^3$ is an unsubstituted heteroalkyl (e.g., 2 to 8 membered, 2 to 6 membered, or 2 to 4 membered heteroalkyl).

In embodiments, $R^3$ is $R^{3E}$-substituted or unsubstituted cycloalkyl (e.g., $C_3$-$C_8$, $C_3$-$C_6$, or $C_5$-$C_6$ cycloalkyl). In embodiments, $R^3$ is $R^{3E}$-substituted cycloalkyl (e.g., $C_3$-$C_8$, $C_3$-$C_6$, or $C_5$-$C_6$ cycloalkyl). In embodiments, $R^3$ is an unsubstituted cycloalkyl (e.g., $C_3$-$C_5$, $C_3$-$C_6$, or $C_5$-$C_6$ cycloalkyl).

In embodiments, $R^3$ is $R^{3E}$-substituted or unsubstituted heterocycloalkyl (e.g., 3 to 8 membered, 3 to 6 membered, or 5 to 6 membered heterocycloalkyl). In embodiments, $R^3$ is $R^{3E}$-substituted heterocycloalkyl (e.g., 3 to 8 membered, 3 to 6 membered, or 5 to 6 membered heterocycloalkyl). In embodiments, $R^3$ is an unsubstituted heterocycloalkyl (e.g., 3 to 8 membered, 3 to 6 membered, or 5 to 6 membered heterocycloalkyl).

In embodiments, $R^3$ is $R^{3E}$-substituted or unsubstituted aryl (e.g., $C_6$-$C_{10}$, $C_{10}$, or phenyl). In embodiments, $R^3$ is $R^{3E}$-substituted aryl (e.g., $C_6$-$C_{10}$, $C_{10}$, or phenyl). In embodiments, $R^3$ is an unsubstituted aryl (e.g., $C_6$-$C_{10}$, $C_{10}$, or phenyl).

In embodiments, $R^3$ is $R^{3E}$-substituted or unsubstituted heteroaryl (e.g., 5 to 10 membered, 5 to 9 membered, or 5 to 6 membered heteroaryl). In embodiments, $R^3$ is $R^{3E}$-substituted heteroaryl (e.g., 5 to 10 membered, 5 to 9 membered, or 5 to 6 membered heteroaryl). In embodiments, $R^3$ is an unsubstituted heteroaryl (e.g., 5 to 10 membered, 5 to 9 membered, or 5 to 6 membered heteroaryl).

$R^{3E}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$N—$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{3F}$-substituted or unsubstituted alkyl (e.g., $C_1$-$C_8$, $C_1$-$C_6$, or $C_1$-$C_4$ alkyl), $R^{3F}$-substituted or unsubstituted heteroalkyl (e.g., 2 to 8 membered, 2 to 6 membered, or 2 to 4 membered heteroalkyl), $R^{3F}$-substituted or unsubstituted cycloalkyl (e.g., $C_3$-$C_8$, $C_3$-$C_6$, or $C_5$-$C_6$ cycloalkyl), $R^{3F}$-substituted or unsubstituted heterocycloalkyl (e.g., 3 to 8 membered, 3 to 6 membered, or 5 to 6 membered heterocycloalkyl), $R^{3F}$-substituted or unsubstituted aryl (e.g., $C_6$-$C_{10}$, $C_{10}$ aryl, or phenyl), or $R^{3F}$-substituted or unsubstituted heteroaryl (e.g., 5 to 10 membered, 5 to 9 membered, or 5 to 6 membered heteroaryl).

$R^{3F}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^3$ may be hydrogen, halogen, or $R^{3E}$-substituted or unsubstituted $C_1$-$C_8$ alkyl. $R^3$ may be hydrogen. $R^3$ may be unsubstituted methyl, unsubstituted ethyl, or unsubstituted propyl.

$R^4$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_5$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^4$ may be halogen, —CF$_3$, —CCl$_3$, —CBr$_3$, —CI$_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^4$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^4$ may be halogen, or substituted or unsubstituted alkyl (e.g., $C_1$-$C_8$, $C_1$-$C_6$, or $C_1$-$C_4$ alkyl). $R^4$ may be halogen, or alkyl (e.g., $C_1$-$C_8$, $C_1$-$C_6$, or $C_1$-$C_4$ alkyl). $R^4$ may be halogen, or substituted or unsubstituted heteroalkyl (e.g., 2 to 8 membered, 2 to 6 membered, or 2 to 4 membered heteroalkyl). $R^4$ may be halogen, unsubstituted heteroalkyl (e.g., 2 to 8 membered, 2 to 6 membered, or 2 to 4 membered heteroalkyl. $R^4$ may be halogen, —CF$_3$, —CCl$_3$, —CBr$_3$, or —CI$_3$. $R^4$ may be hydrogen.

$R^4$ may be hydrogen, $R^{4E}$-substituted or unsubstituted alkyl (e.g., $C_1$-$C_8$, $C_1$-$C_6$, or $C_1$-$C_4$ alkyl), $R^{4E}$-substituted or unsubstituted heteroalkyl (e.g., 2 to 8 membered, 2 to 6 membered, or 2 to 4 membered heteroalkyl), $R^{4E}$-substituted or unsubstituted cycloalkyl (e.g., $C_3$-$C_8$, $C_3$-$C_6$, or $C_5$-$C_6$ cycloalkyl), $R^{4E}$-substituted or unsubstituted heterocycloalkyl (e.g., 3 to 8 membered, 3 to 6 membered, or 5 to 6 membered heterocycloalkyl), $R^{4E}$-substituted or unsubstituted aryl (e.g., $C_6$-$C_{10}$, $C_{10}$ aryl, or phenyl), or $R^{4E}$-substituted or unsubstituted heteroaryl (e.g., 5 to 10 membered, 5 to 9 membered, or 5 to 6 membered heteroaryl). $R^4$ may be $R^{4E}$-substituted or unsubstituted alkyl (e.g., $C_1$-$C_8$, $C_1$-$C_6$, or $C_1$-$C_4$ alkyl), $R^{4E}$-substituted or unsubstituted heteroalkyl (e.g., 2 to 8 membered, 2 to 6 membered, or 2 to 4 membered heteroalkyl), $R^{4E}$-substituted or unsubstituted cycloalkyl (e.g., $C_3$-$C_8$, $C_3$-$C_6$, or $C_5$-$C_6$ cycloalkyl), $R^{4E}$-substituted or unsubstituted heterocycloalkyl (e.g., 3 to 8 membered, 3 to 6 membered, or 5 to 6 membered heterocycloalkyl), $R^{4E}$-substituted or unsubstituted aryl (e.g., $C_6$-$C_{10}$, $C_{10}$ aryl, or phenyl), or $R^{4E}$-substituted or unsubstituted heteroaryl (e.g., 5 to 10 membered, 5 to 9 membered, or 5 to 6 membered heteroaryl).

In embodiments, $R^4$ is $R^{4E}$-substituted or unsubstituted alkyl (e.g., $C_1$-$C_8$, $C_1$-$C_6$, or $C_1$-$C_4$ alkyl). In embodiments, $R^4$ is $R^{4E}$-substituted alkyl (e.g., $C_1$-$C_8$, $C_1$-$C_6$, or $C_1$-$C_4$ alkyl). In embodiments, $R^4$ is an unsubstituted alkyl (e.g., $C_1$-$C_5$, $C_1$-$C_6$, or $C_1$-$C_4$ alkyl).

In embodiments, $R^4$ is $R^{4E}$-substituted or unsubstituted heteroalkyl (e.g., 2 to 8 membered, 2 to 6 membered, or 2 to 4 membered heteroalkyl). In embodiments, $R^4$ is $R^{4E}$-substituted heteroalkyl (e.g., 2 to 8 membered, 2 to 6 membered, or 2 to 4 membered heteroalkyl). In embodiments, $R^4$ is an unsubstituted heteroalkyl (e.g., 2 to 8 membered, 2 to 6 membered, or 2 to 4 membered heteroalkyl).

In embodiments, $R^4$ is $R^{4E}$-substituted or unsubstituted cycloalkyl (e.g., $C_3$-$C_8$, $C_3$-$C_6$, or $C_5$-$C_6$ cycloalkyl). In embodiments, $R^4$ is $R^{4E}$-substituted cycloalkyl (e.g., $C_3$-$C_8$, $C_3$-$C_6$, or $C_5$-$C_6$ cycloalkyl). In embodiments, $R^4$ is an unsubstituted cycloalkyl (e.g., $C_3$-$C_5$, $C_3$-$C_6$, or $C_5$-$C_6$ cycloalkyl).

In embodiments, $R^4$ is $R^{4E}$-substituted or unsubstituted heterocycloalkyl (e.g., 3 to 8 membered, 3 to 6 membered, or 5 to 6 membered heterocycloalkyl). In embodiments, $R^4$ is $R^{4E}$-substituted heterocycloalkyl (e.g., 3 to 8 membered, 3 to 6 membered, or 5 to 6 membered heterocycloalkyl). In embodiments, $R^4$ is an unsubstituted heterocycloalkyl (e.g., 3 to 8 membered, 3 to 6 membered, or 5 to 6 membered heterocycloalkyl).

In embodiments, $R^4$ is $R^{4E}$-substituted or unsubstituted aryl (e.g., $C_6$-$C_{10}$, $C_{10}$, or phenyl). In embodiments, $R^4$ is $R^{4E}$-substituted aryl (e.g., $C_6$-$C_{10}$, $C_{10}$, or phenyl). In embodiments, $R^4$ is an unsubstituted aryl (e.g., $C_6$-$C_{10}$, $C_{10}$, or phenyl).

In embodiments, $R^4$ is $R^{4E}$-substituted or unsubstituted heteroaryl (e.g., 5 to 10 membered, 5 to 9 membered, or 5 to 6 membered heteroaryl). In embodiments, $R^4$ is $R^{4E}$-substituted heteroaryl (e.g., 5 to 10 membered, 5 to 9 membered, or 5 to 6 membered heteroaryl). In embodiments, $R^4$ is an unsubstituted heteroaryl (e.g., 5 to 10 membered, 5 to 9 membered, or 5 to 6 membered heteroaryl).

$R^{4E}$ is independently oxo, halogen, $-CCl_3$, $-CBr_3$, $-CF_3$, $-CI_3$, $-CHF_2$, $-CHCl_2$, $-CHBr_2$, $-CHI_2$, $-CH_2F$, $-CH_2Cl$, $-CH_2Br$, $-OCH_2I$, $-N_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{4F}$-substituted or unsubstituted alkyl (e.g., $C_1$-$C_8$, $C_1$-$C_6$, or $C_1$-$C_4$ alkyl), $R^{4F}$-substituted or unsubstituted heteroalkyl (e.g., 2 to 8 membered, 2 to 6 membered, or 2 to 4 membered heteroalkyl), $R^{4F}$-substituted or unsubstituted cycloalkyl (e.g., $C_3$-$C_5$, $C_3$-$C_6$, or $C_5$-$C_6$ cycloalkyl), $R^{4F}$-substituted or unsubstituted heterocycloalkyl (e.g., 3 to 8 membered, 3 to 6 membered, or 5 to 6 membered heterocycloalkyl), $R^{4F}$-substituted or unsubstituted aryl (e.g., $C_6$-$C_{10}$, $C_{10}$ aryl, or phenyl), or $R^{4F}$-substituted or unsubstituted heteroaryl (e.g., 5 to 10 membered, 5 to 9 membered, or 5 to 6 membered heteroaryl).

$R^{4F}$ is independently oxo, halogen, $-CCl_3$, $-CBr_3$, $-CF_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-N_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_5$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^4$ may be hydrogen, halogen, or $R^{4E}$-substituted or unsubstituted $C_1$-$C_8$ alkyl. $R^4$ may be hydrogen. $R^4$ may be unsubstituted methyl, unsubstituted ethyl, or unsubstituted propyl. In embodiments, $R^3$ and $R^4$ are hydrogen.

$R^5$ may be hydrogen, halogen, $-N_3$, $-CF_3$, $-CCl_3$, $-CBr_3$, $-CI_3$, $-N_3$, $-CN$, $-CHO$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^5$ may be halogen, $-CF_3$, $-CCl_3$, $-CBr_3$, $-CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^5$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^5$ may be halogen, or substituted or unsubstituted alkyl (e.g., $C_1$-$C_8$, $C_1$-$C_6$, or $C_1$-$C_4$ alkyl). $R^5$ may be halogen, or unsubstituted alkyl (e.g., $C_1$-$C_8$, $C_1$-$C_6$, or $C_1$-$C_4$ alkyl). $R^5$ may be halogen, or substituted or unsubstituted heteroalkyl (e.g., 2 to 8 membered, 2 to 6 membered, or 2 to 4 membered heteroalkyl). $R^5$ may be halogen, unsubstituted heteroalkyl (e.g., 2 to 8 membered, 2 to 6 membered, or 2 to 4 membered heteroalkyl. $R^5$ may be halogen, $-CF_3$, $-CCl_3$, $-CBr_3$, or $-CI_3$. $R^5$ may be hydrogen.

$R^5$ may be hydrogen, $R^{5E}$-substituted or unsubstituted alkyl(e.g., $C_1$-$C_8$, $C_1$-$C_6$, or $C_1$-$C_4$ alkyl), $R^{5E}$-substituted or unsubstituted heteroalkyl (e.g., 2 to 8 membered, 2 to 6 membered, or 2 to 4 membered heteroalkyl), $R^{5E}$-substituted or unsubstituted cycloalkyl (e.g., $C_3$-$C_8$, $C_3$-$C_6$, or $C_5$-$C_6$ cycloalkyl), $R^{5E}$-substituted or unsubstituted heterocycloalkyl (e.g., 3 to 8 membered, 3 to 6 membered, or 5 to 6 membered heterocycloalkyl), $R^{5E}$-substituted or unsubstituted aryl (e.g., $C_6$-$C_{10}$, $C_{10}$ aryl, or phenyl), or $R^{5E}$-substituted or unsubstituted heteroaryl (e.g., 5 to 10 membered, 5 to 9 membered, or 5 to 6 membered heteroaryl). $R^5$ may be $R^{5E}$-substituted or unsubstituted alkyl (e.g., $C_1$-$C_8$, $C_1$-$C_6$, or $C_1$-$C_4$ alkyl), $R^{5E}$-substituted heteroalkyl (e.g., 2 to 8 membered, 2 to 6 membered, or 2 to 4 membered heteroalkyl), $R^{5E}$-substituted or unsubstituted cycloalkyl (e.g., $C_3$-$C_8$, $C_3$-$C_6$, or $C_5$-$C_6$ cycloalkyl), $R^{1E}$-substituted or unsubstituted heterocycloalkyl (e.g., 3 to 8 membered, 3 to 6 membered, or 5 to 6 membered heterocycloalkyl), $R^{5E}$-substituted or unsubstituted aryl (e.g., $C_6$-$C_{10}$, $C_{10}$ aryl, or phenyl), or $R^{5E}$-substituted or unsubstituted heteroaryl (e.g., 5 to 10 membered, 5 to 9 membered, or 5 to 6 membered heteroaryl).

In embodiments, $R^5$ is $R^{5E}$-substituted or unsubstituted alkyl (e.g., $C_1$-$C_8$, $C_1$-$C_6$, or $C_1$-$C_4$ alkyl). In embodiments, $R^5$ is $R^{5E}$-substituted alkyl (e.g., $C_1$-$C_8$, $C_1$-$C_6$, or $C_1$-$C_4$ alkyl). In embodiments, $R^5$ is an unsubstituted alkyl (e.g., $C_1$-$C_8$, $C_1$-$C_6$, or $C_1$-$C_4$ alkyl).

In embodiments, $R^5$ is $R^{5E}$-substituted or unsubstituted heteroalkyl (e.g., 2 to 8 membered, 2 to 6 membered, or 2 to 4 membered heteroalkyl). In embodiments, $R^5$ is $R^{5E}$-substituted heteroalkyl (e.g., 2 to 8 membered, 2 to 6 membered, or 2 to 4 membered heteroalkyl). In embodiments, $R^5$ is an unsubstituted heteroalkyl (e.g., 2 to 8 membered, 2 to 6 membered, or 2 to 4 membered heteroalkyl).

In embodiments, $R^5$ is $R^{5E}$-substituted or unsubstituted cycloalkyl (e.g., $C_3$-$C_8$, $C_3$-$C_6$, or $C_5$-$C_6$ cycloalkyl). In embodiments, $R^5$ is $R^{5E}$-substituted cycloalkyl (e.g., $C_3$-$C_8$, $C_3$-$C_6$, or $C_5$-$C_6$ cycloalkyl). In embodiments, $R^5$ is an unsubstituted cycloalkyl (e.g., $C_3$-$C_8$, $C_3$-$C_6$, or $C_5$-$C_6$ cycloalkyl).

In embodiments, $R^5$ is $R^{5E}$-substituted or unsubstituted heterocycloalkyl (e.g., 3 to 8 membered, 3 to 6 membered, or 5 to 6 membered heterocycloalkyl). In embodiments, $R^5$ is $R^{5E}$-substituted heterocycloalkyl (e.g., 3 to 8 membered, 3 to 6 membered, or 5 to 6 membered heterocycloalkyl). In embodiments, $R^5$ is an unsubstituted heterocycloalkyl (e.g., 3 to 8 membered, 3 to 6 membered, or 5 to 6 membered heterocycloalkyl).

In embodiments, $R^5$ is $R^{5E}$-substituted or unsubstituted aryl (e.g., $C_6$-$C_{10}$, $C_{10}$, or phenyl). In embodiments, $R^5$ is $R^{5E}$-substituted aryl (e.g., $C_6$-$C_{10}$, $C_{10}$, or phenyl). In embodiments, $R^5$ is an unsubstituted aryl (e.g., $C_6$-$C_{10}$, $C_{10}$, or phenyl).

In embodiments, $R^5$ is $R^{5E}$-substituted or unsubstituted heteroaryl (e.g., 5 to 10 membered, 5 to 9 membered, or 5 to 6 membered heteroaryl). In embodiments, $R^5$ is $R^{5E}$-substituted heteroaryl (e.g., 5 to 10 membered, 5 to 9 membered, or 5 to 6 membered heteroaryl). In embodiments, $R^5$ is an unsubstituted heteroaryl (e.g., 5 to 10 membered, 5 to 9 membered, or 5 to 6 membered heteroaryl).

$R^{5E}$ is independently oxo, halogen, $-CCl_3$, $-CBr_3$, $-CF_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-N_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{5F}$-substituted or unsubstituted alkyl (e.g., $C_1$-$C_8$, $C_1$-$C_6$, or $C_1$-$C_4$ alkyl), $R^{5F}$-substituted or unsubstituted heteroalkyl (e.g., 2 to 8 membered, 2 to 6 membered, or 2 to 4 membered heteroalkyl), $R^{5F}$-substituted or unsubstituted cycloalkyl (e.g., $C_3$-$C_8$, $C_3$-$C_6$, or $C_5$-$C_6$ cycloalkyl), $R^{5F}$-substituted or unsubstituted heterocycloalkyl (e.g., 3 to 8 membered, 3 to 6 membered, or 5 to 6 membered heterocycloalkyl), $R^{5F}$-substituted or unsubstituted aryl (e.g., $C_6$-$C_{10}$, $C_{10}$ aryl, or phenyl), or $R^{5F}$-substituted or unsubstituted heteroaryl (e.g., 5 to 10 membered, 5 to 9 membered, or 5 to 6 membered heteroaryl).

$R^{5F}$ is independently oxo, halogen, $-CCl_3$, $-CBr_3$, $-CF_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-N_3$, $-CN$, $-OH$, $-NH_2$, $-COOH$, $-CONH_2$, $-NO_2$, $-SH$, $-SO_3H$, $-SO_4H$, $-SO_2N-_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^5$ may be $R^{5E}$-substituted or unsubstituted $C_1$-$C_8$ alkyl, $R^{5E}$-substituted or unsubstituted 2 to 8 membered heteroalkyl, unsubstituted 3 to 5 membered cycloalkyl, or unsubstituted 3 to 5 membered heterocycloalkyl. $R^5$ may be unsubstituted $C_1$-$C_8$ alkyl. $R^5$ may be unsubstituted methyl, unsubstituted ethyl, or unsubstituted propyl. $R^5$ may be methyl, ethyl, or propyl. $R^5$ may be unsubstituted methyl. $R^5$ may be unsubstituted ethyl. $R^5$ may be unsubstituted propyl. $R^5$ may be unsubstituted allyl. $R^5$ may be $R^{5E}$-substituted alkyl. $R^{5E}$ may be unsubstituted 5 or 6 membered heterocycloalkyl. $R^{5E}$ may be unsubstituted morpholino. In embodiments, $R^5$ is substituted or unsubstituted 2 to 8 membered heteroalkyl. $R^5$ may be $-(CH_2)_3N(CH_3)_3$. $R^5$ may be unsubstituted 3 to 5 membered cycloalkyl. In embodiments, $R^5$ is unsubstituted cyclopropyl.

$R^6$ may be hydrogen, halogen, $-N_3$, $-CF_3$, $-CCl_3$, $-CBr_3$, $-CI_3$, $-N_3$, $-CN$, $-CHO$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^6$ may be hydrogen, halogen, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^6$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^6$ may be halogen, or substituted or unsubstituted alkyl (e.g., $C_1$-$C_8$, $C_1$-$C_6$, or $C_1$-$C_4$ alkyl). $R^6$ may be halogen, or unsubstituted alkyl (e.g., $C_1$-$C_8$, $C_1$-$C_6$, or $C_1$-$C_4$ alkyl). $R^6$ may be halogen, or substituted or unsubstituted heteroalkyl (e.g., 2 to 8 membered, 2 to 6 membered, or 2 to 4 membered heteroalkyl). $R^6$ may be halogen, unsubstituted heteroalkyl (e.g., 2 to 8 membered, 2 to 6 membered, or 2 to 4 membered heteroalkyl. $R^6$ may be halogen, $-CF_3$, $-CCl_3$, $-CBr_3$, or $-CI_3$. $R^6$ may be hydrogen.

$R^6$ may be hydrogen, $R^{6E}$-substituted or unsubstituted alkyl (e.g., $C_1$-$C_8$, $C_1$-$C_6$, or $C_1$-$C_4$ alkyl), $R^{6E}$-substituted or unsubstituted heteroalkyl (e.g., 2 to 8 membered, 2 to 6 membered, or 2 to 4 membered heteroalkyl), $R^{6E}$-substituted or unsubstituted cycloalkyl (e.g., $C_3$-$C_8$, $C_3$-$C_6$, or $C_5$-$C_6$ cycloalkyl), $R^{6E}$-substituted or unsubstituted heterocycloalkyl (e.g., 3 to 8 membered, 3 to 6 membered, or 5 to 6 membered heterocycloalkyl), $R^{6E}$-substituted or unsubstituted aryl (e.g., $C_6$-$C_{10}$, $C_{10}$ aryl, or phenyl), or $R^{6E}$-substituted or unsubstituted heteroaryl (e.g., 5 to 10 membered, 5 to 9 membered, or 5 to 6 membered heteroaryl). $R^6$ may be $R^{6E}$-substituted or unsubstituted alkyl (e.g., $C_1$-$C_8$, $C_1$-$C_6$, or $C_1$-$C_4$ alkyl), $R^{6E}$-substituted or unsubstituted heteroalkyl (e.g., 2 to 8 membered, 2 to 6 membered, or 2 to 4 membered heteroalkyl), $R^{6E}$-substituted or unsubstituted cycloalkyl (e.g., $C_3$-$C_8$, $C_3$-$C_6$, or $C_5$-$C_6$ cycloalkyl), $R^{6E}$-substituted or unsubstituted heterocycloalkyl (e.g., 3 to 8 membered, 3 to 6 membered, or 5 to 6 membered heterocycloalkyl), $R^{6E}$-substituted or unsubstituted aryl (e.g., $C_6$-$C_{10}$, $C_{10}$ aryl, or phenyl), or $R^{6E}$-substituted or unsubstituted heteroaryl (e.g., 5 to 10 membered, 5 to 9 membered, or 5 to 6 membered heteroaryl).

In embodiments, $R^6$ is $R^{6E}$-substituted or unsubstituted alkyl (e.g., $C_1$-$C_8$, $C_1$-$C_6$, or $C_1$-$C_4$ alkyl). In embodiments, $R^6$ is $R^{6E}$-substituted alkyl (e.g., $C_1$-$C_8$, $C_1$-$C_6$, or $C_1$-$C_4$ alkyl). In embodiments, $R^6$ is an unsubstituted alkyl (e.g., $C_1$-$C_8$, $C_1$-$C_6$, or $C_1$-$C_4$ alkyl).

In embodiments, $R^6$ is $R^{6E}$-substituted or unsubstituted heteroalkyl (e.g., 2 to 8 membered, 2 to 6 membered, or 2 to 4 membered heteroalkyl). In embodiments, $R^6$ is $R^{6E}$-substituted heteroalkyl (e.g., 2 to 8 membered, 2 to 6 membered, or 2 to 4 membered heteroalkyl). In embodiments, $R^6$ is an unsubstituted heteroalkyl (e.g., 2 to 8 membered, 2 to 6 membered, or 2 to 4 membered heteroalkyl).

In embodiments, $R^6$ is $R^{6E}$-substituted or unsubstituted cycloalkyl (e.g., $C_3$-$C_8$, $C_3$-$C_6$, or $C_5$-$C_6$ cycloalkyl). In embodiments, $R^6$ is $R^{6E}$-substituted cycloalkyl (e.g., $C_3$-$C_5$, $C_3$-$C_6$, or $C_5$-$C_6$ cycloalkyl). In embodiments, $R^6$ is an unsubstituted cycloalkyl (e.g., $C_3$-$C_8$, $C_3$-$C_6$, or $C_5$-$C_6$ cycloalkyl).

In embodiments, $R^6$ is $R^{6E}$-substituted or unsubstituted heterocycloalkyl (e.g., 3 to 8 membered, 3 to 6 membered, or 5 to 6 membered heterocycloalkyl). In embodiments, $R^6$ is $R^{6E}$-substituted heterocycloalkyl (e.g., 3 to 8 membered, 3 to 6 membered, or 5 to 6 membered heterocycloalkyl). In embodiments, $R^6$ is an unsubstituted heterocycloalkyl (e.g., 3 to 8 membered, 3 to 6 membered, or 5 to 6 membered heterocycloalkyl).

In embodiments, $R^6$ is $R^{6E}$-substituted or unsubstituted aryl (e.g., $C_6$-$C_{10}$, $C_{10}$, or phenyl). In embodiments, $R^6$ is $R^{6E}$-substituted aryl (e.g., $C_6$-$C_{10}$, $C_{10}$, or phenyl). In embodiments, $R^6$ is an unsubstituted aryl (e.g., $C_6$-$C_{10}$, $C_{10}$, or phenyl).

In embodiments, $R^6$ is $R^{6E}$-substituted or unsubstituted heteroaryl (e.g., 5 to 10 membered, 5 to 9 membered, or 5 to 6 membered heteroaryl). In embodiments, $R^6$ is $R^{6E}$-substituted heteroaryl (e.g., 5 to 10 membered, 5 to 9 membered, or 5 to 6 membered heteroaryl). In embodiments, $R^6$ is an unsubstituted heteroaryl (e.g., 5 to 10 membered, 5 to 9 membered, or 5 to 6 membered heteroaryl).

$R^{6E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N$—$_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{6F}$-substituted or unsubstituted alkyl (e.g., $C_1$-$C_8$, $C_1$-$C_6$, or $C_1$-$C_4$ alkyl), $R^{6F}$-substituted or unsubstituted heteroalkyl (e.g., 2 to 8 membered, 2 to 6 membered, or 2 to 4 membered heteroalkyl), $R^{6F}$-substituted or unsubstituted cycloalkyl (e.g., $C_3$-$C_8$, $C_3$-$C_6$, or $C_5$-$C_6$ cycloalkyl), $R^{6F}$-substituted or unsubstituted heterocycloalkyl (e.g., 3 to 8 membered, 3 to 6 membered, or 5 to 6 membered heterocycloalkyl), $R^{6F}$-substituted or unsubstituted aryl (e.g., $C_6$-$C_{10}$, $C_{10}$ aryl, or phenyl), or $R^{6F}$-substituted or unsubstituted heteroaryl (e.g., 5 to 10 membered, 5 to 9 membered, or 5 to 6 membered heteroaryl).

$R^{6F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N$—$_2$, —N—$NH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^6$ may be hydrogen, halogen, $R^{6E}$-substituted or unsubstituted $C_1$-$C_8$ alkyl, or unsubstituted phenyl. $R^6$ may be hydrogen. $R^6$ may be halogen. $R^6$ may be $R^{6E}$-substituted or unsubstituted $C_1$-$C_8$ alkyl. $R^6$ may be $R^{6E}$-substituted or unsubstituted $C_1$-$C_5$ alkyl. $R^6$ may be unsubstituted $C_1$-$C_8$ alkyl. $R^6$ may be unsubstituted methyl. $R^6$ may be unsubstituted ethyl. $R^6$ may be unsubstituted propyl. $R^6$ may be unsubstituted allyl. $R^6$ may be unsubstituted aryl. $R^6$ may be unsubstituted phenyl.

$R^5$ and $R^6$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, unsubstituted alkyl, or unsubstituted cycloalkyl. $R^5$ and $R^6$ are independently hydrogen, $C_1$-$C_3$ unsubstituted alkyl or 3 to 5 membered cycloalkyl. $R^5$ and $R^6$ are independently hydrogen, unsubstituted methyl, unsubstituted ethyl, unsubstituted allyl, or unsubstituted cyclopropyl. $R^5$ and $R^6$ may independently be hydrogen or halogen. $R^5$ and $R^6$ may independently be substituted or unsubstituted $C_1$-$C_3$ alkyl. $R^5$ and $R^6$ may be unsubstituted methyl. $R^5$ and $R^6$ may independently be unsubstituted methyl or unsubstituted ethyl.

$R^{16}$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_5$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{16}$ may be substituted or unsubstituted alkyl. $R^{16}$ may be substituted or unsubstituted $C_1$-$C_8$ alkyl. $R^{16}$ may be substituted or unsubstituted $C_1$-$C_5$ alkyl. $R^{16}$ may be substituted or unsubstituted $C_1$-$C_3$ alkyl. $R^{16}$ may be $R^{16E}$-substituted or unsubstituted alkyl. $R^{16}$ may be $R^{16E}$-substituted or unsubstituted $C_1$-$C_8$ alkyl. $R^{16}$ may be $R^{16E}$-substituted or unsubstituted $C_1$-$C_5$ alkyl. $R^{16}$ may be $R^{16E}$-substituted or unsubstituted $C_1$-$C_3$ alkyl. $R^{16}$ may be hydrogen.

$R^{16}$ may be hydrogen, $R^{16E}$-substituted or unsubstituted alkyl (e.g., $C_1$-$C_8$, $C_1$-$C_6$, or $C_1$-$C_4$ alkyl), $R^{16E}$-substituted or unsubstituted heteroalkyl (e.g., 2 to 8 membered, 2 to 6 membered, or 2 to 4 membered heteroalkyl), $R^{16E}$-substituted or unsubstituted cycloalkyl (e.g., $C_3$-$C_8$, $C_3$-$C_6$, or $C_5$-$C_6$ cycloalkyl), $R^{16E}$-substituted or unsubstituted heterocycloalkyl (e.g., 3 to 8 membered, 3 to 6 membered, or 5 to 6 membered heterocycloalkyl), $R^{16E}$-substituted or unsubstituted aryl (e.g., $C_6$-$C_{10}$, $C_{10}$ aryl, or phenyl), or $R^{16E}$-substituted or unsubstituted heteroaryl (e.g., 5 to 10 membered, 5 to 9 membered, or 5 to 6 membered heteroaryl). $R^{16}$ may be $R^{16E}$-substituted or unsubstituted alkyl (e.g., $C_1$-$C_8$, $C_1$-$C_6$, or $C_1$-$C_4$ alkyl), $R^{16E}$-substituted or unsubstituted heteroalkyl (e.g., 2 to 8 membered, 2 to 6 membered, or 2 to 4 membered heteroalkyl), $R^{16E}$-substituted or unsubstituted cycloalkyl (e.g., $C_3$-$C_8$, $C_3$-$C_6$, or $C_5$-$C_6$ cycloalkyl), $R^{16E}$-substituted or unsubstituted heterocycloalkyl (e.g., 3 to 8 membered, 3 to 6 membered, or 5 to 6 membered heterocycloalkyl), $R^{16E}$-substituted or unsubstituted aryl (e.g., $C_6$-$C_{10}$, $C_{10}$ aryl, or phenyl), or $R^{16E}$-substituted or unsubstituted heteroaryl (e.g., 5 to 10 membered, 5 to 9 membered, or 5 to 6 membered heteroaryl).

In embodiments, $R^{16}$ is $R^{16E}$-substituted or unsubstituted alkyl (e.g., $C_1$-$C_8$, $C_1$-$C_6$, or $C_1$-$C_4$ alkyl). In embodiments, $R^{16}$ is $R^{16E}$-substituted alkyl (e.g., $C_1$-$C_5$, $C_1$-$C_6$, or $C_1$-$C_4$ alkyl). In embodiments, $R^{16}$ is an unsubstituted alkyl (e.g., $C_1$-$C_8$, $C_1$-$C_6$, or $C_1$-$C_4$ alkyl).

In embodiments, $R^{16}$ is $R^{16E}$-substituted or unsubstituted heteroalkyl (e.g., 2 to 8 membered, 2 to 6 membered, or 2 to 4 membered heteroalkyl). In embodiments, $R^{16}$ is $R^{16E}$-substituted heteroalkyl (e.g., 2 to 8 membered, 2 to 6 membered, or 2 to 4 membered heteroalkyl). In embodiments, $R^{16}$ is an unsubstituted heteroalkyl (e.g., 2 to 8 membered, 2 to 6 membered, or 2 to 4 membered heteroalkyl).

In embodiments, $R^{16}$ is $R^{16E}$-substituted or unsubstituted cycloalkyl (e.g., $C_3$-$C_8$, $C_3$-$C_6$, or $C_5$-$C_6$ cycloalkyl). In embodiments, $R^{16}$ is $R^{16E}$-substituted cycloalkyl (e.g., $C_3$-$C_8$, $C_3$-$C_6$, or $C_5$-$C_6$ cycloalkyl). In embodiments, $R^{16}$ is an unsubstituted cycloalkyl (e.g., $C_3$—C, $C_3$-$C_6$, or $C_5$-$C_6$ cycloalkyl).

In embodiments, $R^{16}$ is $R^{16E}$-substituted or unsubstituted heterocycloalkyl (e.g., 3 to 8 membered, 3 to 6 membered, or 5 to 6 membered heterocycloalkyl). In embodiments, $R^{16}$ is $R^{16E}$-substituted heterocycloalkyl (e.g., 3 to 8 membered, 3 to 6 membered, or 5 to 6 membered heterocycloalkyl). In embodiments, $R^{16}$ is an unsubstituted heterocycloalkyl (e.g., 3 to 8 membered, 3 to 6 membered, or 5 to 6 membered heterocycloalkyl).

In embodiments, $R^{16}$ is $R^{16E}$-substituted or unsubstituted aryl (e.g., $C_6$-$C_{10}$, $C_{10}$, or phenyl). In embodiments, $R^{16}$ is $R^{16E}$-substituted aryl (e.g., $C_6$-$C_{10}$, $C_{10}$, or phenyl). In embodiments, $R^{16}$ is an unsubstituted aryl (e.g., $C_6$-$C_{10}$, $C_{10}$, or phenyl).

In embodiments, $R^{16}$ is $R^{16E}$-substituted or unsubstituted heteroaryl (e.g., 5 to 10 membered, 5 to 9 membered, or 5 to 6 membered heteroaryl). In embodiments, $R^{16}$ is $R^{16E}$-substituted heteroaryl (e.g., 5 to 10 membered, 5 to 9 membered, or 5 to 6 membered heteroaryl). In embodiments, $R^{16}$ is an unsubstituted heteroaryl (e.g., 5 to 10 membered, 5 to 9 membered, or 5 to 6 membered heteroaryl).

$R^{16E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{16F}$-substituted or unsubstituted alkyl (e.g., $C_1$-$C_8$, $C_1$-$C_6$, or $C_1$-$C_4$ alkyl), $R^{16F}$-substituted or unsubstituted heteroalkyl (e.g., 2 to 8 membered, 2 to 6 membered, or 2 to 4 membered heteroalkyl), $R^{16F}$-substituted or unsubstituted cycloalkyl (e.g., $C_3$-$C_8$, $C_3$-$C_6$, or $C_5$-$C_6$ cycloalkyl), $R^{16F}$-substituted or unsubstituted heterocycloalkyl (e.g., 3 to 8 membered, 3 to 6 membered, or 5 to 6 membered heterocycloalkyl), $R^{16F}$-substituted or unsubstituted aryl (e.g., $C_6$-$C_{10}$, $C_{10}$ aryl, or phenyl), or $R^{16F}$-substituted or unsubstituted heteroaryl (e.g., 5 to 10 membered, 5 to 9 membered, or 5 to 6 membered heteroaryl).

$R^{16F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{16}$ may be hydrogen, halogen or substituted or unsubstituted alkyl. $R^{16}$ may be hydrogen. $R^{16}$ may be halogen. $R^{16}$ may be substituted or unsubstituted alkyl. $R^{16}$ may be substituted or unsubstituted $C_1$-$C_5$ alkyl. $R^{16}$ may be $R^{16E}$-substituted or unsubstituted alkyl. $R^{16}$ may be $R^{16E}$-substituted or unsubstituted $C_1$-$C_5$ alkyl. In embodiments, $R^3$, $R^4$, and $R^{16}$ are hydrogen.

$R^{18}$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{18}$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{18}$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{18}$ may be halogen, or substituted or unsubstituted alkyl (e.g., $C_1$-$C_8$, $C_1$-$C_6$, or $C_1$-$C_4$ alkyl). $R^{18}$ may be halogen, or unsubstituted alkyl (e.g., $C_1$-$C_8$, $C_1$-$C_6$, or $C_1$-$C_4$ alkyl). $R^{18}$ may be halogen, or substituted or unsubstituted heteroalkyl (e.g., 2 to 8 membered, 2 to 6 membered, or 2 to 4 membered heteroalkyl). $R^{18}$ may be halogen, unsubstituted heteroalkyl (e.g., 2 to 8 membered, 2 to 6 membered, or 2 to 4 membered heteroalkyl. $R^{18}$ may be halogen, —$CF_3$, —$CCl_3$, —$CBr_3$, or —$CI_3$. $R^{18}$ may be hydrogen.

$R^{18}$ may be hydrogen, $R^{18E}$-substituted or unsubstituted alkyl (e.g., $C_1$-$C_8$, $C_1$-$C_6$, or $C_1$-$C_4$ alkyl), $R^{18E}$-substituted or unsubstituted heteroalkyl (e.g., 2 to 8 membered, 2 to 6 membered, or 2 to 4 membered heteroalkyl), $R^{18E}$-substituted or unsubstituted cycloalkyl (e.g., $C_3$-$C_8$, $C_3$-$C_6$, or $C_5$-$C_6$ cycloalkyl), $R^{18E}$-substituted or unsubstituted heterocycloalkyl (e.g., 3 to 8 membered, 3 to 6 membered, or 5 to 6 membered heterocycloalkyl), $R^{18E}$-substituted or unsubstituted aryl (e.g., $C_6$-$C_{10}$, $C_{10}$ aryl, or phenyl), or $R^{18E}$-substituted or unsubstituted heteroaryl (e.g., 5 to 10 membered, 5 to 9 membered, or 5 to 6 membered heteroaryl). $R^{18}$ may be $R^{18E}$-substituted or unsubstituted alkyl (e.g., $C_1$-$C_8$, $C_1$-$C_6$, or $C_1$-$C_4$ alkyl), $R^{18E}$-substituted or unsubstituted heteroalkyl (e.g., 2 to 8 membered, 2 to 6 membered, or 2 to 4 membered heteroalkyl), $R^{18E}$-substituted or unsubstituted cycloalkyl (e.g., $C_3$-$C_8$, $C_3$-$C_6$, or $C_5$-$C_6$ cycloalkyl), $R^{18E}$-substituted or unsubstituted heterocycloalkyl (e.g., 3 to 8 membered, 3 to 6 membered, or 5 to 6 membered heterocycloalkyl), $R^{18E}$-substituted or unsubstituted aryl (e.g., $C_6$-$C_{10}$, $C_{10}$ aryl, or phenyl), or $R^{18E}$-substituted or unsubstituted heteroaryl (e.g., 5 to 10 membered, 5 to 9 membered, or 5 to 6 membered heteroaryl).

In embodiments, $R^{18}$ is $R^{18E}$-substituted or unsubstituted alkyl (e.g., $C_1$-$C_8$, $C_1$-$C_6$, or $C_1$-$C_4$ alkyl). In embodiments, $R^{18}$ is $R^{18E}$-substituted alkyl (e.g., $C_1$-$C_8$, $C_1$-$C_6$, or $C_1$-$C_4$ alkyl). In embodiments, $R^{18}$ is an unsubstituted alkyl (e.g., $C_1$-$C_8$, $C_1$-$C_6$, or $C_1$-$C_4$ alkyl).

In embodiments, $R^{18}$ is $R^{18E}$-substituted or unsubstituted heteroalkyl (e.g., 2 to 8 membered, 2 to 6 membered, or 2 to 4 membered heteroalkyl). In embodiments, $R^{18}$ is $R^{18E}$-substituted heteroalkyl (e.g., 2 to 8 membered, 2 to 6 membered, or 2 to 4 membered heteroalkyl). In embodiments, $R^{18}$ is an unsubstituted heteroalkyl (e.g., 2 to 8 membered, 2 to 6 membered, or 2 to 4 membered heteroalkyl).

In embodiments, $R^{18}$ is $R^{18E}$-substituted or unsubstituted cycloalkyl (e.g., $C_3$-$C_8$, $C_3$-$C_6$, or $C_5$-$C_6$ cycloalkyl). In embodiments, $R^{18}$ is $R^{18E}$-substituted cycloalkyl (e.g., $C_3$-$C_8$, $C_3$-$C_6$, or $C_5$-$C_6$ cycloalkyl). In embodiments, $R^{18}$ is an unsubstituted cycloalkyl (e.g., $C_3$-$C_8$, $C_3$-$C_6$, or $C_5$-$C_6$ cycloalkyl).

In embodiments, $R^{18}$ is $R^{18E}$-substituted or unsubstituted heterocycloalkyl (e.g., 3 to 8 membered, 3 to 6 membered, or 5 to 6 membered heterocycloalkyl). In embodiments, $R^{18}$ is $R^{18E}$-substituted heterocycloalkyl (e.g., 3 to 8 membered, 3 to 6 membered, or 5 to 6 membered heterocycloalkyl). In embodiments, $R^{18}$ is an unsubstituted heterocycloalkyl (e.g., 3 to 8 membered, 3 to 6 membered, or 5 to 6 membered heterocycloalkyl).

In embodiments, $R^{18}$ is $R^{18E}$-substituted or unsubstituted aryl (e.g., $C_6$-$C_{10}$, $C_{10}$, or phenyl). In embodiments, $R^{18}$ is $R^{18E}$-substituted aryl (e.g., $C_6$-$C_{10}$, $C_{10}$, or phenyl). In embodiments, $R^{18}$ is an unsubstituted aryl (e.g., $C_6$-$C_{10}$, $C_{10}$, or phenyl).

In embodiments, $R^{18}$ is $R^{18E}$-substituted or unsubstituted heteroaryl (e.g., 5 to 10 membered, 5 to 9 membered, or 5 to 6 membered heteroaryl). In embodiments, $R^{18}$ is $R^{18E}$-substituted heteroaryl (e.g., 5 to 10 membered, 5 to 9 membered, or 5 to 6 membered heteroaryl). In embodiments, $R^{18}$ is an unsubstituted heteroaryl (e.g., 5 to 10 membered, 5 to 9 membered, or 5 to 6 membered heteroaryl).

$R^{18E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{18F}$-substituted or unsubstituted alkyl (e.g., $C_1$-$C_8$, $C_1$-$C_6$, or $C_1$-$C_4$ alkyl), $R^{18F}$-substituted or unsubstituted heteroalkyl (e.g., 2 to 8 membered, 2 to 6 membered, or 2 to 4 membered heteroalkyl), $R^{18F}$-substituted or unsubstituted cycloalkyl (e.g., $C_3$-$C_8$, $C_3$-$C_6$, or $C_5$-$C_6$ cycloalkyl), $R^{18F}$-substituted or unsubstituted heterocycloalkyl (e.g., 3 to 8 membered, 3 to 6 membered, or 5 to 6 membered heterocycloalkyl), $R^{18F}$-substituted or unsubstituted aryl (e.g., $C_6$-$C_{10}$, $C_{10}$ aryl, or phenyl), or $R^{18F}$-substituted or unsubstituted heteroaryl (e.g., 5 to 10 membered, 5 to 9 membered, or 5 to 6 membered heteroaryl).

$R^{18F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{18}$ may be substituted or unsubstituted heterocycloalkyl, substituted or unsubstituted aryl, or substituted or unsubstituted heteroaryl. $R^{18}$ may be $R^{18E}$-substituted or unsubstituted 5 membered heterocycloalkyl, $R^{18E}$-substituted or unsubstituted phenyl, $R^{18E}$-substituted or unsubstituted 6 membered heteroaryl, $R^{18E}$-substituted or unsubstituted 6,6 fused ring aryl-heterocycloalkyl, $R^{18E}$-substituted or unsubstituted 6,5 fused ring aryl-heterocycloalkyl, $R^{18E}$-substituted or unsubstituted 5,6 fused ring aryl-heterocycloalkyl, where $R^{18E}$ and $R^{18F}$ are as described herein, including embodiments thereof.

$R^{18}$ may be $R^{18E}$-substituted or unsubstituted 5 membered heterocycloalkyl, $R^{18E}$-substituted phenyl, $R^{18E}$-substituted or unsubstituted 6 membered heteroaryl, $R^{18E}$-substituted or unsubstituted 6,6 fused ring aryl, $R^{18E}$-substituted or unsubstituted 6,6 fused ring heteroaryl, $R^{18E}$-substituted or unsubstituted 6,5 fused ring aryl, $R^{18E}$-substituted or unsubstituted 6,5 fused ring heteroaryl, $R^{18E}$-substituted or unsubstituted 5,6 fused ring aryl, $R^{18E}$-substituted 5,6 fused ring heteroaryl, $R^{18E}$-substituted or unsubstituted 6,6 fused ring aryl-heterocycloalkyl, $R^{18E}$-substituted or unsubstituted 6,5 fused ring aryl-heterocycloalkyl, or $R^{18E}$-substituted or unsubstituted 5,6 fused ring aryl-heterocycloalkyl.

$R^{18}$ may be $R^{1E}$-substituted or unsubstituted 5 to 6 membered heteroaryl. The $R^{18E}$-substituted or unsubstituted 5 to 6 membered heteroaryl may be $R^{18E}$-substituted or unsubstituted thiophenyl, $R^{18E}$-substituted or unsubstituted thiazolyl, $R^{18E}$-substituted or unsubstituted oxazolyl, $R^{18E}$-substituted or unsubstituted imidazolyl, or derivatives thereof. $R^{18}$ may be $R^{18E}$-substituted or unsubstituted phenyl. $R^{18}$ may be $R^{18E}$-substituted or unsubstituted 6 membered heteroaryl. $R^{18}$ may be $R^{18E}$-substituted or unsubstituted 6,6 fused ring aryl-heterocycloalkyl. The $R^{18E}$-substituted or unsubstituted 6,6 fused ring aryl-heteroaryl may be $R^{18E}$-substituted or unsubstituted dihydrobenzo[1,4]dioxinyl. $R^{18}$ may be $R^{18E}$-substituted or unsubstituted 6,5 fused ring aryl-heterocycloalkyl or $R^{18E}$-substituted or unsubstituted 5,6 fused ring aryl-heterocycloalkyl. The $R^{18E}$-substituted or unsubstituted 6,5 or 5,6 fused ring aryl-heterocycloalkyl may be dihydro-indenyl, benzo[1,3]dioxolyl, or indolyl. $R^{18E}$ may be halogen, $SO_2Ph$, $R^{18}$-substituted or unsubstituted $C_1$-$C_5$ alkyl, or $R^{18F}$-substituted or unsubstituted 2 to 5 membered heteroalkyl.

In one embodiment, $R^1$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In one embodiment, $R^1$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In one embodiment, $R^2$ and $R^{18}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings). In one embodiment, $R^2$ and $R^{16}$ are not joined to form a substituted or unsubstituted cycloalkyl, substituted or unsubstituted heterocycloalkyl, substituted or unsubstituted aryl (including fused cycloalkyl-aryl, heterocycloalkyl-aryl and aryl rings) or substituted or unsubstituted heteroaryl (including fused cycloalkyl-heteroaryl, heterocycloalkyl-heteroaryl and heteroaryl rings).

In one embodiment, $R^1$ and $R^{18}$ are not hydrogen. In one embodiment the compound of formula (I) does not have the formula (3R,8S,8aR)-8-hydroxy-2-methyltetrahydro-1H-3,8a-epidithiopyrrolo[1,2-a]pyrazine-1,4(6H)-dione. In one embodiment, the compound of formula (I) does not have the formula (3R,8S,8aR)-2-methyl-1,4-dioxohexahydro-1H-3,8a-epidithiopyrrolo[1,2-a]pyrazin-8-yl acetate. In one embodiment the compound of formula (I) does not have the formula (3R,6R,8S,8aR)-6-(((tert-butyldiphenylsilyl)oxy)methyl)-8-hydroxy-2-methyltetrahydro-1H-3,8a-epidithiopyrrolo[1,2-a]pyrazine-1,4(6H)-dione. In one embodiment, the compound does not have the formula 2,3-dimethyltetrahydro-1H-3,8a-epidithiopyrrolo[1,2-a]pyrazine-1,4(6H)-dione. In one embodiment, the compound does not have the formula 3-(hydroxymethyl)-2-methyltetrahydro-1H-3,8a-epidithiopyrrolo[1,2-a]pyrazine-1,4(6H)-dione.

The compound of formula (I) may have the formula:

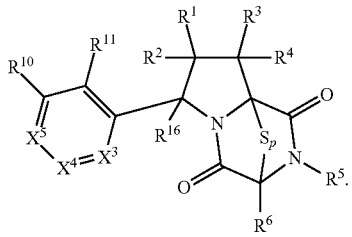

(II)

p, $R^1$, $R^2$, $R^3$, $R^4$, $R^5$, $R^6$ and $R^{16}$ are as described herein.

In the formula (II), $X^3$ is —N= or —CR$^7$=. $X^4$ is —N= or —CR$^8$=. $X^5$ is —N= or —CR$^9$=.

$R^7$ is hydrogen, halogen, —N$_3$, —CF$_3$, —CCl$_3$, —CBr$_3$, —CI$_3$, —CN, —CHO, —OR$^{7A}$, —NR$^{7B}$R$^{7C}$, —COOR$^{7A}$, —CONR$^{7B}$R$^{7C}$, —NO$_2$, —SR$^{7D}$, —SO$_{n7}$R$^{7B}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^8$ is hydrogen, halogen, —N$_3$, —CF$_3$, —CCl$_3$, —CBr$_3$, —CI$_3$, —CN, —CHO, —OR$^{8A}$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{10}$ is hydrogen, halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —CONR$^{10B}$R$^{10C}$, —NO$_2$, —SR$^{10D}$, —SO$_{n10}$R$^{10B}$, —SO$_{v10}$NR$^{10B}$R$^{10C}$, —NHNR$^{10B}$R$^{10C}$, —ONR$^{10B}$R$^{10C}$, —NHC(O)NHNR$^{1B}$R$^{10C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{11}$ is hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —CONR$^{11B}$R$^{11C}$, —NO$_2$, —SR$^{11D}$, —SO$_{n11}$R$^{11B}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, and $R^{11D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbol n7, n8, n9, n10, n11, and n12 are independently an integer from 1 to 4. The symbol v7, v8, v9, v10, v11, and v12 are independently 1 or 2.

$R^7$ and $R^8$ may be joined together to form substituted or unsubstituted cycloalkyl (e.g. 3 to 8 membered cycloalkyl). $R^7$ and $R^8$ may be joined together to form substituted or unsubstituted heterocycloalkyl (e.g. 3 to 8 membered heterocycloalkyl). $R^7$ and $R^8$ may be joined together to form substituted or unsubstituted aryl (e.g. 3 to 8 membered aryl). $R^7$ and $R^8$ may be joined together to form substituted or unsubstituted heteroaryl (e.g. 3 to 8 membered heteroaryl). $R^7$ and $R^8$ may be joined together to form $R^{7E}$-substituted or unsubstituted cycloalkyl (e.g. 3 to 8 membered cycloalkyl). $R^7$ and $R^8$ may be joined together to form $R^{7E}$-substituted or unsubstituted heterocycloalkyl (e.g. 3 to 8 membered heterocycloalkyl). $R^7$ and $R^8$ may be joined together to form $R^{7E}$-substituted or unsubstituted aryl (e.g. 3 to 8 membered aryl). $R^7$ and $R^8$ may be joined together to form $R^{7E}$-substituted or unsubstituted heteroaryl (e.g. 3 to 8 membered heteroaryl).

$R^8$ and $R^9$ may be joined together to form substituted or unsubstituted cycloalkyl (e.g. 3 to 8 membered cycloalkyl). $R^8$ and $R^9$ may be joined together to form substituted or unsubstituted heterocycloalkyl (e.g. 3 to 8 membered heterocycloalkyl). $R^8$ and $R^9$ may be joined together to form substituted or unsubstituted aryl (e.g. 3 to 8 membered aryl). $R^8$ and $R^9$ may be joined together to form substituted or unsubstituted heteroaryl (e.g. 3 to 8 membered heteroaryl). $R^8$ and $R^9$ may be joined together to form $R^{8E}$-substituted or unsubstituted cycloalkyl (e.g. 3 to 8 membered cycloalkyl). $R^8$ and $R^9$ may be joined together to form $R^{8E}$-substituted or unsubstituted heterocycloalkyl (e.g. 3 to 8 membered heterocycloalkyl). $R^8$ and $R^9$ may be joined together to form $R^{8E}$-substituted or unsubstituted aryl (e.g. 3 to 8 membered aryl). $R^8$ and $R^9$ may be joined together to form $R^{8E}$-substituted or unsubstituted heteroaryl (e.g. 3 to 8 membered heteroaryl).

$R^{10}$ and $R^{11}$ may be joined together to form substituted or unsubstituted cycloalkyl (e.g. 3 to 8 membered cycloalkyl). $R^{10}$ and $R^{11}$ may be joined together to form substituted or unsubstituted heterocycloalkyl (e.g. 3 to 8 membered heterocycloalkyl). $R^{10}$ and $R^{11}$ may be joined together to form substituted or unsubstituted aryl (e.g. 3 to 8 membered aryl). $R^{10}$ and $R^{11}$ may be joined together to form substituted or unsubstituted heteroaryl (e.g. 3 to 8 membered heteroaryl). $R^{10}$ and $R^{11}$ may be joined together to form $R^{10E}$-substituted or unsubstituted cycloalkyl (e.g. 3 to 8 membered cycloalkyl). $R^{10}$ and $R^{11}$ may be joined together to form $R^{10E}$-substituted or unsubstituted heterocycloalkyl (e.g. 3 to 8 membered heterocycloalkyl). $R^{10}$ and $R^{11}$ may be joined together to form $R^{10E}$-substituted or unsubstituted aryl (e.g. 3 to 8 membered aryl). $R^{10}$ and $R^{11}$ may be joined together to form $R^{10E}$-substituted or unsubstituted heteroaryl (e.g. 3 to 8 membered heteroaryl).

When $X^3$ is —N=, $X^4$ may be —CR$^8$= and $X^5$ may be —CR$^9$=. When $X^4$ is —N=, $X^3$ may be —CR$^7$= and $X^5$ may be —CR$^9$=. When $X^5$ is —N=, $X^3$ may be —CR$^7$= and $X^4$ may be —CR$^8$=. $X^3$, $X^4$, and $X^5$ may be —CR$^7$=, —CR$^8$=, and —CR$^9$= respectively.

In embodiments, $R^7$ is hydrogen, halogen, —OCH$_3$, —SO$_2$, —SO$_2$—R$^{7B}$, —OR$^{7A}$, —NR$^{7B}$R$^{7C}$, or substituted or unsubstituted aryl (e.g., C$_6$-C$_{10}$ aryl, C$_{10}$ aryl, or phenyl). In embodiments, $R^7$ is hydrogen. In embodiments, $R^7$ is —Br. In embodiments, $R^7$ is —Cl. In embodiments, $R^7$ is —SO$_2$—R$^{7B}$ wherein R$^{7B}$ is substituted or unsubstituted aryl (e.g., C$_6$-C$_{10}$ aryl, C$_{10}$ aryl, or phenyl). In embodiments, $R^7$ is —SO$_2$—R$^{7B}$ wherein R$^{7B}$ is unsubstituted aryl (e.g., C$_6$-C$_{10}$ aryl, C$_{10}$ aryl, or phenyl). In embodiments, $R^7$ is —SO$_2$—R$^{7B}$ wherein R$^{7B}$ is phenyl. In embodiments, $R^7$ is phenyl. In embodiments, $R^7$ is —OR$^{7A}$, wherein R$^{7A}$ is substituted or unsubstituted alkyl (e.g., C$_1$-C$_8$ alkyl, C$_1$-C$_6$ alkyl, or C$_1$-C$_4$ alkyl). In embodiments, $R^7$ is —OR$^{7A}$, wherein R$^{7A}$ is unsubstituted alkyl (e.g., C$_1$-C$_8$ alkyl, C$_1$-C$_6$ alkyl, or C$_1$-C$_4$ alkyl). In embodiments, $R^7$ is —OR$^{7A}$, wherein R$^{7A}$ is substituted or unsubstituted C$_1$-C$_8$ alkyl. In embodiments, $R^7$ is —OR$^{7A}$, wherein R$^{7A}$ is substituted or unsubstituted C$_1$-C$_4$ alkyl. In embodiments, $R^7$ is —OR$^{7A}$, wherein R$^{7A}$ is substituted or unsubstituted C$_1$-C$_2$ alkyl. In embodiments, $R^7$ is —NR$^{7B}$R$^{7C}$, wherein R$^{7B}$ and R$^{7C}$ are unsubstituted alkyl (e.g., C$_1$-C$_8$ alkyl, C$_1$-C$_6$ alkyl, or C$_1$-C$_4$ alkyl). In embodiments, $R^7$ is —NR$^{7B}$R$^{7C}$, wherein R$^{7B}$ and R$^{7C}$ are substituted or unsubstituted C$_1$-C$_8$ alkyl. In embodiments, $R^7$ is —NR$^{7B}$R$^{7C}$, wherein R$^{7B}$ and R$^{7C}$ are substituted or unsubstituted C$_1$-C$_4$ alkyl. In embodiments, $R^7$ is —NR$^{7B}$R$^{7C}$, wherein R$^{7B}$ and R$^{7C}$ are substituted or unsubstituted C$_1$-C$_2$ alkyl.

$R^7$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl). $R^7$ may be halogen, —CF$_3$, —CCl$_3$, —CBr$_3$, —CI$_3$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl). $R^7$ may be halogen, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl). $R^7$ may be halogen, or substituted or unsubstituted alkyl (e.g., C$_1$-C$_8$ alkyl, C$_1$-C$_6$ alkyl, or C$_1$-C$_4$ alkyl). $R^7$ may be halogen, or unsubstituted alkyl (e.g., C$_1$-C$_8$ alkyl, C$_1$-C$_6$ alkyl, or C$_1$-C$_4$ alkyl). $R^7$ may be halogen, or substituted or unsubstituted heteroalkyl (e.g., 2 to 8 membered heteroalkyl, 2 to 6 membered heteroalkyl, or 2 to 4 membered heteroalkyl). $R^7$ may be halogen, unsubstituted heteroalkyl (e.g., 2 to 8 membered heteroalkyl, 2 to 6 membered heteroalkyl, or 2 to 4 membered heteroalkyl. $R^7$ may be halogen, —CF$_3$, —CCl$_3$, —CBr$_3$, or —CI$_3$. $R^7$ may be hydrogen.

$R^7$ may be hydrogen, $R^{7E}$-substituted or unsubstituted alkyl (e.g., C$_1$-C$_8$ alkyl, C$_1$-C$_6$ alkyl, or C$_1$-C$_4$ alkyl), $R^{7E}$-substituted or unsubstituted heteroalkyl (e.g., 2 to 8 membered heteroalkyl, 2 to 6 membered heteroalkyl, or 2 to 4 membered heteroalkyl), $R^{7E}$-substituted or unsubstituted cycloalkyl (e.g., C$_3$-C$_5$ cycloalkyl, C$_3$-C$_6$ cycloalkyl, or C$_5$-C$_6$ cycloalkyl), $R^{7E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7E}$-substituted or unsubstituted aryl (e.g., C$_6$-C$_{10}$ aryl, C$_{10}$ aryl, or phenyl), or $R^{7E}$-substituted or unsubstituted heteroaryl (e.g., 5 to 10 membered heteroaryl, 5 to 9 membered heteroaryl, or 5 to 6 membered heteroaryl). $R^7$ may be $R^{7E}$-substituted or unsubstituted alkyl (e.g., $C_1$-$C_8$ alkyl, $C_1$-$C_6$ alkyl, or $C_1$-$C_4$ alkyl), $R^{7E}$-substituted or unsubstituted heteroalkyl (e.g., 2 to 8 membered heteroalkyl, 2 to 6 membered heteroalkyl, or 2 to 4 membered heteroalkyl), $R^{7E}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{1E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{7E}$-substituted or unsubstituted aryl (e.g., $C_6$-$C_{10}$ aryl, $C_{10}$ aryl, or phenyl), or $R^{7E}$-substituted or unsubstituted heteroaryl (e.g., 5 to 10 membered heteroaryl, 5 to 9 membered heteroaryl, or 5 to 6 membered heteroaryl).

In embodiments, $R^7$ is $R^{7E}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{7E}$-substituted alkyl (e.g., $C_1$-$C_8$ alkyl, $C_1$-$C_6$ alkyl, or $C_1$-$C_4$ alkyl). In embodiments, $R^7$ is an unsubstituted alkyl (e.g., $C_1$-$C_8$ alkyl, $C_1$-$C_6$ alkyl, or $C_1$-$C_4$ alkyl).

In embodiments, $R^7$ is $R^{7E}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{7E}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl).

In embodiments, $R^7$ is $R^{7E}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{7E}$-substituted cycloalkyl (e.g., $C_3$-$C_5$ cycloalkyl, $C_3$-$C_6$ cycloalkyl, or $C_5$-$C_6$ cycloalkyl). In embodiments, $R^7$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^7$ is $R^{7E}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{7E}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^7$ is $R^{7E}$-substituted or unsubstituted aryl (e.g., $C_6$-$C_{10}$ aryl, $C_{10}$ aryl, or phenyl). In embodiments, $R^7$ is $R^{7E}$-substituted aryl (e.g., $C_6$-$C_{10}$ aryl, $C_{10}$ aryl, or phenyl). In embodiments, $R^7$ is an unsubstituted aryl (e.g., $C_6$-$C_{10}$ aryl, $C_{10}$ aryl, or phenyl).

In embodiments, $R^7$ is $R^{7E}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{7E}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl).

$R^{7E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N_{—2}$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$, $R^{7F}$-substituted or unsubstituted alkyl (e.g., $C_1$-$C_8$, $C_1$-$C_6$, or $C_1$-$C_4$ alkyl), $R^{7F}$-substituted or unsubstituted heteroalkyl (e.g., 2 to 8 membered, 2 to 6 membered, or 2 to 4 membered heteroalkyl), $R^{7F}$-substituted or unsubstituted cycloalkyl (e.g., $C_3$-$C_8$, $C_3$-$C_6$, or $C_1$-$C_6$ cycloalkyl), $R^{7F}$-substituted or unsubstituted heterocycloalkyl (e.g., 3 to 8 membered, 3 to 6 membered, or 5 to 6 membered heterocycloalkyl), $R^{7F}$-substituted or unsubstituted aryl (e.g., $C_6$-$C_{10}$ aryl, $C_{10}$ aryl or phenyl), or $R^{7F}$-substituted or unsubstituted heteroaryl (e.g., 5 to 10 membered, 5 to 9 membered, or 5 to 6 membered heteroaryl).

$R^{7F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N_{—2}$, —N—NH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, $R^8$ is hydrogen, halogen, —OCH$_3$, SO$_2$, SO$_2$—$R^{8B}$, —OR$^{8A}$, —NR$^{8B}$SR$^{8C}$, or substituted or unsubstituted aryl (e.g., $C_6$-$C_{10}$ aryl, $C_{10}$ aryl, or phenyl). In embodiments, $R^8$ is hydrogen. In embodiments, $R^8$ is Br. In embodiments, $R^8$ is Cl. In embodiments, $R^8$ is SO$_2$—$R^{8B}$ wherein $R^{8B}$ is substituted or unsubstituted aryl (e.g., $C_6$-$C_{10}$ aryl, $C_{10}$ aryl, or phenyl). In embodiments, $R^8$ is SO$_2$—$R^{8B}$ wherein $R^{8B}$ is unsubstituted aryl (e.g., $C_6$-$C_{10}$ aryl, $C_{10}$ aryl, or phenyl). In embodiments, $R^8$ is SO$_2$—$R^{8B}$ wherein $R^{8B}$ is phenyl. In embodiments, $R^8$ is phenyl. In embodiments, $R^8$ is —OR$^{8A}$, wherein $R^{8A}$ is substituted or unsubstituted alkyl (e.g., $C_1$-$C_8$ alkyl, $C_1$-$C_6$ alkyl, or $C_1$-$C_4$ alkyl). In embodiments, $R^8$ is —OR$^{8A}$, wherein $R^{8A}$ is unsubstituted alkyl (e.g., $C_1$-$C_8$ alkyl, $C_1$-$C_6$ alkyl, or $C_1$-$C_4$ alkyl). In embodiments, $R^8$ is —OR$^{8A}$, wherein $R^{8A}$ is substituted or unsubstituted $C_1$-$C_8$ alkyl. In embodiments, $R^8$ is —OR$^{8A}$, wherein $R^{8A}$ is substituted or unsubstituted $C_1$-$C_4$ alkyl. In embodiments, $R^8$ is —OR$^{8A}$, wherein $R^{8A}$ is substituted or unsubstituted $C_1$-$C_2$ alkyl. In embodiments, $R^8$ is —NR$^{8B}$R$^{8C}$, wherein $R^{8B}$ and $R^{8C}$ are unsubstituted alkyl (e.g., $C_1$-$C_8$ alkyl, $C_1$-$C_6$ alkyl, or $C_1$-$C_4$ alkyl). In embodiments, $R^8$ is —NR$^{8B}$R$^{8C}$, wherein $R^{8B}$ and $R^{8C}$ are substituted or unsubstituted $C_1$-$C_8$ alkyl. In embodiments, $R^8$ is —NR$^{8B}$R$^{8C}$, wherein $R^{8B}$ and $R^{8C}$ are substituted or unsubstituted $C_1$-$C_4$ alkyl. In embodiments, $R^8$ is —NR$^{8B}$R$^{8C}$, wherein $R^{8B}$ and $R^{8C}$ are substituted or unsubstituted $C_1$-$C_2$ alkyl.

$R^8$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —NHNH$_2$, —ONH$_2$, —NHC(O)NHNH$_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^8$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^8$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^8$ may be halogen, or substituted or unsubstituted alkyl (e.g., $C_1$-$C_8$, $C_1$-$C_6$, or $C_1$-$C_4$ alkyl). $R^8$ may be halogen, or unsubstituted alkyl (e.g., $C_1$-$C_8$, $C_1$-$C_6$, or $C_1$-$C_4$ alkyl). $R^8$ may be halogen, or substituted or unsubstituted heteroalkyl (e.g., 2 to 8 membered, 2 to 6 membered, or 2 to 4 membered heteroalkyl). $R^8$ may be halogen, unsubstituted heteroalkyl (e.g., 2 to 8 membered, 2 to 6 membered, or 2 to 4 membered heteroalkyl. $R^8$ may be halogen, —$CF_3$, —$CCl_3$, —$CBr_3$, or —$CI_3$. $R^8$ may be hydrogen.

$R^8$ may be hydrogen, $R^{8E}$-substituted or unsubstituted alkyl (e.g., $C_1$-$C_8$, $C_1$-$C_6$, or $C_1$-$C_4$ alkyl), $R^{8E}$-substituted or unsubstituted heteroalkyl (e.g., 2 to 8 membered, 2 to 6 membered, or 2 to 4 membered heteroalkyl), $R^{8E}$-substituted or unsubstituted cycloalkyl (e.g., $C_3$-$C_8$, $C_3$-$C_6$, or $C_5$-$C_6$ cycloalkyl), $R^{8E}$-substituted or unsubstituted heterocycloalkyl (e.g., 3 to 8 membered, 3 to 6 membered, or 5 to 6 membered heterocycloalkyl), $R^{8E}$-substituted or unsubstituted aryl (e.g., $C_6$-$C_{10}$, $C_{10}$ aryl, or phenyl), or $R^{8E}$-substituted or unsubstituted heteroaryl (e.g., 5 to 10 membered, 5 to 9 membered, or 5 to 6 membered heteroaryl). $R^8$ may be $R^{8E}$-substituted or unsubstituted alkyl(e.g., $C_1$-$C_8$, $C_1$-$C_6$, or $C_1$-$C_4$ alkyl), $R^{8E}$-substituted or unsubstituted heteroalkyl (e.g., 2 to 8 membered, 2 to 6 membered, or 2 to 4 membered heteroalkyl), $R^{8E}$-substituted or unsubstituted cycloalkyl (e.g., $C_3$-$C_8$, $C_3$-$C_6$, or $C_5$-$C_6$ cycloalkyl), $R^{8E}$-substituted or unsubstituted heterocycloalkyl (e.g., 3 to 8 membered, 3 to 6 membered, or 5 to 6 membered heterocycloalkyl), $R^{8E}$-substituted or unsubstituted aryl (e.g., $C_6$-$C_{10}$, $C_{10}$ aryl, or phenyl), or $R^{8E}$-substituted or unsubstituted heteroaryl (e.g., 5 to 10 membered, 5 to 9 membered, or 5 to 6 membered heteroaryl).

In embodiments, $R^8$ is $R^{8E}$-substituted or unsubstituted alkyl (e.g., $C_1$-$C_8$, $C_1$-$C_6$, or $C_1$-$C_4$ alkyl). In embodiments, $R^8$ is $R^{8E}$-substituted alkyl (e.g., $C_1$-$C_8$, $C_1$-$C_6$, or $C_1$-$C_4$ alkyl). In embodiments, $R^8$ is an unsubstituted alkyl (e.g., $C_1$-$C_8$, $C_1$-$C_6$, or $C_1$-$C_4$ alkyl).

In embodiments, $R^8$ is $R^{8E}$-substituted or unsubstituted heteroalkyl (e.g., 2 to 8 membered, 2 to 6 membered, or 2 to 4 membered heteroalkyl). In embodiments, $R^8$ is $R^{8E}$-substituted heteroalkyl (e.g., 2 to 8 membered, 2 to 6 membered, or 2 to 4 membered heteroalkyl). In embodiments, $R^8$ is an unsubstituted heteroalkyl (e.g., 2 to 8 membered, 2 to 6 membered, or 2 to 4 membered heteroalkyl).

In embodiments, $R^8$ is $R^{8E}$-substituted or unsubstituted cycloalkyl (e.g., $C_3$-$C_8$, $C_3$-$C_6$, or $C_5$-$C_6$ cycloalkyl). In embodiments, $R^8$ is $R^{8E}$-substituted cycloalkyl (e.g., $C_3$-$C_8$, $C_3$-$C_6$, or $C_5$-$C_6$ cycloalkyl). In embodiments, $R^8$ is an unsubstituted cycloalkyl (e.g., $C_3$-$C_8$, $C_3$-$C_6$, or $C_5$-$C_6$ cycloalkyl).

In embodiments, $R^8$ is $R^{8E}$-substituted or unsubstituted heterocycloalkyl (e.g., 3 to 8 membered, 3 to 6 membered, or 5 to 6 membered heterocycloalkyl). In embodiments, $R^8$ is $R^{8E}$-substituted heterocycloalkyl (e.g., 3 to 8 membered, 3 to 6 membered, or 5 to 6 membered heterocycloalkyl). In embodiments, $R^8$ is an unsubstituted heterocycloalkyl (e.g., 3 to 8 membered, 3 to 6 membered, or 5 to 6 membered heterocycloalkyl).

In embodiments, $R^8$ is $R^{8E}$-substituted or unsubstituted aryl (e.g., $C_6$-$C_{10}$, $C_{10}$, or phenyl). In embodiments, $R^8$ is $R^{8E}$-substituted aryl (e.g., $C_6$-$C_{10}$, $C_{10}$, or phenyl). In embodiments, $R^8$ is an unsubstituted aryl (e.g., $C_6$-$C_{10}$, $C_{10}$, or phenyl).

In embodiments, $R^8$ is $R^{8E}$-substituted or unsubstituted heteroaryl (e.g., 5 to 10 membered, 5 to 9 membered, or 5 to 6 membered heteroaryl). In embodiments, $R^8$ is $R^{8E}$-substituted heteroaryl (e.g., 5 to 10 membered, 5 to 9 membered, or 5 to 6 membered heteroaryl). In embodiments, $R^8$ is an unsubstituted heteroaryl (e.g., 5 to 10 membered, 5 to 9 membered, or 5 to 6 membered heteroaryl).

$R^{8E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2N$—$_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{8F}$-substituted or unsubstituted alkyl (e.g., $C_1$-$C_8$, $C_1$-$C_6$, or $C_1$-$C_4$ alkyl), $R^{8F}$-substituted or unsubstituted heteroalkyl (e.g., 2 to 8 membered, 2 to 6 membered, or 2 to 4 membered heteroalkyl), $R^{8F}$-substituted or unsubstituted cycloalkyl (e.g., $C_3$-$C_8$, $C_3$-$C_6$, or $C_5$-$C_6$ cycloalkyl), $R^{8F}$-substituted or unsubstituted heterocycloalkyl (e.g., 3 to 8 membered, 3 to 6 membered, or 5 to 6 membered heterocycloalkyl), $R^{8F}$-substituted or unsubstituted aryl (e.g., $C_6$-$C_{10}$, $C_{10}$ aryl, or phenyl), or $R^{8F}$-substituted or unsubstituted heteroaryl (e.g., 5 to 10 membered, 5 to 9 membered, or 5 to 6 membered heteroaryl).

$R^{8F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2N$—$_2$, —$N$—$NH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, $R^9$ is hydrogen, halogen, —$OCH_3$, $SO_2$, $SO_2$—$R^{9B}$, —$OR^{9A}$, —$NR^{9B}R^{9C}$ or substituted or unsubstituted aryl (e.g., $C_6$-$C_{10}$ aryl, $C_{10}$ aryl, or phenyl). In embodiments, $R^9$ is hydrogen. In embodiments, $R^9$ is —Br. In embodiments, $R^9$ is —Cl. In embodiments, $R^9$ is —$SO_2$—$R^{9B}$ wherein $R^{9B}$ is substituted or unsubstituted aryl (e.g., $C_6$-$C_{10}$ aryl, $C_{10}$ aryl, or phenyl). In embodiments, $R^9$ is —$SO_2$—$R^{9B}$ wherein $R^{9B}$ is unsubstituted aryl (e.g., $C_6$-$C_{10}$ aryl, $C_{10}$ aryl, or phenyl). In embodiments, $R^9$ is $SO_2$—$R^{9B}$ wherein $R^{9B}$ is phenyl. In embodiments, $R^9$ is —$OR^{9A}$, wherein $R^{9A}$ is substituted or unsubstituted alkyl (e.g., $C_1$-$C_8$ alkyl, $C_1$-$C_6$ alkyl, or $C_1$-$C_4$ alkyl). In embodiments, $R^9$ is —$OR^{9A}$, wherein $R^{9A}$ is unsubstituted alkyl (e.g., $C_1$-$C_8$ alkyl, $C_1$-$C_6$ alkyl, or $C_1$-$C_4$ alkyl). In embodiments, $R^9$ is —$OR^{9A}$, wherein $R^{9A}$ is substituted or unsubstituted $C_1$-$C_8$ alkyl. In embodiments, $R^9$ is —$OR^{9A}$, wherein $R^{9A}$ is substituted or unsubstituted $C_1$-$C_4$ alkyl. In embodiments, $R^9$ is —$OR^{9A}$, wherein $R^{9A}$ is substituted or unsubstituted $C_1$-$C_2$ alkyl. In embodiments, $R^9$ is —$NR^{9B}R^{9C}$, wherein $R^{9B}$ and $R^{9C}$ are unsubstituted alkyl (e.g., $C_1$-$C_8$ alkyl, $C_1$-$C_6$ alkyl, or $C_1$-$C_4$ alkyl). In embodiments, $R^9$ is —$NR^{9B}R^{9C}$, wherein $R^{9B}$ and $R^{9C}$ are substituted or unsubstituted $C_1$-$C_8$ alkyl. In embodiments, $R^9$ is —$NR^{9B}R^{9C}$, wherein $R^{9B}$ and $R^{9C}$ are substituted or unsubstituted $C_1$-$C_4$ alkyl. In embodiments, $R^9$ is —$NR^{9B}R^{9C}$, wherein $R^{9B}$ and $R^{9C}$ are substituted or unsubstituted $C_1$-$C_2$ alkyl.

$R^9$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^9$ may be halogen, —$CF_3$, —$CCl_3$, —$CBr_3$, —$CI_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl). $R^9$ may be halogen, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl). $R^9$ may be halogen, or substituted or unsubstituted alkyl (e.g., $C_1$-$C_8$ alkyl, $C_1$-$C_6$ alkyl, or $C_1$-$C_4$ alkyl). $R^9$ may be halogen, or unsubstituted alkyl (e.g., $C_1$-$C_8$ alkyl, $C_1$-$C_6$ alkyl, or $C_1$-$C_4$ alkyl). $R^9$ may be halogen, or substituted or unsubstituted heteroalkyl (e.g., 2 to 8 membered heteroalkyl, 2 to 6 membered heteroalkyl, or 2 to 4 membered heteroalkyl). $R^9$ may be halogen, unsubstituted heteroalkyl (e.g., 2 to 8 membered heteroalkyl, 2 to 6 membered heteroalkyl, or 2 to 4 membered heteroalkyl). $R^9$ may be halogen, —$CF_3$, —$CCl_3$, —$CBr_3$, or —$CI_3$. $R^9$ may be hydrogen.

$R^9$ may be hydrogen, $R^{9E}$-substituted or unsubstituted alkyl (e.g., $C_1$-$C_8$, $C_1$-$C_6$, or $C_1$-$C_4$ alkyl), $R^{9E}$-substituted or unsubstituted heteroalkyl (e.g., 2 to 8 membered, 2 to 6 membered, or 2 to 4 membered heteroalkyl), $R^{9E}$-substituted or unsubstituted cycloalkyl (e.g., $C_3$-$C_5$, $C_3$-$C_6$, or $C_5$-$C_6$ cycloalkyl), $R^{9E}$-substituted or unsubstituted heterocycloalkyl (e.g., 3 to 8 membered, 3 to 6 membered, or 5 to 6 membered heterocycloalkyl), $R^{9E}$-substituted or unsubstituted aryl (e.g., $C_6$-$C_{10}$, $C_{10}$ aryl, or phenyl), or $R^{9E}$-substituted or unsubstituted heteroaryl (e.g., 5 to 10 membered, 5 to 9 membered, or 5 to 6 membered heteroaryl). $R^9$ may be $R^{9E}$-substituted or unsubstituted alkyl (e.g., $C_1$-$C_8$, $C_1$-$C_6$, or $C_1$-$C_4$ alkyl), $R^{9E}$-substituted or unsubstituted heteroalkyl (e.g., 2 to 8 membered, 2 to 6 membered, or 2 to 4 membered heteroalkyl), $R^{9E}$-substituted or unsubstituted cycloalkyl (e.g., $C_3$-$C_8$, $C_3$-$C_6$, or $C_5$-$C_6$ cycloalkyl), $R^{9E}$-substituted or unsubstituted heterocycloalkyl (e.g., 3 to 8 membered, 3 to 6 membered, or 5 to 6 membered heterocycloalkyl), $R^{9E}$-substituted or unsubstituted aryl (e.g., $C_6$-$C_{10}$, $C_{10}$ aryl, or phenyl), or $R^{9E}$-substituted or unsubstituted heteroaryl (e.g., 5 to 10 membered, 5 to 9 membered, or 5 to 6 membered heteroaryl).

In embodiments, $R^9$ is $R^{9E}$-substituted or unsubstituted alkyl (e.g., $C_1$-$C_8$, $C_1$-$C_6$, or $C_1$-$C_4$ alkyl). In embodiments, $R^9$ is $R^{9E}$-substituted alkyl(e.g., $C_1$-$C_8$, $C_1$-$C_6$, or $C_1$-$C_4$ alkyl). In embodiments, $R^9$ is an unsubstituted alkyl (e.g., $C_1$-$C_8$, $C_1$-$C_6$, or $C_1$-$C_4$ alkyl).

In embodiments, $R^9$ is $R^{9E}$-substituted or unsubstituted heteroalkyl (e.g., 2 to 8 membered, 2 to 6 membered, or 2 to 4 membered heteroalkyl). In embodiments, $R^9$ is $R^{9E}$-substituted heteroalkyl (e.g., 2 to 8 membered, 2 to 6 membered, or 2 to 4 membered heteroalkyl). In embodiments, $R^9$ is an unsubstituted heteroalkyl (e.g., 2 to 8 membered, 2 to 6 membered, or 2 to 4 membered heteroalkyl).

In embodiments, $R^9$ is $R^{9E}$-substituted or unsubstituted cycloalkyl (e.g., $C_3$-$C_8$, $C_3$-$C_6$, or $C_5$-$C_6$ cycloalkyl). In embodiments, $R^9$ is $R^{9E}$-substituted cycloalkyl (e.g., $C_3$-$C_8$, $C_3$-$C_6$, or $C_5$-$C_6$ cycloalkyl). In embodiments, $R^9$ is an unsubstituted cycloalkyl (e.g., $C_3$-$C_8$, $C_3$-$C_6$, or $C_5$-$C_6$ cycloalkyl).

In embodiments, $R^9$ is $R^{9E}$-substituted or unsubstituted heterocycloalkyl (e.g., 3 to 8 membered, 3 to 6 membered, or 5 to 6 membered heterocycloalkyl). In embodiments, $R^9$ is $R^{9E}$-substituted heterocycloalkyl (e.g., 3 to 8 membered, 3 to 6 membered, or 5 to 6 membered heterocycloalkyl). In embodiments, $R^9$ is an unsubstituted heterocycloalkyl (e.g., 3 to 8 membered, 3 to 6 membered, or 5 to 6 membered heterocycloalkyl).

In embodiments, $R^9$ is $R^{9E}$-substituted or unsubstituted aryl (e.g., $C_6$-$C_{10}$, $C_{10}$, or phenyl). In embodiments, $R^9$ is $R^{9E}$-substituted aryl (e.g., $C_6$-$C_{10}$, $C_{10}$, or phenyl). In embodiments, $R^9$ is an unsubstituted aryl (e.g., $C_6$-$C_{10}$, $C_{10}$, or phenyl).

In embodiments, $R^9$ is $R^{9E}$-substituted or unsubstituted heteroaryl (e.g., 5 to 10 membered, 5 to 9 membered, or 5 to 6 membered heteroaryl). In embodiments, $R^9$ is $R^{9E}$-substituted heteroaryl (e.g., 5 to 10 membered, 5 to 9 membered, or 5 to 6 membered heteroaryl). In embodiments, $R^9$ is an unsubstituted heteroaryl (e.g., 5 to 10 membered, 5 to 9 membered, or 5 to 6 membered heteroaryl).

$R^{9E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{9F}$-substituted or unsubstituted alkyl (e.g., $C_1$-$C_8$, $C_1$-$C_6$, or $C_1$-$C_4$ alkyl), $R^{9F}$-substituted or unsubstituted heteroalkyl (e.g., 2 to 8 membered, 2 to 6 membered, or 2 to 4 membered heteroalkyl), $R^{9F}$-substituted or unsubstituted cycloalkyl (e.g., $C_3$-$C_8$, $C_3$-$C_6$, or $C_5$-$C_6$ cycloalkyl), $R^{9F}$-substituted or unsubstituted heterocycloalkyl (e.g., 3 to 8 membered, 3 to 6 membered, or 5 to 6 membered heterocycloalkyl), $R^{9F}$-substituted or unsubstituted aryl (e.g., $C_6$-$C_{10}$, $C_{10}$ aryl, or phenyl), or $R^{9F}$-substituted or unsubstituted heteroaryl (e.g., 5 to 10 membered, 5 to 9 membered, or 5 to 6 membered heteroaryl).

$R^{9F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N_{—2}$, —$NHNH_2$, —$ONH_2$, —NHC(O)

NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

In embodiments, R$^{10}$ is hydrogen, halogen, —OCH$_3$, —SO$_2$, —SO$_2$—R$^{10B}$, —OR$^{10A}$, —NR$^{10B}$R$^{10C}$, or substituted or unsubstituted aryl (e.g., C$_6$-C$_{10}$ aryl, C$_{10}$ aryl, or phenyl). In embodiments, R$^{10}$ is hydrogen. In embodiments, R$^{10}$ is —Br. In embodiments, R$^{10}$ is —Cl. In embodiments, R$^{10}$ is —SO$_2$—R$^{10B}$ wherein R$^{10B}$ is substituted or unsubstituted aryl (e.g., C$_6$-C$_{10}$ aryl, C$_{10}$ aryl, or phenyl). In embodiments, R$^{10}$ is —SO$_2$—R$^{10B}$ wherein R$^{10B}$ is unsubstituted aryl (e.g., C$_6$-C$_{10}$ aryl, C$_{10}$ aryl, or phenyl). In embodiments, R$^{10}$ is —SO$_2$—R$^{10B}$ wherein R$^{10B}$ is phenyl. In embodiments, R$^{10}$ is phenyl. In embodiments, R$^{10}$ is —OR$^{10A}$, wherein R$^{10A}$ is substituted or unsubstituted alkyl (e.g., C$_1$-C$_8$ alkyl, C$_1$-C$_6$ alkyl, or C$_1$-C$_4$ alkyl). In embodiments, R$^{10}$ is —OR$^{10A}$, wherein R$^{10A}$ is unsubstituted alkyl (e.g., C$_1$-C$_8$ alkyl, C$_1$-C$_6$ alkyl, or C$_1$-C$_4$ alkyl). In embodiments, R$^{10}$ is —OR$^{10A}$, wherein R$^{10A}$ is substituted or unsubstituted C$_1$-C$_8$ alkyl. In embodiments, R$^{10}$ is —OR$^{10A}$, wherein R$^{10A}$ is substituted or unsubstituted C$_1$-C$_4$ alkyl. In embodiments, R$^{10}$ is —OR$^{10A}$, wherein R$^{10A}$ is substituted or unsubstituted C$_1$-C$_2$ alkyl. In embodiments, R$^{10}$ is —NR$^{10B}$R$^{10C}$, wherein R$^{10B}$ and R$^{10C}$ are unsubstituted alkyl (e.g., C$_1$-C$_8$ alkyl, C$_1$-C$_6$ alkyl, or C$_1$-C$_4$ alkyl). In embodiments, R$^{10}$ is —NR$^{10B}$R$^{10C}$, wherein R$^{10B}$ and R$^{10C}$ are substituted or unsubstituted C$_1$-C$_8$ alkyl. In embodiments, R$^{10}$ is —NR$^{10B}$R$^{10C}$ wherein R$^{10B}$ and R$^{10C}$ are substituted or unsubstituted C$_1$-C$_4$ alkyl. In embodiments, R$^{10}$ is —NR$^{10B}$R$^{10C}$, wherein R$^{10B}$ and R$^{10C}$ are substituted or unsubstituted C$_1$-C$_2$ alkyl.

R$^{10}$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., C$_3$-C$_8$, C$_3$-C$_6$, or C$_5$-C$_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., C$_6$-C$_{10}$, C$_{10}$ aryl, or phenyl), or substituted or unsubstituted heteroaryl (e.g., 5 to 10 membered, 5 to 9 membered, or 5 to 6 membered heteroaryl). R$^{10}$ may be halogen, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl). R$^{10}$ may be halogen, or substituted or unsubstituted alkyl (e.g., C$_1$-C$_8$ alkyl, C$_1$-C$_6$ alkyl, or C$_1$-C$_4$ alkyl). R$^{10}$ may be halogen, or unsubstituted alkyl (e.g., C$_1$-C$_8$ alkyl, C$_1$-C$_6$ alkyl, or C$_1$-C$_4$ alkyl). R$^{10}$ may be halogen, or substituted or unsubstituted heteroalkyl (e.g., 2 to 8 membered heteroalkyl, 2 to 6 membered heteroalkyl, or 2 to 4 membered heteroalkyl). R$^{10}$ may be halogen, unsubstituted heteroalkyl (e.g., 2 to 8 membered heteroalkyl, 2 to 6 membered, or 2 to 4 membered heteroalkyl. R$^{10}$ may be halogen, —CF$_3$, —CCl$_3$, —CBr$_3$, or —CI$_3$. R$^1$ may be hydrogen.

R$^{10}$ may be hydrogen, R$^{10E}$-substituted or unsubstituted alkyl (e.g., C$_1$-C$_8$, C$_1$-C$_6$, or C$_1$-C$_4$ alkyl), R$^{10E}$-substituted or unsubstituted heteroalkyl (e.g., 2 to 8 membered, 2 to 6 membered, or 2 to 4 membered heteroalkyl), R$^{1E}$-substituted or unsubstituted cycloalkyl (e.g., C$_3$-C$_8$, C$_3$-C$_6$, or C$_5$-C$_6$ cycloalkyl), R$^{10E}$-substituted or unsubstituted heterocycloalkyl (e.g., 3 to 8 membered, 3 to 6 membered, or 5 to 6 membered heterocycloalkyl), R$^{10E}$-substituted or unsubstituted aryl (e.g., C$_6$-C$_{10}$, C$_{10}$ aryl, or phenyl), or R$^{10E}$-substituted or unsubstituted heteroaryl (e.g., 5 to 10 membered, 5 to 9 membered, or 5 to 6 membered heteroaryl). R$^{10}$ may be R$^{10E}$-substituted or unsubstituted alkyl (e.g., C$_1$-C$_8$, C$_1$-C$_6$, or C$_1$-C$_4$ alkyl), R$^{10E}$-substituted or unsubstituted heteroalkyl (e.g., 2 to 8 membered, 2 to 6 membered, or 2 to 4 membered heteroalkyl), R$^{10E}$-substituted or unsubstituted cycloalkyl (e.g., C$_3$-C$_8$, C$_3$-C$_6$, or C$_5$-C$_6$ cycloalkyl), R$^{10E}$-substituted or unsubstituted heterocycloalkyl (e.g., 3 to 8 membered, 3 to 6 membered, or 5 to 6 membered heterocycloalkyl), R$^{10E}$-substituted or unsubstituted aryl (e.g., C$_6$-C$_{10}$, C$_{10}$ aryl, or phenyl), or R$^{10E}$-substituted or unsubstituted heteroaryl (e.g., 5 to 10 membered, 5 to 9 membered, or 5 to 6 membered heteroaryl).

In embodiments, R$^{10}$ is R$^{10E}$-substituted or unsubstituted alkyl (e.g., C$_1$-C$_8$, C$_1$-C$_6$, or C$_1$-C$_4$ alkyl). In embodiments, R$^{10}$ is R$^{10E}$-substituted alkyl (e.g., C$_1$-C$_8$, C$_1$-C$_6$, or C$_1$-C$_4$ alkyl). In embodiments, R$^{10}$ is an unsubstituted alkyl (e.g., C$_1$-C$_8$, C$_1$-C$_6$, or C$_1$-C$_4$ alkyl).

In embodiments, R$^{10}$ is R$^{10E}$-substituted or unsubstituted heteroalkyl (e.g., 2 to 8 membered, 2 to 6 membered, or 2 to 4 membered heteroalkyl). In embodiments, R$^{10}$ is R$^{10E}$-substituted heteroalkyl (e.g., 2 to 8 membered, 2 to 6 membered, or 2 to 4 membered heteroalkyl). In embodiments, R$^{10}$ is an unsubstituted heteroalkyl (e.g., 2 to 8 membered, 2 to 6 membered, or 2 to 4 membered heteroalkyl).

In embodiments, R$^{10}$ is R$^{10E}$-substituted or unsubstituted cycloalkyl (e.g., C$_3$-C$_8$, C$_3$-C$_6$, or C$_5$-C$_6$ cycloalkyl). In embodiments, R$^{10}$ is R$^{10E}$-substituted cycloalkyl (e.g., C$_3$-C$_8$, C$_3$—C$_6$, or C$_5$-C$_6$ cycloalkyl). In embodiments, R$^{10}$ is an unsubstituted cycloalkyl (e.g., C$_3$-C$_8$, C$_3$-C$_6$, or C$_5$-C$_6$ cycloalkyl).

In embodiments, R$^{10}$ is R$^{10E}$-substituted or unsubstituted heterocycloalkyl (e.g., 3 to 8 membered, 3 to 6 membered, or 5 to 6 membered heterocycloalkyl). In embodiments, R$^{10}$ is R$^{10E}$-substituted heterocycloalkyl (e.g., 3 to 8 membered, 3 to 6 membered, or 5 to 6 membered heterocycloalkyl). In embodiments, R$^{10}$ is an unsubstituted heterocycloalkyl (e.g., 3 to 8 membered, 3 to 6 membered, or 5 to 6 membered heterocycloalkyl).

In embodiments, R$^{10}$ is R$^{10E}$-substituted or unsubstituted aryl (e.g., C$_6$-C$_{10}$, C$_{10}$, or phenyl). In embodiments, R$^{10}$ is R$^{0E}$-substituted aryl (e.g., C$_6$-C$_{10}$, C$_{10}$, or phenyl). In embodiments, R$^{10}$ is an unsubstituted aryl (e.g., C$_6$-C$_{10}$, C$_{10}$, or phenyl).

In embodiments, R$^{10}$ is R$^{10E}$-substituted or unsubstituted heteroaryl (e.g., 5 to 10 membered, 5 to 9 membered, or 5 to 6 membered heteroaryl). In embodiments, R$^{10}$ is R$^{10E}$-substituted heteroaryl (e.g., 5 to 10 membered, 5 to 9 membered, or 5 to 6 membered heteroaryl). In embodiments, R$^{10}$ is an unsubstituted heteroaryl (e.g., 5 to 10 membered, 5 to 9 membered, or 5 to 6 membered heteroaryl).

R$^{10E}$ is independently oxo, halogen, —CCl$_3$, —CBr$_3$, —CF$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{10F}$-substituted or unsubstituted alkyl (e.g., C$_1$-C$_8$, C$_1$-C$_6$, or C$_1$-C$_4$ alkyl), R$^{10F}$-substituted or unsubstituted heteroalkyl (e.g., 2 to 8 membered, 2 to 6 membered, or 2 to 4 membered heteroalkyl), R$^{10F}$-substituted or unsubstituted cycloalkyl (e.g., C$_3$-C$_8$, C$_3$-C$_6$, or C$_5$-C$_6$ cycloalkyl), R$^{10F}$-substituted or unsubstituted heterocycloalkyl (e.g., 3 to 8 membered, 3 to 6 membered, or 5 to 6 membered heterocycloalkyl), R$^{1F}$-substituted or unsubstituted aryl (e.g., C$_6$-C$_{10}$, C$_{10}$ aryl, or phenyl), or R$^{10F}$-substituted or unsubstituted heteroaryl (e.g., 5 to 10 membered, 5 to 9 membered, or 5 to 6 membered heteroaryl).

R$^{10F}$ is independently oxo, halogen, —CCl$_3$, —CBr$_3$, —CF$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, unsubstituted alkyl (e.g., C$_1$-C$_8$, C$_1$—C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

In embodiments, R$^{11}$ is hydrogen, halogen, —OCH$_3$, —SO$_2$, —SO$_2$—R$^{11B}$, —OR$^{11A}$, —NR$^{11B}$R$^{11C}$, or substituted or unsubstituted aryl (e.g., C$_6$-C$_{10}$ aryl, C$_{10}$ aryl, or phenyl). In embodiments, R$^{11}$ is hydrogen. In embodiments, R$^{11}$ is —Br. In embodiments, R$^{11}$ is —Cl. In embodiments, R$^{11}$ is —SO$_2$—R$^{11B}$ wherein R$^{11B}$ is substituted or unsubstituted aryl (e.g., C$_6$-C$_{10}$ aryl, C$_{10}$ aryl, or phenyl). In embodiments, R$^{11}$ is —SO$_2$—R$^{11B}$ wherein R$^{11B}$ is unsubstituted aryl (e.g., C$_6$-C$_{10}$ aryl, C$_{10}$ aryl, or phenyl). In embodiments, R$^{11}$ is —SO$_2$—R$^{11B}$ wherein R$^{11B}$ is phenyl. In embodiments, R$^{11}$ is phenyl. In embodiments, R$^{11}$ is —OR$^{11A}$, wherein R$^{11A}$ is substituted or unsubstituted alkyl (e.g., C$_1$-C$_8$ alkyl, C$_1$-C$_6$ alkyl, or C$_1$-C$_4$ alkyl). In embodiments, R$^{11}$ is —OR$^{11A}$, wherein R$^{11A}$ is unsubstituted alkyl (e.g., C$_1$-C$_8$ alkyl, C$_1$-C$_6$ alkyl, or C$_1$-C$_4$ alkyl). In embodiments, R$^{11}$ is —OR$^{11A}$, wherein R$^{11A}$ is substituted or unsubstituted C$_1$-C$_8$ alkyl. In embodiments, R$^{11}$ is —OR$^{11A}$, wherein R$^{11A}$ is substituted or unsubstituted C$_1$-C$_4$ alkyl. In embodiments, R$^{11}$ is —OR$^{11A}$, wherein R$^{11A}$ is substituted or unsubstituted C$_1$-C$_2$ alkyl. In embodiments, R$^{11}$ is —NR$^{11B}$R$^{11C}$, wherein R$^{11B}$ and R$^{11C}$ are unsubstituted alkyl (e.g., C$_1$-C$_8$ alkyl, C$_1$-C$_6$ alkyl, or C$_1$-C$_4$ alkyl). In embodiments, R$^{11}$ is —NR$^{11B}$R$^{11C}$, wherein R$^{11B}$ and R$^{11C}$ are substituted or unsubstituted C$_1$-C$_8$ alkyl. In embodiments, R$^{11}$ is —NR$^{11B}$R$^{11C}$ wherein R$^{11B}$ and R$^{11C}$ are substituted or unsubstituted C$_1$-C$_4$ alkyl. In embodiments, R$^{11}$ is —NR$^{11B}$R$^{11C}$, wherein R$^{11B}$ and R$^{11C}$ are substituted or unsubstituted C$_1$-C$_2$ alkyl.

R$^{11}$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., C$_3$-C$_5$, C$_3$-C$_6$, or C$_5$-C$_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., C$_6$-C$_{10}$, C$_{10}$ aryl, or phenyl), or substituted or unsubstituted heteroaryl (e.g., 5 to 10 membered, 5 to 9 membered, or 5 to 6 membered heteroaryl). R$^{11}$ may be halogen, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl). R$^{11}$ may be halogen, or substituted or unsubstituted alkyl (e.g., C$_1$-C$_8$ alkyl, C$_1$-C$_6$ alkyl, or C$_1$-C$_4$ alkyl). R$^{11}$ may be halogen, or substituted or unsubstituted alkyl (e.g., C$_1$-C$_8$ alkyl, C$_1$-C$_6$ alkyl, or C$_1$-C$_4$ alkyl). R$^{11}$ may be halogen, or substituted or unsubstituted heteroalkyl (e.g., 2 to 8 membered heteroalkyl, 2 to 6 membered heteroalkyl, or 2 to 4 membered heteroalkyl). R$^{11}$ may be halogen, unsubstituted heteroalkyl (e.g., 2 to 8 membered heteroalkyl, 2 to 6 membered heteroalkyl, or 2 to 4 membered heteroalkyl). Rn may be halogen, —CF$_3$, —CCl$_3$, —CBr$_3$, or —CI$_3$. R$^{11}$ may be hydrogen.

R$^{11}$ may be hydrogen, R$^{11E}$-substituted or unsubstituted alkyl (e.g., C$_1$-C$_8$, C$_1$-C$_6$, or C$_1$-C$_4$ alkyl), R$^{11E}$-substituted or unsubstituted heteroalkyl (e.g., 2 to 8 membered, 2 to 6 membered, or 2 to 4 membered heteroalkyl), R$^{11E}$-substituted or unsubstituted cycloalkyl (e.g., C$_3$-C$_8$, C$_3$-C$_6$, or C$_5$-C$_6$ cycloalkyl), R$^{11E}$-substituted or unsubstituted heterocycloalkyl (e.g., 3 to 8 membered, 3 to 6 membered, or 5 to 6 membered heterocycloalkyl), R$^{11E}$-substituted or unsubstituted aryl (e.g., C$_6$-C$_{10}$, C$_{10}$ aryl, or phenyl), or R$^{11E}$-substituted or unsubstituted heteroaryl (e.g., 5 to 10 membered, 5 to 9 membered, or 5 to 6 membered heteroaryl). R$^{11}$ may be R$^{11E}$-substituted or unsubstituted alkyl (e.g., C$_1$-C$_8$, C$_1$-C$_6$, or C$_1$-C$_4$ alkyl), R$^{11E}$-substituted or unsubstituted heteroalkyl (e.g., 2 to 8 membered, 2 to 6 membered, or 2 to 4 membered heteroalkyl), R$^{11E}$-substituted or unsubstituted cycloalkyl (e.g., C$_3$-C$_8$, C$_3$-C$_6$, or C$_5$-C$_6$ cycloalkyl), R$^{11E}$-substituted or unsubstituted heterocycloalkyl (e.g., 3 to 8 membered, 3 to 6 membered, or 5 to 6 membered heterocycloalkyl), R$^{11E}$-substituted or unsubstituted aryl (e.g., C$_6$-C$_{10}$, C$_{10}$ aryl, or phenyl), or R$^{11E}$-substituted or unsubstituted heteroaryl (e.g., 5 to 10 membered, 5 to 9 membered, or 5 to 6 membered heteroaryl).

In embodiments, R$^{11}$ is R$^{1E}$-substituted or unsubstituted alkyl (e.g., C$_1$-C$_8$, C$_1$-C$_6$, or C$_1$-C$_4$ alkyl). In embodiments, R$^{11}$ is R$^{11E}$-substituted alkyl (e.g., C$_1$-C$_8$, C$_1$-C$_6$, or C$_1$-C$_4$ alkyl). In embodiments, R$^{11}$ is an unsubstituted alkyl (e.g., C$_1$-C$_8$, C$_1$-C$_6$, or C$_1$-C$_4$ alkyl).

In embodiments, R$^{11}$ is R$^{11E}$-substituted or unsubstituted heteroalkyl (e.g., 2 to 8 membered, 2 to 6 membered, or 2 to 4 membered heteroalkyl). In embodiments, R$^{11}$ is R$^{11E}$-substituted heteroalkyl (e.g., 2 to 8 membered, 2 to 6 membered, or 2 to 4 membered heteroalkyl). In embodiments, R$^{11}$ is an unsubstituted heteroalkyl (e.g., 2 to 8 membered, 2 to 6 membered, or 2 to 4 membered heteroalkyl).

In embodiments, R$^{11}$ is R$^{11E}$-substituted or unsubstituted cycloalkyl (e.g., C$_3$-C$_8$, C$_3$-C$_6$, or C$_5$-C$_6$ cycloalkyl). In embodiments, R$^{11}$ is R$^{11E}$-substituted cycloalkyl (e.g., C$_3$-C$_8$, C$_3$-C$_6$, or C$_5$-C$_6$ cycloalkyl). In embodiments, R$^{11}$ is an unsubstituted cycloalkyl (e.g., C$_3$-C$_8$, C$_3$-C$_6$, or C$_5$-C$_6$ cycloalkyl).

In embodiments, R$^{11}$ is R$^{11E}$-substituted or unsubstituted heterocycloalkyl (e.g., 3 to 8 membered, 3 to 6 membered, or 5 to 6 membered heterocycloalkyl). In embodiments, $R^{11}$ is $R^{11E}$-substituted heterocycloalkyl (e.g., 3 to 8 membered, 3 to 6 membered, or 5 to 6 membered heterocycloalkyl). In embodiments, $R^{11}$ is an unsubstituted heterocycloalkyl (e.g., 3 to 8 membered, 3 to 6 membered, or 5 to 6 membered heterocycloalkyl).

In embodiments, $R^{11}$ is $R^{11E}$-substituted or unsubstituted aryl (e.g., $C_6$-$C_{10}$, $C_{10}$, or phenyl). In embodiments, $R^{11}$ is $R^{11E}$-substituted aryl (e.g., $C_6$-$C_{10}$, $C_{10}$, or phenyl). In embodiments, $R^{11}$ is an unsubstituted aryl (e.g., $C_6$-$C_{10}$, $C_{10}$, or phenyl).

In embodiments, $R^{11}$ is $R^{11E}$-substituted or unsubstituted heteroaryl (e.g., 5 to 10 membered, 5 to 9 membered, or 5 to 6 membered heteroaryl). In embodiments, $R^{11}$ is $R^{11E}$-substituted heteroaryl (e.g., 5 to 10 membered, 5 to 9 membered, or 5 to 6 membered heteroaryl). In embodiments, $R^{11}$ is an unsubstituted heteroaryl (e.g., 5 to 10 membered, 5 to 9 membered, or 5 to 6 membered heteroaryl).

$R^{11E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11F}$-substituted or unsubstituted alkyl (e.g., $C_1$-$C_8$, $C_1$-$C_6$, or $C_1$-$C_4$ alkyl), $R^{11F}$-substituted or unsubstituted heteroalkyl (e.g., 2 to 8 membered, 2 to 6 membered, or 2 to 4 membered heteroalkyl), $R^{11F}$-substituted or unsubstituted cycloalkyl (e.g., $C_3$-$C_8$, $C_3$-$C_6$, or $C_5$-$C_6$ cycloalkyl), $R^{11F}$-substituted or unsubstituted heterocycloalkyl (e.g., 3 to 8 membered, 3 to 6 membered, or 5 to 6 membered heterocycloalkyl), $R^{11F}$-substituted or unsubstituted aryl (e.g., $C_6$-$C_{10}$, $C_{10}$ aryl, or phenyl), or $R^{11F}$-substituted or unsubstituted heteroaryl (e.g., 5 to 10 membered, 5 to 9 membered, or 5 to 6 membered heteroaryl).

$R^{11F}$ is independently oxo, halogen, —$CCl_3$, —$CBr_3$, —$CF_3$, —$C_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^9$ and $R^{10}$ may be joined together to form substituted or unsubstituted cycloalkyl (e.g. 3 to 8 membered cycloalkyl). $R^9$ and $R^{10}$ may be joined together to form substituted or unsubstituted heterocycloalkyl (e.g. 3 to 8 membered heterocycloalkyl). $R^9$ and $R^{10}$ may be joined together to form substituted or unsubstituted aryl (e.g. 3 to 8 membered aryl). $R^9$ and $R^{10}$ may be joined together to form substituted or unsubstituted heteroaryl (e.g. 3 to 8 membered heteroaryl). $R^9$ and $R^{10}$ may be joined together to form $R^{9E}$-substituted or unsubstituted cycloalkyl (e.g. 3 to 8 membered cycloalkyl). $R^9$ and $R^{10}$ may be joined together to form $R^{9E}$-substituted or unsubstituted heterocycloalkyl (e.g. 3 to 8 membered heterocycloalkyl). $R^9$ and $R^{10}$ may be joined together to form $R^{9E}$-substituted or unsubstituted aryl (e.g. 3 to 8 membered aryl). $R^9$ and $R^{10}$ may be joined together to form $R^{9E}$-substituted or unsubstituted heteroaryl (e.g. 3 to 8 membered heteroaryl).

$R^{10}$ and $R^{11}$ may be joined together to form substituted or unsubstituted cycloalkyl (e.g. 3 to 8 membered cycloalkyl). $R^{10}$ and $R^{11}$ may be joined together to form substituted or unsubstituted heterocycloalkyl (e.g. 3 to 8 membered heterocycloalkyl). $R^{10}$ and $R^{11}$ may be joined together to form substituted or unsubstituted aryl (e.g. 3 to 8 membered aryl). $R^{10}$ and $R^{11}$ may be joined together to form substituted or unsubstituted heteroaryl (e.g. 3 to 8 membered heteroaryl). $R^{10}$ and $R^{11}$ may be joined together to form $R^{11E}$-substituted or unsubstituted cycloalkyl (e.g. 3 to 8 membered cycloalkyl). $R^{10}$ and $R^{11}$ may be joined together to form $R^{10E}$-substituted or unsubstituted heterocycloalkyl (e.g. 3 to 8 membered heterocycloalkyl). $R^{10}$ and $R^{11}$ may be joined together to form $R^{10E}$-substituted or unsubstituted aryl (e.g. 3 to 8 membered aryl). $R^{10}$ and $R^{11}$ may be joined together to form $R^{10E}$-substituted or unsubstituted heteroaryl (e.g. 3 to 8 membered heteroaryl).

In embodiments, $R^7$, $R^8$, $R^9$, $R^{10}$ and $R''$ are independently hydrogen, halogen, $C_1$-$C_5$ unsubstituted alkyl, 2 to 5 membered unsubstituted heteroalkyl. $R^7$, $R^8$, $R^9$, $R^{10}$ and $R^{11}$ may independently be hydrogen, halogen, unsubstituted methyl, —$OCH_3$ or —$O(CH_2)_2$=$CH_2$. $R^{10}$ and $R^{11}$ may be hydrogen.

The compound of formula (II) may have the formula:

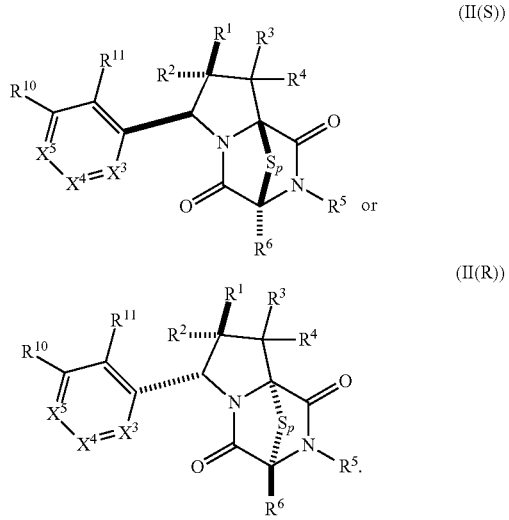

The symbol p, $X^3$, $X^4$, $X^5$, p, $R^1$, $R^2$, $R^3$, $R^4$, $R^5$, $R^6$, $R^7$, $R^8$, $R^9$, $R^{10}$, and $R^{11}$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen.

The compound of formula (II) may have the formula:

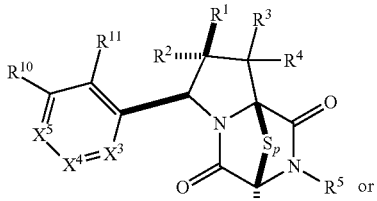
(II(S))

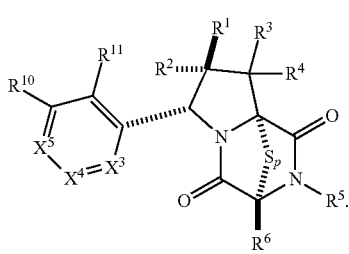
(II(R))

The symbol p, $X^3$, $X^4$, $X^5$, p, $R^1$, $R^2$, $R^3$, $R^4$, $R^5$, $R^6$, $R^7$, $R^8$, $R^9$, $R^{10}$, and $R^{11}$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen.

The compound of formula (II) may have the formula:

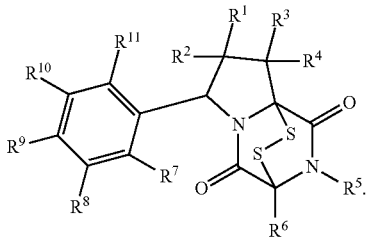
(II1)

In embodiments, $R^8$ is hydrogen or —$OR^{33J}$. $R^9$, $R^{10}$, and $R^{11}$ may independently be hydrogen or halogen. $R^{33J}$ may be hydrogen, or unsubstituted alkyl (e.g. unsubstituted methyl, unsubstituted ethyl, or unsubstituted propyl).

The compound of formula (II) may have the formula:

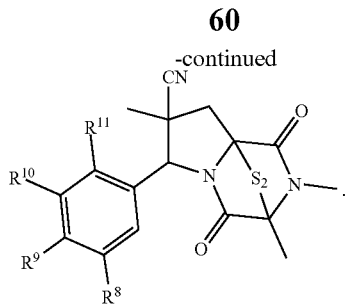

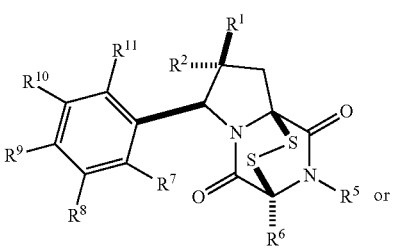

$R^8$ may be hydrogen or —$OR^{8A}$. $R^9$, $R^{10}$, and $R^{11}$ may independently be hydrogen or halogen. $R^{8A}$ may be hydrogen, or unsubstituted alkyl. $R^8$ may be hydrogen.

The compound of formula (II1) may have the formula:

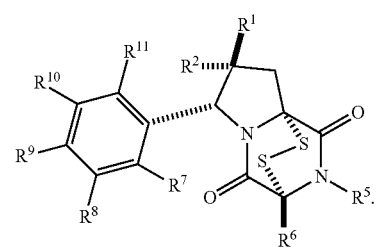
(II1(S))

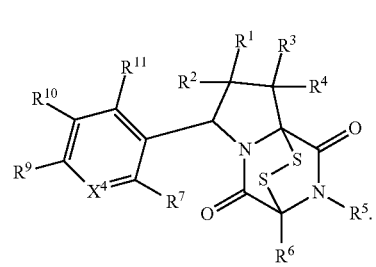
(II1(R))

The compound of formula (II) may have the formula:

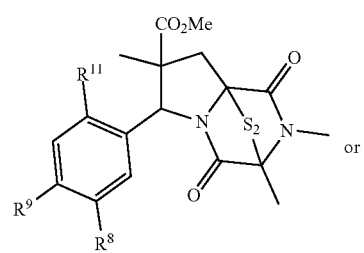
(II2)

The compound of formula (II2) may have the formula:

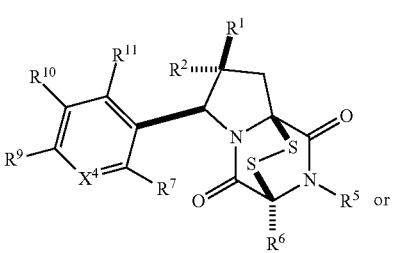
(II2(S))

-continued

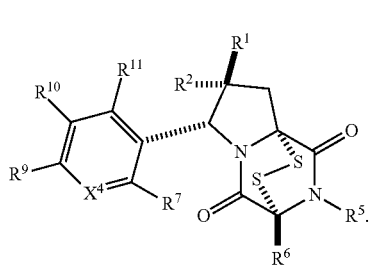
(II2(R))

The compound of formula (II) may have the formula:

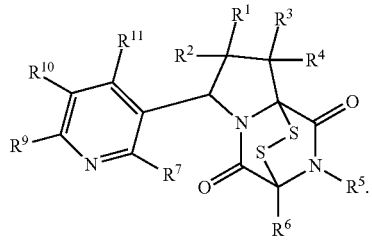
(II3)

The symbol $R^1$, $R^2$, $R^3$, $R^4$, $R^5$, $R^6$, $R^7$, $R^8$, $R^9$, $R^{10}$, and $R^{11}$ are as described herein, including embodiments thereof.

The compound of formula (II3) may have the formula:

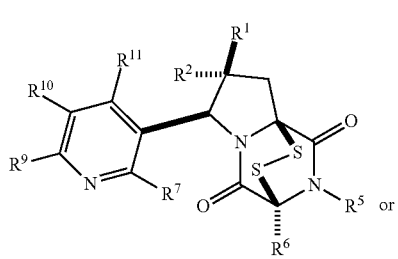
(II3(S))

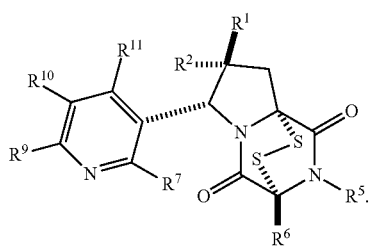
(II3(R))

The compound of formula (II) may have the formula:

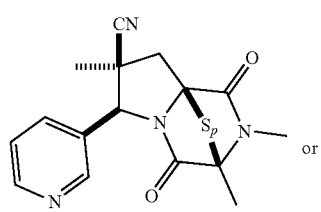
(II4)

or

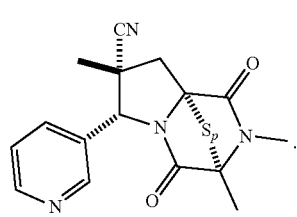
(II5)

p is as described herein.

The compound of formula (I) may have the formula:

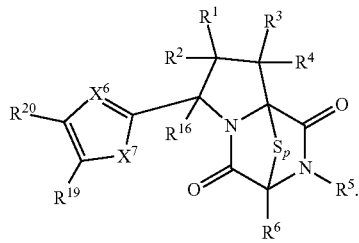
(III)

The symbol p, $R^1$, $R^2$, $R^3$, $R^4$, $R^5$, $R^6$, and $R^{16}$ are as described herein, including embodiments thereof. $R^5$ and $R^6$ may independently be unsubstituted $C_1$-$C_3$ alkyl or unsubstituted 3 to 5 membered cycloalkyl. $R^7$, $R^8$, $R^9$, and $R^{10}$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^{10}$ and $R^{11}$ may be hydrogen.

$X^6$ is —$CR^{23A}$— or —N=. $X^7$ is —$CR^{24A}R^{24B}$, —S—, —O—, or —$NR^{24C}$—.

$R^{19}$ is hydrogen, halogen, —$N_3$, —$CF_3$, —$CCl_3$, —$CBr_3$, —$CI_3$, —CN, —CHO, —$OR^{19A}$, —$NR^{19B}R^{19C}$, —$COOR^{19A}$, —$CONR^{19B}R^{19C}$, —$NO_2$, —$SR^{19D}$, —$SO_{n19}R^{19B}$, —$SO_{v19}NR^{19B}R^{19C}$, —$NHNR^{19B}R^{19C}$, —$ONR^{19B}R^{19C}$, —$NHC(O)NHNR^{19B}R^{19C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_5$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{20}$ is hydrogen, halogen, —$N_3$, —$CF_3$, —$CCl_3$, —$CBr_3$, —$CI_3$, —CN, —CHO, —$OR^{20A}$, —$NR^{20B}R^{20C}$, $COOR^{20A}$, $CONR^{20B}R^{20C}$, —$NO_2$, —$SR^{20D}$, —$SO_{n20}R^{20B}$, —$SO_{v20}NR^{20B}R^{20C}$, —$NHNR^{20B}R^{20C}$, —$ONR^{20B}R^{20C}$, $NHC(O)N$—$NR^{20B}R^{20C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^{19A}$, $R^{19B}$, $R^{19C}$, $R^{19D}$, $R^{20A}$, $R^{20B}$, $R^{20C}$ and $R^{20D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n19 and n20 are independently 1 or 4. v19, and v20 are independently 1 or 2. X is —F, —Cl, —Br, or —I.

$R^{19}$ and $R^{20}$ may optionally be bonded together to form $R^{19E}$— substituted or unsubstituted 3 to 6 membered cycloalkyl, $R^{19E}$— substituted or unsubstituted 3 to 6 membered heterocycloalkyl, $R^{19E}$— substituted or unsubstituted phenyl, or $R^{19E}$-substituted or unsubstituted 5 to 6 membered heteroaryl.

$R^{23A}$, $R^{24A}$, and $R^{24B}$ are independently hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{24C}$ is hydrogen, halogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is —F, —Cl, —Br, or —I.

$R^{23A}$, $R^{24A}$, $R^{24B}$ and $R^{24C}$ may be independently hydrogen, $R^{34}$-substituted or unsubstituted alkyl (e.g., $C_1$-$C_8$, $C_1$-$C_6$, or $C_1$-$C_4$ alkyl), $R^{34}$-substituted or unsubstituted heteroalkyl (e.g., 2 to 8 membered, 2 to 6 membered, or 2 to 4 membered heteroalkyl), $R^{34}$ substituted or unsubstituted cycloalkyl (e.g., $C_3$-$C_8$, $C_3$-$C_6$, or $C_5$-$C_6$ cycloalkyl), $R^{34}$-substituted or unsubstituted heterocycloalkyl (e.g., 3 to 8 membered, 3 to 6 membered, or 5 to 6 membered heterocycloalkyl), $R^{34}$-substituted or unsubstituted aryl (e.g., $C_6$-$C_{10}$, $C_{10}$ aryl, or phenyl), or $R^{34}$-substituted or unsubstituted heteroaryl (e.g., 5 to 10 membered, 5 to 9 membered, or 5 to 6 membered heteroaryl). $R^{23A}$, $R^{24A}$, $R^{24B}$ and $R^{24C}$ may be independently $R^{34}$-substituted or unsubstituted alkyl (e.g., $C_1$-$C_8$, $C_1$-$C_6$, or $C_1$-$C_4$ alkyl), $R^{34}$-substituted or unsubstituted heteroalkyl (e.g., 2 to 8 membered, 2 to 6 membered, or 2 to 4 membered heteroalkyl), $R^{34}$-substituted or unsubstituted cycloalkyl (e.g., $C_3$-$C_8$, $C_3$-$C_6$, or $C_5$-$C_6$ cycloalkyl), $R^{34}$-substituted or unsubstituted heterocycloalkyl (e.g., 3 to 8 membered, 3 to 6 membered, or 5 to 6 membered heterocycloalkyl), $R^{34}$-substituted or unsubstituted aryl (e.g., $C_6$-$C_{10}$, $C_{10}$ aryl, or phenyl), or $R^{34}$-substituted or unsubstituted heteroaryl (e.g., 5 to 10 membered, 5 to 9 membered, or 5 to 6 membered heteroaryl).

In embodiments, $R^{23A}$, $R^{24A}$, $R^{24B}$ and $R^{24C}$ are independently $R^{34}$-substituted or unsubstituted alkyl (e.g., $C_1$-$C_8$, $C_1$-$C_6$, or $C_1$-$C_4$ alkyl). In embodiments, $R^{23A}$, $R^{24A}$, $R^{24B}$ and $R^{24C}$ are independently $R^{34}$-substituted alkyl (e.g., $C_1$-$C_8$, $C_1$-$C_6$, or $C_1$-$C_4$ alkyl). In embodiments, $R^{23A}$, $R^{24A}$, $R^{24B}$ and $R^{24C}$ are independently an unsubstituted alkyl (e.g., $C_1$-$C_8$, $C_1$-$C_6$, or $C_1$-$C_4$ alkyl).

In embodiments, $R^{23A}$, $R^{24A}$, $R^{24B}$ and $R^{24C}$ are independently $R^{34}$-substituted or unsubstituted heteroalkyl (e.g., 2 to 8 membered, 2 to 6 membered, or 2 to 4 membered heteroalkyl). In embodiments, $R^{23A}$, $R^{24A}$, $R^{24B}$ and $R^{24C}$ are independently $R^{34}$-substituted heteroalkyl (e.g., 2 to 8 membered, 2 to 6 membered, or 2 to 4 membered heteroalkyl). In embodiments, $R^{23A}$, $R^{24A}$, $R^{24B}$ and $R^{24C}$ are independently an unsubstituted heteroalkyl (e.g., 2 to 8 membered, 2 to 6 membered, or 2 to 4 membered heteroalkyl).

In embodiments, $R^{23A}$, $R^{24A}$, $R^{24B}$ and $R^{24C}$ are independently $R^{34}$-substituted or unsubstituted cycloalkyl (e.g., $C_3$-$C_8$, $C_3$-$C_6$, or $C_5$-$C_6$ cycloalkyl). In embodiments, $R^{23A}$, $R^{24A}$, $R^{24B}$ and $R^{24C}$ are independently $R^{34}$-substituted cycloalkyl (e.g., $C_3$-$C_8$, $C_3$-$C_6$, or $C_5$-$C_6$ cycloalkyl). In embodiments, $R^{23A}$, $R^{24A}$, $R^{24B}$ and $R^{24C}$ are independently an unsubstituted cycloalkyl (e.g., $C_3$-$C_5$, $C_3$-$C_6$, or $C_5$-$C_6$ cycloalkyl).

In embodiments, $R^{23A}$, $R^{24A}$, $R^{24B}$ and $R^{24C}$ are independently $R^{34}$-substituted or unsubstituted heterocycloalkyl (e.g., 3 to 8 membered, 3 to 6 membered, or 5 to 6 membered heterocycloalkyl). In embodiments, $R^{23A}$, $R^{24A}$, $R^{24B}$ and $R^{24C}$ are independently $R^{34}$-substituted heterocycloalkyl (e.g., 3 to 8 membered, 3 to 6 membered, or 5 to 6 membered heterocycloalkyl). In embodiments, $R^{23A}$, $R^{24A}$, $R^{24B}$ and $R^{24C}$ are independently an unsubstituted heterocycloalkyl (e.g., 3 to 8 membered, 3 to 6 membered, or 5 to 6 membered heterocycloalkyl).

In embodiments, $R^{23A}$, $R^{24A}$, $R^{24B}$ and $R^{24C}$ are independently $R^{34}$-substituted or unsubstituted aryl (e.g., $C_6$-$C_{10}$, $C_{10}$, or phenyl). In embodiments, $R^{23A}$, $R^{24A}$, $R^{24B}$ and $R^{24C}$ are independently $R^{34}$-substituted aryl (e.g., $C_6$-$C_{10}$, $C_{10}$, or phenyl). In embodiments, $R^{23A}$, $R^{24A}$, $R^{24B}$ and $R^{24C}$ are independently an unsubstituted aryl (e.g., $C_6$-$C_{10}$, $C_{10}$, or phenyl).

In embodiments, $R^{23A}$, $R^{24A}$, $R^{24B}$ and $R^{24C}$ are independently $R^{34}$-substituted or unsubstituted heteroaryl (e.g., 5 to 10 membered, 5 to 9 membered, or 5 to 6 membered heteroaryl). In embodiments, $R^{23A}$, $R^{24A}$, $R^{24B}$ and $R^{24C}$ are independently $R^{34}$-substituted heteroaryl (e.g., 5 to 10 membered, 5 to 9 membered, or 5 to 6 membered heteroaryl). In embodiments, $R^{23A}$, $R^{24A}$, $R^{24B}$ and $R^{24C}$ are independently an unsubstituted heteroaryl (e.g., 5 to 10 membered, 5 to 9 membered, or 5 to 6 membered heteroaryl).

$R^{34}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2N$—$_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{34F}$-substituted or unsubstituted alkyl (e.g., $C_1$-$C_8$, $C_1$-$C_6$, or $C_1$-$C_4$ alkyl), $R^{34F}$-substituted or unsubstituted heteroalkyl (e.g., 2 to 8 membered, 2 to 6 membered, or 2 to 4 membered heteroalkyl), $R^{34F}$-substituted or unsubstituted cycloalkyl (e.g., $C_3$-$C_8$, $C_3$-$C_6$, or $C_5$-$C_6$ cycloalkyl), $R^{34F}$-substituted or unsubstituted heterocycloalkyl (e.g., 3 to 8 membered, 3 to 6 membered, or 5 to 6 membered heterocycloalkyl), $R^{34F}$-substituted or unsubstituted aryl (e.g., $C_6$-$C_{10}$, $C_{10}$ aryl, or phenyl), or $R^{34F}$-substituted or unsubstituted heteroaryl (e.g., 5 to 10 membered, 5 to 9 membered, or 5 to 6 membered heteroaryl).

$R^{34F}$ is independently oxo, halogen, —$CCl_3$, —$CBr_3$, —$CF_3$, —$CI_3$, —$CHF_2$, —$CHCl_2$, —$CHBr_2$, —$CHI_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

R$^{19}$ and R$^{24A}$ may optionally be bonded together to form R$^{34}$-substituted or unsubstituted 3 to 6 membered cycloalkyl, R$^{34}$-substituted or unsubstituted 3 to 6 membered heterocycloalkyl, R$^{34}$-substituted or unsubstituted phenyl, or R$^{34}$-substituted or unsubstituted 5 to 6 membered heteroaryl. R$^{20}$ and R$^{23A}$ may optionally be bonded together to form R$^{34}$-substituted or unsubstituted 3 to 6 membered cycloalkyl, R$^{34}$-substituted or unsubstituted 3 to 6 membered heterocycloalkyl, R$^{34}$-substituted or unsubstituted phenyl, or R$^{34}$-substituted or unsubstituted 5 to 6 membered heteroaryl.

When X$^7$ is —S—, X$^6$ may be —N= or —CR$^{23A}$=. When X$^7$ is —NH—, X$^6$ may be —N— or —CR$^{23A}$=. When X$^7$ is NR$^{24C}$—, X$^6$ may —CR$^{23A}$= or —N=. When X$^7$ is —O=, X$^6$ may be —N=, —CH=, or —CR$^{23A}$=. In certain embodiments, X$^7$ is —S— and X$^6$ is —CH=. p may be 2, 3, or 4. In certain embodiments p is 2.

R$^{19}$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., C$_3$-C$_8$, C$_3$-C$_6$, or C$_1$-C$_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., C$_6$-C$_{10}$, C$_{10}$ aryl, or phenyl), or substituted or unsubstituted heteroaryl (e.g., 5 to 10 membered, 5 to 9 membered, or 5 to 6 membered heteroaryl). R$^{19}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —S$_2$Cl, —SO$_3$H, —SO$_4$H, —SO$_2$NH$_2$, —NHNH$_2$, —ONH$_2$, —NHC(O)NHNH$_2$, R$^{19E}$-substituted or unsubstituted alkyl (e.g., C$_1$-C$_8$, C$_1$-C$_6$, or C$_1$-C$_4$ alkyl), or R$^{19E}$-substituted or unsubstituted heteroalkyl (e.g., 2 to 8 membered, 2 to 6 membered, or 2 to 4 membered heteroalkyl). R$^9$ may be halogen, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl). R$^{19}$ may be halogen, or substituted or unsubstituted alkyl (e.g., C$_1$-C$_8$, C$_1$-C$_6$, or C$_1$-C$_4$ alkyl). R$^{19}$ may be halogen, or unsubstituted alkyl (e.g., C$_1$-C$_8$, C$_1$-C$_6$, or C$_1$-C$_4$ alkyl). R$^{19}$ may be halogen, or substituted or unsubstituted heteroalkyl (e.g., 2 to 8 membered, 2 to 6 membered, or 2 to 4 membered heteroalkyl). R$^{19}$ may be halogen, unsubstituted heteroalkyl (e.g., 2 to 8 membered, 2 to 6 membered, or 2 to 4 membered heteroalkyl. R$^{19}$ may be halogen, —CF$_3$, —CCl$_3$, —CBr$_3$, or —CI$_3$. R$^{19}$ may be hydrogen.

R$^{19}$ may be hydrogen, R$^{19E}$-substituted or unsubstituted alkyl (e.g., C$_1$-C$_8$, C$_1$-C$_6$, or C$_1$-C$_4$ alkyl), R$^{19E}$-substituted or unsubstituted heteroalkyl (e.g., 2 to 8 membered, 2 to 6 membered, or 2 to 4 membered heteroalkyl), R$^{19E}$-substituted or unsubstituted cycloalkyl (e.g., C$_3$-C$_5$, C$_3$-C$_6$, or C$_5$-C$_6$ cycloalkyl), R$^{19E}$-substituted or unsubstituted heterocycloalkyl (e.g., 3 to 8 membered, 3 to 6 membered, or 5 to 6 membered heterocycloalkyl), R$^{19E}$-substituted or unsubstituted aryl (e.g., C$_6$-C$_{10}$, C$_{10}$ aryl, or phenyl), or R$^{19E}$-substituted or unsubstituted heteroaryl (e.g., 5 to 10 membered, 5 to 9 membered, or 5 to 6 membered heteroaryl). R$^{19}$ may be R$^{19E}$-substituted or unsubstituted alkyl (e.g., C$_1$-C$_8$, C$_1$-C$_6$, or C$_1$-C$_4$ alkyl), R$^{19E}$-substituted or unsubstituted heteroalkyl (e.g., 2 to 8 membered, 2 to 6 membered, or 2 to 4 membered heteroalkyl), R$^{19E}$-substituted or unsubstituted cycloalkyl (e.g., C$_3$-C$_8$, C$_3$-C$_6$, or C$_5$-C$_6$ cycloalkyl), R$^{19E}$-substituted or unsubstituted heterocycloalkyl (e.g., 3 to 8 membered, 3 to 6 membered, or 5 to 6 membered heterocycloalkyl), R$^{19E}$-substituted or unsubstituted aryl (e.g., C$_6$-C$_{10}$, C$_{10}$ aryl, or phenyl), or R$^{19E}$-substituted or unsubstituted heteroaryl (e.g., 5 to 10 membered, 5 to 9 membered, or 5 to 6 membered heteroaryl).

In embodiments, R$^{19}$ is R$^{19E}$-substituted or unsubstituted alkyl(e.g., C$_1$-C$_8$, C$_1$-C$_6$, or C$_1$-C$_4$ alkyl). In embodiments, R$^{19}$ is R$^{19E}$-substituted alkyl (e.g., C$_1$-C$_8$, C$_1$-C$_6$, or C$_1$-C$_4$ alkyl). In embodiments, R$^{19}$ is an unsubstituted alkyl (e.g., C$_1$-C$_8$, C$_1$-C$_6$, or C$_1$-C$_4$ alkyl).

In embodiments, R$^{19}$ is R$^{19E}$-substituted or unsubstituted heteroalkyl (e.g., 2 to 8 membered, 2 to 6 membered, or 2 to 4 membered heteroalkyl). In embodiments, R$^{19}$ is R$^{19E}$-substituted heteroalkyl (e.g., 2 to 8 membered, 2 to 6 membered, or 2 to 4 membered heteroalkyl). In embodiments, R$^{19}$ is an unsubstituted heteroalkyl (e.g., 2 to 8 membered, 2 to 6 membered, or 2 to 4 membered heteroalkyl).

In embodiments, R$^{19}$ is R$^{19E}$-substituted or unsubstituted cycloalkyl (e.g., C$_3$-C$_8$, C$_3$-C$_6$, or C$_5$-C$_6$ cycloalkyl). In embodiments, R$^{19}$ is R$^{19E}$-substituted cycloalkyl (e.g., C$_3$-C$_8$, C$_3$-C$_6$, or C$_5$-C$_6$ cycloalkyl). In embodiments, R$^{19}$ is an unsubstituted cycloalkyl (e.g., C$_3$-C$_8$, C$_3$-C$_6$, or C$_5$-C$_6$ cycloalkyl).

In embodiments, R$^{19}$ is R$^{19E}$-substituted or unsubstituted heterocycloalkyl (e.g., 3 to 8 membered, 3 to 6 membered, or 5 to 6 membered heterocycloalkyl). In embodiments, R$^{19}$ is R$^{19E}$-substituted heterocycloalkyl (e.g., 3 to 8 membered, 3 to 6 membered, or 5 to 6 membered heterocycloalkyl). In embodiments, R$^{19}$ is an unsubstituted heterocycloalkyl (e.g., 3 to 8 membered, 3 to 6 membered, or 5 to 6 membered heterocycloalkyl).

In embodiments, R$^{19}$ is R$^{19E}$-substituted or unsubstituted aryl (e.g., C$_6$-C$_{10}$, C$_{10}$, or phenyl). In embodiments, R$^{19}$ is R$^{19E}$-substituted aryl (e.g., C$_6$-C$_{10}$, C$_{10}$, or phenyl). In embodiments, R$^{19}$ is an unsubstituted aryl (e.g., C$_6$-C$_{10}$, C$_{10}$, or phenyl).

In embodiments, R$^{19}$ is R$^{19E}$-substituted or unsubstituted heteroaryl (e.g., 5 to 10 membered, 5 to 9 membered, or 5 to 6 membered heteroaryl). In embodiments, R$^{19}$ is R$^{19E}$-substituted heteroaryl (e.g., 5 to 10 membered, 5 to 9 membered, or 5 to 6 membered heteroaryl). In embodiments, R$^{19}$ is an unsubstituted heteroaryl (e.g., 5 to 10 membered, 5 to 9 membered, or 5 to 6 membered heteroaryl).

R$^{19E}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)

—NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{19F}$-substituted or unsubstituted alkyl (e.g., C$_1$-C$_8$, C$_1$-C$_6$, or C$_1$-C$_4$ alkyl), R$^{19F}$-substituted or unsubstituted heteroalkyl (e.g., 2 to 8 membered, 2 to 6 membered, or 2 to 4 membered heteroalkyl), R$^{19F}$-substituted or unsubstituted cycloalkyl (e.g., C$_3$-C$_8$, C$_3$-C$_6$, or C$_5$-C$_6$ cycloalkyl), R$^{19F}$-substituted or unsubstituted heterocycloalkyl (e.g., 3 to 8 membered, 3 to 6 membered, or 5 to 6 membered heterocycloalkyl), R$^{19F}$-substituted or unsubstituted aryl (e.g., C$_6$-C$_{10}$, C$_{10}$ aryl, or phenyl), or R$^{19F}$-substituted or unsubstituted heteroaryl (e.g., 5 to 10 membered, 5 to 9 membered, or 5 to 6 membered heteroaryl).

R$^{19F}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_1$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

R$^{20}$ may be hydrogen, halogen, —N$_3$, —CF$_3$, —CCl$_3$, —CBr$_3$, —CI$_3$, —N$_3$, —CN, —CHO, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., C$_3$-C$_8$, C$_3$-C$_6$, or C$_5$-C$_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., C$_6$-C$_{10}$, C$_{10}$ aryl, or phenyl), or substituted or unsubstituted heteroaryl (e.g., 5 to 10 membered, 5 to 9 membered, or 5 to 6 membered heteroaryl). R$^{20}$ may be halogen, —CF$_3$, —CCl$_3$, —CBr$_3$, —CI$_3$, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl). R$^{20}$ may be halogen, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl). R$^{20}$ may be halogen, or substituted or unsubstituted alkyl (e.g., C$_1$-C$_8$, C$_1$-C$_6$, or C$_1$-C$_4$ alkyl). R$^{20}$ may be halogen, or unsubstituted alkyl (e.g., C$_1$-C$_8$, C$_1$-C$_6$, or C$_1$-C$_4$ alkyl). R$^{20}$ may be halogen, or substituted or unsubstituted heteroalkyl (e.g., 2 to 8 membered, 2 to 6 membered, or 2 to 4 membered heteroalkyl). R$^{20}$ may be halogen, unsubstituted heteroalkyl (e.g., 2 to 8 membered, 2 to 6 membered, or 2 to 4 membered heteroalkyl. R$^{20}$ may be halogen, —CF$_3$, —CCl$_3$, —CBr$_3$, or —CI$_3$. R$^{20}$ may be hydrogen.

R$^{20}$ may be hydrogen, R$^{20E}$-substituted or unsubstituted alkyl (e.g., C$_1$-C$_8$, C$_1$-C$_6$, or C$_1$-C$_4$ alkyl), R$^{20E}$-substituted or unsubstituted heteroalkyl (e.g., 2 to 8 membered, 2 to 6 membered, or 2 to 4 membered heteroalkyl), R$^{20E}$-substituted or unsubstituted cycloalkyl (e.g., C$_3$-C$_8$, C$_3$-C$_6$, or C$_5$-C$_6$ cycloalkyl), R$^{20E}$-substituted or unsubstituted heterocycloalkyl (e.g., 3 to 8 membered, 3 to 6 membered, or 5 to 6 membered heterocycloalkyl), R$^{20E}$-substituted or unsubstituted aryl (e.g., C$_6$-C$_{10}$, C$_{10}$ aryl, or phenyl), or R$^{20E}$-substituted or unsubstituted heteroaryl (e.g., 5 to 10 membered, 5 to 9 membered, or 5 to 6 membered heteroaryl). R$^{20}$ may be R$^{20E}$-substituted or unsubstituted alkyl (e.g., C$_1$-C$_8$, C$_1$-C$_6$, or C$_1$-C$_4$ alkyl), R$^{20E}$-substituted or unsubstituted heteroalkyl (e.g., 2 to 8 membered, 2 to 6 membered, or 2 to 4 membered heteroalkyl), R$^{20E}$-substituted or unsubstituted cycloalkyl (e.g., C$_3$-C$_8$, C$_3$-C$_6$, or C$_5$-C$_6$ cycloalkyl), R$^{20E}$-substituted or unsubstituted heterocycloalkyl (e.g., 3 to 8 membered, 3 to 6 membered, or 5 to 6 membered heterocycloalkyl), R$^{20E}$-substituted or unsubstituted aryl (e.g., C$_6$-C$_{10}$, C$_{10}$ aryl, or phenyl), or R$^{20E}$-substituted or unsubstituted heteroaryl (e.g., 5 to 10 membered, 5 to 9 membered, or 5 to 6 membered heteroaryl).

R$^{20}$ may be hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$C$_1$, —SO$_3$H, —SO$_4$H, —SO$_2$NH$_2$, —NHNH$_2$, —ONH$_2$, —NHC(O)NHNH$_2$, R$^{20E}$-substituted or unsubstituted alkyl (e.g., C$_1$-C$_8$, C$_1$-C$_6$, or C$_1$-C$_4$ alkyl), or R$^{20E}$-substituted or unsubstituted heteroalkyl (e.g., 2 to 8 membered, 2 to 6 membered, or 2 to 4 membered heteroalkyl).

In embodiments, R$^{20}$ is R$^{20E}$-substituted or unsubstituted alkyl (e.g., C$_1$-C$_8$, C$_1$-C$_6$, or C$_1$-C$_4$ alkyl). In embodiments, R$^{20}$ is R$^{20E}$-substituted alkyl (e.g., C$_1$-C$_8$, C$_1$-C$_6$, or C$_1$-C$_4$ alkyl). In embodiments, R$^{20}$ is an unsubstituted alkyl (e.g., C$_1$-C$_8$, C$_1$-C$_6$, or C$_1$-C$_4$ alkyl).

In embodiments, R$^{20}$ is R$^{20E}$-substituted or unsubstituted heteroalkyl (e.g., 2 to 8 membered, 2 to 6 membered, or 2 to 4 membered heteroalkyl). In embodiments, R$^{20}$ is R$^{20E}$-substituted heteroalkyl (e.g., 2 to 8 membered, 2 to 6 membered, or 2 to 4 membered heteroalkyl). In embodiments, R$^{20}$ is an unsubstituted heteroalkyl (e.g., 2 to 8 membered, 2 to 6 membered, or 2 to 4 membered heteroalkyl).

In embodiments, R$^{20}$ is R$^{20E}$-substituted or unsubstituted cycloalkyl (e.g., C$_3$-C$_8$, C$_3$-C$_6$, or C$_5$-C$_6$ cycloalkyl). In embodiments, R$^{20}$ is R$^{20E}$-substituted cycloalkyl (e.g., C$_3$-C$_8$, C$_3$-C$_6$, or C$_5$-C$_6$ cycloalkyl). In embodiments, R$^{20}$ is an unsubstituted cycloalkyl (e.g., C$_3$-C$_8$, C$_3$-C$_6$, or C$_5$-C$_6$ cycloalkyl).

In embodiments, R$^{20}$ is R$^{20E}$-substituted or unsubstituted heterocycloalkyl (e.g., 3 to 8 membered, 3 to 6 membered, or 5 to 6 membered heterocycloalkyl). In embodiments, R$^{20}$ is R$^{20E}$-substituted heterocycloalkyl (e.g., 3 to 8 membered, 3 to 6 membered, or 5 to 6 membered heterocycloalkyl). In embodiments, R$^{20}$ is an unsubstituted heterocycloalkyl (e.g., 3 to 8 membered, 3 to 6 membered, or 5 to 6 membered heterocycloalkyl).

In embodiments, R$^{20}$ is R$^{20E}$-substituted or unsubstituted aryl (e.g., C$_6$-C$_{10}$, C$_{10}$, or phenyl). In embodiments, R$^{20}$ is R$^{20E}$-substituted aryl (e.g., C$_6$-C$_{10}$, C$_{10}$, or phenyl). In embodiments, R$^{20}$ is an unsubstituted aryl (e.g., C$_6$-C$_{10}$, C$_{10}$, or phenyl).

In embodiments, R$^{20}$ is R$^{20E}$-substituted or unsubstituted heteroaryl (e.g., 5 to 10 membered, 5 to 9 membered, or 5 to 6 membered heteroaryl). In embodiments, R$^{20}$ is R$^{20E}$-substituted heteroaryl (e.g., 5 to 10 membered, 5 to 9 membered, or 5 to 6 membered heteroaryl). In embodiments, R$^{20}$ is an unsubstituted heteroaryl (e.g., 5 to 10 membered, 5 to 9 membered, or 5 to 6 membered heteroaryl).

$R^{20E}$ is independently oxo, halogen, —CCl₃, —CBr₃, —CF₃, —CI₃, —CHF₂, —CHCl₂, —CHBr₂, —CHI₂, —CH₂F, —CH₂Cl, —CH₂Br, —CH₂I, —N₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHF₂, —OCHCl₂, —OCHBr₂, —OCHI₂, —OCH₂F, —OCH₂Cl, —OCH₂Br, —OCH₂I, $R^{20F}$-substituted or unsubstituted alkyl (e.g., $C_1$-$C_8$, $C_1$-$C_6$, or $C_1$-$C_4$ alkyl), $R^{20F}$-substituted or unsubstituted heteroalkyl (e.g., 2 to 8 membered, 2 to 6 membered, or 2 to 4 membered heteroalkyl), $R^{20F}$-substituted or unsubstituted cycloalkyl (e.g., $C_3$-$C_8$, $C_3$-$C_6$, or $C_5$-$C_6$ cycloalkyl), $R^{20F}$-substituted or unsubstituted heterocycloalkyl (e.g., 3 to 8 membered, 3 to 6 membered, or 5 to 6 membered heterocycloalkyl), $R^{20F}$-substituted or unsubstituted aryl (e.g., $C_6$-$C_{10}$, $C_{10}$ aryl, or phenyl), or $R^{20F}$-substituted or unsubstituted heteroaryl (e.g., 5 to 10 membered, 5 to 9 membered, or 5 to 6 membered heteroaryl).

$R^{20F}$ is independently oxo, halogen, —CCl₃, —CBr₃, —CF₃, —C₃, —CHF₂, —CHCl₂, —CHBr₂, —CHI₂, —CH₂F, —CH₂Cl, —CH₂Br, —CH₂I, —N₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHF₂, —OCHCl₂, —OCHBr₂, —OCHI₂, —OCH₂F, —OCH₂Cl, —OCH₂Br, —OCH₂I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

The compound of formula (III) may have the formula:

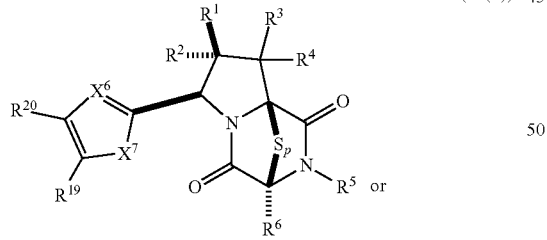

(III(S))

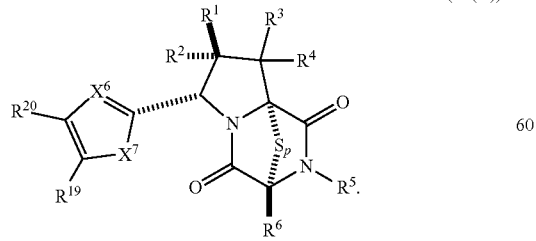

(III(R))

The compound of formula (III) may have the formula:

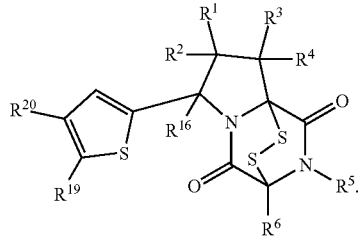

(III1)

The compound of formula (III1) may have the formula:

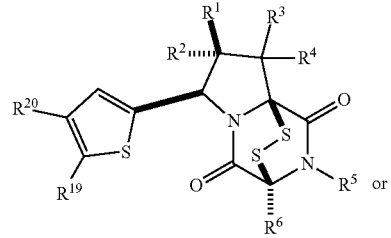

(III1(S))

or

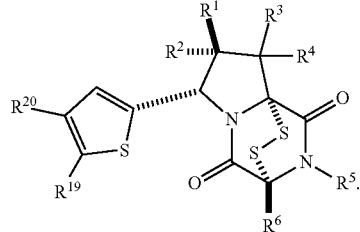

(III1(R))

The compound of formula (III) may have the formula:

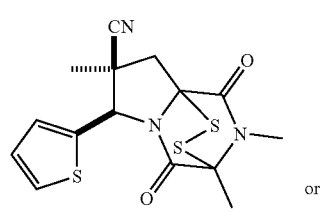

(ETP204)

or

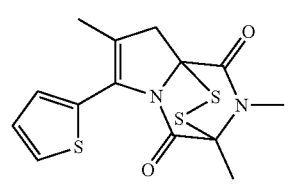

(ETP206)

The compound of formula (I) may have the formula:

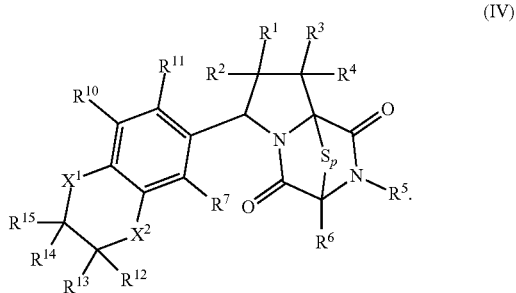

(IV)

The symbol p, $R^1$, $R^2$, $R^3$, $R^4$, $R^5$, $R^6$, $R^7$, $R^{10}$, $R^{11}$, and $R^{16}$ are as described herein, including embodiments thereof. $X^1$ is —$CR^{21A}R^{21B}$—, —O—, —$NR^{21C}$—, or —S—. $X^2$ is —$CR^{22A}R^{22B}$—, —O—, —$NR^{22C}$—, or —S—.

$R^{21A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{21A}$ is hydrogen.

$R^{21B}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{21B}$ is hydrogen.

$R^{21C}$ is hydrogen, —$CX_3$, —CN, —COOH, —$CONH_2$, —$CHX_2$, —$CH_2X$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). X is independently —F, —Cl, —Br, or —I. In embodiments, $R^{21C}$ is hydrogen.

$R^{22A}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{22A}$ is hydrogen.

$R^{22B}$ is hydrogen, halogen, —$N_3$, —$CF_3$, —$CCl_3$, —$CBr_3$, —$CI_3$, —CN, —CHO, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{22B}$ is hydrogen.

$R^{22C}$ is hydrogen, —$CX_3$, —CN, —COOH, —$CONH_2$, —$CHX_2$, —$CH_2X$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). X is independently —F, —Cl, —Br, or —I. In embodiments, $R^{22C}$ is hydrogen.

$R^{12}$ is hydrogen, halogen, —$N_3$, —$CF_3$, —$CCl_3$, —$CBr_3$, —$CI_3$, —CN, —CHO, —$OR^{12A}$, —$NR^{12B}R^{12C}$, —$COOR^{12A}$, —$CONR^{12B}R^{12C}$, —$NO_2$, —$SR^{12D}$, —$SO_{n12}R^{12B}$, —$SO_{v12}NR^{12B}R^{12C}$, —$NHNR^{12B}R^{12C}$, —ONR$^{12B}$R$^{12C}$, —NHC(O)NHNR$^{12B}$R$^{12C}$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, —NO$_2$, —SR$^{13D}$, —SO$_{n13}$R$^{13B}$, —SO$_{v13}$NR$^{13B}$R$^{13C}$, —NHNR$^{13B}$R$^{13C}$, —ONR$^{13B}$R$^{13C}$, —NHC(O)N—R$^{13B}$R$^{13C}$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

R$^{14}$ is hydrogen, halogen, —N$_3$, —CF$_3$, —CCl$_3$, —CBr$_3$, —CI$_3$, —CN, —CHO, —OR$^{14A}$, —NR$^{14B}$R$^{14C}$, —COOR$^{14A}$, CONR$^{14B}$R$^{14C}$, —NO$_2$, —SR$^{14D}$, SO$_{n14}$R$^{14B}$, SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

R$^{15}$ is hydrogen, halogen, —N$_3$, —CF$_3$, —CCl$_3$, —CBr$_3$, —CI$_3$, —CN, —CHO, —OR$^{15A}$, —NR$^{15B}$R$^{15C}$, —COOR$^{15A}$, CONR$^{15B}$R$^{15C}$, —NO$_2$, —SR$^{15D}$, —SO$_{n15}$R$^{15B}$, —SO$_{v15}$NR$^{15B}$R$^{15C}$, —NHNR$^{15B}$R$^{15C}$, ONR$^{15B}$R$^{15C}$, —NHC(O)NHNR$^{15B}$R$^{15C}$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, and R$^{15D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^5$ and R$^6$ may independently be unsubstituted C$_1$-C$_3$ alkyl or unsubstituted 3 to 5 membered cycloalkyl. R$^7$, R$^8$, R$^9$, and R$^{10}$ may independently be hydrogen, halogen, unsubstituted methyl, —OCH$_3$ or —O(CH$_2$)$_2$=CH$_2$. R$^1$ may be —CN or unsubstituted 2 to 5 membered heteroalkyl. R$^1$ may be —CN. R$^1$ may be —COOCH$_3$. R$^1$ may be unsubstituted methyl. R$^2$ may be C$_1$-C$_3$ unsubstituted alkyl. When R$^1$ is —CN, R$^2$ may be unsubstituted methyl. R$^3$ and R$^4$ may be hydrogen. R$^{10}$ and R$^{11}$ may be hydrogen. R$^{12}$, R$^{13}$, R$^{14}$, and R$^{15}$ may be hydrogen.

R$^{21A}$, R$^{21B}$, R$^{22A}$, and R$^{22B}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, R$^{34}$-substituted or unsubstituted alkyl (e.g., C$_1$-C$_8$ alkyl, C$_1$-C$_6$ alkyl, or C$_1$-C$_4$ alkyl), R$^{34}$-substituted or unsubstituted heteroalkyl (e.g., 2 to 8 membered heteroalkyl, 2 to 6 membered heteroalkyl, or 2 to 4 membered heteroalkyl), R$^{34}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{34}$-substituted or unsubstituted heterocycloalkyl (e.g., 3 to 8 membered heterocycloalkyl, 3 to 6 membered heterocycloalkyl, or 5 to 6 membered heterocycloalkyl), R$^{34}$-substituted or unsubstituted aryl (e.g., C$_6$-C$_{10}$ aryl, C$_{10}$ aryl, or phenyl), or R$^{34}$-substituted or unsubstituted heteroaryl (e.g., 5 to 10 membered heteroaryl, 5 to 9 membered heteroaryl, or 5 to 6 membered heteroaryl).

R$^{21C}$ and R$^{22C}$ are independently hydrogen, —CX$_3$, —CN, —COOH, —CONH$_2$, —CHX$_2$, —CH$_2$X, R$^{34}$-substituted or unsubstituted alkyl (e.g., C$_1$-C$_5$ alkyl, C$_1$-C$_6$ alkyl, or C$_1$-C$_4$ alkyl), R$^{34}$-substituted or unsubstituted heteroalkyl (e.g., 2 to 8 membered heteroalkyl, 2 to 6 membered heteroalkyl, or 2 to 4 membered heteroalkyl), R$^{34}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{34}$-substituted or unsubstituted heterocycloalkyl (e.g., 3 to 8 membered heterocycloalkyl, 3 to 6 membered heterocycloalkyl, or 5 to 6 membered heterocycloalkyl), R$^{34}$-substituted or unsubstituted aryl (e.g., C$_6$-C$_{10}$ aryl, C$_{10}$ aryl, or phenyl), or R$^{34}$-substituted or unsubstituted heteroaryl (e.g., 5 to 10 membered heteroaryl, 5 to 9 membered heteroaryl, or 5 to 6 membered heteroaryl). X is independently —F, —Cl, —Br, or —I.

R$^{21A}$, R$^{21B}$, R$^{21C}$, R$^{22A}$, R$^{22B}$, and R$^{22C}$ may be independently hydrogen, substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., C$_3$-C$_8$, C$_3$-C$_6$, or C$_5$-C$_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., C$_6$-C$_{10}$, C$_{10}$ aryl, or phenyl), or substituted or unsubstituted heteroaryl (e.g., 5 to 10 membered, 5 to 9 membered, or 5 to 6 membered heteroaryl). R$^{21A}$, R$^{21B}$, R$^{22A}$, R$^{22B}$, and R$^{22C}$ may be independently substituted or unsubstituted alkyl (e.g., C$_1$-C$_8$, C$_1$-C$_6$, or C$_1$-C$_4$ alkyl), substituted or unsubstituted heteroalkyl (e.g., 2 to 8 membered, 2 to 6 membered, or 2 to 4 membered heteroalkyl). R$^{21A}$, R$^{21B}$, R$^{22A}$, and R$^{22B}$ may be independently hydrogen, halogen, substituted or unsubstituted alkyl (e.g., $C_1$-$C_8$, $C_1$-$C_6$, or $C_1$-$C_4$ alkyl), or substituted or unsubstituted heteroalkyl (e.g., 2 to 8 membered, 2 to 6 membered, or 2 to 4 membered heteroalkyl). $R^{21A}$, $R^{21B}$, $R^{21C}$, $R^{22A}$, $R^{22B}$, and $R^{22C}$ may be independently hydrogen, or substituted or unsubstituted alkyl (e.g., $C_1$-$C_8$, $C_1$-$C_6$, or $C_1$-$C_4$ alkyl). $R^{21A}$, $R^{21B}$, $R^{21C}$, $R^{22A}$, $R^{22B}$, and $R^{22C}$ may be independently hydrogen, or unsubstituted alkyl (e.g., $C_1$-$C_8$, $C_1$-$C_6$, or $C_1$-$C_4$ alkyl). $R^{21A}$, $R^{21B}$, $R^{21C}$, $R^{22A}$, $R^{22B}$, and $R^{22C}$ may be independently hydrogen, or substituted or unsubstituted heteroalkyl (e.g., 2 to 8 membered, 2 to 6 membered, or 2 to 4 membered heteroalkyl). $R^{21A}$, $R^{21B}$, $R^{21C}$, $R^{22A}$, $R^{22B}$, and $R^{22C}$ may be independently hydrogen, or unsubstituted heteroalkyl (e.g., 2 to 8 membered, 2 to 6 membered, or 2 to 4 membered heteroalkyl. $R^{21A}$, $R^{21B}$, $R^{21C}$, $R^{22A}$, $R^{22B}$, and $R^{22C}$ may be independently hydrogen, —$CF_3$, —$CCl_3$, —$CBr_3$, or —$CI_3$.

$R^{21A}$, $R^{21B}$, $R^{21C}$, $R^{22A}$, $R^{22B}$, and $R^{22C}$ may be independently hydrogen, $R^{34}$-substituted or unsubstituted alkyl (e.g., $C_1$-$C_8$, $C_1$-$C_6$, or $C_1$-$C_4$ alkyl), $R^{34}$-substituted or unsubstituted heteroalkyl (e.g., 2 to 8 membered, 2 to 6 membered, or 2 to 4 membered heteroalkyl), $R^{34}$-substituted or unsubstituted cycloalkyl (e.g., $C_3$-$C_8$, $C_3$-$C_6$, or $C_5$-$C_6$ cycloalkyl), $R^{34}$-substituted or unsubstituted heterocycloalkyl (e.g., 3 to 8 membered, 3 to 6 membered, or 5 to 6 membered heterocycloalkyl), $R^{34}$-substituted or unsubstituted aryl (e.g., $C_6$-$C_{10}$, $C_{10}$ aryl, or phenyl), or $R^{34}$-substituted or unsubstituted heteroaryl (e.g., 5 to 10 membered, 5 to 9 membered, or 5 to 6 membered heteroaryl). $R^{21A}$, $R^{21B}$, $R^{21C}$, $R^{22A}$, $R^{22B}$ and $R^{22C}$ may be independently $R^{34}$-substituted or unsubstituted alkyl (e.g., $C_1$-$C_8$, $C_1$-$C_6$, or $C_1$-$C_4$ alkyl), $R^{34}$-substituted or unsubstituted heteroalkyl (e.g., 2 to 8 membered, 2 to 6 membered, or 2 to 4 membered heteroalkyl), $R^{34}$-substituted or unsubstituted cycloalkyl (e.g., $C_3$-$C_8$, $C_3$-$C_6$, or $C_5$-$C_6$ cycloalkyl), $R^{34}$-substituted or unsubstituted heterocycloalkyl (e.g., 3 to 8 membered, 3 to 6 membered, or 5 to 6 membered heterocycloalkyl), $R^{34}$-substituted or unsubstituted aryl (e.g., $C_6$-$C_{10}$, $C_{10}$ aryl, or phenyl), or $R^{34}$-substituted or unsubstituted heteroaryl (e.g., 5 to 10 membered, 5 to 9 membered, or 5 to 6 membered heteroaryl).

In embodiments, $R^{21A}$, $R^{21B}$, $R^{21C}$, $R^{22A}$, $R^{22B}$, and $R^{22C}$ are independently $R^{34}$-substituted or unsubstituted alkyl (e.g., $C_1$-$C_8$, $C_1$-$C_6$, or $C_1$-$C_4$ alkyl). In embodiments, $R^{21A}$, $R^{21B}$, $R^{21C}$, $R^{22A}$, $R^{22B}$, and $R^{22C}$ are independently $R^{34}$-substituted alkyl (e.g., $C_1$-$C_8$, $C_1$-$C_6$, or $C_1$-$C_4$ alkyl). In embodiments, $R^{21A}$, $R^{21B}$, $R^{21C}$, $R^{22A}$, $R^{22B}$, and $R^{22C}$ are independently an unsubstituted alkyl (e.g., $C_1$-$C_8$, $C_1$-$C_6$, or $C_1$-$C_4$ alkyl).

In embodiments, $R^{21A}$, $R^{21B}$, $R^{21C}$, $R^{22A}$, $R^{22B}$, and $R^{22C}$ are independently $R^{34}$-substituted or unsubstituted heteroalkyl (e.g., 2 to 8 membered, 2 to 6 membered, or 2 to 4 membered heteroalkyl). In embodiments, $R^{21A}$, $R^{21B}$, $R^{21C}$, $R^{22A}$, $R^{22B}$, and $R^{22C}$ are independently $R^{34}$-substituted heteroalkyl (e.g., 2 to 8 membered, 2 to 6 membered, or 2 to 4 membered heteroalkyl). In embodiments, $R^{21A}$, $R^{21B}$, $R^{21C}$, $R^{22A}$, $R^{22B}$, and $R^{22C}$ are independently an unsubstituted heteroalkyl (e.g., 2 to 8 membered, 2 to 6 membered, or 2 to 4 membered heteroalkyl).

In embodiments, $R^{21A}$, $R^{21B}$, $R^{21C}$, $R^{22A}$, $R^{22B}$, and $R^{22C}$ are independently $R^{34}$-substituted or unsubstituted cycloalkyl (e.g., $C_3$-$C_8$, $C_3$-$C_6$, or $C_5$-$C_6$ cycloalkyl). In embodiments, $R^{21A}$, $R^{21B}$, $R^{21C}$, $R^{22A}$, $R^{22B}$, and $R^{22C}$ are independently $R^{34}$-substituted cycloalkyl (e.g., $C_3$-$C_8$, $C_3$-$C_6$, or $C_5$-$C_6$ cycloalkyl). In embodiments, $R^{21A}$, $R^{21B}$, $R^{21C}$, $R^{22A}$, $R^{22B}$, and $R^{22C}$ are independently an unsubstituted cycloalkyl (e.g., $C_3$-$C_8$, $C_3$-$C_6$, or $C_5$-$C_6$ cycloalkyl).

In embodiments, $R^{21A}$, $R^{21B}$, $R^{21C}$, $R^{22A}$, $R^{22B}$, and $R^{22C}$ are independently $R^{34}$-substituted or unsubstituted heterocycloalkyl (e.g., 3 to 8 membered, 3 to 6 membered, or 5 to 6 membered heterocycloalkyl). In embodiments, $R^{21A}$, $R^{21B}$, $R^{21C}$, $R^{22A}$, $R^{22B}$, and $R^{22C}$ are independently $R^{34}$-substituted heterocycloalkyl (e.g., 3 to 8 membered, 3 to 6 membered, or 5 to 6 membered heterocycloalkyl). In embodiments, $R^{21A}$, $R^{21B}$, $R^{21C}$, $R^{22A}$, $R^{22B}$, and $R^{22C}$ are independently an unsubstituted heterocycloalkyl (e.g., 3 to 8 membered, 3 to 6 membered, or 5 to 6 membered heterocycloalkyl).

In embodiments, $R^{21A}$, $R^{21B}$, $R^{21C}$, $R^{22A}$, $R^{22B}$, and $R^{22C}$ are independently $R^{34}$-substituted or unsubstituted aryl (e.g., $C_6$-$C_{10}$, $C_{10}$, or phenyl). In embodiments, $R^{21A}$, $R^{21B}$, $R^{21C}$, $R^{22A}$, $R^{22B}$, and $R^{22C}$ are independently $R^{34}$-substituted aryl (e.g., $C_6$-$C_{10}$, $C_{10}$, or phenyl). In embodiments, $R^{21A}$, $R^{21B}$, $R^{21C}$, $R^{22A}$, $R^{22B}$, and $R^{22C}$ are independently an unsubstituted aryl (e.g., $C_6$-$C_{10}$, $C_{10}$, or phenyl).

In embodiments, $R^{21A}$, $R^{21B}$, $R^{21C}$, $R^{22A}$, $R^{22B}$, and $R^{22C}$ are independently $R^{34}$-substituted or unsubstituted heteroaryl (e.g., 5 to 10 membered, 5 to 9 membered, or 5 to 6 membered heteroaryl). In embodiments, $R^{21A}$, $R^{21B}$, $R^{21C}$, $R^{22A}$, $R^{22B}$, and $R^{22C}$ are independently $R^{34}$-substituted heteroaryl (e.g., 5 to 10 membered, 5 to 9 membered, or 5 to 6 membered heteroaryl). In embodiments, $R^{21A}$, $R^{21B}$, $R^{21C}$, $R^{22A}$, $R^{22B}$, and $R^{22C}$ are independently an unsubstituted heteroaryl (e.g., 5 to 10 membered, 5 to 9 membered, or 5 to 6 membered heteroaryl).

$R^{21A}$, $R^{21B}$, $R^{21C}$, $R^{22A}$, $R^{22B}$, and/or $R^{22C}$ may be fused to form $R^{34}$-substituted or unsubstituted 5 or 6 membered heterocycloalkyl, a substituted or unsubstituted phenyl, or a substituted or unsubstituted 5 or 6 membered heteroaryl. $R^{21C}$ and $R^{22C}$ are independently hydrogen, halogen, —$CX_3$, —CN, —COOH, —$CONH_2$, —$CHX_2$, —$CH_2X$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_1$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

n12, n13, n14 and n15 are independently 1 or 4. v12, v13, v14, and v15 are independently 1 or 2.

$R^{12}$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{12}$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^1$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^1$ may be halogen, or substituted or unsubstituted alkyl (e.g., $C_1$-$C_8$, $C_1$-$C_6$, or $C_1$-$C_4$ alkyl). $R^{12}$ may be halogen, or unsubstituted alkyl (e.g., $C_1$-$C_8$, $C_1$-$C_6$, or $C_1$-$C_4$ alkyl). $R^{12}$ may be halogen, or substituted or unsubstituted heteroalkyl (e.g., 2 to 8 membered, 2 to 6 membered, or 2 to 4 membered heteroalkyl). $R^{12}$ may be halogen, unsubstituted heteroalkyl (e.g., 2 to 8 membered, 2 to 6 membered, or 2 to 4 membered heteroalkyl. $R^{12}$ may be halogen, —$CF_3$, —$CCl_3$, —$CBr_3$, or —$CI_3$. $R^{12}$ may be hydrogen.

$R^{12}$ may be hydrogen, $R^{12E}$-substituted or unsubstituted alkyl (e.g., $C_1$-$C_8$, $C_1$-$C_6$, or $C_1$-$C_4$ alkyl), $R^{12E}$-substituted or unsubstituted heteroalkyl (e.g., 2 to 8 membered, 2 to 6 membered, or 2 to 4 membered heteroalkyl), $R^{12E}$-substituted or unsubstituted cycloalkyl (e.g., $C_3$-$C_8$, $C_3$-$C_6$, or $C_5$-$C_6$ cycloalkyl), $R^{12E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{12E}$-substituted or unsubstituted heteroaryl (e.g., 5 to 10 membered, 5 to 9 membered, or 5 to 6 membered heteroaryl). $R^1$ may be $R^{12E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{12E}$-substituted or unsubstituted cycloalkyl (e.g., $C_3$-$C_8$, $C_3$-$C_6$, or $C_5$-$C_6$ cycloalkyl), $R^{12E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{12E}$-substituted or unsubstituted heteroaryl (e.g., 5 to 10 membered, 5 to 9 membered, or 5 to 6 membered heteroaryl).

In embodiments, $R^{12}$ is $R^{12E}$-substituted or unsubstituted alkyl (e.g., $C_1$-$C_8$, $C_1$-$C_6$, or $C_1$-$C_4$ alkyl). In embodiments, $R^{12}$ is $R^{12E}$-substituted alkyl (e.g., $C_1$-$C_8$, $C_1$-$C_6$, or $C_1$-$C_4$ alkyl). In embodiments, $R^{12}$ is an unsubstituted alkyl (e.g., $C_1$-$C_8$, $C_1$-$C_6$, or $C_1$-$C_4$ alkyl).

In embodiments, $R^{12}$ is $R^{12E}$-substituted or unsubstituted heteroalkyl (e.g., 2 to 8 membered, 2 to 6 membered, or 2 to 4 membered heteroalkyl). In embodiments, $R^{12}$ is $R^{12E}$-substituted heteroalkyl (e.g., 2 to 8 membered, 2 to 6 membered, or 2 to 4 membered heteroalkyl). In embodiments, $R^{12}$ is an unsubstituted heteroalkyl (e.g., 2 to 8 membered, 2 to 6 membered, or 2 to 4 membered heteroalkyl).

In embodiments, $R^{12}$ is $R^{12E}$-substituted or unsubstituted cycloalkyl (e.g., $C_3$-$C_8$, $C_3$-$C_6$, or $C_5$-$C_6$ cycloalkyl). In embodiments, $R^{12}$ is $R^{12E}$-substituted cycloalkyl (e.g., $C_3$-$C_8$, $C_3$-$C_6$, or $C_5$-$C_6$ cycloalkyl). In embodiments, $R^{12}$ is an unsubstituted cycloalkyl (e.g., $C_3$-$C_8$, $C_3$-$C_6$, or $C_5$-$C_6$ cycloalkyl).

In embodiments, $R^{12}$ is $R^{12E}$-substituted or unsubstituted heterocycloalkyl (e.g., 3 to 8 membered, 3 to 6 membered, or 5 to 6 membered heterocycloalkyl). In embodiments, $R^1$ is $R^{12E}$-substituted heterocycloalkyl (e.g., 3 to 8 membered, 3 to 6 membered, or 5 to 6 membered heterocycloalkyl). In embodiments, $R^{12}$ is an unsubstituted heterocycloalkyl (e.g., 3 to 8 membered, 3 to 6 membered, or 5 to 6 membered heterocycloalkyl).

In embodiments, $R^{12}$ is $R^{12E}$-substituted or unsubstituted aryl (e.g., $C_6$-$C_{10}$, $C_{10}$, or phenyl). In embodiments, $R^1$ is $R^{12E}$-substituted aryl (e.g., $C_6$-$C_{10}$, $C_{10}$, or phenyl). In embodiments, $R^{12}$ is an unsubstituted aryl (e.g., $C_6$-$C_{10}$, $C_{10}$, or phenyl).

In embodiments, $R^{12}$ is $R^{12E}$-substituted or unsubstituted heteroaryl (e.g., 5 to 10 membered, 5 to 9 membered, or 5 to 6 membered heteroaryl). In embodiments, $R^{12}$ is $R^{12E}$-substituted heteroaryl (e.g., 5 to 10 membered, 5 to 9 membered, or 5 to 6 membered heteroaryl). In embodiments, $R^{12}$ is an unsubstituted heteroaryl (e.g., 5 to 10 membered, 5 to 9 membered, or 5 to 6 membered heteroaryl).

$R^{12E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{12F}$-substituted or unsubstituted alkyl (e.g., $C_1$-$C_8$, $C_1$-$C_6$, or $C_1$-$C_4$ alkyl), $R^{12F}$-substituted or unsubstituted heteroalkyl (e.g., 2 to 8 membered, 2 to 6 membered, or 2 to 4 membered heteroalkyl), $R^{12F}$-substituted or unsubstituted cycloalkyl (e.g., $C_3$-$C_8$, $C_3$-$C_6$, or $C_5$-$C_6$ cycloalkyl), $R^{12F}$-substituted or unsubstituted heterocycloalkyl (e.g., 3 to 8 membered, 3 to 6 membered, or 5 to 6 membered heterocycloalkyl), $R^{2F}$-substituted or unsubstituted aryl (e.g., $C_6$-$C_{10}$, $C_{10}$ aryl, or phenyl), or $R^{12F}$-substituted or unsubstituted heteroaryl (e.g., 5 to 10 membered, 5 to 9 membered, or 5 to 6 membered heteroaryl).

$R^{12F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_1$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{13}$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{13}$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^1$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{13}$ may be halogen, or substituted or unsubstituted alkyl (e.g., $C_1$-$C_8$, $C_1$-$C_6$, or $C_1$-$C_4$ alkyl). $R^{13}$ may be halogen, or unsubstituted alkyl (e.g., $C_1$-$C_8$, $C_1$-$C_6$, or $C_1$-$C_4$ alkyl). $R^{13}$ may be halogen, or substituted or unsubstituted heteroalkyl (e.g., 2 to 8 membered, 2 to 6 membered, or 2 to 4 membered heteroalkyl). $R^{13}$ may be halogen, unsubstituted heteroalkyl (e.g., 2 to 8 membered, 2 to 6 membered, or 2 to 4 membered heteroalkyl. $R^{13}$ may be halogen, —$CF_3$, —$CCl_3$, —$CBr_3$, or —$C_3$. $R^{13}$ may be hydrogen.

$R^{13}$ may be hydrogen, $R^{13E}$-substituted or unsubstituted alkyl (e.g., $C_1$-$C_8$, $C_1$-$C_6$, or $C_1$-$C_4$ alkyl), $R^{13E}$-substituted or unsubstituted heteroalkyl (e.g., 2 to 8 membered, 2 to 6 membered, or 2 to 4 membered heteroalkyl), $R^{13E}$-substituted or unsubstituted cycloalkyl (e.g., $C_3$-$C_8$, $C_3$-$C_6$, or $C_5$-$C_6$ cycloalkyl), $R^{13E}$-substituted or unsubstituted heterocycloalkyl (e.g., 3 to 8 membered, 3 to 6 membered, or 5 to 6 membered heterocycloalkyl), $R^{13E}$-substituted or unsubstituted aryl (e.g., $C_6$-$C_{10}$, $C_{10}$ aryl, or phenyl), or $R^{13E}$-substituted or unsubstituted heteroaryl (e.g., 5 to 10 membered, 5 to 9 membered, or 5 to 6 membered heteroaryl). $R^3$ may be $R^{13E}$-substituted or unsubstituted alkyl (e.g., $C_1$-$C_8$, $C_1$-$C_6$, or $C_1$-$C_4$ alkyl), $R^{13E}$-substituted or unsubstituted heteroalkyl (e.g., 2 to 8 membered, 2 to 6 membered, or 2 to 4 membered heteroalkyl), $R^{13E}$-substituted or unsubstituted cycloalkyl (e.g., $C_3$-$C_8$, $C_3$-$C_6$, or $C_5$-$C_6$ cycloalkyl), $R^{13E}$-substituted or unsubstituted heterocycloalkyl (e.g., 3 to 8 membered, 3 to 6 membered, or 5 to 6 membered heterocycloalkyl), $R^{13E}$-substituted or unsubstituted aryl (e.g., $C_6$-$C_{10}$, $C_{10}$ aryl, or phenyl), or $R^{13E}$-substituted or unsubstituted heteroaryl (e.g., 5 to 10 membered, 5 to 9 membered, or 5 to 6 membered heteroaryl).

In embodiments, $R^{13}$ is $R^{13E}$-substituted or unsubstituted alkyl (e.g., $C_1$-$C_8$, $C_1$-$C_6$, or $C_1$-$C_4$ alkyl). In embodiments, $R^{13}$ is $R^{13E}$-substituted alkyl (e.g., $C_1$-$C_8$, $C_1$-$C_6$, or $C_1$-$C_4$ alkyl). In embodiments, $R^{13}$ is an unsubstituted alkyl (e.g., $C_1$-$C_8$, $C_1$-$C_6$, or $C_1$-$C_4$ alkyl).

In embodiments, $R^{13}$ is $R^{13E}$-substituted or unsubstituted heteroalkyl (e.g., 2 to 8 membered, 2 to 6 membered, or 2 to 4 membered heteroalkyl). In embodiments, $R^{13}$ is $R^{13E}$-substituted heteroalkyl (e.g., 2 to 8 membered, 2 to 6 membered, or 2 to 4 membered heteroalkyl). In embodiments, $R^{13}$ is an unsubstituted heteroalkyl (e.g., 2 to 8 membered, 2 to 6 membered, or 2 to 4 membered heteroalkyl).

In embodiments, $R^{13}$ is $R^{13E}$-substituted or unsubstituted cycloalkyl (e.g., $C_3$-$C_8$, $C_3$-$C_6$, or $C_5$-$C_6$ cycloalkyl). In embodiments, $R^{13}$ is $R^{13E}$-substituted cycloalkyl (e.g., $C_3$-$C_8$, $C_3$-$C_6$, or $C_5$-$C_6$ cycloalkyl). In embodiments, $R^{13}$ is an unsubstituted cycloalkyl (e.g., $C_3$-$C_8$, $C_3$-$C_6$, or $C_5$-$C_6$ cycloalkyl).

In embodiments, $R^{13}$ is $R^{13E}$-substituted or unsubstituted heterocycloalkyl (e.g., 3 to 8 membered, 3 to 6 membered, or 5 to 6 membered heterocycloalkyl). In embodiments, $R^{13}$ is $R^{13E}$-substituted heterocycloalkyl (e.g., 3 to 8 membered, 3 to 6 membered, or 5 to 6 membered heterocycloalkyl). In embodiments, $R^{13}$ is an unsubstituted heterocycloalkyl (e.g., 3 to 8 membered, 3 to 6 membered, or 5 to 6 membered heterocycloalkyl).

In embodiments, $R^{13}$ is $R^{13F}$-substituted or unsubstituted aryl (e.g., $C_6$-$C_{10}$, $C_{10}$, or phenyl). In embodiments, $R^{13}$ is $R^{13E}$-substituted aryl (e.g., $C_6$-$C_{10}$, $C_{10}$, or phenyl). In embodiments, $R^{13}$ is an unsubstituted aryl (e.g., $C_6$-$C_{10}$, $C_{10}$, or phenyl).

In embodiments, $R^{13}$ is $R^{13E}$-substituted or unsubstituted heteroaryl (e.g., 5 to 10 membered, 5 to 9 membered, or 5 to 6 membered heteroaryl). In embodiments, $R^{13}$ is $R^{13E}$-substituted heteroaryl (e.g., 5 to 10 membered, 5 to 9 membered, or 5 to 6 membered heteroaryl). In embodiments, $R^{13}$ is an unsubstituted heteroaryl (e.g., 5 to 10 membered, 5 to 9 membered, or 5 to 6 membered heteroaryl).

$R^{13E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{13F}$-substituted or unsubstituted alkyl (e.g., $C_1$-$C_8$, $C_1$-$C_6$, or $C_1$-$C_4$ alkyl), $R^{13F}$-substituted or unsubstituted heteroalkyl (e.g., 2 to 8 membered, 2 to 6 membered, or 2 to 4 membered heteroalkyl), $R^{13F}$-substituted or unsubstituted cycloalkyl (e.g., $C_3$-$C_8$, $C_3$-$C_6$, or $C_5$-$C_6$ cycloalkyl), $R^{13F}$-substituted or unsubstituted heterocycloalkyl (e.g., 3 to 8 membered, 3 to 6 membered, or 5 to 6 membered heterocycloalkyl), $R^{13F}$-substituted or unsubstituted aryl (e.g., $C_6$-$C_{10}$, $C_{10}$ aryl, or phenyl), or $R^{13F}$-substituted or unsubstituted heteroaryl (e.g., 5 to 10 membered, 5 to 9 membered, or 5 to 6 membered heteroaryl).

$R^{13F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{14}$ may be hydrogen, halogen, —$N_3$, —$CF_3$, —$CCl_3$, —$CBr_3$, —$CI_3$, —$N_3$, —$CN$, —$CHO$, —$OH$, —$NH_2$, —$COOH$, —$CONH_2$, —$NO_2$, —$SH$, —$SO_3H$, —$SO_4H$, —$S_2NH_2$, —$NHNH_2$, —$ONH_2$, —$NHC(O)NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{14}$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{14}$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{14}$ may be halogen, or substituted or unsubstituted alkyl (e.g., $C_1$-$C_8$, $C_1$-$C_6$, or $C_1$-$C_4$ alkyl). $R^{14}$ may be halogen, or unsubstituted alkyl (e.g., $C_1$-$C_8$, $C_1$-$C_6$, or $C_1$-$C_4$ alkyl). $R^{14}$ may be halogen, or substituted or unsubstituted heteroalkyl (e.g., 2 to 8 membered, 2 to 6 membered, or 2 to 4 membered heteroalkyl). $R^{14}$ may be halogen, unsubstituted heteroalkyl (e.g., 2 to 8 membered, 2 to 6 membered, or 2 to 4 membered heteroalkyl. $R^{14}$ may be halogen, —$CF_3$, —$CCl_3$, —$CBr_3$, or —$CI_3$. $R^{14}$ may be hydrogen.

$R^{14}$ may be hydrogen, $R^{14E}$-substituted or unsubstituted alkyl (e.g., $C_1$-$C_8$, $C_1$-$C_6$, or $C_1$-$C_4$ alkyl), $R^{14E}$-substituted or unsubstituted heteroalkyl (e.g., 2 to 8 membered, 2 to 6 membered, or 2 to 4 membered heteroalkyl), $R^{14E}$-substituted or unsubstituted cycloalkyl (e.g., $C_3$-$C_8$, $C_3$-$C_6$, or $C_5$-$C_6$ cycloalkyl), $R^{14E}$-substituted or unsubstituted heterocycloalkyl (e.g., 3 to 8 membered, 3 to 6 membered, or 5 to 6 membered heterocycloalkyl), $R^{14E}$-substituted or unsubstituted aryl (e.g., $C_6$-$C_{10}$, $C_{10}$ aryl, or phenyl), or $R^{14E}$-substituted or unsubstituted heteroaryl (e.g., 5 to 10 membered, 5 to 9 membered, or 5 to 6 membered heteroaryl). $R^{14}$ may be $R^{14E}$-substituted or unsubstituted alkyl (e.g., $C_1$-$C_8$, $C_1$-$C_6$, or $C_1$-$C_4$ alkyl), $R^{14E}$-substituted or unsubstituted heteroalkyl (e.g., 2 to 8 membered, 2 to 6 membered, or 2 to 4 membered heteroalkyl), $R^{14E}$-substituted or unsubstituted cycloalkyl (e.g., $C_3$-$C_8$, $C_3$-$C_6$, or $C_5$-$C_6$ cycloalkyl), $R^{14E}$-substituted or unsubstituted heterocycloalkyl (e.g., 3 to 8 membered, 3 to 6 membered, or 5 to 6 membered heterocycloalkyl), $R^{14E}$-substituted or unsubstituted aryl (e.g., $C_6$-$C_{10}$, $C_{10}$ aryl, or phenyl), or $R^{14E}$-substituted or unsubstituted heteroaryl (e.g., 5 to 10 membered, 5 to 9 membered, or 5 to 6 membered heteroaryl).

In embodiments, $R^{14}$ is $R^{14E}$-substituted or unsubstituted alkyl (e.g., $C_1$-$C_8$, $C_1$-$C_6$, or $C_1$-$C_4$ alkyl). In embodiments, $R^{14}$ is $R^{14E}$-substituted alkyl (e.g., $C_1$-$C_8$, $C_1$-$C_6$, or $C_1$-$C_4$ alkyl). In embodiments, $R^{14}$ is an unsubstituted alkyl (e.g., $C_1$-$C_8$, $C_1$-$C_6$, or $C_1$-$C_4$ alkyl).

In embodiments, $R^{14}$ is $R^{14E}$-substituted or unsubstituted heteroalkyl (e.g., 2 to 8 membered, 2 to 6 membered, or 2 to 4 membered heteroalkyl). In embodiments, $R^{14}$ is $R^{14E}$-substituted heteroalkyl (e.g., 2 to 8 membered, 2 to 6 membered, or 2 to 4 membered heteroalkyl). In embodiments, $R^{14}$ is an unsubstituted heteroalkyl (e.g., 2 to 8 membered, 2 to 6 membered, or 2 to 4 membered heteroalkyl).

In embodiments, $R^{14}$ is $R^{14E}$-substituted or unsubstituted cycloalkyl (e.g., $C_3$-$C_8$, $C_3$-$C_6$, or $C_5$-$C_6$ cycloalkyl). In embodiments, $R^{14}$ is $R^{14E}$-substituted cycloalkyl (e.g., $C_3$-$C_8$, $C_3$-$C_6$, or $C_5$-$C_6$ cycloalkyl). In embodiments, $R^{14}$ is an unsubstituted cycloalkyl (e.g., $C_3$-$C_8$, $C_3$-$C_6$, or $C_5$-$C_6$ cycloalkyl).

In embodiments, $R^{14}$ is $R^{14E}$-substituted or unsubstituted heterocycloalkyl (e.g., 3 to 8 membered, 3 to 6 membered, or 5 to 6 membered heterocycloalkyl). In embodiments, $R^{14}$ is $R^{14E}$-substituted heterocycloalkyl (e.g., 3 to 8 membered, 3 to 6 membered, or 5 to 6 membered heterocycloalkyl). In embodiments, $R^{14}$ is an unsubstituted heterocycloalkyl (e.g., 3 to 8 membered, 3 to 6 membered, or 5 to 6 membered heterocycloalkyl).

In embodiments, $R^{14}$ is $R^{14E}$-substituted or unsubstituted aryl (e.g., $C_6$-$C_{10}$, $C_{10}$, or phenyl). In embodiments, $R^{14}$ is $R^{14E}$-substituted aryl (e.g., $C_6$-$C_{10}$, $C_{10}$, or phenyl). In embodiments, $R^{14}$ is an unsubstituted aryl (e.g., $C_6$-$C_{10}$, $C_{10}$, or phenyl).

In embodiments, $R^{14}$ is $R^{14E}$-substituted or unsubstituted heteroaryl (e.g., 5 to 10 membered, 5 to 9 membered, or 5 to 6 membered heteroaryl). In embodiments, $R^{14}$ is $R^{14E}$-substituted heteroaryl (e.g., 5 to 10 membered, 5 to 9 membered, or 5 to 6 membered heteroaryl). In embodiments, $R^{14}$ is an unsubstituted heteroaryl (e.g., 5 to 10 membered, 5 to 9 membered, or 5 to 6 membered heteroaryl).

$R^{14E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{14F}$-substituted or unsubstituted alkyl (e.g., $C_1$-$C_8$, $C_1$-$C_6$, or $C_1$-$C_4$ alkyl), $R^{14F}$-substituted or unsubstituted heteroalkyl (e.g., 2 to 8 membered, 2 to 6 membered, or 2 to 4 membered heteroalkyl), $R^{14F}$-substituted or unsubstituted cycloalkyl (e.g., $C_3$-$C_8$, $C_3$-$C_6$, or $C_5$-$C_6$ cycloalkyl), $R^{14F}$-substituted or unsubstituted heterocycloalkyl (e.g., 3 to 8 membered, 3 to 6 membered, or 5 to 6 membered heterocycloalkyl), $R^{14F}$-substituted or unsubstituted aryl (e.g., $C_6$-$C_{10}$, $C_{10}$ aryl, or phenyl), or $R^{14F}$-substituted or unsubstituted heteroaryl (e.g., 5 to 10 membered, 5 to 9 membered, or 5 to 6 membered heteroaryl).

$R^{14F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_1$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{15}$ may be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2Cl$, —$SO_3H$, —$SO_4H$, —$SO_2NH_2$, $R^{15}$ may be hydrogen, halogen, —$N_3$, —$CF_3$, —$CCl_3$, —$CBr_3$, —$CI_3$, —$N_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl), substituted or unsubstituted cycloalkyl (e.g., $C_3$-$C_8$, $C_3$-$C_6$, or $C_5$-$C_6$ cycloalkyl), substituted or unsubstituted heterocycloalkyl (e.g., 3 to 8 membered, 3 to 6 membered, or 5 to 6 membered heterocycloalkyl), substituted or unsubstituted aryl (e.g., $C_6$-$C_{10}$, $C_{10}$ aryl, or phenyl), or substituted or unsubstituted heteroaryl (e.g., 5 to 10 membered, 5 to 9 membered, or 5 to 6 membered heteroaryl). $R^{15}$ may be halogen, —$CF_3$, —$CCl_3$, —$CBr_3$, —$CI_3$, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{15}$ may be halogen, substituted or unsubstituted alkyl (e.g., $C_1$-$C_8$, $C_1$-$C_6$, or $C_1$-$C_4$ alkyl), substituted or unsubstituted heteroalkyl (e.g., 2 to 8 membered, 2 to 6 membered, or 2 to 4 membered heteroalkyl). $R^{15}$ may be halogen, or substituted or unsubstituted alkyl (e.g., $C_1$-$C_8$, $C_1$-$C_6$, or $C_1$-$C_4$ alkyl). $R^{15}$ may be halogen, or unsubstituted alkyl (e.g., $C_1$-$C_8$, $C_1$-$C_6$, or $C_1$-$C_4$ alkyl). $R^{15}$ may be halogen, or substituted or unsubstituted heteroalkyl (e.g., 2 to 8 membered, 2 to 6 membered, or 2 to 4 membered heteroalkyl). $R^{15}$ may be halogen, unsubstituted heteroalkyl (e.g., 2 to 8 membered, 2 to 6 membered, or 2 to 4 membered heteroalkyl. $R^{15}$ may be halogen, —$CF_3$, —$CCl_3$, —$CBr_3$, or —$C_3$. $R^{15}$ may be hydrogen.

$R^{15}$ may be hydrogen, $R^{15E}$-substituted or unsubstituted alkyl (e.g., $C_1$-$C_8$, $C_1$-$C_6$, or $C_1$-$C_4$ alkyl), $R^{15E}$-substituted or unsubstituted heteroalkyl (e.g., 2 to 8 membered, 2 to 6 membered, or 2 to 4 membered heteroalkyl), $R^{15E}$-substituted or unsubstituted cycloalkyl (e.g., $C_3$-$C_8$, $C_3$-$C_6$, or $C_5$-$C_6$ cycloalkyl), $R^{15E}$-substituted or unsubstituted heterocycloalkyl (e.g., 3 to 8 membered, 3 to 6 membered, or 5 to 6 membered heterocycloalkyl), $R^{15E}$-substituted or unsubstituted aryl (e.g., $C_6$-$C_{10}$, $C_{10}$ aryl, or phenyl), or $R^{15E}$-substituted or unsubstituted heteroaryl (e.g., 5 to 10 membered, 5 to 9 membered, or 5 to 6 membered heteroaryl). $R^{15}$ may be $R^{15E}$-substituted or unsubstituted alkyl (e.g., $C_1$-$C_8$, $C_1$-$C_6$, or $C_1$-$C_4$ alkyl), $R^{15E}$-substituted or unsubstituted heteroalkyl (e.g., 2 to 8 membered, 2 to 6 membered, or 2 to 4 membered heteroalkyl), $R^{15E}$-substituted or unsubstituted cycloalkyl (e.g., $C_3$-$C_8$, $C_3$-$C_6$, or $C_5$-$C_6$ cycloalkyl), $R^{15E}$-substituted or unsubstituted heterocycloalkyl (e.g., 3 to 8 membered, 3 to 6 membered, or 5 to 6 membered heterocycloalkyl), $R^{15E}$-substituted or unsubstituted aryl (e.g., $C_6$-$C_{10}$, $C_{10}$ aryl, or phenyl), or $R^{15E}$-substituted or unsubstituted heteroaryl (e.g., 5 to 10 membered, 5 to 9 membered, or 5 to 6 membered heteroaryl).

In embodiments, $R^{15}$ is $R^{15E}$-substituted or unsubstituted alkyl (e.g., $C_1$-$C_8$, $C_1$-$C_6$, or $C_1$-$C_4$ alkyl). In embodiments, $R^{15}$ is $R^{15E}$-substituted alkyl (e.g., $C_1$-$C_8$, $C_1$-$C_6$, or $C_1$-$C_4$ alkyl). In embodiments, $R^{15}$ is an unsubstituted alkyl (e.g., $C_1$-$C_8$, $C_1$-$C_6$, or $C_1$-$C_4$ alkyl).

In embodiments, $R^{15}$ is $R^{15E}$-substituted or unsubstituted heteroalkyl (e.g., 2 to 8 membered, 2 to 6 membered, or 2 to 4 membered heteroalkyl). In embodiments, $R^1$ is $R^{15E}$-substituted heteroalkyl (e.g., 2 to 8 membered, 2 to 6 membered, or 2 to 4 membered heteroalkyl). In embodiments, $R^{15}$ is an unsubstituted heteroalkyl (e.g., 2 to 8 membered, 2 to 6 membered, or 2 to 4 membered heteroalkyl).

In embodiments, $R^{15}$ is $R^{15E}$-substituted or unsubstituted cycloalkyl (e.g., $C_3$-$C_8$, $C_3$-$C_6$, or $C_5$-$C_6$ cycloalkyl). In embodiments, $R^{15}$ is $R^{15E}$-substituted cycloalkyl (e.g., $C_3$-$C_8$, $C_3$-$C_6$, or $C_5$-$C_6$ cycloalkyl). In embodiments, $R^{15}$ is an unsubstituted cycloalkyl (e.g., $C_3$-$C_8$, $C_3$-$C_6$, or $C_5$-$C_6$ cycloalkyl).

In embodiments, $R^{15}$ is $R^{15E}$-substituted or unsubstituted heterocycloalkyl (e.g., 3 to 8 membered, 3 to 6 membered, or 5 to 6 membered heterocycloalkyl). In embodiments, $R^1$ is $R^{15E}$-substituted heterocycloalkyl (e.g., 3 to 8 membered, 3 to 6 membered, or 5 to 6 membered heterocycloalkyl). In embodiments, $R^{15}$ is an unsubstituted heterocycloalkyl (e.g., 3 to 8 membered, 3 to 6 membered, or 5 to 6 membered heterocycloalkyl).

In embodiments, $R^{15}$ is $R^{15E}$-substituted or unsubstituted aryl (e.g., $C_6$-$C_{10}$, $C_{10}$, or phenyl). In embodiments, $R^1$ is $R^{15E}$-substituted aryl (e.g., $C_6$-$C_{10}$, $C_{10}$, or phenyl). In embodiments, $R^{15}$ is an unsubstituted aryl (e.g., $C_6$-$C_{10}$, $C_{10}$, or phenyl).

In embodiments, $R^{15}$ is $R^{15E}$-substituted or unsubstituted heteroaryl (e.g., 5 to 10 membered, 5 to 9 membered, or 5 to 6 membered heteroaryl). In embodiments, $R^{15}$ is $R^{15E}$-substituted heteroaryl (e.g., 5 to 10 membered, 5 to 9 membered, or 5 to 6 membered heteroaryl). In embodiments, $R^{15}$ is an unsubstituted heteroaryl (e.g., 5 to 10 membered, 5 to 9 membered, or 5 to 6 membered heteroaryl).

$R^{15E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{15F}$-substituted or unsubstituted alkyl (e.g., $C_1$-$C_8$, $C_1$-$C_6$, or $C_1$-$C_4$ alkyl), $R^{15F}$-substituted or unsubstituted heteroalkyl (e.g., 2 to 8 membered, 2 to 6 membered, or 2 to 4 membered heteroalkyl), $R^{15F}$-substituted or unsubstituted cycloalkyl (e.g., $C_3$-$C_8$, $C_3$-$C_6$, or $C_5$-$C_6$ cycloalkyl), $R^{15F}$-substituted or unsubstituted heterocycloalkyl (e.g., 3 to 8 membered, 3 to 6 membered, or 5 to 6 membered heterocycloalkyl), $R^{15F}$-substituted or unsubstituted aryl (e.g., $C_6$-$C_{10}$, $C_{10}$ aryl, or phenyl), or $R^{15F}$-substituted or unsubstituted heteroaryl (e.g., 5 to 10 membered, 5 to 9 membered, or 5 to 6 membered heteroaryl).

$R^{15F}$ is independently oxo, halogen, —$CCl_3$, —$CBr_3$, —$CF_3$, —$C_3$, —$CHF_2$, —$CHCl_2$, —$CHBr_2$, —$CHI_2$, —$CH_2F$, —$CH_2Cl$, —$CH_2Br$, —$CH_2I$, —$N_3$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OC_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

The compound of formula (IV) may have the formula:

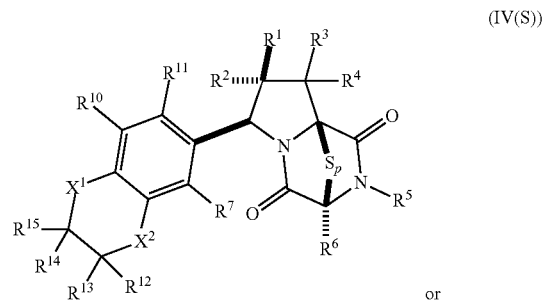

(IV(S))

or (IV(R))

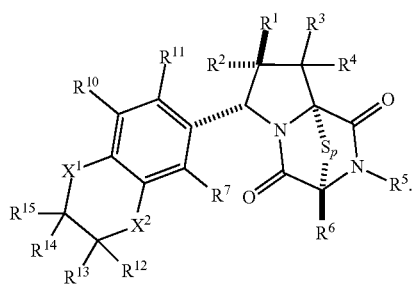

The symbol p, $X^1$, $X^2$, $R^1$, $R^2$, $R^3$, $R^4$, $R^5$, $R^6$, $R^7$, $R^{10}$, $R^{11}$, $R^{12}$, $R^{13}$, $R^{14}$ and $R^{15}$ are as described herein, including embodiments thereof.

The compound of formula (IV) may have the formula:

(IV1)

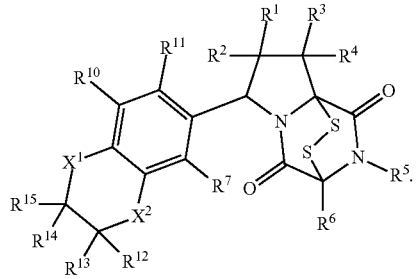

The symbol $X^1$, $X^2$, $R^1$, $R^2$, $R^3$, $R^4$, $R^5$, $R^6$, $R^7$, $R^{10}$, $R^{11}$, $R^{12}$, $R^{13}$, $R^{14}$ and $R^{15}$ are as described herein, including embodiments thereof.

The compound of formula (IV1) may have the formula:

(IV1(S))

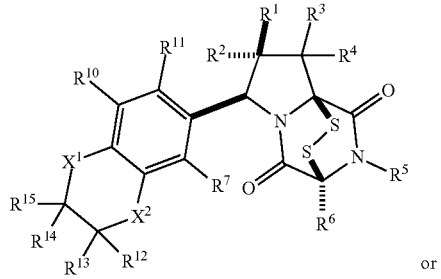

or (IV1(R))

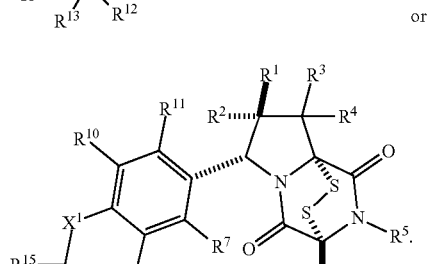

The compound of formula (IV1) may have the formula:

(IV2)

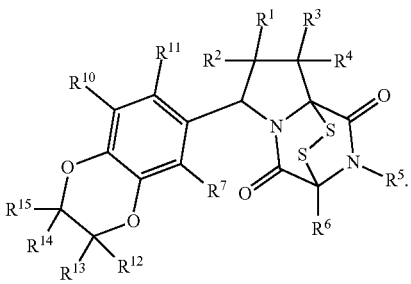

The symbol $R^1$, $R^2$, $R^3$, $R^4$, $R^5$, $R^6$, $R^7$, $R^{10}$, $R^{11}$, $R^{12}$, $R^{13}$, $R^{14}$ and $R^{15}$ are as described herein, including embodiments thereof.

The compound of formula (IV2) may have the formula:

(IV2(S))

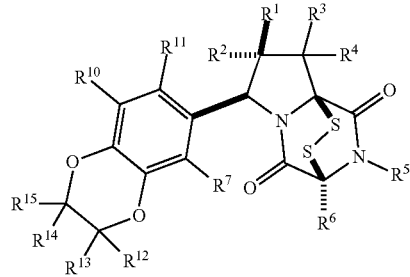

or (IV2(R))

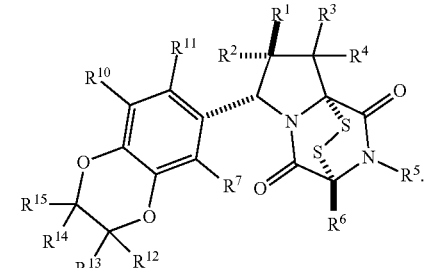

The compound of formula (IV2) may have the formula:

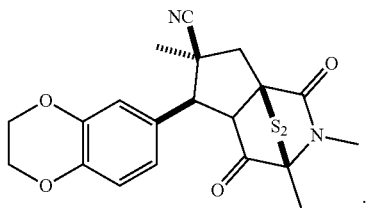

In some embodiments, the compound of formula (I) has the structure of formula (V):

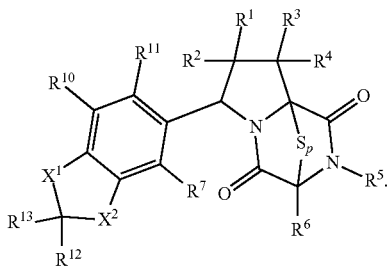

(V)

The symbol $X^1$, $X^2$, $R^1$, $R^2$, $R^3$, $R^4$, $R^5$, $R^6$, $R^7$, $R^{10}$, $R^{11}$, $R^{12}$, and $R^{13}$ are as described herein, including embodiments thereof.

In some embodiments, $R^5$ and $R^6$ are independently unsubstituted $C_1$-$C_3$ alkyl or unsubstituted 3 to 5 membered cycloalkyl. In some embodiments, $R^7$, $R^{10}$, and $R^{11}$ and independently hydrogen, halogen, unsubstituted methyl, —$OCH_3$ or —$O(CH_2)_2$=$CH_2$. In some embodiments, $R^1$ is —CN or unsubstituted 2 to 5 membered heteroalkyl. In some embodiments, $R^1$ is —CN. In some embodiments, $R^1$ is —$COOCH_3$. In some embodiments, $R^1$ is unsubstituted methyl. In some embodiments, $R^2$ is $C_1$-$C_3$ unsubstituted alkyl. In some embodiments, when $R^1$ is —CN, $R^2$ may be unsubstituted methyl. In some embodiments, $R^3$ and $R^4$ are hydrogen. In some embodiments, $R^{10}$ and $R^{11}$ are hydrogen. In some embodiments, $R^{12}$ and $R^{13}$ are hydrogen.

In some embodiments, the compound of formula (V) has the structure of formula (V(S)):

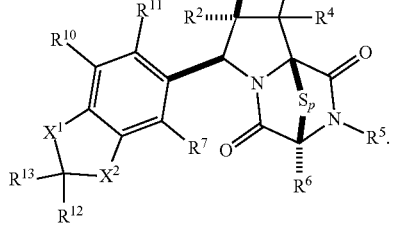

(V(S))

In some embodiments of a compound of formula (V (S)), $X^1$ and $X^2$ are independently O or S. In some embodiments of a compound of formula (V (S)), p is 2. In some embodiments of a compound of formula (V (S)), p is 3.

In some embodiments, the compound of formula (V) has the structure of formula (V(R)):

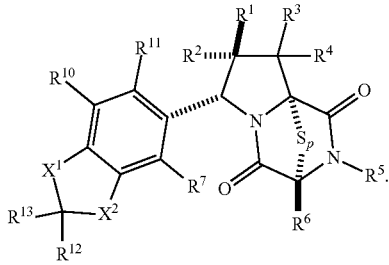

(V(R))

In some embodiments of a compound of formula (V(R)), $X^1$ and $X^2$ are independently O or S. In some embodiments of a compound of formula (V(R)), p is 2. In some embodiments of a compound of formula (V(R)), p is 3.

In some embodiments, the compound of formula (V) has the structure of formula (V1):

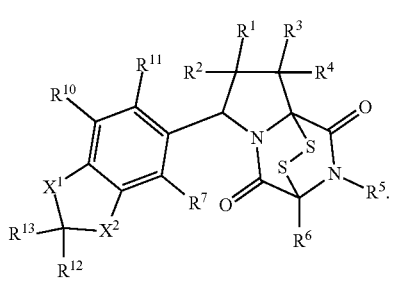

(V1)

In some embodiments, the compound of formula (VI) has the structure of formula (V-1(S)):

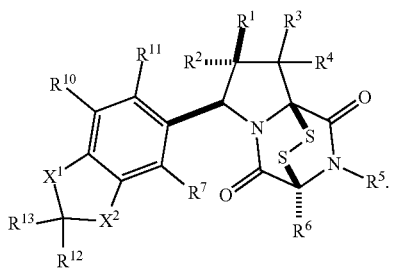

(V1(S))

In some embodiments, the compound of formula (VI) has the structure of formula (V-1(R)):

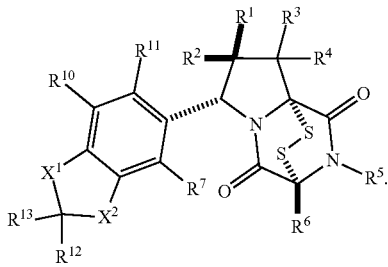

(V1(R))

In some embodiments, the compound of formula (VI) has the structure of formula (V2):

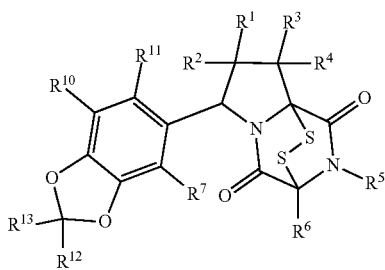

In some embodiments of a method of treating T-cell lymphoma, the compound of formula (V2(S)) has the structure of formula (V2(S)):

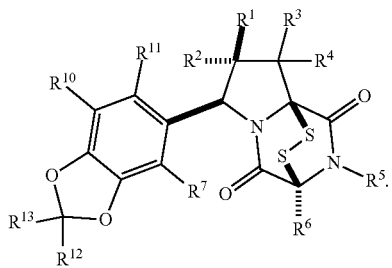

In some embodiments of a compound of formula (V2(S)), $R^1$ is —CN, —OR$^{1A}$, —COOR$^{1A}$, or —CONR$^{1B}$R$^{1C}$, wherein $R^{1A}$, $R^{1B}$, and $R^{1C}$ are independently hydrogen, or substituted or unsubstituted alkyl. In some embodiments of a compound of formula (V2(S)), $R^1$ is —CN. In some embodiments of a compound of formula (V2(S)), $R^2$ is —CF$_3$, substituted or unsubstituted alkyl, substituted or unsubstituted heteroalkyl, substituted or unsubstituted cycloalkyl, or substituted or unsubstituted heterocycloalkyl. In some embodiments of a compound of formula (V2(S)), $R^2$ is substituted or unsubstituted alkyl or substituted or unsubstituted heteroalkyl. In some embodiments of a compound of formula (V2(S)), $R^2$ is methyl. In some embodiments of a compound of formula (V2(S)), $R^3$ and $R^4$ are independently hydrogen. In some embodiments of a compound of formula (V2(S)), $R^{12}$ and $R^{11}$ are independently hydrogen. In some embodiments of a compound of formula (V2(S)), $R^{10}$ and $R^{11}$ are independently hydrogen.

In some embodiments, the compound of formula (V1(R)) has the structure of formula (V2(R)):

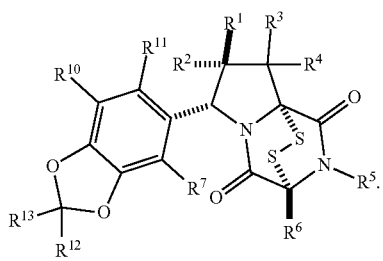

In some embodiments of a compound of formula (V2(R)), $R^1$ is —CN, —OR$^{1A}$, —COOR$^{1A}$, or —CONR$^{1B}$R$^{1C}$, wherein $R^{1A}$, $R^{1B}$, and $R^{1C}$ are independently hydrogen, or substituted or unsubstituted alkyl. In some embodiments of a compound of formula (V2(R)), $R^1$ is —CN. In some embodiments of a compound of formula (V2(R)), $R^2$ is —CF$_3$, substituted or unsubstituted alkyl, substituted or unsubstituted heteroalkyl, substituted or unsubstituted cycloalkyl, or substituted or unsubstituted heterocycloalkyl. In some embodiments of a compound of formula (V2(R)), $R^2$ is substituted or unsubstituted alkyl or substituted or unsubstituted heteroalkyl. In some embodiments of a compound of formula (V2(R)), $R^2$ is methyl. In some embodiments of a compound of formula (V2(R)), $R^3$ and $R^4$ are independently hydrogen. In some embodiments of a compound of formula (V2(R)), $R^{12}$ and $R^{11}$ are independently hydrogen. In some embodiments of a compound of formula (V2(R)), $R^{10}$ and $R^{11}$ are independently hydrogen.

In some embodiments, the compound of formula (V) may have the structure of formula:

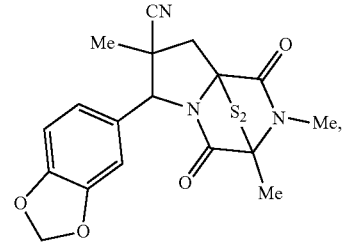

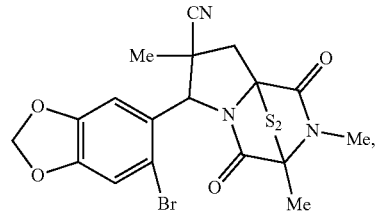

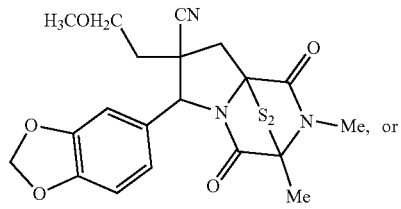

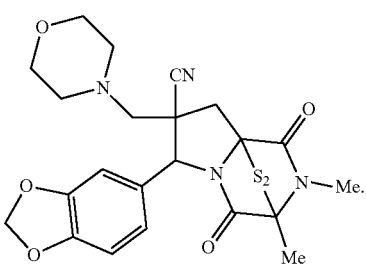

In some embodiments, the compound of formula (V) may have the structure of formula:

(1)
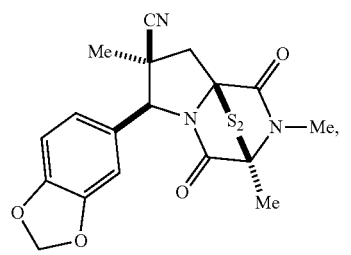
(2)
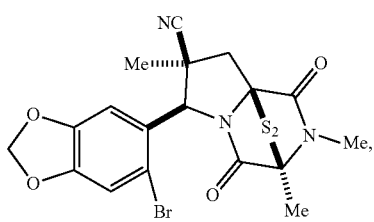
(3)
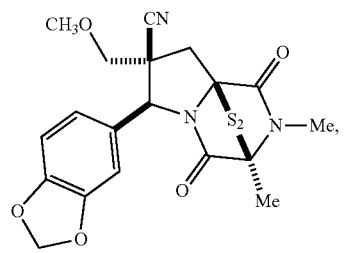
(4)
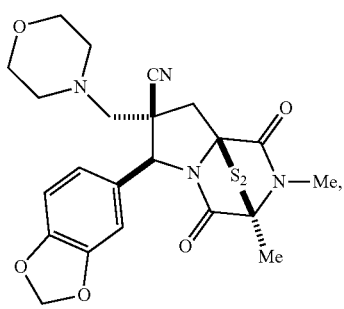
(5)
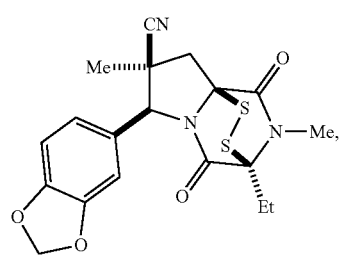
(6)
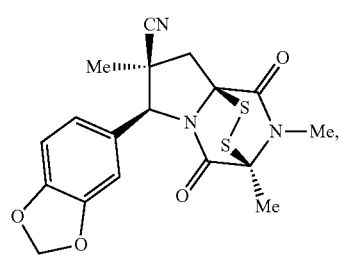
(7)
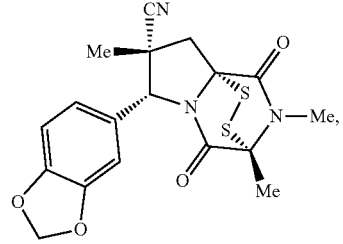
(8)
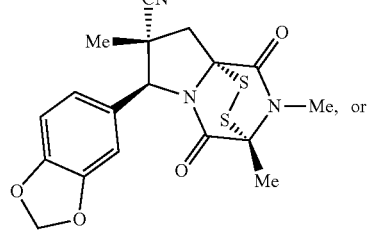
(9)
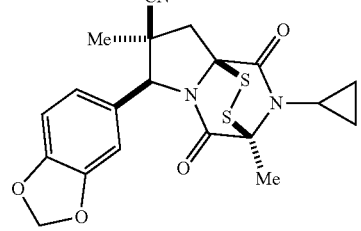
In some embodiments, the compound of formula (V) has the structure of formula (V3):
(V3)
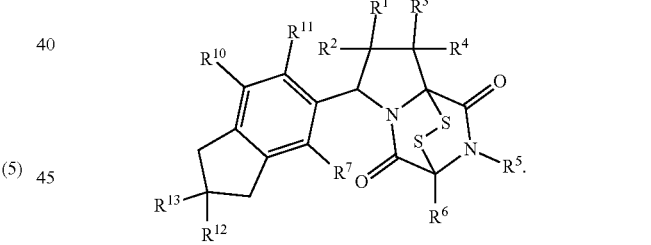
In some embodiments, the compound of formula (V3) may have the structure of formula (V3(S)):
(V3(S))
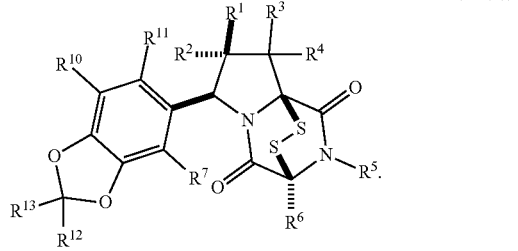
In some embodiments, the compound of formula (V3) may have the structure of formula (IV(R)):

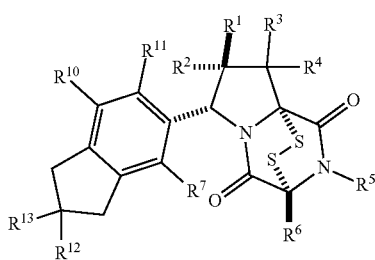
(V3(R))

The compound of formula (VI) may have the formula:

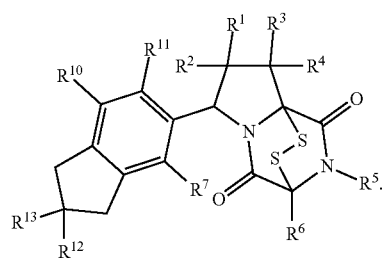
(V4)

The compound of formula (V4) may have the formula:

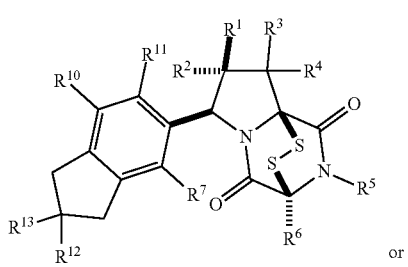
(V4(S))

or

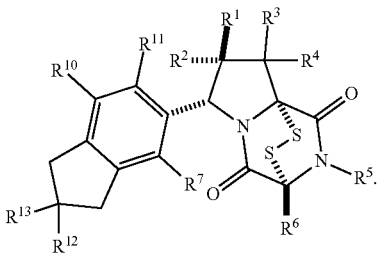
(V4(R))

In some embodiments, the compound of formula (V4) may have the structure of formula:

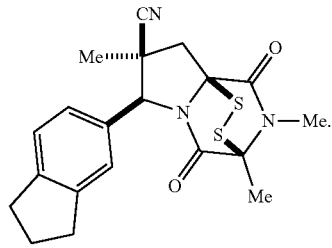
(10)

The compound of formula (I) may have the formula:

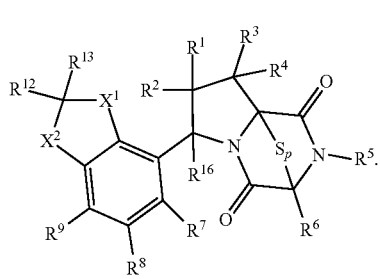
(VI)

The symbols $X^1$, $X^2$, p, $R^1$, $R^2$, $R^3$, $R^4$, $R^5$, $R^6$, $R^7$, $R^8$, $R^9$, $R^{12}$, $R^{13}$, and $R^{16}$ are as described herein, including embodiments thereof.

$R^5$ and $R^6$ may independently be unsubstituted $C_1$-$C_3$ alkyl or unsubstituted 3 to 5 membered cycloalkyl. $R^7$, $R^8$, and $R^9$ may independently be hydrogen, halogen, unsubstituted methyl, —$OCH_3$ or —$O(CH_2)_2$=$CH_2$. $R^1$ may be —CN or unsubstituted 2 to 5 membered heteroalkyl. $R^1$ may be —CN. $R^1$ may be —$COOCH_3$. $R^1$ may be unsubstituted methyl. $R^2$ may be $C_1$-$C_3$ unsubstituted alkyl. When $R^1$ is —CN, $R^2$ may be unsubstituted methyl. $R^3$ and $R^4$ may be hydrogen. $R^7$ and $R^8$ may be hydrogen. $R^{12}$ and $R^{13}$ may be hydrogen. $R^7$, $R^8$, and $R^9$ may be hydrogen.

The compound of formula (VI) may have the formula:

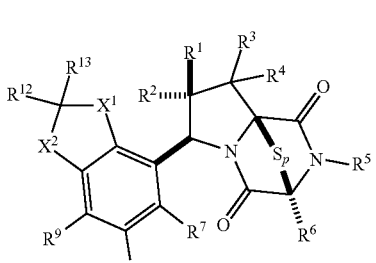
(VI(S))

or

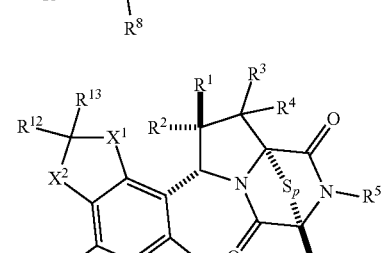
(VI(R))

The compound formula (VI) may have the formula:

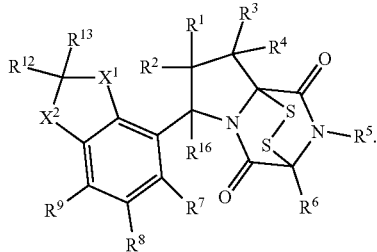
(VI1)

The compound of formula (VI1) may have the formula:

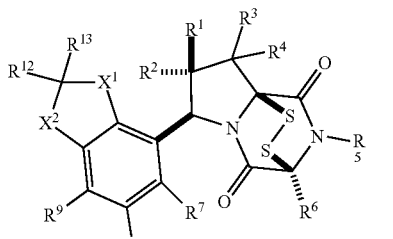
(VI1(S))

or

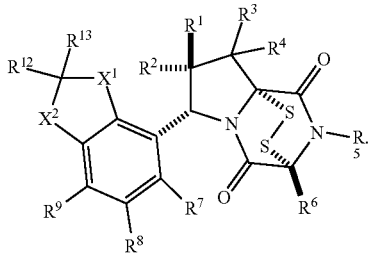
(VI1(R))

The compound of formula (VI) may have the formula:

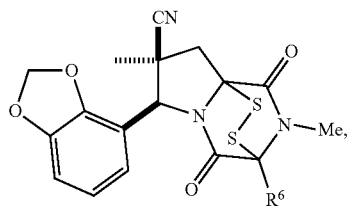
(11)

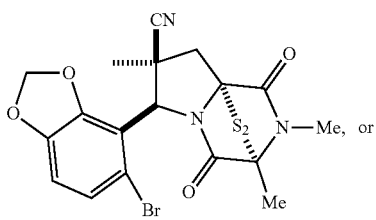
(12)

or

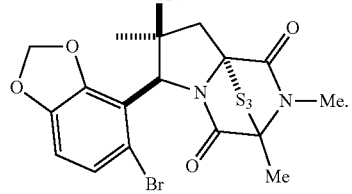
(13)

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$, $R^{20D}$, $R^{21C}$, $R^{22C}$, and $R^{24C}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$, $R^{20D}$, $R^{21C}$, $R^{22C}$, and $R^{24C}$ are independently hydrogen, —$CX_3$, —CN, —COOH, —$CONH_2$, —$CHX_2$, —$CH_2X$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$$R^{7B}$$R^{7C}$, $R^{7D}$, $R^{8A}$, $R^{8B}$$R^{8C}$, $R^{8D}$, $R^{9A}$, $R^{9B}$$R^{9C}$, $R^{9D}$, $R^{11A}$, $R^{11B}$, $R^{11C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$, $R^{20D}$D, $R^{21C}$, $R^{22C}$, and $R^{24C}$ are independently hydrogen, —$CX_3$, —CN, —COOH, —$CONH_2$, —$CHX_2$, —$CH_2X$, unsubstituted alkyl, unsubstituted heteroalkyl, unsubstituted cycloalkyl, unsubstituted heterocycloalkyl, unsubstituted aryl, or unsubstituted heteroaryl.

In embodiments, n1 is 1. In embodiments, n1 is 2. In embodiments, n1 is 3. In embodiments, n1 is 4. In embodiments, n2 is 1. In embodiments, n2 is 2. In embodiments, n2 is 3. In embodiments, n2 is 4. In embodiments, n3 is 1. In embodiments, n3 is 2. In embodiments, n3 is 3. In embodiments, n3 is 4. In embodiments, n4 is 1. In embodiments, n4 is 2. In embodiments, n4 is 3. In embodiments, n4 is 4. In embodiments, n5 is 1. In embodiments, n5 is 2. In embodiments, n5 is 3. In embodiments, n5 is 4. In embodiments, n6 is 1. In embodiments, n6 is 2. In embodiments, n6 is 3. In embodiments, n6 is 4. In embodiments, n7 is 1. In embodiments, n7 is 2. In embodiments, n7 is 3. In embodiments, n7 is 4. In embodiments, n8 is 1. In embodiments, n8 is 2. In embodiments, n8 is 3. In embodiments, n8 is 4. In embodiments, n9 is 1. In embodiments, n9 is 2. In embodiments, n9 is 3. In embodiments, n9 is 4. In embodiments, n10 is 1. In embodiments, n10 is 2. In embodiments, n10 is 3. In embodiments, n10 is 4. In embodiments, n11 is 1. In embodiments, n11 is 2. In embodiments, n11 is 3. In embodiments, n11 is 4. In embodiments, n12 is 1. In embodiments, n12 is 2. In embodiments, n12 is 3. In embodiments, n12 is 4. In embodiments, n13 is 1. In embodiments, n13 is 2. In embodiments, n13 is 3. In embodiments, n13 is 4. In embodiments, n14 is 1. In embodiments, n14 is 2. In embodiments, n14 is 3. In embodiments, n14 is 4. In embodiments, n15 is 1. In embodiments, n15 is 2. In embodiments, n15 is 3. In embodiments, n15 is 4. In embodiments, n16 is 1. In embodiments, n16 is 2. In embodiments, n16 is 3. In embodiments, n16 is 4. In embodiments, n19 is 1. In embodiments, n19 is 2. In embodiments, n19 is 3. In embodiments, n19 is 4. In embodiments, n20 is 1. In embodiments, n20 is 2. In embodiments, n20 is 3. In embodiments, n20 is 4.

In embodiments, v1 is 1. In embodiments, v is 2. In embodiments, v2 is 1. In embodiments, v2 is 2. In embodiments, v3 is 1. In embodiments, v3 is 2. In embodiments, v4 is 1. In embodiments, v4 is 2. In embodiments, v5 is 1. In embodiments, v5 is 2. In embodiments, v6 is 1. In embodiments, v6 is 2. In embodiments, v7 is 1. In embodiments, v7 is 2. In embodiments, v8 is 1. In embodiments, v8 is 2. In embodiments, v9 is 1. In embodiments, v9 is 2. In embodiments, v10 is 1. In embodiments, v10 is 2. In embodiments, v11 is 1. In embodiments, v11 is 2. In embodiments, v12 is 1. In embodiments, v12 is 2. In embodiments, v3 is 1. In embodiments, v13 is 2. In embodiments, v14 is 1. In embodiments, v4 is 2. In embodiments, v15 is 1. In embodiments, v15 is 2. In embodiments, v is 16. In embodiments, v16 is 2. In embodiments, v is 18. In embodiments, v8 is 2. In embodiments, v19 is 1. In embodiments, v9 is 2. In embodiments, v20 is 1. In embodiments, v20 is 2.

Non-Bridged Forms of Compounds

In an aspect is provided a compound (ETP compound) for use in the methods provided herein having the formula (XXI):

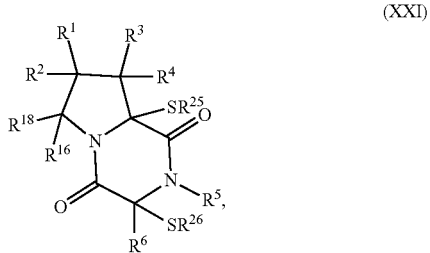

(XXI)

or a pharmaceutically acceptable salt thereof. $R^1$, $R^2$, $R^3$, $R^4$, $R^5$, $R^6$, $R^{16}$, $R^{18}$, $R^{25}$ and $R^{26}$ are as described above.

In embodiments, $R^6$ is hydrogen, —$CF_3$, —$CCl_3$, —$CBr_3$, —$CI_3$, —CN, —CHO, —$COOR^{64}$, —$CONR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^6$ is substituted or unsubstituted $C_1$-$C_3$ alkyl. In embodiments, $R^6$ is s unsubstituted $C_1$-$C_3$ alkyl. In embodiments, $R^6$ is methyl.

In embodiments, $R^5$ is substituted or unsubstituted $C_1$-$C_3$ alkyl. In embodiments, $R^5$ is s unsubstituted $C_1$-$C_3$ alkyl. In embodiments, $R^5$ is methyl.

In embodiments, $R^2$ is —C(O)-$L^1$-$R^{32}$ or —C(S)-$L^1$-$R^{32}$. In embodiments, $R^{26}$ is —C(O)-$L^2$-$R^{33}$ or —C(S)-$L^2$-$R^{33}$. In embodiments, $R^{25}$ and $R^{26}$ are joined to form:

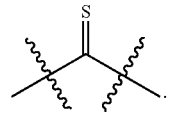 [SMILES: *C(*)=S]

In embodiments, $L^1$ is a bond, —O—, —NH—, substituted or unsubstituted alkylene, substituted or unsubstituted heteroalkylene. In embodiments, $L^2$ is a bond, —O—, —NH—, substituted or unsubstituted alkylene, substituted or unsubstituted heteroalkylene. In embodiments, $R^{25}$ and $R^{26}$ are joined to form:

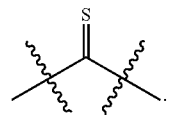 [SMILES: *C(*)=S]

In embodiments, $R^{32}$ and $R^{33}$ are independently hydrogen, halogen, OH, substituted or unsubstituted alkyl, substituted or unsubstituted aryl. In embodiments, $R^{32}$ and $R^{33}$ are independently halogen, OH, substituted or unsubstituted alkyl, substituted or unsubstituted aryl. In embodiments, $R^{32}$ is hydrogen. In embodiments, $R^{32}$ is halogen. In embodiments, $R^{32}$ is —OH. In embodiments, $R^{32}$ is substituted or unsubstituted alkyl. In embodiments, $R^{32}$ is substituted or unsubstituted $C_1$-$C_3$ alkyl. In embodiments, $R^{32}$ is unsubstituted $C_1$-$C_3$ alkyl. In embodiments, $R^{32}$ is substituted or unsubstituted phenyl. In embodiments, $R^{32}$ is unsubstituted phenyl. In embodiments, $R^{33}$ is hydrogen. In embodiments, $R^{33}$ is halogen. In embodiments, $R^{33}$ is —OH. In embodiments, $R^{33}$ is substituted or unsubstituted alkyl. In embodiments, $R^{33}$ is substituted or unsubstituted $C_1$-$C_3$ alkyl. In embodiments, $R^{33}$ is unsubstituted $C_1$-$C_3$ alkyl. In embodiments, $R^{33}$ is substituted or unsubstituted phenyl. In embodiments, $R^{33}$ is unsubstituted phenyl.

In embodiments, $R^{32}$ and $R^{33}$ are independently halogen. In embodiments $R^{32}$ and $R^3$ are independently —Cl. In embodiments $R^{32}$ and $R^{33}$ are independently —OH. In embodiments, $R^{32}$ and $R^{33}$ are independently substituted or unsubstituted $C_1$-$C_3$ alkyl or substituted or unsubstituted aryl. In embodiments, $R^{32}$ and $R^{33}$ are independently unsubstituted $C_1$-$C_3$ alkyl or unsubstituted aryl.

In embodiments, $R^5$ is hydrogen. In embodiments, $R^6$ is hydrogen. In embodiments, $R^{18}$ is hydrogen.

In embodiments, the compound has the formula:

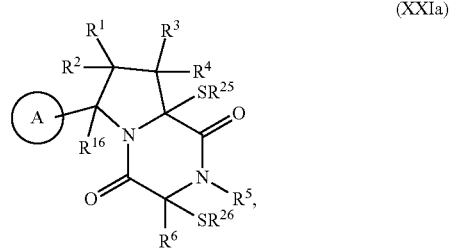

(XXIa)

or a pharmaceutically acceptable salt thereof, wherein $R^1$, $R^2$, $R^3$, $R^4$, $R^5$, $R^6$, $R^{16}$, $R^{25}$ and $R^{26}$ are as described herein.

In embodiments, Ring A is a substituted or unsubstituted cycloalkyl, substituted or unsubstituted heterocycloalkyl, substituted or unsubstituted aryl, or substituted or unsubstituted heteroaryl. In embodiments, Ring A is substituted or unsubstituted phenyl, substituted or unsubstituted pyridyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted furanyl, substituted or unsubstituted pyrrolyl, or substituted or unsubstituted thienyl. In embodiments, Ring A is substituted or unsubstituted phenyl, pyridinyl, pyridazinyl, pyrimidinyl, pyrazinyl, or triazinyl.

In embodiments, Ring A is a $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, Ring A is a $R^{35}$-substituted cycloalkyl, $R^{35}$-substituted heterocycloalkyl, $R^{35}$-substituted aryl, or $R^{35}$-substituted heteroaryl. In embodiments, Ring A is a unsubstituted cycloalkyl, unsubstituted heterocycloalkyl, unsubstituted aryl, or unsubstituted heteroaryl. In embodiments, Ring A is $R^{35}$-substituted or unsubstituted phenyl, $R^{35}$-substituted or unsubstituted pyridyl, $R^{35}$-substituted or unsubstituted pyrazolyl, $R^{35}$-substituted or unsubstituted imidazolyl, $R^{35}$-substituted or unsubstituted oxazolyl, $R^{35}$-substituted or unsubstituted isoxazolyl, $R^{35}$-substituted or unsubstituted thiazolyl, $R^{35}$-substituted or unsubstituted furanyl, $R^{35}$-substituted or unsubstituted pyrrolyl, or $R^{35}$-substituted or unsubstituted thienyl. In embodiments, Ring A is $R^{35}$-substituted or unsubstituted pyridinyl. In embodiments, Ring A is $R^{35}$-substituted or unsubstituted pyridazinyl. In embodiments, Ring A is $R^{35}$-substituted or unsubstituted pyrimidinyl. In embodiments, Ring A is $R^{35}$-substituted or unsubstituted pyrazinyl. In embodiments, Ring A is $R^{35}$-substituted or unsubstituted triazinyl. In embodiments, Ring A is $R^{35}$-substituted phenyl, $R^{35}$-substituted pyridyl, $R^{35}$-substituted pyrazolyl, $R^{35}$-substituted imidazolyl, $R^{35}$-substituted oxazolyl, $R^{35}$-substituted isoxazolyl, $R^{35}$-substituted thiazolyl, $R^{35}$-substituted furanyl, $R^{35}$-substituted pyrrolyl, or $R^{35}$-substituted thienyl. In embodiments, Ring A is $R^{35}$-substituted pyridinyl. In embodiments, Ring A is $R^{35}$-substituted pyridazinyl. In embodiments, Ring A is $R^{35}$-substituted pyrimidinyl. In embodiments, Ring A is $R^{35}$-substituted pyrazinyl. In embodiments, Ring A is $R^{35}$-substituted triazinyl. In embodiments, Ring A is unsubstituted phenyl, unsubstituted pyridyl, unsubstituted pyrazolyl, unsubstituted imidazolyl, unsubstituted oxazolyl, unsubstituted isoxazolyl, unsubstituted thiazolyl, unsubstituted furanyl, unsubstituted pyrrolyl, or unsubstituted thienyl. In embodiments, Ring A is unsubstituted pyridinyl. In embodiments, Ring A is unsubstituted pyridazinyl. In embodiments, Ring A is unsubstituted pyrimidinyl. In embodiments, Ring A is unsubstituted pyrazinyl. In embodiments, Ring A is unsubstituted triazinyl.

$R^{35}$ is independently oxo, halogen, $-CCl_3$, $-CBr_3$, $-CF_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-N_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{35F}$-substituted or unsubstituted alkyl (e.g., $C_1$-$C_8$, $C_1$-$C_6$, or $C_1$-$C_4$ alkyl), $R^{35F}$-substituted or unsubstituted heteroalkyl (e.g., 2 to 8 membered, 2 to 6 membered, or 2 to 4 membered heteroalkyl), $R^{35F}$-substituted or unsubstituted cycloalkyl (e.g., $C_3$-$C_8$, $C_3$-$C_6$, or $C_5$-$C_6$ cycloalkyl), $R^{35F}$-substituted or unsubstituted heterocycloalkyl (e.g., 3 to 8 membered, 3 to 6 membered, or 5 to 6 membered heterocycloalkyl), $R^{35F}$-substituted or unsubstituted aryl (e.g., $C_6$-$C_{10}$, $C_{10}$ aryl, or phenyl), or $R^{35F}$-substituted or unsubstituted heteroaryl (e.g., 5 to 10 membered, 5 to 9 membered, or 5 to 6 membered heteroaryl).

$R^{35F}$ is independently oxo, halogen, $-CCl_3$, $-CBr_3$, $-CF_3$, $-C_3$, $-CHF_2$, $-CHCl_2$, $-CHBr_2$, $-CHI_2$, $-CH_2F$, $-CH_2Cl$, $-CH_2Br$, $-CH_2I$, $-N_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, the compound or pharmaceutically acceptable salt thereof, has the formula:

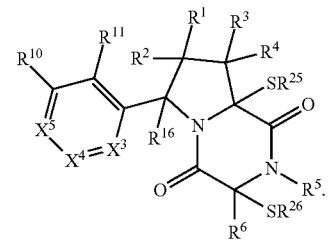

(XXII)

$R^1$, $R^2$, $R^3$, $R^4$, $R^5$, $R^6$, $R^{16}$, $R^{25}$ and $R^{26}$ areas described herein.

In embodiments, $X^3$ is $-N=$ or $-CR^7=$. In embodiments, $X^4$ is $-N=$ or $-CR^8=$. In embodiments, $X^5$ is $-N=$ or $-CR^9=$. $R^7$, $R^8$, $R^9$, $R^{10}$, and $R^{11}$ are as described herein. In embodiments, $X^3$ is $-CR^7=$ and $X^5$ is $-CR^9=$. In embodiments, $X^3$ is $-CR^7=$; $X^4$ is $-N=$; $X^5$ is $-CR^9=$; $R^{10}$, $R^{11}$ and $R^7$ are independently hydrogen; and $R^9$ is $-OCH_3$.

In embodiments, $R^7$ and $R^8$ may optionally be joined to forma substituted or unsubstituted cycloalkyl, substituted or unsubstituted heterocycloalkyl. In embodiments, $R^8$ and $R^9$ may optionally be joined to form a substituted or unsubstituted cycloalkyl, substituted or unsubstituted heterocycloalkyl.

In embodiments, $R^{7B}$ and $R^{7C}$, $R^{8B}$ and $R^{8C}$, $R^{9B}$ and $R^{9C}$, $R^{10B}$ and $R^{10C}$, and $R^{11B}$ and $R^{11C}$, substituents bonded to the same nitrogen atom may optionally be joined to form a substituted or unsubstituted heterocycloalkyl or substituted or unsubstituted heteroaryl.

As described above, the symbols n6, n7, n8, n9, n10 and n11 are independently an integer from 1 to 4. Each occurrence of v6, v7, v8, v9, v10 and v11 is independently 1 or 2.

In embodiments, the compound or the pharmaceutically acceptable salt thereof has the formula:

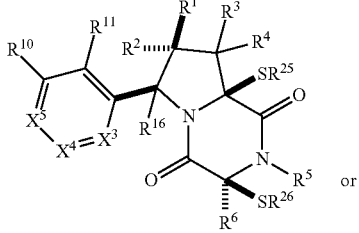

(XXII(S))

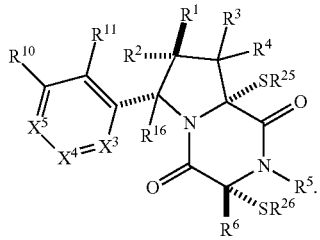

(XXII(R))

$R^1$, $R^2$, $R^3$, $R^4$, $R^5$, $R^6$, $R^{10}$, $R^{11}$, $R^{16}$, $R^{25}$, $R^{26}$, $X^3$, $X^4$ and $X^5$ are as described herein.

In embodiments, $R^7$ and $R^8$ or $R^8$ and $R^9$ are optionally joined to form a substituted or unsubstituted cycloalkyl or substituted or unsubstituted heterocycloalkyl having structural formula:

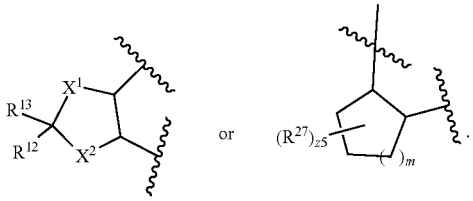

In embodiments, $R^7$ and $R^8$ are optionally joined to form a substituted or unsubstituted cycloalkyl or substituted or unsubstituted heterocycloalkyl having structural formula:

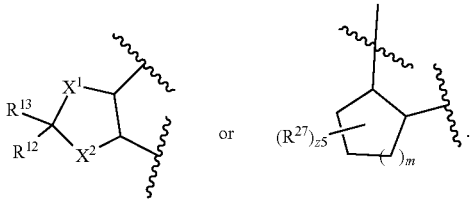

In embodiments, $R^8$ and $R^9$ are optionally joined to form a substituted or unsubstituted cycloalkyl or substituted or unsubstituted heterocycloalkyl having structural formula:

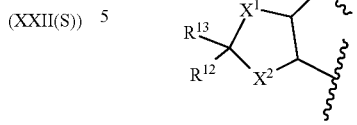 or 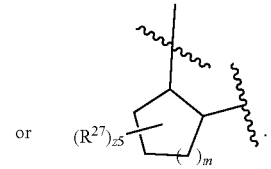

In embodiments, $R^7$ and $R^8$ or $R^8$ and $R^9$ are optionally joined to form a substituted or unsubstituted cycloalkyl or substituted or unsubstituted heterocycloalkyl having structural formula:

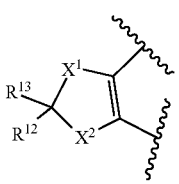 or 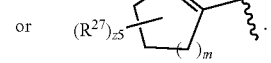

In embodiments, $R^7$ and $R^8$ are optionally joined to form a substituted or unsubstituted cycloalkyl or substituted or unsubstituted heterocycloalkyl having structural formula:

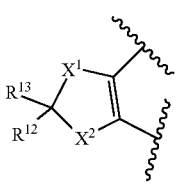 or 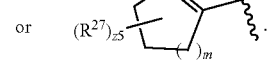

In embodiments, $R^8$ and $R^9$ are optionally joined to form a substituted or unsubstituted cycloalkyl or substituted or unsubstituted heterocycloalkyl having structural formula:

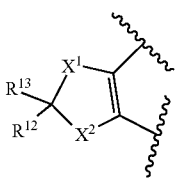 or 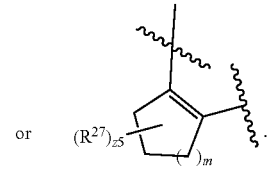

$X^1$ is —$CR^{21A}R^{21B}$—, —O—, —$NR^{21C}$— or —S—. $X^2$ is —$CR^{22A}R^{22B}$—, —O—, —$NR^{22C}$—, or —S—. The symbol z5 is an integer from 0 to 8. The symbol m is 1 or 2. $R^{12}$, $R^{13}$, $R^{21A}$, $R^{21B}$, $R^{21C}$, $R^{22A}$, $R^{22B}$, and $R^{22C}$ are as described herein.

In embodiments, $X^1$ is —O—, —$NR^{21C}$—, or S. In embodiments, $X^2$ is —O—, —$NR^{22C}$—, or S. In embodiments, m is 1 and z5 is an integer from 0 to 6. In embodiments, m is 2 and z5 is an integer from 0 to 8. In embodiments, z5 is 0.

$R^{27}$ is halogen, —$N_3$, —$CF_3$, —$CCl_3$, —$CBr_3$, —$CI_3$, —CN, —CHO, —$OR^{27A}$, —$NR^{27B}R^{27C}$, —$COOR^{27A}$, —$CONR^{27B}R^{27C}$, —$NO_2$, —$SR^{27D}$, —$SO_{n27}R^{27B}$, —$SO_{v27}NR^{27B}R^{27C}$, —$NHNR^{27B}R^{27C}$, —$ONR^{27B}R^{27C}$, —$NHC(O)NHNR^{27B}R^{27C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{27}$ is halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{27E}$-substituted or unsubstituted alkyl (e.g., $C_1$-$C_8$ alkyl, $C_1$-$C_6$ alkyl, or $C_1$-$C_4$ alkyl), $R^{27E}$-substituted or unsubstituted heteroalkyl (e.g., 2 to 8 membered heteroalkyl, 2 to 6 membered heteroalkyl, or 2 to 4 membered heteroalkyl), $R^{27E}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27E}$-substituted or unsubstituted aryl (e.g., $C_6$-$C_{10}$ aryl, $C_{10}$ aryl, or phenyl), or $R^{27E}$-substituted or unsubstituted heteroaryl (e.g., 5 to 10 membered heteroaryl, 5 to 9 membered heteroaryl, or 5 to 6 membered heteroaryl).

In embodiments, $R^{27}$ is $R^{27E}$-substituted or unsubstituted alkyl (e.g., $C_1$-$C_8$ alkyl, $C_1$-$C_6$ alkyl, or $C_1$-$C_4$ alkyl), $R^{27E}$-substituted or unsubstituted heteroalkyl (e.g., 2 to 8 membered heteroalkyl, 2 to 6 membered heteroalkyl, or 2 to 4 membered heteroalkyl), $R^{27E}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27E}$-substituted or unsubstituted aryl (e.g., $C_6$-$C_{10}$ aryl, $C_{10}$ aryl, or phenyl), or $R^{27E}$-substituted or unsubstituted heteroaryl (e.g., 5 to 10 membered heteroaryl, 5 to 9 membered heteroaryl, or 5 to 6 membered heteroaryl).

In embodiments, $R^{27}$ is $R^{27E}$-substituted or unsubstituted alkyl (e.g., $C_1$-$C_8$ alkyl, $C_1$-$C_6$ alkyl, or $C_1$-$C_4$ alkyl). In embodiments, $R^{27}$ is $R^{27E}$-substituted alkyl (e.g., $C_1$-$C_8$ alkyl, $C_1$-$C_6$ alkyl, or $C_1$-$C_4$ alkyl). In embodiments, $R^{27}$ is an unsubstituted alkyl (e.g., $C_1$-$C_8$ alkyl, $C_1$-$C_6$ alkyl, or $C_1$-$C_4$ alkyl).

In embodiments, $R^{27}$ is $R^{27E}$-substituted or unsubstituted heteroalkyl (e.g., 2 to 8 membered heteroalkyl, 2 to 6 membered heteroalkyl, or 2 to 4 membered heteroalkyl). In embodiments, $R^{27}$ is $R^{27E}$-substituted heteroalkyl (e.g., 2 to 8 membered heteroalkyl, 2 to 6 membered heteroalkyl, or 2 to 4 membered heteroalkyl). In embodiments, $R^{27}$ is an unsubstituted heteroalkyl (e.g., 2 to 8 membered heteroalkyl, 2 to 6 membered heteroalkyl, or 2 to 4 membered heteroalkyl).

In embodiments, $R^{27}$ is $R^{27E}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is $R^{27E}$-substituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{27}$ is $R^{27E}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{27}$ is $R^{27E}$-substituted heterocycloalkyl (e.g., 3 to 8 membered heterocycloalkyl, 3 to 6 membered heterocycloalkyl, or 5 to 6 membered heterocycloalkyl). In embodiments, $R^{27}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{27}$ is $R^{27E}$-substituted or unsubstituted aryl (e.g., $C_6$-$C_{10}$ aryl, $C_{10}$ aryl, or phenyl). In embodiments, $R^{27}$ is $R^{27E}$-substituted aryl (e.g., $C_6$-$C_{10}$ aryl, $C_{10}$ aryl, or phenyl). In embodiments, $R^{27}$ is an unsubstituted aryl (e.g., $C_6$-$C_{10}$ aryl, $C_{10}$ aryl, or phenyl).

In embodiments, $R^{27}$ is $R^{27E}$-substituted or unsubstituted heteroaryl (e.g., 5 to 10 membered heteroaryl, 5 to 9 membered heteroaryl, or 5 to 6 membered heteroaryl). In embodiments, $R^{27}$ is $R^{27E}$-substituted heteroaryl (e.g., 5 to 10 membered heteroaryl, 5 to 9 membered heteroaryl, or 5 to 6 membered heteroaryl). In embodiments, $R^{27}$ is an unsubstituted heteroaryl (e.g., 5 to 10 membered heteroaryl, 5 to 9 membered heteroaryl, or 5 to 6 membered heteroaryl).

$R^{27E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{27F}$-substituted or unsubstituted alkyl (e.g., $C_1$-$C_8$, $C_1$-$C_6$, or $C_1$-$C_4$ alkyl), $R^{27F}$-substituted or unsubstituted heteroalkyl (e.g., 2 to 8 membered, 2 to 6 membered, or 2 to 4 membered heteroalkyl), $R^{27F}$-substituted or unsubstituted cycloalkyl (e.g., $C_3$-$C_8$, $C_3$-$C_6$, or $C_5$-$C_6$ cycloalkyl), $R^{27F}$-substituted or unsubstituted heterocycloalkyl (e.g., 3 to 8 membered, 3 to 6 membered, or 5 to 6 membered heterocycloalkyl), $R^{27F}$-substituted or unsubstituted aryl (e.g., $C_6$-$C_{10}$ aryl, $C_{10}$ or phenyl), or $R^{27F}$-substituted or unsubstituted heteroaryl (e.g., 5 to 10 membered, 5 to 9 membered, or 5 to 6 membered heteroaryl).

$R^{27F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, the compound or pharmaceutically acceptable salt thereof, has the

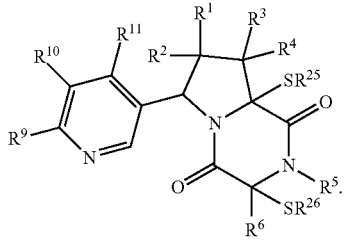

(XXIIa)

$R^1$, $R^2$, $R^3$, $R^4$, $R^5$, $R^6$, $R^{10}$, $R^{11}$, $R^{16}$, $R^{25}$, and $R^{26}$ are as described herein.

In embodiments, the compound or pharmaceutically acceptable salt thereof, has the formula:

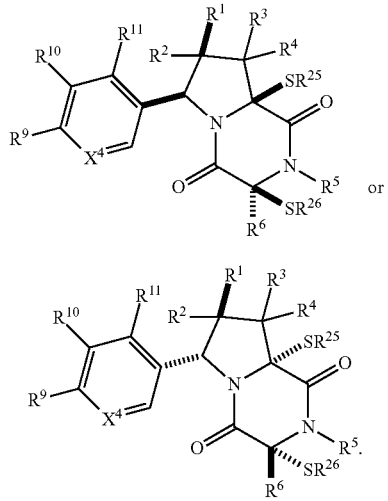

(XXIIa(S))

or (XXIIa(R))

In some embodiments, $R^{16}$ is hydrogen, halogen, —$CF_3$, —$CCl_3$, —$CBr_3$, —$CI_3$, —CN, —CHO, —$COOR^{16A}$, —$CONR^{16B}R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{v1}NR^{1B}R^{1C}$, —$NHNR^{1B}R^{1C}$, —$ONR^{1B}R^{1C}$, —$NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is —CN. In embodiments, $R^1$ is —CN and $R^2$ is an unsubstituted $C_1$-$C_3$ alkyl. In embodiments, $R^1$ is —CN and $R^2$ is methyl.

In some embodiments, $R^1$ is hydrogen, —CN, —CHO, —$OR^{1A}$, —$NR^{1B}R^{1C}$, —$C(O)OR^{1A}$, —$C(O)NR^{1B}R^{1C}$, —$NO_2$, —$SR^{1D}$, —$S(O)_{n1}R^{1B}$, —$SO_{v1}NR^{1B}R^{1C}$, —$NHNR^{1B}R^{1C}$, $ONR^{1B}R^{1C}$, —$NHC(O)NHNR^{1B}R^{1C}$, or substituted or unsubstituted alkyl. In embodiments, $R^1$ is hydrogen, —CN, —CHO, —$OCH_3$, —$N(CH_3)_2$, —$NH_2$, —$C(O)OCH_3$, —$S(O)_2R^{1B}$, or substituted or unsubstituted alkyl. In embodiments, $R^1$ is —$C(O)OR^{1A}$ wherein $R^{1A}$ is substituted or unsubstituted alkyl (e.g., $C_1$-$C_8$ alkyl, $C_1$-$C_6$ alkyl, or $C_1$-$C_4$ alkyl). In embodiments, $R^1$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

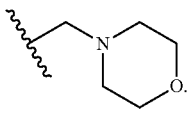

In some embodiments, $R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$, —$COOR^{2A}$, —$CONR^{2B}R^{2C}$, —$NO_2$, —$SR^{2D}$, —$SO_{n2}R^{2B}$, —$SO_{v2}NR^{2B}R^{2C}$, —$NHNR^{2B}R^{2C}$, —$ONR^{2B}R^{2C}$, —$NHC(O)NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is —CN. In embodiments, $R^2$ is an unsubstituted $C_1$-$C_3$ alkyl.

In some embodiments, $R^2$ is hydrogen, —CN, —CHO, —$OR^{2A}$, —$NR^{2B}R^{2C}$, —$C(O)OR^{2A}$, —$C(O)NR^{2B}R^{2C}$, —$NO_2$, —$SR^{2D}$, —$S(O)_{v1}NR^{2B}SO_{v1}NR^{2B}R^{2C}$, $R^{2B}R^{2C}$, $ONR^{2B}R^{2C}$, —$NHC(O)NHNR^{2B}R^{2C}$, or substituted or unsubstituted alkyl. In embodiments, $R^2$ is hydrogen, —CN, —CHO, —$OCH_3$, —$N(CH_3)_2$, —$NH_2$, —$C(O)OCH_3$, —$S(O)_2R^{2B}$, or substituted or unsubstituted alkyl. In embodiments, $R^2$ is —$C(O)OR^{2A}$ wherein $R^{2A}$ is substituted or unsubstituted alkyl (e.g., $C_1$-$C_8$ alkyl, $C_1$-$C_6$ alkyl, or $C_1$-$C_4$ alkyl). In embodiments, $R^2$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

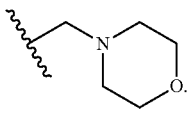

In some embodiments, $R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_{n3}R^{3B}$, —$SO_{v3}NR^{3B}R^{3C}$, —$NHNR^{3B}R^{3C}$, —$ONR^{3B}R^{3C}$, —$NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^4$ is hydrogen, halogen, —$N_3$, —$CF_3$, —$CCl_3$, —$CBr_3$, —$CI_3$, —CN, —CHO, —$OR^{4A}$, —$NR^{4B}R^{4C}$, —$COOR^{4A}$, —$CONR^{4B}R^{4C}$, —$NO_2$, —$SR^{4D}$, —$SO_{n4}R^{4B}$, —$SO_{v4}NR^{4B}R^{4C}$, —$NHNR^{4B}R^{4C}$, —$ONR^{4B}R^{4C}$, —$NHC(O)NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{1A}$, $R^{1B}$, $R^{1C}$, $R^{2A}$, $R^{2B}$, $R^{2C}$, $R^{2D}$, $R^{3A}$, $R^{3B}$, $R^{3C}$, $R^{3D}R^{4A}$, $R^{4B}$, $R^{4C}$, $R^{4D}$, $R^{16A}$, $R^{16B}$ and $R^{16C}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{16B}$ and $R^{16C}$, $R^{2B}$ and $R^{2C}$, and $R^{1B}$ and $R^{1C}$ substituents bonded to the same nitrogen atom may optionally be joined to form a substituted or unsubstituted heterocycloalkyl or substituted or unsubstituted heteroaryl. The symbols n1, n2, n3, and n4 are independently an integer from 1 to 4. The symbols, v1, v2, v3, and v4 are independently 1 or 2.

In some embodiments, $L^1$ is a bond, —O—, —NH—, substituted or unsubstituted alkylene, substituted or unsubstituted heteroalkylene. In some embodiments, $L^2$ is a bond, —O—, —NH—, substituted or unsubstituted alkylene, substituted or unsubstituted heteroalkylene.

In some embodiments, $L^1$ is —O—. In some embodiments, $L^1$ is —NH—. In some embodiments, $L^1$ is a bond. In some embodiments, $L^2$ is —O—. In some embodiments, $L^2$ is —NH—. In some embodiments, $L^2$ is a bond.

In embodiments, the compound or the pharmaceutically acceptable salt thereof has the formula:

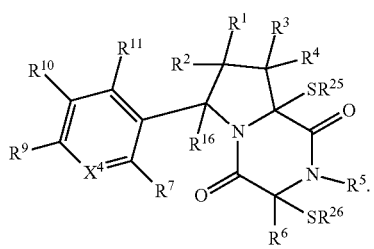

(XXIII)

$R^1$, $R^2$, $R^3$, $R^4$, $R^5$, $R^6$, $R^7$, $R^9$, $R^{10}$, $R^{11}$, $R^{16}$, $R^{25}$, $R^{26}$ and $X^4$ are as described herein.

In embodiments, $R^5$ is hydrogen. In embodiments, $R^6$ is hydrogen. In embodiments, $R^7$ is hydrogen. In embodiments, $R^9$ is hydrogen. In embodiments, $R^{10}$ is hydrogen. In embodiments, $R^{11}$ is hydrogen.

In embodiments, the compound or the pharmaceutically acceptable salt thereof has the formula:

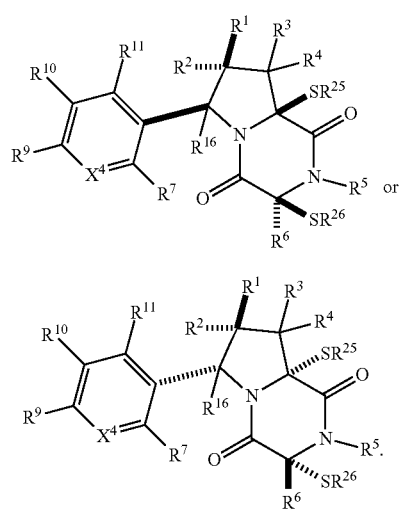

(XXIII(S))

or (XXIII(R))

$R^1$, $R^2$, $R^3$, $R^4$, $R^5$, $R^6$, $R^7$, $R^9$, $R^{10}$, $R^{11}$, $R^{16}$, $R^{25}$, $R^{26}$ and $X^4$ are as described herein.

In embodiments, the compound or the pharmaceutically acceptable salt thereof has the formula:

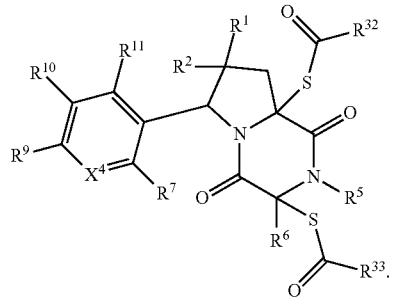

(XXIV)

$R^1$, $R^2$, $R^5$, $R^6$, $R^7$, $R^9$, $R^{10}$, $R^{11}$, $R^{25}$, $R^{26}$, $R^{32}$ and $R^{33}$ and $X^4$ are as described herein. In embodiments, $R^5$ is hydrogen. In embodiments, $R^6$ is hydrogen. In embodiments, $R^7$ is hydrogen. In embodiments, $R^9$ is hydrogen. In embodiments, $R^{10}$ is hydrogen. In embodiments, $R^{11}$ is hydrogen.

In embodiments, the compound or the pharmaceutically acceptable salt thereof has the

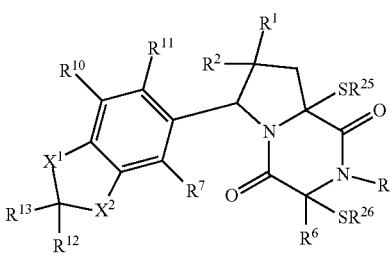

(XXV)

$R^1$, $R^2$, $R^5$, $R^6$, $R^7$, $R^{10}$, $R^{11}$, $R^{12}$, $R^{13}$, $R^{25}$, $R^{26}$, $X^1$ and $X^2$ are as described herein. In embodiments, $R^5$ is hydrogen. In embodiments, $R^6$ is hydrogen. In embodiments, $R^7$ is hydrogen. In embodiments, $R^{10}$ is hydrogen. In embodiments, $R^{11}$ is hydrogen.

In embodiments, the compound or the pharmaceutically acceptable salt thereof has the formula:

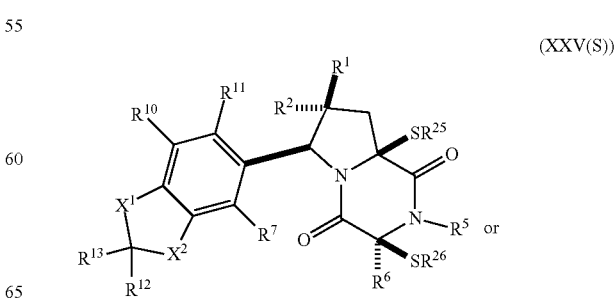

(XXV(S))

or

-continued

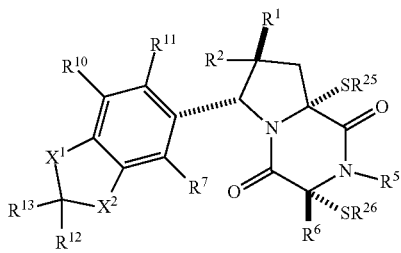
(XXV(R))

In embodiments, the compound or the pharmaceutically acceptable salt thereof has the formula:

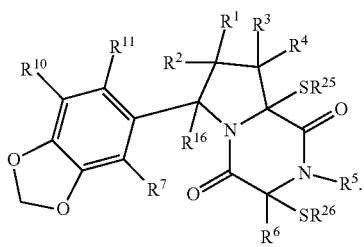
(XXVI)

$R^1$, $R^2$, $R^3$, $R^4$, $R^5$, $R^6$, $R^{10}$, $R^{11}$, $R^{16}$, $R^{25}$ and $R^{26}$ are as described herein. In embodiments, $R^{10}$ is hydrogen. In embodiments, $R^{11}$ is hydrogen.

In embodiments, $R^5$ is hydrogen. In embodiments, $R^6$ is hydrogen. In embodiments, $R^7$ is hydrogen. In embodiments, $R^9$ is hydrogen. In embodiments, $R^{10}$ is hydrogen. In embodiments, $R^{11}$ is hydrogen.

In embodiments, the compound or the pharmaceutically acceptable salt thereof has the formula:

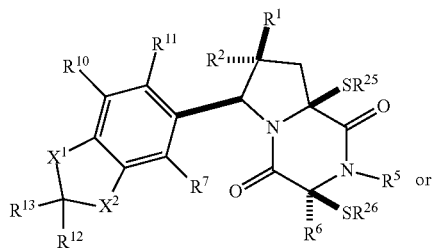
(XXV(S))

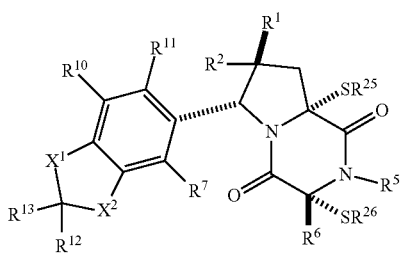
(XXV(R))

$R^1$, $R^2$, $R^5$, $R^6$, $R^7$, $R^{10}$, $R^{11}$, $R^{12}$, $R^{13}$, $R^{25}$, $R^{26}$, $X^1$ and $X^2$ are as described herein.

In embodiments, the compound or the pharmaceutically acceptable salt thereof has the formula:

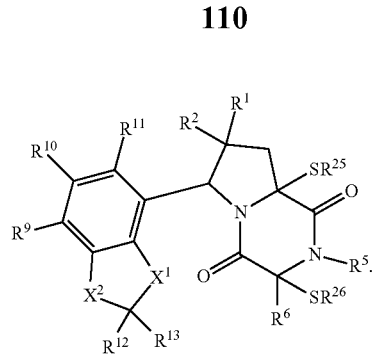
(XXVII)

$R^1$, $R^2$, $R^5$, $R^6$, $R^9$, $R^{10}$, $R^{11}$, $R^{12}$, $R^{13}$, $R^{25}$, $R^{26}$, $X^1$ and $X^2$ are as described herein.

In embodiments, $R^5$ is hydrogen. In embodiments, $R^6$ is hydrogen. In embodiments, $R^9$ is hydrogen. In embodiments, $R^{10}$ is hydrogen. In embodiments, $R^{11}$ is hydrogen.

In embodiments, the compound or the pharmaceutically acceptable salt thereof has the formula:

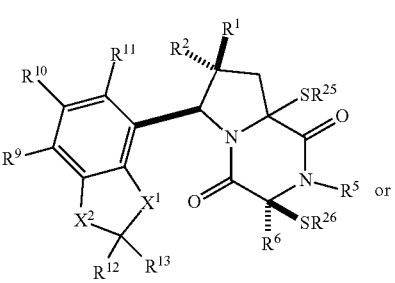
(XXVII(S))

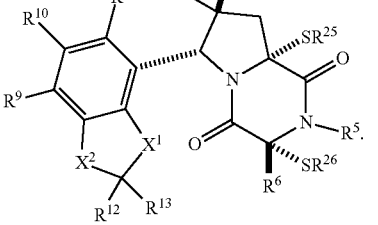
(XXVII(R))

In embodiments, the compound or the pharmaceutically acceptable salt thereof has the

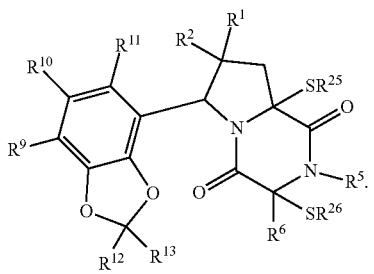
(XXVIIa)

$R^1$, $R^2$, $R^5$, $R^6$, $R^9$, $R^{10}$, $R^{11}$, $R^{12}$, $R^{13}$, $R^{25}$, and $R^{26}$ are as described herein.

In embodiments, $R^5$ is hydrogen. In embodiments, $R^6$ is hydrogen. In embodiments, $R^9$ is hydrogen. In embodiments, $R^{10}$ is hydrogen. In embodiments, $R^{11}$ is hydrogen.

In embodiments, the compound or the pharmaceutically acceptable salt thereof has the formula:

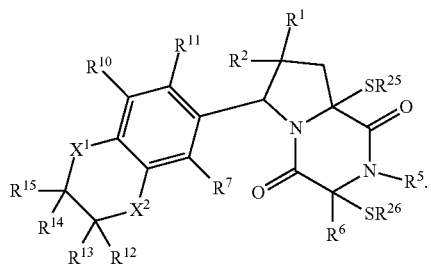

(XXVIII)

$R^1$, $R^2$, $R^5$, $R^6$, $R^7$, $R^{10}$, $R^{11}$, $R^{12}$, $R^{13}$, $R^{14}$, $R^{15}$, $R^{25}$, $R^{26}$, $X^1$ and $X^2$ are as described herein are as described herein. In embodiments, R is hydrogen. In embodiments, $R^6$ is hydrogen. In embodiments, $R^7$ is hydrogen. In embodiments, $R^{10}$ is hydrogen. In embodiments, $R^{11}$ is hydrogen.

In embodiments, the compound or the pharmaceutically acceptable salt thereof has the formula:

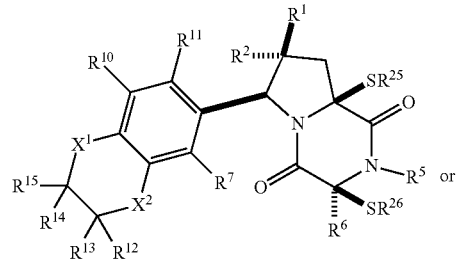

(XXVIII(S))

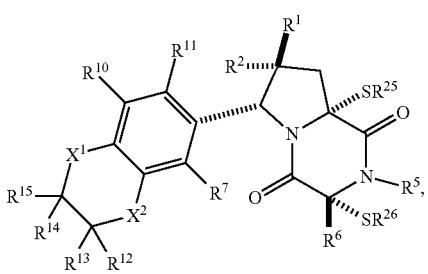

(XXVIII(R))

wherein $R^1$, $R^2$, $R^5$, $R^6$, $R^7$, $R^{10}$, $R^{11}$, $R^{12}$, $R^{13}$, $R^{14}$, $R^{15}$, $R^{25}$, $R^{26}$, $X^1$ and $X^2$ are as described herein.

In embodiments, the compound or the pharmaceutically acceptable salt thereof has the formula:

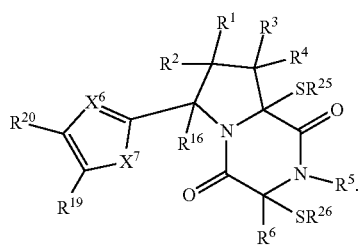

(XXIX)

$X^6$, $X^7$, $R^1$, $R^2$, $R^3$, $R^4$, $R^5$, $R^6$, $R^{19}$, $R^{20}$, $R^{25}$, and $R^{26}$ are as described herein.

In embodiments, $X^6$ is —N=. In embodiments, $X^6$ is —$CR^{23A}$=. In embodiments, $X^7$ is —$CR^{24A}R^{24B}$—. In embodiments, $X^7$ is —S—. In embodiments, $X^7$ is —O—. In embodiments, $X^7$ is —$NR^{24C}$—. In embodiments, $X^6$ is —CH=. In embodiments, $X^7$ is —$CHR^{24B}$—. In embodiments, $X^7$ is —$CH_2$—. In embodiments, $X^7$ is —NH—. $R^{23A}$, $R^{24A}$, $R^{24B}$, and $R^{24C}$ are as described herein.

In embodiments, $R^5$ is hydrogen. In embodiments, $R^6$ is hydrogen. In embodiments, $R^{19}$ is hydrogen. In embodiments, $R^{20}$ is hydrogen. In embodiments, $R^{23A}$ is hydrogen. In embodiments, $R^{24A}$ is hydrogen. In embodiments, $R^{24B}$ is hydrogen. In embodiments, $R^{24C}$ is hydrogen.

In embodiments, the compound or the pharmaceutically acceptable salt thereof has the formula:

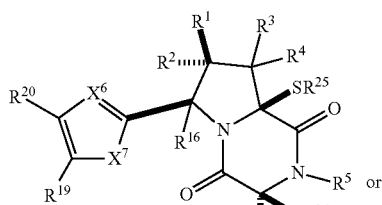

(XXIX(S))

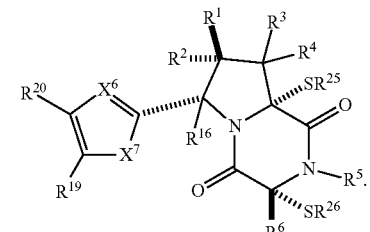

(XXIX(R))

In embodiments, $R^1$ is substituted or unsubstituted alkyl (e.g., $C_1$-$C_8$ alkyl, $C_1$-$C_6$ alkyl, or $C_1$-$C_4$ alkyl). In embodiments, $R^1$ is substituted alkyl (e.g., $C_1$-$C_8$ alkyl, $C_1$-$C_6$ alkyl, or $C_1$-$C_4$ alkyl). In embodiments, $R^1$ is unsubstituted alkyl (e.g., $C_1$-$C_8$ alkyl, $C_1$-$C_6$ alkyl, or $C_1$-$C_4$ alkyl). In embodiments, $R^1$ is substituted or unsubstituted $C_1$-$C_6$ alkyl. In embodiments, $R^1$ is substituted or unsubstituted $C_1$-$C_4$ alkyl. In embodiments, $R^1$ is unsubstituted $C_1$-$C_6$ alkyl. In embodiments, $R^1$ is unsubstituted $C_1$-$C_4$ alkyl. In embodiments, $R^1$ is —CN or —$CH_3$. In embodiments, $R^1$ is —CN. In embodiments, $R^1$ is —$CH_3$.

In some embodiments, $R^1$ is hydrogen, —CN, —CHO, —$OR^{1A}$, —$NR^{1B}R^{1C}$, —C(O)$OR^{1A}$, —C(O)$NR^{1B}R^{1C}$, —$NO_2$, —$SR^{1D}$, —S(O)$_{n1}R^{1B}$, —$SO_{v1}NR^{1B}R^{1C}$, —$NHNR^{1B}R^{1C}$, $ONR^{1B}R^{1C}$, —NHC(O)$NHNR^{1B}R^{1C}$, or substituted or unsubstituted alkyl. In embodiments, $R^1$ is hydrogen, —CN, —CHO, —$OCH_3$, —$N(CH_3)_2$, —$NH_2$, —$C(O)OCH_3$, —$S(O)_2R^{1B}$, or substituted or unsubstituted alkyl. In embodiments, $R^1$ is —C(O)$OR^{1A}$ wherein $R^{1A}$ is substituted or unsubstituted alkyl (e.g., $C_1$-$C_8$ alkyl, $C_1$-$C_6$ alkyl, or $C_1$-$C_4$ alkyl). In embodiments, R is hydrogen, —$CH_3$, —$N(CH_3)_2$, —CN, —$CH_2OCH_3$, —$C(O)OCH_3$, —$C(O)OCH_2CH_2CH_3$, —$C(O)OC(CH_3)_4$, or

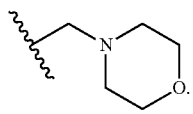 [SMILES: *CN1CCOCC1]

In embodiments, $R^2$ is substituted or unsubstituted alkyl (e.g., $C_1$-$C_8$ alkyl, $C_1$-$C_6$ alkyl, or $C_1$-$C_4$ alkyl). In embodiments, $R^2$ is substituted alkyl (e.g., $C_1$-$C_8$ alkyl, $C_1$-$C_6$ alkyl, or $C_1$-$C_4$ alkyl). In embodiments, $R^2$ is unsubstituted alkyl (e.g., $C_1$-$C_8$ alkyl, $C_1$-$C_6$ alkyl, or $C_1$-$C_4$ alkyl). In embodiments, $R^2$ is substituted or unsubstituted $C_1$-$C_6$ alkyl. In embodiments, $R^2$ is substituted or unsubstituted $C_1$-$C_4$ alkyl. In embodiments, $R^2$ is unsubstituted $C_1$-$C_6$ alkyl. In embodiments, $R^2$ is unsubstituted $C_1$-$C_4$ alkyl. In embodiments, $R^2$ is —CN or —$CH_3$. In embodiments, $R^2$ is —CN. In embodiments, $R^2$ is —$CH_3$.

In some embodiments, $R^2$ is hydrogen, —CN, —CHO, —$OR^{2A}$, —$NR^{2B}R^{2C}$, —$C(O)OR^{2A}$, —$C(O)NR^{2B}R^{2C}$, —$NO_2$, —$SR^{2D}$, —$S(O)_{n2}R^{2B}$, —$SO_{v2}NR^{2B}R^{2C}$, —N—$R^{2B}R^{2C}$, $ONR^{2B}R^{2C}$, —$NHC(O)NHNR^{2B}R^{2C}$, or substituted or unsubstituted alkyl. In embodiments, $R^2$ is hydrogen, —CN, —CHO, —$OCH_3$, —$N(CH_3)_2$, —$NH_2$, —$C(O)OCH_3$, —$S(O)_2R^{2B}$, or substituted or unsubstituted alkyl. In embodiments, $R^2$ is —$C(O)OR^{2A}$ wherein $R^{2A}$ is substituted or unsubstituted alkyl (e.g., $C_1$-$C_8$ alkyl, $C_1$-$C_6$ alkyl, or $C_1$-$C_4$ alkyl). In embodiments, $R^2$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

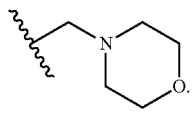

In embodiments, $R^3$ is substituted or unsubstituted alkyl (e.g., $C_1$-$C_8$ alkyl, $C_1$-$C_6$ alkyl, or $C_1$-$C_4$ alkyl). In embodiments, $R^3$ is substituted alkyl (e.g., $C_1$—C alkyl, $C_1$-$C_6$ alkyl, or $C_1$-$C_4$ alkyl). In embodiments, $R^3$ is unsubstituted alkyl (e.g., $C_1$-$C_8$ alkyl, $C_1$-$C_6$ alkyl, or $C_1$-$C_4$ alkyl). In embodiments, $R^3$ is substituted or unsubstituted $C_1$-$C_6$ alkyl. In embodiments, $R^3$ is substituted or unsubstituted $C_1$-$C_4$ alkyl. In embodiments, $R^3$ is unsubstituted $C_1$-$C_6$ alkyl. In embodiments, $R^3$ is unsubstituted $C_1$-$C_4$ alkyl. In embodiments, $R^3$ is —CN or —$CH_3$. In embodiments, $R^3$ is —CN. In embodiments, $R^3$ is —$CH_3$.

In some embodiments, $R^3$ is hydrogen, —CN, —CHO, —$OR^{3A}$, —$NR^{3B}R^{3C}$, —$C(O)OR^{3A}$, —$C(O)NR^{3B}R^{3C}$, —$NO_2$, —$SR^{3D}$, —$S(O)_{n3}R^{3B}$, —$SO_{v3}NR^{3B}R^{3C}$, —$NHNR^{3B}R^{3C}$, $ONR^{3B}R^{3C}$, —$NHC(O)NHNR^{3B}R^{3C}$, or substituted or unsubstituted alkyl. In embodiments, $R^3$ is hydrogen, —CN, —CHO, —$OCH_3$, —$N(CH_3)_2$, —$NH_2$, —$C(O)OCH_3$, —$S(O)_2R^{3B}$, or substituted or unsubstituted alkyl. In embodiments, $R^3$ is —$C(O)OR^{3A}$ wherein $R^{3A}$ is substituted or unsubstituted alkyl (e.g., $C_1$-$C_8$ alkyl, $C_1$-$C_6$ alkyl, or $C_1$-$C_4$ alkyl). In embodiments, $R^3$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

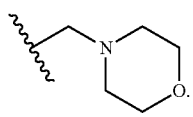 [SMILES: *CN1CCOCC1]

In embodiments, $R^4$ is substituted or unsubstituted alkyl (e.g., $C_1$-$C_8$ alkyl, $C_1$-$C_6$ alkyl, or $C_1$-$C_4$ alkyl). In embodiments, $R^4$ is substituted alkyl (e.g., $C_1$-$C_8$ alkyl, $C_1$-$C_6$ alkyl, or $C_1$-$C_4$ alkyl). In embodiments, $R^4$ is unsubstituted alkyl (e.g., $C_1$-$C_8$ alkyl, $C_1$-$C_6$ alkyl, or $C_1$-$C_4$ alkyl). In embodiments, $R^4$ is substituted or unsubstituted $C_1$-$C_6$ alkyl. In embodiments, $R^4$ is substituted or unsubstituted $C_1$-$C_4$ alkyl. In embodiments, $R^4$ is unsubstituted $C_1$-$C_6$ alkyl. In embodiments, $R^4$ is unsubstituted $C_1$-$C_4$ alkyl. In embodiments, $R^4$ is —CN or —$CH_3$. In embodiments, $R^4$ is —CN. In embodiments, $R^4$ is —$CH_3$.

In some embodiments, $R^4$ is hydrogen, —CN, —CHO, —$OR^{4A}$, —$NR^{4B}R^{4C}$, —$C(O)OR^{4A}$, —$C(O)NR^{4B}R^{4C}$, —$NO_2$, —$SR^{4D}$, —$S(O)_{n4}R^{4B}$, —$SO_{v4}NR^{4B}R^{4C}$, —$NHNR^{4B}R^{4C}$, $ONR^{4B}R^{4C}$, —$NHC(O)NHNR^{4B}R^{4C}$, or substituted or unsubstituted alkyl. In embodiments, $R^4$ is hydrogen, —CN, —CHO, —$OCH_3$, —$N(CH_3)_2$, —$NH_2$, —$C(O)OCH_3$, —$S(O)_2R^{4B}$, or substituted or unsubstituted alkyl. In embodiments, $R^4$ is —$C(O)OR^{4A}$ wherein $R^{4A}$ is substituted or unsubstituted alkyl (e.g., $C_1$-$C_8$ alkyl, $C_1$-$C_6$ alkyl, or $C_1$-$C_4$ alkyl). In embodiments, $R^4$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

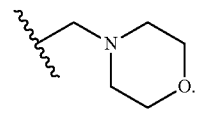

In embodiments, $R^5$ is substituted or unsubstituted alkyl (e.g., $C_1$-$C_8$ alkyl, $C_1$-$C_6$ alkyl, or $C_1$-$C_4$ alkyl). In embodiments, $R^5$ is substituted alkyl (e.g., $C_1$-$C_8$ alkyl, $C_1$-$C_6$ alkyl, or $C_1$-$C_4$ alkyl). In embodiments, $R^5$ is unsubstituted alkyl (e.g., $C_1$-$C_8$ alkyl, $C_1$-$C_6$ alkyl, or $C_1$-$C_4$ alkyl). In embodiments, $R^5$ is substituted or unsubstituted $C_1$-$C_6$ alkyl. In embodiments, $R^5$ is substituted or unsubstituted $C_1$-$C_4$ alkyl. In embodiments, R is unsubstituted $C_1$-$C_6$ alkyl. In embodiments, $R^5$ is unsubstituted $C_1$-$C_4$ alkyl. In embodiments, $R^5$ is —$CH_3$.

In some embodiments, $R^5$ is an unsubstituted cyclopropyl. In embodiments, $R^5$ is an unsubstituted cyclobutyl. In embodiments, $R^5$ is an unsubstituted cyclopentyl. In embodiments, $R^5$ is an unsubstituted cyclohexyl. In embodiments, $R^5$ is an unsubstituted $C_2$-$C_4$ alkylene. In embodiments, $R^5$ is an unsubstituted $C_4$ alkylene.

In embodiments, $R^6$ is substituted or unsubstituted alkyl (e.g., $C_1$-$C_8$ alkyl, $C_1$-$C_6$ alkyl, or $C_1$-$C_4$ alkyl). In embodiments, $R^6$ is substituted alkyl (e.g., $C_1$-$C_8$ alkyl, $C_1$-$C_6$ alkyl, or $C_1$-$C_4$ alkyl). In embodiments, $R^6$ is unsubstituted alkyl (e.g., $C_1$-$C_8$ alkyl, $C_1$-$C_6$ alkyl, or $C_1$-$C_4$ alkyl). In embodiments, $R^6$ is substituted or unsubstituted $C_1$-$C_6$ alkyl. In embodiments, $R^6$ is substituted or unsubstituted $C_1$-$C_4$ alkyl. In embodiments, $R^6$ is unsubstituted $C_1$-$C_6$ alkyl. In embodiments, $R^6$ is unsubstituted $C_1$-$C_4$ alkyl. In embodiments, $R^6$ is —$CH_3$.

In some embodiments, $R^6$ is an unsubstituted cyclopropyl. In embodiments, $R^6$ is an unsubstituted cyclobutyl. In embodiments, $R^6$ is an unsubstituted cyclopentyl. In embodiments, $R^6$ is an unsubstituted cyclohexyl. In embodiments, $R^6$ is an unsubstituted $C_2$-$C_4$ alkylene. In embodiments, $R^6$ is an unsubstituted $C_4$ alkylene.

In some embodiments, $R^{16}$ is substituted or unsubstituted alkyl (e.g., $C_1$-$C_8$ alkyl, $C_1$-$C_6$ alkyl, or $C_1$-$C_4$ alkyl). In embodiments, $R^{16}$ is substituted alkyl (e.g., $C_1$-$C_8$ alkyl, $C_1$-$C_6$ alkyl, or $C_1$-$C_4$ alkyl). In embodiments, $R^{16}$ is unsubstituted alkyl (e.g., $C_1$-$C_8$ alkyl, $C_1$-$C_6$ alkyl, or $C_1$-$C_4$ alkyl). In embodiments, $R^{16}$ is substituted or unsubstituted $C_1$-$C_6$ alkyl. In embodiments, $R^{16}$ is substituted or unsubstituted $C_1$-$C_4$ alkyl. In embodiments, $R^6$ is unsubstituted $C_1$-$C_6$ alkyl. In embodiments, $R^{16}$ is unsubstituted $C_1$-$C_4$ alkyl. In embodiments, $R^{16}$ is —CN or —$CH_3$. In embodiments, $R^{16}$ is —CN. In embodiments, $R^{16}$ is —$CH_3$.

In embodiments, $R^{18}$ is $R^{18E}$-substituted or unsubstituted alkyl (e.g., $C_1$-$C_8$ alkyl, $C_1$-$C_6$ alkyl, or $C_1$-$C_4$ alkyl), $R^{18E}$-substituted or unsubstituted heteroalkyl (e.g., 2 to 8 membered heteroalkyl, 2 to 6 membered heteroalkyl, or 2 to 4 membered heteroalkyl), $R^{18E}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{18E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{18E}$-substituted or unsubstituted aryl (e.g., $C_6$-$C_{10}$ aryl, $C_{10}$ aryl, or phenyl), or $R^{18E}$-substituted or unsubstituted heteroaryl (e.g., 5 to 10 membered heteroaryl, 5 to 9 membered heteroaryl, or 5 to 6 membered heteroaryl).

In some embodiments, $R^{18}$ is Ring A. In embodiments, Ring A is a substituted or unsubstituted cycloalkyl, substituted or unsubstituted heterocycloalkyl, substituted or unsubstituted aryl, or substituted or unsubstituted heteroaryl. In embodiments, Ring A is $R^{18E}$-substituted or unsubstituted heteroaryl (e.g., 5 to 10 membered heteroaryl, 5 to 9 membered heteroaryl, or 5 to 6 membered heteroaryl). In embodiments, Ring A is $R^{18E}$-substituted heteroaryl (e.g., 5 to 10 membered heteroaryl, 5 to 9 membered heteroaryl, or 5 to 6 membered heteroaryl). In embodiments, Ring A is an unsubstituted heteroaryl (e.g., 5 to 10 membered heteroaryl, 5 to 9 membered heteroaryl, or 5 to 6 membered heteroaryl).

In embodiments, Ring A is substituted or unsubstituted phenyl, substituted or unsubstituted pyridyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted furanyl, substituted or unsubstituted pyrrolyl, or substituted or unsubstituted thienyl. In embodiments, Ring A is substituted or unsubstituted phenyl, pyridinyl, pyridazinyl, pyrimidinyl, pyrazinyl, or triazinyl.

In embodiments, $R^{25}$ is —C(O)-$L^1$-$R^{32}$ or —C(S)-$L^1$-$R^{32}$. $R^{26}$ is —C(O)-$L^2$-$R^{33}$ or —C(S)-$L^2$-$R^{33}$. In embodiments, $R^{25}$ and $R^{26}$ are joined together to form:

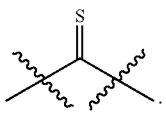

In embodiments, $R^{25}$ and $R^{26}$ are independently, hydrogen, trityl, para-methoxybenzyl, para-methylbenzyl, acetamidomethyl, tert-butyl, tert-butyl thiol, unsubstituted benzyl, unsubstituted methyl, phenylacyl, or unsubstituted benzyloxycarbonyl.

In embodiments, $L^1$ is -$L^{1A}$-$L^{1B}$-, wherein $L^{1A}$ is bonded to —C(O)— or —C(S)—. $L^{1A}$ is a bond or —$(CH_2)_{z1}$—. In embodiments, $L^2$ is -$L^{2A}$-$L^{2B}$-, wherein $L^{2A}$ is bonded to —C(O)— or —C(S)—. $L^{1B}$ is a bond, —O—, or —$NR^{30B}$—, $L^{2A}$ is a bond or —$(CH_2)_{z2}$—. $L^{2B}$ is a bond, —O—, or —$NR^{31B}$— $R^{30B}$ and $R^{31B}$ are independently hydrogen or substituted or unsubstituted alkyl. The symbols z1 and z2 are independently an integer from 1 to 10. In embodiments, $L^{1A}$ is —$CH_2$—. In embodiments, $L^{2A}$ is —$CH_2$—. In embodiments, $L^{1A}$ and $L^{2A}$ are independently —$CH_2$—. In embodiments, $L^{1A}$ is —$CH_2$—. In embodiments, $L^{2A}$ is —$CH_2$—.

In embodiments, $R^{25}$ has the formula:

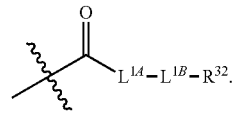

In embodiments, $R^{25}$ has the formula:

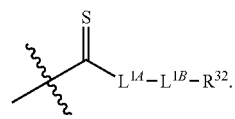

In embodiments, $R^{25}$ has the formula:

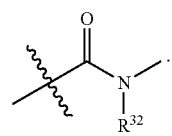

In embodiments, $R^{25}$ has the formula:

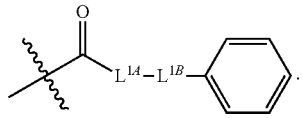

In embodiments, $R^{26}$ has the formula:

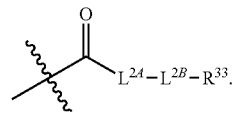

In embodiments, $R^{26}$ has the formula:

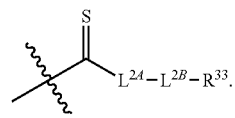

In embodiments, $R^{26}$ has the formula:

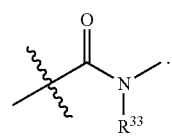

In embodiments, $R^{26}$ has the formula:

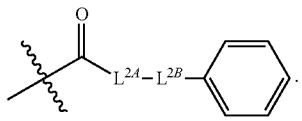

In embodiments, $L^{1B}$ is —$NR^{30B}$—; $L^{2B}$ is —$NR^{31B}$—; and $R^{30B}$ and $R^{31B}$ are independently unsubstituted $C_1$-$C_3$ alkyl.

In embodiments, $R^{25}$ is —C(O)-$L^1$-$R^{32}$. In embodiments, $R^{25}$ is —C(S)-$L^1$-$R^{32}$. In embodiments, $R^{26}$ is —C(O)-$L^2$-$R^{33}$. In embodiments, $R^{26}$ is —C(S)-$L^2$-$R^{33}$. In embodiments, $R^{25}$ is —C(O)-$L^1$-$R^{32}$ and $R^{26}$ is —C(O)-$L^2$-$R^{33}$. In embodiments, $R^{25}$ is —C(S)-$L^1$-$R^{32}$ and $R^{26}$ is —C(S)-$L^2$-$R^{33}$.

In embodiments, $R^{25}$ is

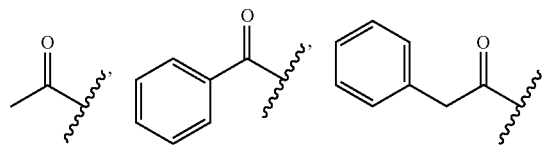

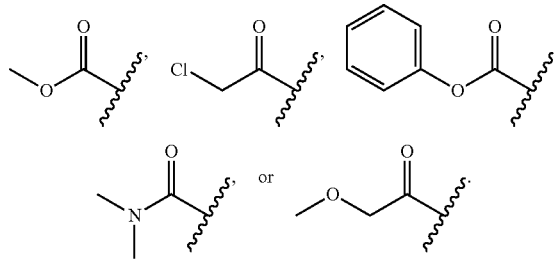

In embodiments, $R^{25}$ is

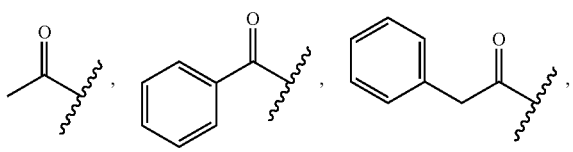

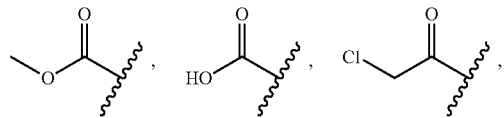

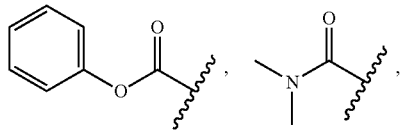

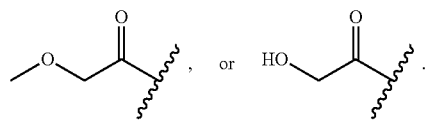

In embodiments, $R^{25}$ is

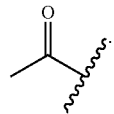

In embodiments, $R^{25}$ is

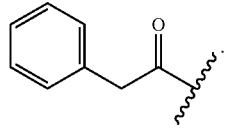 [SMILES: *C(=O)Cc1ccccc1 ; "."]

In embodiments, $R^{25}$ is

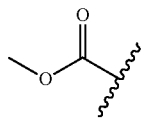

In embodiments, $R^{25}$ is

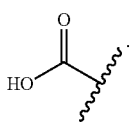

In embodiments, $R^{25}$ is

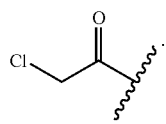 [SMILES: *C(=O)CCl ; "."]

In embodiments, $R^{25}$ is

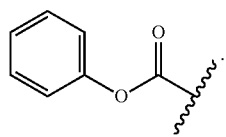 [SMILES: *C(=O)Oc1ccccc1 ; "."]

In embodiments, $R^{25}$ is
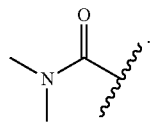
In embodiments, $R^{25}$ is
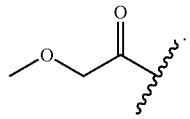
In embodiments, $R^{25}$ is
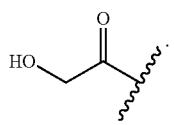 [SMILES: *C(=O)CO ; "."]
In embodiments, $R^{26}$ is
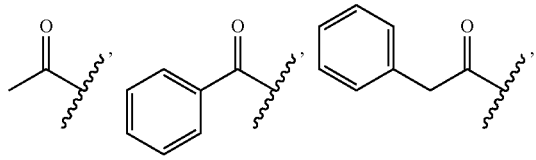
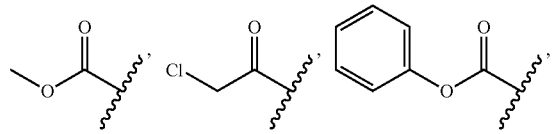
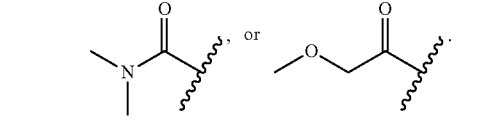
In embodiments, $R^{26}$ is
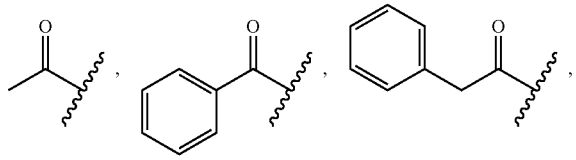
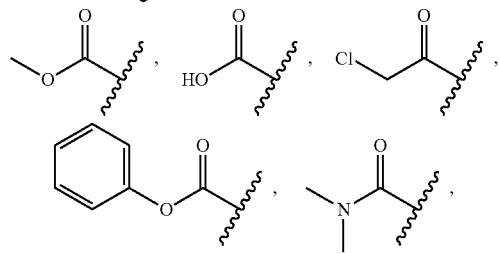
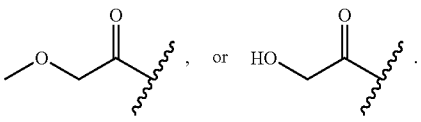
In embodiments, $R^{26}$ is
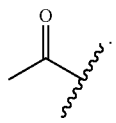
In embodiments, $R^{26}$ is
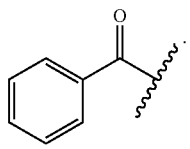
In embodiments, $R^{26}$ is
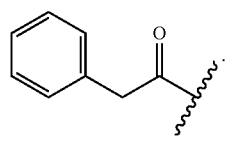 [SMILES: *C(=O)Cc1ccccc1 ; "."]
In embodiments, $R^{26}$ is
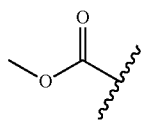
In embodiments, $R^{26}$ is
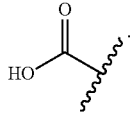
In embodiments, $R^{26}$ is
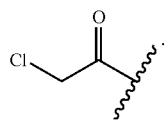

In embodiments, $R^{26}$ is

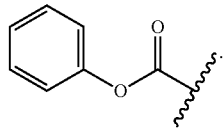 [SMILES: *C(=O)Oc1ccccc1]

In embodiments, $R^{26}$ is

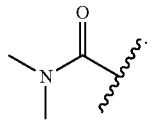 [SMILES: *C(=O)N(C)C]

In embodiments, $R^{26}$ is

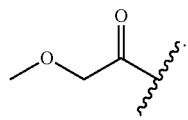 [SMILES: *C(=O)COC]

In embodiments, $R^{26}$ is

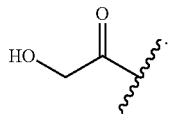

In embodiments, $R^{32}$ is halogen, substituted or unsubstituted $C_1$-$C_3$ alkyl, substituted or unsubstituted aryl. In embodiments, $R^{32}$ is substituted or unsubstituted aryl (e.g., $C_6$-$C_{10}$ aryl, $C_{10}$ aryl, or phenyl). In embodiments, $R^{32}$ is halogen. In embodiments, $R^{32}$ is substituted or unsubstituted phenyl. In embodiments, $R^{32}$ is unsubstituted phenyl. In embodiments, $R^{32}$ is Cl. In embodiments, $R^{32}$ is substituted or unsubstituted $C_1$-$C_3$ alkyl. In embodiments, $R^{32}$ is unsubstituted $C_1$-$C_3$ alkyl. In embodiments, $R^{32}$ is substituted $C_1$-$C_3$ alkyl. In embodiments, $R^{32}$ is an unsubstituted $C_3$ alkyl. In embodiments, $R^{32}$ is —Cl. In embodiments, $R^{32}$ is —F. In embodiments, $R^{32}$ is —CH$_3$. In embodiments, $R^{32}$ is hydrogen.

In embodiments, $R^{32}$ is hydrogen, halogen, $R^{32E}$-substituted or unsubstituted $C_1$-$C_3$ alkyl, or $R^{32E}$-substituted or unsubstituted aryl. In embodiments, $R^{32}$ is halogen, $R^{32E}$-substituted or unsubstituted $C_1$-$C_3$ alkyl, or $R^{32E}$-substituted or unsubstituted aryl. In embodiments, $R^{32}$ is $R^{32E}$-substituted or unsubstituted aryl (e.g., $C_6$-$C_{10}$ aryl, $C_{10}$ aryl, or phenyl). In embodiments, $R^{32}$ is $R^{32E}$-substituted or unsubstituted phenyl. In embodiments, $R^{32}$ is $R^{32E}$-substituted or unsubstituted $C_1$-$C_3$ alkyl. In embodiments, $R^{32}$ is $R^{32E}$-substituted or unsubstituted $C_1$-$C_3$ alkyl, or $R^{32E}$-substituted or unsubstituted aryl. In embodiments, $R^{32}$ is $R^{32E}$-substituted or unsubstituted aryl (e.g., $C_6$-$C_{10}$ aryl, $C_{10}$ aryl, or phenyl). In embodiments, $R^{32}$ is $R^{32E}$-substituted or unsubstituted phenyl. In embodiments, $R^{32}$ is $R^{32E}$-substituted or unsubstituted $C_1$-$C_3$ alkyl.

$R^{32E}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{32F}$-substituted or unsubstituted alkyl (e.g., $C_1$-$C_8$ alkyl, $C_1$-$C_6$ alkyl, or $C_1$-$C_4$ alkyl), $R^{32F}$-substituted or unsubstituted heteroalkyl (e.g., 2 to 8 membered heteroalkyl, 2 to 6 membered heteroalkyl, or 2 to 4 membered heteroalkyl), $R^{32F}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32F}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32F}$-substituted or unsubstituted aryl (e.g., $C_6$-$C_{10}$ aryl, $C_{10}$ aryl, or phenyl), or $R^{32F}$-substituted or unsubstituted heteroaryl (e.g., 5 to 10 membered heteroaryl, 5 to 9 membered heteroaryl, or 5 to 6 membered heteroaryl).

$R^{32F}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, $R^{33}$ is hydrogen, halogen, substituted or unsubstituted $C_1$-$C_3$ alkyl, or substituted or unsubstituted aryl. In embodiments, $R^{33}$ is substituted or unsubstituted aryl (e.g., $C_6$-$C_{10}$ aryl, $C_{10}$ aryl, or phenyl). In embodiments, $R^{33}$ is halogen. In embodiments, $R^{33}$ is substituted or unsubstituted phenyl. In embodiments, $R^{33}$ is unsubstituted phenyl. In embodiments, $R^{33}$ is $R^{33E}$-substituted or unsubstituted $C_1$-$C_3$ alkyl. In embodiments, $R^{33}$ is unsubstituted $C_1$-$C_3$ alkyl. In embodiments, $R^2$ is an unsubstituted $C_3$ alkyl. In embodiments, $R^{33}$ is —Cl. In embodiments, $R^{33}$ is —F. In embodiments, $R^{33}$ is —CH$_3$. In embodiments, $R^{33}$ is hydrogen.

In embodiments, $R^{33}$ is hydrogen, halogen, $R^{33E}$-substituted or unsubstituted $C_1$-$C_3$ alkyl, or $R^{33E}$-substituted or unsubstituted aryl. In embodiments, $R^{33}$ is halogen, $R^{33E}$-substituted or unsubstituted $C_1$-$C_3$ alkyl, or $R^{33E}$-substituted or unsubstituted aryl. In embodiments, $R^{33}$ is $R^{33E}$-substituted or unsubstituted aryl (e.g., $C_6$-$C_{10}$ aryl, $C_{10}$ aryl, or phenyl). In embodiments, $R^{33}$ is $R^{33E}$-substituted or unsubstituted phenyl. In embodiments, $R^{33}$ is $R^{33E}$-substituted or unsubstituted $C_1$-$C_3$ alkyl. In embodiments, $R^{33}$ is halogen, $R^{33E}$-substituted or unsubstituted $C_1$-$C_3$ alkyl, or $R^{33E}$-substituted or unsubstituted aryl. In embodiments, $R^{33}$ is $R^{33E}$-substituted or unsubstituted aryl (e.g., $C_6$-$C_{10}$ aryl, $C_{10}$ aryl, or phenyl). In embodiments, $R^{33}$ is $R^{33E}$-substituted or unsubstituted phenyl. In embodiments, $R^{33}$ is $R^{33E}$-substituted or unsubstituted $C_1$-$C_3$ alkyl.

$R^{33E}$ is independently oxo, halogen, —CCl$_3$, —CBr$_3$, —CF$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{33F}$-substituted or unsubstituted alkyl (e.g., $C_1$-$C_8$, $C_1$-$C_6$, or $C_1$-$C_4$ alkyl), $R^{33F}$-substituted or unsubstituted heteroalkyl (e.g., 2 to 8 membered, 2 to 6 membered, or 2 to 4 membered), $R^{33F}$-substituted or unsubstituted cycloalkyl (e.g., $C_3$-$C_8$, $C_3$-$C_6$, or $C_5$-$C_6$ cycloalkyl), $R^{33F}$-substituted or unsubstituted heterocycloalkyl (e.g., 3 to 8 membered, 3 to 6 membered, or 5 to 6 membered heterocycloalkyl), $R^{33F}$-substituted or unsubstituted aryl (e.g., $C_6$-$C_{10}$ aryl, $C_{10}$ aryl, or phenyl), or $R^{33F}$-substituted or unsubstituted heteroaryl (e.g., 5 to 10 membered, 5 to 9 membered, or 5 to 6 membered heteroaryl).

$R^{33F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_5$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{25}$ may be hydrogen, $R^{25E}$-substituted or unsubstituted alkyl (e.g., $C_1$-$C_8$, $C_1$-$C_6$, or $C_1$-$C_4$ alkyl), $R^{25E}$-substituted or unsubstituted heteroalkyl (e.g., 2 to 8 membered, 2 to 6 membered, or 2 to 4 membered heteroalkyl), $R^{2E}$-substituted or unsubstituted aryl (e.g., $C_6$-$C_{10}$, $C_{10}$ aryl, or phenyl), or $R^{25E}$-substituted or unsubstituted heteroaryl (e.g., 5 to 10 membered, 5 to 9 membered, or 5 to 6 membered heteroaryl). $R^{25}$ may be $R^{25E}$-substituted or unsubstituted alkyl (e.g., $C_1$-$C_8$, $C_1$-$C_6$, or $C_1$-$C_4$ alkyl), $R^{25E}$-substituted or unsubstituted heteroalkyl (e.g., 2 to 8 membered, 2 to 6 membered, or 2 to 4 membered heteroalkyl), $R^{25E}$-substituted or unsubstituted aryl (e.g., $C_6$-$C_{10}$, $C_{10}$ aryl, or phenyl), or $R^{25E}$-substituted or unsubstituted heteroaryl (e.g., 5 to 10 membered, 5 to 9 membered, or 5 to 6 membered heteroaryl).

In embodiments, $R^{25}$ is $R^{25E}$-substituted or unsubstituted alkyl, $R^{25E}$-substituted or unsubstituted heteroalkyl, $R^{25E}$-substituted or unsubstituted aryl, or $R^{25E}$-substituted or unsubstituted heteroaryl.

In embodiments, $R^{25}$ is $R^{25E}$-substituted or unsubstituted alkyl (e.g., $C_1$-$C_8$ alkyl, $C_1$-$C_6$ alkyl, or $C_1$-$C_4$ alkyl). In embodiments, $R^{25}$ is $R^{25E}$-substituted alkyl (e.g., $C_1$-$C_8$ alkyl, $C_1$-$C_6$ alkyl, or $C_1$-$C_4$ alkyl). In embodiments, $R^{25}$ is an unsubstituted alkyl (e.g., $C_1$-$C_8$ alkyl, $C_1$-$C_6$ alkyl, or $C_1$-$C_4$ alkyl).

In embodiments, $R^{25}$ is $R^{25E}$-substituted or unsubstituted heteroalkyl (e.g., 2 to 8 membered heteroalkyl, 2 to 6 membered heteroalkyl, or 2 to 4 membered heteroalkyl). In embodiments, $R^{25}$ is $R^{25E}$-substituted heteroalkyl (e.g., 2 to 8 membered heteroalkyl, 2 to 6 membered heteroalkyl, or 2 to 4 membered heteroalkyl). In embodiments, $R^{25}$ is an unsubstituted heteroalkyl (e.g., 2 to 8 membered heteroalkyl, 2 to 6 membered heteroalkyl, or 2 to 4 membered heteroalkyl).

In embodiments, $R^{25}$ is $R^{25E}$-substituted or unsubstituted aryl (e.g., $C_6$-$C_{10}$ aryl, $C_{10}$ aryl, or phenyl). In embodiments, $R^{25}$ is $R^{25E}$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^{25}$ is $R^{25E}$-substituted or unsubstituted heteroaryl (e.g., 5 to 10 membered heteroaryl, 5 to 9 membered heteroaryl, or 5 to 6 membered heteroaryl). In embodiments, $R^{25}$ is $R^{25E}$-substituted heteroaryl (e.g., 5 to 10 membered heteroaryl, 5 to 9 membered heteroaryl, or 5 to 6 membered heteroaryl). In embodiments, $R^{25}$ is an unsubstituted heteroaryl (e.g., 5 to 10 membered heteroaryl, 5 to 9 membered heteroaryl, or 5 to 6 membered heteroaryl).

$R^{25E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{25F}$-substituted or unsubstituted alkyl (e.g., $C_1$-$C_8$ alkyl, $C_1$-$C_6$ alkyl, or $C_1$-$C_4$ alkyl), $R^{25F}$-substituted or unsubstituted heteroalkyl (e.g., 2 to 8 membered heteroalkyl, 2 to 6 membered heteroalkyl, or 2 to 4 membered heteroalkyl), $R^{25F}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25F}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25F}$-substituted or unsubstituted aryl (e.g., $C_6$-$C_{10}$ aryl, $C_{10}$ aryl, or phenyl), or $R^{25F}$-substituted or unsubstituted heteroaryl (e.g., 5 to 10 membered heteroaryl, 5 to 9 membered heteroaryl, or 5 to 6 membered heteroaryl).

$R^{25F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{26}$ may be hydrogen, $R^{26E}$-substituted or unsubstituted alkyl (e.g., $C_1$-$C_8$, $C_1$-$C_6$, or $C_1$-$C_4$ alkyl), $R^{26E}$-substituted or unsubstituted heteroalkyl (e.g., 2 to 8 membered, 2 to 6 membered, or 2 to 4 membered heteroalkyl), $R^{26E}$-substituted or unsubstituted aryl (e.g., $C_6$-$C_{10}$, $C_{10}$ aryl, or phenyl), or $R^{26E}$-substituted or unsubstituted heteroaryl (e.g., 5 to 10 membered, 5 to 9 membered, or 5 to 6 membered heteroaryl). $R^{26}$ may be $R^{26E}$-substituted or unsubstituted alkyl (e.g., $C_1$-$C_8$, $C_1$-$C_6$, or $C_1$-$C_4$ alkyl), $R^{26E}$-substituted or unsubstituted heteroalkyl (e.g., 2 to 8 membered, 2 to 6 membered, or 2 to 4 membered heteroalkyl), $R^{26E}$-substituted or unsubstituted aryl (e.g., $C_6$-$C_{10}$, $C_{10}$ aryl, or phenyl), or $R^{26E}$-substituted or unsubstituted heteroaryl (e.g., 5 to 10 membered, 5 to 9 membered, or 5 to 6 membered heteroaryl).

In embodiments, $R^{26}$ is $R^{26E}$-substituted or unsubstituted alkyl(e.g., $C_1$-$C_8$ alkyl, $C_1$-$C_6$ alkyl, or $C_1$-$C_4$ alkyl). In embodiments, $R^{26}$ is $R^{26E}$-substituted alkyl (e.g., $C_1$-$C_8$ alkyl, $C_1$-$C_6$ alkyl, or $C_1$-$C_4$ alkyl). In embodiments, $R^{26}$ is an unsubstituted alkyl (e.g., $C_1$-$C_8$ alkyl, $C_1$-$C_6$ alkyl, or $C_1$-$C_4$ alkyl).

In embodiments, $R^{26}$ is $R^{26E}$-substituted or unsubstituted heteroalkyl (e.g., 2 to 8 membered heteroalkyl, 2 to 6 membered heteroalkyl, or 2 to 4 membered heteroalkyl). In embodiments, $R^{26}$ is $R^{26E}$-substituted heteroalkyl (e.g., 2 to 8 membered heteroalkyl, 2 to 6 membered heteroalkyl, or 2 to 4 membered heteroalkyl). In embodiments, $R^{26}$ is an unsubstituted heteroalkyl (e.g., 2 to 8 membered heteroalkyl, 2 to 6 membered heteroalkyl, or 2 to 4 membered heteroalkyl).

In embodiments, $R^{26}$ is $R^{26E}$-substituted or unsubstituted aryl (e.g., $C_6$-$C_{10}$ aryl, $C_{10}$ aryl, or phenyl). In embodiments, $R^{26}$ is $R^{26E}$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^{26}$ is $R^{26E}$-substituted or unsubstituted heteroaryl (e.g., 5 to 10 membered heteroaryl, 5 to 9 membered heteroaryl, or 5 to 6 membered heteroaryl). In embodiments, $R^{26}$ is $R^{26E}$-substituted heteroaryl (e.g., 5 to 10 membered heteroaryl, 5 to 9 membered heteroaryl, or 5 to 6 membered heteroaryl). In embodiments, $R^{26}$ is an unsubstituted heteroaryl (e.g., 5 to 10 membered heteroaryl, 5 to 9 membered heteroaryl, or 5 to 6 membered heteroaryl).

$R^{26E}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{26F}$-substituted or unsubstituted alkyl (e.g., $C_1$-$C_8$ alkyl, $C_1$-$C_6$ alkyl, or $C_1$-$C_4$ alkyl), $R^{26F}$-substituted or unsubstituted heteroalkyl (e.g., 2 to 8 membered heteroalkyl, 2 to 6 membered heteroalkyl, or 2 to 4 membered heteroalkyl), $R^{26F}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26F}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26F}$-substituted or unsubstituted aryl (e.g., $C_6$-$C_{10}$ aryl, $C_{10}$ aryl, or phenyl), or $R^{26F}$-substituted or unsubstituted heteroaryl (e.g., 5 to 10 membered heteroaryl, 5 to 9 membered heteroaryl, or 5 to 6 membered heteroaryl).

$R^{26F}$ is independently oxo, halogen, —$CCl_3$, —$CBr_3$, —$CF_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —$N_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{16A}$, $R^{16B}$, $R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$ and $R^{20D}$ are independently hydrogen, hydrogen, —$CX_3$, —CN, —COOH, —$CONH_2$, —$CHX_2$, —$CH_2X$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$$R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{16A}$, $R^{16B}$, $R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$, and $R^{20D}$ are independently hydrogen, —$CX_3$, —CN, —COOH, —$CONH_2$, —$CHX_2$, —$CH_2X$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{7B}$ and $R^{7C}$, $R^{8B}$ and $R^{8C}$, $R^{9B}$ and $R^{9C}$, $R^{10B}$ and $R^{10C}$, $R^{11B}$ and $R^{11C}$, $R^{16B}$ and $R^{16C}$, and $R^{18B}$ and $R^{18C}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{1A}$, $R^{1B}$, $R^{1C}$, $R^{1D}$, $R^{2A}$, $R^{2B}$, $R^{2C}$, $R^{2D}$, $R^{3A}$, $R^{3B}$$R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$$R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{16A}$, $R^{16B}$$R^{16C}$, $R^{16D}$, $R^{18A}$, $R^{18B}$, $R^{18C}$, $R^{18D}$, $R^{19A}$, $R^{19B}$, $R^{19C}$, $R^{19D}$, $R^{20A}$, $R^{20B}$, $R^{20C}$, and $R^{20D}$ are independently hydrogen.

In embodiments, the compound or pharmaceutically acceptable salt thereof, has the formula:

(XXII)

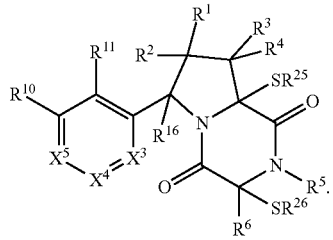

$R^1$, $R^2$, $R^3$, $R^4$, $R^5$, $R^6$, $R^{16}$, $R^{25}$ and $R^{26}$ are as described herein.

In embodiments, $X^3$ is —$CR^7$=. In embodiments, $X^3$ is —N=. $X^4$ is —N= or —$CR^8$—. In embodiments, $X^4$ is —$CR^8$=. In embodiments, $X^4$ is —N=. In embodiments, $X^5$ is —$CR^9$=. In embodiments, $X^5$ is —N=. In embodiments, $X^3$ is —$CR^7$= and $X^4$ is —N= and $X^5$ is —$CR^9$= and $R^7$, $R^{10}$ and $R^{11}$ are independently hydrogen and $R^9$ is —$OCH_3$. In embodiments, $X^3$ is —CH= and $X^4$ is —N= and $X^5$ is —CH= and $R^{10}$ and $R^{11}$ are independently hydrogen. In embodiments, $X^3$ is —$CR^7$= and $X^5$ is —$CR^9$=. In embodiments, $X^3$ is —CH= and $X^5$ is —CH=.

In embodiments, $R^7$ and $R^8$ are optionally joined to form a substituted or unsubstituted cycloalkyl or substituted or unsubstituted heterocycloalkyl having structural formula:

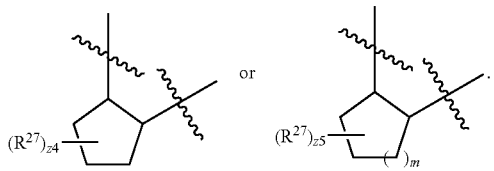

The symbols $R^{27}$ and z5 are as described herein. z4 may be an integer from 0 to 6.

In embodiments, $R^7$ and $R^8$ are optionally joined to form a substituted or unsubstituted cycloalkyl or substituted or unsubstituted heterocycloalkyl having structural formula:

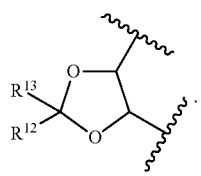

In embodiments, $R^7$ and $R^8$ are optionally joined to form a substituted or unsubstituted cycloalkyl or substituted or unsubstituted heterocycloalkyl having structural formula:

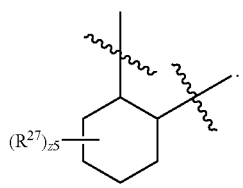

In embodiments, $R^8$ and $R^9$ are optionally joined to form a substituted or unsubstituted cycloalkyl or substituted or unsubstituted heterocycloalkyl having structural formula:

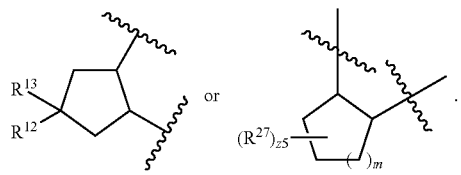

The symbols $R^{27}$ and z5 are as described herein. In embodiments, $R^8$ and $R^9$ are optionally joined to form a substituted or unsubstituted cycloalkyl or substituted or unsubstituted heterocycloalkyl having structural formula:

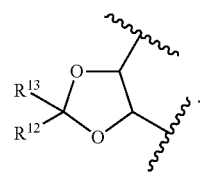

In embodiments, $R^8$ and $R^9$ are optionally joined to form a substituted or unsubstituted cycloalkyl or substituted or unsubstituted heterocycloalkyl having structural

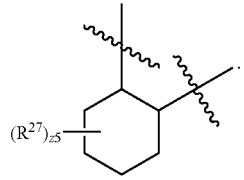

In embodiments, $R^7$ and $R^8$ are optionally joined to form a substituted or unsubstituted cycloalkyl or substituted or unsubstituted heterocycloalkyl having structural formula:

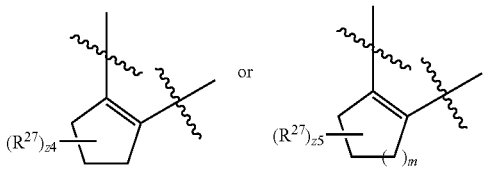

The symbols $R^{27}$ z4 and z5 are as described herein. In embodiments, $R^7$ and $R^8$ are optionally joined to form a substituted or unsubstituted cycloalkyl or substituted or unsubstituted heterocycloalkyl having structural formula:

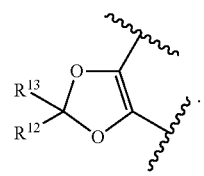

In embodiments, $R^7$ and $R^8$ are optionally joined to form a substituted or unsubstituted cycloalkyl or substituted or unsubstituted heterocycloalkyl having structural formula:

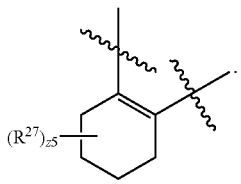

In embodiments, $R^8$ and $R^9$ are optionally joined to form a substituted or unsubstituted cycloalkyl or substituted or unsubstituted heterocycloalkyl having structural formula:

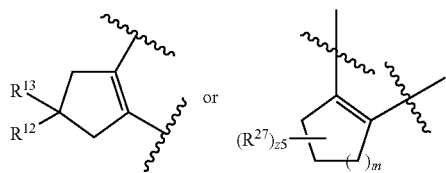

In embodiments, $R^8$ and $R^9$ are optionally joined to form a substituted or unsubstituted cycloalkyl or substituted or unsubstituted heterocycloalkyl having structural formula:

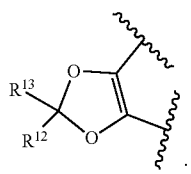

In embodiments, $R^8$ and $R^9$ are optionally joined to form a substituted or unsubstituted cycloalkyl or substituted or unsubstituted heterocycloalkyl having structural formula:

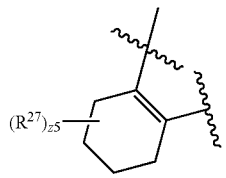

In embodiments, $L^1$ is a bond, —O—, —NH—, $R^{30}$-substituted or unsubstituted alkylene, $R^3$-substituted or unsubstituted heteroalkylene. In embodiments, $L^2$ is a bond, —O—, —NH—, $R^{31}$-substituted or unsubstituted alkylene, $R^{31}$-substituted or unsubstituted heteroalkylene.

$R^{30}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{30E}$-substituted or unsubstituted alkyl (e.g., C$_1$-C$_8$ alkyl, C$_1$-C$_6$ alkyl, or C$_1$-C$_4$ alkyl), $R^{30E}$-substituted or unsubstituted heteroalkyl (e.g., 2 to 8 membered heteroalkyl, 2 to 6 membered heteroalkyl, or 2 to 4 membered heteroalkyl), $R^{30E}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{30E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30E}$-substituted or unsubstituted aryl (e.g., C$_6$-C$_{10}$ aryl, C$_{10}$ aryl, or phenyl), or $R^{30E}$-substituted or unsubstituted heteroaryl (e.g., 5 to 10 membered heteroaryl, 5 to 9 membered heteroaryl, or 5 to 6 membered heteroaryl).

$R^{30B}$ may be hydrogen, or $R^{30E}$-substituted or unsubstituted alkyl (e.g., C$_1$-C$_8$ alkyl, C$_1$-C$_6$ alkyl, or C$_1$-C$_4$ alkyl). $R^{30B}$ may be $R^{30E}$-substituted or unsubstituted alkyl (e.g., C$_1$-C$_8$ alkyl, C$_1$-C$_6$ alkyl, or C$_1$-C$_4$ alkyl). $R^{3B}$ may be $R^{30E}$-substituted alkyl (e.g., C$_1$-C$_5$ alkyl, C$_1$-C$_6$ alkyl, or C$_1$-C$_4$ alkyl). $R^{30B}$ may be unsubstituted alkyl (e.g., C$_1$-C$_8$ alkyl, C$_1$-C$_6$ alkyl, or C$_1$-C$_4$ alkyl). In embodiments, $R^{30B}$ is hydrogen, or $R^{30E}$-substituted or unsubstituted C$_1$-C$_4$ alkyl. In embodiments, $R^{30B}$ is hydrogen, or $R^{30E}$-substituted or unsubstituted C$_1$-C$_3$ alkyl. In embodiments, $R^{30B}$ is hydrogen. In embodiments, $R^{30B}$ is $R^{30E}$-substituted C$_1$-C$_3$ alkyl. In embodiments, $R^{30B}$ is unsubstituted C$_1$-C$_3$ alkyl. In embodiments, $R^{30B}$ is hydrogen. In embodiments, $R^{30B}$ is —CH$_3$.

$R^{30E}$ is independently oxo, halogen, —CCl$_3$, —CBr$_3$, —CF$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{30F}$-substituted or unsubstituted alkyl (e.g., C$_1$-C$_8$ alkyl, C$_1$-C$_6$ alkyl, or C$_1$-C$_4$ alkyl), $R^{30F}$-substituted or unsubstituted heteroalkyl (e.g., 2 to 8 membered heteroalkyl, 2 to 6 membered heteroalkyl, or 2 to 4 membered heteroalkyl), $R^{30F}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{30F}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30F}$-substituted or unsubstituted aryl (e.g., C$_6$-C$_{10}$ aryl, C$_{10}$ aryl, or phenyl), or $R^{30F}$-substituted or unsubstituted heteroaryl (e.g., 5 to 10 membered heteroaryl, 5 to 9 membered heteroaryl, or 5 to 6 membered heteroaryl).

$R^{30F}$ is independently oxo, halogen, —CCl$_3$, —CBr$_3$, —CF$_3$, —C$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

$R^{31}$ is independently oxo, halogen, —CCl₃, —CBr₃, —CF₃, —CI₃, —CHF₂, —CHCl₂, —CHBr₂, —CHI₂, —CH₂F, —CH₂Cl, —CH₂Br, —CH₂I, —N₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHF₂, —OCHCl₂, —OCHBr₂, —OCHI₂, —OCH₂F, —OCH₂Cl, —OCH₂Br, —OCH₂I, $R^{31E}$-substituted or unsubstituted alkyl (e.g., $C_1$-$C_8$ alkyl, $C_1$-$C_6$ alkyl, or $C_1$-$C_4$ alkyl), $R^{31E}$-substituted or unsubstituted heteroalkyl (e.g., 2 to 8 membered heteroalkyl, 2 to 6 membered heteroalkyl, or 2 to 4 membered heteroalkyl), $R^{31E}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31E}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31E}$-substituted or unsubstituted aryl (e.g., $C_6$-$C_{10}$ aryl, $C_{10}$ aryl, or phenyl), or $R^{3E}$-substituted or unsubstituted heteroaryl (e.g., 5 to 10 membered heteroaryl, 5 to 9 membered heteroaryl, or 5 to 6 membered heteroaryl).

$R^{31B}$ may be hydrogen, or $R^{31E}$-substituted or unsubstituted alkyl (e.g., $C_1$-$C_8$ alkyl, $C_1$-$C_6$ alkyl, or $C_1$-$C_4$ alkyl). $R^{31B}$ may be $R^{31E}$-substituted or unsubstituted alkyl (e.g., $C_1$-$C_8$ alkyl, $C_1$-$C_6$ alkyl, or $C_1$-$C_4$ alkyl). $R^{31B}$ may be $R^{31E}$-substituted alkyl (e.g., $C_1$-$C_8$ alkyl, $C_1$-$C_6$ alkyl, or $C_1$-$C_4$ alkyl). $R^{31B}$ may be unsubstituted alkyl (e.g., $C_1$-$C_8$ alkyl, $C_1$-$C_6$ alkyl, or $C_1$-$C_4$ alkyl). In embodiments, $R^{31B}$ is hydrogen, or $R^{31E}$-substituted or unsubstituted $C_1$-$C_4$ alkyl. In embodiments, $R^{31B}$ is hydrogen, or $R^{3E}$-substituted or unsubstituted $C_1$-$C_3$ alkyl. In embodiments, $R^{31B}$ is hydrogen. In embodiments, $R^{31B}$ is $R^{31E}$-substituted $C_1$-$C_3$ alkyl. In embodiments, $R^{31B}$ is unsubstituted $C_1$-$C_3$ alkyl. In embodiments, $R^{31B}$ is hydrogen. In embodiments, $R^{31B}$ is —CH₃.

$R^{31E}$ is independently oxo, halogen, —CCl₃, —CBr₃, —CF₃, —C₃, —CHF₂, —CHCl₂, —CHBr₂, —CHI₂, —CH₂F, —CH₂Cl, —CH₂Br, —CH₂I, —N₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCl₃, —OCHF₂, —OCHCl₂, —OCHBr₂, —OCHI₂, —OCH₂F, —OCH₂Cl, —OCH₂Br, —OCH₂I, $R^{31F}$-substituted or unsubstituted alkyl (e.g., $C_1$-$C_8$ alkyl, $C_1$-$C_6$ alkyl, or $C_1$-$C_4$ alkyl), $R^{31F}$-substituted or unsubstituted heteroalkyl (e.g., 2 to 8 membered heteroalkyl, 2 to 6 membered heteroalkyl, or 2 to 4 membered heteroalkyl), $R^{31F}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31F}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31F}$-substituted or unsubstituted aryl (e.g., $C_6$-$C_{10}$ aryl, $C_{10}$ aryl, or phenyl), or $R^{31F}$-substituted or unsubstituted heteroaryl (e.g., 5 to 10 membered heteroaryl, 5 to 9 membered heteroaryl, or 5 to 6 membered heteroaryl).

$R^{31F}$ is independently oxo, halogen, —CCl₃, —CBr₃, —CF₃, —C₃, —CHF₂, —CHCl₂, —CHBr₂, —CHI₂, —CH₂F, —CH₂Cl, —CH₂Br, —CH₂I, —N₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCl₃, —OCHF₂, —OCHCl₂, —OCHBr₂, —OCHI₂, —OCH₂F, —OCH₂Cl, —OCH₂Br, —OCH₂I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

In embodiments, the compound or pharmaceutically acceptable salt has the formula having the formula:

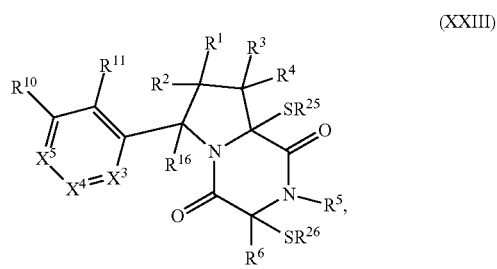

(XXIII)

wherein $X^3$, $X^4$, $X^5$, $R^1$, $R^2$, $R^3$, $R^4$, $R^5$, $R^6$, $R^{10}$, $R^{11}$, $R^{16}$, $R^{25}$ and $R^{26}$ are as described herein.

$R^{16}$ is hydrogen, halogen, —CF₃, —CCl₃, —CBr₃, —CI₃, —CN, —CHO, —COOR¹⁶ᴬ, —CONR¹⁶ᴮR¹⁶ᶜ, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^1$ is hydrogen, halogen, —N₃, —CF₃, —CCl₃, —CBr₃, —CI₃, —CN, —CHO, —OR¹ᴬ, —NR¹ᴮR¹ᶜ, —COOR¹ᴬ, —CONR¹ᴮR¹ᶜ, —NO₂, —SR¹ᴰ, —SO$_n$R¹ᴮ, —SO$_{v1}$NR¹ᴮR¹ᶜ, —NHNR¹ᴮR¹ᶜ, ONR¹ᴮR¹ᶜ, —NHC(O)NHNR¹ᴮR¹ᶜ, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^1$ is —CN. In embodiments, $R^1$ is —CN and $R^{1.2}$ is an unsubstituted $C_1$-$C_3$ alkyl. In embodiments, $R^1$ is —CN and $R^{1.2}$ is methyl. In embodiments, $R^1$ is hydrogen, —CN, —CHO, —OR¹ᴬ, —NR¹ᴮR¹ᶜ, —C(O)OR¹ᴬ, —C(O)NR¹ᴮR¹ᶜ, —NO₂, —SR¹ᴰ, —S(O)$_n$R¹ᴮ, —SO$_{v1}$NR¹ᴮR¹ᶜ, —R¹ᴮR¹ᶜ, ONR¹ᴮR¹ᶜ, —NHC(O)NHNR¹ᴮR¹ᶜ, or substituted or unsubstituted alkyl. In embodiments, $R^1$ is hydrogen, —CN, —CHO, —OCH₃, —N(CH₃)₂, —NH₂, —C(O)OCH₃, —S(O)₂R¹ᴮ, or substituted or unsubstituted alkyl. In embodiments, $R^1$ is —C(O)

$OR^{1A}$ wherein $R^{1A}$ is substituted or unsubstituted alkyl (e.g., $C_1$-$C_8$ alkyl, $C_1$-$C_6$ alkyl, or $C_1$-$C_4$ alkyl). In embodiments, $R^1$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

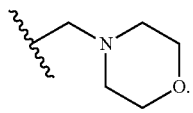 [SMILES: *CN1CCOCC1]

In embodiments, $R^1$ is hydrogen. In embodiments, $R^1$ is —$CH_3$. In embodiments, $R^1$ is —$N(CH_3)_2$. In embodiments, $R^1$ is —CN. In embodiments, R is —$CH_2OCH_3$. In embodiments, $R^1$ is —$C(O)OCH_3$. In embodiments, $R^1$ is —$C(O)OCH_2CH_2CH_2CH_3$. In embodiments, $R^1$ is —$C(O)OC(CH_3)_4$. In embodiments, $R^1$ is

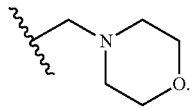 [SMILES: *CN1CCOCC1]

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$, —$COOR^{2A}$, —$CONR^{2B}R^{2C}$, —$NO_2$, —$SR^{2D}$, —$SO_{n2}R^{2B}$, —$SO_{v2}NR^{2B}R^{2C}$, —$NHNR^{2B}R^{2C}$, —$ONR^{2B}R^{2C}$, —$NHC(O)NHNR^{2B}R^{2C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^2$ is —CN. In embodiments, $R^2$ is an unsubstituted $C_1$-$C_3$ alkyl. In embodiments, $R^2$ is hydrogen, —CN, —CHO, —$OR^{2A}$, —$NR^{2B}R^{2C}$, —$C(O)OR^{2A}$, $C(O)NR^{2B}R^{2C}$—$NO_2$, —$SR^{2D}$, —$S(O)_{n1}R^{2B}$, —$SO_{v1}NR^{2B}R^{2C}$, —$NHNR^{2B}R^{2C}$, $ONR^{2B}R^{2C}$, —$NHC(O)NHNR^{2B}R^{2C}$, or substituted or unsubstituted alkyl. In embodiments, $R^2$ is hydrogen, —CN, —CHO, —$OCH_3$, —$N(CH_3)_2$, —$NH_2$, —$C(O)OCH_3$, —$S(O)_2R^{2B}$, or substituted or unsubstituted alkyl. In embodiments, $R^2$ is —$C(O)OR^{2A}$ wherein $R^{2A}$ is substituted or unsubstituted alkyl (e.g., $C_1$-$C_8$ alkyl, $C_1$-$C_6$ alkyl, or $C_1$-$C_4$ alkyl). In embodiments, $R^2$ is hydrogen, —$CH_3$, —$N(CH_3)_2$, —CN, —$CH_2OCH_3$, —$C(O)OCH_3$, —$C(O)OCH_2CH_2CH_2CH_3$, —$C(O)OC(CH_3)_4$, or

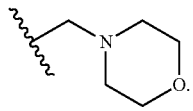 [SMILES: *CN1CCOCC1]

In embodiments, $R^2$ is hydrogen. In embodiments, $R^2$ is —$CH_3$. In embodiments, $R^2$ is —$N(CH_3)_2$. In embodiments, $R^2$ is —CN. In embodiments, $R^2$ is —$CH_2OCH_3$. In embodiments, $R^2$ is —$C(O)OCH_3$. In embodiments, $R^2$ is —$C(O)OCH_2CH_2CH_2CH_3$. In embodiments, $R^2$ is —$C(O)OC(CH_3)_4$. In embodiments, $R^2$ is

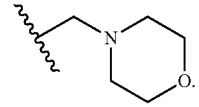

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_{n3}R^{3B}$, —$SO_{v3}NR^{3B}R^{3C}$, —$NHNR^{3B}R^{3C}$, —$ONR^{3B}R^{3C}$, —$NHC(O)NHNR^{3B}R^{3C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^4$ is hydrogen, halogen, —$N_3$, —$CF_3$, —$CCl_3$, —$CBr_3$, —$CI_3$, —CN, —CHO, —$OR^{4A}$, —$NR^{4B}R^{4C}$, —$COOR^{4A}$, —$CONR^{4B}R^{4C}$, —$NO_2$, —$SR^{4D}$, —$SO_{n4}R^{4B}$, —$SO_{v4}NR^{4B}R^{4C}$, —$NHNR^{4B}R^{4C}$, —$ONR^{4B}R^{4C}$, —$NHC(O)NHNR^{4B}R^{4C}$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the compound has the formula:

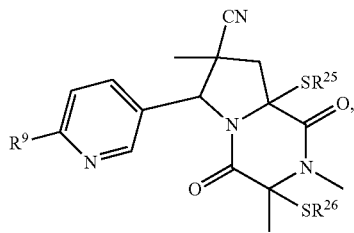

(XXX)

wherein $R^{12}$, $R^{25}$, and $R^{26}$ are as described herein. In embodiments, $R^{25}$ and $R^{26}$ are independently —$C(O)CH_3$. In embodiments, $R^{25}$ and $R^{26}$ are both —$C(O)CH_3$. In embodiments, $R^9$ is —$OCH_3$. In embodiments, $R^{25}$ and $R^{26}$ are independently —$C(O)CH_3$, —$C(O)OPh$, —$C(O)CH_2OCH_3$, $C(O)NHPh$, or —$C(S)OPh$.

In embodiments, the compound has the formula:

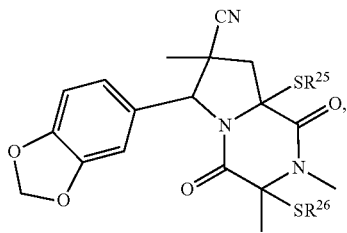

(XXXI)

wherein $R^{25}$ and $R^{26}$ are as described herein. In embodiments, $R^{25}$ and $R^{26}$ are independently —C(O)CH$_3$. In embodiments, $R^{25}$ and $R^{26}$ are both —C(O)CH$_3$. In embodiments, $R^{25}$ and $R^{26}$ are independently —C(O)CH$_3$, —C(O)OPh, —C(O)CH$_2$OCH$_3$, C(O)NHPh, or —C(S)OPh.

In embodiments, the compound or pharmaceutically acceptable salt thereof, has the formula:

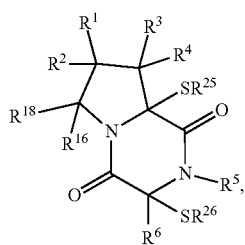

(XXI')

wherein $R^1$, $R^2$, $R^3$, $R^4$, $R^5$, $R^6$, $R^{16}$, $R^{18}$, $R^{25}$ and $R^{26}$ are as described herein, or a pharmaceutically acceptable salt thereof.

In embodiments, $R^1$ is hydrogen, halogen, —N$_3$, —CF$_3$, —CCl$_3$, —CBr$_3$, —CI$_3$, —CN, —CHO, —OR$^{1A}$, —NR$^{1B}$R$^{1C}$, —COOR$^{1A}$, —CONR$^{1B}$R$^{1C}$, —NO$_2$, —SR$^{1D}$, —SO$_{n1}$R$^{1B}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is hydrogen, halogen, —N$_3$, —CF$_3$, —CCl$_3$, —CBr$_3$, —CI$_3$, —CN, —CHO, —OR$^{2A}$, —NR$^{2B}$R$^{2C}$, —COOR$^{2A}$, —CONR$^{2B}$R$^{2C}$, —NO$_2$, —SR$^{2D}$, —SO$_{n2}$R$^{2B}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is hydrogen, halogen, —N$_3$, —CF$_3$, —CCl$_3$, —CBr$_3$, —CI$_3$, —CN, —CHO, —OR$^{3A}$, —NR$^{3B}$R$^{3C}$, —COOR$^{1A}$, —CONR$^{3B}$R$^{3C}$, —NO$_2$, —SR$^{3D}$, —SO$_{n3}$R$^{3B}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, halogen, —N$_3$, —CF$_3$, —CCl$_3$, —CBr$_3$, —CI$_3$, —CN, —CHO, —OR$^{4A}$, —NR$^{4B}$R$^{4C}$, —COOR$^{4A}$, —CONR$^{4B}$R$^{4C}$, —NO$_2$, —SR$^{4D}$, —SO$_{n4}$R$^{4B}$, —SO$_{v4}$NR$^{4B}$R$^{4C}$, —NHNR$^{4B}$R$^{4C}$, —ONR$^{4B}$R$^{4C}$, —NHC(O)NHNR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{16}$ is hydrogen, halogen, —CF$_3$, —CCl$_3$, —CBr$_3$, —CI$_3$, —CN, —CHO, —COOR$^{6A}$, —CONR$^{16B}$R$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{16A}$, $R^{16B}$, and $R^{16C}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{16B}$ and $R^{16C}$, $R^{2B}$ and $R^{2C}$, $R^{1B}$ and $R^{1C}$, $R^{3B}$ and $R^{3C}$, and $R^{4B}$ and $R^{4C}$ substituents bonded to the same nitrogen atom may optionally be joined to form a substituted or unsubstituted heterocycloalkyl or substituted or unsubstituted heteroaryl;

In embodiments, $R^5$ is hydrogen, halogen, —N$_5$, —CF$_5$, —CCl$_5$, —CBr$_5$, —CI$_5$, —CN, —CHO, —OR$^{5A}$, —NR$^{5B}$R$^{5C}$, —COOR$^{5A}$, —CONR$^{5B}$R$^{5C}$, —NO$_2$, —SR$^{5D}$, —SO$_{n5}$R$^{5B}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^6$ is hydrogen, —CF$_3$, —CCl$_3$, —CBr$_3$, —CI$_3$, —CN, —CHO, —COOR$^{6A}$, —CONR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{25}$ is —C(O)-L$^1$-R$^{32}$ or —C(S)-L-R$^{32}$. In embodiments, $R^{26}$ is —C(O)-L$^2$-R$^3$ or —C(S)-L$^2$-R$^{33}$. In embodiments, $R^{25}$ and $R^{26}$ may optionally be joined to form

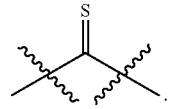

.

In embodiments, L is a bond, —O—, —NH—, substituted or unsubstituted alkylene, substituted or unsubstituted heteroalkylene. In embodiments, L$^2$ is a bond, —O—, —NH—, substituted or unsubstituted alkylene, substituted or unsubstituted heteroalkylene. In embodiments, $R^{32}$ and $R^{33}$ are independently hydrogen, halogen, substituted or unsubstituted C$_1$-C$_3$ alkyl, substituted or unsubstituted aryl. In embodiments, $R^{32}$ and $R^{33}$ are independently halogen, substituted or unsubstituted C$_1$-C$_3$ alkyl, substituted or unsubstituted aryl. In embodiments, $R^{18}$ is hydrogen, halogen, —N$_3$, —CF$_3$, —CCl$_3$, —CBr$_3$, —CI$_3$, —CN, —CHO, —OR$^{18A}$, —NR$^{18B}$R$^{18C}$, —C(O)OR$^{19A}$, C(O)NR$^{18B}$R$^{18C}$, —NO$_2$, —SR$^{18D}$, —S(O)$_{n18}$R$^{18B}$, —SO$_{v1}$NR$^{18B}$R$^{18C}$, —NHNR$^{18B}$R$^{18C}$, ONR$^{18B}$R$^{18C}$, —NHC(O)NHNR$^{18B}$R$^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{16A}$, $R^{16B}$, $R^{16C}$, $R^{18A}$, $R^{18B}$, $R^{18C}$, and $R^{18D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{7B}$ and $R^{7C}$, $R^{8B}$ and $R^{8C}$, $R^{9B}$ and $R^{9C}$, $R^{10B}$ and $R^{10C}$, $R^{11B}$ and $R^{11C}$, $R^{16B}$ and $R^{16C}$, and $R^{18B}$ and $R^{18C}$ substituents bonded to the same nitrogen atom may optionally be joined to form a substituted or unsubstituted heterocycloalkyl or substituted or unsubstituted heteroaryl. In embodiments, n1, n2, n3, n4, n5, n16, and n18 are independently an integer from 1 to 4; and v1, v2, v3, v4, n5, v16, and v18, and independently 1 or 2.

In embodiments, the compound or pharmaceutically acceptable salt thereof, has the formula:

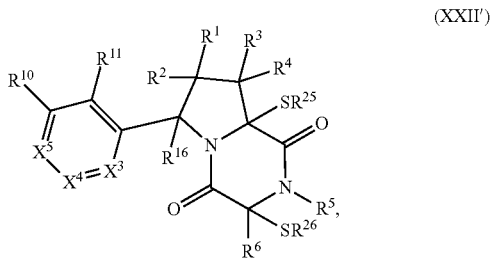

(XXII')

wherein $X^3$, $X^4$, $X^5$, $R^1$, $R^2$, $R^3$, $R^4$, $R^5$, $R^6$, $R^{10}$, $R^{11}$, $R^{16}$, $R^{25}$ and $R^{26}$ are as described herein, or a pharmaceutically acceptable salt thereof.

In embodiments, $X^3$ is $-N=$ or $-CR^7=$. In embodiments, $X^4$ is $-N=$ or $-CR^8=$. In embodiments, $X^5$ is $-N=$ or $-CR^9=$. In embodiments, $R^7$ is hydrogen, halogen, $-N_3$, $-CF_3$, $-CCl_3$, $-CBr_3$, $-CI_3$, $-CN$, $-CHO$, $-OR^{7A}$, $-NR^{7B}R^{7C}$, $-COOR^{7A}$, $-CONR^{7B}R^{7C}$, $-NO_2$, $-SR^{7D}$, $-SO_{n7}R^{7B}$, $-SO_{v7}NR^{7B}R^{7C}$, $-NR^{7B}R^{7C}$, $-ONR^{7B}R^{7C}$, $-NHC(O)NHNR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^8$ is hydrogen, halogen, $-N_3$, $-CF_3$, $-CCl_3$, $-CBr_3$, $-CI_3$, $-CN$, $-CHO$, $-OR^{8A}$, $-NR^{8B}R^{8C}$, $-COOR^{8A}$, $-CONR^{8B}R^{8C}$, $-NO_2$, $-SR^{8D}$, $-SO_{n8}R^{8B}$, $-SO_{v8}NR^{8B}R^{8C}$, $-NHNR^{8B}R^{8C}$, $-ONR^{8B}R^{8C}$, $-NHC(O)NHNR^{8B}R^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$ and $R^8$ may optionally be joined to form a substituted or unsubstituted cycloalkyl or substituted or unsubstituted heterocycloalkyl.

In embodiments, $R^9$ is hydrogen, halogen, $-N_3$, $-CF_3$, $-CCl_3$, $-CBr_3$, $-CI_3$, $-CN$, $-CHO$, $-OR^{9A}$, $-NR^{9B}R^{9C}$, $-COOR^{9A}$, $-CONR^{9B}R^{9C}$, $-NO_2$, $-SR^{9D}$, $-SO_{n9}R^{9B}$, $-SO_{v9}NR^{9B}R^{9C}$, $-NHNR^{9B}R^{9C}$, $-ONR^{9B}R^{9C}$, $-NHC(O)NHNR^{9B}R^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ and $R^9$ may optionally be joined to form a substituted or unsubstituted cycloalkyl, substituted or unsubstituted heterocycloalkyl.

In embodiments, $R^{10}$ is hydrogen, halogen, $-N_3$, $-CF_3$, $-CCl_3$, $-CBr_3$, $-CI_3$, $-CN$, $-CHO$, $-OR^{10A}$, $-NR^{10B}R^{10C}$, $-COOR^{10A}$, $-CONR^{10B}R^{10C}$, $-NO_2$, $-SR^{10D}$, $-SO_{n10}R^{10B}$, $-SO_{v10}NR^{10B}R^{10C}$, $-NHNR^{10B}R^{10C}$, $-ONR^{10B}R^{10C}$, $-NHC(O)NHNR^{10B}R^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{11}$ is hydrogen, halogen, $-N_3$, $-CF_3$, $-CCl_3$, $-CBr_3$, $-CI_3$, $-CN$, $-CHO$, $-OR^{11A}$, $-NR^{11B}R^{11C}$, $-COOR^{11A}$, $-CONR^{11B}R^{11C}$, $-NO_2$, $-SR^{11D}$, $-SO_{n11}R^{11B}$, $-SO_{v11}NR^{11B}R^{11C}$, $-NHNR^{11B}R^{11C}$, $-ONR^{11B}R^{11C}$, $-NHC(O)NHNR^{11B}R^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{7A}$, $R^{7B}$, $R^{7C}$, $R^{7D}$, $R^{8A}$, $R^{8B}$, $R^{8C}R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, and $R^{11D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{7B}$ and $R^{7C}$, $R^{8B}$ and $R^{8C}$, and $R^{9B}$ and $R^{9C}$, $R^{10B}$ and $R^{10C}$, and $R^{11B}$ and $R^{11C}$, substituents bonded to the same nitrogen atom may optionally be joined to form a substituted or unsubstituted heterocycloalkyl or substituted or unsubstituted heteroaryl. In embodiments, n7, n8, n9, n10, and n11 are independently an integer from 1 to 4. In embodiments, v7, v8, v9, v10 and v11 are independently 1 or 2.

In embodiments, the compound or pharmaceutically acceptable salt thereof, has the formula:

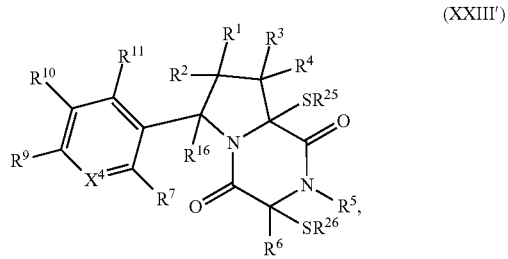

(XXIII')

wherein $X^4$, $R^1$, $R^2$, $R^3$, $R^4$, $R^5$, $R^6$, $R^7$, $R^9$, $R^{10}$, $R^{11}$, $R^{16}$, $R^{25}$ and $R^{26}$ are as described herein.

In some embodiments, $R^7$ and $R^8$ or $R^8$ and $R^9$ are optionally joined to form a substituted or unsubstituted cycloalkyl or substituted or unsubstituted heterocycloalkyl having structural formula:

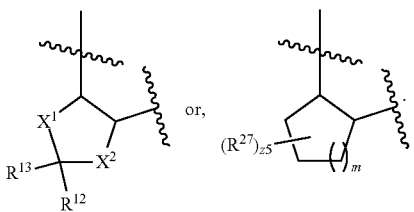

In some embodiments, $R^7$ and $R^8$ or $R^8$ and $R^9$ are optionally joined to form a substituted or unsubstituted cycloalkyl or substituted or unsubstituted heterocycloalkyl having structural formula:

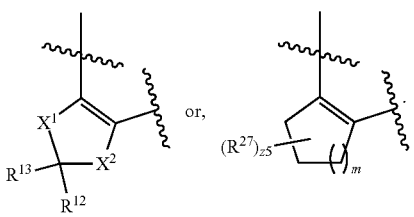

In embodiments, $X^1$ is —O—, —NR$^{21C}$—, or —S—. In embodiments, $X^2$ is —O—, —NR$^{22C}$—, or —S—. In embodiments, z5 is an integer from 0 to 8. In embodiments, m is 1 or 2.

In embodiments, $R^{12}$ and $R^{13}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound or pharmaceutically acceptable salt thereof, has the formula:

(XXXIII'(S))

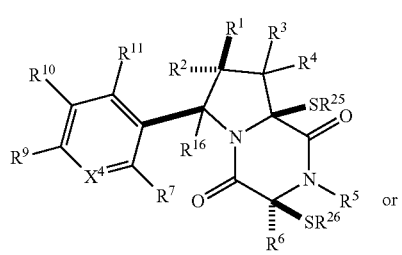

or (XXIII'(R))

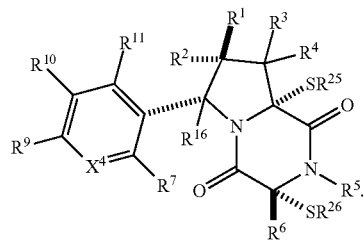

In embodiments, the compound or pharmaceutically acceptable salt thereof, has the formula:

(XXIV')

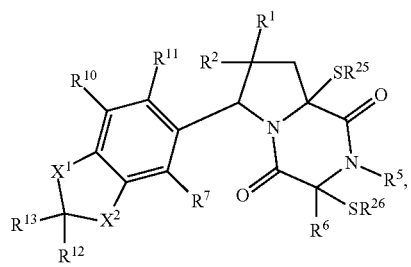

wherein $X^1$, $X^2$, $R^1$, $R^2$, R, $R^6$, $R^7$, $R^{10}$, $R^{11}$, $R^{12}$, $R^{13}$, $R^{25}$ and $R^{26}$ are as described herein.

In embodiments, the compound or pharmaceutically acceptable salt thereof, has the formula:

(XXIV'(S))

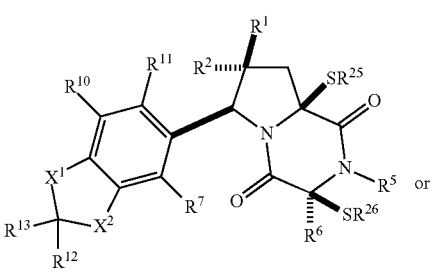

or (XXIV'(R))

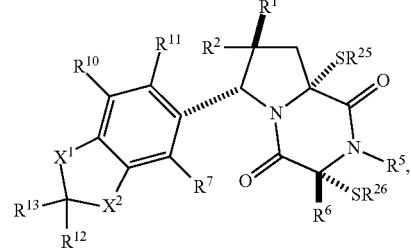

In embodiments, the compound or pharmaceutically acceptable salt thereof, has the formula:

(XXVI'(S))

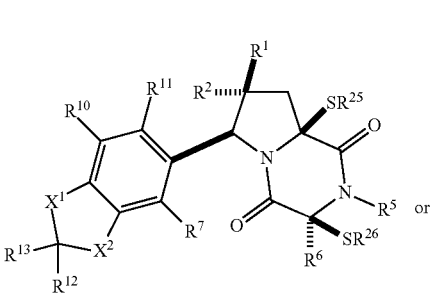

or

-continued

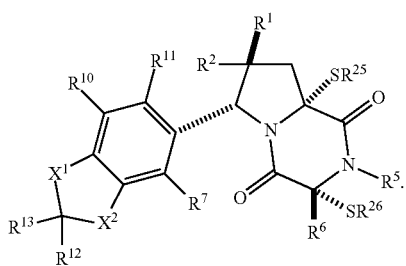
(XXVI'(R))

In embodiments the compound or pharmaceutically acceptable salt thereof, has the formula:

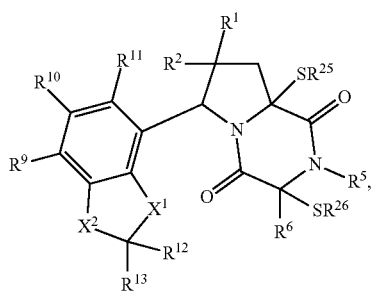
(XXV')

wherein $X^1$, $X^2$, $R^1$, $R^2$, $R^5$, $R^6$, $R^9$, $R^{10}$, $R^{11}$, $R^{12}$, $R^{13}$, $R^{25}$ and $R^{26}$ are as described herein.

In embodiments, the compound or pharmaceutically acceptable salt thereof, has the formula:

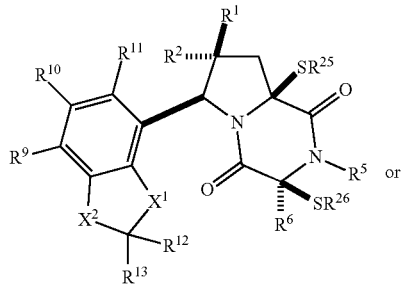
(XXV'(S))

or

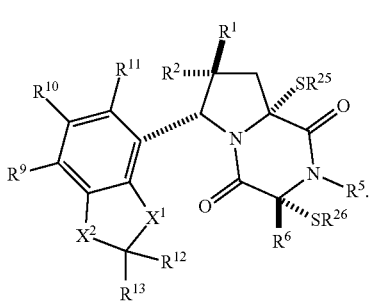
(XXV'(R))

In embodiments, the compound or pharmaceutically acceptable salt thereof, has the formula:

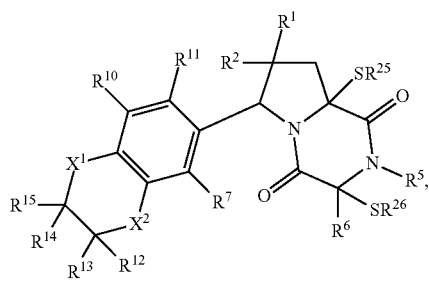
(XXVI')

wherein $X^1$, $X^2$, $R^1$, $R^2$, $R^5$, $R^6$, $R^7$, $R^{10}$, $R^{11}$, $R^{12}$, $R^{13}$, $R^{25}$ and $R^{26}$ are as described herein.

In embodiments, the compound or pharmaceutically acceptable salt thereof, has the formula:

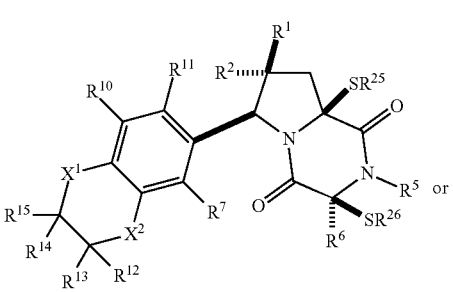
(XXVI'(S))

or

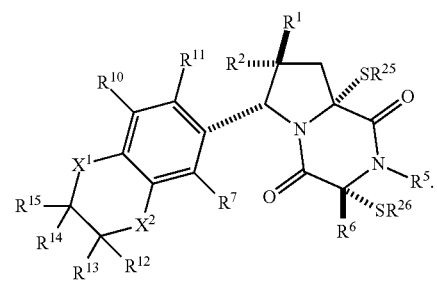
(XXVI'(R))

In embodiments, the compound or pharmaceutically acceptable salt thereof, has the formula:

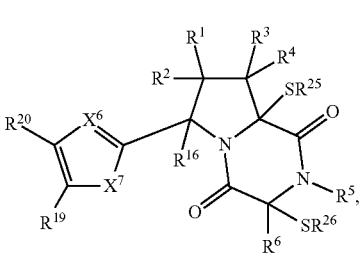
(XXVII')

wherein $X^6$, $X^7$, $R^1$, $R^2$, $R^3$, $R^4$, $R^5$, $R^6$, $R^{16}$, $R^{19}$, $R^{20}$, $R^{25}$ and $R^{26}$ are as described herein.

In embodiments, the compound or pharmaceutically acceptable salt thereof, has the formula:

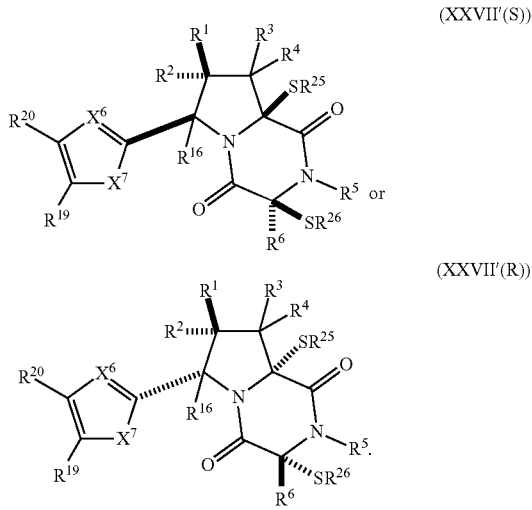

(XXVII'(S))

(XXVII'(R))

In some embodiments, $R^{10}$ and $R^{11}$ are independently hydrogen. In some embodiments, $X^4$ is —N=. In some embodiments, $R^9$ is —OCH$_3$. In some embodiments, $R^2$ is substituted or unsubstituted alkyl.

In some embodiments, $R^2$ is substituted or unsubstituted $C_1$-$C_3$ alkyl. In some embodiments, $R^2$ is methyl. In some embodiments, $R^1$ is —CN. In some embodiments, $R^{25}$ is —C(O)-L$^1$-R$^{32}$ or —C(S)-L$^1$-R$^{32}$; and $R^{26}$ is —C(O)-L$^2$-R$^{33}$ or —C(S)-L$^2$-R$^{33}$.

In some embodiments, $R^{25}$ is —C(O)-L$^1$-R$^{32}$; and $R^{26}$ is —C(O)-L$^2$-R$^{33}$.

In some embodiments, $R^{25}$ is —C(S)-L$^1$-R$^{32}$; and $R^{26}$ is —C(S)-L$^2$-R$^{33}$.

In some embodiments, $L^1$ and $L^2$ are independently —O—.

In some embodiments, $L^1$ and $L^2$ are independently —NH—.

In some embodiments, $L^1$ and $L^2$ are independently a bond.

In some embodiments, $L^1$ is -L$^{1A}$-L$^{1B}$, wherein L$^{1A}$ is bonded to —C(O)— or —C(S)—; and $L^2$ is -L$^{2A}$-L$^{2B}$-, wherein L$^{2A}$ is bonded to —C(O)— or —C(S)—; L$^{1A}$ is a bond or —(CH$_2$)$_{z1}$—; L$^{1B}$ is a bond, —O— or —NR$^{30B}$—. L$^{2A}$ is a bond or —(CH$_2$)$_{z2}$—; L$^{2B}$ is a bond, —O— or —NR$^{31B}$—; z1 and z2 are independently an integer from 1 to 10; and $R^{30}$ and $R^{31}$ are independently hydrogen or substituted or unsubstituted alkyl.

In some embodiments, L$^{1A}$ and L$^{2A}$ are independently —CH$_2$—.

In some embodiments, L$^{1B}$ is —NR$^{30B}$—, L$^{2B}$ is —NR$^{31B}$—; and R$^{30B}$ and R$^{31B}$ are independently unsubstituted $C_1$-$C_3$ alkyl.

In some embodiments, $R^{32}$ and $R^{33}$ are independently unsubstituted $C_1$-$C_3$ alkyl or unsubstituted aryl.

In some embodiments, $R^{32}$ and $R^{33}$ are independently unsubstituted aryl.

In some embodiments, $R^{32}$ and $R^{33}$ are independently halogen. In some embodiments, $R^{32}$ and $R^{33}$ are independently hydrogen.

In some embodiments, $R^{25}$ and $R^{26}$ are joined together to form:

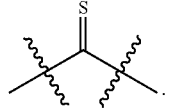

In some embodiments, $R^6$ is methyl.

In some embodiments, the compound or pharmaceutically acceptable salt thereof, has the structure:

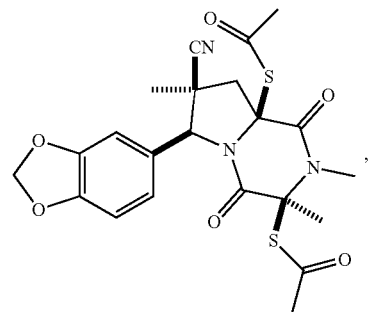

,

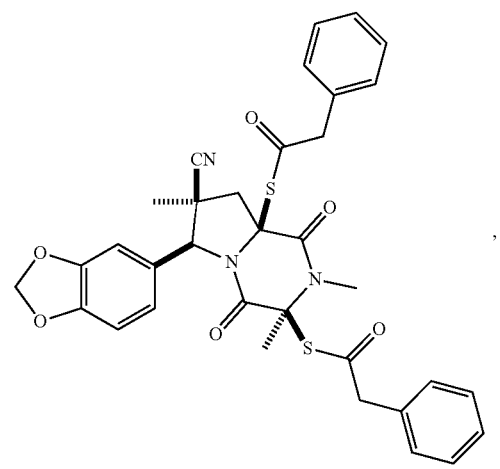

,

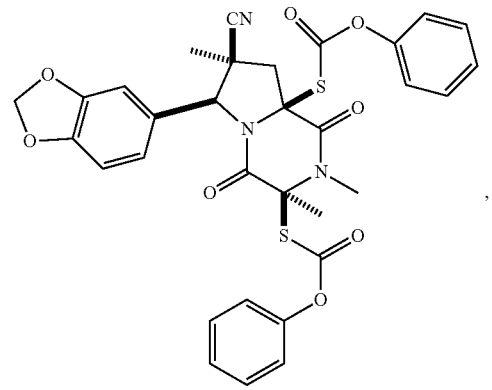

,

145
-continued
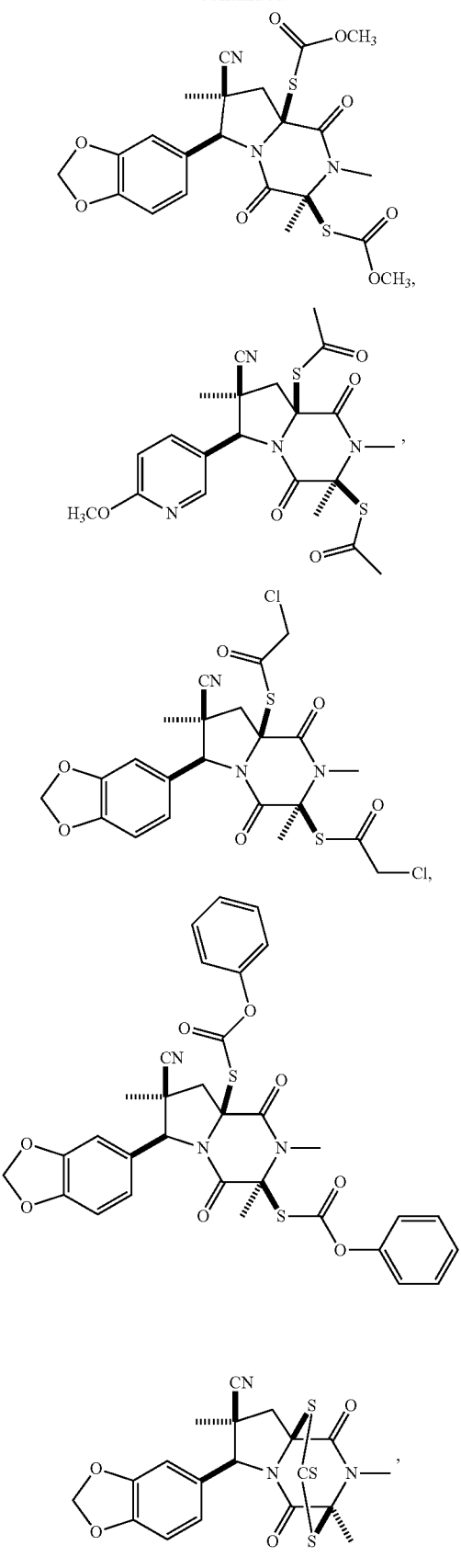
146
-continued
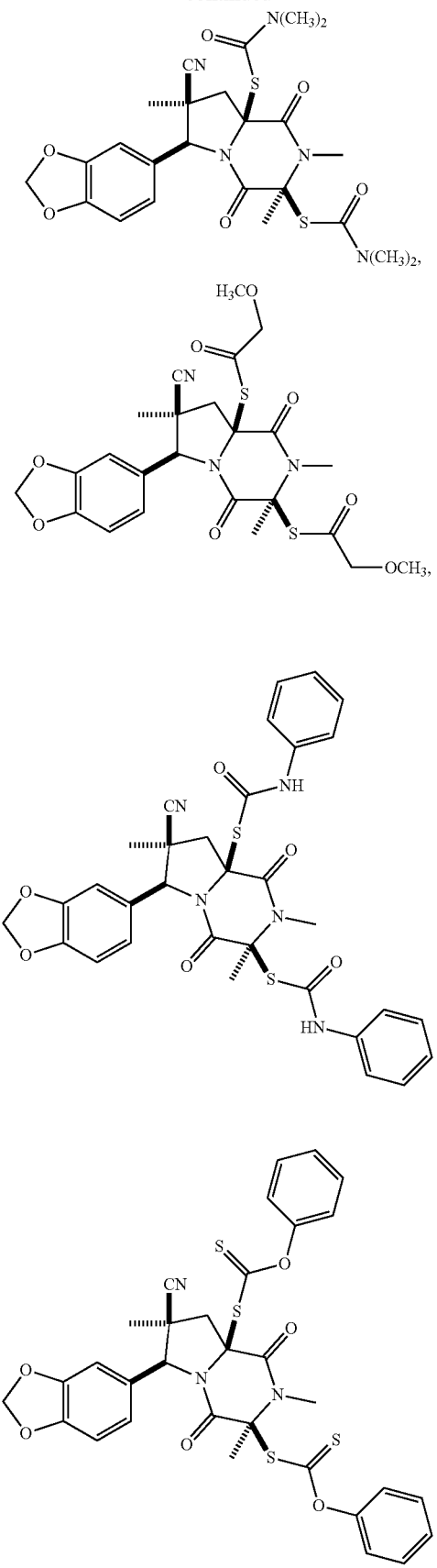

147
-continued
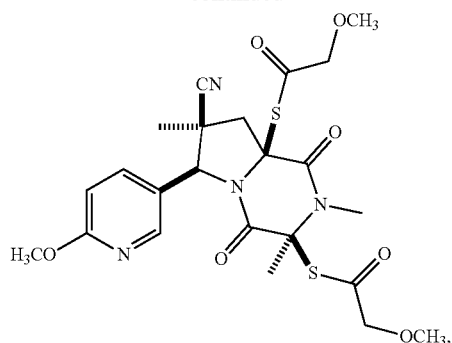
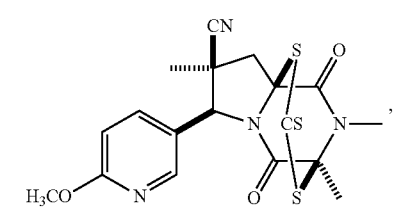
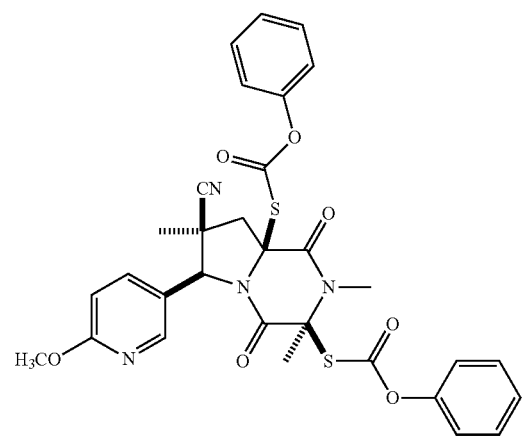
,
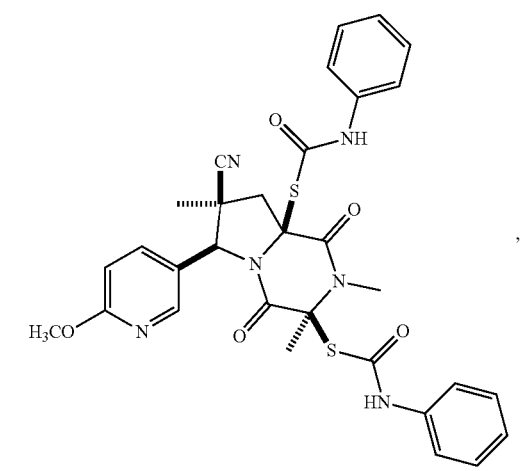
,
148
-continued
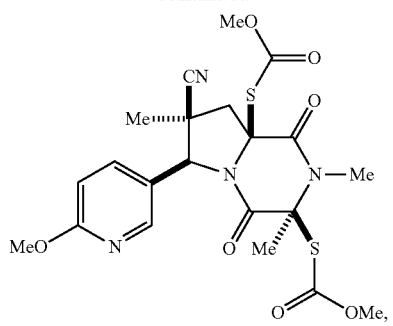
, or
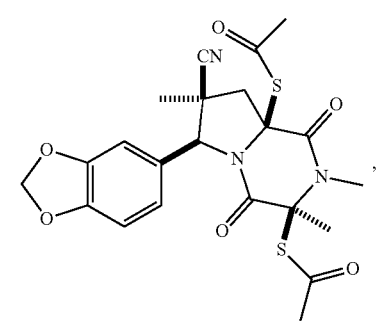
In embodiments, the compound has the structure 149
-continued
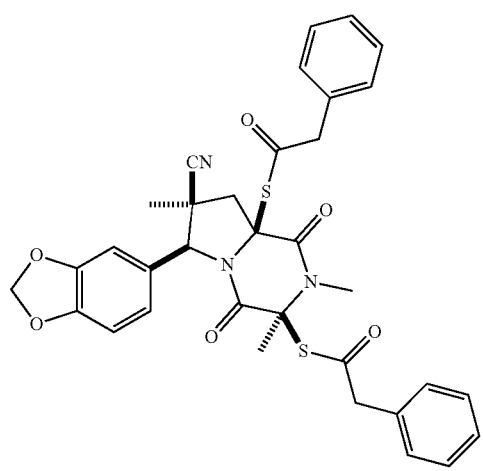
,
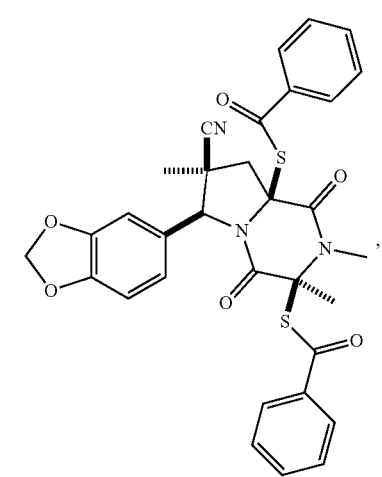
,
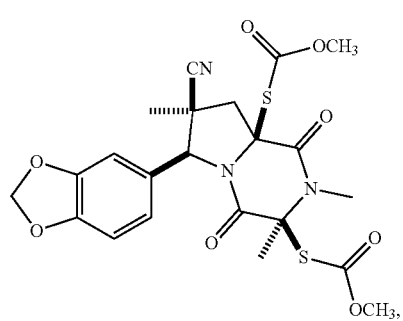
,
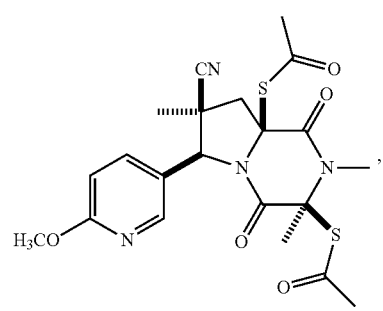
150
-continued
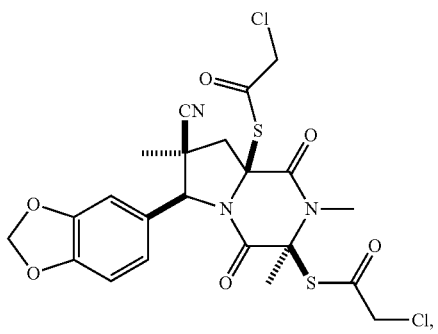
,
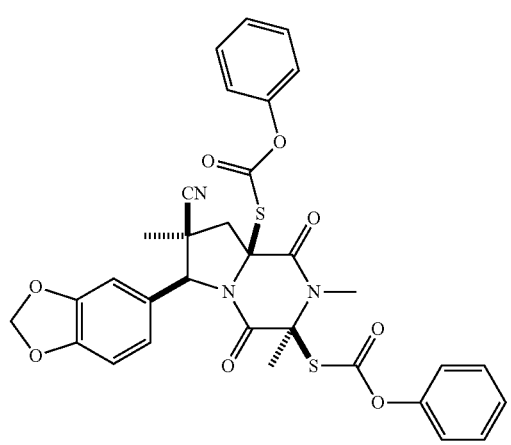
,
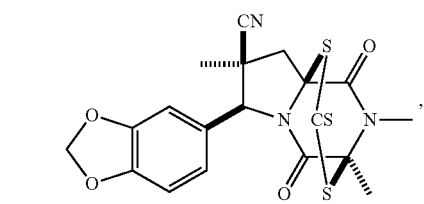
,
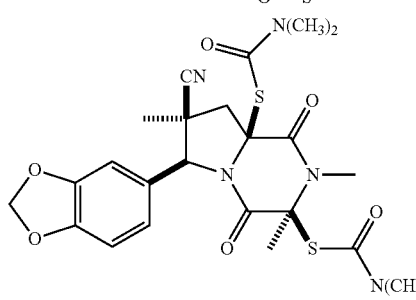
,
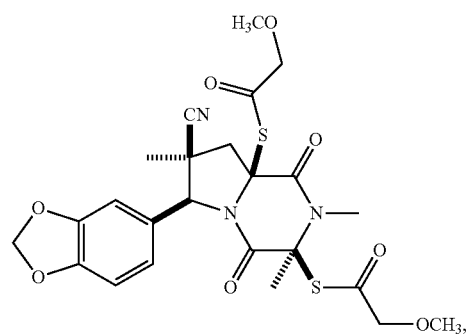
, 151
-continued
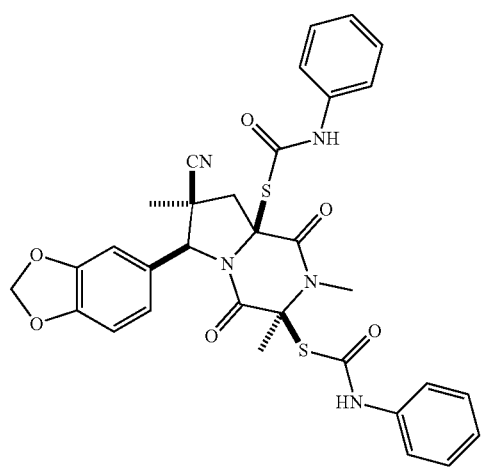
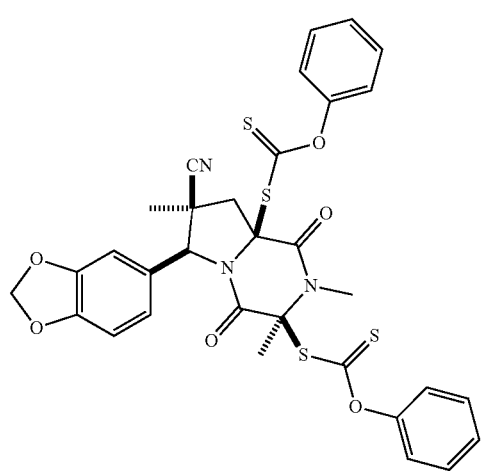
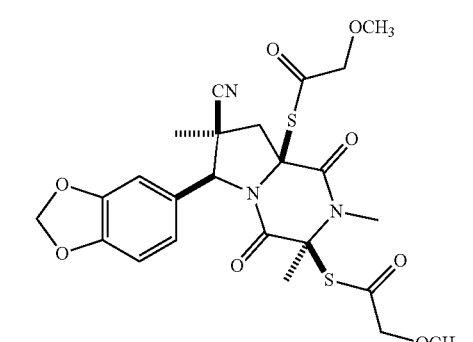
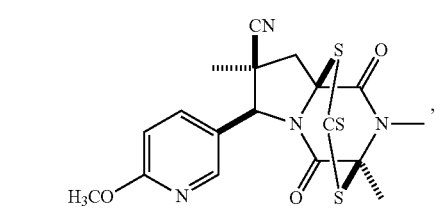
152
-continued
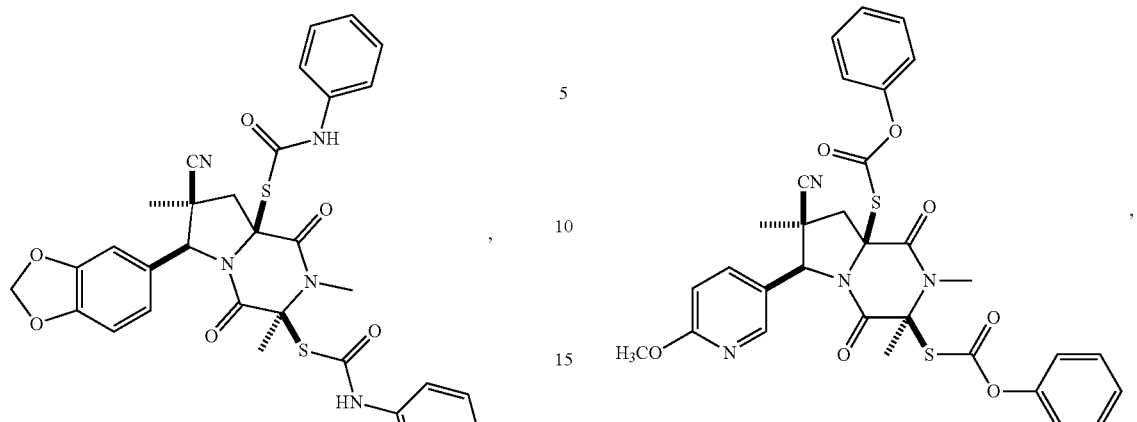
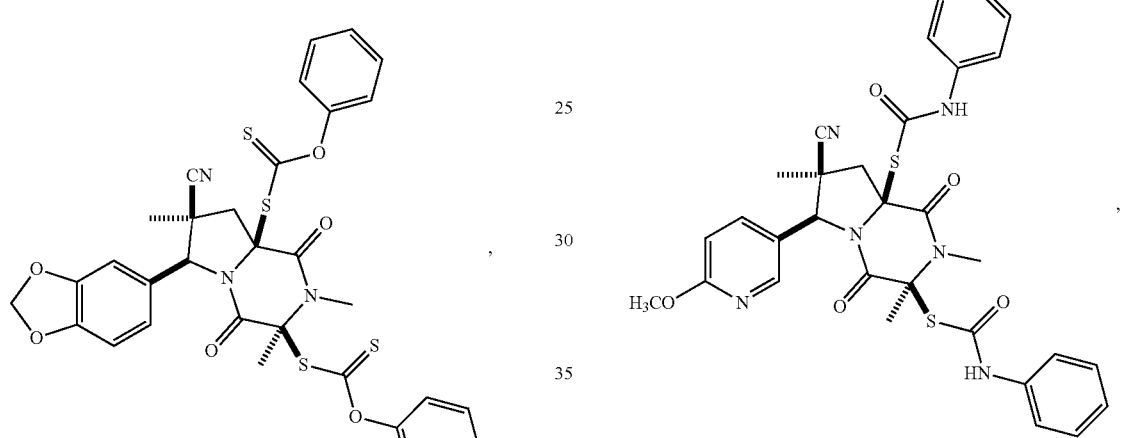
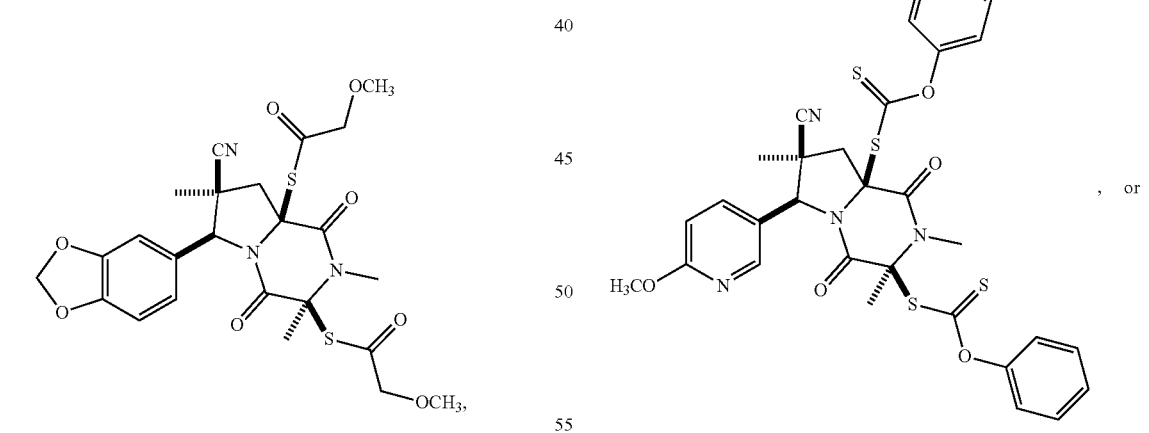
, or
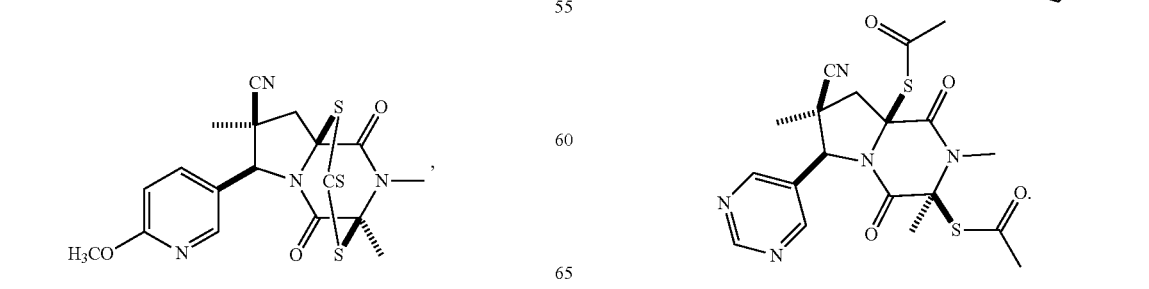

In embodiments, the compound has the structure:
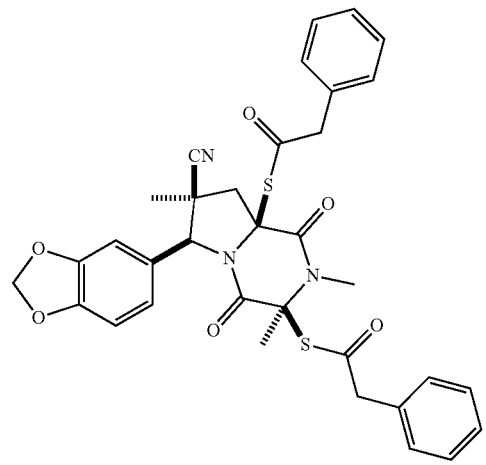
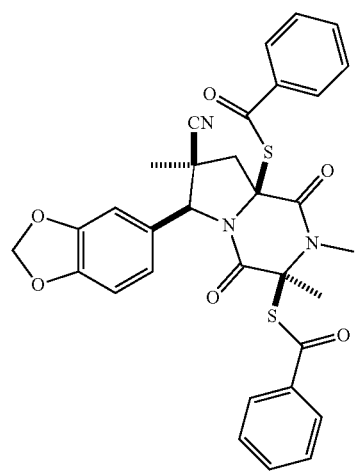
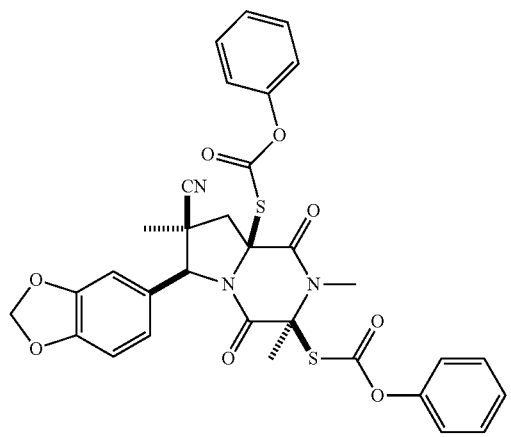
-continued
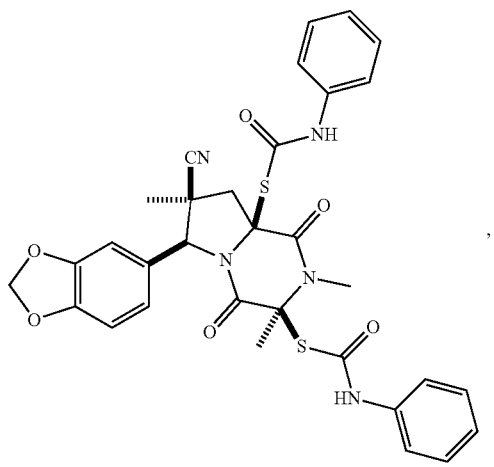
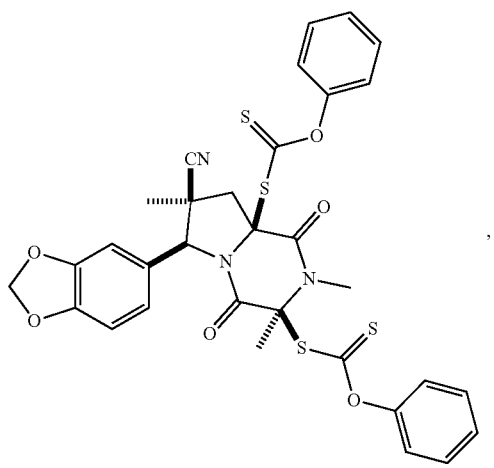
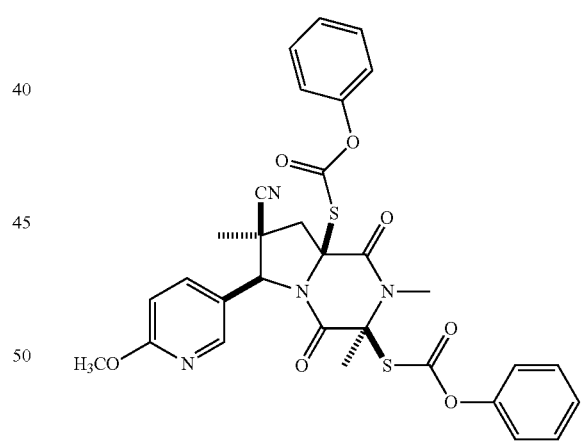
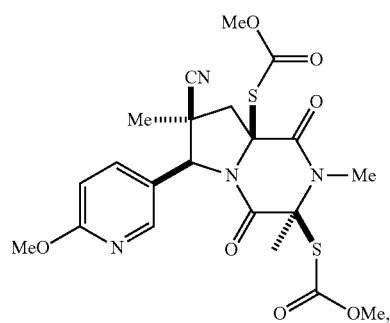

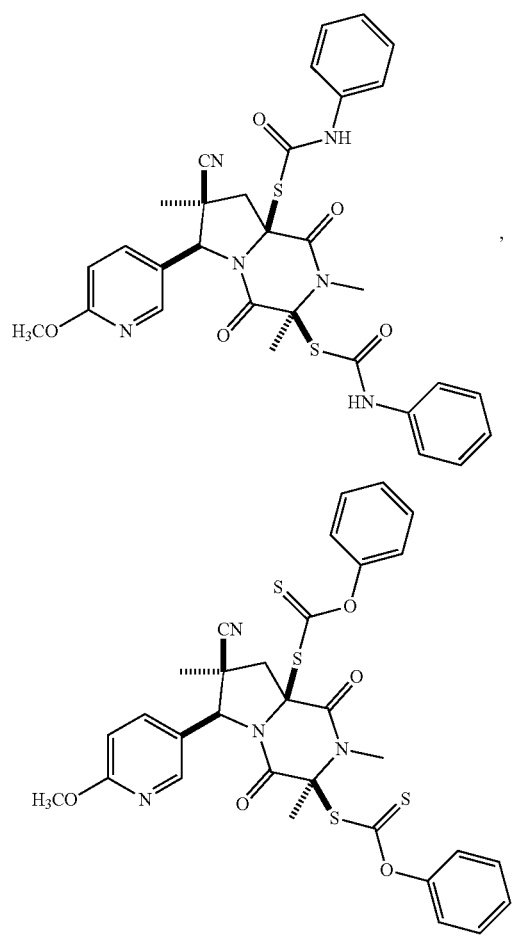
In embodiments, the compound has the structure:
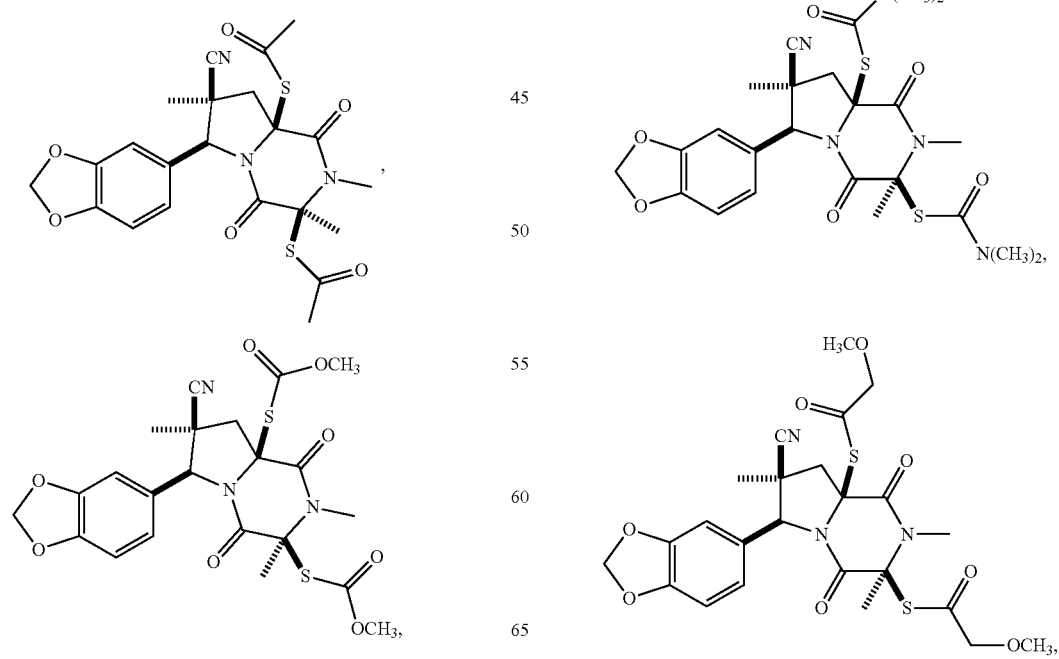
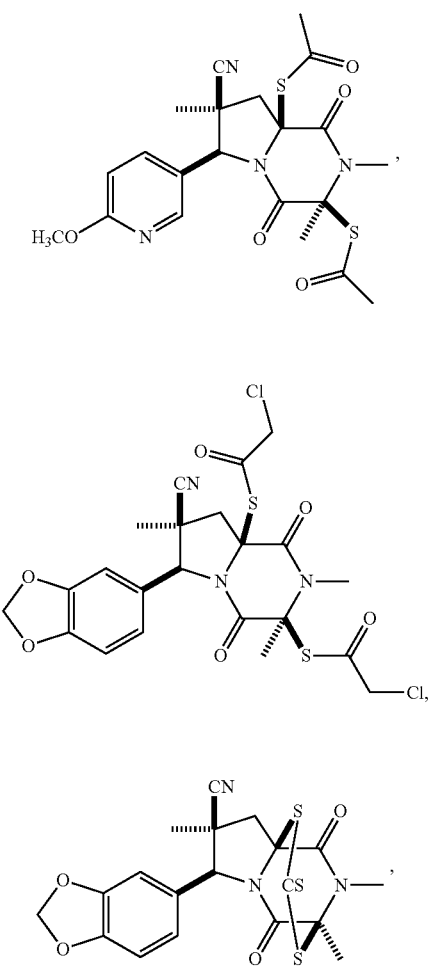

-continued

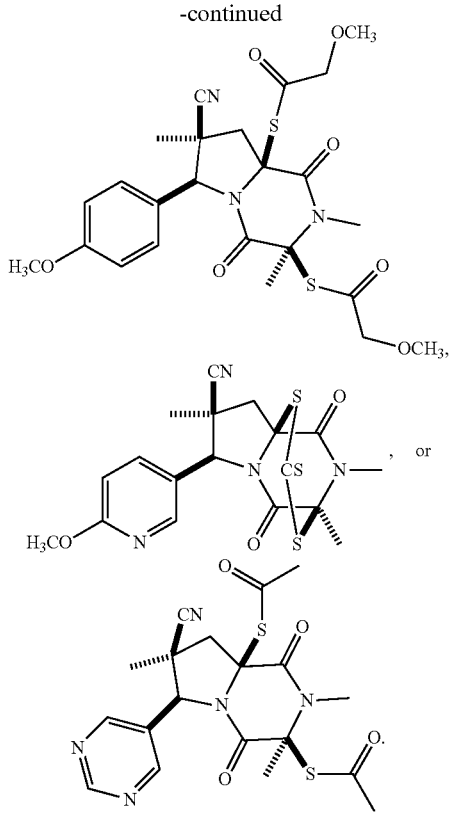

Further Forms of Compounds
Isomers

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or a combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

Tautomers

In some situations, compounds may exist as tautomers. All tautomers are included within the formula described herein.

Labelled Compounds

The compounds described herein may be labeled isotopically (e.g. with a radioisotope) or by other means, including, but not limited to, the use of chromophores or fluorescent moieties, bioluminescent labels, or photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, such as, for example, increased in vivo half-life or reduced dosage requirements.

Salts

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, or tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

Solvates

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein is accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in FIESER AND FIESER'S REAGENTS FOR ORGANIC SYNTHESIS, Volumes 1-17 (John Wiley and Sons, 1991); RODD'S CHEMISTRY OF CARBON COMPOUNDS, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989); March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); and Green and Wuts, PROTECTIVE GROUPS IN ORGANIC SYNTHESIS 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide, the following synthetic methods may be utilized as described in International Patent Application PCT/US2013/066252, which is herein incorporated by reference for this disclosure.

In certain embodiments, the compound is a compound as set forth in Table 1.

TABLE 1

Exemplary embodiments of compounds provided herein.

| Structure | Reference |
|---|---|
| 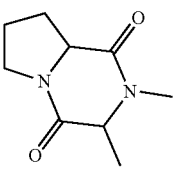 | ETP6 |
| 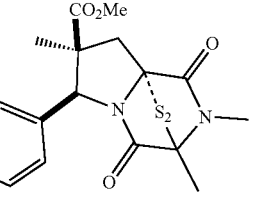 | ETP8 |
| 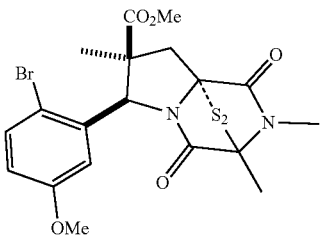 | ETP12 |

TABLE 1-continued

Exemplary embodiments of compounds provided herein.

| Structure | Reference |
|---|---|
| 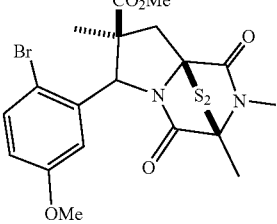 | ETP14 |
| 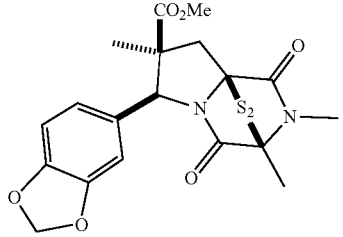 | ETP27 |
| 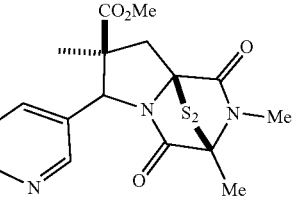 | ETP49 |
| 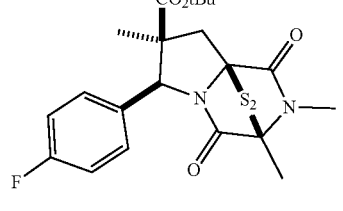 | ETP56 |
| 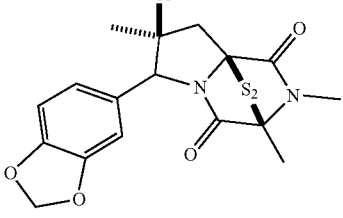 | ETP69 |
| 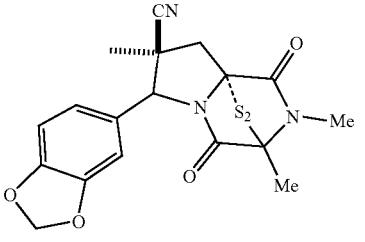 | ETP95 |

TABLE 1-continued
Exemplary embodiments of compounds provided herein.
| Structure | Reference |
|---|---|
| 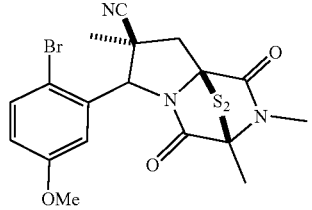 | ETP100 |
| 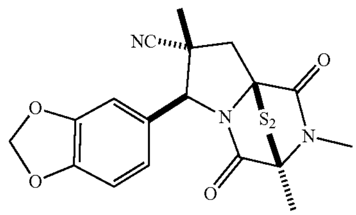 | ETP120 |
| 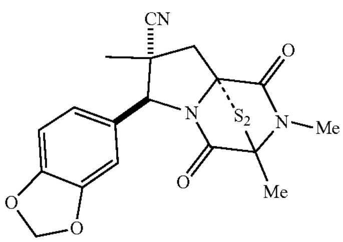 | ETP125 |
| 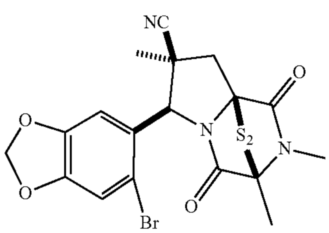 | ETP128 |
| 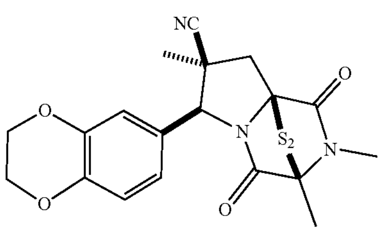 | ETP130 |
| 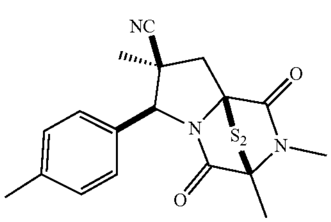 | ETP154 |
TABLE 1-continued
Exemplary embodiments of compounds provided herein.
| Structure | Reference |
|---|---|
| 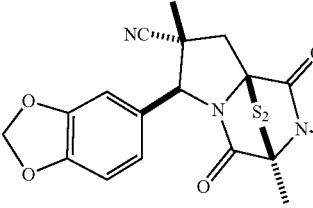 | ETP167 |
| 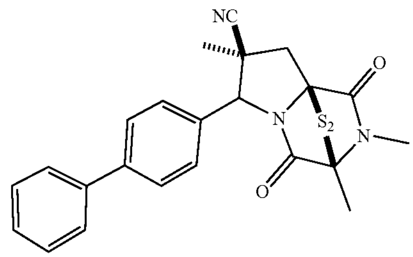 | ETP178 |
| 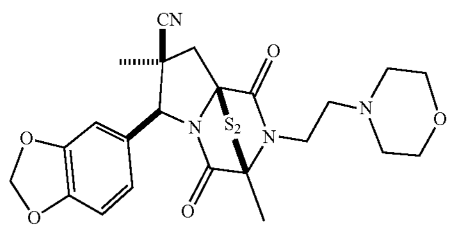 | ETP195 |
| 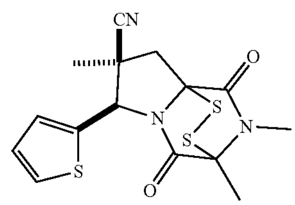 [SMILES: CN1C(=O)C23C[C@](C)(C#N)[C@H](c4cccs4)N2C(=O)C1(C)SS3] | ETP204 |
| 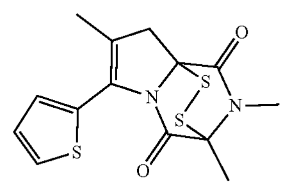 [SMILES: CC1=C(c2cccs2)N2C(=O)C3(C)SSC2(C1)C(=O)N3C] | ETP206 |
| 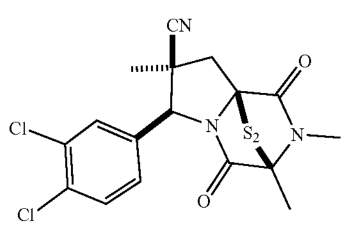 | ETP214 |
| 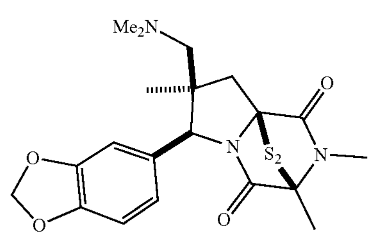 | ETP218 |

TABLE 1-continued

Exemplary embodiments of compounds provided herein.

| Structure | Reference |
|---|---|
| (structure) | ETP223 |
| (structure) | ETP229 |
| (structure) | ETP303 |
| (structure) 3:1 mix spimers | ETP309 |
| (structure) 3:1 mix spimers | ETP313 |
| (structure) | ETP328 |
| (structure) | ETP331 |
| (structure) | ETP341 |
| (structure) | ETP344 |
| (structure) | ETP356 |
| (structure) | ETP359 |
| (structure) | ETP365 |
| (structure) | ETP382 |

TABLE 1-continued
Exemplary embodiments of compounds provided herein.
| Structure | Reference |
|---|---|
| 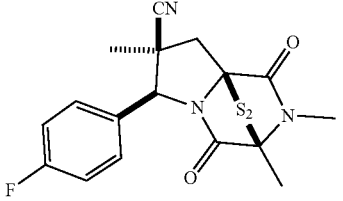 | ETP384 |
| 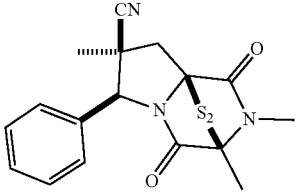 | ETP390 |
| 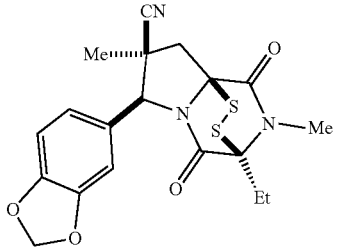 | ETP406 |
| 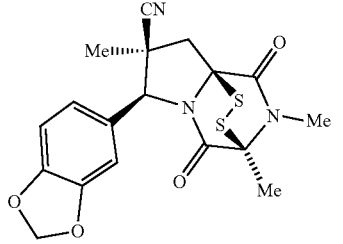 [SMILES: CN1C(=O)[C@@]23C[C@](C)(C#N)[C@H](c4ccc5c(c4)OCO5)N2C(=O)[C@]1(C)SS3] | ETP417 |
| 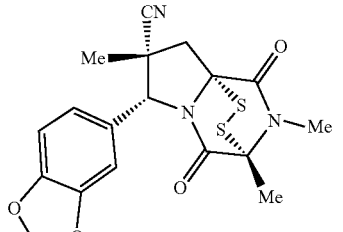 | ETP422 |
| 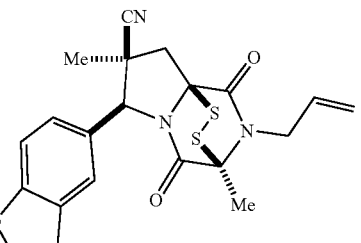 | ETP425 |
| 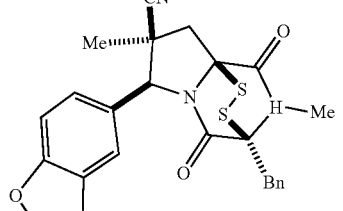 | ETP442 |
| 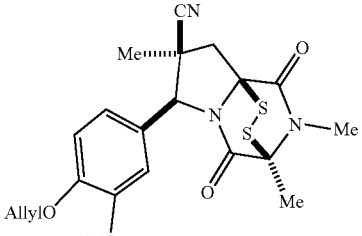 | ETP450 |
| 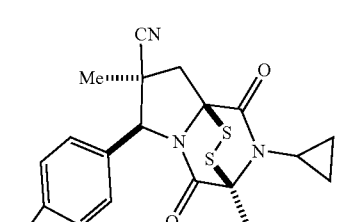 | ETP452 |
| 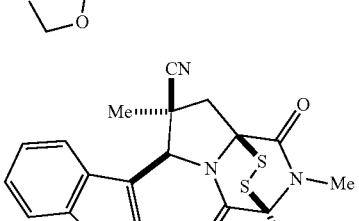 | ETP469 |
| 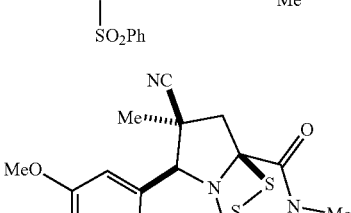 | ETP484 |
| 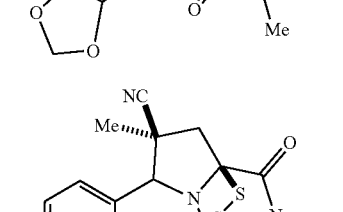 | ETP493 |

Pharmaceutical Composition

Described herein are pharmaceutical compositions comprising a compound (ETP compound) provided herein, including a bridged ETP compound (e.g. formula (1), (I), (I(S)), (I(R)), (II), (II(S)), (II(R)), (II1), (II1(S)), (II1(R)), (II2), (II2(S)), (II2(R)), (II3), (II3(S)), (II3(R)), (II4), (II5), (III), (III(S)), (III(R)), (III1), (III1(S)), (III1(R)), (IV), (IV(S)), (IV(R)), (IV1), (IV1(S)), (IV1(R)), (IV2), (IV2(S)), (IV2(R)), (V), (V(S)), (V(R)), (V1), (V1(S)), (V1(R)), (V2), (V2(S)), (V2(R)), (V3), (V3(S)), (V3(R)), (V4), (V4(S)), (V4(R)), (VI), (VI(S)), (VI(R)), (VI1), (VI1(S)), (VI1(R))), (XXI), (XXIa), (XXII), (XXII(S)), (XXII(R)), (XXIII), (XXIII(S)), (XXIII(R)), (XXIV), (XXIV(S)), (XXIV(R)), (XXV), (XXV(S)), (XXV(R)), (XXVI), (XXVI(S)), (XXVI(R)), (XXVII), (XXVII(S)), (XXVII (R)), (XXVIII), (XXVII(S)), (XXVIII(R)), (XXIX), (XXIX (S)), (XXIX (R)), (XXX), (XXXI), (XXI'), (XXII'), (XXIII'), (XXIII'(S)), (XXIII'(R)), (XXIV'), (XXIV'(S)), (XXIV'(R)), (XXV'), (XXV'(S)), (XXV'(R)), (XXVI'), (XXVI'(S)), and (XXVI' (R)), described herein. In some embodiments, the pharmaceutical composition refers to a mixture of a bridged ETP compound described herein with an excipient. In some embodiments, the excipient is a carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, antifoaming agent, antioxidant, preservative, or one or more combination thereof. The pharmaceutical composition facilitates administration of the ETP compound described herein to an organism. In practicing the methods of treatment or use provided herein, therapeutically effective amounts of the ETP compound described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The ETP compound described herein can be used singly or in combination with one or more therapeutic agents as components of mixtures (as in combination therapy).

The pharmaceutical compositions described herein are administered to a subject by multiple administration routes, including, but not limited to, oral, parenteral (e.g., intravenous, subcutaneous, intramuscular), intranasal, inhalation, buccal, topical, rectal, or transdermal administration routes. In some embodiments, pharmaceutical compositions described herein, which include a bridged ETP compound described herein, are formulated into any suitable dosage form, including, but not limited to, emulsions suitable for injection, nanosuspensions suitable for injection, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulates formulations, and mixed immediate release and controlled release formulations.

Described herein are pharmaceutical compositions comprising a compound (ETP compound) provided herein, including a bridged ETP compound (e.g. formula (1), (I), (I(S)), (I(R)), (II), (II(S)), (II(R)), (II1), (II1(S)), (II1(R)), (II2), (II2(S)), (II2(R)), (II3), (II3(S)), (II3(R)), (II4), (II5), (III), (III(S)), (III(R)), (III1), (III1(S)), (III1(R)), (IV), (IV(S)), (IV(R)), (IV1), (IV(S)), (IV1(R)), (IV2), (V2(S)), (V2 (R)), (V), (V(S)), (V(R)), (VI), (VI(S)), (V1(R)), (V2), (V2(S)), (V2(R)), (V3), (V3(S)), (V3(R)), (V4), (V4(S)), (V4(R)), (VI), (VI(S)), (VI(R)), (VI1), (VI1(S)), (VII(R))), (XXI), (XXIa), (XXII), (XXII(S)), (XXII(R)), (XXIII), (XXIII(S)), (XXIII(R)), (XXIV), (XXIV(S)), (XXIV(R)), (XXV), (XXV(S)), (XXV(R)), (XXVI), (XXVI(S)), (XXVI (R)), (XXVII), (XXVII(S)), (XXVII (R)), (XXVIII), (XXVIII(S)), (XXVIII(R)), (XXIX), (XXIX (S)), (XXIX (R)), (XXX), (XXXI), (XXI'), (XXII'), (XXIII'), (XXIII'(S)), (XXIII'(R)), (XXIV'), (XXIV'(S)), (XXIV'(R)), (XXV'), (XXV'(S)), (XXV'(R)), (XXVI'), (XXVI'(S)), and (XXVI' (R)), described herein formulated for oral administration. In some embodiments, the pharmaceutical composition for oral use is a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In some embodiments, the pharmaceutical composition for oral use is a solid dosage form, e.g., tablets, effervescent tablets, and capsules. In some embodiments, the solid dosage form are prepared by mixing particles of a bridged ETP compound described herein, with one or more pharmaceutical excipients to form a bulk blend composition. When referring to these bulk blend compositions as homogeneous, it is meant that the particles of the ETP compound described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application may depend, inter alia, on the condition being treated. When administered in methods to treat a disease, such compositions may contain an amount of active ingredient effective to achieve the desired result, e.g., modulating the activity of a target molecule, and/or reducing, eliminating, or slowing the progression of disease symptoms.

Generally, the ETP compound described herein is administered in an amount effective for amelioration of the symptoms of the disease or disorder (i.e., a therapeutically effective amount). In some embodiments, the therapeutically effective amount is an amount that is capable of at least partially preventing or reversing a disease or disorder. In some embodiments, the dose required to obtain an effective amount varies depending on the agent, formulation, disease or disorder, and individual to whom the ETP compound described herein is administered.

In some embodiments, the determination of the effective amount involves in vitro assays in which varying doses of the ETP compound described herein are administered to cells in culture and the concentration of agent effective for ameliorating some or all symptoms is determined in order to calculate the concentration required in vivo. In some embodiments, the effective amounts are based on in vivo animal studies.

In some embodiments, the ETP compound described herein is administered prior to, concurrently with, and subsequent to the appearance of symptoms of a disease or disorder. In some embodiments, the ETP compound described herein is administered to a subject with a family history of the disease or disorder, or who has a phenotype that may indicate a predisposition to a disease or disorder, or who has a genotype which predisposes the subject to the disease or disorder.

Methods

Described herein are methods for treating T-cell lymphoma in a subject in need thereof, comprising administering to the subject in need thereof, a therapeutically effective amount of a compound (ETP compound) provided herein, including compounds having the structure of formula (e.g. formula (1), (I), (I(S)), (I(R)), (II), (II(S)), (II(R)), (II1), (II1(S)), (II1(R)), (II2), (II2(S)), (II2(R)), (II3), (II3(S)), (II3(R)), (II4), (II5), (III), (III(S)), (III(R)), (III1), (III1(S)), (III1(R)), (IV), (IV(S)), (IV(R)), (IV1), (IV1(S)), (IV1(R)), (IV2), (IV2(S)), (IV2(R)), (V), (V(S)), (V(R)), (V1), (V1(S)), (V1(R)), (V2), (V2(S)), (V2(R)), (V3), (V3(S)), (V3(R)), (V4), (V4(S)), (V4(R)), (VI), (VI(S)), (VI(R)), (VI1), (VI1(S)), (VI1(R))), (XXI), (XXIa), (XXII), (XXII(S)), (XXII(R)), (XXIII), (XXIII(S)), (XXIII(R)), (XXIV), (XXIV(S)), (XXIV(R)), (XXV), (XXV(S)), (XXV(R)), (XXVI), (XXVI(S)), (XXVI(R)), (XXVII), (XXVII(S)), (XXVII (R)), (XXVIII), (XXVIII(S)), (XXVIII(R)), (XXIX), (XXIX (S)), (XXIX (R)), (XXX), (XXXI), (XXI'), (XXII'), (XXIII'), (XXIII'(S)), (XXIII'(R)), (XXIV'), (XXIV' (S)), (XXIV'(R)), (XXV'), (XXV'(S)), (XXV'(R)), (XXVI'), (XXVI'(S)), and (XXVI'(R)), including embodiments thereof. In some embodiments of a method of treating T-cell lymphoma, the compound has the structure of formula (1), including embodiments thereof. In some embodiments of a method of treating T-cell lymphoma, the compound has the structure of formula (I), including embodiments thereof. In some embodiments of a method of treating T-cell lymphoma, the compound has the structure of formula (I(S)), including embodiments thereof. In some embodiments of a method of treating T-cell lymphoma, the compound has the structure of formula (I(R)), including embodiments thereof. In some embodiments of a method of treating T-cell lymphoma, the compound has the structure of formula (II), including embodiments thereof. In some embodiments of a method of treating T-cell lymphoma, the compound has the structure of formula (II(S)), including embodiments thereof. In some embodiments of a method of treating T-cell lymphoma, the compound has the structure of formula (II(R)), including embodiments thereof. In some embodiments of a method of treating T-cell lymphoma, the compound has the structure of formula (III), including embodiments thereof. In some embodiments of a method of treating T-cell lymphoma, the compound has the structure of formula (III(S)), including embodiments thereof. In some embodiments of a method of treating T-cell lymphoma, the compound has the structure of formula (III(R)), including embodiments thereof. In some embodiments of a method of treating T-cell lymphoma, the compound has the structure of formula (IV), including embodiments thereof. In some embodiments of a method of treating T-cell lymphoma, the compound has the structure of formula (IV(S)), including embodiments thereof. In some embodiments of a method of treating T-cell lymphoma, the compound has the structure of formula (IV(R)), including embodiments thereof. In some embodiments of a method of treating T-cell lymphoma, the compound has the structure of formula (V), including embodiments thereof. In some embodiments of a method of treating T-cell lymphoma, the compound has the structure of formula (V(S)), including embodiments thereof. In some embodiments of a method of treating T-cell lymphoma, the compound has the structure of formula (V(R)), including embodiments thereof. In some embodiments of a method of treating T-cell lymphoma, the compound has the structure of formula (VI), including embodiments thereof. In some embodiments of a method of treating T-cell lymphoma, the compound has the structure of formula (VI(S)), including embodiments thereof. In some embodiments of a method of treating T-cell lymphoma, the compound has the structure of formula (VI(R)), including embodiments thereof. In some embodiments of a method of treating T-cell lymphoma, the compound has the structure of formula (XXI), including embodiments thereof. In some embodiments of a method of treating T-cell lymphoma, the compound has the structure of formula (XXIa), including embodiments thereof. In some embodiments of a method of treating T-cell lymphoma, the compound has the structure of formula (XXII), including embodiments thereof. In some embodiments of a method of treating T-cell lymphoma, the compound has the structure of formula (XXII(S)), including embodiments thereof. In some embodiments of a method of treating T-cell lymphoma, the compound has the structure of formula (XXII(R)), including embodiments thereof. In some embodiments of a method of treating T-cell lymphoma, the compound has the structure of formula (XXIII), including embodiments thereof. In some embodiments of a method of treating T-cell lymphoma, the compound has the structure of formula (XXIII(S)), including embodiments thereof. In some embodiments of a method of treating T-cell lymphoma, the compound has the structure of formula (XXIII(R)), including embodiments thereof. In some embodiments of a method of treating T-cell lymphoma, the compound has the structure of formula (XXIV), including embodiments thereof. In some embodiments of a method of treating T-cell lymphoma, the compound has the structure of formula (XXIV(S)), including embodiments thereof. In some embodiments of a method of treating T-cell lymphoma, the compound has the structure of formula (XXIV(R)), including embodiments thereof. In some embodiments of a method of treating T-cell lymphoma, the compound has the structure of formula (XXV), including embodiments thereof. In some embodiments of a method of treating T-cell lymphoma, the compound has the structure of formula (XXV(S)), including embodiments thereof. In some embodiments of a method of treating T-cell lymphoma, the compound has the structure of formula (XXV(R)), including embodiments thereof. In some embodiments of a method of treating T-cell lymphoma, the compound has the structure of formula (XXVI(S)), including embodiments thereof. In some embodiments of a method of treating T-cell lymphoma, the compound has the structure of formula (XXVI (R)), including embodiments thereof. In some embodiments of a method of treating T-cell lymphoma, the compound has the structure of formula (XXVII), including embodiments thereof. In some embodiments of a method of treating T-cell lymphoma, the compound has the structure of formula (XXVII(S)), including embodiments thereof. In some embodiments of a method of treating T-cell lymphoma, the compound has the structure of formula (XXVII (R)), including embodiments thereof. In some embodiments of a method of treating T-cell lymphoma, the compound has the structure of formula (XXVIII), including embodiments thereof. In some embodiments of a method of treating T-cell lymphoma, the compound has the structure of formula (XXVIII (S)), including embodiments thereof. In some embodiments of a method of treating T-cell lymphoma, the compound has the structure of formula (XXVIII(R)), including embodiments thereof. In some embodiments of a method of treating T-cell lymphoma, the compound has the structure of formula (XXIX), including embodiments thereof. In some embodiments of a method of treating T-cell lymphoma, the compound has the structure of formula (XXIX (S)), including embodiments thereof. In some embodiments of a method of treating T-cell lymphoma, the compound has the structure of formula (XXIX (R)), including embodiments thereof.

In some embodiments of a method of treating T-cell lymphoma, the compound has the structure of formula (XXX), including embodiments thereof. In some embodiments of a method of treating T-cell lymphoma, the compound has the structure of formula (XXXI), including embodiments thereof. In some embodiments of a method of treating T-cell lymphoma, the compound has the structure of formula (XXI'), including embodiments thereof. In some embodiments of a method of treating T-cell lymphoma, the compound has the structure of formula (XXII'), including embodiments thereof. In some embodiments of a method of treating T-cell lymphoma, the compound has the structure of formula (XXIII'), including embodiments thereof. In some embodiments of a method of treating T-cell lymphoma, the compound has the structure of formula (XXIII'(S)), including embodiments thereof. In some embodiments of a method of treating T-cell lymphoma, the compound has the structure of formula (XXIII'(R)), including embodiments thereof. In some embodiments of a method of treating T-cell lymphoma, the compound has the structure of formula (XXIV'), including embodiments thereof. In some embodiments of a method of treating T-cell lymphoma, the compound has the structure of formula (XXIV'(S)), including embodiments thereof. In some embodiments of a method of treating T-cell lymphoma, the compound has the structure of formula (XXV'), including embodiments thereof. In some embodiments of a method of treating T-cell lymphoma, the compound has the structure of formula (XXV'(S)), including embodiments thereof. In some embodiments of a method of treating T-cell lymphoma, the compound has the structure of formula (XXV'(R)), including embodiments thereof. In some embodiments of a method of treating T-cell lymphoma, the compound has the structure of formula (XXVI'), including embodiments thereof. In some embodiments of a method of treating T-cell lymphoma, the compound has the structure of formula (XXVI'(S)), including embodiments thereof. In some embodiments of a method of treating T-cell lymphoma, the compound has the structure of formula (XXVI'(R)), including embodiments thereof.

Also described herein are methods of treating T-cell lymphoma in a subject in need thereof, comprising administering to the subject in need thereof, a bridged ETP compound described herein. In some embodiments of a method of treating T-cell lymphoma, the compound has the structure of formula (1), including embodiments thereof. In some embodiments, the ETP compound is a compound having the structure of formula (I), or a pharmaceutically acceptable salt or a pharmaceutically acceptable solvate thereof. In some embodiments, the ETP compound is a compound having the structure of formula (I(S)), or a pharmaceutically acceptable salt or a pharmaceutically acceptable solvate thereof. In some embodiments, the ETP compound is a compound having the structure of formula (I(R)), or a pharmaceutically acceptable salt or a pharmaceutically acceptable solvate thereof. In some embodiments, the ETP compound is a compound having the structure of formula (II), or a pharmaceutically acceptable salt or a pharmaceutically acceptable solvate thereof. In some embodiments, the ETP compound is a compound having the structure of formula (II(S)), or a pharmaceutically acceptable salt or a pharmaceutically acceptable solvate thereof. In some embodiments, the ETP compound is a compound having the structure of formula (II(R)), or a pharmaceutically acceptable salt or a pharmaceutically acceptable solvate thereof. In some embodiments, the ETP compound is a compound having the structure of formula (III), or a pharmaceutically acceptable salt or a pharmaceutically acceptable solvate thereof. In some embodiments, the ETP compound is a compound having the structure of formula (III(S)), or a pharmaceutically acceptable salt or a pharmaceutically acceptable solvate thereof. In some embodiments, the ETP compound is a compound having the structure of formula (III(R)), or a pharmaceutically acceptable salt or a pharmaceutically acceptable solvate thereof. In some embodiments, the ETP compound is a compound having the structure of formula (IV), or a pharmaceutically acceptable salt or a pharmaceutically acceptable solvate thereof. In some embodiments, the ETP compound is a compound having the structure of formula (IV(S)), or a pharmaceutically acceptable salt or a pharmaceutically acceptable solvate thereof. In some embodiments, the ETP compound is a compound having the structure of formula (IV(R)), or a pharmaceutically acceptable salt or a pharmaceutically acceptable solvate thereof. In some embodiments, the ETP compound is a compound having the structure of formula (V), or a pharmaceutically acceptable salt or a pharmaceutically acceptable solvate thereof. In some embodiments, the ETP compound is a compound having the structure of formula (V(S)), or a pharmaceutically acceptable salt or a pharmaceutically acceptable solvate thereof. In some embodiments, the ETP compound is a compound having the structure of formula (V(R)), or a pharmaceutically acceptable salt or a pharmaceutically acceptable solvate thereof. In some embodiments, the ETP compound is a compound having the structure of formula (VI), or a pharmaceutically acceptable salt or a pharmaceutically acceptable solvate thereof. In some embodiments, the ETP compound is a compound having the structure of formula (VI(S)), or a pharmaceutically acceptable salt or a pharmaceutically acceptable solvate thereof. In some embodiments, the ETP compound is a compound having the structure of formula (VI(R)), or a pharmaceutically acceptable salt or a pharmaceutically acceptable solvate thereof. In some embodiments, the ETP compound is a compound having the structure of formula (XXI), or a pharmaceutically acceptable salt or a pharmaceutically acceptable solvate thereof. In some embodiments, the ETP compound is a compound having the structure of formula (XXIa), or a pharmaceutically acceptable salt or a pharmaceutically acceptable solvate thereof. In some embodiments, the ETP compound is a compound having the structure of formula (XXII), or a pharmaceutically acceptable salt or a pharmaceutically acceptable solvate thereof. In some embodiments, the ETP compound is a compound having the structure of formula (XXII(S)), or a pharmaceutically acceptable salt or a pharmaceutically acceptable solvate thereof. In some embodiments, the ETP compound is a compound having the structure of formula (XXII(R)), or a pharmaceutically acceptable salt or a pharmaceutically acceptable solvate thereof. In some embodiments, the ETP compound is a compound having the structure of formula (XXIII), or a pharmaceutically acceptable salt or a pharmaceutically acceptable solvate thereof. In some embodiments, the ETP compound is a compound having the structure of formula (XXIII(S)), or a pharmaceutically acceptable salt or a pharmaceutically acceptable solvate thereof. In some embodiments, the ETP compound is a compound having the structure of formula (XXIII(R)), or a pharmaceutically acceptable salt or a pharmaceutically acceptable solvate thereof. In some embodiments, the ETP compound is a compound having the structure of formula (XXIV), or a pharmaceutically acceptable salt or a pharmaceutically acceptable solvate thereof. In some embodiments, the ETP compound is a compound having the structure of formula (XXIV(S)), or a pharmaceutically acceptable salt or a pharmaceutically acceptable solvate thereof. In some embodiments, the ETP compound is a compound having the structure of formula (XXIV(R)), or a pharmaceutically acceptable salt or a pharmaceutically acceptable solvate thereof. In some embodiments, the ETP compound is a compound having the structure of formula (XXV), or a pharmaceutically acceptable salt or a pharmaceutically acceptable solvate thereof. In some embodiments, the ETP compound is a compound having the structure of formula (XXV(S)), or a pharmaceutically acceptable salt or a pharmaceutically acceptable solvate thereof. In some embodiments, the ETP compound is a compound having the structure of formula (XXV(R)), or a pharmaceutically acceptable salt or a pharmaceutically acceptable solvate thereof. In some embodiments, the ETP compound is a compound having the structure of formula (XXVI), or a pharmaceutically acceptable salt or a pharmaceutically acceptable solvate thereof. In some embodiments, the ETP compound is a compound having the structure of formula (XXVI(S)), or a pharmaceutically acceptable salt or a pharmaceutically acceptable solvate thereof. In some embodiments, the ETP compound is a compound having the structure of formula (XXVI(R)), or a pharmaceutically acceptable salt or a pharmaceutically acceptable solvate thereof. In some embodiments, the ETP compound is a compound having the structure of formula (XXVII), or a pharmaceutically acceptable salt or a pharmaceutically acceptable solvate thereof. In some embodiments, the ETP compound is a compound having the structure of formula (XXVII(S)), or a pharmaceutically acceptable salt or a pharmaceutically acceptable solvate thereof. In some embodiments, the ETP compound is a compound having the structure of formula (XXVII(R)), or a pharmaceutically acceptable salt or a pharmaceutically acceptable solvate thereof. In some embodiments, the ETP compound is a compound having the structure of formula (XXVIII), or a pharmaceutically acceptable salt or a pharmaceutically acceptable solvate thereof. In some embodiments, the ETP compound is a compound having the structure of formula (XXVIII(S)), or a pharmaceutically acceptable salt or a pharmaceutically acceptable solvate thereof. In some embodiments, the ETP compound is a compound having the structure of formula (XXVIII(R)), or a pharmaceutically acceptable salt or a pharmaceutically acceptable solvate thereof. In some embodiments, the ETP compound is a compound having the structure of formula (XXIX), or a pharmaceutically acceptable salt or a pharmaceutically acceptable solvate thereof. In some embodiments, the ETP compound is a compound having the structure of formula (XXIX (S)), or a pharmaceutically acceptable salt or a pharmaceutically acceptable solvate thereof. In some embodiments, the ETP compound is a compound having the structure of formula (XXIX (R)), or a pharmaceutically acceptable salt or a pharmaceutically acceptable solvate thereof. In some embodiments, the ETP compound is a compound having the structure of formula (XXX), or a pharmaceutically acceptable salt or a pharmaceutically acceptable solvate thereof. In some embodiments, the ETP compound is a compound having the structure of formula (XXXI), or a pharmaceutically acceptable salt or a pharmaceutically acceptable solvate thereof. In some embodiments, the ETP compound is a compound having the structure of formula (XXI'), or a pharmaceutically acceptable salt or a pharmaceutically acceptable solvate thereof. In some embodiments, the ETP compound is a compound having the structure of formula (XXII'), or a pharmaceutically acceptable salt or a pharmaceutically acceptable solvate thereof. In some embodiments, the ETP compound is a compound having the structure of formula (XXIII'), or a pharmaceutically acceptable salt or a pharmaceutically acceptable solvate thereof. In some embodiments, the ETP compound is a compound having the structure of formula (XXIII'(S)), or a pharmaceutically acceptable salt or a pharmaceutically acceptable solvate thereof. In some embodiments, the ETP compound is a compound having the structure of formula (XXIII'(R)), or a pharmaceutically acceptable salt or a pharmaceutically acceptable solvate thereof. In some embodiments, the ETP compound is a compound having the structure of formula (XXIV'), or a pharmaceutically acceptable salt or a pharmaceutically acceptable solvate thereof. In some embodiments, the ETP compound is a compound having the structure of formula (XXIV'(S)), or a pharmaceutically acceptable salt or a pharmaceutically acceptable solvate thereof. In some embodiments, the ETP compound is a compound having the structure of formula (XXIV'(R)), or a pharmaceutically acceptable salt or a pharmaceutically acceptable solvate thereof. In some embodiments, the ETP compound is a compound having the structure of formula (XXV'), or a pharmaceutically acceptable salt or a pharmaceutically acceptable solvate thereof. In some embodiments, the ETP compound is a compound having the structure of formula (XXV'(S)), or a pharmaceutically acceptable salt or a pharmaceutically acceptable solvate thereof. In some embodiments, the ETP compound is a compound having the structure of formula (XXV'(R)), or a pharmaceutically acceptable salt or a pharmaceutically acceptable solvate thereof. In some embodiments, the ETP compound is a compound having the structure of formula (XXVI'), or a pharmaceutically acceptable salt or a pharmaceutically acceptable solvate thereof. In some embodiments, the ETP compound is a compound having the structure of formula (XXVI'(S)), or a pharmaceutically acceptable salt or a pharmaceutically acceptable solvate thereof. In some embodiments, the ETP compound is a compound having the structure of formula (XXVI'(R)), or a pharmaceutically acceptable salt or a pharmaceutically acceptable solvate thereof.

In some embodiments of a method of treating T-cell lymphoma, the T-cell lymphoma is cutaneous T-cell lymphoma. In some embodiments of a method of treating T-cell lymphoma, the cutaneous T-cell lymphoma is Sezary syndrome. In some embodiments of a method of treating T-cell lymphoma, the cutaneous T-cell lymphoma is mycosis fungoides. In some embodiments of a method of treating T-cell lymphoma, the cutaneous T-cell lymphoma is folliculotropic mycosis fungoides. In some embodiments of a method of treating T-cell lymphoma, the cutaneous T-cell lymphoma is pagetoid reticulosis. In some embodiments of a method of treating T-cell lymphoma, the cutaneous T-cell lymphoma is granulomatous slack skin. In some embodiments of a method of treating T-cell lymphoma, the cutaneous T-cell lymphoma is primary cutaneous CD30+ T-cell lymphoproliferative disorder. In some embodiments of a method of treating T-cell lymphoma, the cutaneous T-cell lymphoma is lymphomatoid papulosis. In some embodiments of a method of treating T-cell lymphoma, the cutaneous T-cell lymphoma is primary cutaneous anaplastic large-cell lymphoma. In some embodiments of a method of treating T-cell lymphoma, the cutaneous T-cell lymphoma is primary cutaneous γδ T-cell lymphoma. In some embodiments of a method of treating T-cell lymphoma, the cutaneous T-cell lymphoma is primary cutaneous CD8+ aggressive epidermotropic lymphoma. In some embodiments of a method of treating T-cell lymphoma, the cutaneous T-cell lymphoma is primary cutaneous CD8+ aggressive epidermotropic cytotoxic T-cell lymphoma. In some embodiments of a method of treating T-cell lymphoma, the cutaneous T-cell lymphoma is primary cutaneous CD4+ small/medium T-cell lymphoma.

In some embodiments of a method of treating T-cell lymphoma, the T-cell lymphoma is nodal T-cell lymphoma. In some embodiments of a method of treating T-cell lymphoma, the nodal T-cell lymphoma is follicular T-cell lymphoma. In some embodiments of a method of treating T-cell lymphoma, the nodal T-cell lymphoma is angioimmunoblastic T-cell lymphoma. In some embodiments of a method of treating T-cell lymphoma, the nodal T-cell lymphoma is nodal peripheral T-cell lymphoma with TFH phenotype. In some embodiments of a method of treating T-cell lymphoma, the nodal T-cell lymphoma is anaplastic large cell lymphoma ALK+. In some embodiments of a method of treating T-cell lymphoma, the nodal T-cell lymphoma is anaplastic large cell lymphoma ALK–. In some embodiments of a method of treating T-cell lymphoma, the nodal T-cell lymphoma is breast implant-associated anaplastic large-cell lymphoma. In some embodiments of a method of treating T-cell lymphoma, the nodal T-cell lymphoma is peripheral T-cell lymphoma not otherwise specified (PTCL-NOS).

In some embodiments of a method of treating T-cell lymphoma, the T-cell lymphoma is extranodal T-cell lymphoma. In some embodiments of a method of treating T-cell lymphoma, the extranodal T-cell lymphoma is systemic EBV+ T-cell lymphoma of childhood. In some embodiments of a method of treating T-cell lymphoma, the extranodal T-cell lymphoma is hydroa vacciniforme-like lymphoproliferative disorder. In some embodiments of a method of treating T-cell lymphoma, the extranodal T-cell lymphoma is extranodal NK/T-cell lymphoma nasal type. In some embodiments of a method of treating T-cell lymphoma, the extranodal T-cell lymphoma is enteropathy-associated T-cell lymphoma. In some embodiments of a method of treating T-cell lymphoma, the extranodal T-cell lymphoma is hepatosplenic T-cell lymphoma. In some embodiments of a method of treating T-cell lymphoma, the extranodal T-cell lymphoma is subcutaneous panniculitis-like T-cell lymphoma.

In some embodiments of a method of treating T-cell lymphoma, the T-cell lymphoma is leukemic T-cell lymphoma. In some embodiments of a method of treating T-cell lymphoma, the leukemic T-cell lymphoma is T-cell prolymphocytic leukemia. In some embodiments of a method of treating T-cell lymphoma, the leukemic T-cell lymphoma is T-cell large-granular lymphocytic leukemia. In some embodiments of a method of treating T-cell lymphoma, the leukemic T-cell lymphoma is adult T-cell leukemia/lymphoma.

In some embodiments of a method of treating T-cell lymphoma, the T-cell lymphoma is monomorphic epitheliotropic intestinal T-cell lymphoma. In some embodiments of a method of treating T-cell lymphoma, the T-cell lymphoma is indolent T-cell lymphoproliferative disorder of the gastrointestinal tract.

In some embodiments of a method of treating T-cell lymphoma, the T-cell lymphoma is peripheral T-cell lymphoma, anaplastic large-cell lymphoma, angioimmunoblastic T-cell lymphoma, adult T-cell Leukemia/Lymphoma, blastic natural killer (NK) cell lymphoma, enteropathy-associated T-cell lymphoma, hepatosplenic T-cell lymphoma, lymphoblastic lymphoma, or nasal natural killer (NK)/T-cell lymphoma.

Also described herein are methods for treating T-cell lymphoma in a subject in need thereof, comprising administering to the subject in need thereof, a bridged ETP compound described herein, thereby reducing, ameliorating or eliminating a symptom or manifestation of T-cell lymphoma. In some embodiments of a method of treating T-cell lymphoma, the subject in need thereof is predisposed to T-cell lymphoma, but does not yet manifest a symptom of T-cell lymphoma. In some embodiments of a method of treating T-cell lymphoma, the administration of a bridged ETP compound described herein effectively prevents or delays development of symptoms associated with T-cell lymphoma. In some embodiments of a method of treating T-cell lymphoma, the symptoms of T-cell lymphoma comprise at least one of the following symptoms: chest pain, coughing, difficulty breathing, fatigue, loss of appetite, weight loss, alopecia, follicular cysts, comedolike lesions, nail dystrophy, fever, night sweats, itchy skin, swollen lymph nodes, lymphadenopathy, hepatosplenomegaly, autoimmune phenomena, swollen abdomen, painful abdomen, edematous skin, atopic dermatitis, nonspecific dermatitis, nonspecific chronic dermatitis, parapsoriasis, patches on lower trunk, patches on buttocks, palmar hyperkeratosis, plantar hyperkeratosis, minimal/absent pruritus, and intensely pruritic plaques.

In some embodiments of a method of treating T-cell lymphoma, the T-cell lymphoma is associated with at least one of the following conditions: smoking, obesity, infection, HIV, Epstein-Barr virus, human T-lymphotropic virus, *Helicobacter pyroli* infection, chronic *Helicobacter pyroli* infection, exposure to chemicals, exposure to insecticides, exposure to pesticides, use of immunosuppressant drugs, weakened immune system, genetic disorders, previous chemotherapy, and previous radiation therapy. In some embodiments of a method of treating T-cell lymphoma, the T-cell lymphoma is associated with smoking. In some embodiments of a method of treating T-cell lymphoma, the T-cell lymphoma is associated with obesity. In some embodiments of a method of treating T-cell lymphoma, the T-cell lymphoma is associated with infection. In some embodiments of a method of treating T-cell lymphoma, the T-cell lymphoma is associated with HIV. In some embodiments of a method of treating T-cell lymphoma, the T-cell lymphoma is associated with Epstein-Barr virus. In some embodiments of a method of treating T-cell lymphoma, the T-cell lymphoma is associated with human T-lymphotropic virus. In some embodiments of a method of treating T-cell lymphoma, the T-cell lymphoma is associated with *Helicobacter pyroli* infection. In some embodiments of a method of treating T-cell lymphoma, the T-cell lymphoma is associated with chronic *Helicobacter pyroli* infection. In some embodiments of a method of treating T-cell lymphoma, the T-cell lymphoma is associated with exposure to chemicals. In some embodiments of a method of treating T-cell lymphoma, the T-cell lymphoma is associated with exposure to insecticides. In some embodiments of a method of treating T-cell lymphoma, the T-cell lymphoma is associated with exposure to pesticides. In some embodiments of a method of treating T-cell lymphoma, the T-cell lymphoma is associated with use of immunosuppressant drugs. In some embodiments of a method of treating T-cell lymphoma, the T-cell lymphoma is associated with weakened immune system. In some embodiments of a method of treating T-cell lymphoma, the T-cell lymphoma is associated with genetic disorders. In some embodiments of a method of treating T-cell lymphoma, the T-cell lymphoma is associated with previous chemotherapy. In some embodiments of a method of treating T-cell lymphoma, the T-cell lymphoma is associated with previous radiation therapy.

In some embodiments of a method of treating T-cell lymphoma, the treatment of T-cell lymphoma in a subject in need thereof comprises the steps of: (a) identifying a subject in need of treatment of T-cell lymphoma, and (b) administering a therapeutically effective amount of a bridged ETP compound to said subject, thereby treating the T-cell lymphoma.

In some embodiments of a method of treating T-cell lymphoma, the method further comprises administering an additional therapeutic agent. In some embodiments, the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

In some embodiments of a method of treating T-cell lymphoma, the treatment of T-cell lymphoma in a subject in need thereof results in reduction or minimization of undesired side effects in the subject associated with chemotherapy, chemotherapy, radiotherapy, or cancer therapy. In some embodiments, the undesired side effects in the subject associated with chemotherapy, chemotherapy, radiotherapy, or cancer therapy comprise fatigue, anemia, appetite changes, bleeding problems, diarrhea, constipation, hair loss, nausea, vomiting, pain, peripheral neuropathy, swelling, skin and nail changes, urinary and bladder changes, and trouble swallowing.

Embodiments P

Embodiment P1. A method for treating T-cell lymphoma in a subject in need thereof, comprising administering to the subject, a compound having the structure of formula (I):

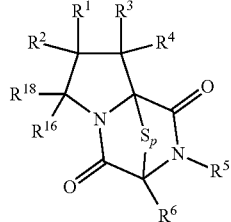

wherein, $R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{n1}OR^{1B}$, —$SO_{v1}NR^{1B}R^{1C}$, —$NHNR^{1B}R^{1C}$, —$ONR^{1B}R^{1C}$, —NHC(O)NHNR$^{1B}R^{1C}$-substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$— $COOR^{2A}$, —$CONR^{2B}R^{2C}$, —$NO_2$, —$SR^{2D}$, —$SO_{n2}R^{2B}$, —$SO_{n2}OR^{2B}$, —$SO_{v2}NR^{2B}R^{2C}$, —$NHNR^{2B}R^{2C}$, —$ONR^{2B}R^{2C}$, —NHC(O)NHNR$^{2B}R^{2C}$-substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_3R^{3B}$, —$SO_{n3}OR^{3B}$, —$SO_{v3}NR^{3B}R^{3C}$, —$NHNR^{3B}R^{3C}$, $ONR^{3B}R^{3C}$, —NHC(O)NHNR$^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{4A}$, —$NR^{34}R^{4C}$, —$COOR^{4A}$, —$CONR^{4B}R^{4C}$, —$NO_2$, —$SR^{4D}$, —$SO_{n4}R^{4B}$, —$SO_{n4}OR^{4B}$, —$SO_{v4}NR^{4B}R^{4C}$, —$NHNR^{4B}R^{4C}$, —$ONR^{4B}R^{4C}$, —NHC(O) NHNR$^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$N_3$, —$CF_3$, —$CCl_3$, —$CBr_3$, —$CI_3$, —CN, —CHO, —$OR^{5A}$, —$NR^{5B}R^{5C}$, —$COOR^{5A}$, —$CONR^{5B}R^{5C}$, —$NO_2$, —$SR^{5D}$, —$SO_{n5}R^{5B}$, —$SO_{n5}OR^{5B}$, —$SO_{v5}NR^{5B}R^{5C}$, —$NHNR^{5B}R^{5C}$, —$ONR^{5B}R^{5C}$, —NHC(O) NHNR$^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{v6}NR^{6B}R^{6C}$, —NHNR$^{6B}$R$^{6C}$, —ONR$^{6B}$R$^{6C}$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —N$_3$, —CF$_3$, —CCl$_3$, —CBr$_3$, —CI$_3$, —CN, —CHO, —OR$^{16A}$, —NR$^{16B}$R$^{6C}$, —COOR$^{16A}$, —CONR$^{16B}$R$^{16C}$, —NO$_2$, —SR$^{16D}$, —SO$_{n16}$R$^{16B}$, —SO$_{n16}$OR$^{16B}$, —SO$_{v16}$NR$^{16B}$R$^{16C}$, —NHNR$^{16B}$R$^{16C}$, —ONR$^{16B}$R$^{16C}$, —NHC(O)NHNR$^{16B}$R$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{18}$ is hydrogen, halogen, —N$_3$, —CF$_3$, —CCl$_3$, —CBr$_3$, —CI$_3$, —CN, —CHO, —OR$^{18A}$, —NR$^{18B}$R$^{18C}$, —COOR$^{18A}$, —CONR$^{18B}$R$^{18C}$, —NO$_2$, —SR$^{18D}$, —SO$_{18}$R$^{8B}$, —SO$_{n18}$OR$^{10B}$, —SO$_{v18}$NR$^{18B}$R$^{18C}$, —NHNR$^{18B}$R$^{18C}$, —ONR$^{18B}$R$^{18C}$, —NHC(O)NHNR$^{18B}$R$^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{16A}$, R$^{16B}$, R$^{16C}$, R$^{16D}$, R$^{18A}$, R$^{18B}$, R$^{18C}$ and R$^{18D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;

n1, n2, n3, n4, n5, n6, n16, and n18 are an integer from 0 to 4;

v1, v2, v3, v4, v5, v6, v16, and v18 are independently 1 or 2; and p is 2, 3, or 4;

or a pharmaceutically acceptable salt thereof.

Embodiment P2. The method of Embodiment P1, wherein R$^{18}$ is substituted or unsubstituted heterocycloalkyl, substituted or unsubstituted aryl, or substituted or unsubstituted heteroaryl.

Embodiment P3. The method of anyone of Embodiments P1-P2, wherein R$^{16}$ is hydrogen.

Embodiment P4. The method of anyone of Embodiments P1-P3, wherein R$^3$ and R$^4$ are independently hydrogen or methyl.

Embodiment P5. The method of anyone of Embodiments P1-P4, wherein R$^1$ is —CN, —COOR$^{1A}$, —CONR$^{1B}$R$^{1C}$, or substituted or unsubstituted heteroalkyl.

Embodiment P6. The method of anyone of Embodiments P1-P5, wherein R$^1$ is —CN.

Embodiment P7. The method of anyone of Embodiments P1-P6, wherein R$^2$ is —CF$_3$, substituted or unsubstituted alkyl, substituted or unsubstituted heteroalkyl, substituted or unsubstituted cycloalkyl, or substituted or unsubstituted heterocycloalkyl.

Embodiment P8. The method of anyone of Embodiments P1-P7, wherein R$^2$ is substituted or unsubstituted alkyl or substituted or unsubstituted heteroalkyl Embodiment P9. The method of any one of Embodiments P1-P8, wherein R$^2$ is methyl or methoxy.

Embodiment P10. The method of anyone of Embodiments P1-P9, wherein R$^5$ and R$^6$ are independently hydrogen, halogen, substituted or unsubstituted alkyl, or substituted or unsubstituted cycloalkyl.

Embodiment P11. The method of anyone of Embodiments P1-P10, wherein R$^5$ and R$^6$ are independently hydrogen, methyl, ethyl, allyl, or cyclopropyl.

Embodiment P12. The method of anyone of Embodiments P1-P11, wherein R$^5$ and R$^6$ are independently hydrogen or methyl.

Embodiment P13. The method of anyone of Embodiments P1-P12, wherein p is 2.

Embodiment P14. The method of Embodiment P1, wherein the compound of formula (I) has the structure of formula (II):

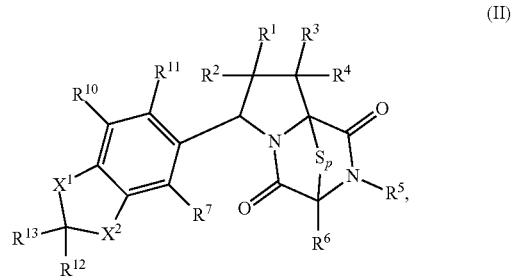

wherein,

X$^1$ is —CR$^{21A}$R$^{21B}$—, —O—, —NR$^{21C}$— or —S—;

X$^2$ is —CR$^{22A}$R$^{22B}$, —O— NR$^{22C}$— or —S—;

R$^7$ is hydrogen, halogen, —N$_3$, —CF$_3$, —CCl$_3$, —CBr$_3$, —CI$_3$, —CN, —CHO, —OR$^{7A}$, —NR$^{7B}$R$^{7C}$, —COOR$^{7A}$, —CONR$^{7B}$R$^{7C}$, —NO$_2$, —SR$^{7D}$, —SO$_{n7}$R$^{7B}$, —SO$_{n7}$OR$^{7B}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —CONR$^{10B}$R$^{10C}$, —NO$_2$, —SR$^{10D}$, —SO$_{n10}$R$^{10B}$, —SO$_{n10}$OR$^{10B}$, —SO$_{v10}$NR$^{10B}$R$^{10C}$, —NR$^{10B}$R$^{10C}$, —ONR$^{10B}$R$^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —CONR$^{11B}$R$^{11C}$, —NO$_2$, —SR$^{11D}$, —SO$_{n11}$R$^{11B}$, —SO$_{n11}$OR$^{11B}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ and R$^{11}$ are optionally joined together to form a substituted or unsubstituted cycloalkyl, a substituted or unsubstituted heterocycloalkyl, a substituted or unsubstituted aryl, or a substituted or unsubstituted heteroaryl;

R¹² is hydrogen, halogen, —N₃, —CF₃, —CCl₃, —CBr₃, —CI₃, —CN, —CHO, —OR¹²ᴬ, —NR¹²ᴮR¹²ᶜ, —COOR¹²ᴬ, —CONR¹²ᴮR¹²ᶜ, —NO₂, —SR¹²ᴰ, —SO$_{n12}$R¹²ᴮ, —SO$_{n12}$OR¹²ᴮ, —SO$_{v12}$NR¹²ᴮR¹²ᶜ, —NHNR¹²ᴮR¹²ᶜ, —ONR¹²ᴮR¹²ᶜ, —NHC(O) NHNR¹²ᴮR¹²ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹³ is hydrogen, halogen, —N₃, —CF₃, —CCl₃, —CBr₃, —CI₃, —CN, —CHO, —OR¹³ᴬ, —NR¹³ᴮR¹³ᶜ, —COOR¹³ᴬ, —CONR¹³ᴮR¹³ᶜ, —NO₂, —SR¹³ᴰ, —SO$_{n13}$R¹³ᴮ, —SO$_{n13}$OR¹³ᴮ, —SO$_{v13}$NR¹³ᴮR¹³ᶜ, —NHNR¹³ᴮR¹³ᶜ, —ONR¹³ᴮR¹³ᶜ, —NHC(O) NHNR¹³ᴮR¹³ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{21A}$, $R^{21B}$, $R^{22A}$, and $R^{22B}$, are independently hydrogen, halogen, —N₃, —CF₃, —CCl₃, —CBr₃, —CI₃, —CN, —CHO, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O) NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{7A}$, $R^{7B}$, $R^{7C}$, $R^{7C}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{21C}$ and $R^{22C}$ are independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n7, n10, n11, n12 and n13 are independently 0 or 4;
v7, v10, v11, v12 and v13 are independently 1 or 2; and
p is 2 or 3;
or a pharmaceutically acceptable salt thereof.

Embodiment P15. The method of Embodiment P14, wherein the compound of formula (II) has the structure of formula:

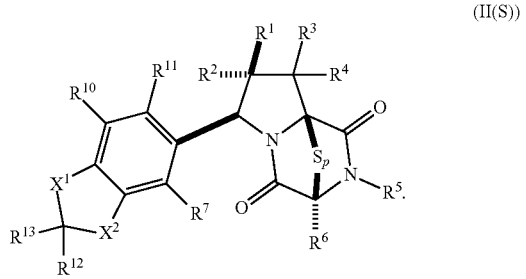

(II(S))

Embodiment P16. The method of Embodiment P15, wherein X¹ and X² are independently —O— or —S—.

Embodiment P17. The method of Embodiment P15, wherein p is 2.

Embodiment P18. The method of Embodiment P15, wherein the compound of formula (II(S)) has the structure of formula (III(S)):

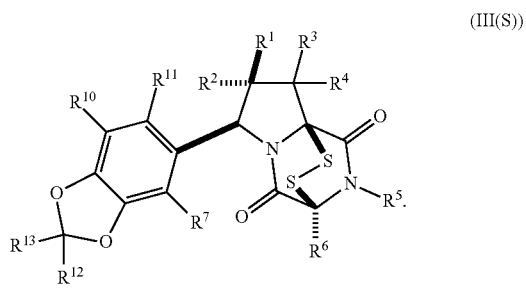

(III(S))

Embodiment P19. The method of Embodiment P18, wherein R¹ is —CN, —OR¹ᴬ, —COOR¹ᴬ, or —CONR¹ᴮR¹ᶜ, and wherein R¹ᴬ, R¹ᴮ, and R¹ᶜ are independently hydrogen, or substituted or unsubstituted alkyl.

Embodiment P20. The method of Embodiment P18 or P19, wherein R¹ is —CN.

Embodiment P21. The method of anyone of Embodiments P18-P20, wherein R² is —CF₃, substituted or unsubstituted alkyl, substituted or unsubstituted heteroalkyl, substituted or unsubstituted cycloalkyl, or substituted or unsubstituted heterocycloalkyl.

Embodiment P22. The method of anyone of Embodiments P18-P21, wherein R² is substituted or unsubstituted alkyl or substituted or unsubstituted heteroalkyl.

Embodiment P23. The method of anyone of Embodiments P18-P22, wherein R² is methyl.

Embodiment P24. The method of anyone of Embodiments 19-24, wherein R³ and R⁴ are hydrogen.

Embodiment P25. The method of anyone of Embodiments P18-P24, wherein R¹² and R¹³ are independently hydrogen or methyl.

Embodiment P26. The method of anyone of Embodiments P18-P25, wherein R¹⁰ and R¹¹ are hydrogen.

Embodiment P27. The method of any one of Embodiments P1-P14, wherein the compound has the structure of formula:

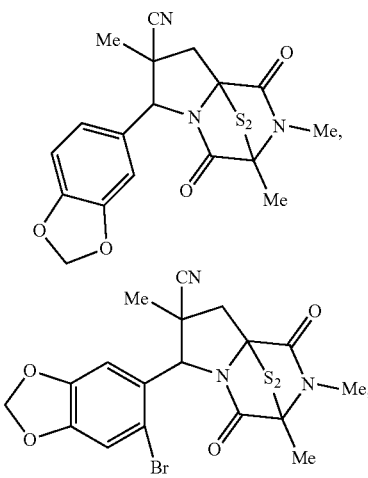

-continued
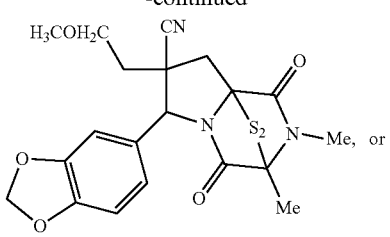
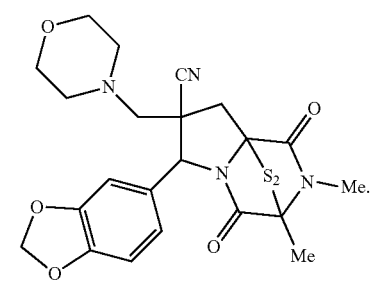
Embodiment P28. The method of Embodiment P18, wherein the compound has the structure of formula:
(1)
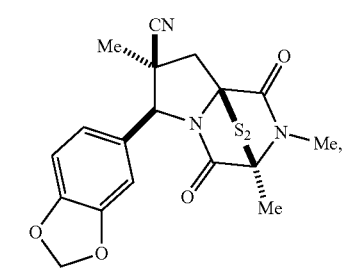
(2)
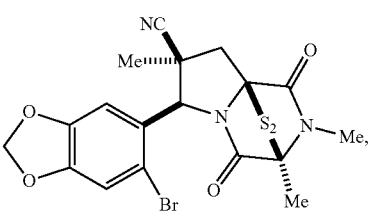
(3)
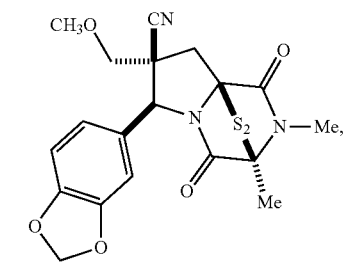
-continued
(4)
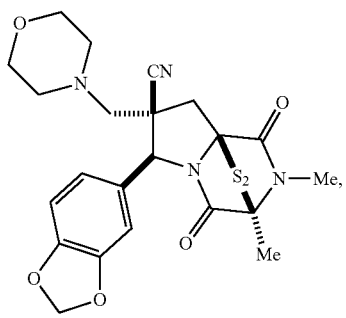
(5)
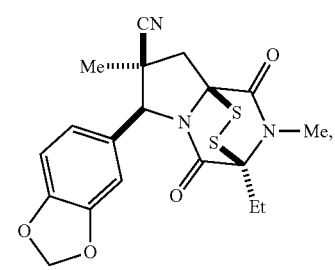
(6)
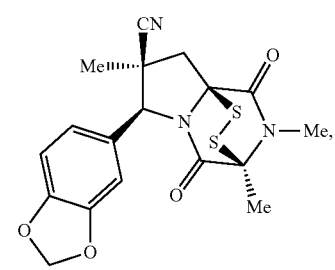
(7)
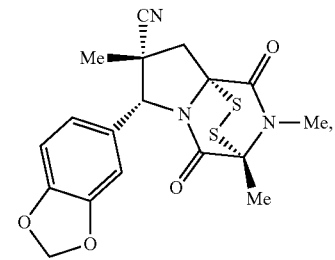
(8)
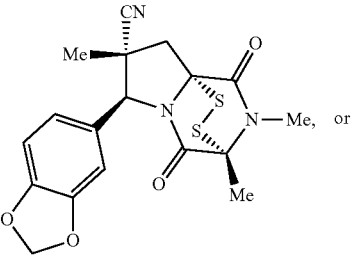

(9)

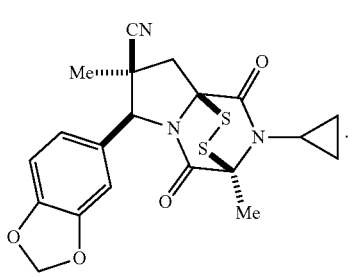

Embodiment P29. The method of any one of Embodiments P1-P28, wherein the T-cell lymphoma is cutaneous T-cell lymphoma (CTCL), peripheral T-cell lymphoma, anaplastic large-cell lymphoma, angioimmunoblastic T-cell lymphoma, adult T-cell Leukemia/Lymphoma, blastic natural killer (NK) cell lymphoma, enteropathy-associated T-cell lymphoma, hepatosplenic T-cell lymphoma, lymphoblastic lymphoma, or nasal natural killer (NK)/T-cell lymphoma.

Embodiment P30. The method of Embodiment P29, wherein the cutaneous T-cell lymphoma is Sezary syndrome, mycosis fungoides, folliculotropic mycosis fungoides, pagetoid reticulosis, granulomatous slack skin, primary cutaneous CD30+ T-cell lymphoproliferative disorders, lymphomatoid papulosis, primary cutaneous anaplastic large-cell lymphoma, primary cutaneous γδ T-cell lymphoma, primary cutaneous CD8+ aggressive epidermotropic lymphoma, primary cutaneous CD8+ aggressive epidermotropic cytotoxic T-cell lymphoma, or primary cutaneous CD4+ small/medium T-cell lymphoma.

Embodiment P31. The method of anyone of Embodiments P1-P30, wherein the T-cell lymphoma is associated with at least one of the following conditions: smoking, obesity, infection, HIV, Epstein-Barr virus, human T-lymphotropic virus, *Helicobacter pyroli* infection, chronic *Helicobacter pyroli* infection, exposure to chemicals, exposure to insecticides, exposure to pesticides, use of immunosuppressant drugs, weakened immune system, genetic disorders, previous chemotherapy, and previous radiation therapy.

Embodiment P32. The method of any one of Embodiments P1-P31, further comprising administering to the subject an additional therapeutic agent used in the treatment of T-cell lymphoma.

Embodiment P33. The method of Embodiment P32, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

Embodiment P34. A pharmaceutical composition for treating T-cell lymphoma comprising an ETP derivative, at least one additional therapeutic agent used in the treatment of T-cell lymphoma, and at least one pharmaceutically acceptable excipient.

Embodiment P35. The pharmaceutical composition of Embodiment P34, wherein the ETP derivative is a compound having the structure of formula (I):

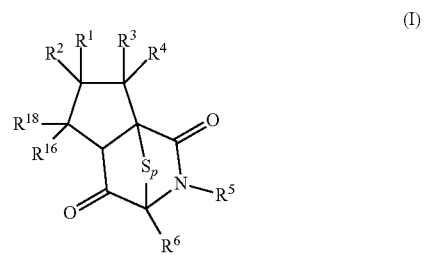

(I)

wherein, $R^1$ is hydrogen, halogen, $-N_3$, $-CF_3$, $-CCl_3$, $-CBr_3$, $-CI_3$, $-CN$, $-CHO$, $-OR^{1A}$, $-NR^{1B}R^{1C}$, $-COOR^{1A}$, $-CONR^{1B}R^{1C}$, $-NO_2$, $-SR^{1D}$, $-SO_{n1}R^{1B}$, $-SO_{n1}OR^{1B}$, $-SO_{n1}NR^{1B}R^{1C}$, $-NHNR^{1B}R^{1C}$, $-ONR^{1B}R^{1C}$, $-NHC(O)NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-N_3$, $-CF_3$, $-CCl_3$, $-CBr_3$, $-CI_3$, $-CN$, $-CHO$, $-OR^{2A}$, $-NR^{2B}R^{2C}$, $-COOR^{2A}$, $-CONR^{2B}R^{2C}$, $-NO_2$, $-SR^{2D}$, $-SO_{n2}R^{2B}$, $-SO_{n2}OR^{2B}$, $-SO_{n2}NR^{2B}R^{2C}$, $-NHNR^{2B}R^{2C}$, $-ONR^{2B}R^{2C}$, $-NHC(O)NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{3A}$, $-NR^{3B}R^{3C}$, $-COOR^{3A}$, $-CONR^{3B}R^{3C}$, $-NO_2$, $-SR^{3D}$, $-SO_{n3}R^{3B}$, $-SO_{n3}OR^{3B}$, $-SO_{n3}NR^{3B}R^{3C}$, $-NHNR^{3B}R^{3C}$, $ONR^{3B}R^{3C}$, $-NHC(O)NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-CHO$, $-OR^{4A}$, $-NR^{34}R^{4C}$, $-COOR^{4A}$, $-CONR^{4B}R^{4C}$, $-NO_2$, $-SR^{4D}$, $-SO_{n4}R^{4B}$, $-SO_{n4}OR^{4B}$, $-SO_{n4}NR^{4B}R^{4C}$, $-NHNR^{4B}R^{4C}$, $ONR^{4B}R^{4C}$, $-NHC(O)NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-N_3$, $-CF_3$, $-CCl_3$, $-CBr_3$, $-CI_3$, $-CN$, $-CHO$, $-OR^{5A}$, $-NR^{1B}R^{5C}$, $-COOR^{5A}$, $-CONR^{5B}R^{5C}$, $-NO_2$, $-SR^{5D}$, $-SO_{n5}R^{5B}$, $-SO_{n5}OR^{5B}$, $-SO_{n5}NR^{5B}R^{5C}$, $-NHNR^{5B}R^{5C}$, $-ONR^{5B}R^{5C}$, $-NHC(O)NHNR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n16}OR^{6B}$, —$SO_{n6}NR^{6B}R^{6C}$, —$NHNR^{6B}R^{6C}$, —$ONR^{6B}R^{6C}$, —NHC(O)NHNR$^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$N_3$, —$CF_3$, —$CCl_3$, —$CBr_3$, —$CI_3$, —CN, —CHO, —$OR^{6A}$, —$NR^{16B}R^{16C}$, —$COOR^{16A}$, —$CONR^{16B}R^{6C}$, —$NO_2$, —$SR^{16D}$, —$SO_{n16}R^{16B}$, —$SO_{n16}OR^{16B}$, —$SO_{n16}NR^{16B}R^{16C}$, —$NHNR^{16B}R^{16C}$, —$ONR^{16B}R^{16C}$, —NHC(O)NHNR$^{16B}R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$N_3$, —$CF_3$, —$CCl_3$, —$CBr_3$, —$CI_3$, —CN, —CHO, —$OR^{18A}$, —$NR^{18B}R^{18C}$, —$COOR^{18A}$, —$CONR^{18B}R^{18C}$, —$NO_2$, —$SR^{18D}$, —$SO_{n18}OR^{18B}$, —$SO_{n18}OR^{18B}$, —$SO_{n18}NR^{18B}R^{18C}$, —$NHNR^{18B}R^{18C}$, —$ONR^{18B}R^{18C}$, —NHC(O)NHNR$^{18B}R^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{16A}$, $R^{16B}$, $R^{16C}$, $R^{16D}$, $R^{18A}$, $R^{18B}$, $R^{18C}$, and $R^{18D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;

n1, n2, n3, n4, n5, n6, n16, and n18 are an integer from 0 to 4;

v1, v2, v3, v4, v5, v6, v16, and v18 are independently 1 or 2; and p is 2, 3, or 4;

or a pharmaceutically acceptable salt thereof.

Embodiment P36. The pharmaceutical composition of Embodiments P34-P35, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

Embodiments Q

Embodiment Q1. A method for treating T-cell lymphoma in a subject in need thereof, comprising administering to the subject, a compound having the structure of formula (XXI):

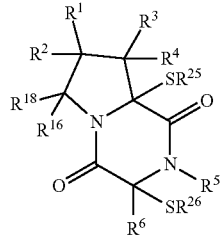

(XXI)

wherein, $R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{n1}OR^{1B}$, —$SO_{v1}NR^{1B}R^{1C}$, —$NHNR^{1B}R^{1C}$, —$ONR^{1B}R^{1C}$, —NHC(O)NHNR$^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$— $COOR^{2A}$, —$CONR^{2B}R^{2C}$, —$NO_2$, —$SR^{2D}$, —$SO_{n2}R^{2B}$, —$SO_{n2}OR^{2B}$, —$SO_{v2}NR^{2B}R^{2C}$, —$NHNR^{2B}R^{2C}$, —$ONR^{2B}R^{2C}$, —NHC(O)NHNR$^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$— $COOR^{3A}$, —$CONR^{3B}R^{3C}$, —$NO_2$, —$SR^{3D}$, —$SO_{n3}R^{3B}$, —$SO_{n3}OR^{3B}$, —$SO_{v3}NR^{3B}R^{3C}$, —$NHNR^{3B}R^{3C}$, $ONR^{3B}R^{3C}$, —NHC(O)NHNR$^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{4A}$, —$NR^{34}R^{4C}$, —$COOR^{4A}$, —$CONR^{4B}R^{4C}$, —$NO_2$, —$SR^{4D}$, —$SO_{n4}R^{4B}$, —$SO_{n4}OR^{4B}$, —$SO_{v4}NR^{4B}R^{4C}$, —$NHNR^{4B}R^{4C}$, —$ONR^{4B}R^{4C}$, —NHC(O)NHNR$^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$N_3$, —$CF_3$, —$CCl_3$, —$CBr_3$, —$CI_3$, —CN, —CHO, —$OR^{5A}$, —$NHNR^{5B}R^{5C}$, —$COOR^{5A}$, —$CONR^{5B}R^{5C}$, —$NO_2$, —$SR^{5D}$, —$SO_{n5}R^{5B}$, —$SO_{n5}OR^{5B}$, —$SO_{v5}NR^{5B}R^{5C}$, —$NHNR^{5B}R^{5C}$, —$ONR^{5B}R^{5C}$, —NHC(O)NHNR$^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —SO$_{n6}$R$^{6B}$, —SO$_{n6}$OR$^{6B}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —N$_3$, —CF$_3$, —CCl$_3$, —CBr$_3$, —CI$_3$, —CN, —CHO, —OR$^{16A}$, —NR$^{16B}$R$^{16C}$, —COOR$^{16A}$, —CONR$^{16B}$R$^{16C}$, —NO$_2$, —SR$^{16D}$, —SO$_{n16}$R$^{16B}$, —SO$_{n16}$OR$^{16B}$, —SO$_{v16}$NR$^{16B}$R$^{16C}$, —NHNR$^{16B}$R$^{16C}$, —ONR$^{16B}$R$^{16C}$, —NHC(O)NHNR$^{16B}$R$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{18}$ is hydrogen, halogen, —N$_3$, —CF$_3$, —CCl$_3$, —CBr$_3$, —CI$_3$, —CN, —CHO, —OR$^{18A}$, —NR$^{18B}$R$^{18C}$, —COOR$^{18A}$, —CONR$^{18B}$R$^{18C}$, —NO$_2$, —SR$^{18D}$, —SO$_{n18}$R$^{18B}$, —SO$_{n18}$OR$^{18B}$, —SO$_{v18}$NR$^{18B}$R$^{18C}$, —NHNR$^{18B}$R$^{18C}$, —ONR$^{18B}$R$^{18C}$, —NHC(O)NHNR$^{18B}$R$^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{25}$ is hydrogen —C(O)-L$^1$-R$^{32}$, —C(S)-L$^1$-R$^{32}$, substituted or unsubstituted alkyl, substituted or unsubstituted heteroalkyl, substituted or unsubstituted aryl, or substituted or unsubstituted heteroaryl;

R$^{26}$ is hydrogen, —C(O)-L$^2$-R$^{33}$, —C(S)-L$^2$-R$^{33}$, substituted or unsubstituted alkyl, substituted or unsubstituted heteroalkyl, substituted or unsubstituted aryl, or substituted or unsubstituted heteroaryl;

R$^{25}$ and R$^{26}$ may optionally be joined to form

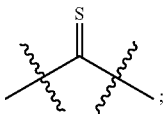 [SMILES: *C(*)=S]

L$^1$ is a bond, —O—, —NH—, substituted or unsubstituted alkylene, substituted or unsubstituted heteroalkylene;

L$^2$ is a bond, —O—, —NH—, substituted or unsubstituted alkylene, substituted or unsubstituted heteroalkylene;

R$^{32}$ and R$^{33}$ are independently halogen, substituted or unsubstituted C$_1$-C$_3$ alkyl, substituted or unsubstituted aryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{16A}$, R$^{16B}$, R$^{16C}$, R$^{16D}$, R$^{18A}$, R$^{18B}$, R$^{18C}$, and R$^{18D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;
n1, n2, n3, n4, n5, n6, n16, and n18 are independently an integer from 0 to 4; and v1, v2, v3, v4, v5, v6, v16, and v18 are independently 1 or 2;

or a pharmaceutically acceptable salt thereof.

Embodiment Q2. The method of Embodiment Q1, wherein R$^{18}$ is substituted or unsubstituted heterocycloalkyl, substituted or unsubstituted aryl, or substituted or unsubstituted heteroaryl.

Embodiment Q3. The method of Embodiment Q1 or Q2, wherein R$^{16}$ is hydrogen.

Embodiment Q4. The method of Embodiment Q1, wherein the compound has the formula:

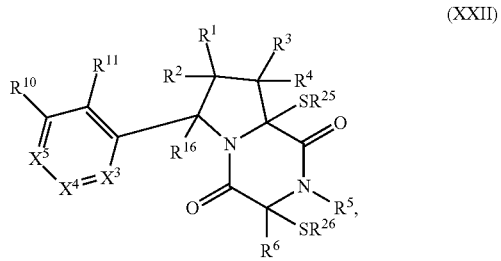

(XXII)

wherein:
X$^3$ is —N═ or —CR$^7$═;
X$^4$ is —N═ or —CR$^8$═;
X$^5$ is —N═ or —CR$^9$═;
R$^7$ is hydrogen, halogen, —N$_3$, —CF$_3$, —CCl$_3$, —CBr$_3$, —CI$_3$, —CN, —CHO, —OR$^{7A}$, —NR$^{7B}$R$^{7C}$, —COOR$^{7A}$, —CONR$^{7B}$R$^{7C}$, —NO$_2$, —SR$^{7D}$, —SO$_{n7}$R$^{7B}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —N$_3$, —CF$_3$, —CCl$_3$, —CBr$_3$, —CI$_3$, —CN, —CHO, —OR$^A$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ may optionally be joined to form a substituted or unsubstituted cycloalkyl, substituted or unsubstituted heterocycloalkyl;

R$^9$ is hydrogen, halogen, —N$_3$, —CF$_3$, —CCl$_3$, —CBr$_3$, —CI$_3$, —CN, —CHO, —OR$^{9A}$, —NR$^{9B}$R$^{9C}$, —COOR$^{9A}$, —CONR$^{9B}$R$^{9C}$, —NO$_2$, —SR$^{9D}$, —SO$_{v9}$R$^{9B}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^8$ and R$^9$ may optionally be joined to form a substituted or unsubstituted cycloalkyl, substituted or unsubstituted heterocycloalkyl;

R$^{10}$ is hydrogen, halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —CONR$^{10B}$R$^{10C}$, —NO$_2$, —SR$^{10D}$, —SO$_{n10}$R$^{10B}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —CONR$^{11B}$R$^{11C}$, —NO$_2$, —SR$^{11D}$, —SO$_{n11}$R$^{11B}$, —SO$_{v11}$NR$^{11B}$R$^{11C}$, —R$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$ and R$^{11D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{7B}$ and R$^{7C}$, R$^{8B}$ and R$^{8C}$, R$^{9B}$ and R$^{9C}$, R$^{10B}$ and R$^{10C}$, and R$^{11B}$ and R$^{11C}$, substituents bonded to the same nitrogen atom may optionally be joined to form a substituted or unsubstituted heterocycloalkyl or substituted or unsubstituted heteroaryl; n7, n8, n9, n10 and n11 are independently an integer from 0 to 4; and v7, v8, v9, v10 and v11 are independently 1 or 2.

Embodiment Q5. The method of any one of Embodiments Q2 to Q4, wherein R$^7$ and R$^8$ or R$^8$ and R$^9$ are joined to form a substituted or unsubstituted cycloalkyl or substituted or unsubstituted heterocycloalkyl having structural formula:

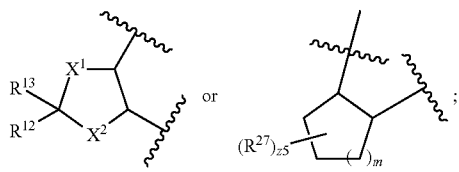

wherein:
X$^1$ is —CR$^{21A}$R$^{21B}$—, —O—, —NR$^{21C}$— or —S—;
X$^2$ is —CR$^{22A}$R$^{22B}$—, —O—, —NR$^{22C}$—, or —S—;
R$^{12}$ is hydrogen, halogen, —N$_3$, —CF$_3$, —CCl$_3$, —CBr$_3$, —CI$_3$, —CN, —CHO, —OR$^{12A}$, —NR$^{12B}$R$^{12C}$, —COOR$^{12A}$, —CONR$^{12B}$R$^{12C}$, —NO$_2$, —SR$^{12D}$, —SO$_{n12}$R$^{12B}$, —SO$_{n12}$OR$^{12B}$, —SO$_{v12}$NR$^{12B}$R$^{12C}$, —NHNR$^{12B}$R$^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{3A}$, —CONR$^{13B}$R$^{13C}$, —NO$_2$, —SR$^{13D}$, —SO$_{n13}$R$^{3B}$, —SO$_{v12}$OR$^{13B}$, —SO$_{v12}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{27}$ is hydrogen, halogen, —N$_3$, —CF$_3$, —CCl$_3$, —CBr$_3$, —CI$_3$, —CN, —CHO, —OR$^{27A}$, —NR$^{27B}$R$^{27C}$, —COOR$^{27A}$, —CONR$^{27B}$R$^{27C}$, —NO$_2$, —SR$^{27D}$, —SO$_{n27}$R$^{27B}$, —SO$_{n27}$OR$^{27B}$, —SO$_{v27}$NR$^{27B}$R$^{27C}$, —NHNR$^{27B}$R$^{27C}$, —ONR$^{27B}$R$^{27C}$, —NHC(O)NHNR$^{27B}$R$^{27C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21A}$, R$^{21B}$, R$^{22A}$, and R$^{22B}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21C}$, R$^{22C}$, R$^{27A}$, R$^{27B}$, R$^{27C}$, and R$^{27D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n12, n13, and n27 are independently an integer from 0 to 4;

v12, v13 and v27 are independent 1 or 2;

m is 1 or 2;

z5 is an integer from 0 to 8;

or a pharmaceutically acceptable salt thereof.

Embodiment Q6. The method of any one of Embodiments Q1-Q5, wherein the compound has the formula:

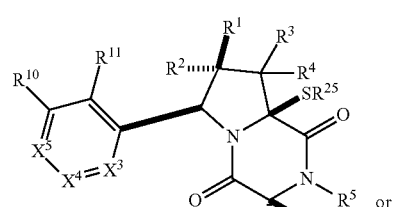

(XXII(S))

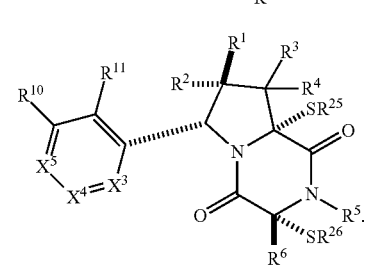

(XXII(R))

Embodiment Q7. The method of any one of Embodiments Q1-Q5, wherein the compound has the formula:

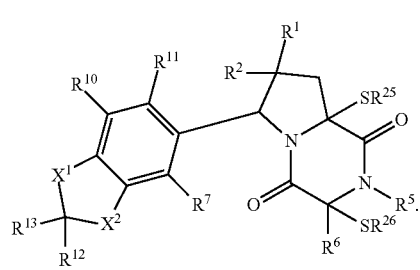

(XXV)

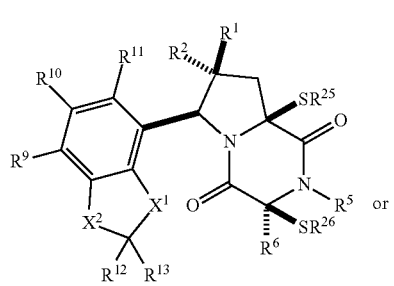

(XXVII(S))

or

Embodiment Q8. The method of any one of Embodiments Q1-Q6, wherein the compound has the formula:

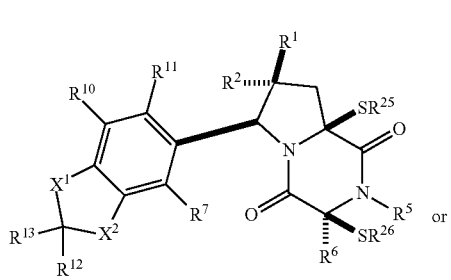

(XXV(S))

or

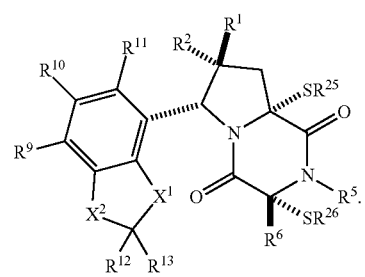

(XXVII(R))

Embodiment Q11. The method of any one of Embodiments Q1-Q5, wherein the compound has the formula:

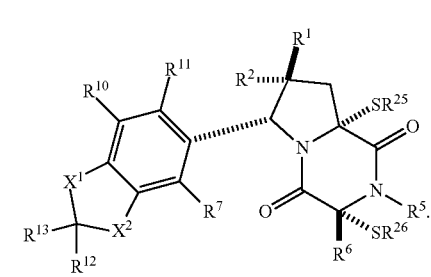

(XXV(R))

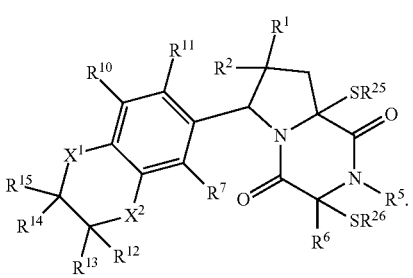

(XXVIII)

Embodiment Q9. The method of any one of Embodiments Q1-Q5, wherein the compound has the formula:

Embodiment Q12. The method of any one of Embodiments Q1-Q11, wherein the compound has the formula:

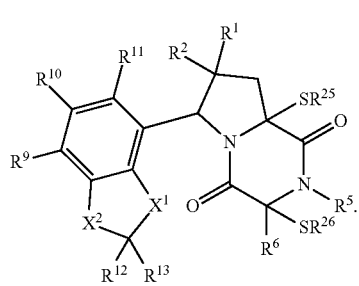

(XXVII)

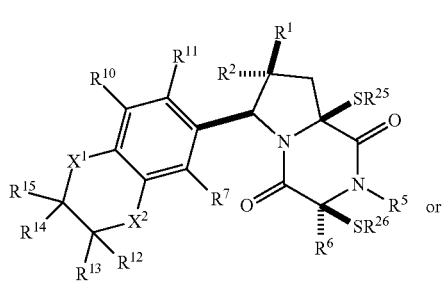

(XXVIII(S))

or

Embodiment Q10. The method of any one of Embodiments Q1-Q9, wherein the compound is -continued (XXVIII(R))

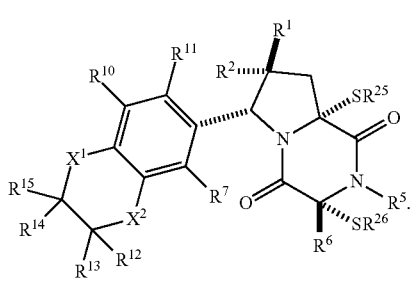

Embodiment Q13. The method of any one of Embodiments Q1-Q5, wherein the compound has the formula:

(XXIX)

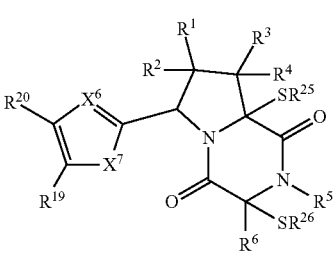

wherein:
$X^6$ is —N= or —CR$^{23A}$=;
$X^7$ is —CR$^{24A}$R$^{24B}$—, —S—, —O—, or —NR$^{24C}$—;
$R^{19}$ is hydrogen, halogen, —N$_3$, —CF$_3$, —CCl$_3$, —CBr$_3$, —CI$_3$, —CN, —CHO, —OR$^{19A}$, —NR$^{19B}$R$^{19C}$, —COOR$^{19A}$, —CONR$^{19B}$R$^{19C}$, —NO$_2$, —SR$^{19D}$, —SO$_{n19}$R$^{19B}$, —SO$_{v19}$NR$^{19B}$R$^{19C}$, —NR$^{19B}$R$^{19C}$C, —ONR$^{19B}$R$^{19C}$, —NHC(O)NHNR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{20}$ is hydrogen, halogen, —N$_3$, —CF$_3$, —CCl$_3$, —CBr$_3$, —CI$_3$, —CN, —CHO, —OR$^{20A}$, —NR$^{20B}$R$^{20C}$, COOR$^{20A}$, CONR$^{20B}$R$^{20C}$, —NO$_2$, —SR$^{20D}$, —SO$_{n20}$R$^{20B}$, —SO$_{v20}$NR$^{20B}$R$^{20C}$, —NHNR$^{20B}$R$^{20C}$, —ONR$^{20B}$R$^{20C}$, —NHC(O)NHNR$^{20B}$R$^{20C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{23A}$, $R^{24A}$, and $R^{24B}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{19A}$, $R^{19B}$, $R^{19C}$, $R^{19D}$, $R^{20A}$, $R^{20B}$, $R^{20C}$, $R^{20D}$, and $R^{24C}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
n19 and n20 are independently an integer from 0 to 4; and v19 and v20 are independent 1 or 2.

Embodiment Q14. The method of any one of Embodiments Q1-Q13, wherein the compound has the formula:

(XXIX(S))

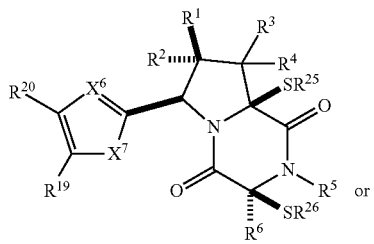

or (XXIX(R))

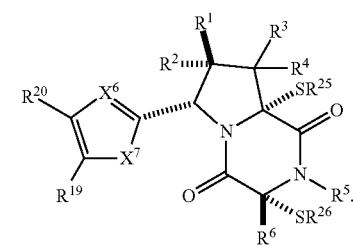

Embodiment Q15. The method of anyone of Embodiments Q1-Q12, wherein $R^{10}$ and $R^{11}$ are independently hydrogen.
Embodiment Q16. The method of anyone of Embodiments Q2-Q6, wherein $X^4$ is —N=.
Embodiment Q17. The method of anyone of Embodiments Q2-Q6, wherein $R^9$ is —OCH$_3$.
Embodiment Q18. The method of anyone of Embodiments Q1-Q17, wherein $R^2$ is substituted or unsubstituted alkyl.
Embodiment Q19. The method of anyone of Embodiments Q1-Q18, wherein $R^2$ is substituted or unsubstituted $C_1$-$C_3$ alkyl.
Embodiment Q20. The method of anyone of Embodiments Q1-Q19, wherein $R^2$ is methyl.
Embodiment Q21. The method of anyone of Embodiments Q1-Q17, wherein $R^2$ is substituted or unsubstituted alkyl.
Embodiment Q22. The method of anyone of Embodiments Q1-Q21, wherein $R^1$ is —CN.
Embodiment Q23. The method of any one of Embodiments Q1-Q22, wherein:
$R^{25}$ is —C(O)-L$^1$-R$^{32}$ or —C(S)-L$^1$-R$^{32}$; and
$R^{26}$ is —C(O)-L$^2$-R$^{33}$ or —C(S)-L$^2$-R$^{33}$.
Embodiment Q24. The method of any one of Embodiments Q1-Q23, wherein L and L$^2$ are independently a bond, —O—, or —NH—.
Embodiment Q25. The method of any one of Embodiments Q1-Q23, wherein:
L$^1$ is -L$^{1A}$-L$^{1B}$, wherein L$^{1A}$ is bonded to —C(O)— or —C(S)—; and
L$^2$ is -L$^{2A}$-L$^{2B}$-, wherein L$^{2A}$ is bonded to —C(O)— or —C(S)—;
L$^{1A}$ is a bond or —(CH$_2$)$_{z1}$—;

$L^{1B}$ is a bond, —O— or —NR$^{30B}$—;
$L^{2A}$ is a bond or —(CH$_2$)$_{z2}$—;
$L^{2B}$ is a bond, —O— or —NR$^{31B}$—;
z1 and z2 are independently an integer from 1 to 10; and
R$^{30B}$ and R$^{31B}$ are independently hydrogen or substituted or unsubstituted alkyl.

Embodiment Q26. The method of Embodiment Q25, wherein $L^{1A}$ and $L^{2A}$ are independently —CH$_2$—.

Embodiment Q27. The method of Embodiment Q25 or Q26, wherein:
$L^{1B}$ is —NR$^{30B}$—.
$L^{2B}$ is —NR$^{31B}$—; and
R$^{30B}$ and R$^{31B}$ are independently unsubstituted C$_1$-C$_3$ alkyl.

Embodiment Q28. The method of anyone of Embodiments Q1-Q27, wherein R$^{32}$ and R$^{33}$ are independently unsubstituted C$_1$-C$_3$ alkyl or unsubstituted aryl.

Embodiment Q29. The method of any one of Embodiments Q1 to Q28, wherein R$^{32}$ and R$^{33}$ are independently halogen.

Embodiment Q30. The method of any one of Embodiments Q1 to Q21, wherein R$^{25}$ and R$^{26}$ are joined together to form:

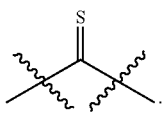 [SMILES: *C(*)=S]

Embodiment Q31. The method of anyone of Embodiments Q1-Q30, wherein R$^6$ is methyl.

Embodiment Q32. The method of any one of Embodiments Q1-Q31, wherein the compound has the structure:

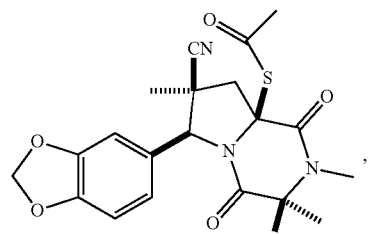

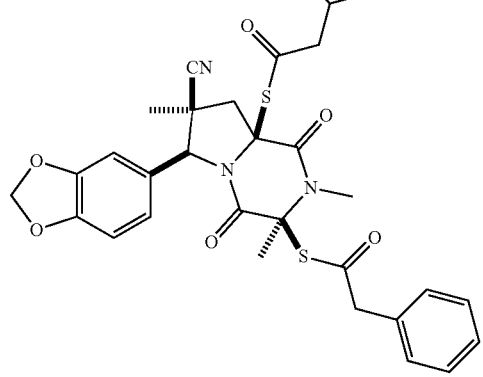

-continued

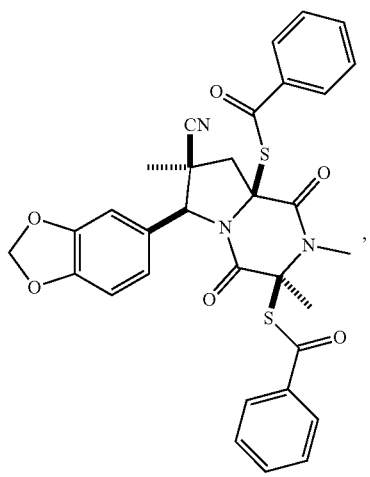

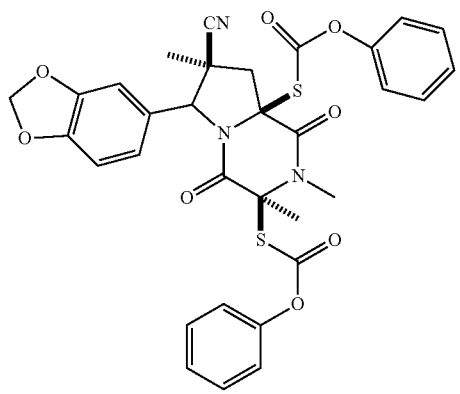

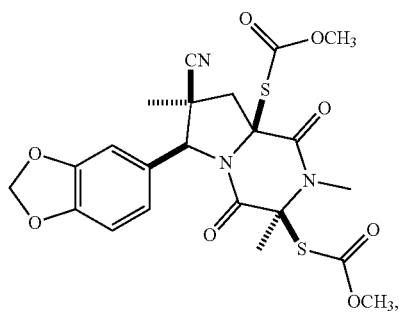

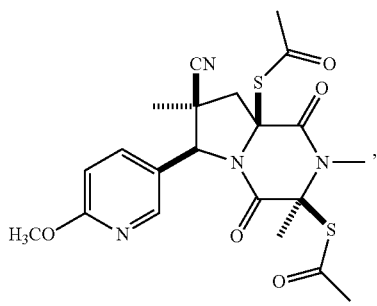

199
-continued
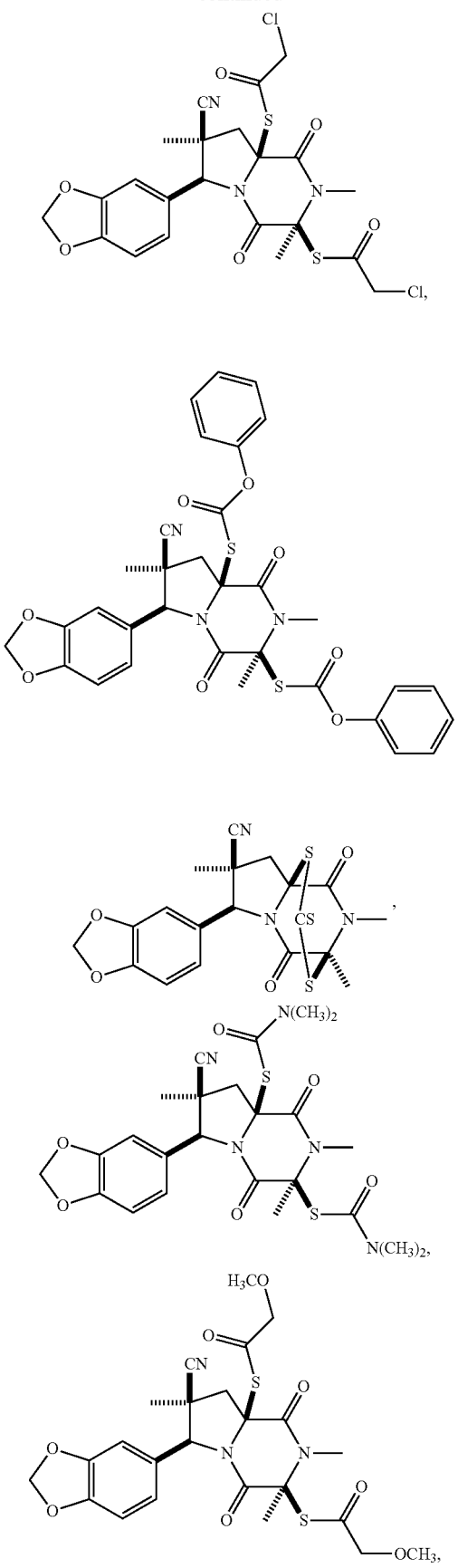
200
-continued
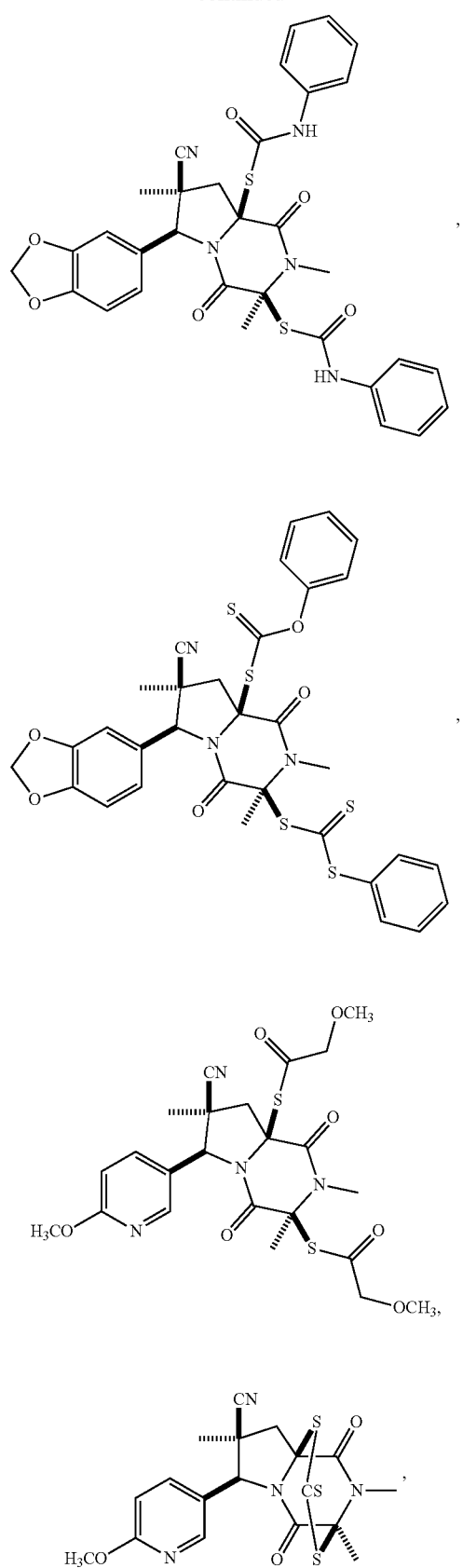

201
-continued

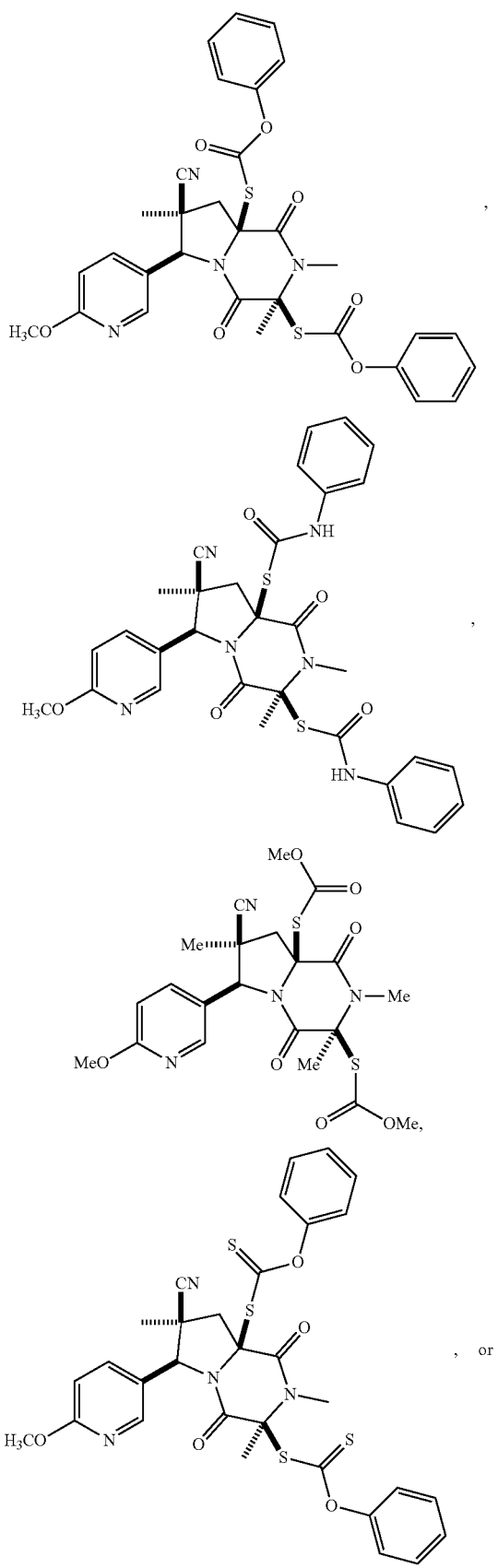

,

202
-continued

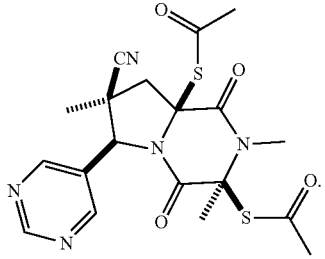

Embodiment Q33. The method of any one of Embodiments Q1-Q32, wherein the T-cell lymphoma is cutaneous T-cell lymphoma (CTCL), peripheral T-cell lymphoma, anaplastic large-cell lymphoma, angioimmunoblastic T-cell lymphoma, adult T-cell Leukemia/Lymphoma, blastic natural killer (NK) cell lymphoma, enteropathy-associated T-cell lymphoma, hepatosplenic T-cell lymphoma, lymphoblastic lymphoma, or nasal natural killer (NK)/T-cell lymphoma.

Embodiment Q34. The method of Embodiment Q33, wherein the cutaneous T-cell lymphoma is Sezary syndrome, mycosis fungoides, folliculotropic mycosis fungoides, pagetoid reticulosis, granulomatous slack skin, primary cutaneous CD30+ T-cell lymphoproliferative disorders, lymphomatoid papulosis, primary cutaneous anaplastic large-cell lymphoma, primary cutaneous γδ T-cell lymphoma, primary cutaneous CD8+ aggressive epidermotropic lymphoma, primary cutaneous CD8+ aggressive epidermotropic cytotoxic T-cell lymphoma, or primary cutaneous CD4+ small/medium T-cell lymphoma.

Embodiment Q35. The method of anyone of Embodiments Q1-Q34, wherein the T-cell lymphoma is associated with at least one of the following conditions: smoking, obesity, infection, HIV, Epstein-Barr virus, human T-lymphotropic virus, *Helicobacter pyroli* infection, chronic *Helicobacter pyroli* infection, exposure to chemicals, exposure to insecticides, exposure to pesticides, use of immunosuppressant drugs, weakened immune system, genetic disorders, previous chemotherapy, and previous radiation therapy.

Embodiment Q36. The method of any one of Embodiments Q1-Q35, further comprising administering to the subject an additional therapeutic agent used in the treatment of T-cell lymphoma.

Embodiment Q37. The method of Embodiment Q36, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

Embodiment Q38. A pharmaceutical composition for treating T-cell lymphoma comprising an ETP derivative, at least one additional therapeutic agent used in the treatment of T-cell lymphoma, and at least one pharmaceutically acceptable excipient.

Embodiment Q39. The pharmaceutical composition of Embodiment Q38, wherein the ETP derivative is a compound having the structure of formula (XXI):

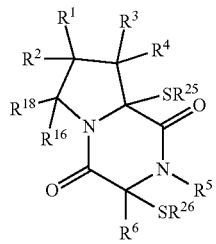

(XXI)

wherein, $R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{n1}OR^{1B}$, —$SO_{v1}NR^{1B}R^{1C}$, —$NHNR^{1B}R^{1C}$, —$ONR^{1B}R^{1C}$, —NHC(O)NHNR$^{1B}$R$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$, —$COOR^{2A}$, —$CONR^{2B}R^{2C}$, —$NO_2$, —$SR^{2D}$, —$SO_{n2}R^{2B}$, —$SO_{n2}OR^{2B}$, —$SO_{v2}NR^{2B}R^{2C}$, —$NHNR^{2B}R^{2C}$, —$ONR^{2B}R^{2C}$, —NHC(O)NHNR$^{2B}$R$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_3R^{3B}$, —$SO_{n3}OR^{3B}$, —$SO_{v3}NR^{3B}R^{3C}$, —$NHNR^{3B}R^{3C}$, —$ONR^{3B}R^{3C}$, —NHC(O)NHNR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{4A}$, —$NR^{34}R^{4C}$, —$COOR^{4A}$, —$CONR^{4B}R^{4C}$, —$NO_2$, —$SR^{4D}$, —$SO_{n4}R^{4B}$, —$SO_{n4}OR^{4B}$, —$SO_{v4}NR^{4B}R^{4C}$, —$NHNR^{4B}R^{4C}$, —$ONR^{4B}R^{4C}$, —NHC(O)NHNR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$N_3$, —$CF_3$, —$CCl_3$, —$CBr_3$, —$CI_3$, —CN, —CHO, —$OR^{5A}$, —$NR^{5B}R^{5C}$, —$COOR^{5A}$, —$CONR^{5B}R^{5C}$, —$NO_2$, —$SR^{5D}$, —$SO_{n5}R^{5B}$, —$SO_{n5}OR^{5B}$, —$SO_{v5}NR^{5B}R^{5C}$, —$NHNR^{5B}R^{5C}$, —$ONR^{5B}R^{5C}$, —NHC(O)NHNR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{v6}NR^{6B}R^{6C}$, —$NHNR^{6B}R^{6C}$, —$ONR^{6B}R^{6C}$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$N_3$, —$CF_3$, —$CCl_3$, —$CBr_3$, —$CI_3$, —CN, —CHO, —$OR^{6A}$, —$NR^{16B}R^{16C}$, —$COOR^{16A}$, —$CONR^{16B}R^{16C}$, —$NO_2$, —$SR^{16D}$, —$SO_{n16}R^{16B}$, —$SO_{n16}OR^{16B}$, —$SO_{v16}NR^{16B}R^{16C}$, —$NHNR^{16B}R^{16C}$, —$ONR^{16B}R^{16C}$, —NHC(O)NHNR$^{16B}$R$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$N_3$, —$CF_3$, —$CCl_3$, —$CBr_3$, —$CI_3$, —CN, —CHO, —$OR^{18A}$, —$NR^{18B}R^{18C}$, —$COOR^{18A}$, —$CONR^{18B}R^{18C}$, —$NO_2$, —$SR^{18D}$, —$SO_{n18}R^{18B}$, —$SO_{n18}OR^{18B}$, —$SO_{v18}NR^{18B}R^{18C}$, —$NHNR^{18B}R^{18C}$, —$ONR^{18B}R^{18C}$, —NHC(O)NHNR$^{18B}$R$^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{25}$ is hydrogen —C(O)-$L^1$-$R^{32}$, —C(S)-$L^1$-$R^{32}$, substituted or unsubstituted alkyl, substituted or unsubstituted heteroalkyl, substituted or unsubstituted aryl, or substituted or unsubstituted heteroaryl;

$R^{26}$ is hydrogen, —C(O)-$L^2$-$R^{33}$, —C(S)-$L^2$-$R^{33}$, substituted or unsubstituted alkyl, substituted or unsubstituted heteroalkyl, substituted or unsubstituted aryl, or substituted or unsubstituted heteroaryl;

$R^{25}$ and $R^{26}$ may optionally be joined to form

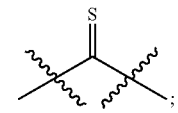 [SMILES: *C(*)=S]

;

$L^1$ is a bond, —O—, —NH—, substituted or unsubstituted alkylene, substituted or unsubstituted heteroalkylene;

$L^2$ is a bond, —O—, —NH—, substituted or unsubstituted alkylene, substituted or unsubstituted heteroalkylene;

$R^{32}$ and $R^{33}$ are independently halogen, substituted or unsubstituted $C_1$-$C_3$ alkyl, substituted or unsubstituted aryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{16A}$, $R^{16B}$, $R^{16C}$, $R^{16D}$, $R^{18A}$, $R^{18B}$, $R^{18C}$, and $R^{18D}$ are independently hydrogen, halogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;

n1, n2, n3, n4, n5, n6, n16, and n18 are independently an integer from 0 to 4; and v1, v2, v3, v4, v5, v6, v16, and v18 are independently 1 or 2;

or a pharmaceutically acceptable salt thereof.

Embodiment Q40. The pharmaceutical composition of Embodiment Q38 or Q39, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

EMBODIMENTS

Embodiment 1. A method for treating T-cell lymphoma in a subject in need thereof, comprising administering to the subject, a compound having the structure of formula (1):

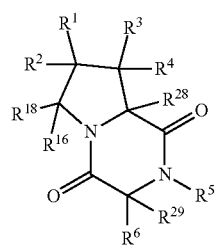

(1)

wherein, $R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{n1}OR^{1B}$, —$SO_{v1}NR^{1B}R^{1C}$, —$NHNR^{1B}R^{1C}$, $ONR^{1B}R^{1C}$, —NHC(O)$NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$, —$COOR^{2A}$, —$CONR^{2B}R^{2C}$, —$NO_2$, —$SR^{2D}$, —$SO_{n2}R^{2B}$, —$SO_{n2}OR^{2B}$, —$SO_{v2}NR^{2B}R^{2C}$, —$NHNR^{2B}R^{2C}$, —$ONR^{2B}R^{2C}$, —NHC(O)$NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$—$COOR^{3A}$, —$CONR^{3B}R^{3C}$, —$NO_2$, —$SR^{3D}$, —$SO_{n3}R^{3B}$, —$SO_{n3}OR^{3B}$, —$SO_{v3}NR^{3B}R^{3C}$, —$NHNR^{3B}R^{3C}$, —$ONR^{3B}R^{3C}$, —NHC(O)$NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{4A}$, —$NR^{4B}R^{4C}$, —$COOR^{4A}$, —$CONR^{4B}R^{4C}$, —$NO_2$, —$SR^{4D}$, —$SO_{n4}R^{4B}$, —$SO_{n4}OR^{4B}$, —$SO_{v4}NR^{4B}R^{4C}$, —$NHNR^{4B}R^{4C}$, $ONR^{4B}R^{4C}$, —NHC(O)$NHNR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$N_3$, —$CF_3$, —$CCl_3$, —$CBr_3$, —$CI_3$, —CN, —CHO, —$OR^{1A}$, —$NR^{5B}R^{5C}$, —$COOR^{5A}$, —$CONR^{5B}R^{5C}$, —$NO_2$, —$SR^{5D}$, —$SO_{n5}R^{5B}$, —$SO_{n5}OR^{5B}$, —$SO_{v5}NR^{5B}R^{5C}$, —$NHNR^{5B}R^{5C}$, —$ONR^{5B}R^{5C}$, —NHC(O)$NHNR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$N_3$, —$CF_3$, —$CCl_3$, —$CBr_3$, —$CI_3$, —CN, —CHO, —$OR^{6A}$, —$NR^{6B}R^{6C}$, —$COOR^{6A}$, —$CONR^{6B}R^{6C}$, —$NO_2$, —$SR^{6D}$, —$SO_{n6}R^{6B}$, —$SO_{n6}OR^{6B}$, —$SO_{v6}NR^{6B}R^{6C}$, —$NHNR^{6B}R^{6C}$, —$ONR^{6B}R^{6C}$, —NHC(O)$NHNR^{6B}R^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$N_3$, —$CF_3$, —$CCl_3$, —$CBr_3$, —$CI_3$, —CN, —CHO, —$OR^{16A}$, —$NR^{16B}R^{16C}$, —$COOR^{16A}$, —$CONR^{16B}R^{16C}$, —$NO_2$, —$SR^{16D}$, —$SO_{n16}R^{16B}$, —$SO_{n16}OR^{16B}$, —$SO_{v16}NR^{16B}R^{16C}$, —$NHNR^{16B}R^{16C}$, —$ONR^{16B}R^{16C}$, —NHC(O)$NHNR^{16B}R^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$N_3$, —$CF_3$, —$CCl_3$, —$CBr_3$, —$CI_3$, —CN, —CHO, —$OR^{18A}$, —$NR^{18B}R^{18C}$, —$COOR^{18A}$, —$CONR^{18B}R^{18C}$, —$NO_2$, —$SR^{18D}$, —$SO_{n18}R^{18B}$, —$SO_{n18}OR^{18B}$, —$SO_{v18}NR^{18B}R^{18C}$, —$NHNR^{18B}R^{18C}$, $ONR^{18B}R^{18C}$, —NHC(O)$NHNR^{18B}R^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{28}$ is —$SR^{25}$ and $R^{29}$ is —$SR^{26}$, wherein $R^{28}$ and $R^{29}$ are optionally joined to form *—$S_p$—* wherein p is an integer from 2 to 4 and each * represents the point of attachment to the remainder of the compound;

$R^{25}$ is hydrogen, —C(O)-$L^1$-$R^{32}$, —C(S)-$L^1$-$R^{32}$, substituted or unsubstituted alkyl, substituted or unsubstituted heteroalkyl, substituted or unsubstituted aryl, or substituted or unsubstituted heteroaryl;

$R^{26}$ is hydrogen, —C(O)-$L^2$-$R^{33}$, —C(S)-$L^2$-$R^{33}$, substituted or unsubstituted alkyl, substituted or unsubstituted heteroalkyl, substituted or unsubstituted aryl, or substituted or unsubstituted heteroaryl;

$R^{25}$ and $R^{26}$ may optionally be joined to form

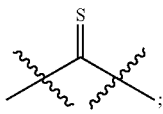

$L^1$ is a bond, —O—, —NH—, substituted or unsubstituted alkylene, substituted or unsubstituted heteroalkylene;

$L^2$ is a bond, —O—, —NH—, substituted or unsubstituted alkylene, substituted or unsubstituted heteroalkylene;

$R^{32}$ and $R^{33}$ are independently halogen, substituted or unsubstituted $C_1$-$C_3$ alkyl, substituted or unsubstituted aryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{16A}$, $R^{16B}$, $R^{16C}$, $R^{16D}$, $R^{18A}$, $R^{18B}$, $R^{18C}$, and $R^{18D}$ are independently hydrogen, halogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;

n1, n2, n3, n4, n5, n6, n16, and n18 are independently an integer from 1 to 4; and v1, v2, v3, v4, v5, v6, v16, and v18 are independently 1 or 2;

or a pharmaceutically acceptable salt thereof.

Embodiment 2. The method of Embodiment 1, wherein $R^{18}$ is substituted or unsubstituted heterocycloalkyl, substituted or unsubstituted aryl, or substituted or unsubstituted heteroaryl.

Embodiment 3. The method of Embodiment 1, wherein $R^{16}$ is hydrogen.

Embodiment 4. The method of Embodiments 1-3, wherein the compound having the structure of formula (I):

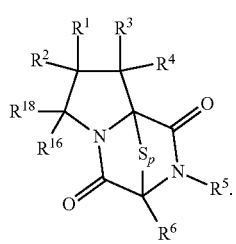

(I)

Embodiment 5. The method of Embodiment 4, wherein $R^3$ and $R^4$ are independently hydrogen or unsubstituted methyl.

Embodiment 6. The method of Embodiments 4-5, wherein R is —CN, —COOR$^{1A}$, —CONR$^{1B}$R$^{1C}$, or substituted or unsubstituted heteroalkyl.

Embodiment 7. The method of Embodiments 4-6, wherein $R^1$ is —CN.

Embodiment 8. The method of Embodiments 4-7, wherein $R^2$ is —$CF_3$, substituted or unsubstituted alkyl, substituted or unsubstituted heteroalkyl, substituted or unsubstituted cycloalkyl, or substituted or unsubstituted heterocycloalkyl.

Embodiment 9. The method of Embodiments 4-8, wherein $R^2$ is substituted or unsubstituted alkyl or substituted or unsubstituted heteroalkyl.

Embodiment 10. The method of Embodiments 4-9, wherein $R^2$ is methyl or methoxy.

Embodiment 11. The method of Embodiments 4-10, wherein $R^5$ and $R^6$ are independently hydrogen, halogen, substituted or unsubstituted alkyl, or substituted or unsubstituted cycloalkyl.

Embodiment 12. The method of Embodiments 4-11, wherein $R^5$ and $R^6$ are independently hydrogen, methyl, ethyl, allyl, or cyclopropyl.

Embodiment 13. The method of Embodiments 4-12, wherein $R^5$ and $R^6$ are independently hydrogen or unsubstituted methyl.

Embodiment 14. The method of Embodiments 4-13, wherein p is 2.

Embodiment 15. The method of Embodiment 4, wherein the compound of formula (I) has the structure of formula (II):

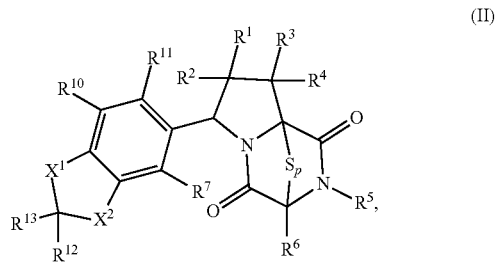

(II)

wherein, $X^1$ is —$CR^{21A}R^{21B}$—, —O—, —$NR^{21C}$— or —S—;

$X^2$ is —$CR^{22A}R^{22B}$—, —O—, —$NR^{22C}$—, or —S—;

$R^7$ is hydrogen, halogen, —$N_3$, —$CF_3$, —$CCl_3$, —$CBr_3$, —$CI_3$, —CN, —CHO, —$OR^{7A}$, —$NR^{7B}R^{7C}$, —$COOR^{7A}$, —$CONR^{7B}R^{7C}$, —$NO_2$, —$SR^{7D}$, —$SO_{n7}R^{7B}$, —$SO_{n7}OR^{7B}$, —$SO_{v7}NR^{7B}R^{7C}$, —$NHNR^{7B}R^{7C}$, —$ONR^{7B}R^{7C}$, —NHC(O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$N_3$, —$CF_3$, —$CCl_3$, —$CBr_3$, —$CI_3$, —CN, —CHO, —$OR^{10A}$, —$NR^{10B}R^{10C}$, —$COOR^{10A}$, —$CONR^{10B}R^{10C}$, —$NO_2$, —$SR^{10D}$, —$SO_{n10}R^{10B}$, —$SO_{n10}OR^{10B}$, —$SO_{v10}NR^{10B}R^{10C}$, —$NHNR^{10B}R^{10C}$, —$ONR^{10B}R^{10C}$, —NHC(O) NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$N_3$, —$CF_3$, —$CCl_3$, —$CBr_3$, —$CI_3$, —CN, —CHO, —$OR^{11A}$, —$NR^{11B}R^{11C}$, —$COOR^{11A}$, —$CONR^{11B}R^{11C}$, —$NO_2$, —$SR^{11D}$, —$SO_{n11}R^{11B}$, —$SO_{n11}OR^{11B}$, —$SO_{v11}NR^{11B}R^{11C}$, —$NHNR^{11B}R^{11C}$, —$ONR^{11B}R^{11C}$, —NHC(O)

NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ and R$^{11}$ are optionally joined together to form a substituted or unsubstituted cycloalkyl, a substituted or unsubstituted heterocycloalkyl, a substituted or unsubstituted aryl, or a substituted or unsubstituted heteroaryl;

R$^{12}$ is hydrogen, halogen, —N$_3$, —CF$_3$, —CCl$_3$, —CBr$_3$, —CI$_3$, —CN, —CHO, —OR$^{12A}$, —NR$^{12B}$R$^{12C}$, —COOR$^{12A}$, —CONR$^{12B}$R$^{12C}$, —NO$_2$, —SR$^{12D}$, —SO$_{n12}$R$^{12B}$, —SO$_{n12}$OR$^{12B}$, —SO$_{v12}$NR$^{12B}$R$^{12C}$, —NHNR$^{12B}$R$^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —N$_3$, —CF$_3$, —CCl$_3$, —CBr$_3$, —CI$_3$, —CN, —CHO, —OR$^{13A}$, —NR$^{13B}$R$^{13C}$, —COOR$^{13A}$, —CONR$^{13B}$R$^{13C}$, —NO$_2$, —SR$^{13D}$, —SO$_{n13}$R$^{13B}$, —SO$_{n13}$OR$^{13B}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21A}$, R$^{21B}$, R$^{22A}$, and R$^{22B}$, are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{7A}$, R$^{7B}$, R$^{7C}$, R$^{7C}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{21C}$, and R$^{22C}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n7, n10, n11, n12 and n13 are independently 1 or 4;

v7, v10, v11, v12 and v13 are independently 1 or 2; and p is 2 or 3;

or a pharmaceutically acceptable salt thereof.

Embodiment 16. The method of Embodiment 15, wherein the compound of formula (II) has the structure of formula:

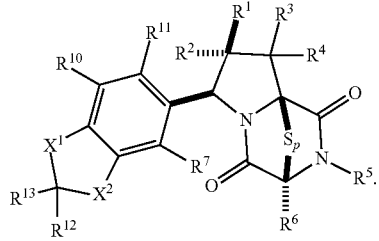

(II(S))

Embodiment 17. The method of Embodiment 16, wherein X$^1$ and X$^2$ are independently —O— or —S—.

Embodiment 18. The method of Embodiments 15-17, wherein p is 2.

Embodiment 19. The method of Embodiments 16-17, wherein the compound of formula (II(S)) has the structure of formula (III(S)):

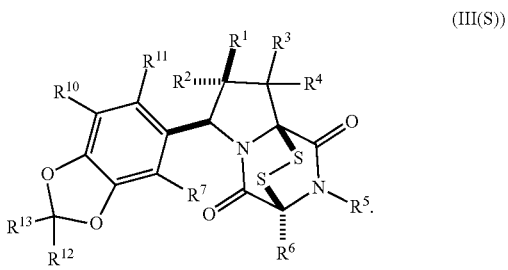

(III(S))

Embodiment 20. The method of Embodiment 19, wherein R$^1$ is —CN, —OR$^{1A}$, —COOR$^{1A}$, or —CONR$^{1B}$R$^{1C}$, and wherein R$^{1A}$, R$^{1B}$, and R$^{1C}$ are independently hydrogen, or substituted or unsubstituted alkyl.

Embodiment 21. The method of Embodiments 19 or 20, wherein R$^1$ is —CN.

Embodiment 22. The method of Embodiments 19-21, wherein R$^2$ is —CF$_3$, substituted or unsubstituted alkyl, substituted or unsubstituted heteroalkyl, substituted or unsubstituted cycloalkyl, or substituted or unsubstituted heterocycloalkyl.

Embodiment 23. The method of Embodiments 19-22, wherein R$^2$ is substituted or unsubstituted alkyl or substituted or unsubstituted heteroalkyl.

Embodiment 24. The method of Embodiments 19-23, wherein R$^2$ is methyl.

Embodiment 25. The method of Embodiments 19-24, wherein R$^3$ and R$^4$ are hydrogen.

Embodiment 26. The method of Embodiments 19-25, wherein R$^{12}$ and R$^{13}$ are independently hydrogen or unsubstituted methyl.

Embodiment 27. The method of Embodiments 19-27, wherein R$^{10}$ and R$^{11}$ are hydrogen.

Embodiment 28. The method of Embodiments 4-27, wherein the compound is:

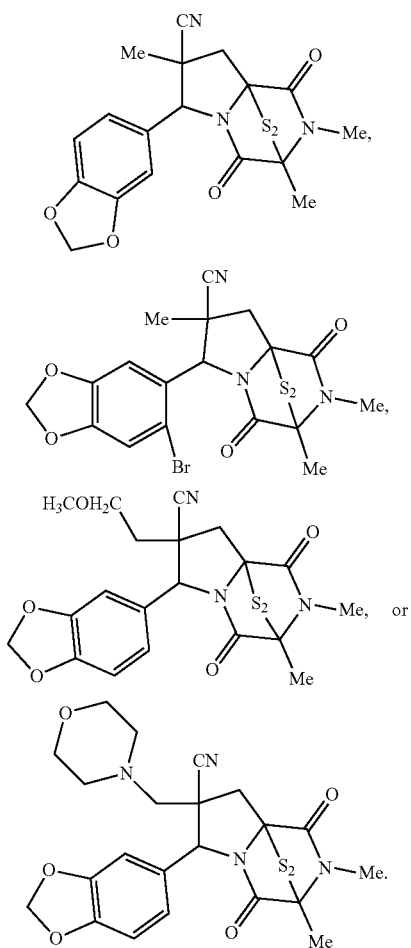
Embodiment 29. The method of Embodiment 28, wherein the compound is:
(1)
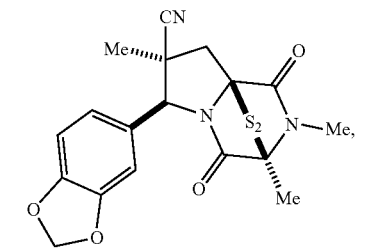
(2)
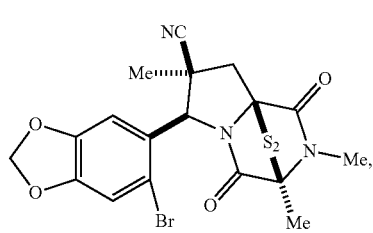
-continued
(3)
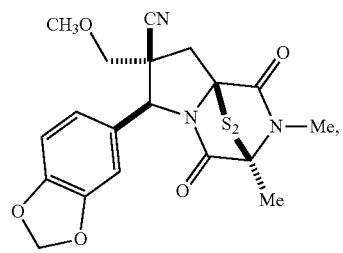
(4)
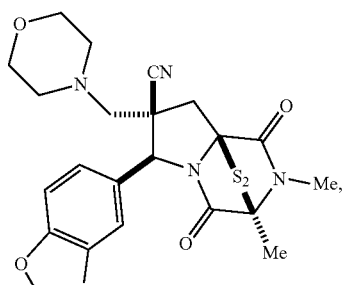
(5)
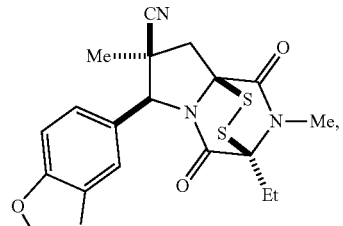
(6)
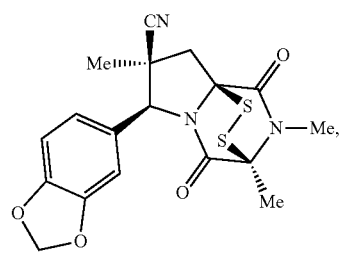
(7)
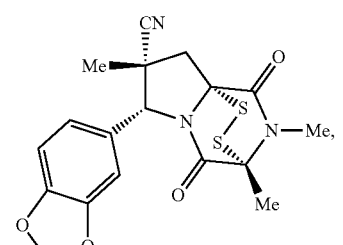
(8)
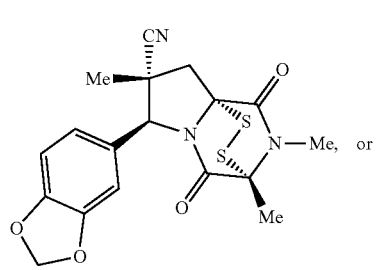

-continued (9)

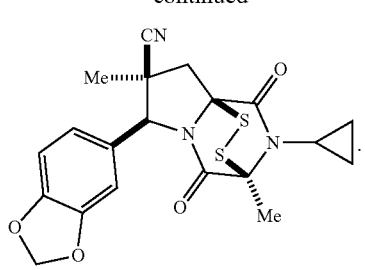

Embodiment 30. The method of Embodiments 1-3, a compound having the structure of formula (XXI):

(XXI)

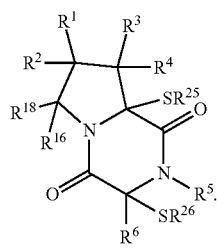

Embodiment 31. The method of Embodiment 30, wherein the compound has the formula:

(XXII)

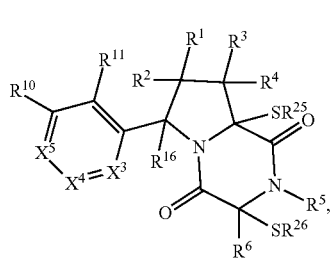

wherein:
$X^3$ is —N= or —CR$^7$=;
$X^4$ is —N= or —CR$^8$=;
$X^5$ is —N= or —CR$^9$=;
$R^7$ is hydrogen, halogen, —N$_3$, —CF$_3$, —CCl$_3$, —CBr$_3$, —CI$_3$, —CN, —CHO, —OR$^{7A}$, —NR$^{7B}$R$^{7C}$, —COOR$^{7A}$, —CONR$^{7B}$R$^{7C}$, —NO$_2$, —SR$^{7D}$, —SO$_{n7}$R$^{7B}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^8$ is hydrogen, halogen, —N$_3$, —CF$_3$, —CCl$_3$, —CBr$_3$, —CI$_3$, —CN, —CHO, —OR$^{8A}$, —NR$^{8B}$R$^{8C}$, —COOR$^{8A}$, —CONR$^{8B}$R$^{8C}$, —NO$_2$, —SR$^{8D}$, —SO$_{n8}$R$^{8B}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ may optionally be joined to form a substituted or unsubstituted cycloalkyl, substituted or unsubstituted heterocycloalkyl;
$R^9$ is hydrogen, halogen, —N$_3$, —CF$_3$, —CCl$_3$, —CBr$_3$, —CI$_3$, —CN, —CHO, —OR$^{9A}$—NR$^{9B}$R$^{9C}$, —COOR$^{9A}$, —CONR$^{9B}$R$^{9C}$, —NO$_2$, —SR$^{9D}$, —SO$_{n9}$R$^{9B}$, —SO$_{v9}$NR$^{9B}$R$^{9C}$, —R$^{9B}$R$^{9C}$—ONR$^{9B}$R$^{9C}$, —NHC(O)NHNR$^{9B}$R$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ and $R^9$ may optionally be joined to form a substituted or unsubstituted cycloalkyl, substituted or unsubstituted heterocycloalkyl;
$R^{10}$ is hydrogen, halogen, —N$_3$, —CF$_3$, —CCl$_3$, —CBr$_3$, —CI$_3$, —CN, —CHO, —OR$^{10A}$, —NR$^{10B}$R$^{10C}$, —COOR$^{10A}$, —CONR$^{10B}$R$^{10C}$, —NO$_2$, —SR$^{10D}$, —SO$_{n10}$R$^{10B}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, —N$_3$, —CF$_3$, —CCl$_3$, —CBr$_3$, —CI$_3$, —CN, —CHO, —OR$^{11A}$, —NR$^{11B}$R$^{11C}$, —COOR$^{11A}$, —CONR$^{11B}$R$^{11C}$, —NO$_2$, —SR$^{11D}$, —SO$_{n11}$R$^{11B}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{7B}$ and $R^{7C}$, $R^{8B}$ and $R^{8C}$, $R^{9B}$ and $R^{9C}$, $R^{10B}$ and $R^{10C}$, and $R^{11B}$ and $R^{11C}$, substituents bonded to the same nitrogen atom may optionally be joined to form a substituted or unsubstituted heterocycloalkyl or substituted or unsubstituted heteroaryl;
n7, n8, n9, n10 and n11 are independently an integer from 1 to 4; and
v7, v8, v9, v10 and v11 are independently 1 or 2.

Embodiment 32. The method of Embodiment 31, wherein $R^7$ and $R^8$ or $R^8$ and $R^9$ are joined to form a substituted or unsubstituted cycloalkyl or substituted or unsubstituted heterocycloalkyl having structural formula:

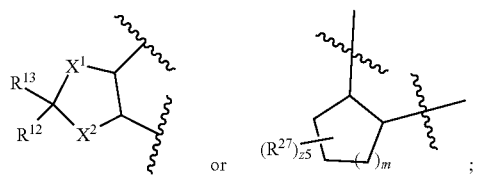

wherein:

X$^1$ is —CR$^{21A}$R$^{21B}$—, —O—, —NR$^{21C}$—, or —S—;

X$^2$ is —CR$^{22A}$R$^{22B}$, —O—, —NR$^{22C}$—, or —S—;

R$^{12}$ is hydrogen, halogen, —N$_3$, —CF$_3$, —CCl$_3$, —CBr$_3$, —CI$_3$, —CN, —CHO, —OR$^{12A}$, —NR$^{12B}$R$^{12C}$, —COOR$^{12A}$, —CONR$^{12B}$R$^{12C}$, —NO$_2$, —SR$^{12D}$, —SO$_{n2}$R$^{12B}$, —SO$_{n12}$OR$^{12B}$, —SO$_{v12}$NR$^{12B}$R$^{12C}$, —NHNR$^{12B}$R$^{12C}$, —ONR$^{12B}$R$^{12C}$, —NHC(O)NHNR$^{12B}$R$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —N$_3$, —CF$_3$, —CCl$_3$, —CBr$_3$, —CI$_3$, —CN, —CHO, —OR$^{3A}$, —NR$^{13B}$R$^{13C}$, —COOR$^{13A}$, —CONR$^{13B}$R$^{13C}$, —NO$_2$, —SR$^{13D}$, —SO$_{n13}$R$^{13B}$, —SO$_{v12}$OR$^{13B}$, —SO$_{v12}$NR$^{13B}$R$^{13C}$, —NHNR$^{13B}$R$^{13C}$, —ONR$^{13B}$R$^{13C}$, —NHC(O)NHNR$^{13B}$R$^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{27}$ is halogen, —N$_3$, —CF$_3$, —CCl$_3$, —CBr$_3$, —CI$_3$, —CN, —CHO, —OR$^{27A}$, —NR$^{27B}$R$^{27C}$, —COOR$^{27A}$, —CONR$^{27B}$R$^{27C}$, —NO$_2$, —SR$^{27D}$, —SO$_{n27}$R$^{27B}$, —SO$_{n27}$OR$^{27B}$, —SO$_{v27}$NR$^{27B}$R$^{27C}$, —NHNR$^{27B}$R$^{27C}$, —ONR$^{27B}$R$^{27C}$, —NHC(O)NHNR$^{27B}$R$^{27C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21A}$, R$^{21B}$, R$^{22A}$, and R$^{22B}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{21C}$, R$^{22C}$, R$^{27A}$, R$^{27B}$, R$^{27C}$, and R$^{27D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n12, n13, and n27 are independently an integer from 1 to 4;

v12, v13 and v27 are independent 1 or 2;

m is 1 or 2;

z5 is an integer from 0 to 8;

or a pharmaceutically acceptable salt thereof.

Embodiment 33. The method of Embodiments 30-32, wherein the compound has the formula:

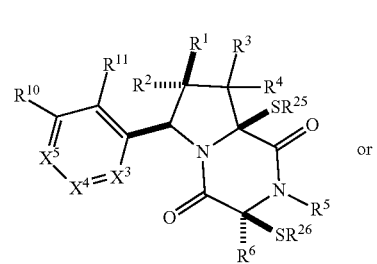

(XXII(S))

or

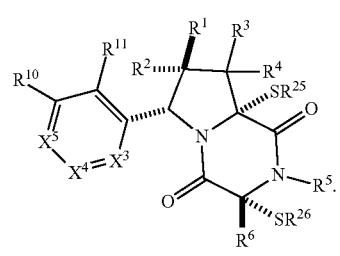

(XXII(R))

Embodiment 34. The method of Embodiment 31, wherein the compound has the formula:

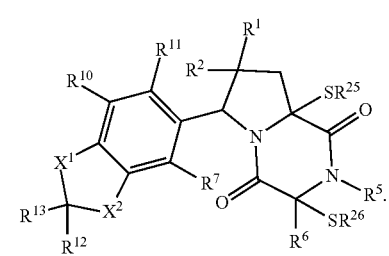

(XXV)

Embodiment 35. The method of Embodiment 31, wherein the compound has the formula:

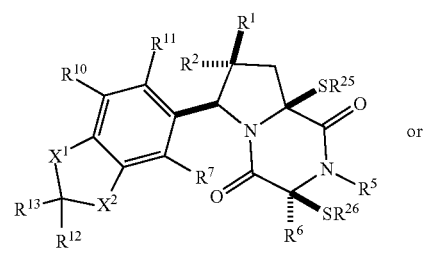

(XXV(S))

or

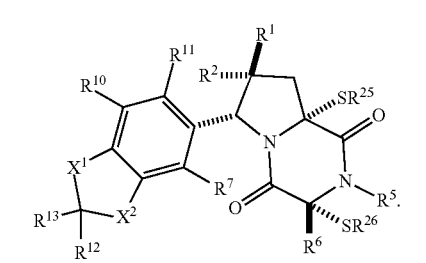

(XXV(R))

Embodiment 36. The method of Embodiment 31, wherein the compound has the formula:

(XXVII)

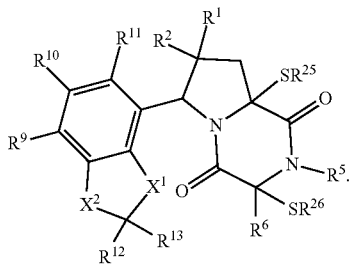

(XXVIII(S))

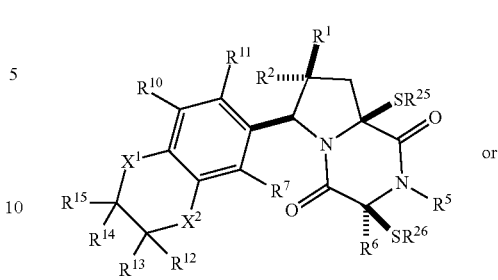

or

Embodiment 37. The method of Embodiment 36, wherein the compound is (XXVII(S))

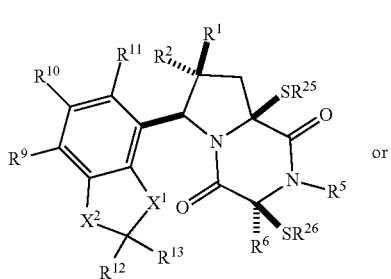

or (XXVIII(R))

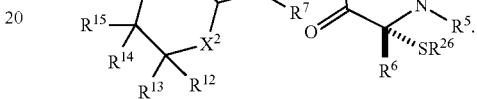

Embodiment 40. The method of Embodiment 30, wherein the compound has the formula:

(XXIX)

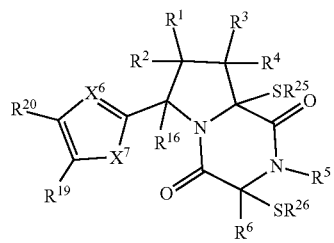

(XXVII(R))

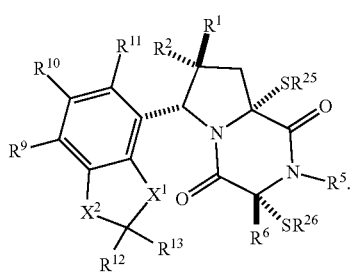

Embodiment 38. The method of Embodiment 31, wherein the compound has the formula:

(XXVIII)

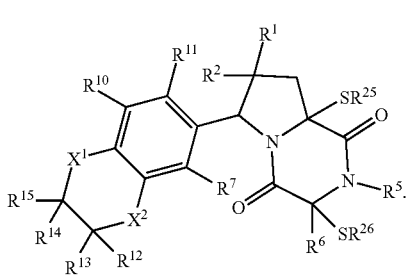

Embodiment 39. The method of Embodiment 38, wherein the compound has the wherein:

$X^6$ is —N= or —CR$^{23A}$=;

$X^7$ is —CR$^{24A}$R$^{24B}$—, —S—, —O—, or —NR$^{24C}$—.

$R^{19}$ is hydrogen, halogen, —N$_3$, —CF$_3$, —CCl$_3$, —CBr$_3$, —CI$_3$, —CN, —CHO, —OR$^{19A}$, —NR$^{19B}$R$^{9C}$, —COOR$^{19A}$, —CONR$^{19B}$R$^{19C}$, —NO$_2$, —SR$^{19D}$, —SO$_{n19}$R$^{19B}$, —SO$_{v19}$NR$^{19B}$R$^{19C}$, —NHNR$^{19B}$R$^{19C}$, —ONR$^{19B}$R$^{19C}$, —NHC(O)NHNR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{20}$ is hydrogen, halogen, —N$_3$, —CF$_3$, —CCl$_3$, —CBr$_3$, —CI$_3$, —CN, —CHO, —OR$^{20A}$, —NR$^{20B}$R$^{20C}$, COOR$^{20A}$, CONR$^{20B}$R$^{20C}$, —NO$_2$, —SR$^{20D}$, —SO$_{n20}$R$^{20B}$, —SO$_{v20}$NR$^{20B}$R$^{20C}$, —NHNR$^{20B}$R$^{20C}$, —ONR$^{20B}$R$^{20C}$, —NHC(O)NHNR$^{20B}$R$^{20C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23A}$, $R^{24A}$, and $R^{24B}$ are independently hydrogen, halogen, —N$_3$, —CF$_3$, —CCl$_3$, —CBr$_3$, —CI$_3$, —CN, —CHO, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19A}$, $R^{19B}$, $R^{19C}$, $R^{19D}$, $R^{20A}$, $R^{20B}$, $R^{20C}$, $R^{20D}$, and $R^{24C}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n19 and n20 are independently an integer from 1 to 4; and v19 and v20 are independent 1 or 2.

Embodiment 41. The method of Embodiment 40, wherein the compound has the formula:

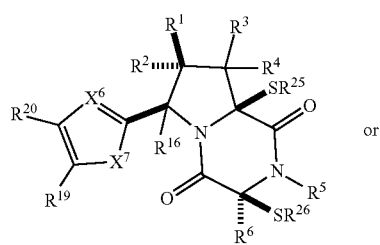

(XXIX (S))

or

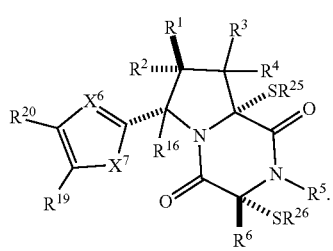

(XXIX (R))

Embodiment 42. The method of Embodiments 30-39, wherein $R^{10}$ and $R^{11}$ are independently hydrogen.

Embodiment 43. The method of Embodiments 30-33, wherein $X^4$ is —N=.

Embodiment 44. The method of Embodiments 30-33, wherein $R^9$ is —OCH$_3$.

Embodiment 45. The method of Embodiments 30-44, wherein $R^2$ is substituted or unsubstituted alkyl.

Embodiment 46. The method of Embodiments 30-45, wherein $R^2$ is substituted or unsubstituted C$_1$-C$_3$ alkyl.

Embodiment 47. The method of Embodiments 30-46, wherein $R^2$ is methyl.

Embodiment 48. The method of Embodiments 30-47, wherein $R^1$ is —CN.

Embodiment 49. The method of Embodiments 30-49, wherein:

$R^{25}$ is —C(O)-L$^1$-R$^{32}$ or —C(S)-L$^1$-R$^{32}$; and $R^{26}$ is —C(O)-L$^2$-R$^{33}$ or —C(S)-L$^2$-R$^{33}$;

Embodiment 50. The method of Embodiments 30-49, wherein L$^1$ and L$^2$ are independently a bond, —O—, or —NH—;

Embodiment 51. The method of Embodiments 30-49, wherein:

L$^1$ is -L$^{1A}$-L$^{1B}$-, wherein L$^{1A}$ is bonded to —C(O)— or —C(S)—; and L$^2$ is -L$^{2A}$-L$^{2B}$-, wherein L$^{2A}$ is bonded to —C(O)— or —C(S)—;

L$^{1A}$ is a bond or —(CH$_2$)$_{z1}$—;

L$^{1B}$ is a bond, —O— or —NR$^{30B}$—;

L$^{2A}$ is a bond or —(CH$_2$)$_{z2}$—;

L$^{2B}$ is a bond, —O— or —NR$^{31B}$—;

z1 and z2 are independently an integer from 30 to 10; and $R^{30B}$ and $R^{31B}$ are independently hydrogen or substituted or unsubstituted alkyl.

Embodiment 52. The method of Embodiment 51, wherein L$^{1A}$ and L$^{2A}$ are independently —CH$_2$—.

Embodiment 53. The method of Embodiments 51 or 52, wherein:

L$^{31B}$ is —NR$^{30B}$—;

L$^{2B}$ is —NR$^{31B}$—; and $R^{30B}$ and $R^{31B}$ are independently unsubstituted C$_1$-C$_3$ alkyl.

Embodiment 54. The method of Embodiments 30-53, wherein $R^{32}$ and $R^{33}$ are independently unsubstituted C$_1$-C$_3$ alkyl or unsubstituted aryl.

Embodiment 55. The method of Embodiments 30-53, $R^{32}$ and $R^{33}$ are independently halogen.

Embodiment 56. The method of Embodiments 30-48, wherein $R^2$ and $R^{26}$ are joined together to form:

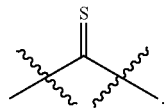 [SMILES: *C(*)=S]

Embodiment 57. The method of Embodiments 30-56, wherein $R^6$ is methyl.

Embodiment 58. The method of Embodiments 30-57, wherein the compound has the structure:

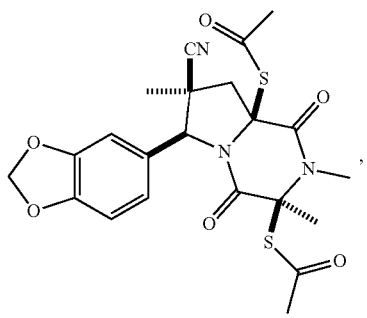

-continued
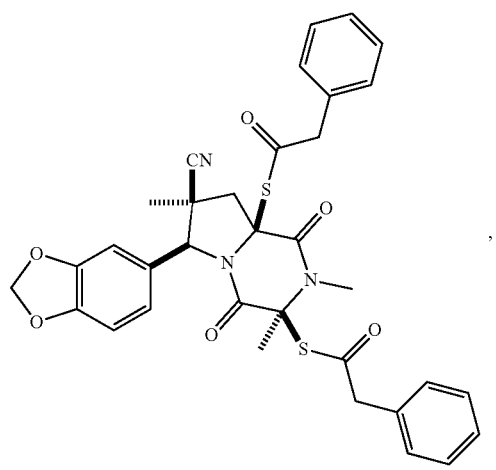
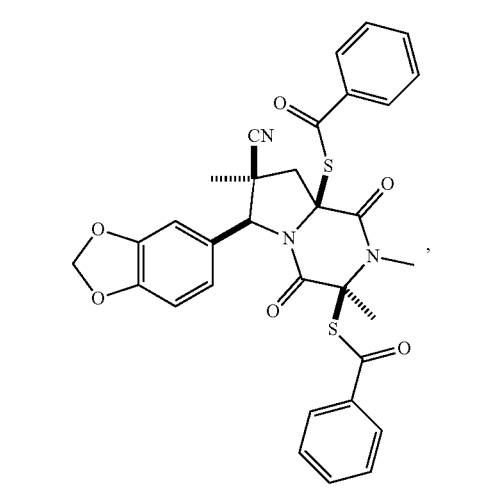
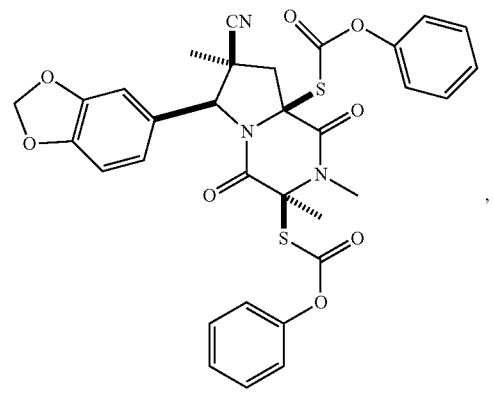
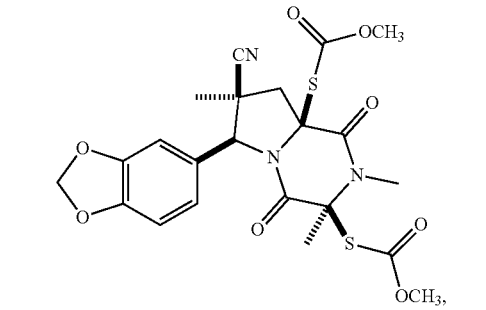
-continued
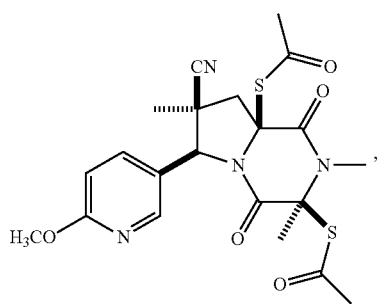
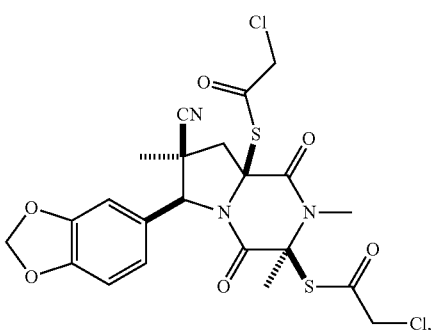
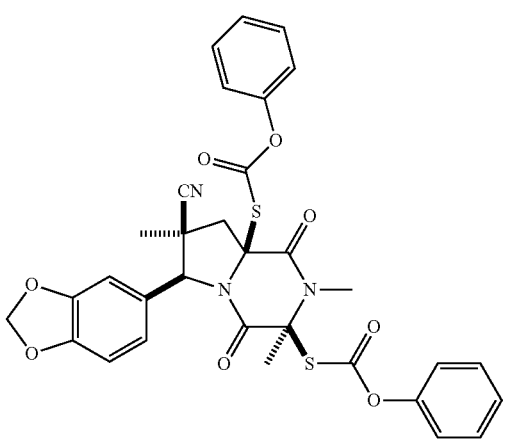
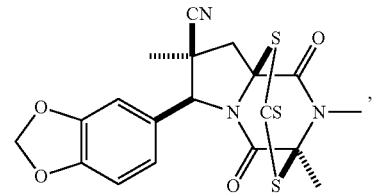
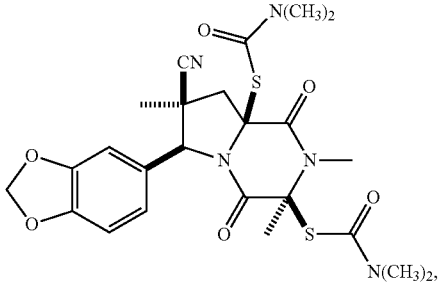

223
-continued
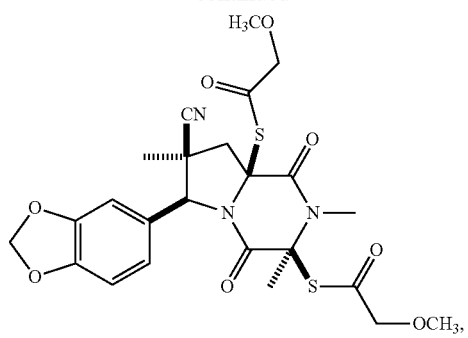
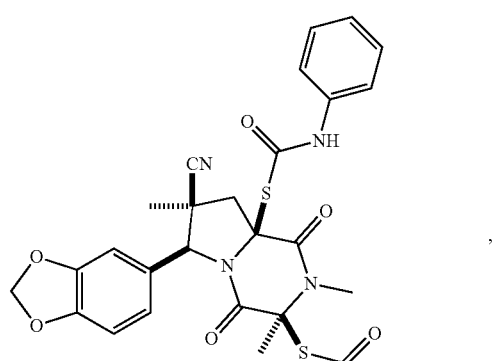
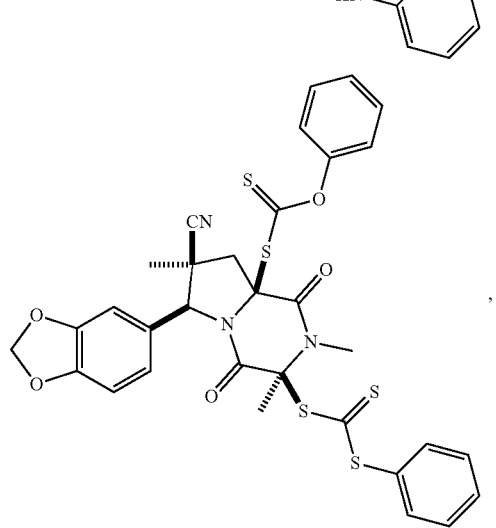
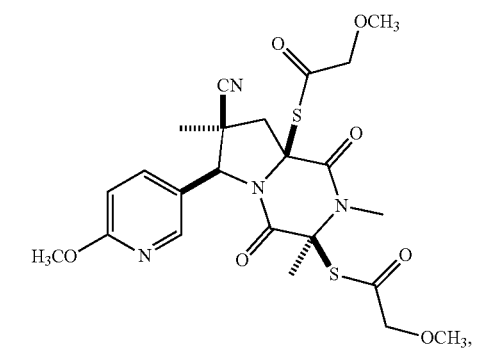
224
-continued
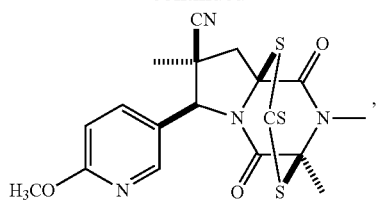
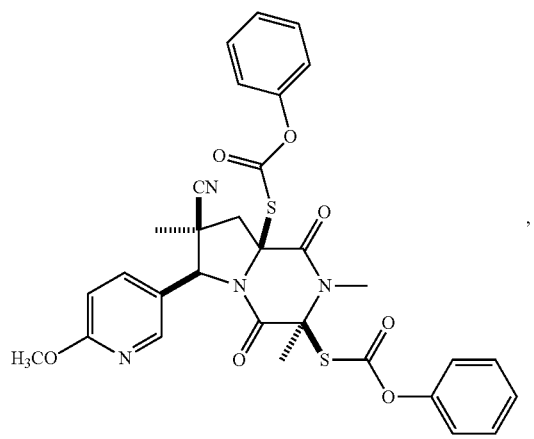
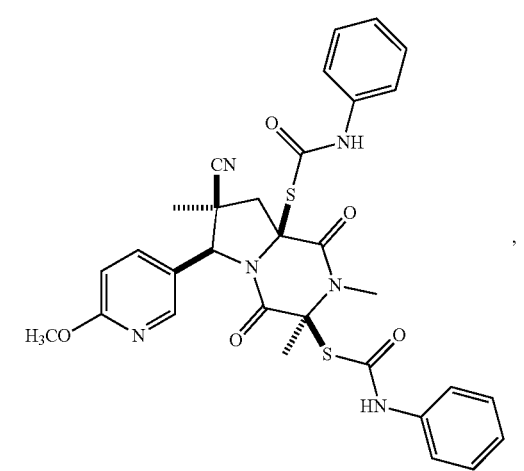
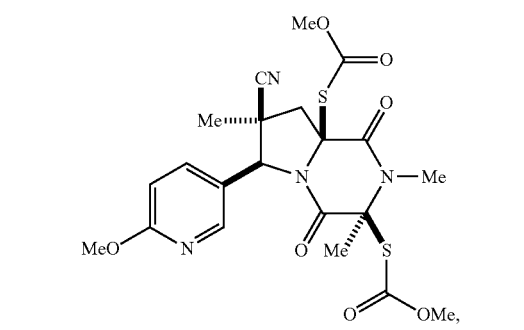

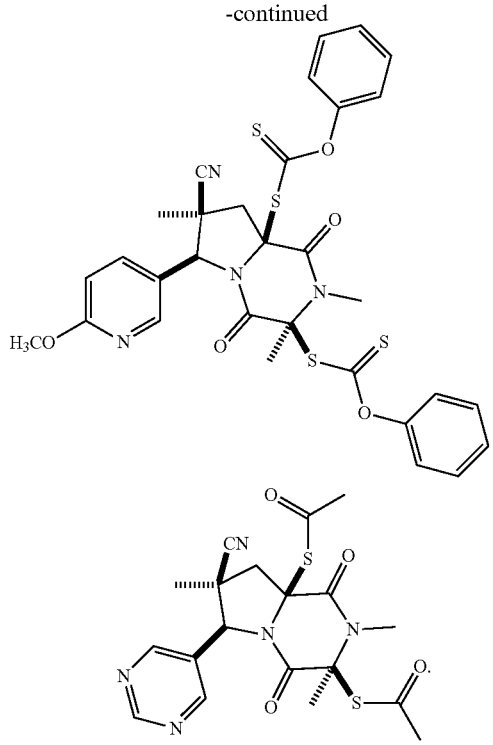

Embodiment 59. The method of Embodiments 1-58, wherein the T-cell lymphoma is cutaneous T-cell lymphoma (CTCL), peripheral T-cell lymphoma, anaplastic large-cell lymphoma, angioimmunoblastic T-cell lymphoma, adult T-cell Leukemia/Lymphoma, blastic natural killer (NK) cell lymphoma, enteropathy-associated T-cell lymphoma, hepatosplenic T-cell lymphoma, lymphoblastic lymphoma, or nasal natural killer (NK)/T-cell lymphoma.

Embodiment 60. The method of Embodiments 59, wherein the cutaneous T-cell lymphoma is Sezary syndrome, mycosis fungoides, folliculotropic mycosis fungoides, pagetoid reticulosis, granulomatous slack skin, primary cutaneous CD30+ T-cell lymphoproliferative disorders, lymphomatoid papulosis, primary cutaneous anaplastic large-cell lymphoma, primary cutaneous γδ T-cell lymphoma, primary cutaneous CD8+ aggressive epidermotropic lymphoma, primary cutaneous CD8+ aggressive epidermotropic cytotoxic T-cell lymphoma, or primary cutaneous CD4+ small/medium T-cell lymphoma.

Embodiment 61. The method of Embodiments 1-60, wherein the T-cell lymphoma is associated with at least one of the following conditions: smoking, obesity, infection, HIV, Epstein-Barr virus, human T-lymphotropic virus, *Helicobacter pyroli* infection, chronic *Helicobacter pyroli* infection, exposure to chemicals, exposure to insecticides, exposure to pesticides, use of immunosuppressant drugs, weakened immune system, genetic disorders, previous chemotherapy, and previous radiation therapy.

Embodiment 62. The method of Embodiments 1-61, further comprising administering to the subject an additional therapeutic agent used in the treatment of T-cell lymphoma.

Embodiment 63. The method of Embodiment 62, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

Embodiment 64. A pharmaceutical composition for treating T-cell lymphoma comprising an ETP derivative, at least one additional therapeutic agent used in the treatment of T-cell lymphoma, and at least one pharmaceutically acceptable excipient.

Embodiment 65. The pharmaceutical composition of Embodiment 64, wherein the ETP derivative is a compound having the structure of formula (1):

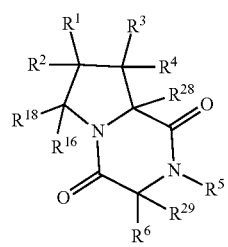

(1)

wherein:
$R^1$ is hydrogen, halogen, —$N_3$, —$CF_3$, —$CCl_3$, —$CBr_3$, —$CI_3$, —CN, —CHO, —$OR^{1A}$, —$NR^{1B}R^{1C}$, —$COOR^{1A}$, —$CONR^{1B}R^{1C}$, —$NO_2$, —$SR^{1D}$, —$SO_{n1}R^{1B}$, —$SO_{v1}OR^{1B}$, —$SO_{v1}NR^{1B}R^{1C}$, —$NHNR^{1B}R^{1C}$, $ONR^{1B}R^{1C}$, —NHC(O)$NHNR^{1B}R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —CHO, —$OR^{2A}$, —$NR^{2B}R^{2C}$, —$COOR^{2A}$, —$CONR^{2B}R^{2C}$, —$NO_2$, —$SR^{2D}$, —$SO_{n2}R^{2B}$, —$SO_{n2}OR^{2B}$, —$SO_{v2}NR^{2B}R^{2C}$, —$NHNR^{2B}R^{2C}$, —$ONR^{2B}R^{2C}$, —NHC(O)$NHNR^{2B}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —CHO, —$OR^{3A}$, —$NR^{3B}R^{3C}$, —$COOR^{3A}$, —$CONR^{3B}R^{3C}$, —$NO_2$, —$SR^{3D}$, —$SO_{n3}R^{3B}$, —$SO_{n3}OR^{3B}$, —$SO_{v3}NR^{3B}R^{3C}$, —$NHNR^{3B}R^{3C}$, —$ONR^{3B}R^{3C}$, —NHC(O)$NHNR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —CHO, —$OR^{4A}$, —$NR^{4B}R^{4C}$, —$COOR^{4A}$, —$CONR^{4B}R^{4C}$, —$NO_2$, —$SR^{4D}$, —$SO_{n4}R^{4B}$, —$SO_{n4}OR^{4B}$, —$SO_{v4}NR^{4B}R^{4C}$, —$NHNR^{4B}R^{4C}$, —$ONR^{4B}R^{4C}$, —NHC(O)

NHNR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —N$_3$, —CF$_3$, —CCl$_3$, —CBr$_3$, —CI$_3$, —CN, —CHO, —OR$^{5A}$, —NR$^{5B}$R$^{5C}$, —COOR$^{5A}$, —CONR$^{5B}$R$^{5C}$, —NO$_2$, —SR$^{5D}$, —SO$_{n5}$R$^{5B}$, —SO$_{n5}$OR$^{5B}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —N$_3$, —CF$_3$, —CCl$_3$, —CBr$_3$, —CI$_3$, —CN, —CHO, —OR$^{6A}$, —NR$^{6B}$R$^{6C}$, —COOR$^{6A}$, —CONR$^{6B}$R$^{6C}$, —NO$_2$, —SR$^{6D}$, —SO$_{n6}$R$^{6B}$, —SO$_{n6}$OR$^{6B}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —N$_3$, —CF$_3$, —CCl$_3$, —CBr$_3$, —CI$_3$, —CN, —CHO, —OR$^{16A}$, —NR$^{16B}$R$^{16C}$, —COOR$^{16A}$, —CONR$^{16B}$R$^{16C}$, —NO$_2$, —SR$^{16D}$, —SO$_{n16}$R$^{16B}$, —SO$_{n16}$OR$^{16B}$, —SO$_{v16}$NR$^{16B}$R$^{16C}$, —NHNR$^{16B}$R$^{16C}$, —ONR$^{16B}$R$^{16C}$, —NHC(O)NHNR$^{16B}$R$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{18}$ is hydrogen, halogen, —N$_3$, —CF$_3$, —CCl$_3$, —CBr$_3$, —CI$_3$, —CN, —CHO, —OR$^{18A}$, —NR$^{18B}$R$^{18C}$, —COOR$^{18A}$, —CONR$^{18B}$R$^{18C}$, —NO$_2$, —SR$^{18D}$, —SO$_{n18}$R$^{18B}$, —SO$_{n18}$OR$^{18B}$, —SO$_{v18}$NR$^{18B}$R$^{18C}$, —NHNR$^{18B}$R$^{18C}$, —OTR$^{18B}$R$^{18C}$, —NHC(O)NHNR$^{18B}$R$^{18C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{28}$ is —SR$^{25}$ and R$^{29}$ is —SR$^{26}$, wherein R$^{28}$ and R$^{29}$ are optionally joined to form *—S$_p$—* wherein p is an integer from 2 to 4 and each * represents the point of attachment to the remainder of the compound;

R$^{25}$ is hydrogen, —C(O)-L$^1$-R$^{32}$, —C(S)-L$^1$-R$^{32}$, substituted or unsubstituted alkyl, substituted or unsubstituted heteroalkyl, substituted or unsubstituted aryl, or substituted or unsubstituted heteroaryl;

R$^{26}$ is hydrogen, —C(O)-L$^2$-R$^{33}$, —C(S)-L$^2$-R$^{33}$, substituted or unsubstituted alkyl, substituted or unsubstituted heteroalkyl, substituted or unsubstituted aryl, or substituted or unsubstituted heteroaryl;

R$^{25}$ and R$^{26}$ may optionally be joined to form

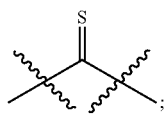 [SMILES: *C(*)=S]

;

L$^1$ is a bond, —O—, —NH—, substituted or unsubstituted alkylene, substituted or unsubstituted heteroalkylene;

L$^2$ is a bond, —O—, —NH—, substituted or unsubstituted alkylene, substituted or unsubstituted heteroalkylene;

R$^{32}$ and R$^{33}$ are independently halogen, substituted or unsubstituted C$_1$-C$_3$ alkyl, substituted or unsubstituted aryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{16A}$, R$^{16B}$, R$^{16C}$, R$^{16D}$, R$^{18A}$, R$^{18B}$, R$^{18C}$, and R$^{18D}$ are independently hydrogen, halogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br, or —I;

n1, n2, n3, n4, n5, n6, n16, and n18 are independently an integer from 1 to 4; and v1, v2, v3, v4, v5, v6, v16, and v18 are independently 1 or 2;

or a pharmaceutically acceptable salt thereof.

Embodiment 66. The pharmaceutical composition of Embodiments 64-65, wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

EXAMPLES

Example 1

The compounds of Formulae I-XVIII can be prepared in a number of ways well known to those skilled in the art, including both solid phase and solution phase techniques. The compounds can be synthesized, for example, by the methods described below, or variations thereof as appreciated by the skilled artisan. Although these syntheses are illustrated for preparation of ETPs having substituted aryl substituents at C$_6$, identical sequences can be employed to prepare ETPs with substituted heteroaryl substituents at C$_6$. See e.g. Martins, M. M.; Carvalho *Tetrahedron* 2007, 63, 9923-9932; Borthwick, A. D. *Chem Rev* 2012, 112, 3641-3716; Iwasa, E.; Hamashima, Y.; Sodeoka, M. Isr. *J. Chem.* 2011, 51, 420-433; Nicolaou, K. C.; Lu, M.; Totokotsopoulos, S.; Heretsch, P.; Giguère, D.; Sun, Y.-P.; Sarlah, D.; Nguyen, T. H.; Wolf, I. C.; Smee, D. F.; Day, C. W.; Bopp, S.; Winzeler, E. A. *J. Am. Chem. Soc.* 2012, 134, 17320-17332. All processes disclosed in association with the present invention are contemplated to be practiced on any scale, including milligram, gram, multigram, kilogram, multikilogram or commercial industrial scale.

Scheme 1: Synthesis of racemic ETP derivatives described herein.

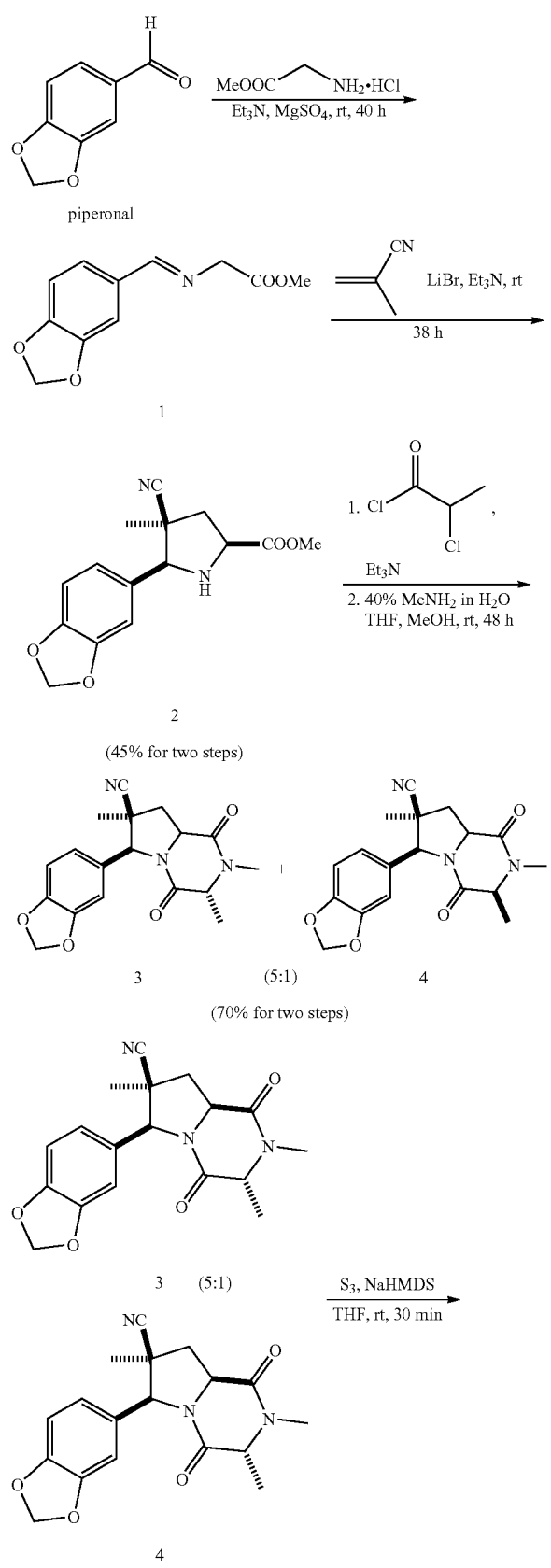

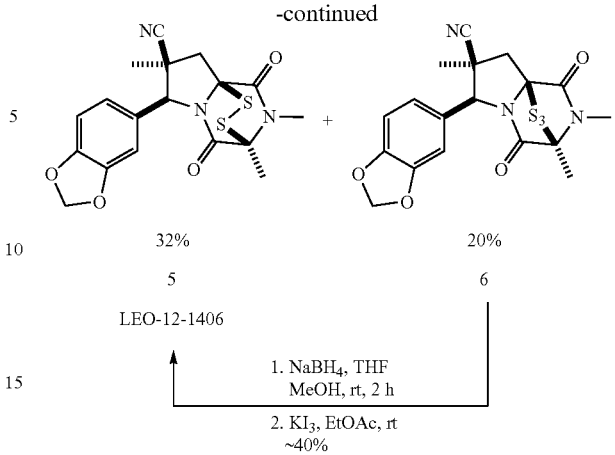

LEO-12-1406

1. NaBH₄, THF
   MeOH, rt, 2 h
2. KI₃, EtOAc, rt
   ~40%

Embodiments of Formula I may be prepared as shown in Scheme 1 above. Dehydrative condensation of an aldehyde with a glycine derivative renders an intermediate imine such as 1, which when treated with base in the presence of lithium bromide generates an azomethine ylide that subsequently undergoes a dipolar cycloaddition reaction to generate the desired pyrrolidine product such as 2. The azomethine ylide can be generated and the cycloaddition accomplished in many ways known in the art (Grigg, R. and V. Sridharan (1993). Azomethine Ylide Cycloadditions via 1,2-Prototropy and Metallo-Dipole Formation from Imines. *Advances in Cycloaddition*. D. P. Curran. Greenwich, CT, Jai Press Inc. 3: 161-204). For example, the cycloaddition may be carried out by simply heating the components in a solvent or by the use of other metal complexes or salts and other bases. Compounds 2 are typically generated as mixtures of diastereoisomers, the isomer exemplified by 2 can be separated from the mixture based on its reduced solubility in solvent mixtures like MeOH/DCM (1:1). If required, the diastereoisomer products can be obtained in high purity by column chromatography; the subsequent steps can be performed with the separated stereoisomers or carried out with the mixture of stereoisomers with separation being accomplished by column chromatography, crystallization or other common techniques after the polysulfur bridge is incorporated.

The product of this cycloaddition reaction is a pyrrolidine ester, which can be converted to a dioxopiperazine in many well-known ways (Martins, M. B., Ivone, C. (2007) Diketopiperazines: biological activity and synthesis. *Tetrahedron* 63, 9923-9932). For example, the pyrrolidine ester can be acylated on the free nitrogen with an α-halo acid chloride to yield the corresponding amide. These compounds can be treated with an excess of a primary amine to undergo a cyclocondensation reaction furnishing the desired diketopiperazine ring, compounds, exemplified by 3 and 4. In general the diketopiperazine was isolated as mixture of diastereoisomers which need not be separated at this stage. Alternatively, the pyrrolidine ester can be coupled with an α-aminoester (typically protected on nitrogen) to give a dipeptide, which directly or upon removal of the nitrogen-protecting group can be cyclized to the dioxopiperazine intermediate.

The diketopiperazine then undergoes a sulfidation process, one example of which is illustrated in Scheme 1, to yield the desired ETP. Alternatively, the intermediate in this sequence, can be reduced and the dithiol product protected on the two sulfur atoms. The conversion of the diooxopiperazine intermediate to an ETP product can be accomplished in many ways well known in the art (Iwasa, E.; Hamashima, Y.; Sodeoka, M. (2011) Epipolythiodiketopiperazine Alkaloids: Total Syntheses and Biological Activities Isr. *J. Chem.* 51, 420-433. Nicolaou, K. C., et al. (2011) Synthesis and Biological Evaluation of Epidithio-, Epitetrathio-, and bis-(Methylthio)diketopiperazines: Synthetic Methodology, Enantioselective Total Synthesis of Epicoccin G, 8,8'-epi-ent-Rostratin B, Gliotoxin, Gliotoxin G, Emethallicin E, and Haematocin and Discovery of New Antiviral and Antimalarial Agents *J. Am. Chem. Soc.,* 133, 8150-8153.)

Synthetic scheme for enantioselective synthesis of ETP analogues described herein.

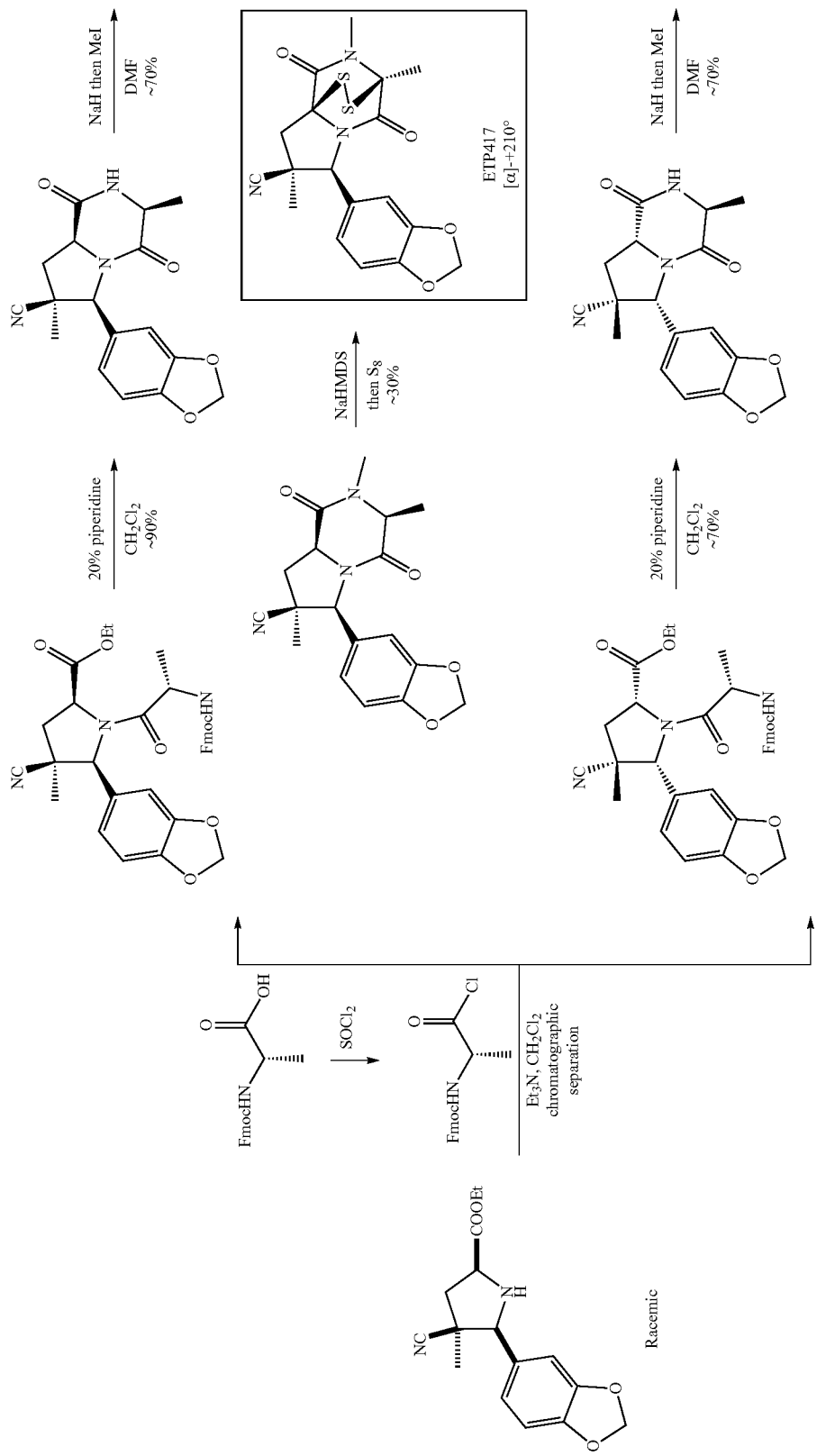

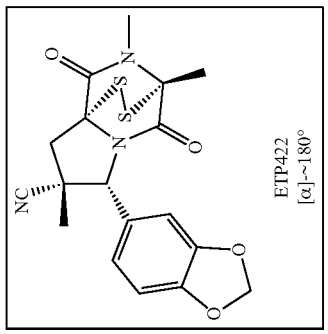
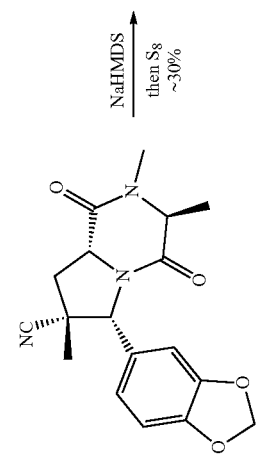
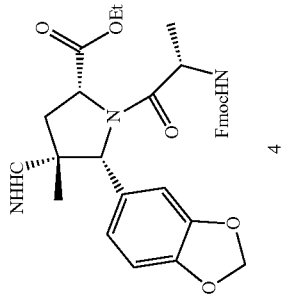
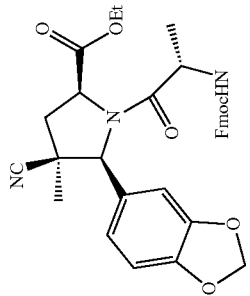
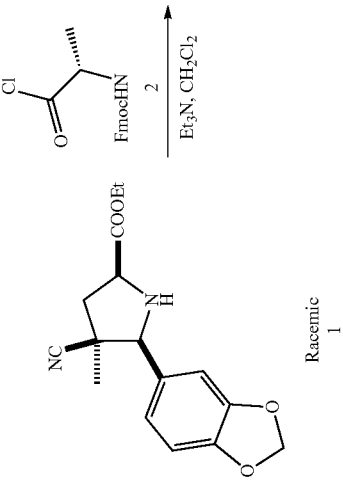

To a stirred solution of racemic 1 (2.1 g, 7 mmol) in CH$_2$Cl$_2$ (14 mL) were added Et$_3$N (1.4 g, 14 mmol) and acyl chloride 2 (3.25 g, 10 mmol) in CH$_2$Cl$_2$ (14 mL) at 0° C. The reaction was stirred overnight. The reaction was quenched with sat. NaHCO$_3$ and extracted with CH$_2$Cl$_2$. The combined organic layer was dried over MgSO$_4$ and evaporated to dryness. The crude product was purified by silica gel column chromatography by elution with 33% EtOAc/Hexane to afford 1.9 g (46%) of compound 3 and 1.7 g (40%) of compound 4. For compound 3: $^1$H NMR (400 MHz, CDCl$_3$) δ/ppm 7.75 (d, 2H, J=7.4 Hz), 7.55 (d, 2H, J=7.4 Hz), 7.40 (t, 2H, J=7.4 Hz), 7.30 (t, 2H, J=7.4 Hz), 7.30 (s, 1H), 7.19 (dd, 1H, J=1.4, 8.0 Hz), 6.86 (d, 2H, J=7.8 Hz), 6.00 (d, 2H, J=6.6 Hz), 5.22 (s, 1H), 5.19 (d, 2H, J=7.8 Hz), 4.60 (dd, 1H, J=7.4, 9.8 Hz), 4.39-4.22 (m, 4H), 4.20-4.14 (m, 2H), 2.59 (dd, 1H, J=9.8, 13.8 Hz), 2.35 (dd, 1H, J=7.0, 13.8 Hz), 1.61 (s, 3H), 1.35 (t, 3H, J=7.0 Hz), 0.98 (d, 3H, J=7.0 Hz); $^{13}$C NMR (100 MHz, CDCl$_3$) δ/ppm 174.0, 170.2, 156.1, 148.31, 148.27, 143.70, 143.65, 141.3, 131.8, 127.75, 127.72, 127.0, 125.1, 125.0, 121.3, 120.0, 108.6, 107.8, 101.4, 70.3, 67.2, 61.9, 58.2, 47.8, 47.0, 44.5, 37.3, 24.3, 17.4, 14.1;

For compound 4 (main rotamer): $^1$H NMR (400 MHz, CDCl$_3$) δ/ppm 7.75 (d, 2H, J=7.4 Hz), 7.55 (d, 2H, J=7.4 Hz), 7.40 (t, 2H, J=7.4 Hz), 7.30 (t, 2H, J=7.4 Hz), 7.30 (s, 1H), 7.19 (dd, 1H, J=1.4, 8.0 Hz), 7.03 (s, 1H), 6.93 (d, 1H, J=7.8 Hz), 6.80 (d, 1H, J=8.2 Hz), 5.95 (d, 2H, J=2.2 Hz), 5.37 (dd, 1H, J=3.4, 8.2 Hz), 5.27 (d, 1H, J=7.6 Hz), 4.76 (s, 1H), 4.40-4.10 (m, 6H), 2.90 (dd, 1H, J=3.4, 13.2 Hz), 2.41 (dd, 1H, J=2.3, 13.2 Hz), 1.62 (s, 3H), 1.40 (d, 3H, J=7.0 Hz), 1.39 (t, 3H, J=7.0 Hz); $^{13}$C NMR (100 MHz, CDCl$_3$) δ/ppm 174.0, 170.9, 156.3, 147.9, 147.7, 143.64, 143.62, 141.3, 130.6, 127.8, 127.7, 127.0, 125.1, 125.0, 120.2, 120.0, 108.3, 107.0, 101.1, 70.8, 67.2, 62.6, 59.3, 48.4, 47.0, 43.4, 40.8, 23.1, 17.8, 14.1;

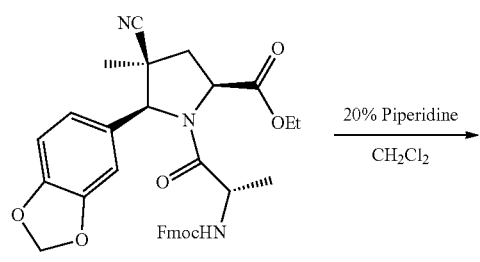

3

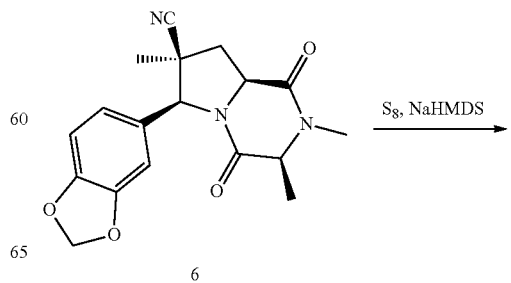

5

To a stirred solution of compound 3 (2.8 g, 4.7 mmol) in CH$_2$Cl$_2$ (18 mL) was added piperidine (4.0 g, 47 mmol). After 30 min, the solvent was removed. The crude product was purified by silica gel column chromatography by elution with 3% MeOH/CH$_2$Cl$_2$ to afford 1.4 g (91%) of compound 5 as white solid. $^1$H NMR (400 MHz, CDCl$_3$) δ/ppm 6.79 (d, 2H, J=7.8 Hz), 6.63 (dd, 1H, J=2.0, 8.2 Hz), 6.57 (d, 2H, J=2.0 Hz), 5.96 (s, 2H), 5.91 (s, 1H), 4.87 (s, 1H), 4.43 (dd, 1H, J=6.6, 11.0 Hz), 4.17 (q, 1H, J=6.6 Hz), 2.82 (dd, 1H, J=11.4, 13.4 Hz), 2.35 (dd, 1H, J=6.6, 13.4 Hz), 1.68 (s, 3H), 1.44 (d, 3H, J=6.6 Hz); $^{13}$C NMR (100 MHz, CDCl$_3$) δ/ppm 168.9, 166.9, 148.3, 148.2, 130.8, 119.7, 108.7, 106.2, 101.4, 69.3, 57.5, 51.6, 42.8, 35.8, 25.3, 15.4;

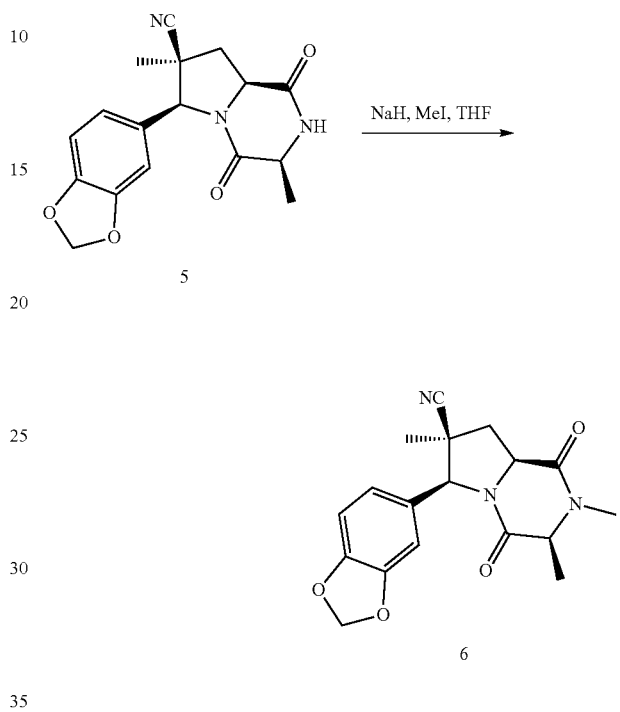

To a stirred solution of compound 5 (1.4 g, 4.3 mmol) in THF (43 mL) was added NaH (60%, 260 mg, 6.5 mmol) at 0° C. After 20 min at 23° C., MeI (1.85 g, 13 mmol) was added at 0° C. After 2 h at 23° C., the reaction was quenched with sat. NH4Cl. The solvent was removed and the residue was extracted with CH$_2$Cl$_2$. The combined organic layer was dried over MgSO$_4$ and evaporated to dryness. The crude product was purified by silica gel column chromatography by elution with 25% EtOAc/Hexane to afford 1.25 g (86%) of compound 6. $^1$H NMR (400 MHz, CDCl$_3$) δ/ppm 6.82 (d, 2H, J=8.2 Hz), 6.73 (d, 1H, J=2.0 Hz), 6.71 (s, 1H), 5.98 (s, 2H), 4.73 (dd, 1H, J=6.2, 10.6 Hz), 3.88 (q, 1H, J=7.0 Hz), 3.01 (s, 3H), 2.93 (dd, 1H, J=6.2, 13.0 Hz), 2.26 (dd, 1H, J=10.6, 13.0 Hz), 1.60 (s, 3H), 1.54 (d, 3H, J=7.4 Hz); $^{13}$C NMR (100 MHz, CDCl$_3$) δ/ppm 165.9, 165.2, 148.2, 148.1, 129.3, 120.3, 119.4, 108.6, 106.1, 101.4, 70.2, 60.6, 58.4, 44.1, 41.6, 32.1, 22.7, 16.7;

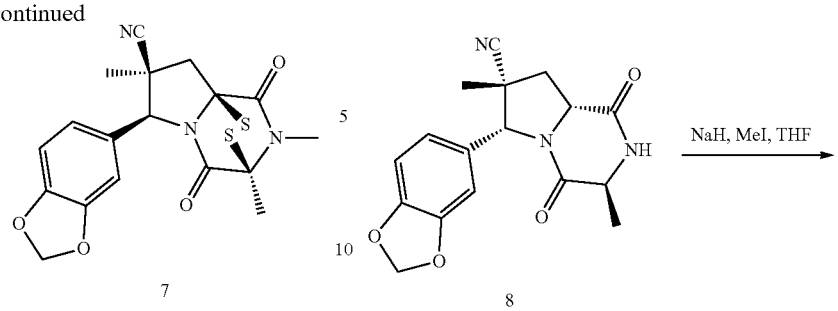

To a suspension of elemental sulfur (300 mg, 9.4 mmol) in dry THF (10 mL) NaHMDS (0.6 M in toluene, 7.40 mL) is being added dropwise. The resulting yellow reaction mixture is stirred at ambient temperature for one minute and then combined with a slurry of the substrate 6 (340 mg, 1.0 mmol in 5 mL dry THF). A second portion of NaHMDS (0.6 M in toluene, 4.8 mL) is subsequently added resulting in an orange mixture which is stirred at ambient temperature for 30 minutes. After quenching with saturated aqueous ammonium chloride, the solvent was removed and the residue was extracted with $CH_2Cl_2$. The combined organic layer was dried over $MgSO_4$ and evaporated to dryness. The crude product was purified by silica gel column chromatography by elution with 2% EtOAc/$CH_2Cl_2$ to afford 129 mg (32%) of compound 7. $^1$H-NMR (400 MHz, $CDCl_3$): δ/ppm 6.96 (s, 1H), 6.91 (s, 2H), 6.06 (s, 2H), 4.89 (s, 1H), 3.36 (d, 1H, J=14.5 Hz), 3.14 (s, 3H), 3.06 (d, 1H, J=14.5 Hz), 2.00 (s, 3H), 1.73 (s, 3H); $^{13}$C-NMR (100 MHz, $CDCl_3$): δ/ppm 165.6, 162.1, 148.6, 148.3, 127.5, 120.7, 120.3, 108.6, 107.2, 101.6, 73.4, 73.3, 72.4, 44.4, 42.8, 27.8, 24.8, 18.1. $^α[D]_{20}$=+240°, ee %>99%

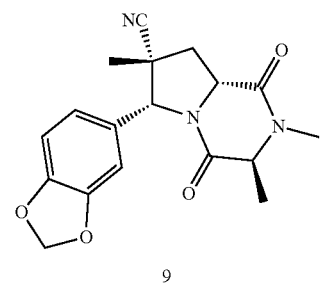

See procedure as preparing compound 6. $^1$H-NMR (400 MHz, $CDCl_3$): δ/ppm 6.79 (d, 1H, J=9.0 Hz), 6.63 (d, 1H, J=9.0 Hz), 6.57 (s, 1H), 5.96 (s, 2H), 4.82 (s, 1H), 4.36 (dd, 1H, J=6.5, 11.0 Hz), 3.90 (q, 1H, J=7.0 Hz), 3.04 (s, 3H), 2.76 (t, 1H, J=7.0 Hz), 2.45 (dd, 1H, J=6.5, 13.5 Hz), 1.66 (s, 3H), 1.47 (d, 3H, J=7.0 Hz); $^{13}$C-NMR (100 MHz, $CDCl_3$): δ/ppm 166.6, 166.0, 148.2, 148.1, 130.8, 119.9, 119.8, 108.6, 106.2, 101.4, 69.6, 60.8, 56.1, 42.6, 36.7, 32.0, 25.1, 15.3;

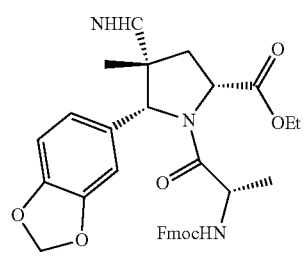

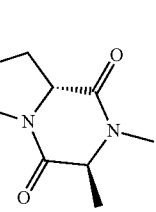

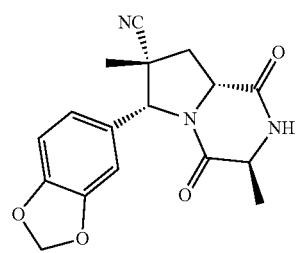

See procedure as preparing compound 5. $^1$H NMR (400 MHz, DMSO-$d_6$) δ/ppm 8.45 (d, 1H, J=4.2 Hz), 6.88 (d, 1H, J=8.2 Hz), 6.70 (s, 1H), 6.60 (d, 1H, J=7.4 Hz), 6.00 (s, 2H), 4.87 (s, 1H), 4.73 (dd, 1H, J=6.6, 11.0 Hz), 3.78-3.70 (m, 1H), 2.42-2.26 (m, 2H), 1.62 (s, 3H), 1.35 (d, 3H, J=7.4 Hz); $^{13}$C NMR (100 MHz, DMSO-$d_6$) δ/ppm 168.6, 167.6, 147.7, 147.4, 133.2, 121.4, 119.8, 108.6, 107.1, 101.7, 68.3, 55.8, 53.5, 42.6, 36.1, 24.4, 18.8;

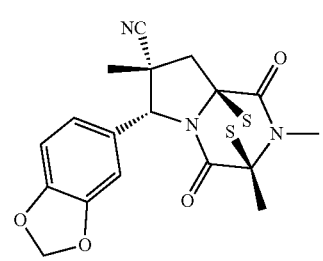

See procedure as preparing compound 7. $^1$H-NMR (400 MHz, $CDCl_3$): δ/ppm 6.96 (s, 1H), 6.91 (s, 2H), 6.06 (s, 2H), 4.89 (s, 1H), 3.36 (d, 1H, J=14.5 Hz), 3.14 (s, 3H), 3.06 (d, 1H, J=14.5 Hz), 2.00 (s, 3H), 1.73 (s, 3H); $^{13}$C-NMR (100 MHz, $CDCl_3$): δ/ppm 165.6, 162.1, 148.6, 148.3, 127.5, 120.7, 120.3, 108.6, 107.2, 101.6, 73.4, 73.3, 72.4, 44.4, 42.8, 27.8, 24.8, 18.1. $^α[D]_{20}$=−216°, ee %>95%.

Example 2

General Procedure for the Synthesis of Polyfunctionalized Pyrrolidine Esters.

Dimethyl rac-(2S,4S,5S)-5-(4-Fluorophenyl)-4-methylpyrrolidine-2,4-dicarboxylate

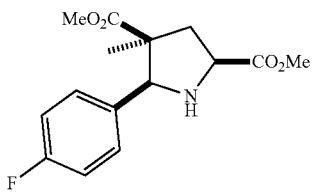

Chemical Formula: $C_{15}H_{18}FNO_4$
Exact Mass: 295.12

4-Fluorobenzaldehyde (1.24 g, 10 mmol) was dissolved in 15 mL of MeCN containing triethylamine (1.5 mL, 11 mmol) and glycine methyl ester hydrochloride (1.35 g, 11 mmol). The reaction mixture was stirred for 5 h at room temperature. After removing the solvent in vacuo, the solid residue was re-dissolved in $CH_2Cl_2$ and washed twice from water to give the imine intermediate as colourless oil. To a solution of this material in 20 mL of THF, solid LiBr (1.1 g, 12 mmol) and triethylamine (1.7 mL, 12 mmol) were added portionwise. After 2 min, methyl methacrylate (1.5 g, 15 mmol) was added and the resulting solution was stirred at room temperature for 8 h. After evaporation of the solvent in vacuo and extractive work-up (3 times, $CH_2Cl_2$/water), the desired product was isolated as yellow oil (2.6 g, 90% yield, as a single diastereomer). In some cases the cycloadduct was isolated as a mixture of C4 epimers, which were separated by crystallization or chromatography $^1$H-NMR (500 MHz, $CDCl_3$): δ/ppm 7.30 (2H, m), 7.03 (2H, t, J=8.5 Hz), 4.09 (1H, s), 4.06 (1H, t, J=7.0 Hz), 3.86 (3H, s), 3.30 (3H, s), 2.95 (1H, br. s, NH), 2.76 (1H, dd, J=7.0, 13.5 Hz), 2.14 (1H, dd, J=13.0, 13.5 Hz), 1.43 (s, 3H); $^{13}$C-NMR (125 MHz, $CDCl_3$): δ/ppm 174.6 (C), 174.3 (C), 162.3 (C, $J_{C-F}$=245 Hz), 134.7 (C, $J_{C-F}$=3 Hz), 128.4 (2CH, d, $J_{C-F}$=8 Hz), 115.0 (2CH, d, $J_{C-F}$=21 Hz), 73.1 (CH), 58.8 (CH), 54.6 (C), 52.3 ($CH_3$), 51.5 ($CH_3$), 41.1 ($CH_2$), 22.5 ($CH_3$). LR-MS: 295.96; HR-MS (ESI) calculated for $C_{15}H_{18}NO_4FCl$: 296.1298 (M+H$^+$), found: 296.1302.

2-Ethyl rac-4-Methyl (2S,4S,5S)-4-methyl-5-(pyridin-3-yl)pyrrolidine-2,4-dicarboxylate

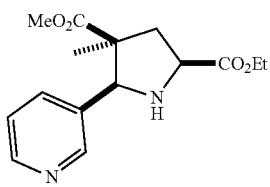

Chemical Formula: $C_{15}H_{20}N_2O_4$
Exact Mass: 292.14

Isolated as pale yellow oil, dr (diastereomer ratio)>9:1. $^1$H-NMR (500 MHz, $CDCl_3$): δ/ppm 8.26 (1H, s), 8.23 (1H, dd, J=1.5, 4.5 Hz), 7.45 (1H, dd, J=1.5, 8.0 Hz), 6.98 (1H, dd, J=4.5, 9.0 Hz), 4.00-4.12 (2H, m), 3.85 (2H, s), 3.78 (1H, app. t, J=7.5 Hz), 2.99 (3H, s), 2.48 (1H, dd, J=8.0, 13.0 Hz), 1.86 (1H, dd, J=8.0, 13.0 Hz), 1.17 (3H, s), 1.07 (3H, t, J=7.0 Hz); $^{13}$C-NMR (125 MHz, $CDCl_3$): δ/ppm 173.9 (C), 173.3 (C), 148.9 (CH), 148.6 (CH), 134.9 (C), 133.9 (CH), 122.8 (CH), 70.7 (CH), 60.8 ($CH_2$), 58.5 (CH), 54.4 (C), 51.1 ($CH_3$), 40.3 ($CH_2$), 22.4 ($CH_3$), 14.0 ($CH_3$). IR (film): v/cm$^{-1}$ 3380, 2981, 2950, 1732, 1430, 1210, 1110, 1029, 716. LR-MS: 293.1 (M+H$^+$); HR-MS (ESI) calculated for $C_{15}H_{20}N_2O_4Na$: 315.1321 (M+Na$^+$), found: 315.1315.

2-Ethyl 4-Methyl rac-(2S,4S,5S)-5-(5-Bromo-2-methoxyphenyl)-4-methylpyrrolidine-2,4-dicarboxylate

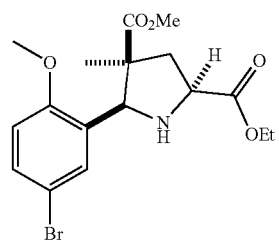

Chemical Formula: $C_{17}H_{22}BrNO_5$
Exact Mass: 399.07

Isolated as brown oil (single diastereomer). $^1$H-NMR (500 MHz, $CDCl_3$): δ/ppm 7.45 (1H, d, J=2.5 Hz), 7.28 (1H, dd, J=2.5, 9.0 Hz), 6.70 (1H, d, J=9.0 Hz), 4.45 (1H, s), 4.25 (2H, q, J=7.0 Hz), 3.96 (1H, app. t, J=8.0 Hz), 3.74 (3H, s), 3.30 (3H, s), 2.72 (1H, dd, J=9.0, 13.0 Hz), 2.05 (1H, dd, J=9.0, 13.0 Hz), 1.36 (3H, s), 1.24 (3H, t, J=7.0 Hz); $^{13}$C-NMR (125 MHz, $CDCl_3$): δ/ppm 174.7 (C), 173.4 (C), 156.3 (C), 131.1 (CH), 130.4 (CH), 129.4 (C), 112.7 (C), 112.0 (CH), 66.8 (CH), 61.0 ($CH_2$), 59.0 ($CH_3$), 55.4 ($CH_3$), 54.5 (C), 51.3 (CH), 41.7 ($CH_2$), 22.8 ($CH_3$), 14.2 ($CH_3$). IR (film): v/cm$^{-1}$ 3366, 2980, 2938, 2839, 2236, 1736, 1486, 1252, 1202, 1134, 1028, 809. LR-MS: 389.0 (M+Na$^+$); HR-MS (ESI) calculated for $C_{16}H_{19}N_2O_3BrNa$: 389.0477 (M+Na$^+$), found: 389.0471.

4-(tert-Butyl) 2-Ethyl rac-(2S,4S,5S)-5-(4-Fluorophenyl)-4-methylpyrrolidine-2,4-dicarboxylate

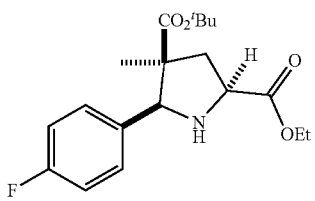

Chemical Formula: $C_{19}H_{26}FNO_4$
Exact Mass: 351.18

Isolated as yellow oil (dr>9:1). $^1$H-NMR (500 MHz, $CDCl_3$): δ/ppm 7.37 (2H, dd, J=5.5, 8.0 Hz), 7.04 (2H, app. t, J=8.0 Hz), 4.31 (2H, q, J=7.0 Hz), 4.08 (1H, q, J=7.0 Hz), 4.03 (1H, t, J=8.5 Hz), 2.69 (1H, br. s), 2.66 (1H, dd, J=9.0, 13.0 Hz), 2.12 (1H, dd, J=8.5, 13.0 Hz), 1.49 (3H, s), 1.36 (3H, t, J=7.0 Hz), 1.13 (9H, s); $^{13}$C-NMR (125 MHz, $CDCl_3$): δ/ppm 173.7 (C), 173.4 (C), 162.3 (C, d, J=244 Hz), 135.9 (C), 128.9 (2CH, d, J=8 Hz), 114.9 (2CH, d, J=21 Hz), 80.8 (C), 72.3 (CH), 61.2 (CH$_2$), 58.9 (CH), 55.1 (C), 41.9 (CH$_2$), 27.6 (3CH$_3$), 24.3 (CH$_3$), 14.3 (CH$_3$). IR (film): v/cm$^{-1}$ 3368, 2979, 2935, 1724, 1511, 1369, 1224, 1154. LR-MS: 352.2 M+H$^+$; HR-MS (ESI) calculated for C$_{19}$H$_{26}$NO$_4$FNa: 374.1743 (M+Na$^+$), found: 374.1742.

Ethyl rac-(2S,4S,5S)-4-Cyano-4-methyl-5-phenylpyrrolidine-2-carboxylate

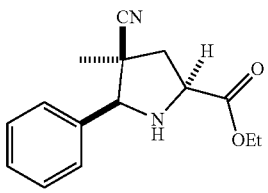

Chemical Formula: C$_{15}$H$_{18}$N$_2$O$_2$
Exact Mass: 258.1368

$^1$H-NMR (500 MHz, CDCl$_3$): δ/ppm 7.52 (2H, d, J=7.1 Hz), 7.41-7.34 (3H, m), 4.34-4.24 (2H, m), 3.98 (1H, dd, J=4.2, 9.7 Hz), 3.93 (1H, s), 2.90 (1H, s), 2.82 (1H, dd, J=4.2, 13.6 Hz), 2.29 (1H, dd, J=9.6, 13.6 Hz), 1.42 (3H, s), 1.34 (3H, t, J=7.1 Hz); $^{13}$C-NMR (125 MHz, CDCl$_3$): δ/ppm 173.0 (C), 136.5 (C), 128.9 (CH), 128.6 (2CH), 127.6 (2CH), 121.9 (C), 72.4 (CH), 61.7 (CH$_2$), 57.3 (CH), 44.1 (C), 42.5 (CH$_2$), 22.0 (CH$_3$), 14.2 (CH$_3$); IR (film): v/cm–$^1$ 3348, 2980, 2234, 1734, 1454; LR-MS: 281.1 [M+Na]$^+$; HR-MS (ESI) calculated for C$_{15}$H$_{18}$N$_2$O$_2$Na: 281.1266, found: 281.1263.

Ethyl rac-(2S,4S,5S)-4-Cyano-5-(4-fluorophenyl)-4-methylpyrrolidine-2-carboxylate

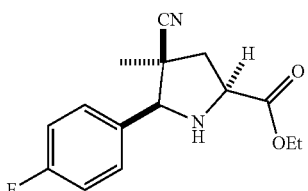

Chemical Formula: C$_{15}$H$_{17}$FN$_2$O$_2$
Exact Mass: 276.1274

$^1$H-NMR (500 MHz, CDCl$_3$): δ/ppm 7.52 (2H, dd, J=5.4, 8.7 Hz), 7.09 (2H, t, J=8.7 Hz), 4.34-4.24 (2H, m), 4.00 (1H, dd, J=4.2, 9.6 Hz), 3.95 (1H, s), 2.83 (1H, dd, J=4.2, 13.7 Hz), 2.82 (1H, s), 2.30 (1H, dd, J=9.6, 13.7 Hz), 1.41 (3H, s), 1.34 (3H, t, J=7.1 Hz); $^{13}$C-NMR (125 MHz, CDCl$_3$): δ/ppm 172.9 (C), 163.2 (C, d, J=246 Hz), 132.4 (C), 129.4 (2CH, d, J=8 Hz), 121.8 (C), 115.7 (2CH, d, J=22 Hz), 71.7 (CH), 61.9 (CH$_2$), 57.3 (CH), 44.0 (C), 42.2 (CH$_2$), 22.0 (CH$_3$), 14.3 (CH$_3$); IR (film): v/cm$^{-1}$ 3348, 2982, 2235, 1736, 1605, 1510; LR-MS: 299.1 [M+Na]$^+$; HR-MS (ESI) calculated for C$_5$H$_{17}$FN$_2$O$_2$Na: 299.1172, found: 299.1177.

Ethyl rac-(2S,4S,5S)-5-(Benzo[d][1,3]dioxol-5-yl)-4-cyano-4-methylpyrrolidine-2-carboxylate

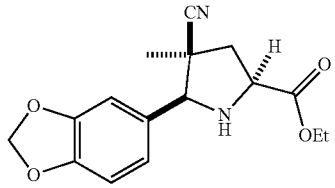

Chemical Formula: C$_{16}$H$_{18}$N$_2$O$_4$
Exact Mass: 302.1267

Isolated as brown oil (dr=3:2). $^1$H-NMR (500 MHz, CDCl$_3$): δ/ppm 7.12 (1H, s), 6.98 (1H, d, J=8.5 Hz), 6.83 (1H, d, J=8.5 Hz), 5.99 (2H, s), 4.31 (2H, q, J=7.0 Hz), 3.98 (1H, dd, J=4.5, 9.5 Hz), 3.89 (1H, s), 2.83 (1H, dd, J=4.0, 13.5 Hz), 2.75 (1H, br. s), 2.29 (1H, dd, J=9.5, 13.5 Hz), 1.44 (3H, s), 1.36 (3H, t, J=7.0 Hz); $^{13}$C-NMR (125 MHz, CDCl$_3$): δ/ppm 173.0 (C), 148.0 (C), 147.9 (C), 130.6 (C), 122.1 (C), 121.1 (CH), 108.2 (CH), 107.9 (CH), 101.3 (CH$_2$), 72.1 (CH), 61.6 (CH$_2$), 57.0 (CH), 43.8 (C), 42.1 (CH$_2$), 22.1 (CH$_3$), 14.2 (CH$_3$). IR (film): v/cm$^{-1}$3361, 2984, 2900, 2254, 1734, 1490, 1447, 1265, 1041, 909. LR-MS: 325.1 M+Na$^+$; HR-MS (ESI) calculated for C$_{16}$H$_{18}$N$_2$O$_4$Na: 325.1164 (M+Na$^+$), found: 325.1161.

Ethyl rac-(2S,4S,5R)-5-(6-Bromobenzo[d][1,3]dioxol-5-yl)-4-cyano-4-methylpyrrolidine-2-carboxylate

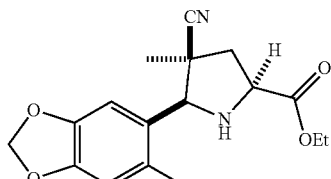

Chemical Formula: C$_{16}$H$_{17}$BrN$_2$O$_4$
Exact Mass: 380.0372

Isolated as brown oil (single diastereomer). $^1$H-NMR (500 MHz, CDCl$_3$): δ/ppm 7.48 (1H, s), 6.96 (1H, s), 5.97 (1H, s), 5.92 (1H, s), 4.56 (1H, s), 4.20 (2H, q, J=7.0 Hz), 4.00 (1H, m), 2.67 (1H, dd, J=6.0, 8.0 Hz), 2.65 (1H, broad s), 2.27 (1H, dd, J=9.0, 13.5 Hz), 1.53 (3H, s), 1.27 (3H, t, J=7.0 Hz); $^{13}$C-NMR (125 MHz, CDCl$_3$): δ/ppm 172.8 (C), 148.3 (C), 147.6 (C), 130.9 (C), 122.0 (C), 114.5 (C), 112.4 (CH), 109.4 (CH), 102.0 (CH$_2$), 68.5 (CH), 61.4 (CH$_2$), 57.1 (CH), 44.3 (C), 41.4 (CH$_2$), 23.3 (CH$_3$), 14.2 (CH$_3$). IR (film): v/cm$^{-1}$ 3366, 2981, 2904, 2237, 1737, 1504, 1477, 1408, 1241, 1205, 1117, 1037, 931, 846. LR-MS: 381.2 M+Na$^+$.

Ethyl rac-(2S,4S,5R)-5-(5-Bromo-2-methoxyphenyl)-4-cyano-4-methylpyrrolidine-2-carboxylate

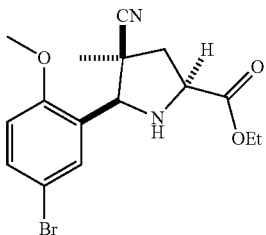

Chemical Formula: $C_{16}H_{19}BrN_2O_3$
Exact Mass: 366.0579

Isolated as brown oil (single diastereomer). $^1$H-NMR (500 MHz, CDCl$_3$): δ/ppm 7.89 (1H, d, J=2.5 Hz), 7.37 (1H, dd, J=2.5, 9.0 Hz), 6.77 (1H, d, J=9.0 Hz), 4.47 (1H, s), 4.27 (2H, q, J=7.5 Hz), 3.98 (1H, t, J=7.5 Hz), 3.83 (3H, s), 2.71 (1H, br s), 2.62 (1H, dd, J=7.0, 13.0 Hz), 2.26 (1H, dd, J=8.5, 13.0 Hz), 1.49 (3H, s), 1.34 (3H, t, J=7.5 Hz); $^{13}$C-NMR (125 MHz, CDCl$_3$): δ/ppm 172.7 (C), 156.4 (C), 131.9 (CH), 131.1 (CH), 129.1 (C), 122.3 (C), 113.1 (C), 112.2 (CH), 64.5 (CH), 61.5 (CH$_2$), 57.7 (CH), 55.5 (CH$_3$), 43.9 (C), 41.8 (CH$_2$), 23.6 (CH$_3$), 14.3 (CH$_3$). IR (film): ν/cm$^{-1}$ 3366, 2980, 2938, 2904, 2839, 2236, 1736, 1486, 1463, 1252, 1202, 1134, 1028, 809. LR-MS: 389.0 M+Na$^+$; HR-MS (ESI) calculated for C$_{16}$H$_{19}$N$_2$O$_3$Na: 389.0477, found: 389.0471.

Ethyl rac-(2S,4S,5S)-4-Cyano-5-(2,2-difluorobenzo[d][1,3]dioxol-5-yl)-4-methylpyrrolidine-2-carboxylate

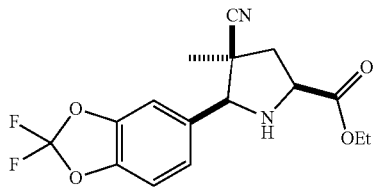

Chemical Formula: $C_{16}H_{16}F_2N_2O_4$
Exact Mass: 338.1078

Isolated as yellow oil (dr=4:1). $^1$H-NMR (500 MHz, CDCl$_3$): δ/ppm 7.38 (1H, s), 7.22 (1H, d, J=8.5 Hz), 7.06 (1H, d, J=8.5 Hz), 4.24-4.34 (2H, m), 3.97 (1l, s), 3.95-4.01 (1H, m), 2.84 (1H, dd, J=4.5, 9.0 Hz), 2.68 (1H, s), 2.29 (1H, dd, J=4.5, 8.5 Hz), 1.44 (3H, s), 1.33 (3H, t, J=9.0 Hz); $^{13}$C-NMR (125 MHz, CDCl$_3$): δ/ppm 172.7 (C), 144.1 (C), 133.7 (C), 133.3 (C), 131.8 (C, t, J=250 Hz), 123.1 (CH), 121.6 (C), 109.3 (CH), 109.1 (CH), 71.9 (CH), 61.8 (CH$_2$), 57.0 (CH), 43.9 (C), 41.8 (CH$_2$), 22.1 (CH$_3$), 14.2 (CH$_3$). IR (film): ν/cm$^{-1}$ 3351, 3078, 2983, 2236, 1738, 1497, 1448, 1382, 1239, 1148, 1034, 818, 703.

Ethyl rac-(2S,4S,5S)-5-(3,4-Bis(allyloxy)phenyl)-4-cyano-4-methylpyrrolidine-2-carboxylate

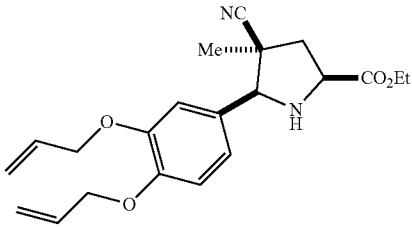

Chemical Formula: $C_{21}H_{26}N_2O_4$
Exact Mass: 370.1893
Molecular Weight: 370.4490

Isolated as yellow oil (dr=4:1). $^1$H-NMR (500 MHz, CDCl$_3$) δ/ppm 7.17 (d, J=1.5 Hz, 1H), 7.01-6.99 (m, 1H), 6.89 (d, J=8.2 Hz, 1H), 6.13-6.04 (m, 2H), 5.47-5.40 (m, 2H), 5.31-5.26 (m, 2H), 4.66-4.60 (m, 4H), 4.33-4.26 (m, 2H), 3.96 (dd, J=9.6, 3.9 Hz, 1H), 3.85 (s, 1H), 2.82 (dd, J=13.6, 4.1 Hz, 1H), 2.75 (broads, 1H), 2.27 (dd, J=13.6, 9.7 Hz, 1H), 1.40 (s, 3H), 1.33 (t, J=7.6 Hz, 3H) ppm; $^{13}$C-NMR (126 MHz, CDCl$_3$) δ/ppm 173.2 (C), 149.1 (C), 148.6 (C), 133.5 (2×CH), 129.4 (C), 122.2 (C), 120.5 (CH), 118.0 (CH$_2$), 117.8 (CH$_2$), 113.8 (CH), 113.4 (CH), 72.4 (CH), 70.2 (CH$_2$), 70.0 (CH$_2$), 61.8 (CH$_2$), 57.3 (CH), 44.0 (C), 42.5 (C$_2$), 22.1 (CH$_3$), 14.3 (C$_3$) ppm; IR (film) ν/cm$^{-1}$ 2982, 2936, 1735, 1649, 1513, 1454, 1426, 1378, 1265, 1217, 1138, 1021, 997, 929, 810 cm$^{-1}$; HRMS (ESI) calcd for C$_{21}$H$_{26}$N$_2$O$_4$Na$^+$ (M+Na) 393.1790, found 393.1796.

Ethyl rac-(2S,4S,5S)-4-Cyano-5-(7-methoxybenzo[d][1,3]dioxol-5-yl)-4-methylpyrrolidine-2-carboxylate

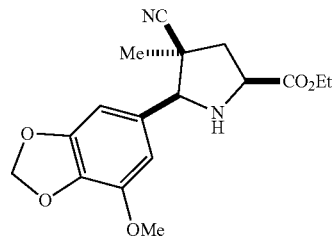

Chemical Formula: $C_{17}H_{20}N_2O_5$
Exact Mass: 332.1372
Molecular Weight: 332.3560

Isolated as yellow oil (dr=3:2). $^1$H-NMR (500 MHz, CDCl$_3$) δ/ppm 6.78 (s, 1H), 6.67 (s, 1H), 5.96 (s, 2H), 4.29-4.22 (m, 2H), 3.93 (dd, J=9.5, 4.3 Hz, 1H), 3.91 (s, 3H), 3.82 (s, 1H), 2.78 (dd, J=13.6, 4.3 Hz, 1H), 2.68 (broad s, 1H), 2.24 (dd, J=13.6, 9.6 Hz, 1H), 1.40 (s, 3H), 1.31 (t, J=7.2 Hz, 3H) ppm; $^{13}$C-NMR (126 MHz, CDCl$_3$) δ/ppm 172.9 (C), 148.8 (C), 143.6 (C), 135.6 (C), 131.4 (C), 122.0 (C), 107.1 (CH), 101.9 (CH), 101.7 (CH$_2$), 72.3 (CH), 61.7 (CH$_2$), 57.1 (CH$_3$), 56.7 (CH), 43.9 (C), 42.1 (CH$_2$), 22.2 (CH$_3$), 14.2 (CH$_3$) ppm; IR (film) ν/cm$^{-1}$ 2979, 2235, 1735, 1635, 1510, 1452, 1381, 1323, 1291, 1202, 1138, 1094, 1043, 929, 855, 831, 733 cm$^{-1}$; HRMS (ESI) calcd for C$_{17}$H$_{20}$N$_2$O$_5$Na$^+$ (M+Na) 355.1270, found 355.1261.

247

Ethyl rac-(2S,4S,5S)-4-Cyano-5-(2,3-dihydro-1H-inden-5-yl)-4-methylpyrrolidine-2-carboxylate

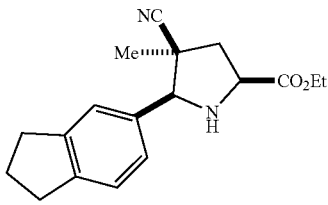

Chemical Formula: C$_{18}$H$_{22}$N$_2$O$_2$
Exact Mass: 298.1681
Molecular Weight: 298.3860

Isolated as yellow oil (dr=1:1). $^1$H-NMR (500 MHz, CDCl$_3$) δ 7.40 (s, 1H), 7.27-7.23 (m, 2H), 4.34-4.26 (m, 2H), 3.98 (dd, J=9.6, 3.9 Hz, 1H), 3.90 (s, 1H), 2.97-2.89 (m, 4H), 2.83 (dd, J=13.8, 4.2 Hz, 1H), 2.30 (dd, J=13.8, 9.7 Hz, 1H), 2.09 (app. quintet, J=7.4 Hz, 2H), 1.62 (broad s, 1H), 1.42 (s, 3H), 1.35 (t, J=7.3 Hz, 3H) ppm; $^{13}$C-NMR (126 MHz, CDCl$_3$) δ 173.2 (C), 145.3 (C), 144.8 (C), 134.3 (C), 125.6 (CH), 124.5 (CH), 123.4 (CH), 122.2 (C), 72.8 (CH), 61.8 (CH$_2$), 57.5 (CH), 44.2 (C), 42.8 (CH$_2$), 33.0 (CH$_2$), 32.8 (CH$_2$), 25.6 (CH$_2$), 22.1 (CH$_3$), 14.4 (CH$_3$) ppm; IR (film) v/cm$^{-1}$ 2940, 2234, 1735, 1447, 1378, 1209, 1139, 1097, 1032, 826 cm$^{-1}$; HRMS (ESI) calcd for CH$_{22}$N$_2$O$_2$Na$^+$ (M+Na) 321.1579, found 321.1577.

Ethyl rac-(2S,4S,5S)-4-Cyano-4-methyl-5-(1-(phenylsulfonyl)-1H-indol-3-yl)pyrrolidine-2-carboxylate

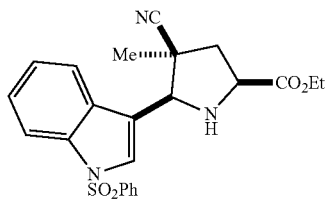

Chemical Formula: C$_{23}$H$_{23}$N$_3$O$_4$S
Exact Mass: 437.1409
Molecular Weight: 437.5140

Isolated as a yellow, highly viscous oil. $^1$H-NMR (500 MHz, CDCl$_3$) δ 7.98 (d, J=6.4 Hz, 2H), 7.93 (d, J=8.3 Hz, 2H), 7.59 (d, J=7.9 Hz, 1H), 7.52 (t, J=7.4 Hz, 1H), 7.43 (t, J=7.8 Hz, 2H), 7.32 (t, J=7.7 Hz, 1H), 7.23 (t, J=7.6 Hz, 1H), 4.35-4.28 (m, 2H), 4.27 (d, J=5.6 Hz, 1H), 4.04-4.00 (m, 1H), 2.88 (dd, J=13.7, 4.3 Hz, 1H), 2.81 (broad s, 1H), 2.33 (dd, J=13.7, 9.8 Hz, 1H), 1.46 (s, 3H), 1.37 (t, J=7.1 Hz, 3H) ppm; $^{13}$C-NMR (126 MHz, CDCl$_3$) δ 172.7 (C), 137.9 (C), 135.1 (C), 134.0 (CH), 129.8 (C), 129.4 (CH), 127.2 (CH), 125.2 (CH), 125.1 (CH), 123.4 (CH), 122.2 (C), 119.8 (CH), 119.1 (C), 113.9 (CH), 64.6 (CH), 61.9 (CH$_2$), 57.4 (CH), 44.6 (C), 42.6 (CH$_2$), 22.4 (CH$_3$), 14.3 (CH$_3$) ppm; IR (film) v/cm$^{-1}$ 2980, 2235, 1735, 1606, 1447, 1369, 1273, 1212, 1176, 1125, 1092, 1024, 979, 858, 750, 722 cm$^{-1}$; HRMS (ESI) calcd for C$_{23}$H$_{23}$N$_3$O$_4$SNa$^+$ (M+Na) 460.1307, found 460.1305.

248

Example 3

General Procedure for Forming Diketopiperazines by Sequential Reaction of Pyrrolidine Esters with 2-Chloroalkanonyl Chlorides and Amines.

Methyl rac-(3R,6S,7S,8aS)-6-(4-Fluorophenyl)-2,3,7-trimethyl-1,4-dioxooctahydropyrrolo[1,2-a]pyrazine-7-carboxylate

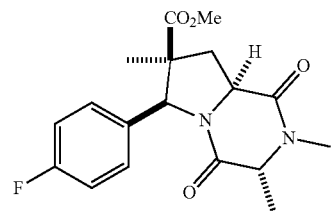

Chemical Formula: C$_{18}$H$_{21}$FN$_2$O$_4$
Exact Mass: 348.1485

The corresponding pyrrolidine (1.0 equiv) was dissolved in 10 mL of CH$_2$Cl$_2$ and cooled to 0° C. with an ice-bath. Triethylamine (1.2 equiv) was added, followed by dropwise addition of a solution of 2-chloropropionyl chloride (1.2 equiv, 50% v/v in CH$_2$Cl$_2$). This mixture was stirred for 1 h with cooling, followed by 1 h after removal of the ice-bath. The intermediate α-chloroimide is then directly extracted (3×CH$_2$Cl$_2$) and isolated as brownish foam after removal of the volatiles in vacuo. The corresponding amide was re-dissolved in 10 mL of CH$_2$Cl$_2$ and combined with the equivalent volume of 40% aq MeNH$_2$ solution to give a biphasic mixture, which was stirred at rt for 12-16 h. Extraction of this mixture gives the crude diketopiperazine (DKP) product as yellow foam (purity 50-80%). This residue was stirred with MeOH (1 M) for 1 h, whereupon a colorless solid was obtained 70% yield. Trituration of this material from a methanolic solution in CH$_2$Cl$_2$ (often accelerated by vigorous stirring) gave the major DKP stereoisomer as a colorless solid after filtration and drying under high vacuum. Either the pure DKP steroisomer, or the solid 5:1 mixture of DKP isomers, could be employed in the subsequent sulfidation step.

$^1$H-NMR (500 MHz, CDCl$_3$): δ/ppm 7.00-7.10 (2H, m), 6.91 (2H, t, J=8.5 Hz), 4.81 (1H, s), 4.36 (1H, dd, J=6.5, 11.5 Hz), 3.81 (1H, q, J=9.0 Hz), 3.22 (3H, s), 2.94 (3H, s), 2.90-2.95 (1H, m), 2.16 (1H, dd, J=6.5, 14.0 Hz), 1.53 (3H, s), 1.44 (3H, d, J=9.0 Hz); $^{13}$C-NMR (125 MHz, CDCl$_3$): δ/ppm 172.1 (C), 167.3 (C), 166.9 (C), 162.3 (C, d, J=249 Hz), 133.6 (C, d, J=3 Hz), 128.3 (2 CH, d, J=8 Hz), 115.2 (2 CH, d, J=21 Hz), 69.4 (CH), 60.9 (CH), 56.9 (CH), 53.3 (C), 51.9 (CH$_3$), 34.4 (CH$_2$), 32.0 (CH$_3$), 24.2 (CH$_3$), 15.3 (CH$_3$). IR (film): v/cm$^{-4}$ 2975, 2929, 1736, 1677, 1605, 1509, 1433, 1401, 1299, 1248, 1225, 1126, 1158, 849. LR-MS: 371.07 (M+Na$^+$); HR-MS (ESI) calculated for C$_{18}$H$_{22}$N$_2$O$_4$F: 349.1564 (M+H$^+$), found: 349.1570.

tert-Butyl rac-(3R,6S,7S,8aS)-6-(4-Fluorophenyl)-2,3,7-trimethyl-1,4-dioxooctahydropyrrolo[1,2-a]pyrazine-7-carboxylate

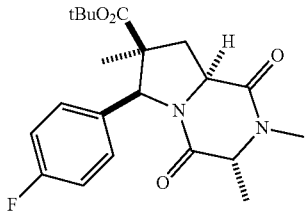

Chemical Formula: $C_{21}H_{27}FN_2O_4$
Exact Mass: 390.1955

$^1$H-NMR (500 MHz, CDCl$_3$): δ/ppm 7.06-7.13 (2H, m), 6.91-6.95 (2H, m), 4.76 (1H, s), 4.34 (1H, dd, J=7.0, 12.0 Hz), 3.79 (1H, q, J=7.0 Hz), 3.00 (3H, s), 2.92-3.00 (1H, m), 2.17 (1H, dd, J=6.5, 14.0 Hz), 1.51 (3H, s), 1.45 (3H, d, J=7.0 Hz), 1.05 (9H, s); $^{13}$C-NMR (125 MHz, CDCl$_3$): δ/ppm 170.8 (C), 167.3 (C), 166.7 (C), 162.3 (C, d, J=250 Hz), 134.2 (C), 129.2 (2CH), 115.1 (2CH, d, J=21 Hz), 81.4 (C), 69.3 (CH), 60.8 (CH), 56.7 (CH), 53.4 (C), 34.8 (CH$_2$), 31.9 (CH$_3$), 27.3 (3CH$_3$), 25.2 (CH$_3$), 15.2 (CH$_3$). IR (film): v/cm$^{-1}$ 2977, 2934, 1724, 1673, 1510, 1452, 1430, 1401, 1369, 1304, 1250, 1228, 1167, 1124, 848, 734. LR-MS: 413.2 (M+Na$^+$); HR-MS (ESI) calculated for $C_{21}H_{27}N_2O_4$FNa: 413.1852 (M+Na$^+$), found: 413.1846.

Methyl rac-(3R,6S,7S,8aS)-6-(Benzo[d][1,3]dioxol-5-yl)-2,3,7-trimethyl-1,4-dioxooctahydropyrrolo-[1,2-a]pyrazine-7-carboxylate

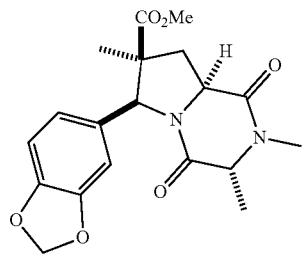

Chemical Formula: $C_{19}H_{22}N_2O_6$
Exact Mass: 374.1478

Isolated as an 8:1 mixture of diastereomers, data for the major isomer is reported. $^1$H-NMR (500 MHz, CDCl$_3$): δ/ppm 6.68 (1H, d, J=8.0 Hz), 6.54 (1H, d, J=8.0 Hz), 6.51 (1H, s), 5.90 (2H, s), 4.78 (1H), 4.36 (1H, dd, J=6.5, 11.5 Hz), 3.85 (1H, app. t, J=7.0 Hz), 3.32 (3H, s), 3.03 (3H, s), 2.90-3.00 (1H, m), 2.16 (1H, dd, J=6.5, 8.5 Hz), 1.53 (3H, s), 1.41 (3H, s); $^{13}$C-NMR (125 MHz, CDCl$_3$): δ/ppm 172.09 (C), 167.2 (C), 166.8 (C), 147.5 (C), 147.3 (C), 131.4 (C), 120.3 (CH), 108.0 (CH), 106.9 (CH), 101.1 (CH$_2$), 69.8 (CH), 60.8 (CH), 56.8 (CH$_3$), 53.2 (C), 51.9 (CH), 34.2 (CH$_2$), 32.0 (CH$_3$), 24.1 (CH$_3$), 15.2 (CH$_3$). LR-MS: 416.1 M+Na$^+$; IR (film): v/cm$^{-1}$ 2953, 2949, 1735, 1672, 1490, 1432, 1294, 1245, 1122, 1037. HR-MS (ESI) calculated for $C_{19}H_{22}N_2O_6$Na: 397.1375 (M+Na$^+$), found: 397.1367.

Rac-(3R,6S,7S,8aS)-2,3,7-trimethyl-1,4-dioxo-6-phenyloctahydropyrrolo-[1,2-a]pyrazine-7-carbonitrile

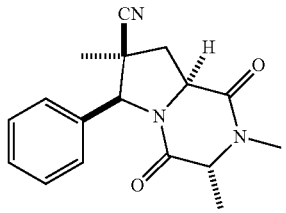

Chemical Formula: $C_{17}H_{19}N_3O_2$
Exact Mass: 297.1477

$^1$H-NMR (600 MHz, CDCl$_3$): δ/ppm 7.39-7.33 (3H, m), 7.12 (2H, d, J=7.2 Hz), 4.91 (1H, s), 4.40 (1H, dd, J=6.6, 11.4 Hz), 3.91 (1H, q, J=3.6, 7.2 Hz), 3.05 (3H, s), 2.79 (1H, t, J=11.4 Hz), 2.46 (1H, dd, J=6.6, 13.2 Hz), 1.69 (3H, s), 1.48 (3H, d, J=7.2 Hz); $^{13}$C-NMR (125 MHz, CDCl$_3$): δ/ppm 166.7 (C), 166.2 (C), 136.9 (C), 129.2 (2CH), 129.1 (2CH), 126.1 (CH), 119.9 (C), 69.8 (CH), 60.9 (CH), 56.3 (CH), 42.6 (C), 36.7 (CH$_2$), 32.2 (CH$_3$), 25.3 (CH$_3$), 15.4 (CH$_3$); IR (film): v/cm$^{-1}$ 2981, 2937, 2244, 1673; LR-MS: 320.1 [M+Na]$^+$; HR-MS (ESI) calculated for $C_{17}H_{19}N_3O_2$Na: 320.1375, found: 320.1380.

Rac-(3R,6S,7S,8aS)-6-(4-fluorophenyl)-2,3,7-trimethyl-1,4-dioxooctahydropyrrolo-[1,2-a]pyrazine-7-carbonitrile

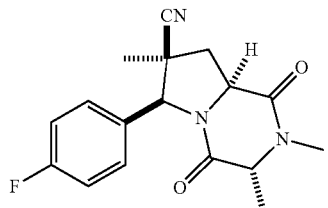

Chemical Formula: $C_{17}H_{18}FN_3O_2$
Exact Mass: 315.1383

$^1$H-NMR (500 MHz, CDCl$_3$): δ/ppm 7.13-7.05 (4H, m), 4.90 (1H, s), 4.39 (1H, dd, J=6.5, 11.0 Hz), 3.90 (1H, q, J=7.0 Hz), 3.06 (3H, s), 2.76 (1H, t, J=12.0 Hz), 2.47 (1H, dd, J=6.5, 13.5 Hz), 1.69 (3H, s), 1.49 (3H, d, J=7.5 Hz); $^{13}$C-NMR (125 MHz, CDCl$_3$): δ/ppm 166.8 (C), 166.1 (C), 163.0 (C, d, J=247 Hz), 132.8 (C, d, J=3 Hz), 127.9 (2CH, d, J=8 Hz), 119.8 (C), 116.2 (2CH, d, J=22 Hz), 69.2 (CH), 60.9 (CH), 56.3 (CH), 42.6 (C), 36.8 (CH$_2$), 32.2 (CH$_3$), 25.3 (CH$_3$), 15.4 (CH$_3$); IR (film): v/cm$^{-1}$ 2989, 2940, 2241, 1681; LR-MS: 338.1 [M+Na]$^+$; HR-MS (ESI) calculated for $C_{17}H_{18}FN_3O_2$Na: 338.1281, found: 338.1283.

251

Rac-(3R,6S,7S,8aS)-6-(Benzo[d][1,3]dioxol-5-yl)-2,3,7-trimethyl-1,4-dioxooctahydropyrrolo[1,2-a]-pyrazine-7-carbonitrile

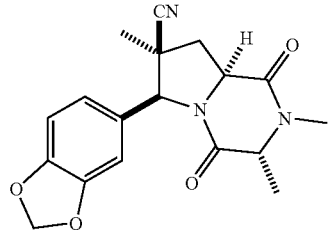

Chemical Formula: $C_{18}H_{19}N_3O_4$
Exact Mass: 341.1376

$^1$H-NMR (500 MHz, CDCl$_3$): δ/ppm 6.79 (1H, d, J=9.0 Hz), 6.63 (1H, d, J=9.0 Hz), 6.57 (1H, s), 5.96 (2H, s), 4.82 (1H, s), 4.36 (1H, dd, J=6.5, 11.0 Hz), 3.90 (1H, app q, J=7.0 Hz), 3.04 (3H, s), 2.76 (1H, app t, J=7.0 Hz), 2.45 (1H, dd, J=6.5, 13.5 Hz), 1.66 (3H, s), 1.47 (3H, d, J=7.0 Hz); $^{13}$C-NMR (125 MHz, CDCl$_3$): δ/ppm 166.6 (C), 166.0 (C), 148.2 (C), 148.1 (C), 130.8 (C), 119.9 (CH), 119.8 (C), 108.6 (CH), 106.2 (CH), 101.4 (CH$_2$), 69.6 (CH), 60.8 (CH), 56.1 (CH), 42.6 (C), 36.7 (CH$_2$), 32.0 (CH$_3$), 25.1 (CH$_3$), 15.3 (CH$_3$). LR-MS: 364.0 M+Na$^+$; IR (film) v/cm$^{-1}$: 2982, 2917, 2244, 1671, 1491, 1447, 1246, 1037, 925, 721 v/cm$^{-1}$. HR-MS (ESI) calculated for $C_{18}H_{19}N_3O_4Na$: 364.1273 (M+Na$^+$), found: 364.1273.

Rac-(6R,7S,8aS)-2,3,7-Trimethyl-1,4-dioxo-6-(thiophen-2-yl)octahydropyrrolo[1,2-a]pyrazine-7-carbonitrile

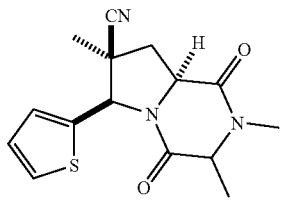

Chemical Formula: $C_{15}H_{17}N_3O_2S$
Exact Mass: 303.1041

$^1$H-NMR (500 MHz, CDCl$_3$): δ/ppm 7.31 (1H, m), 7.11 (1H, s), 7.06 (1H, m), 5.27 (1H, s), 4.39 (1H, dd, J=6.5, 11.0 Hz), 3.95 (1H, q, J=7.5 Hz), 3.08 (3H, s), 3.00 (1H, app t, J=13.0 Hz), 2.56 (1H, dd, J=6.5, 13.0 Hz), 1.72 (3H, s), 1.52 (3H, d, J=7.5 Hz); $^{13}$C-NMR (125 MHz, CDCl$_3$): δ/ppm 166.9 (C), 166.0 (C), 140.4 (C), 127.5 (CH), 127.0 (CH), 125.5 (CH), 119.6 (C), 65.3 (CH), 60.8 (CH), 55.8 (CH), 42.9 (C), 36.8 (CH$_2$), 32.2 (CH$_3$), 24.5 (CH$_3$), 15.4 (CH$_3$). IR (film): v/cm$^{-1}$ 2981, 2935, 2246, 1672, 1447, 1428, 1402, 1301, 1229, 1065, 915, 722. LR-MS: 326.0 M+Na$^+$. HR-MS (ESI) calculated for $C_{15}H_{17}N_3O_2SNa$: 326.0939 (M+Na$^+$), found: 326.0942.

252

Rac-(6S,7S,8aS)-6-(4-Chlorophenyl)-2,3,7-trimethyl-1,4-dioxooctahydropyrrolo[1,2-a]pyrazine-7-carbonitrile

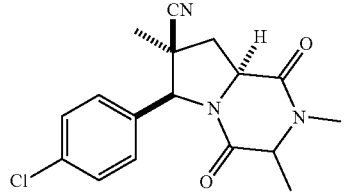

Chemical Formula: $C_{17}H_{18}ClN_3O_2$
Exact Mass: 331.1088

$^1$H-NMR (500 MHz, CDCl$_3$): δ/ppm 7.35 (2H, d, J=8.5 Hz), 7.07 (2H, d, J=8.5 Hz), 4.88 (1H, s), 4.39 (1H, dd, J=6.5, 11.5 Hz), 3.90 (1H, q, J=7.5 Hz), 3.06 (3H, s), 2.76 (1H, app t, J=12.0 Hz), 2.48 (1H, dd, J=6.5, 8.5 Hz), 1.70 (3H, s), 1.49 (3H, d, J=7.5 Hz); $^{13}$C-NMR (125 MHz, CDCl$_3$): δ/ppm 166.7 (C), 166.0 (C), 135.4 (C), 135.1 (C), 129.4 (2CH), 127.5 (2CH), 119.7 (C), 69.2 (CH), 60.9 (CH), 56.3 (CH), 42.4 (C), 36.8 (CH$_2$), 32.2 (CH$_3$), 25.3 (CH$_3$), 15.4 (CH$_3$). IR (film): v/cm$^{-1}$ 2981, 2919, 2852, 2246, 1673, 1490, 1430, 1303, 1235, 1093, 731. LR-MS: 354.0 M+Na$^+$. HR-MS (ESI) calculated for $C_{17}H_{18}N_3O_2ClNa$: 354.0985 (M+Na$^+$), found: 354.0981.

Rac-(3R,6S,7S,8aS)-6-(Benzo[d][1,3]dioxol-5-yl)-2-(3-(dimethylamino)propyl)-3,7-dimethyl-1,4-dioxooctahydropyrrolo[1,2-a]pyrazine-7-carbonitrile

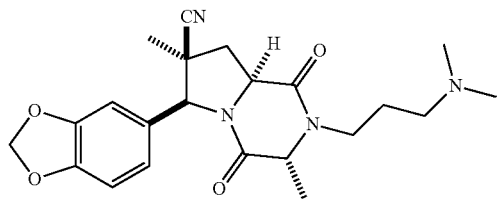

Chemical Formula: $C_{22}H_{28}N_4O_4$
Exact Mass: 412.2111

Isolated as an 8:1 mixture of diastereomers, data for the major isomer is reported. $^1$H-NMR (500 MHz, CDCl$_3$): δ/ppm 6.74 (1H, d, J=8.0 Hz), 6.56 (1H, d, J=8.0 Hz), 6.52 (1H, s), 5.91 (2H, s), 4.80 (1H, s), 4.35 (1H, dd, J=6.5, 11.0 Hz), 4.02 (1H, q, J=7.5 Hz), 3.83 (1H, dt, J=7.5, 13.5 Hz), 3.00 (1H, dt, J=7.5, 13.5 Hz), 2.74 (1H, app t, J=12.0 Hz), 2.40 (1H, dd, J=6.5, 13.5 Hz), 2.20-2.30 (2H, m), 2.14 (6H, s), 1.70-1.80 (2H, m), 1.62 (3H, s), 1.43 (3H, d, J=6.5 Hz); $^{13}$C-NMR (125 MHz, CDCl$_3$): δ/ppm 167.1 (C), 166.3 (C), 148.3 (C), 148.2 (C), 131.0 (C), 119.9 (C), 119.7 (CH), 108.6 (CH), 106.3 (CH), 101.5 (CH$_2$), 69.4 (CH), 59.3 (CH), 56.3 (CH$_2$), 56.2 (CH), 45.4 (2CH$_3$), 43.3 (C), 42.7 (CH$_2$), 36.6 (CH$_2$), 25.9 (CH$_2$), 25.1 (CH$_3$), 16.0 (CH$_3$). IR (film): v/cm$^{-1}$ 2979, 2943, 2822, 2781, 2244, 1672, 1491, 1448, 1427, 1245, 1037, 929, 811, 735. LR-MS: 435.3 M+Na$^+$. HR-MS (ESI) calculated for $C_{22}H_{28}N_4O_4Na$: 435.2008 (M+Na$^+$), found: 435.2015.

253

Rac-(3R,6R,7S,8aS)-6-(6-Bromobenzo[d][1,3]di-oxol-5-yl)-2,3,7-trimethyl-1,4-dioxooctahydro-pyrrolo[1,2-a]pyrazine-7-carbonitrile

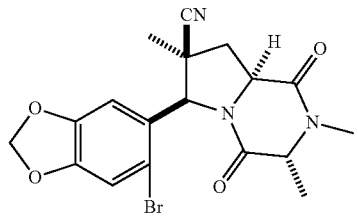

Chemical Formula: $C_{18}H_{18}BrN_3O_4$
Exact Mass: 419.0481

Isolated as a 3:1 mixture of diastereomers, data for the major isomer is reported. $^1$H-NMR (500 MHz, CDCl$_3$): δ/ppm 7.07 (1H, s), 6.34 (1H, s), 5.98 (2H, s), 5.34 (1H, s), 4.36 (1H, dd, J=6.5, 12.0 Hz), 3.92 (1H, q, J=7.0 Hz), 3.04 (3H, s), 2.66 (1H, app t, J=13.0 Hz), 2.48 (1H, dd, J=6.5, 13.0 Hz), 1.74 (3H, s), 1.47 (3H, d, J=7.0 Hz); $^{13}$C-NMR (125 MHz, CDCl$_3$): δ/ppm 166.5 (C), 166.0 (C), 148.7 (C), 148.1 (C), 129.1 (C), 119.7 (C), 115.0 (C), 113.5 (CH), 105.0 (CH), 102.3 (CH$_2$), 68.2 (CH), 60.8 (CH), 56.4 (CH), 42.2 (C), 37.4 (CH$_2$), 31.8 (CH$_3$), 24.9 (CH$_3$), 15.5 (CH$_3$). IR (film): v/cm$^{-1}$ 2982, 2246, 1675, 1503, 1478, 1429, 1402, 1307, 1248, 1120, 1036, 928. LR-MS: 435.3 HR-MS (ESI) calculated for $C_{18}H_{18}BrN_3O_4Na$: 442.0378 (M+Na$^+$), found: 442.0369.

Rac-(3R,6S,7S,8aS)-2,3,7-Trimethyl-1,4-dioxo-6-(p-tolyl)octahydropyrrolo[1,2-a]pyrazine-7-carbonitrile

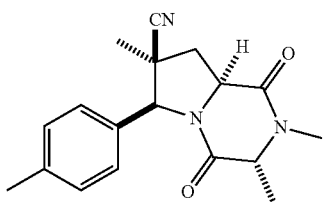

Chemical Formula: $C_{18}H_{21}N_3O_2$
Exact Mass: 311.1634

$^1$H-NMR (500 MHz, CDCl$_3$): δ/ppm 7.17 (2H, d, J=7.5 Hz), 7.01 (2H, d, J=7.5 Hz), 4.88 (1H, s), 4.38 (1H, dd, J=7.0, 11.0 Hz), 3.89 (1H, q, J=7.0 Hz), 3.04 (3H, s), 2.79 (1H, app t, J=12.5 Hz), 2.44 (1H, dd, J=6.5, 12.5 Hz), 2.32 (3H, s), 1.67 (3H, s), 1.47 (3H, d, J=7.0 Hz); $^{13}$C-NMR (125 MHz, CDCl$_3$): δ/ppm 166.7 (C), 166.2 (C), 138.9 (C), 134.0 (C), 129.8 (2CH), 125.9 (2CH), 120.0 (C), 69.6 (CH), 60.9 (CH), 56.2 (CH), 42.6 (C), 36.7 (CH$_2$), 32.1 (CH$_3$), 25.2 (CH$_3$), 21.3 (CH$_3$), 15.4 (CH$_3$). IR (film): v/cm$^{-1}$ 3054, 2982, 2935, 2877, 2243, 1681, 1515, 1452, 1430, 1402, 1306, 1246, 1230, 1063, 804, 734. LR-MS: 334.0 M+Na$^+$. HR-MS (ESI) calculated for $C_{18}H_{21}N_3O_2Na$: 334.1531, found: 334.1536. The structure and relative configuration of this sample was confirmed by single-crystal X-ray analysis.

254

Rac-(3R,6S,7S,8aS)-6-(2,3-Dihydrobenzo[b][1,4]dioxin-6-yl)-2,3,7-trimethyl-1,4-dioxooctahydro-pyrrolo[1,2-a]pyrazine-7-carbonitrile

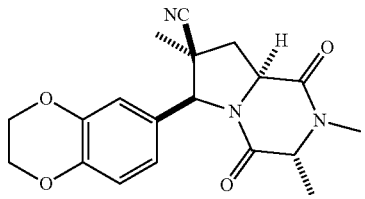

Chemical Formula: $C_{19}H_{21}N_3O_4$
Exact Mass: 355.1532

$^1$H-NMR (500 MHz, 1:1 d$_4$-MeOD/CDCl$_3$): δ/ppm 6.61 (1H, d, J=7.0 Hz), 6.38 (2H, m), 4.59 (1H, s), 4.28 (1H, m), 4.00 (4H, m), 3.69 (1H, q, J=9.0 Hz), 2.82 (3H, s), 2.48 (1H, app t, J=12.0 Hz), 2.23 (1H, dd, J=8.5, 12.0 Hz), 1.45 (3H, s), 1.26 (3H, d, J=9.0 Hz); $^{13}$C-NMR (125 MHz, CDCl$_3$): δ/ppm 167.3 (C), 166.6 (C), 144.0 (C), 143.7 (C), 130.2 (C), 120.0 (C), 119.1 (CH), 117.6 (CH), 114.9 (CH), 69.3 (CH), 64.3 (2CH$_2$), 60.8 (CH), 56.1 (CH), 42.7 (C), 36.5 (CH$_2$), 31.9 (CH$_3$), 24.7 (CH$_3$), 14.9 (CH$_3$). IR (film): v/cm$^{-1}$ 3056.3, 2982.2, 2936.7, 2878.2, 2244.2, 1672.0, 1509.0, 1450.8, 1432.5, 1307.3, 1287.9, 1067.0, 886.5. LR-MS: 378.1 M+Na$^+$. HR-MS (ESI) calculated for $C_{19}H_{21}N_3O_4Na$: 378.1430, found: 378.1433.

Rac-(3R,6S,7S,8aS)-6-(Benzo[d][1,3]dioxol-5-yl)-3,7-dimethyl-2-(2-morpholinoethyl)-1,4-dioxooctahydropyrrolo[1,2-a]pyrazine-7-carbonitrile

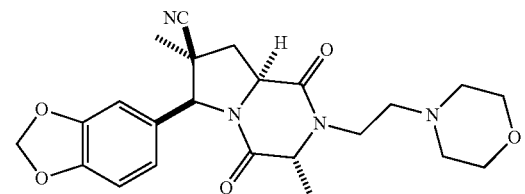

Chemical Formula: $C_{23}H_{28}N_4O_5$
Exact Mass: 440.2060

$^1$H-NMR (500 MHz, 1:1 d$_4$-MeOD/CDCl$_3$): δ/ppm 6.61 (1H, d, J=9.5 Hz), 6.49 (1H, d, J=9.5 Hz), 6.36 (1H, s), 5.77 (2H, s), 4.67 (1H, s), 4.31 (1H, dd, J=6.5, 11.0 Hz), 3.88 (1H, q, J=9.0 Hz), 3.80 (1H, m), 3.44-3.50 (4H, m), 2.88-2.95 (1H, m), 2.55 (1H, app t, J=6.5 Hz), 2.20-2.45 (7H, m), 1.49 (3H, s), 1.31 (3H, d, J=9.0 Hz); $^{13}$C-NMR (125 MHz, CDCl$_3$): δ/ppm 167.4 (C), 166.5 (C), 148.2 (C), 148.1 (C), 131.0 (C), 120.2 (CH), 120.0 (C), 108.5 (CH), 105.8 (CH), 101.5 (CH$_2$), 69.4 (CH), 66.9 (2CH$_2$), 59.7 (CH), 56.4 (CH$_2$), 56.1 (CH), 53.7 (2CH$_2$), 42.8 (C), 41.6 (CH$_2$), 36.5 (CH$_2$), 24.8 (CH$_3$), 15.6 (CH$_3$). IR (film): v/cm$^{-1}$ 2955.4, 2858.2, 2812.5, 2243.7, 1672.0, 1491.0, 1448.4, 1426.9, 1295.8, 1245.8, 1115.3, 1036.5, 922.1. LR-MS: 441.3 M+H$^+$. HR-MS (ESI) calculated for $C_{23}H_{28}N_4O_5Na$: 463.1957, found 463.1946.

Rac-(3R,6S,7S,8aS)-6-(2,2-Difluorobenzo[d][1,3]dioxol-5-yl)-2,3,7-trimethyl-1,4-dioxooctahydropyrrolo[1,2-a]pyrazine-7-carbonitrile

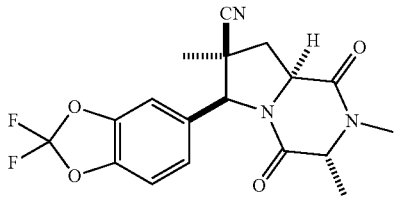

Chemical Formula: $C_{18}H_{17}F_2N_3O_4$
Molecular Weight: 377.3478

$^1$H-NMR (500 MHz, CDCl$_3$): δ/ppm 7.07 (1H, d, J=8.0 Hz), 6.90 (1H, d, J=8.0 Hz), 6.83 (1H, s), 4.88 (1H, s), 4.36-4.43 (1H, dd, J=6.5, 11.5 Hz), 3.92 (1H, q, J=7.0 Hz), 3.07 (3H, s), 2.76 (1H, app t, J=12.0 Hz), 2.51 (1H, dd, J=6.5, 13.5 Hz), 1.71 (3H, s), 1.50 (3H, d, J=7.0 Hz); $^{13}$C-NMR (125 MHz, CDCl$_3$): δ/ppm 166.8 (C), 165.9 (C), 144.2 (C), 144.1 (C), 133.3 (C), 131.7 (CF$_2$, t, J=255 Hz), 121.9 (CH), 119.6 (C), 110.0 (CH), 107.4 (CH), 69.4 (CH), 60.5 (CH), 56.3 (CH), 42.6 (C), 36.9 (CH$_2$), 32.2 (CH$_3$), 25.3 (CH$_3$), 15.4 (CH$_3$). IR (film): v/cm$^{-1}$ 2984, 2939, 2246, 1674, 1500, 1452, 1429, 1403, 1241, 1150, 912, 732. LR-MS: 400.2 (M+Na$^+$); HR-MS (ESI) calculated for $C_{18}H_{17}N_3O_4F_2Na$: 400.1085, found: 400.1092.

Rac-(3R,6S,7R,8aS)-6-(Benzo[d][1,3]dioxol-5-yl)-7-(((tert-butyldimethylsilyl)oxy)methyl)-2,3-dimethyl-1,4-dioxooctahydropyrrolo[1,2-a]pyrazine-7-carbonitrile

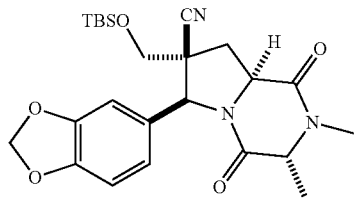

Chemical Formula: $C_{24}H_{33}N_3O_5Si$
Molecular Weight: 471.6290

$^1$H-NMR (500 MHz, CDCl$_3$): δ/ppm 6.73 (1H, d, J=9.0 Hz), 6.2-7.0 (2H, br s), 5.95 (2H, d, J=9.0 Hz), 5.35 (1H, s), 4.62 (1H,1H, m), 3.88 (1H, q, J=7.5 Hz), 3.29 (1H, d, J=9.5 Hz), 3.21 (1H, d, J=9.5 Hz), 3.05 (3H, s), 2.58-2.62 (1H, m), 2.26 (1H, app t, J=12.0 Hz), 1.52 (3H, d, J=7.5 Hz), 0.88 (9H, s), 0.01 (3H, s), −0.02 (3H, s); $^{13}$C-NMR (125 MHz, CDCl$_3$): δ/ppm 166.4 (C), 166.2 (C), 148.0 (2C), 128.2 (C), 121.7 (C), 108.5 (CH), 101.5 (CH$_2$), 66.6 (CH), 63.5 (CH$_2$), 61.1 (CH), 57.0 (CH), 49.2 (C), 33.1 (CH$_2$), 32.1 (CH$_3$), 25.7 (3CH$_3$), 18.2 (C), 15.4 (CH$_3$), −5.6 (2CH$_3$), 2 aromatic CH not seen. IR (film): v/cm$^{-1}$ 2930, 2884, 2857, 2240, 1678, 1490, 1448, 1402, 1245, 1105, 1039, 928, 840, 780, 732. LR-MS: 494.3 (M+Na$^+$); HR-MS (ESI) calculated for $C_{24}H_{33}N_3O_5SiNa$: 494.2087, found: 494.2068.

Rac-(3R,6S,7R,8aS)-6-(Benzo[d][1,3]dioxol-5-yl)-7-(methoxymethyl)-2,3-dimethyl-1,4-dioxo-octahydropyrrolo[1,2-a]pyrazine-7-carbonitrile

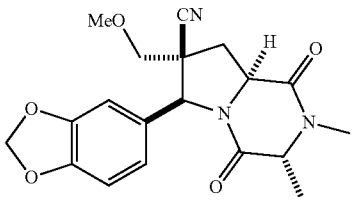

Chemical Formula: $C_{19}H_{21}N_3O_5$
Molecular Weight: 371.3930

$^1$H-NMR (500 MHz, CDCl$_3$): δ/ppm 6.78 (1H, d, J=8.0 Hz), 6.65 (1H, d, J=8.0 Hz), 6.59 (1H, s), 5.95 (2H, s), 5.03 (1H, s), 4.36 (1H, dd, J=7.0, 11.0 Hz), 3.88 (1H, q, J=7.0 Hz), 3.62 (2H, s), 3.48 (3H, s), 3.02 (3H, s), 2.74 (1H, app t, J=11.5 Hz), 2.67 (1H, dd, J=7.5, 14.0 Hz), 1.44 (3H, d, J=7.0 Hz); $^{13}$C-NMR (125 MHz, CDCl$_3$): δ/ppm 166.7 (C), 166.2 (C), 148.3 (C), 148.2 (C), 130.8 (C), 120.0 (CH), 118.3 (C), 108.8 (CH), 106.4 (CH), 101.5 (CH$_2$), 74.8 (CH$_2$), 65.4 (CH), 60.8 (CH), 59.8 (CH$_3$), 56.8 (CH), 48.7 (C), 33.7 (CH$_2$), 32.1 (CH$_3$), 15.3 (CH$_3$).

Rac-(3R,6R,7S,8aS)-6-(Benzo[d][1,3]dioxol-4-yl)-2,3,7-trimethyl-1,4-dioxooctahydropyrrolo[1,2-a]pyrazine-7-carbonitrile

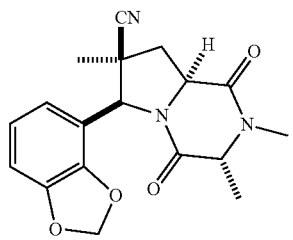

Chemical Formula: $C_{18}H_{19}N_3O_4$
Molecular Weight: 341.3670

$^1$H-NMR (500 MHz, d$_6$-DMSO, 390K): δ/ppm 6.85 (2H, br s), 6.65 (1H, br s), 6.00 (1H, s), 5.92 (1H, s), 4.96 (1H, s), 4.67 (1H, dd, J=6.5, 10.5 Hz), 3.95 (1H, q, J=7.0 Hz), 2.97 (3H, s), 2.58-2.67 (1H, m), 2.44-2.55 (1H, m), 1.72 (3H, s), 1.46 (3H, d, J=7.0 Hz); $^{13}$C-NMR (125 MHz, d$_6$-DMSO, 390K): δ/ppm 166.8 (C), 166.6 (C), 147.9 (C), 145.0 (C), 122.1 (CH), 121.1 (CH), 120.5 (CH), 108.7 (CH), 101.4 (CH$_2$), 65.6 (CH), 60.6 (CH), 56.4 (CH), 42.7 (C), 38.1 (CH$_2$), 31.8 (CH$_3$), 25.0 (CH$_3$), 15.6 (CH$_3$). IR (film): v/cm$^{-1}$ 3056, 2981, 2895, 2244, 1672, 1460, 1432, 1402, 1251, 1066, 928, 731. LR-MS: 342.1 (M+H$^+$); HR-MS (ESI) calculated for $C_{18}H_{19}N_3O_4Na$: 364.1273, found: 364.1267.

Rac-(3R,6S,7S,8aS)-6-(benzo[d][1,3]dioxol-5-yl)-2-butyl-3,7-dimethyl-1,4-dioxo-octahydropyrrolo[1,2-a]pyrazine-7-carbonitrile

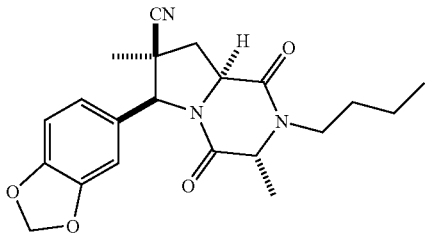 [SMILES: CCCCN1C(=O)[C@@H]2C[C@](C)(C#N)[C@H](c3ccc4c(c3)OCO4)N2C(=O)[C@H]1C]

¹H-NMR (500 MHz, CDCl₃): δ/ppm 6.79 (1H, d, J=9.0 Hz), 6.60 (1H, d, J=9.0 Hz), 6.55 (1H, s), 5.96 (2H, s), 4.82 (1H, s), 4.38 (1H, dd, J=6.5, 11.0 Hz), 3.95 (1H, app q, J=7.0 Hz), 2.99 (1H, m), 2.81 (1H, app t, J=7.0 Hz), 2.43 (1H, dd, J=6.5, 13.5 Hz), 1.60 (2H, m), 1.56 (3H, s), 1.45 (3H, d, J=7.0 Hz) 1.38 (2H, m), 0.96 (3H, t, J=7.2 Hz); ¹³C-NMR (125 MHz, CDCl₃): δ/ppm 167.2 (C), 166.3 (C), 148.6 (C), 148.4 (C), 131.1 (C), 120.0 (CH), 119.9 (C), 108.8 (CH), 106.4 (CH), 101.7 (CH₂), 69.7 (CH), 59.0 (CH), 56.5 (CH), 44.8 (C), 42.9 (CH₂), 36.9 (CH₂), 30.0 (CH₂), 25.4 (CH₃), 20.2 (CH₂), 16.2 (CH₃). 13.9 (CH₃), LR-MS: 406.2 M+Na⁺; IR (film): v/cm⁻¹ 2982, 2917, 2244, 1671, 1491, 1447, 1246, 1037, 925, 721 v/cm⁻¹. HR-MS (ESI) calculated for C₂₁H₂₅N₃O₄Na: 406.1713 (M+Na⁺), found: 406.1730.

Rac-(3R,6S,7S,8aS)-6-(4-methoxyphenyl)-2,3,7-trimethyl-1,4-dioxooctahydropyrrolo[1,2-a]pyrazine-7-carbonitrile

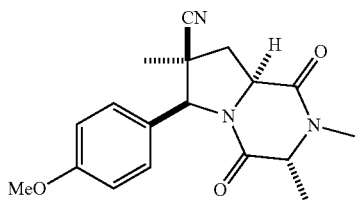 [SMILES: COc1ccc([C@@H]2N3C(=O)[C@@H](C)N(C)C(=O)[C@@H]3C[C@]2(C)C#N)cc1]

¹H-NMR (500 MHz, CDCl₃): δ/ppm 7.05 (2H, d, J=8.5 Hz), 6.88 (2H, d, J=8.5 Hz), 4.88 (1H, s), 4.39 (1H, dd, J=6.5, 11.5 Hz), 3.90 (1H, q, J=7.5 Hz), 3.79 (3H, s), 3.05 (3H, s), 2.80 (1H, app t, J=12.0 Hz), 2.46 (1H, dd, J=6.5, 8.5 Hz), 1.70 (3H, s), 1.48 (3H, d, J=7.5 Hz); ¹³C-NMR (125 MHz, CDCl₃): δ/ppm 166.6 (C), 166.2 (C), 159.9 (C), 128.9 (C), 127.2 (2CH), 119.9 (C), 114.4 (2CH), 69.3 (CH), 60.9 (CH), 56.1 (CH), 55.2 (CH₃), 42.6 (C), 36.6 (CH₂), 32.1 (CH₃), 25.1 (CH₃), 15.3 (CH₃). IR (film): v/cm⁻¹ 2981, 2919, 2852, 2246, 1673, 1490, 1303, 1235, 1093, 756. HR-MS (ESI) calculated for C₁₈H₂₁N₃O₃Na: 350.1475 (M+Na⁺), found: 350.1465.

Rac-(3R,6S,7S,8aS)-6-(benzo[d][1,3]dioxol-5-yl)-3-ethyl-2,7-dimethyl-1,4-dioxo-octahydropyrrolo[1,2-a]pyrazine-7-carbonitrile

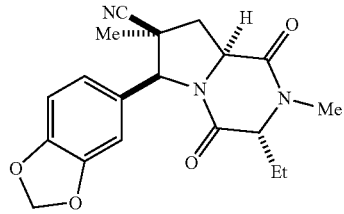

Chemical Formula: C₁₉H₂₁N₃O₄
Exact Mass: 355.1532
Molecular Weight: 355.3940

Prepared from the corresponding pyrrolidine ester and 2-chlorobutanoyl chloride by conducting the reaction with methylamine at 60° C. overnight. Isolated as a 9:1 mixture of diastereomers; NMR data for the major isomer is reported. ¹H-NMR (600 MHz, CDCl₃) δ 6.79 (d, J=8.0 Hz, 1H), 6.63 (dd, J=8.0, 1.9 Hz, 1H), 6.56 (t, J=1.9 Hz, 1H), 5.96 (s, 2H), 4.83 (s, 1H), 4.41 (dd, J=8.0, 1.9 Hz, 1H), 3.77 (dd, J=7.5, 6.3 Hz, 1H), 3.08 (s, 3H), 2.76 (dd, J=13.0, 11.7 Hz, 1H), 2.45 (dd, J=13.2, 6.7 Hz, 1H), 1.95-1.92 (m, 1H), 1.91-1.85 (m, 1H), 1.66 (s, 3H), 1.07 (t, J=7.4 Hz, 3H) ppm; ¹³C-NMR (126 MHz, CDCl₃) δ 166.4 (C), 166.2 (C), 148.4 (C), 148.3 (C), 131.0 (C), 120.0 (CH), 119.9 (C), 108.8 (CH), 106.3 (CH), 101.6 (CH₂), 69.9 (CH), 66.8 (CH), 56.3 (CH), 42.7 (C), 37.0 (CH₂), 33.5 (CH₃), 25.4 (CH₃), 24.4 (CH₂), 10.6 (CH₃) ppm; IR (film) v/cm⁻¹ 2929, 2245, 1672, 1491, 1446, 1402, 1246, 1038, 916, 821, 730 cm⁻¹; HRMS (ESI) calcd for C₁₉H₂₁N₃O₄Na⁺ (M+Na) 378.1430, found 378.1433.

Rac-(3R,6S,7S,8aS)-2-allyl-6-(benzo[d][1,3]dioxol-5-yl)-3,7-dimethyl-1,4-dioxo-octahydropyrrolo[1,2-a]pyrazine-7-carbonitrile

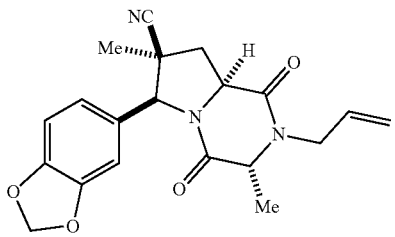

Chemical Formula: C₂₀H₂₁N₃O₄
Exact Mass: 367.1532
Molecular Weight: 367.4050

The cyclization to the diketopiperazine was performed in a THF/H₂O (1:1) solvent mixture at 80° C., overnight. ¹H-NMR (600 MHz, CDCl₃) δ 6.80-6.78 (m, 1H), 6.63-6.61 (m, 1H), 6.56 (d, J=1.6 Hz, 1H), 5.98-5.96 (m, 2H), 5.81-5.74 (m, 1H), 5.27 (dd, J=10.2, 1.1 Hz, 1H), 5.24 (dd, J=17.0, 1.1 Hz, 1H), 4.84 (s, 1H), 4.50 (ddt, J=15.3, 5.3, 1.4 Hz, 1H), 4.41 (dd, J=11.7, 6.7 Hz, 1H), 3.97 (q, J=7.4 Hz, 1H), 3.68 (dd, J=15.2, 6.8 Hz, 1H), 2.82 (dd, J=13.3, 11.5 Hz, 1H), 2.46 (dd, J=13.3, 6.8 Hz, 1H), 1.68 (s, 3H), 1.48 (d, J=7.4 Hz, 3H) ppm; $^{13}$C-NMR (126 MHz, CDCl$_3$) δ 167.0 (C), 166.1 (C), 148.4 (C), 148.3 (C), 131.8 (CH), 131.0 (C), 119.9 (CH), 119.3 (CH$_2$), 108.8 (CH), 106.3 (CH), 101.6 (CH$_2$), 69.6 (CH), 58.2 (CH), 56.3 (CH), 54.7 (C), 47.1 (CH$_2$), 42.8 (C), 36.7 (CH$_2$), 25.4 (CH$_3$), 16.0 (CH$_3$) ppm; IR (film) v/cm$^{-1}$ 2924, 2853, 2244, 1674, 1505, 1448, 1427, 1294, 1246, 1184, 1101, 1038, 933, 859, 809, 735 cm$^{-1}$; HRMS (ESI) calcd for C$_{20}$H$_{21}$N$_3$O$_4$Na$^+$ (M+Na) 390.1430, found 390.1438.

Rac-(3R,6S,7S,8aS)-6-(benzo[d][1,3]dioxol-5-yl)-2-cyclopropyl-3,7-dimethyl-1,4-dioxooctahydropyrrolo[1,2-a]pyrazine-7-carbonitrile

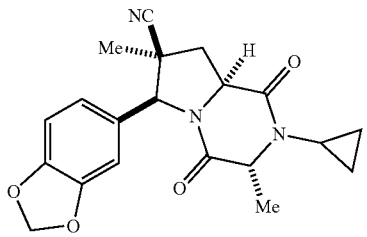

Chemical Formula: C$_{20}$H$_{21}$N$_3$O$_4$
Exact Mass: 367.1532
Molecular Weight: 367.4050

Cyclization to the diketopiperazine was performed using cyclopropylamine (3.5 equiv) in a THF/H$_2$O (1:1) solvent mixture that was heated from 80-100° C. over 2 d. $^1$H-NMR (500 MHz, CDCl$_3$) δ 6.76 (d, J=8.0 Hz, 1H), 6.56 (d, J=8.0 Hz, 1H), 6.47 (s, 1H), 5.95 (s, 2H), 4.80 (s, 1H), 4.38 (dd, J=11.3, 6.7 Hz, 1H), 3.98 (q, J=7.3 Hz, 1H), 2.74-2.69 (m, 2H), 2.45 (dd, J=13.3, 6.7 Hz, 1H), 1.65 (s, 3H), 1.49 (d, J=7.3 Hz, 3H), 1.09 (dq, J=9.5, 6.6 Hz, 1H), 0.88-0.83 (m, 1H), 0.79 (dq, J=9.5, 6.5 Hz, 1H), 0.58 (dq, J=10.4, 5.2 Hz, 1H) ppm; $^{13}$C-NMR (126 MHz, CDCl$_3$) δ168.2 (C), 167.2 (C), 148.3 (C), 148.2 (C), 130.9 (C), 119.9 (CH), 119.8 (CH), 108.7 (CH), 106.1 (CH), 101.5 (CH$_2$), 69.4 (CH), 59.8 (CH), 56.7 (CH), 42.7 (C), 36.7 (CH$_2$), 28.0 (CH), 25.2 (CH$_3$), 16.2 (CH$_3$), 8.7 (CH$_2$), 5.7 (CH$_2$) ppm; IR (film) v/cm$^{-1}$ 2984, 1675, 1490, 1424, 1376, 1245, 1189, 1036, 932, 733 cm$^{-1}$; HRMS (ESI) calcd for C$_{20}$H$_{21}$N$_3$O$_4$Na$^+$ (M+Na) 390.1430, found 390.1433.

Rac-(3R,6S,7S,8aS)-6-(3,4-bis(allyloxy)phenyl)-2,3,7-trimethyl-1,4-dioxooctahydro-pyrrolo[1,2-a]pyrazine-7-carbonitrile

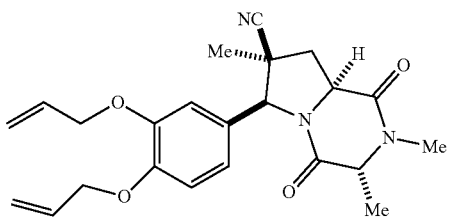

Chemical Formula: C$_{23}$H$_{27}$N$_3$O$_4$
Exact Mass: 409.2002
Molecular Weight: 409.4860

$^1$H-NMR (500 MHz, CDCl$_3$) δ 6.86 (d, J=8.2 Hz, 1H), 6.65-6.63 (m, 2H), 6.09-6.01 (m, 2H), 5.39 (dd, J=17.2 Hz, 1.1 Hz, 1H), 5.37 (dd, J=17.3 Hz, 1.2 Hz, 1H), 5.26 (app. dt, J=10.6, 0.2 Hz, 2H), 4.85 (s, 1H), 4.60-4.57 (m, 4H), 4.37 (dd, J=11.3, 6.8 Hz, 1H), 3.91 (q, J=7.2 Hz, 1H), 3.06 (s, 3H), 2.78 (app t, J=12.2 Hz, 1H), 2.44 (dd, J=13.3, 6.8 Hz, 1H), 1.68 (s, 3H), 1.49 (d, J=7.2 Hz, 3H) ppm; $^{13}$C-NMR (126 MHz, CDCl$_3$) δ166.8 (C), 166.3 (C), 149.2 (C), 148.7 (C), 133.4 (CH), 133.4 (CH), 129.6 (C), 119.9 (C), 118.7 (CH), 117.9 (CH$_2$), 117.9 (CH$_2$), 113.9 (CH), 112.4 (CH), 70.2 (CH$_2$), 69.9 (CH$_2$), 69.5 (CH), 61.1 (CH), 56.2 (CH), 42.7 (C), 36.7 (CH$_2$), 32.3 (CH$_3$), 25.3 (CH$_3$), 15.4 (CH$_3$) ppm; IR (film) v/cm$^{-1}$ 2983, 1672, 1515, 1451, 1426, 1306, 1259, 1224, 1206, 1139, 1017, 996, 924, 806, 732 cm$^{-1}$; HRMS (ESI) calcd for C$_{23}$H$_{27}$N$_3$O$_4$Na$^+$ (M+Na) 432.1899, found 432.1888.

Rac-(3R,6S,7S,8aS)-6-(7-methoxybenzo[d][1,3]dioxol-5-yl)-2,3,7-trimethyl-1,4-dioxooctahydropyrrolo[1,2-a]pyrazine-7-carbonitrile

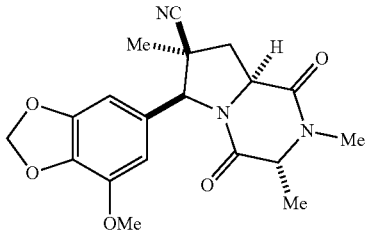

Chemical Formula: C$_{19}$H$_{21}$N$_3$O$_5$
Exact Mass: 371.1481
Molecular Weight: 371.3930

Isolated as an 8:1 mixture of diasteromers; NMR data for the major isomer is reported. $^1$H-NMR (500 MHz, CDCl$_3$) δ 6.34 (s, 1H), 6.24 (s, 1H), 5.97 (s, 2H), 4.81 (s, 1H), 4.36 (dd, J=11.3, 6.6 Hz, 1H), 3.92 (q, J=7.3 Hz, 1H), 3.89 (s, 3H), 3.05 (s, 3H), 2.78 (app. t, J=12.4 Hz, 1H), 2.46 (dd, J=13.3, 6.6 Hz, 1H), 1.68 (s, 3H), 1.49 (d, J=7.3 Hz, 3H) ppm; $^{13}$C-NMR (126 MHz, CDCl$_3$) δ166.9 (C), 166.2 (C), 149.5 (C), 143.8 (C), 135.9 (C), 131.6 (C), 119.9 (C), 107.0 (CH), 102.0 (CH$_2$), 99.7 (CH), 69.8 (CH), 61.0 (CH), 56.8 (CH$_2$), 56.3 (CH), 42.8 (C), 36.8 (CH$_2$), 32.3 (CH$_3$), 25.4 (CH$_3$), 15.5 (CH$_3$) ppm; IR (film) v/cm$^{-1}$ 2981, 1143, 1673, 1512, 1452, 1433, 1402, 1324, 1240, 1199, 1135, 1093, 1043, 927, 735 cm$^{-1}$; HRMS (ESI) calcd for C$_{19}$H$_{21}$N$_3$O$_5$Na$^+$ (M+Na) 394.1379, found 394.1371.

Rac-(3R,6S,7S,8aS)-6-(2,3-dihydro-1H-inden-5-yl)-2,3,7-trimethyl-1,4-dioxooctahydro-pyrrolo[1,2-a]pyrazine-7-carbonitrile

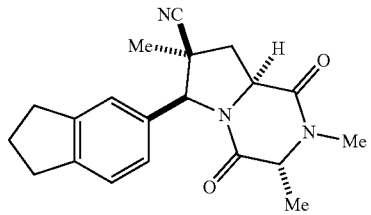

Chemical Formula: $C_{20}H_{23}N_3O_2$
Exact Mass: 337.1790
Molecular Weight: 337.4230

$^1$H-NMR (500 MHz, CDCl$_3$) □ 7.19 (d, J=7.7 Hz, 1H), 6.96 (s, 1H), 6.93 (d, J=7.7 Hz, 1H), 4.89 (s, 1H), 4.38 (dd, J=11.6, 6.7 Hz, 1H), 3.91 (q, J=7.3 Hz, 1H), 3.07 (s, 3H), 2.90-2.80 (m, 5H), 2.45 (dd, J=13.3, 6.6 Hz, 1H), 2.05 (app. quintet, J=7.5 Hz, 2H), 1.69 (s, 3H), 1.49 (d, J=7.3 Hz, 3H) ppm; $^{13}$C-NMR (126 MHz, CDCl$_3$) δ166.8 (C), 166.3 (C), 145.5 (C), 145.2 (C), 134.8 (C), 125.0 (CH), 123.9 (CH), 122.1 (CH), 120.1 (C), 70.1 (CH), 61.0 (CH), 56.3 (CH), 42.8 (C), 36.8 (CH$_2$), 33.0 (CH$_2$), 32.8 (CH$_2$), 32.2 (CH$_3$), 25.4 (CH$_3$), 25.4 (CH$_2$), 15.5 (CH$_2$) ppm; IR (film) v/cm$^{-1}$ 1940, 1673, 1431, 1402, 1306, 1239, 1062, 814, 733 cm$^{-1}$; HRMS (ESI) calcd for $C_{20}H_{23}N_3O_2Na^+$ (M+Na) 360.1688, found 360.1684.

Rac (3R,6S,7S,8aS)-2,3,7-trimethyl-1,4-dioxo-6-(1-(phenylsulfonyl)-1H-indol-3-yl)octahydropyrrolo[1,2-a]pyrazine-7-carbonitrile

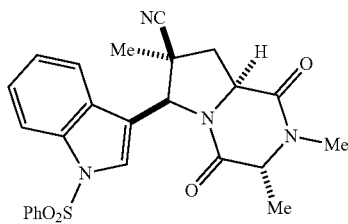

Chemical Formula: $C_{25}H_{24}N_4O_4S$
Exact Mass: 476.1518
Molecular Weight: 476.5510

Isolated as an 7:1 mixture of diasteromers; NMR data for the major isomer is reported. $^1$H-NMR (500 MHz, CDCl$_3$) δ 7.89 (d, J=8.2 Hz, 1H), 7.77 (d, J=7.5 Hz, 2H), 7.51 (app. t, J=7.3 Hz, 1H), 7.46-7.39 (m, 4H), 7.31 (app. t, J=7.3 Hz, 1H), 7.25 (app. t, J=7.3 Hz, 1H), 5.18 (s, 1H), 4.40 (dd, J=12.4, 6.3 Hz, 1H), 3.92 (q, J=7.4 Hz, 1H), 3.09 (s, 3H), 2.83 (app. t, J=11.9 Hz, 1H), 2.57 (dd, J=13.3, 6.3 Hz, 1H), 1.73 (s, 3H), 1.49 (s, 3H) ppm; $^{13}$C-NMR (126 MHz, CDCl$_3$) δ166.7 (C), 166.0 (C), 137.9 (C), 135.4 (C), 134.1 (CH), 129.5 (CH), 126.8 (CH), 125.6 (CH), 124.1 (CH), 123.9 (CH), 119.9 (CH), 119.6 (C), 119.5 (C), 119.4 (C), 114.1 (CH), 62.4 (CH), 60.9 (CH), 56.2 (CH), 42.2 (C), 38.1 (CH$_2$), 32.3 (CH$_3$), 25.1 (CH$_3$), 15.7 (CH$_3$) ppm; IR (film) v/cm$^{-1}$ 2982, 1675, 1448, 1367, 1307, 1175, 1124, 1095, 977, 748, 725 cm$^{-1}$; HRMS (ESI) calcd for $C_{25}H_{24}N_4O_4SNa^+$ (M+Na) 499.1416, found 499.1412.

Alternate Procedure for Forming Diketopiperazines from Substituted Prolidine Esters and Protected α-Amino Acids.

Rac-(3R,6S,7S,8aS)-6-(benzo[d][1,3]dioxol-5-yl)-3-benzyl-2,7-dimethyl-1,4-dioxooctahydropyrrolo[1,2-a]pyrazine-7-carbonitrile

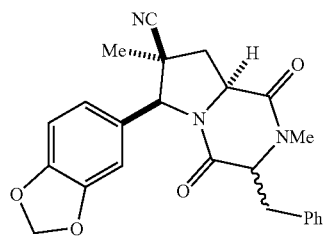

Chemical Formula: $C_{24}H_{23}N_3O_4$
Exact Mass: 417.1689
Molecular Weight: 417.4650

To a solution of N-Boc-phenylalanine (263 mg, 1.00 mmol, 1.5 equiv) in dry CH$_2$Cl$_2$ (2 mL) at 0° C. was added N,N-diisopropylethylamine (0.12 mL, 0.66 mmol, 1 equiv) and BOPCl (253 mg, 1.00 mmol, 1.5 equiv) and the reaction was allowed to warm to room temperature over 1 h. After recooling to 0° C. additional N,N-diisopropylethylamine (0.23 mL, 1.3 mmol, 2 equiv) was added, followed by the dropwise addition of a solution of the corresponding pyrrolidine ester (200 mg, 0.66 mmol, 1 equiv) in CH$_2$Cl$_2$ (1.3 mL). The reaction was allowed to warm to room temperature overnight, after which time TLC analysis showed full conversion of the starting material. After an extractive work-up (CH$_2$Cl$_2$/water), the crude product was filtered through a silica gel plug using hexanes/ethyl acetate (1:1) as the eluent and the volatiles were removed in vacuo. The crude acylated pyrrolidine ester was dissolved in dry CH$_2$Cl$_2$ (2.1 mL) and cooled to 0° C. Trifluoroacetic acid (0.8 mL) was added, the reaction allowed to warm to rt over 3 h, and the volatiles were removed under reduced pressure. The resulting residue was dissolved in a 4:1 mixture i-BuOH/toluene (18 mL) containing N,N-diisopropylethylamine (0.46 mL, 2.65 mmol, 4 equiv). The vial was sealed with a teflon cap and heated to 100° C. overnight. After an extractive work up (CH$_2$Cl$_2$/water) and concentration, two diastereomeric DKPs were separated by silica gel chromatography (eluent: hexanes/EtOAc 1:3).

NMR data for diastereomer A: $^1$H-NMR (600 MHz, CDCl$_3$) δ 7.38-7.35 (m, 3H), 7.26-7.25 (m, 2H), 7.00 (d, J=3.7 Hz, 1H), 6.78 (d, J=8.0 Hz, 1H), 6.63 (d, J=7.2 Hz, 1H), 6.55 (s, 1H), 5.92 (s, 2H), 4.71 (s, 1H), 4.29 (app. q, J=4.2 Hz, 1H), 3.31 (dd, J=13.9, 4.6 Hz, 1H), 2.95 (dd, J=13.9, 4.4 Hz, 1H), 2.64 (dd, J=11.9, 6.2 Hz, 1H), 2.44 (app. t, J=12.5 Hz, 1H), 2.05 (dd, J=13.0, 6.3 Hz, 1H), 1.32 (s, 3H) ppm. NMR data for diastereomer B: $^1$H-NMR (600 MHz, CDCl$_3$) δ 7.37-7.34 (m, 2H), 7.32-7.29 (m, 1H), 7.22-7.19 (m, 2H), 6.81 (d, J=8.0 Hz, 1H), 6.64 (dd, J=8.8, 1.7 Hz, 1H), 6.60 (d, J=1.8 Hz, 1H), 6.00 (d, J=1.5 Hz, 1H), 5.99 (d, J=1.5 Hz, 1H), 5.69 (broad s, 1H), 4.91 (s, 1H), 4.40 (dd, J=11.3, 6.9 Hz, 1H), 4.32 (dd, J=10.2, 4.2 Hz, 1H), 3.51 (dd, J=14.7, 3.9 Hz, 1H), 2.79 (dd, J=11.5, 4.1 Hz, 1H), 2.77 (dd, J=10.3, 4.4 Hz, 1H), 2.40 (dd, J=13.4, 6.8 Hz, 1H), 1.68 (s, 3H) ppm.

Both DKP products were individually methylated in a separate reaction vessel by the following procedure: To the intermediate DKP (91 mg, 0.23 mmol, 1 equiv) in acetone (2.8 mL) was added $K_2CO_3$ (620 mg, 4.5 mmol, 20 equiv) and MeI (1.4 mL, 23 mmol, 100 equiv) and the reaction was stirred for 2 d at room temperature with the exclusion of light. After an extractive work up ($CH_2Cl_2$/water), each diasteromeric DKP was obtained as amorphous solid.

Diastereomer A: $^1$H-NMR (500 MHz, $CDCl_3$) δ 7.34-7.31 (m, 3H), 7.18-7.13 (m, 2H), 6.77 (d, J=7.8 Hz, 1H), 6.59 (d, J=7.8 Hz, 1H), 6.51 (s, 1H), 5.95 (s, 2H), 4.65 (s, 1H), 4.18 (t, J=4.1 Hz, 1H), 3.28 (dd, J=14.1, 3.9 Hz, 1H), 3.14-3.10 (m, 4H), 2.40-2.39 (m, 2H), 2.04-2.01 (m, 1H), 1.26 (s, 3H) ppm; $^{13}$C-NMR (126 MHz, $CDCl_3$) δ166.5 (C), 165.5 (C), 148.3 (C), 148.2 (C), 135.4 (C), 131.1 (C), 129.9 (CH), 129.2 (CH), 128.1 (CH), 120.0 (C), 119.9 (CH), 108.8 (CH), 106.1 (CH), 101.5 ($CH_2$), 69.5 (CH), 66.4 (CH), 55.4 (CH), 42.3 (C), 36.8 ($CH_2$), 36.4 ($CH_2$), 32.4 ($CH_3$), 24.8 ($CH_3$) ppm; IR (film) v/cm$^{-1}$ 2934, 2247, 1673, 1505, 1491, 1446, 1403, 1304, 1247, 1102, 1053 cm$^{-1}$; HRMS (ESI) calcd for $C_{24}H_{23}N_3O_4Na^+$ (M+Na) 440.1586, found 440.1580. Diastereomer B: $^1$H-NMR (500 MHz, $CDCl_3$) δ 7.26-7.19 (m, 3H), 7.14-7.11 (m, 2H), 6.76 (d, J=8.0 Hz, 1H), 6.55 (d, J=8.4 Hz, 1H), 6.52 (s, 1H), 5.99-5.96 (m, 2H), 4.82 (s, 1H), 4.43 (t, J=5.2 Hz, 1H), 4.37 (dd, J=11.3, 6.8 Hz, 1H), 3.48 (dd, J=16.0, 5.6 Hz, 1H), 3.42 (dd, J=16.0, 5.5 Hz, 1H), 3.04 (s, 3H), 2.81 (dd, J=13.1, 11.5 Hz, 1H), 2.46 (dd, J=13.4, 6.6 Hz, 1H), 1.66 (s, 3H) ppm; $^{13}$C-NMR (126 MHz, $CDCl_3$) δ168.1 (C), 165.8 (C), 148.3 (2×C), 136.5 (C), 130.8 (C), 129.0 (CH), 128.8 (CH), 127.1 (CH), 120.1 (C), 120.0 (CH), 108.8 (CH), 106.7 (CH), 101.2 ($CH_2$), 69.8 (CH), 61.3 (CH), 57.4 (CH), 42.8 (C), 37.0 ($CH_2$), 33.5 ($CH_2$), 30.9 ($CH_3$), 25.6 ($CH_3$) ppm; IR (film) v/cm$^{-1}$ 1675, 1504, 1491, 1448, 1390, 1306, 1244, 1039, 912, 733, 700 cm$^{-1}$; HRMS (ESI) calcd for $C_{24}H_{23}N_3O_4Na^+$ (M+Na) 440.1586, found 440.1577.

Example 4

General Procedure for Synthesis of Epidithiodiketopiperazines.

Methyl Rac-(3S,6S,7S,8aS)-6-(4-fluorophenyl)-2,3,7-trimethyl-1,4-dioxohexahydro-6H-3,8a-epidithiopyrrolo[1,2-a]pyrazine-7-carboxylate

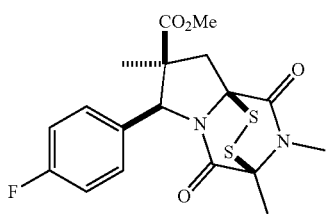

Chemical Formula: $C_{18}H_{19}FN_2O_4S_2$
Exact Mass: 410.0770

To a suspension of elemental sulfur (32 mg, 1.0 mmol) in dry THF (5 mL) was added a solution of NaHMDS (0.25 mL, 2 M in THF) at room temperature. After 1 min, a solution of the diketopiperazine (35 mg, 0.1 mmol, in 2 mL THF) was added, followed by a second aliquot of NaHMDS (0.25 mL, 2 M in THF) within another 2 min. The resulting orange-brown solution was stirred for 30 min at rt, cooled to 0° C. and quenched by addition of aqueous $NH_4Cl$. After extractive work-up ($CH_2Cl_2$/water) and evaporation of the solvent, a yellow residue was obtained. This residue was re-dissolved in a mixture of MeOH/THF (5 mL) to which $NaBH_4$ (350 mg, 1 mmol) was added portionwise at 0° C. After stirring for 30 min, this mixture was quenched with aqueous $NH_4Cl$, extracted ($CH_2Cl_2$/water) and the extract was dried over $Na_2SO_4$. After evaporation of the solvent, a yellow residue was obtained, which was subsequently dissolved in EtOAc (10 mL). A solution of $KI_3$ (0.5 M, 2 mL) in water was added and the biphasic system was stirred at rt for 15 min, after which time 3 mL of saturated aqueous $Na_2S_2O_3$ was added to give a pale yellow EtOAc layer. Aqueous extraction and evaporation of the organic phase gives a yellow oil, which was purified by preparative TLC ($Et_2O/CH_2Cl_2$) to give the title compound as a yellow oil.

$^1$H-NMR (500 MHz, $CDCl_3$): δ/ppm 7.41 (2H, m), 7.03 (2H, t, J=9.0 Hz), 5.09 (1H, s), 3.36 (3H, s), 3.34 (1H, d, J=14.5 Hz), 3.25 (1H, d, J=14.5 Hz), 3.11 (3H, s), 1.97 (3H, s), 1.55 (3H, s); $^{13}$C-NMR (125 MHz, $CDCl_3$): δ/ppm 171.89 (C), 166.2 (C), 163.1 (C), 162.6 (C, d, J=250 Hz), 131.8 (C), 129.4 (2CH, d, J=8 Hz), 115.5 (2CH, d, J=22 Hz), 74.6 (C), 73.4 (C), 72.4 (CH), 55.1 (C), 52.3 ($CH_3$), 38.9 ($CH_2$), 27.8 ($CH_3$), 25.5 ($CH_3$), 18.4 ($CH_3$). IR (film): v/cm$^{-1}$ 2951, 1736, 1692, 1606, 1511, 1255, 1228, 1161, 1129, 848, 733. LR-MS: 432.85 (M+Na$^+$); HR-MS (ESI) calculated for $C_{18}H_{19}N_2O_4FS_2Na$: 433.0668, found: 433.0660.

Example 5

Alternate Simplified General Procedure for Synthesis of Epidithiodiketopiperazines.

Rac-(3S,6S,7S,8aS)-6-(benzo[d][1,3]dioxol-5-yl)-3-ethyl-2,7-dimethyl-1,4-dioxo-hexahydro-6H-3,8a-epidithiopyrrolo[1,2-a]pyrazine-7-carbonitrile To a suspension of $S_8$ (83 mg, 0.32 mmol) in dry THF (3.4 mL) was added a solution of NaHMDS (1.7 mL, 0.93 mmol, 3.3 equiv, 0.56 M in toluene) at room temperature over 40 sec. After 1 min, a solution of the diketopiperazine (100 mg, 0.28 mmol, in 2.6 mL THF) was added dropwise, followed by a second aliquot of NaHMDS (1.1 mL, 0.62 mmol, 2.2 equiv, 0.56 M in toluene) within another 30-40 sec. The resulting orange-yellow solution was stirred for 50 min at rt and quenched by addition of saturated aqueous $NH_4Cl$. After extractive work-up ($CH_2Cl_2$/water) and evaporation of the solvent, a yellow-brown amorphous residue was obtained. This residue was evaporated onto 2.2 g $SiO_2$ and placed on top of a filter frit containing 12 g $SiO_2$. Washing of this $SiO_2$ plug with 150 mL of hexanes removes the majority of HMDS-related material. Subsequent washing with 150 mL of MeCN elutes the sulfidated products as a mixture of epidi- and epitrisulfide products (epidi:epitri usually ~9:1). These products were separated by preparative TLC (2-4% EtOAc/$CH_2Cl_2$). The desired epidisulfide product ($R_f$~0.3) was isolated as an off-white solid (purity 95%) after removal of the volatiles in vacuo.

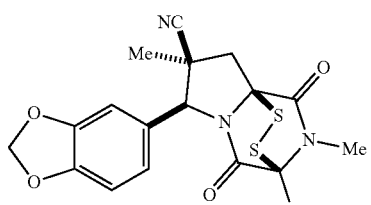

Chemical Formula: C$_{19}$H$_{19}$N$_3$O$_4$S$_2$
Exact Mass: 417.0817
Molecular Weight: 417.4980

$^1$H-NMR (600 MHz, CDCl$_3$) δ 6.88 (s, 1H), 6.84 (app. s, 2H), 5.99 (app. m, 2H), 4.83 (s, 1H), 3.28 (d, J 15.0 Hz, 1H), 3.10 (s, 3H), 3.01 (d, J=15.0 Hz, 1H), 2.39 (m, 1H), 2.30 (m, 1H), 1.68 (s, 3H), 1.25 (t, J=7.2 Hz, 3H) ppm; $^{13}$C-NMR (126 MHz, CDCl$_3$) δ 166.6 (C), 161.0 (C), 148.6 (C), 148.3 (C), 127.5 (C), 120.8 (CH), 120.4 (C), 108.6 (CH), 107.3 (CH), 101.6 (CH$_2$), 78.0 (C), 73.5 (C), 72.6 (CH), 44.5 (C), 42.9 (CH$_2$), 28.8 (CH$_3$), 25.4 (CH$_2$), 24.9 (CH$_3$), 9.9 (CH$_3$) ppm; IR (film) v/cm$^{-1}$ 2917, 1685, 1558, 1506, 1491, 1357, 1249, 1001, 928 cm$^{-1}$; HRMS (ESI) calcd for C$_{19}$H$_{19}$N$_3$O$_4$S$_2$Na$^+$ (M+Na) 440.0715, found 440.0718.

At the end of the concentration process, MeOH (1-2 mL) and CH$_2$Cl$_2$ (1-2 mL) can be added and then again removed in vacuo to facilitate the formation of a colorless powder. In other cases, the epidi- and epitrisulfide products can be separated by column chromatography on silica gel using a mixtures of CH$_2$Cl$_2$ and EtOAc as the eluent. Generally either of the two procedures described above can be used to prepare the epidithiodiketopiperazine products.

tert-Butyl Rac-(3S,6S,7S,8aS)-6-(4-fluorophenyl)-2,3,7-trimethyl-1,4-dioxohexahydro-6H-3,8a-epidithiopyrrolo[1,2-a]pyrazine-7-carboxylate

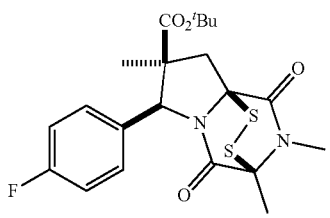

Chemical Formula: C$_{21}$H$_{25}$FN$_2$O$_4$S$_2$
Exact Mass: 452.1240

$^1$H-NMR (500 MHz, CDCl$_3$): δ/ppm 7.52-7.55 (2H, m), 7.09 (2H, t, J=8.5 Hz), 5.04 (1H, s), 3.36 (1H, d, J=14.5 Hz), 3.31 (1H, d, J=14.5 Hz), 3.14 (3H, s), 1.99 (3H, s), 1.56 (3H, s), 1.17 (9H, s); $^{13}$C-NMR (125 MHz, CDCl$_3$): δ/ppm 170.4 (C), 166.3 (C), 163.0 (C), 161.7 (C, d, J=247 Hz), 132.3 (C), 130.4 (2CH, d, J=8 Hz), 115.5 (2CH, d, J=22 Hz), 82.2 (C), 74.4 (C), 73.5 (C), 72.2 (CH), 55.0 (C), 39.4 (CH$_2$), 27.8 (CH$_3$), 27.5 (3CH$_3$), 26.6 (CH$_3$), 18.3 (CH$_3$). IR (film): v/cm$^{-1}$ 2977, 2935, 1693, 1511, 1367, 1310, 1229, 1132, 847. LR-MS: 475.1 (M+Na); HR-MS (ESI) calculated for C$_{21}$H$_{25}$N$_2$O$_4$FS$_2$Na: 475.1137, found: 475.1132.

Methyl Rac-(3S,6S,7S,8aS)-6-(benzo[d][1,3]dioxol-5-yl)-2,3,7-trimethyl-1,4-dioxohexahydro-6H-3,8a-epidithiopyrrolo[1,2-a]pyrazine-7-carboxylate

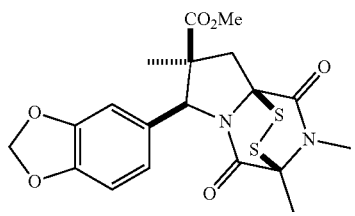

Chemical Formula: C$_{19}$H$_{20}$N$_2$O$_6$S$_2$
Exact Mass: 436.0763

$^1$H-NMR (500 MHz, CDCl$_3$): δ/ppm 6.98 (1, s), 6.87 (1H, d, J=8.0 Hz), 6.76 (1H, d, J=8.0 Hz), 5.96 (2H, s), 5.03 (1H, s), 3.42 (3H, s), 3.34 (1H, d, J=14.0 Hz), 3.22 (1H, d, J=14.0 Hz), 3.10 (3H, s), 1.96 (3H, s), 1.52 (3H); $^{13}$C-NMR (125 MHz, CDCl$_3$): δ/ppm 171.6 (C), 166.3 (C), 163.1 (C), 147.9 (C), 147.6 (C), 129.6 (C), 121.3 (CH), 108.2 (CH), 108.0 (CH), 101.3 (CH$_2$), 74.6 (C), 73.4 (C), 72.9 (CH), 55.1 (C), 52.3 (CH$_3$), 38.8 (CH$_2$), 27.8 (CH$_3$), 25.4 (CH$_3$), 18.4 (CH$_3$). IR (film): v/cm$^{-1}$ 2953, 1736, 1692, 1490, 1447, 1356, 1250, 1038. LR-MS: 459.2 M+Na$^+$; HR-MS (ESI) calculated for C$_{19}$H$_{20}$N$_2$O$_6$S$_2$Na: 459.0660, found: 459.0652.

Methyl Rac-(3S,6S,7S,8aS)-6-(5-bromo-2-methoxyphenyl)-2,3,7-trimethyl-1,4-dioxohexahydro-6H-3,8a-epidithiopyrrolo[1,2-a]pyrazine-7-carboxylate

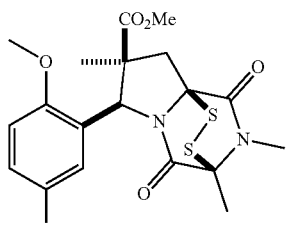

Chemical Formula: C$_{19}$H$_{21}$BrN$_2$O$_5$S$_2$
Exact Mass: 500.0075

$^1$H-NMR (500 MHz, CDCl$_3$): δ/ppm 7.54 (1H, s), 7.34 (1H, d, J=9.0 Hz), 6.70 (1H, d, J=9.0 Hz), 5.52 (11, s), 3.78 (3H, s), 3.33 (3H, s), 3.26 (11, d, J=14.5 Hz), 3.21 (1H, d, J=14.5 Hz), 3.09 (3H, s), 1.96 (3H, s), 1.52 (3H, s); $^{13}$C-NMR (125 MHz, CDCl$_3$): δ/ppm 171.7 (C), 166.3 (C), 162.8 (C), 155.5 (C), 132.1 (CH), 130.9 (CH), 126.9 (C), 113.2 (C), 111.8 (CH), 74.8 (C), 73.3 (C), 67.2 (CH), 55.7 (CH$_3$), 54.4 (C), 52.2 (CH$_3$), 40.6 (CH$_2$), 27.8 (CH$_3$), 25.0 (CH$_3$), 18.4 (CH$_3$). IR (film): v/cm$^{-1}$ 2939, 1734, 1692, 1489, 1356, 1253, 1129, 1028, 914. LR-MS: 523.2 (M+Na$^+$); HR-MS (ESI) calculated for C$_{19}$H$_{21}$N$_2$O$_5$S$_2$BrNa: 522.9973 (M+Na$^+$), found: 522.9972.

267

Methyl Rac-(3S,6S,7S,8aS)-2,3,7-trimethyl-1,4-dioxo-6-(pyridin-3-yl)hexahydro-6H-3,8a-epidithiopyrrolo[1,2-a]pyrazine-7-carboxylate

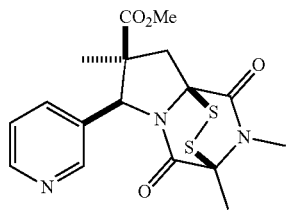

Chemical Formula: $C_{17}H_{19}N_3O_4S_2$
Exact Mass: 393.0817

Isolated as a 4:1 mixture of diastereomers, data for the major isomer is reported. $^1$H-NMR (500 MHz, CDCl$_3$): δ/ppm 8.63 (1H, d, J=2.0 Hz), 8.54 (1H, dd, J=2.0, 5.0 Hz), 7.81 (1H, d, J=8.0 Hz), 7.27-7.30 (1H, m), 5.10 (1H, s), 3.36 3H, s), 3.25-3.34 (2H, m), 3.10 (3H, s), 1.96 (3H, s), 1.57 (3H, s); $^{13}$C-NMR (125 MHz, CDCl$_3$): δ/ppm 171.4 (C), 166.2 (C), 163.1 (C), 149.8 (CH), 149.2 (CH), 135.1 (CH), 131.8 (C), 123.5 (CH), 74.6 (C), 73.4 (C), 70.5 (CH), 55.1 (C), 52.5 (CH$_3$), 39.1 (CH$_2$), 27.8 (CH$_3$), 25.5 (CH$_3$), 18.3 (CH$_3$). IR (film): v/cm$^{-1}$ 2927, 1735, 1690, 1354, 1309, 1261, 1129, 916. LR-MS: 416.1 (M+Na$^+$); HR-MS (ESI) calculated for $C_{17}H_{19}N_3O_4S_2$Na: 416.0715 (M+Na$^+$), found: 416.0715.

Rac-(3S,6S,7S,8aS,9S)-2,3,7-trimethyl-1,4-dioxo-6-phenylhexahydro-6H-3,8a-epidithiopyrrolo[1,2-a]pyrazine-7-carbonitrile

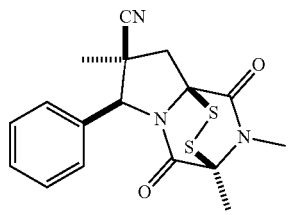

Chemical Formula: $C_{17}H_{17}N_3O_2S_2$
Exact Mass: 359.0762

$^1$H-NMR (500 MHz, CDCl$_3$): δ/ppm 7.46-7.38 (5H, m), 4.91 (1H, s), 3.32 (1H, d, J=14.5 Hz), 3.09 (3H, s), 3.00 (1H, d, J=14.9 Hz), 1.94 (3H, s), 1.69 (3H, s); $^{13}$C-NMR (125 MHz, CDCl$_3$): δ/ppm 165.7 (C), 162.2 (C), 133.8 (C), 129.6 (CH), 129.1 (2CH), 126.9 (2CH), 120.2 (C), 73.4 (C), 72.5 (CH), 44.5 (C), 43.0 (CH$_2$) 29.8 (C), 27.9 (CH$_3$), 24.9 (CH$_3$), 18.2 (CH$_3$); IR (film): v/cm$^{-1}$ 2917, 2849, 2361, 2341, 2241, 1705, 1680; LR-MS: 382.0 [M+Na]$^+$; HR-MS (ESI) calculated for $C_{17}H_{17}N_3O_2S_2$Na: 382.0660, found: 382.0671.

268

Rac (3S,6S,7S,8aS,9S)-6-(4-fluorophenyl)-2,3,7-trimethyl-1,4-dioxohexahydro-6H-3,8a-epidithiopyrrolo[1,2-a]pyrazine-7-carbonitrile

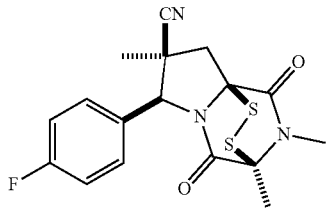

Chemical Formula: $C_{17}H_{16}FN_3O_2S_2$
Exact Mass: 377.0668

$^1$H-NMR (500 MHz, CDCl$_3$): δ/ppm 7.37 (2H, dd, J=5.4, 8.4 Hz), 7.13 (2H, t, J=8.7 Hz), 4.89 (1H, s), 3.31 (1H, d, J=14.7 Hz), 3.08 (3H, s), 2.99 (1H, d, J=15.0 Hz), 1.94 (3H, s), 1.68 (3H, s); $^{13}$C-NMR (125 MHz, CDCl$_3$): δ/ppm 165.6 (C), 163.4 (C, d, J=247 Hz), 162.2 (C), 129.6 (C, d, J=3 Hz), 128.8 (2CH, d, J=8 Hz), 120.2 (C), 116.2 (2CH, d, J=22 Hz), 73.52 (C), 73.46 (C), 71.9 (CH), 44.5 (C), 42.9 (CH$_2$), 27.9 (CH$_3$), 24.7 (CH$_3$), 18.2 (CH$_3$); IR (film): v/cm$^{-1}$ 2991, 2356, 2239, 1706, 1682, 1512; LR-MS: 400.0 [M+Na]$^+$; HR-MS (ESI) calculated for $C_{17}H_{16}FN_3O_2S_2$: 400.0566, found: 400.0582.

Rac-(3S,6S,7S,8aS)-6-(Benzo[d][1,3]dioxol-5-yl)-2,3,7-trimethyl-1,4-dioxohexahydro-6H-3,8a-epidithiopyrrolo[1,2-a]pyrazine-7-carbonitrile

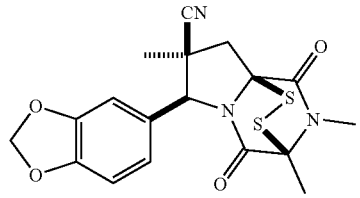

Chemical Formula: $C_{18}H_{17}N_3O_4S_2$
Exact Mass: 403.0660

Major ETP stereoisomer. $^1$H-NMR (500 MHz, CDCl$_3$): δ/ppm 6.96 (1H, s), 6.91 (2H, app. s), 6.06 (2H, s), 4.89 (1H, s), 3.36 (1H, d, J=14.5 Hz), 3.14 (3H, s), 3.06 (1H, d, J=14.5 Hz), 2.00 (3H, s), 1.73 (3H, s); $^{13}$C-NMR (125 MHz, CDCl$_3$): δ/ppm 165.6 (C), 162.1 (C), 148.6 (C), 148.3 (C), 127.5 (C), 120.7 (CH), 120.3 (C), 108.6 (CH), 107.2 (CH), 101.6 (CH$_2$), 73.4 (C), 73.3 (C), 72.4 (CH), 44.4 (C), 42.8 (CH$_2$), 27.8 (CH$_3$), 24.8 (CH$_3$), 18.1 (CH$_3$). IR (film): v/cm$^{-1}$ 2984, 2902, 2250, 1688, 1491, 1446, 1358, 1250, 1038, 731. LR-MS: 426.1 M+Na$^+$; HR-MS (ESI) calculated for $C_{18}H_{17}N_3O_4S_2$Na: 426.0558, found: 426.0555. The constitution and relative configuration of this product was confirmed by single-crystal X-ray analysis.

269

Rac-(3R,6S,7S,8aR)-6-(Benzo[d][1,3]dioxol-5-yl)-2,3,7-trimethyl-1,4-dioxohexahydro-6H-3,8a-epidithiopyrrolo[1,2-a]pyrazine-7-carbonitrile

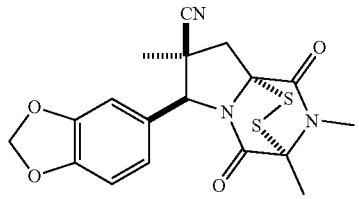

Chemical Formula: $C_{18}H_{17}N_3O_4S_2$
Exact Mass: 403.0660

Minor ETP stereoisomer. $^1$H-NMR (500 MHz, CDCl$_3$): δ/ppm 6.80 (1H, d, J=8.0 Hz), 6.60 (1H, d, J=8.0 Hz), 6.55 (1H, s), 5.99 (2H, s), 5.03 (1H, s), 3.80 (1H, d, J=15.0 Hz), 3.12 (3H, s), 2.51 (1H, d, J=15.0 Hz), 1.99 (3H, s), 1.94 (3H, s); $^{13}$C-NMR (125 MHz, CDCl$_3$): δ/ppm 165.3 (C), 162.4 (C), 148.6 (C), 148.5 (C), 129.4 (C), 120.1 (CH), 119.6 (C), 108.9 (CH), 106.3 (CH), 101.6 (CH$_2$), 73.8 (C), 73.7 (C), 71.6 (CH), 43.8 (C), 42.3 (CH$_2$), 27.9 (CH$_3$), 27.2 (CH$_3$), 18.3 (CH$_3$). IR (film): v/cm$^{-1}$ 2988, 2940, 2900, 2249, 1694, 1504, 1448, 1355, 1248, 1111, 1038, 912, 731. LR-MS: 426.0 M+Na$^+$; HR-MS (ESI) calculated for $C_{18}H_{17}N_3O_4S_2$Na: 426.0558, found: 426.0553.

Rac-(3S,6R,7S,8aS)-6-(5-Bromo-2-methoxyphenyl)-2,3,7-trimethyl-1,4-dioxohexahydro-6H-3,8a-epidithiopyrrolo[1,2-a]pyrazine-7-carbonitrile

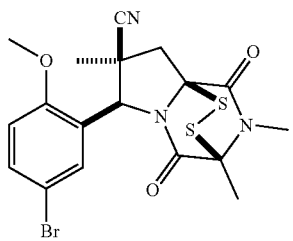

Chemical Formula: $C_{18}H_{18}BrN_3O_3S_2$
Exact Mass: 466.9973

$^1$H-NMR (500 MHz, CDCl$_3$): δ/ppm 7.50 (1H, s), 7.45 (1H, dd, J=2.0, 8.5 Hz), 6.83 (1H, d, J=8.5 Hz), 5.49 (1H, s), 3.90 (3H, s), 3.45 (1H, d, J=14.5 Hz), 3.10 (3H, s), 2.91 (1H, d, J=14.5 Hz), 1.98 (3H, s), 1.65 (3H, s); $^{13}$C-NMR (125 MHz, CDCl$_3$): δ/ppm 165.7 (C), 162.7 (C), 155.8 (C), 133.2 (CH), 129.9 (CH), 120.0 (C), 113.4 (C), 112.5 (CH), 73.7 (C), 73.3 (C), 65.5 (CH), 55.6 (CH$_3$), 43.5 (C), 41.9 (CH$_2$), 27.9 (CH$_3$), 25.7 (CH$_3$), 18.3 (CH$_3$). IR (film): v/cm$^{-1}$ 2937, 2359, 1692, 1488, 1359, 1252, 729. LR-MS: 490.0 (M+Na); HR-MS (ESI) calculated for $C_{18}H_{18}N_3O_3BrS_2$Na: 489.9871, found: 489.9862.

270

Rac-(3S,6R,7S,8aS)-2,3,7-Trimethyl-1,4-dioxo-6-(thiophen-2-yl)hexahydro-6H-3,8a-epidithiopyrrolo[1,2-a]pyrazine-7-carbonitrile

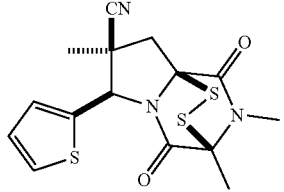

Chemical Formula: $C_{15}H_{15}N_3O_2S_3$
Exact Mass: 365.0326

$^1$H-NMR (500 MHz, CDCl$_3$): δ/ppm 7.36 (1H, d, J=4.5 Hz), 7.30 (1H, br. s), 7.07 (1H, t, J=4.5 Hz), 5.30 (1H, s), 3.43 (1H, d, J=14.5 Hz), 3.00-3.15 (4H, m), 1.96 (3H, s), 1.66 (3H, s); $^{13}$C-NMR (125 MHz, CDCl$_3$): δ/ppm 165.5 (C), 162.2 (C), 136.2 (C), 127.7 (CH), 127.6 (CH), 126.8 (CH), 119.6 (C), 73.4 (C), 72.9 (C), 67.3 (CH), 44.3 (C), 42.0 (CH$_2$), 27.9 (CH$_3$), 25.2 (CH$_3$), 18.2 (CH$_3$). IR (film): v/cm$^{-1}$ 2917, 2361, 1699, 1403, 1360, 1251, 1068, 848. LR-MS: 388.1 (M+Na$^+$); HR-MS (ESI) calculated for $C_{15}H_{15}N_3O_2S_3$Na: 388.0224, found: 388.0221.

Rac-(3S,6S,7S,8aS)-6-([1,1'-Biphenyl]-4-yl)-2,3,7-trimethyl-1,4-dioxohexahydro-6H-3,8a-epidithiopyrrolo[1,2-a]pyrazine-7-carbonitrile

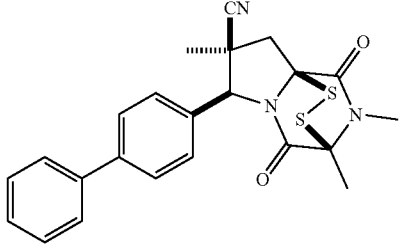

Chemical Formula: $C_{23}H_{21}N_3O_2S_2$
Exact Mass: 435.1075

$^1$H-NMR (500 MHz, CDCl$_3$): δ/ppm 7.72 (2H, d, J=8.5 Hz), 7.66 (2H, d, J=8.5 Hz), 7.45-7.53 (4H, m), 7.41 (1H, t, J=7.5 Hz), 5.02 (1H, s), 3.41 (1H, d, J=15.0 Hz), 3.16 (3H, s), 3.09 (1H, d, J=15.0 Hz), 2.02 (3H, s), 1.78 (3H, s); C-NMR (125 MHz, CDCl$_3$): δ/ppm 165.6 (C), 162.2 (C), 142.3 (C), 140.4 (C), 132.6 (C), 128.8 (2CH), 127.7 (2CH), 127.6 (2CH), 127.2 (CH+2CH), 120.2 (C), 73.5 (C), 73.4 (C), 72.2 (CH), 44.4 (C), 42.9 (CH$_2$), 27.8 (CH$_3$), 24.8 (CH$_3$), 18.1 (CH$_3$). IR (film): v/cm$^{-1}$ 2935, 2250, 1689, 1488, 1448, 1414, 1358, 1252, 910. LR-MS: 458.2 (M+Na$^+$); HR-MS (ESI) calculated for $C_{23}H_{21}N_3O_2S_2$Na: 458.0973, found: 458.0972.

271

Rac-(3S,6S,7S,8aS)-2,3,7-Trimethyl-1,4-dioxo-6-(p-tolyl)hexahydro-6H-3,8a-epidithiopyrrolo[1,2-a]pyrazine-7-carbonitrile

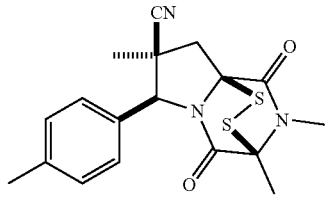

Chemical Formula: $C_{18}H_{19}N_3O_2S_2$
Exact Mass: 373.0919

$^1$H-NMR (500 MHz, CDCl$_3$): δ/ppm 7.28-7.35 (4H, m), 4.94 (1H, s), 3.37 (1H, d, J=15.0 Hz), 3.14 (3H, s), 3.06 (1H, d, J=15.0 Hz), 2.43 (3H, s), 2.00 (3H, s), 1.74 (3H, s); $^{13}$C-NMR (125 MHz, CDCl$_3$): δ/ppm 165.7 (C), 162.1 (C), 139.3 (C), 130.7 (C), 129.7 (2CH), 126.7 (2CH), 120.3 (C), 73.5 (C), 73.3 (C), 72.4 (CH), 44.5 (C), 42.9 (CH$_2$), 27.8 (CH$_3$), 24.7 (CH$_3$), 21.4 (CH$_3$), 18.1 (CH$_3$). IR (film): ν/cm$^{-1}$ 2990, 2921, 2245, 1685, 1516, 1358, 1253, 816. LR-MS: 396.2 (M+Na$^+$); HR-MS (ESI) calculated for $C_{18}H_{19}N_3O_2S_2Na$: 396.0816, found: 396.0800. The constitution and relative configuration of this product was confirmed by single-crystal X-ray analysis.

Rac-(3S,6S,7S,8aS)-6-(2,3-Dihydrobenzo[b][1,4]dioxin-6-yl)-2,3,7-trimethyl-1,4-dioxohexahydro-6H-3,8a-epidithiopyrrolo[1,2-a]pyrazine-7-carbonitrile

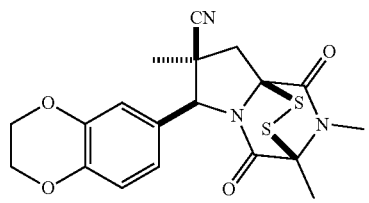

Chemical Formula: $C_{19}H_{19}N_3O_4S_2$
Exact Mass: 417.0817

$^1$H-NMR (500 MHz, CDCl$_3$): δ/ppm 6.90-7.00 (3H, m), 4.88 (1H, s), 4.32 (4H, m), 3.36 (1H, d, J=14.5 Hz), 3.14 (3H, s), 3.05 (1H, d, J=14.5 Hz), 2.00 (3H, s), 1.72 (3H, s); $^{13}$C-NMR (125 MHz, CDCl$_3$): δ/ppm 165.7 (C), 162.2 (C), 144.4 (C), 143.7 (C), 126.9 (C), 120.2 (C), 119.9 (CH), 117.9 (CH), 115.9 (CH), 73.4 (C), 73.3 (C), 72.0 (CH), 64.3 (2CH$_2$), 44.4 (C), 42.7 (CH$_2$), 27.8 (CH$_3$), 24.9 (CH$_3$), 18.1 (CH$_3$). IR (film): ν/cm$^{-1}$ 2984, 2938, 2251, 1690, 1592, 1509, 1360, 1288, 1260, 1067, 912. LR-MS: 439.9 (M+Na$^+$); HR-MS (ESI) calculated for $C_{19}H_{19}N_3O_4S_2Na$: 440.0715, found: 440.0728.

272

Rac-(3S,6S,7S,8aS)-6-(4-Chlorophenyl)-2,3,7-trimethyl-1,4-dioxohexahydro-6H-3,8a-epidithiopyrrolo[1,2-a]pyrazine-7-carbonitrile

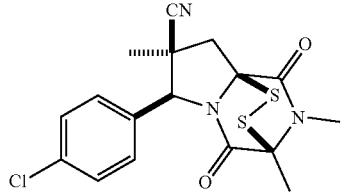

Chemical Formula: $C_{17}H_{16}ClN_3O_2S_2$
Exact Mass: 393.0372

$^1$H-NMR (500 MHz, CDCl$_3$): δ/ppm 7.42 (2H, d, J=8.5 Hz), 7.32 (2H, d, J=8.5 Hz), 4.87 (1H, s), 3.32 (1H, d, J=15.0 Hz), 3.08 (3H, s), 2.99 (1H, d, J=15.0 Hz), 1.94 (3H, s), 1.68 (3H, s); $^{13}$C-NMR (125 MHz, CDCl$_3$): δ/ppm 165.5 (C), 162.1 (C), 135.5 (C), 132.2 (C), 129.3 (2CH), 128.2 (2CH), 120.0 (C), 73.5 (C), 73.4 (C), 71.8 (CH), 44.3 (C), 42.9 (CH$_2$), 27.8 (CH$_3$), 24.7 (CH$_3$), 18.1 (CH$_3$). IR (film): ν/cm$^{-1}$ 2992, 2941, 2246, 1690, 1493, 1359, 1255, 1090, 825. LR-MS: 416.2 (M+Na$^+$); HR-MS (ESI) calculated for $C_{17}H_{16}N_3O_2ClS_2Na$: 416.0270, found: 416.0261.

Rac-(3S,6S,7S,8aS)-6-(3,4-Dichlorophenyl)-2,3,7-trimethyl-1,4-dioxohexahydro-6H-3,8a-epidithiopyrrolo[1,2-a]pyrazine-7-carbonitrile

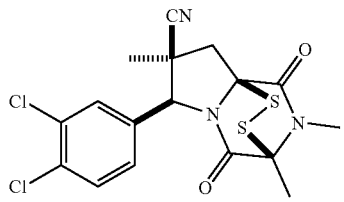

Chemical Formula: $C_{17}H_{15}Cl_2N_3O_2S_2$
Exact Mass: 426.9983

$^1$H-NMR (500 MHz, CDCl$_3$): δ/ppm 7.53 (1H, d, J=8.0 Hz), 7.46 (1H, s), 7.25 (1H, d, J=8.0 Hz), 4.85 (1H, s), 3.33 (1H, d, J=15.0 Hz), 3.09 (3H, s), 3.00 (1H, d, J=15.0 Hz), 1.95 (3H, s), 1.70 (3H, s); $^{13}$C-NMR (125 MHz, CDCl$_3$): δ/ppm 165.4 (C), 162.0 (C), 133.9 (2C), 133.2 (C), 131.2 (CH), 129.0 (CH), 126.2 (CH), 119.8 (C), 73.4 (2C), 71.2 (CH), 44.2 (C), 42.9 (CH$_2$), 27.9 (CH$_3$), 24.8 (CH$_3$), 18.1 (CH$_3$). IR (film): ν/cm$^{-1}$ 2936, 2250, 1696, 1472, 1359, 1252, 1136, 1031, 912, 730. LR-MS: 449.9 (M+Na$^+$); HR-MS (ESI) calculated for $C_{17}H_{15}N_3O_2Cl_2S_2Na$: 449.9880, found: 449.9853.

Rac-(3S,6R,7S,8aS)-6-(6-Bromobenzo[d][1,3]di-oxol-5-yl)-2,3,7-trimethyl-1,4-dioxohexahydro-6H-3,8a-epidithiopyrrolo[1,2-a]pyrazine-7-carbonitrile

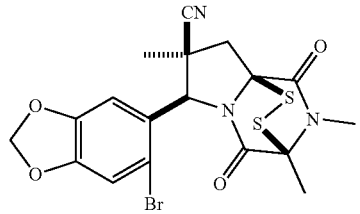

Chemical Formula: C₁₈H₁₆BrN₃O₄S₂
Exact Mass: 480.9766

$^1$H-NMR (500 MHz, CDCl$_3$): δ/ppm 7.07 (1H, s), 7.05 (1H, s), 6.02 (2H, s), 5.22 (1H, s), 3.41 (1H, d, J=15.0 Hz), 3.08 (3H, s), 2.98 (1H, d, J=15.0 Hz), 1.95 (3H, s), 1.75 (3H, s); $^{13}$C-NMR (125 MHz, CDCl$_3$): δ/ppm 165.5 (C), 162.2 (C), 149.1 (C), 148.3 (C), 126.8 (C), 120.0 (C), 114.4 (C), 113.2 (CH), 108.0 (CH), 102.3 (CH$_2$), 73.6 (C), 73.3 (C), 71.0 (CH), 44.2 (C), 42.8 (CH$_2$), 27.8 (CH$_3$), 25.5 (CH$_3$), 18.1 (CH$_3$). IR (film): v/cm$^{-1}$ 3043, 2986, 2913, 2243, 1694, 1504, 1480, 1355, 1242, 1118, 1037, 931, 734. LR-MS: 504.1 (M+Na$^+$); HR-MS (ESI) calculated for C$_{18}$H$_{16}$N$_3$O$_4$BrS$_2$Na: 503.9663, found: 503.9647.

Rac-(3S,6S,7R,8aS)-6-(Benzo[d][1,3]dioxol-5-yl)-7-((dimethylamino)methyl)-2,3,7-trimethyl-tetrahydro-6H-3,8a-epidithiopyrrolo[1,2-a]pyrazine-1,4-dione

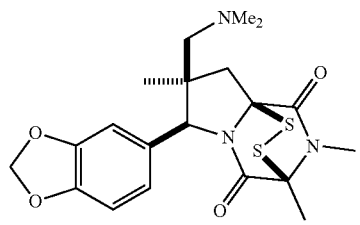

Chemical Formula: C₂₀H₂₅N₃O₄S₂
Exact Mass: 435.1286

Prepared from rac-(3R,6S,7S,8aS)-6-(Benzo[d][1,3]di-oxol-5-yl)-2,3,7-trimethyl-1,4-dioxo-octahydropyrrolo[1,2-a]-pyrazine-7-carbonitrile by conventional NiCl$_2$/NaBH$_4$ reduction of the nitrile, Eschweiler-Clarke dimethylation of the resulting primary amine and sulfidation.

H-NMR (500 MHz, CDCl$_3$): δ/ppm 6.91 (1H, s), 6.76-6.83 (2H, m), 5.97 (2H, s), 4.77 (1H, s), 3.18 (1H, d, J=14.5 Hz), 3.07 (3H, s), 2.55 (1H, d, J=14.5 Hz), 2.15 (6H, s), 1.97 (2H, s), 1.94 (3H, s), 1.27 (3H, s); $^{13}$C-NMR (125 MHz, CDCl$_3$): δ/ppm 166.6 (C), 163.1 (C), 148.0 (C), 147.3 (C), 130.0 (C), 121.3 (CH), 108.4 (CH), 108.1 (CH), 101.3 (CH$_2$), 74.9 (C), 74.2 (CH), 73.5 (C), 66.1 (CH$_2$), 8.2 (2CH$_3$), 47.8 (C), 41.8 (CH$_2$), 27.7 (CH$_3$), 26.5 (CH$_3$), 18.4 (CH$_3$). IR (film): v/cm$^{-1}$ 2940, 2821, 2770, 1690, 1490, 1445, 1379, 1353, 1249, 1104, 1038, 932, 734. LR-MS: 458.2 (M+Na$^+$); HR-MS (ESI) calculated for C$_{20}$H$_{25}$N$_3$O$_4$S$_2$Na: 458.1184, found: 458.1185.

Rac-(3S,6R,7S,8aS)-6-(4-Methoxybenzo[d][1,3]dioxol-5-yl)-2,3,7-trimethyl-1,4-dioxohexahydro-6H-3,8a-epidithiopyrrolo[1,2-a]pyrazine-7-carbonitrile

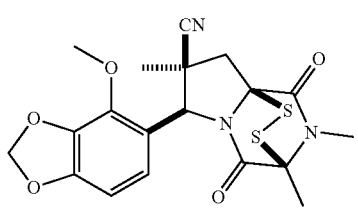

Chemical Formula: C₁₉H₁₉N₃O₅S₂
Exact Mass: 433.4970

$^1$H-NMR (500 MHz, CDCl$_3$): δ/ppm 6.52-6.62 (2H, m), 6.01 (2H, s), 4.84 (1H, s), 3.89 (3H, s), 3.31 (1H, d, J=15.0 Hz), 3.09 (3H, s), 3.01 (1H, d, J=15.0 Hz), 1.96 (3H, s), 1.68 (3H, s); $^{13}$C-NMR (125 MHz, CDCl$_3$): δ/ppm 165.5 (C), 162.0 (C), 149.2 (C), 143.8 (C), 136.0 (C), 128.1 (C), 120.2 (C), 106.1 (CH), 102.1 (CH$_2$), 101.2 (CH), 73.6 (C), 73.5 (C), 72.4 (CH), 56.6 (CH$_3$), 44.5 (C), 42.7 (CH$_2$), 27.9 (CH$_3$), 25.1 (CH$_3$), 18.2 (CH$_3$). IR (film): v/cm$^{-1}$ 2940, 2902, 2241, 1696, 1636, 1513, 1453, 1358, 1250, 1201, 1130, 1093, 1044, 874, 734. LR-MS: 456.0 M+Na$^+$; HR-MS (ESI) calculated for C$_{19}$H$_{19}$N$_3$O$_5$S$_2$Na: 456.0664, found: 456.0653.

Rac-(3S,6S,7R,8aS)-6-(Benzo[d][1,3]dioxol-5-yl)-7-(methoxymethyl)-2,3-dimethyl-1,4-dioxohexahydro-6H-3,8a-epidithiopyrrolo[1,2-a]pyrazine-7-carbonitrile

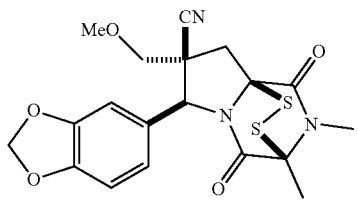

Chemical Formula: C₁₉H₁₉N₃O₅S₂
Exact Mass: 433.4970

$^1$H-NMR (500 MHz, CDCl$_3$): δ/ppm 6.91 (1H, s), 6.80-6.88 (2H, m), 5.99 (2H, s), 5.26 (1H, s), 3.61 (1H, d, J=9.5 Hz), 3.58 (1H, d, J=15.0 Hz), 3.54 (1H, d, J=9.5 Hz), 3.47 (3H, s), 3.08 (3H, s), 2.88 (1H, d, J=15.0 Hz), 1.94 (3H, s); $^{13}$C-NMR (125 MHz, CDCl$_3$): δ/ppm 165.5 (C), 162.0 (C), 148.4 (C), 148.3 (C), 128.0 (C), 120.9 (CH), 118.4 (C), 108.7 (CH), 107.4 (CH), 101.5 (CH$_2$), 73.8 (C), 73.5 (C), 73.0 (CH$_2$), 67.2 (CH), 59.7 (CH$_3$), 49.6 (C), 38.5 (CH$_2$), 27.8 (CH$_3$), 18.1 (CH$_3$). IR (film): v/cm$^{-1}$ 2993, 2928, 2898, 2250, 1693, 1497, 1491, 1447, 1358, 1250, 1118, 1038, 914, 731. LR-MS: 456.0 M+Na$^+$; HR-MS (ESI) calculated for C$_{19}$H$_{19}$N$_3$O$_5$S$_2$Na: 456.0664, found: 456.0650.

275

Rac-(3S,6S,7S,8aS)-6-(2,2-Difluorobenzo[d][1,3]dioxol-5-yl)-2,3,7-trimethyl-1,4-dioxohexahydro-6H-3,8a-epidithiopyrrolo[1,2-a]pyrazine-7-carbonitrile

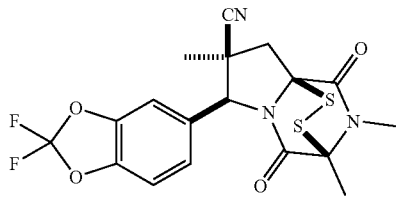

Chemical Formula: $C_{18}H_{15}F_2N_3O_4S_2$
Exact Mass: 439.4518

$^1$H-NMR (500 MHz, CDCl$_3$): δ/ppm 7.09-7.15 (3H, m), 4.89 (1H, s), 3.33 (1H, d, J=14.5 Hz), 3.08 (3H, s), 3.00 (1H, d, J=14.5 Hz), 1.95 (3H, s), 1.69 (3H, s); $^{13}$C-NMR (125 MHz, CDCl$_3$): δ/ppm 165.4 (C), 162.1 (C), 144.4 (C), 144.2 (C), 131.7 (C, t, J=255 Hz), 130.0 (C), 122.6 (CH), 119.9 (C), 109.8 (CH), 108.3 (CH), 77.3 (C), 73.4 (C), 72.0 (C), 44.4 (C), 42.9 (CH$_2$), 27.9 (CH$_3$), 24.8 (CH$_3$), 18.1 (CH$_3$). IR (film): ν/cm$^{-1}$ 2986, 2942, 2253, 1697, 1501, 1450, 1358, 1240, 1154, 1034, 903, 731. LR-MS: 462.0 M+Na$^+$; HR-MS (ESI) calculated for $C_{18}H_{15}N_3O_4F_2S_2$Na: 462.0370, found: 462.0377.

Rac-(3R,6R,7S,8aR)-6-(5-Bromobenzo[d][1,3]dioxol-4-yl)-2,3,7-trimethyl-1,4-dioxohexahydro-6H-3,8a-epidithiopyrrolo[1,2-a]pyrazine-7-carbonitrile

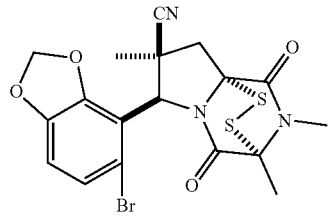

Chemical Formula: $C_{18}H_{16}BrN_3O_4S_2$
Exact Mass: 482.3670

$^1$H-NMR (500 MHz, CDCl$_3$): δ/ppm 7.13 (1H, d, J=8.5 Hz), 6.69 (1H, d, J=8.5 Hz), 5.90 (1H, s), 5.80 (1H, s), 5.65 (1H, s), 3.88 (1H, d, J=15.5 Hz), 3.06 (3H, s), 2.57 (1H, d, J=15.5 Hz), 2.12 (3H, s), 1.95 (3H, s); $^{13}$C-NMR (125 MHz, CDCl$_3$): δ/ppm 165.5 (C), 161.6 (C), 147.6 (C), 145.1 (C), 126.4 (CH), 119.6 (C), 117.7 (C), 114.9 (C), 110.5 (CH), 102.1 (CH$_2$), 74.6 (C), 73.7 (C), 68.5 (CH), 44.3 (CH$_2$), 43.1 (C), 27.6 (CH$_3$), 27.5 (CH$_3$), 18.3 (CH$_3$). IR (film): ν/cm$^{-1}$ 2986, 2880, 2250, 1695, 1457, 1357, 1242, 1059, 1035, 932, 731. LR-MS: 503.9 M+Na$^+$; HR-MS (ESI) calculated for $C_{18}H_{16}N_3O_4S_2$BrNa: 503.9663, found: 503.9655. The constitution and relative configuration of this product was confirmed by single-crystal X-ray analysis.

276

Rac-(3S,6R,7S,8aS)-6-(Benzo[d][1,3]dioxol-4-yl)-2,3,7-trimethyl-1,4-dioxohexahydro-6H-3,8a-epidithiopyrrolo[1,2-a]pyrazine-7-carbonitrile

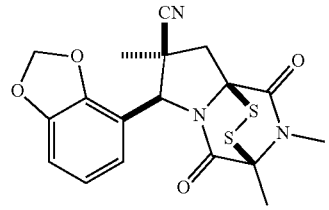

Chemical Formula: $C_{18}H_{17}N_3O_4S_2$
Molecular Weight: 403.4710

$^1$H-NMR (500 MHz, CDCl$_3$): δ/ppm 6.80-6.96 (3H, m), 6.02 (1H, s), 6.00 (1H, s), 5.22 (1H, s), 3.35 (1H, d, J=15.0 Hz), 3.08 (3H, s), 2.98 (1H, d, J=15.0 Hz), 1.95 (3H, s), 1.70 (3H, s); $^{13}$C-NMR (125 MHz, CDCl$_3$): δ/ppm 165.6 (C), 162.2 (C), 147.6 (C), 145.2 (C), 122.3 (CH), 120.1 (C), 119.5 (CH), 115.7 (C), 109.5 (CH), 101.3 (CH$_2$), 73.6 (C), 73.3 (C), 66.2 (CH), 44.1 (C), 42.7 (CH$_2$), 27.8 (CH$_3$), 25.1 (CH$_3$), 18.2 (CH$_3$). IR (film): ν/cm$^{-1}$ 12991, 2905, 2241, 1697, 1462, 1357, 1249, 1063, 1029, 931, 731. LR-MS: 426.0 M+Na$^+$; HR-MS (ESI) calculated for $C_{18}H_{17}N_3O_4S_2$Na: 426.0558, found: 426.0552. The constitution and relative configuration of this product was confirmed by single-crystal X-ray analysis.

Rac-(3S,6S,7R,8aS)-6-(Benzo[d][1,3]dioxol-5-yl)-2,3-dimethyl-7-(morpholinomethyl)-1,4-dioxohexahydro-6H-3,8a-epidithiopyrrolo[1,2-a]pyrazine-7-carbonitrile

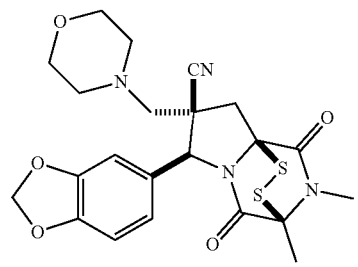

Chemical Formula: $C_{22}H_{24}N_4O_5S_2$
Molecular Weight: 488.5770

$^1$H-NMR (500 MHz, CDCl$_3$): δ/ppm 6.96 (1H, s), 6.91 (1H, d, J=8.0 Hz), 6.84 (1H, d, J=7.0 Hz), 5.99 (2H, s), 5.17 (1H, s), 3.65-3.74 (4H, m), 3.56 (1H, d, J=14.5 Hz), 3.04 (3H, s), 2.92 (1H, d, J=14.5 Hz), 2.70-2.80 (2H, m), 2.60-2.75 (4H, m), 1.94 (3H, s); $^{13}$C-NMR (125 MHz, CDCl$_3$): δ/ppm 165.6 (C), 162.2 (C), 148.4 (C), 148.3 (C), 128.2 (C), 121.1 (CH), 119.7 (C), 108.7 (CH), 107.6 (CH), 101.5 (CH$_2$), 73.7 (C), 73.5 (C), 68.7 (CH), 67.1 (2CH$_2$), 63.4 (CH$_2$), 55.3 (2CH$_2$), 49.6 (C), 39.5 (CH$_2$), 27.9 (CH$_3$), 18.2 (CH$_3$). IR (film): ν/cm$^{-1}$ 2958, 2855, 2816, 2248, 1688, 1491, 1447, 1356, 1260, 1116, 1037, 914, 864, 730. LR-MS: 511.1 M+Na$^+$; HR-MS (ESI) calculated for $C_{22}H_{24}N_4O_5S_2$Na: 511.1086, found: 511.1068.

277

Rac-(3S,6S,7S,8aS)-6-(benzo[d][1,3]dioxol-5-yl)-2-butyl-3,7-dimethyl-1,4-dioxohexahydro-1H-3,8a-epidithiopyrrolo[1,2-a]pyrazine-7-carbonitrile

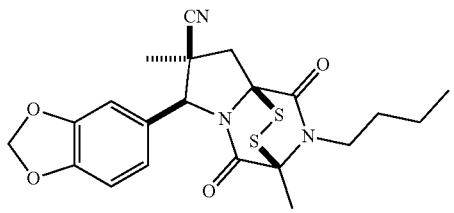

$^1$H-NMR (500 MHz, CDCl$_3$): δ/ppm 6.88 (1H, s), 6.82 (2H, app. s), 5.99 (2H, s), 4.81 (1H, s), 3.78, (1H, m), 3.30 (1H, d, J=14.5 Hz), 2.99 (1H, d, J=14.5 Hz), 1.98 (3H, s), 1.66 (3H, s), 1.62 (2H, m), 1.38 (2H, m), 0.96 (3H, t, J=7.2 Hz); $^{13}$C-NMR (125 MHz, CDCl$_3$): δ/ppm 165.2 (C), 162.4 (C), 148.7 (C), 148.4 (C), 127.7 (C), 120.8 (CH), 120.5 (C), 108.7 (CH), 107.4 (CH), 101.7 (CH$_2$), 73.8 (C), 73.0 (C), 72.5 (CH), 44.6 (C), 43.3 (CH$_2$), 43.0 (CH$_2$), 29.9 (CH$_2$), 25.0 (CH$_3$), 24.8 (CH$_2$), 20.4 (CH$_2$), 17.8 (CH$_3$), 14.0 (CH$_3$). IR (film): v/cm$^{-1}$ 2984, 2902, 2250, 1688, 1491, 1446, 1358, 1250, 1038, 731. HR-MS (ESI) calculated for C$_{21}$H$_{23}$N$_3$O$_4$S$_2$Na: 468.1022, found: 468.1018.

Rac-(3S,6S,7S,8aS)-6-(4-methoxyphenyl)-2,3,7-trimethyl-1,4-dioxohexahydro-1H-3,8a-epidithiopyrrolo[1,2-a]pyrazine-7-carbonitrile

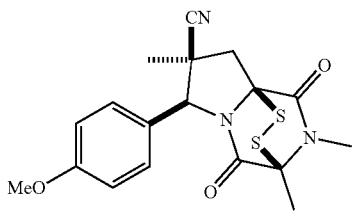

$^1$H-NMR (500 MHz, CDCl$_3$): δ/ppm 7.30 (2H, d, J=8.5 Hz), 6.96 (2H, d, J=8.5 Hz), 4.85 (1H, s), 3.79 (3H, s), 3.28 (1H, d, J=15.0 Hz), 3.08 (3H, s), 2.99 (1H, d, J=15.0 Hz), 1.94 (3H, s), 1.66 (3H, s); $^{13}$C-NMR (125 MHz, CDCl$_3$): δ/ppm 165.0 (C), 162.3 (C), 159.9 (C), 128.7 (C), 127.3 (2CH), 117.8 (C), 114.7 (2CH), 73.6 (C), 73.4 (C), 72.0 (CH), 55.2 (CH$_3$), 44.2 (C), 42.7 (CH$_2$), 27.7 (CH$_3$), 24.8 (CH$_3$), 18.0 (CH$_3$). IR (film): v/cm$^1$ 2988, 2940, 2246, 1690, 1493, 1359, 1255, 1093, 756. HR-MS (ESI) calculated for C$_{18}$H$_{19}$N$_3$O$_3$S$_2$Na: 412.0760, found: 412.0753.

278

Rac-(3S,6S,7S,8aS)-6-(benzo[d][1,3]dioxol-5-yl)-3-benzyl-2,7-dimethyl-1,4-dioxohexahydro-6H-3,8a-epidithiopyrrolo[1,2-a]pyrazine-7-carbonitrile

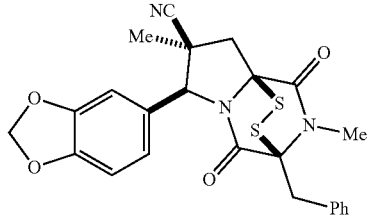

Chemical Formula: C$_{24}$H$_{21}$N$_3$O$_4$S$_2$
Exact Mass: 479.0973
Molecular Weight: 479.5690

$^1$H-NMR (500 MHz, CDCl$_3$) δ 7.33-7.31 (m, 2H), 7.29-7.24 (m, 3H), 6.86 (s, 1H), 6.82-6.81 (m, 2H), 5.99-5.98 (m, 2H), 4.90 (s, 1H), 3.82 (d, J=15.3 Hz, 1H), 3.75 (d, J=15.3 Hz, 1H), 3.32 (d, J=14.9 Hz, 1H), 3.07 (s, 3H), 3.02 (d, J=14.9 Hz, 1H), 1.70 (s, 3H) ppm; $^{13}$C-NMR (126 MHz, CDCl$_3$) δ 166.4 (C), 161.4 (C), 148.6 (C), 148.3 (C), 133.6 (C), 129.9 (CH), 128.7 (CH), 127.8 (CH), 127.4 (C), 120.8 (CH), 120.3 (C), 108.7 (CH), 107.4 (CH), 101.6 (CH$_2$), 77.8 (C), 73.5 (C), 72.7 (CH), 44.5 (C), 42.9 (CH$_2$), 36.6 (CH$_2$), 29.4 (CH$_3$), 25.0 (CH$_3$) ppm; IR (film) v/cm$^{-1}$ 2917, 1695, 1491, 1447, 1357, 1249, 1190, 1037, 931, 817 cm$^{-1}$; HRMS (ESI) calcd for C$_{24}$H$_{21}$N$_3$O$_4$S$_2$Na$^+$ (M+Na) 502.0871, found 502.0867.

Rac-(3S,6S,7S,8aS)-2-allyl-6-(benzo[d][1,3]dioxol-5-yl)-3,7-dimethyl-1,4-dioxohexahydro-6H-3,8a-epidithiopyrrolo[1,2-a]pyrazine-7-carbonitrile

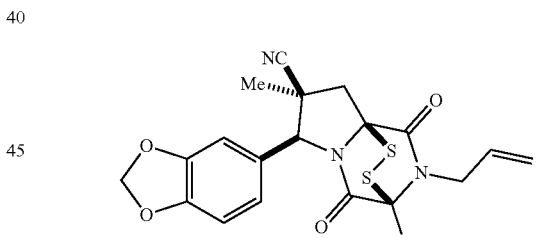

Chemical Formula: C$_{20}$H$_{19}$N$_3$O$_4$S$_2$
Exact Mass: 429.0817
Molecular Weight: 429.5090

$^1$H-NMR (500 MHz, CDCl$_3$) δ 6.88 (s, 1H), 6.84 (app. s, 2H), 5.99 (s, 2H), 5.89-5.82 (m, 1H), 5.28 (d, J=17.6 Hz, 1H), 5.25 (d, J=10.6 Hz, 1H), 4.83 (s, 1H), 4.41-4.37 (m, 1H), 4.02 (dd, J=16.2, 5.6 Hz 1H), 3.30 (d, J=14.9 Hz, 1H), 3.01 (d, J=14.9 Hz, 1H), 1.98 (s, 3H), 1.66 (s, 3H) ppm; $^{13}$C-NMR (126 MHz, CDCl$_3$) δ 165.1 (C), 162.2 (C), 148.6 (C), 148.3 (C), 131.5 (CH), 127.6 (C), 120.7 (CH), 120.4 (C), 118.4 (CH$_2$), 108.6 (CH), 107.2 (CH), 101.6 (CH$_2$), 73.6 (C), 73.1 (C), 72.4 (CH), 45.2 (CH$_2$), 44.5 (C), 42.9 (CH$_2$), 24.8 (CH$_3$), 17.5 (CH$_3$) ppm; IR (film) v/cm$^{-1}$ 1688, 1491, 1446, 1359, 1249, 1191, 1103, 1038, 929 cm$^{-1}$; HRMS (ESI) calcd for C$_{20}$H$_{19}$N$_3$O$_4$S$_2$Na+(M+Na) 452.0715, found 452.0719.

279

Rac-(3S,6S,7S,8aS)-6-(benzo[d][1,3]dioxol-5-yl)-2-cyclopropyl-3,7-dimethyl-1,4-dioxohexahydro-6H-3,8a-epidithiopyrrolo[1,2-a]pyrazine-7-carbonitrile

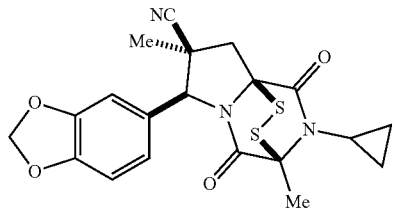

Chemical Formula: $C_{20}H_{19}N_3O_4S_2$
Exact Mass: 429.0817
Molecular Weight: 429.5090

$^1$H-NMR (500 MHz, CDCl$_3$) δ 6.87 (s, 1H), 6.84-6.81 (app. s, 2H), 5.99 (s, 2H), 4.80 (s, 1H), 3.27 (d, J=14.9 Hz, 1H), 2.93 (d, J=14.9 Hz, 1H), 2.57-2.53 (m, 1H), 2.12 (s, 3H), 1.66 (s, 3H), 1.29-1.24 (m, 1H), 1.06-0.97 (m, 2H), 0.96-0.90 (m, 1H) ppm; 13C-NMR (126 MHz, CDCl$_3$) δ 165.7 (C), 162.3 (C), 148.6 (C), 148.3 (C), 127.6 (C), 120.7 (CH), 120.4 (C), 108.6 (CH), 107.2 (CH), 101.6 (CH$_2$), 74.4 (C), 74.1 (C), 72.4 (CH), 44.5 (C), 42.9 (CH$_2$), 25.8 (CH), 24.8 (CH$_3$), 17.8 (CH$_3$), 8.2 (CH$_2$), 7.7 (CH$_2$) ppm; IR (film) v/cm$^{-1}$ 1696, 1491, 1446, 1348, 1248, 1189, 1037, 930, 735 cm$^{-1}$; HRMS (ESI) calcd for $C_{20}H_{19}N_3O_4S_2Na^+$ (M+Na) 452.0715, found 452.0702.

280

Rac-(3S,6S,7S,8aS)-6-(7-methoxybenzo[d][1,3]dioxol-5-yl)-2,3,7-trimethyl-1,4-dioxohexa-hydro-6H-3,8a-epidithiopyrrolo[1,2-a]pyrazine-7-carbonitrile

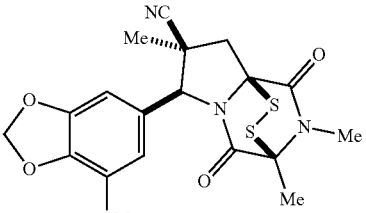

Chemical Formula: $C_{19}H_{19}N_3O_5S_2$
Exact Mass: 433.0766
Molecular Weight: 433.4970

$^1$H-NMR (500 MHz, CDCl$_3$) δ 6.60 (s, 1H), 6.58 (s, 1H), 6.00 (m, 2H), 4.84 (s, 1H), 3.89 (s, 3H), 3.31 (d, J=14.8 Hz, 1H), 3.08 (s, 3H), 2.99 (d, J=14.8 Hz, 1H), 1.95 (s, 3H), 1.67 (s, 3H) ppm; $^{13}$C-NMR (126 MHz, CDCl$_3$) δ 165.5 (C), 162.1 (C), 149.3 (C), 143.9 (C), 136.1 (C), 128.2 (C), 120.2 (C), 106.5 (CH), 102.0 (CH$_2$), 101.3 (CH), 73.7 (C), 73.6 (C), 72.5 (CH$_2$), 56.7 (CH$_3$), 44.5 (C), 42.8 (CH$_2$), 27.9 (CH$_3$), 25.2 (CH$_3$), 18.2 (CH$_3$) ppm; IR (film) v/cm$^{-1}$ 2984, 2250, 1696, 1637, 1512, 1453, 1358, 1246, 1201, 1129, 1093, 1044, 913, 731 cm$^{-1}$; HRMS (ESI) calcd for $C_{19}H_{19}N_3O_5S_2Na^+$ (M+Na) 456.0664, found 456.0648.

Rac-(3S,6S,7S,8aS)-6-(3,4-bis(allyloxy)phenyl)-2,3,7-trimethyl-1,4-dioxohexahydro-6H-3,8a-epidithiopyrrolo[1,2-a]pyrazine-7-carbonitrile

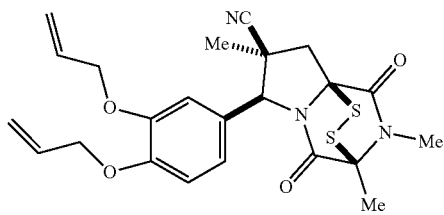

Chemical Formula: $C_{23}H_{25}N_3O_4S_2$
Exact Mass: 471.1286
Molecular Weight: 471.5900

$^1$H-NMR (500 MHz, CDCl$_3$) δ 6.95 (s, 1H), 6.92-6.88 (m, 2H), 6.11-6.03 (m, 2H), 5.45-5.38 (m, 2H), 5.29-5.24 (m, 2H), 4.87 (s, 1H), 4.63-4.60 (m, 4H), 3.31 (d, J=14.8 Hz, 1H), 3.08 (s, 3H), 2.98 (d, J=14.8 Hz, 1H), 1.95 (s, 3H), 1.66 (s, 3H) ppm; $^{13}$C-NMR (126 MHz, CDCl$_3$) δ165.6 (C), 162.2 (C), 149.3 (C), 148.8 (C), 133.4 (CH), 133.3 (CH), 126.5 (C), 120.3 (CH), 119.8 (CH$_2$), 117.9 (CH$_2$), 117.8 (CH$_2$), 113.7 (CH), 112.2 (CH), 73.8 (C), 73.6 (C), 72.4 (C), 70.0 (CH$_2$), 69.9 (CH$_2$), 44.5 (C), 42.8 (CH$_2$), 27.9 (CH$_3$), 25.1 (CH$_3$), 18.3 (CH$_3$) ppm; IR (film) v/cm$^{-1}$ 1695, 1607, 1593, 1516, 1424, 1380, 1360, 1262, 1218, 1141, 996, 919, 731 cm$^{-1}$; HRMS (ESI) calcd for $C_{23}H_{25}N_3O_4S_2Na^+$ (M+Na) 494.1184, found 494.1188.

Rac-(3S,6S,7S,8aS)-6-(2,3-dihydro-1H-inden-5-yl)-2,3,7-trimethyl-1,4-dioxohexahydro-6H-3,8a-epidithiopyrrolo[1,2-a]pyrazine-7-carbonitrile

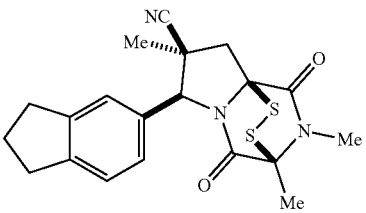

Chemical Formula: $C_{20}H_{21}N_3O_2S_2$
Exact Mass: 399.1075
Molecular Weight: 399.5270

$^1$H-NMR (500 MHz, CDCl$_3$) δ 7.26 (d, J=7.2 Hz, 1H), 7.20 (s, 1H), 7.15 (d, J=7.2 Hz, 1H), 4.87 (s, 1H), 3.30 (d, J=14.9 Hz, 1H), 3.07 (s, 3H), 3.00 (d, J=14.9 Hz, 1H), 2.94-2.89 (m, 4H), 2.08 (app. quintet, J=7.5 Hz, 2H), 1.93 (s, 3H), 1.67 (s, 3H) ppm; $^{13}$C-NMR (126 MHz, CDCl$_3$) δ 165.8 (C), 162.2 (C), 145.8 (C), 145.0 (C), 131.5 (C), 124.9 (CH), 124.8 (CH), 122.9 (CH), 120.5 (C), 73.6 (C), 73.4 (C), 72.8 (CH), 44.6 (C), 43.0 (CH$_2$), 33.0 (CH$_2$), 32.8 (CH$_2$), 27.9 (CH$_3$), 25.4 (CH$_2$), 24.8 (CH$_3$), 18.2 (CH$_3$) ppm; IR (film) v/cm$^{-1}$ 2941, 2251, 1696, 1440, 1359, 1254, 1202, 1145, 1112, 1067, 1030, 911, 731 cm$^{-1}$; HRMS (ESI) calcd for $C_{20}H_{21}N_3O_2S_2Na^+$ (M+Na) 422.0973, found 422.0965.

Rac-(3S,6S,7S,8aS)-2,3,7-trimethyl-1,4-dioxo-6-(1-(phenylsulfonyl)-1H-indol-3-yl)hexahydro-6H-3,8a-epidithiopyrrolo[1,2-a]pyrazine-7-carbonitrile

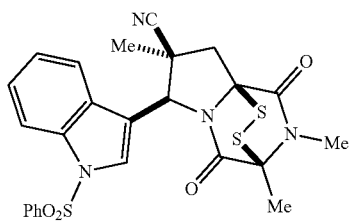

Chemical Formula: $C_{25}H_{22}N_4O_4S_3$
Exact Mass: 538.0803
Molecular Weight: 538.6550

$^1$H-NMR (500 MHz, CDCl$_3$) δ 7.96 (d, J=8.4 Hz, 1H), 7.86-7.84 (m, 3H), 7.55 (d, J=8.0 Hz, 1H), 7.52 (d, J=8.0 Hz, 1H), 7.42 (t, J=7.8 Hz, 2H), 7.34 (t, J=7.7 Hz, 1H), 7.28 (d, J=7.8 Hz, 1H), 5.29 (s, 1H), 3.43 (d, J=14.7 Hz, 1H), 3.10 (s, 3H), 3.05 (d, J=14.7 Hz, 1H), 1.96 (s, 3H), 1.70 (s, 3H) ppm; $^{13}$C-NMR (126 MHz, CDCl$_3$) δ165.5 (C), 162.0 (C), 137.8 (C), 135.3 (C), 134.2 (CH), 129.4 (CH), 128.9 (C), 127.1 (CH), 125.8 (CH), 125.5 (CH), 123.8 (CH), 120.1 (C), 119.5 (CH), 116.6 (C), 114.1 (CH), 73.6 (C), 73.3 (C), 64.2 (CH), 43.8 (C), 42.8 (CH$_2$), 28.0 (CH$_3$), 25.2 (CH$_3$), 18.3 (CH$_3$) ppm; IR (film) v/cm$^{-1}$ 2360, 1696, 1447, 1361, 1214, 1176, 1120, 1095, 974, 747, 725, 684 cm$^{-1}$; HRMS (ESI) calcd for $C_{25}H_{22}N_4O_4S_3Na^+$ (M+Na) 561.0701, found 561.0703.

Example 6

Separation of Enantiomers of ETP Products.

Isolation of (3S,6S,7S,8aS)- and (3R,6R,7R,8aR)-6-(benzo[d][1,3]dioxol-5-yl)-2,3,7-trimethyl-1,4-dioxohexahydro-6H-3,8a-epidithiopyrrolo[1,2-a]pyrazine-7-carbonitriles

LEO-13-1721

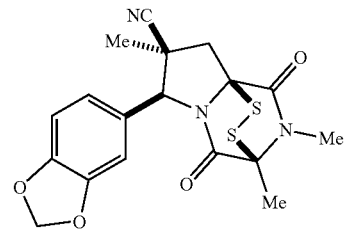

Chemical Formula: $C_{18}H_{17}N_3O_4S_2$
Exact Mass: 403.0660
Molecular Weight: 403.4710

LEO-13-1722

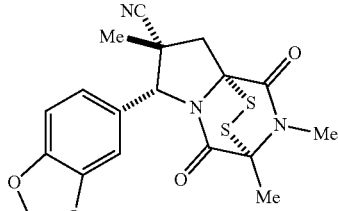

Chemical Formula: $C_{18}H_{17}N_3O_4S_2$
Exact Mass: 403.0660
Molecular Weight: 403.4710

The two enantiomers were separated by preparative chiral HPLC (stationary phase: CHIRALPAK IA (250×50 mm i.d., 5 micron), mobile phase: reagent alcohol 100%), flow rate 2.5 mL/min). The enantiomeric excess was determined by means of analytical chiral HPLC (stationary phase CHIRALPAK IA-3 (50×4.6 mm i.d., 3 micron), mobile phase: reagent alcohol 100%, flow rate 1 mL/min, 254 nm): (3S,6S,7S,8aS)-enantiomer: $t_{ret}$=1.40 min; (3R,6R,7R,8aR)-enantiomer: $t_{ret}$=2.11 min.

Absolute configuration was assigned on the basis of CD data and existing precedent [Carmack, M.; Neubert, L. A. *J. Am. Chem. Soc.* 1967, 89, 7134-7136. Hauser, D.; Weber, H. P.; Sigg, H. *P. Helv. Chim. Acta* 1970, 53, 1061-1073. Minato, H.; Matsumoto, M.; Katayama, T. *J. Chem. Soc.* D. 1971, 44-45. Nagarajan, R.; Woody, R. W. *J. Am. Chem. Soc.* 1973, 95, 7212-7222. Woody, R. W. *Tetrahedron* 1973, 29, 1273-1283].

Example 7

Cell Viability Assay of Compound (1) against CTCL

Figure 1B:
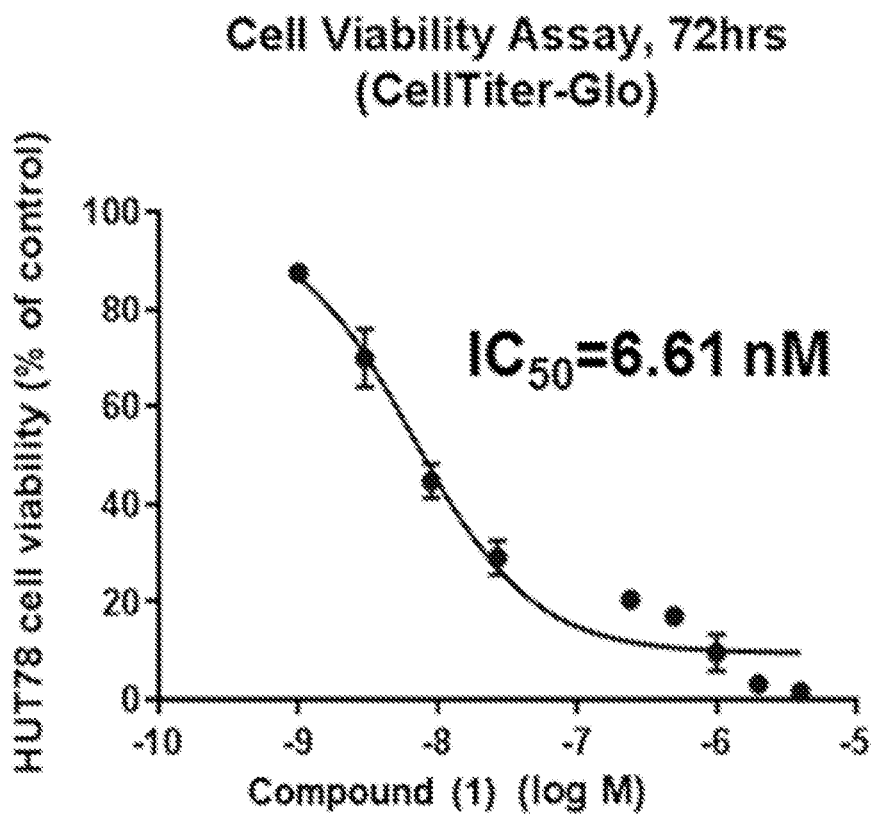
FIG. 1B shows compound (1) activity against HUT78 CTCL cells.
Figure 1C:
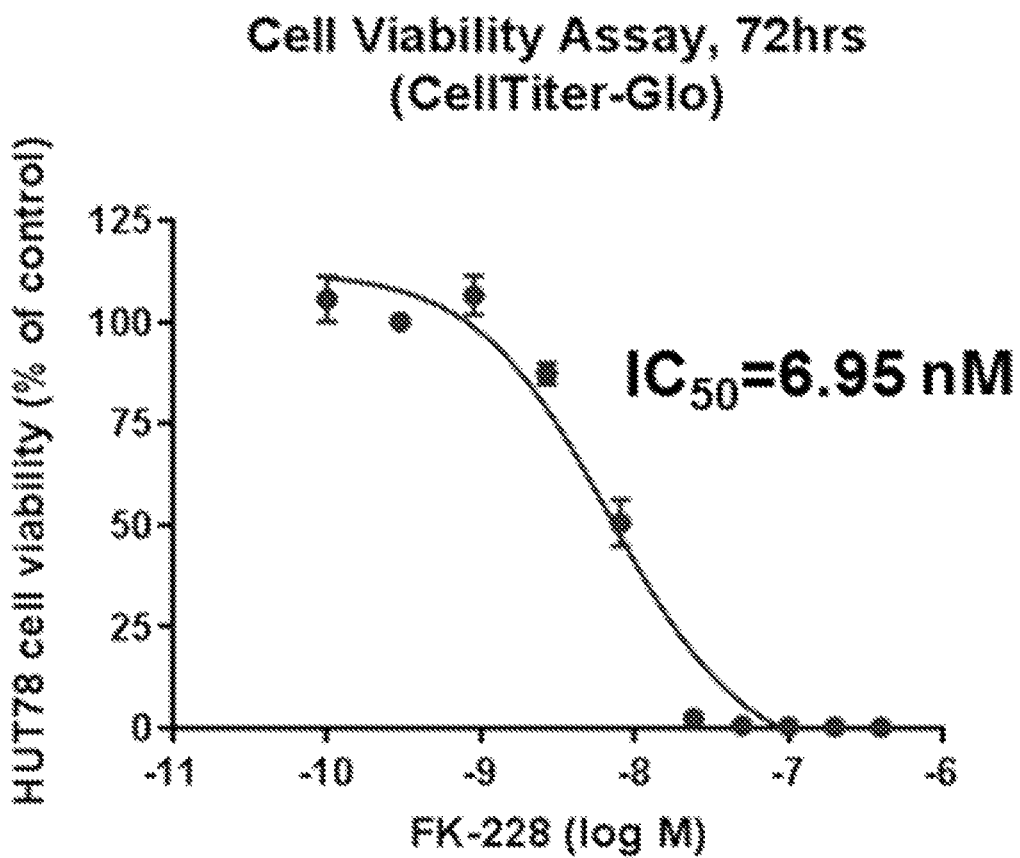
FIG. 1C shows Romidepsin (FK-228) activity against HUT78 CTCL cells.
Figure 2A:
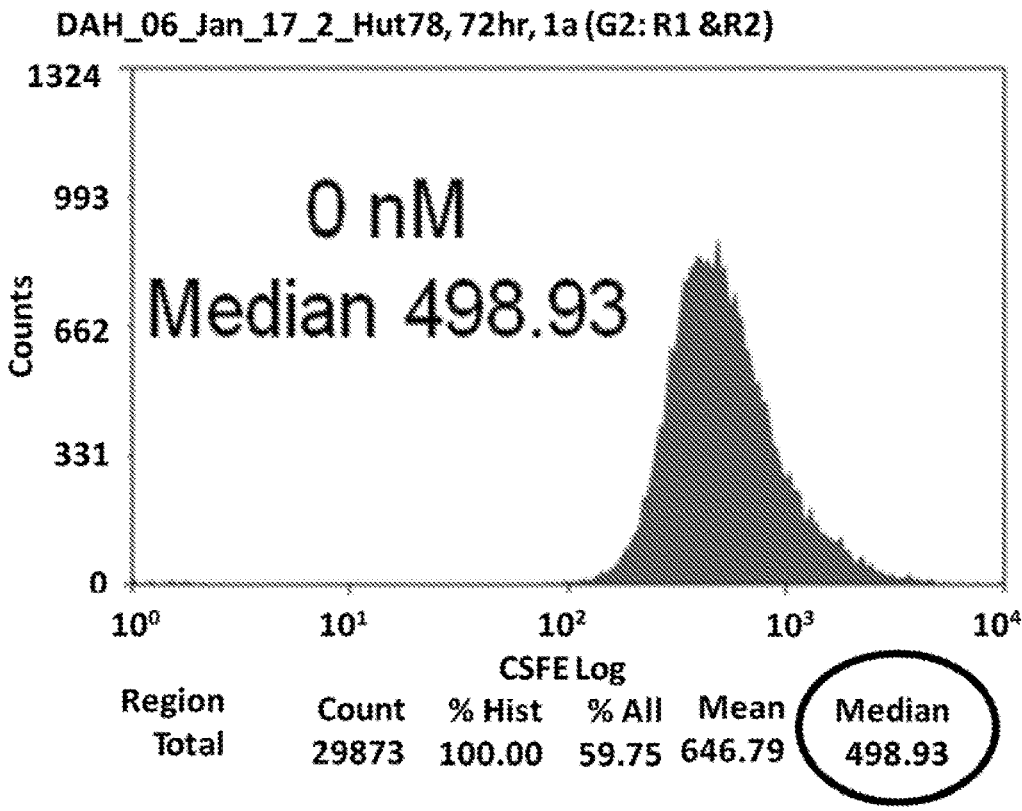
FIGS. 2A-2D show compound (1) dose-dependent HUT78 CTCL cell proliferation using carboxy-fluorescein succinimidyl ester (CFSE) staining cell proliferation assay.
Figure 2B:
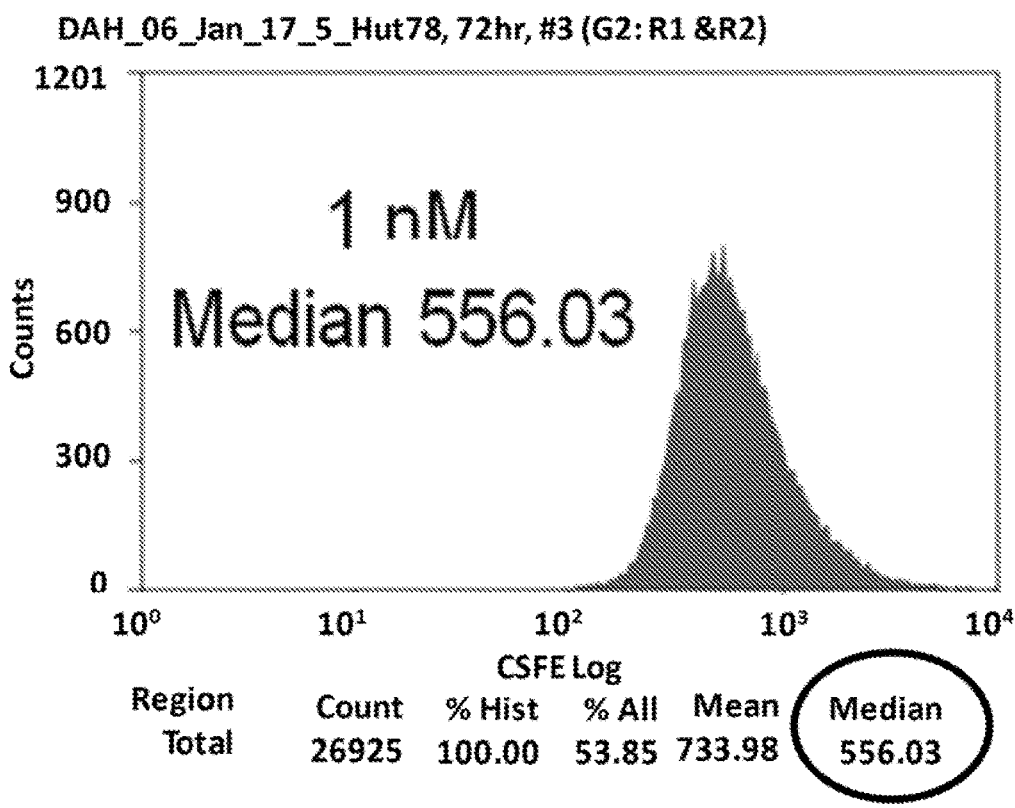
Figure 2C:
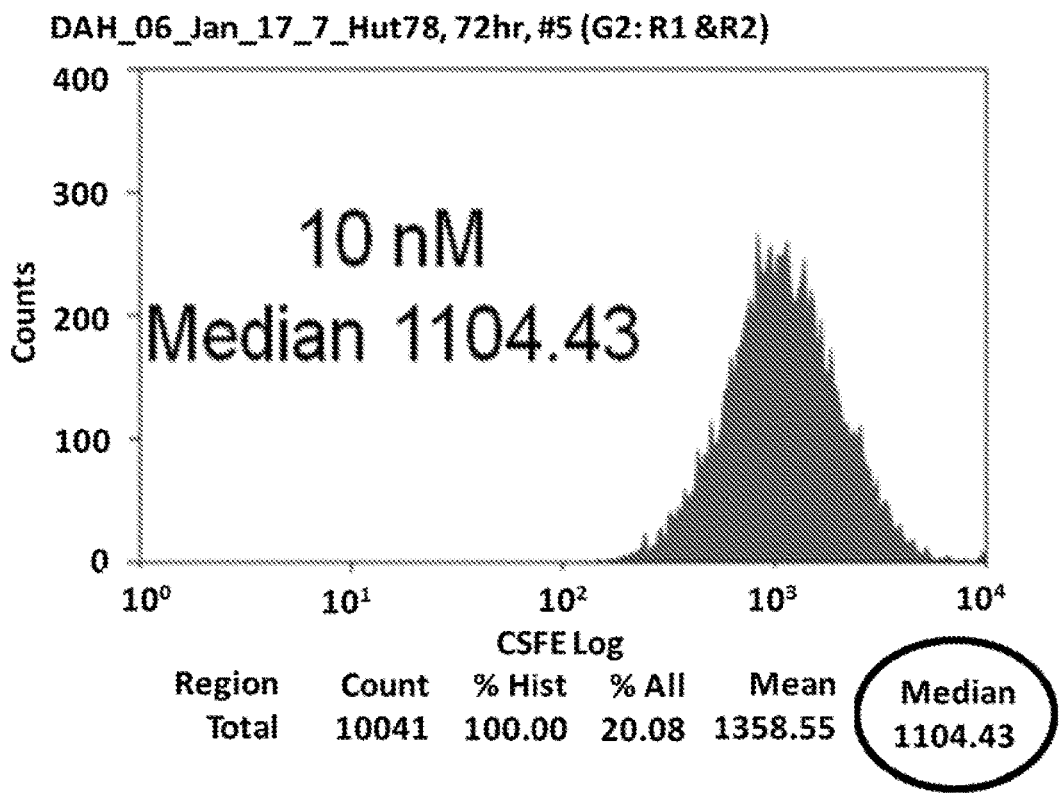
Figure 2D:
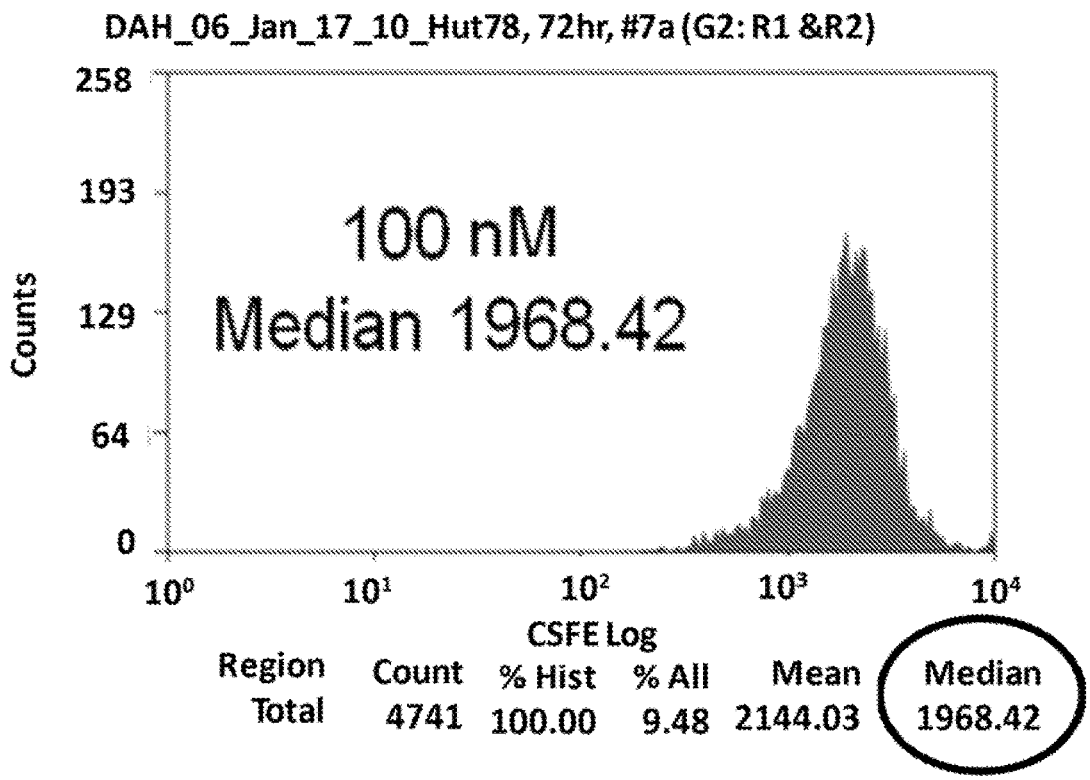

Compound (1) and FK-228 (an anticancer agent used in CTCL) were tested in a cell viability assay using HUT78 cells in a CELLTITER-GLO® assay. An IC$_{50}$ value of 6.61 nM was determined for compound (1). See, FIG. 1B. An IC$_{50}$ value of 6.95 nM was determined for FK-228. See FIG. 1C. Analysis of the results demonstrates that the compound (1) has potent antitumor activities against CTCL.

Example 8

Carboxy-Fluorescein Succinimidyl Ester (CFSE) Staining Cell Proliferation Assay

Compound (1) was tested in a carboxy-fluorescein succinimidyl ester (CFSE) stained HUT78 CTCL proliferation assay. HUT78 cells were stained with CFSE dye. The CFSE stained cells were plated into 96-well plates in growth medium. The resulted cells were treated with 1.0, 10, or 100 nM solution of compound (1), and then incubated for 72 h under the growth conditions. After, optical densities were read on a multiwell scanning spectrophotometer at wavelength 488 nm. Cells cultured in the absence of compound (1) served as a control. Analysis of the results demonstrates that the compound (1) inhibits proliferation of HUT78 CTCL cells (see FIG. 2).

Example 9

Figure 3:
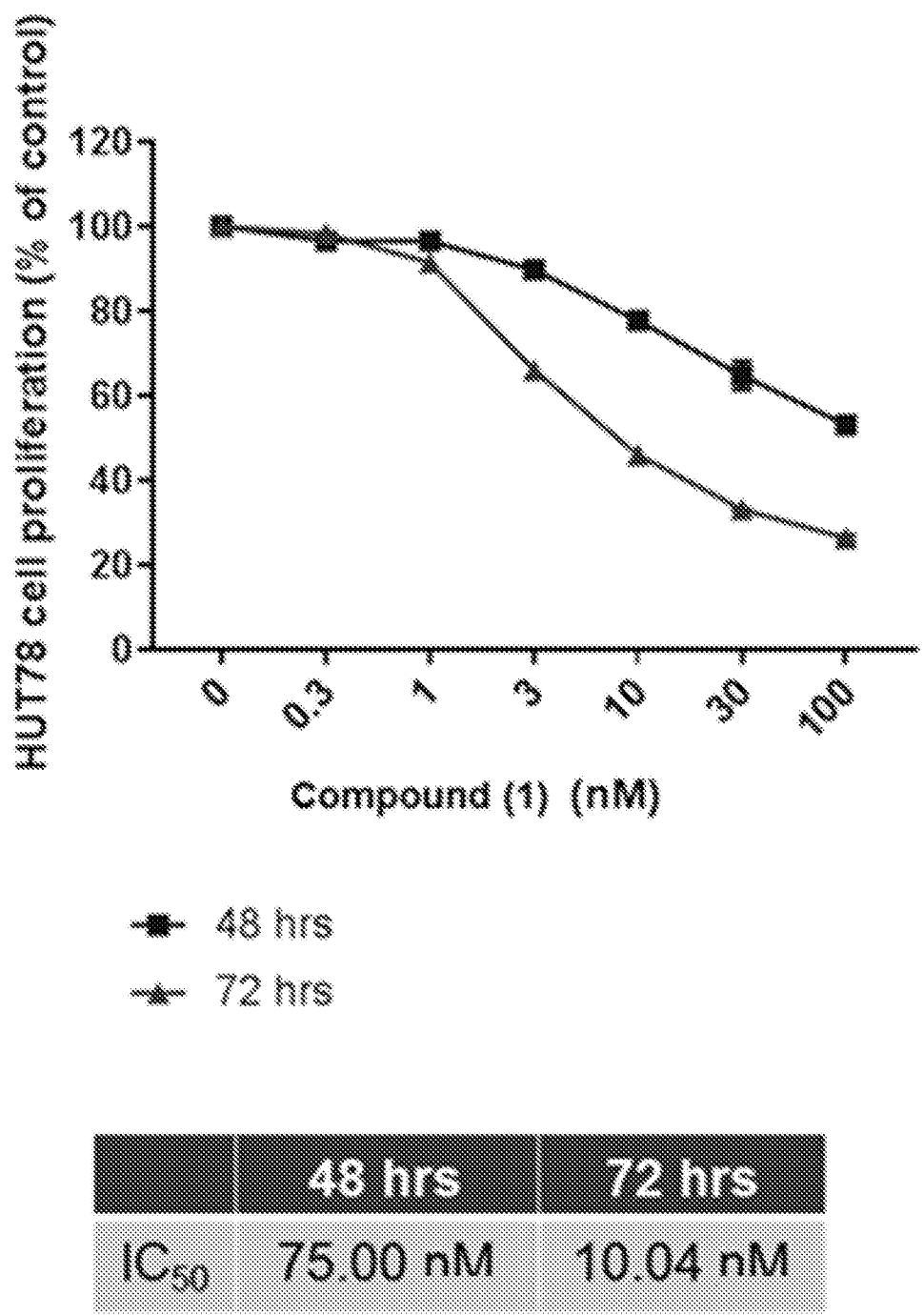
FIG. 3 illustrates inhibition of HUT78 CTCL cell proliferation by compound (1) in a dose-and-time-dependent manner.

Effects of Compound (1) on HUT78 CTCL cells
Compound (1) was tested in a cell proliferation assay using HUT78 CTCL cells. The cells were treated with 0.3, 1, 3, 10, 30, or 100 nM concentration of compound (1), and then incubated for 48 h or 72 h under the growth conditions. An $IC_{50}$ value of 75.00 nM was determined when the cells were incubated in the growth media for 48 h. An $IC_{50}$ value of 10.04 nM was determined when the cells were incubated in the growth media for 72 h. Cells cultured in the absence of compound (1) served as a control. Analysis of the results demonstrates that the compound (1) inhibits proliferation of HUT78 CTCL cells in a dose- and time-dependent manner (see FIG. 3)

Example 10

Induction of Apoptosis by Compound (1)

Figure 4:
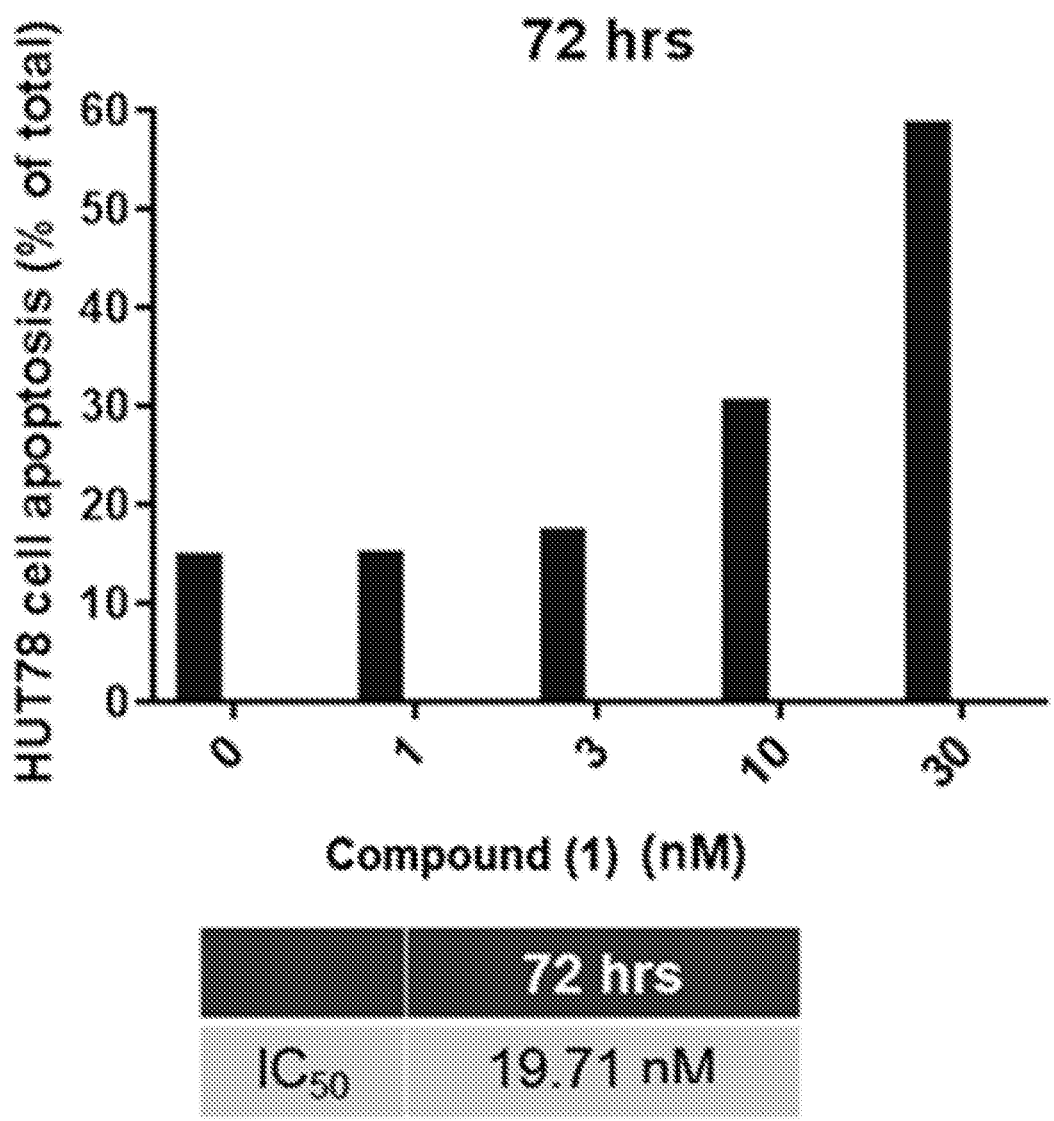
FIG. 4 illustrates apoptosis of HUT78 CTCL cells by compound (1) in a dose-dependent manner.

Compound (1) was tested in a cell apoptosis assay using HUT78 CTCL cells. The cells were treated with 1, 3, 10, or 100 nM concentration of compound (1), and then incubated for 72 h under the growth conditions. An $IC_{50}$ value of 19.71 nM was determined after the cells were incubated in the growth media for 72 h. Cells cultured in the absence of compound (1) served as a control. Analysis of the results demonstrates that the compound (1) induces apoptosis of HUT78 CTCL cells in a dose-dependent manner (see FIG. 4).

Example 11

Figure 5:
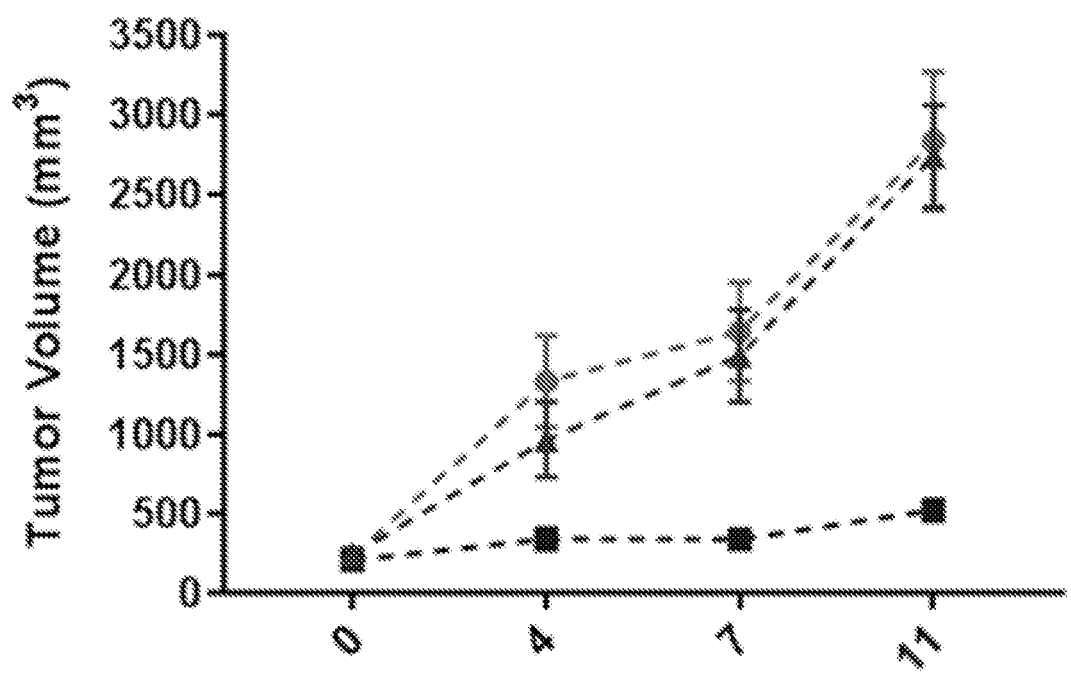
FIG. 5 illustrates tumor volume comparison in compound (1) regimen (squares) versus FK-228 regimen (triangles) using a HUT78 CTCL mouse xenograft model.
Figure 6:
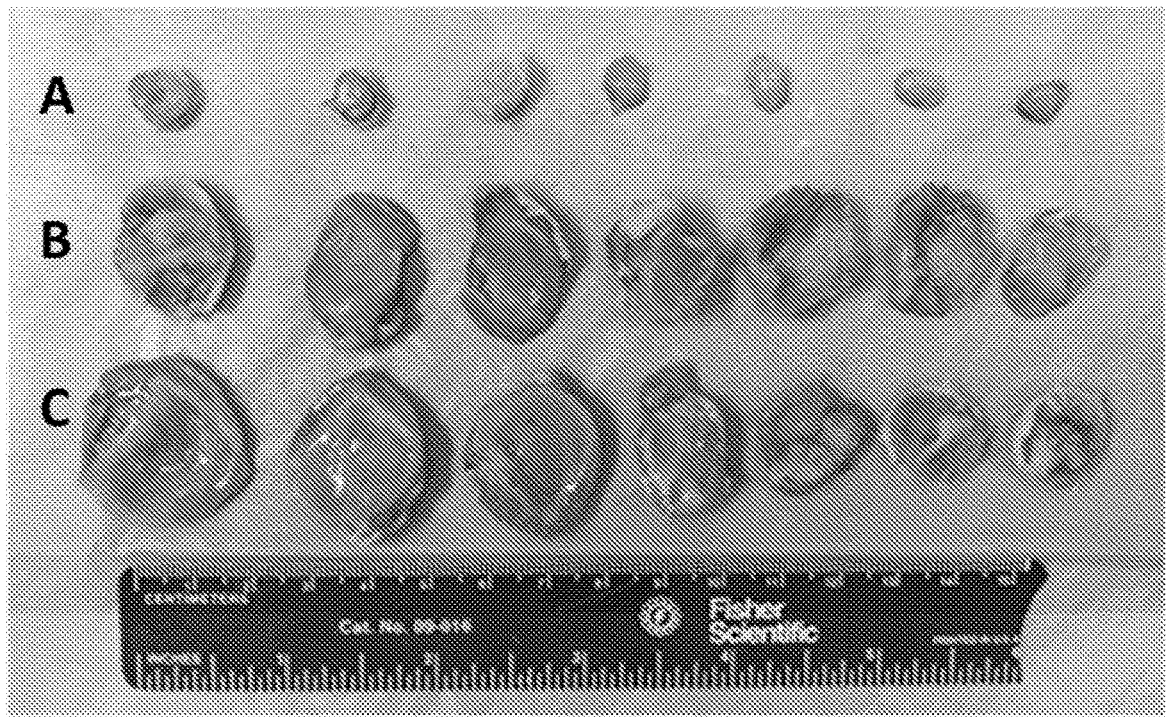
FIG. 6 illustrates tumor size comparison in compound (1) regimen versus FK-228 regimen using a HUT78 CTCL mouse xenograft model.

Tumor Volume, Size, and Weight Comparison in Compound (1) Regimen Versus FK-228 Regimen in HUT78 CTCL Mouse Xenograft Model Compound (1) and FK-228 were tested for tumor growth inhibition in CTCL mouse xenograft models. One group of mice was treated with 20 mg/kg of compound (1) using gavage during 3 consecutive days, followed by 3 consecutive days of break. Another group of mice was treated with 2 mg/kg of FK-228 intraperitoneal, twice weekly. Mice with no treatment served as a control. The tumor volume, size, and weight were compared 12 days after the treatments started. Analysis of the results demonstrates that compound (1) regimen (squares) results in tumor growth inhibition, compared to the FK-228 regimen (triangles), and to the vehicle (circles) (FIG. 5). Compound (1) regimen also results in the reduction of the tumor size (FIG. 6).

Figure 7:
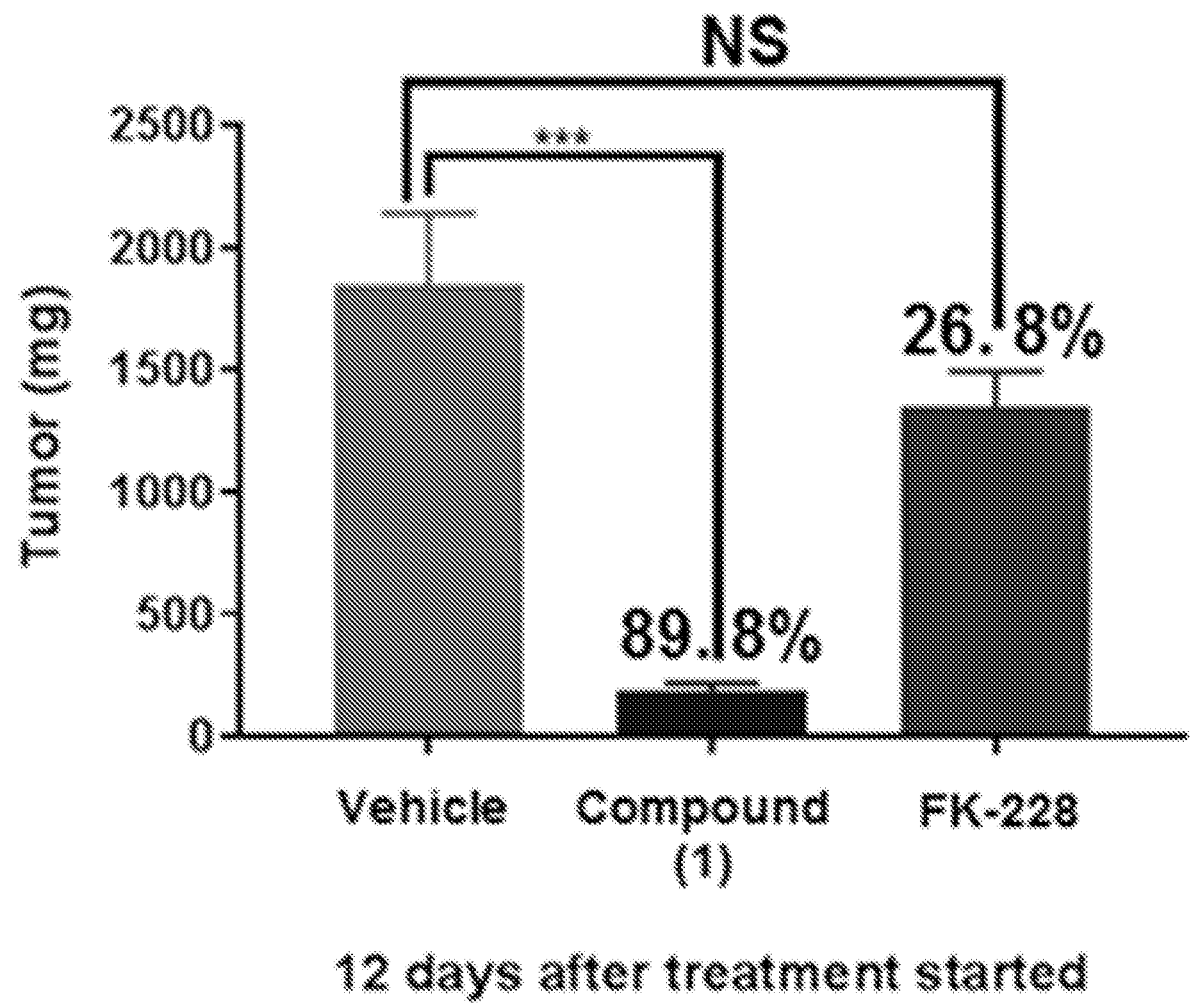
FIG. 7 illustrates tumor weight comparison in compound (1) regimen versus FK-228 regimen using a HUT78 CTCL mouse xenograft model.

Ascites and diarrhea in mice were observed in romidespin regimen, suggesting drug associated toxicity, while no toxicity was observed in compound (1) regimen. The tumor weight inhibition in a HUT78 CTCL mouse xenograft model was 89.8% in compound (1) regimen (P<0.001), suggesting compound (1) exhibited significantly more potent in vivo efficacy than romidepsin (FIG. 7).

Example 12

Phase 1/2 Study to Evaluate Safety of Compound 1 in Subjects with Cutaneous T-Cell Lymphoma (CTCL)

The primary objective of this study is to characterize the safety, tolerability, and dose-limiting toxicities (DLTs) of compound (1) when administered orally to patients with CTCL that has relapsed (returned after responding to previous treatment) or is refractory (has not responded to previous treatment).

Study Objectives

The safety and tolerability of multiple doses of compound (1);

The effect of multiple doses of compound (1) on relapsed CTCL; and

The effect of multiple doses of compound (1) on refractory CTCL.

Patients: Eligible subjects will be men and women 18 years and old. Healthy volunteers are not eligible.

Inclusion Criteria:

Histologically confirmed diagnosis of CTCL including:
  a. Mycosis fungoides
  b. Sézary syndrome
  c. Primary cutaneous anaplastic large cell Stage Ib to IVb disease Progression of disease (PD) or relapse of disease after at least 1 previous systemic therapy, PD after last prior treatment regimen, and recovered from the toxic effects of prior therapy Eastern Cooperative Oncology Group (ECOG) Performance Status ≤2

Age >18 years, of either sex

Life expectancy ≥3 months

Adequate blood, liver, and kidney function as determined by laboratory tests

Female patients with childbearing potential must be using a hormonal contraceptive, intra uterine device, diaphragm with spermicide, or condom with spermicide for the duration of the study. Women of childbearing potential must have a negative serum or urinary hCG pregnancy test Male patients, who are not surgically sterile, must use a condom with spermicide for the duration of the study Have given written informed consent, prior to any study related procedure not part of the patient's normal medical care, with the understanding that consent may be withdrawn by the patient at any time without prejudice to future medical care Exclusion Criteria:

Active concurrent malignancy (except non-melanoma skin cancer or carcinoma in situ of the cervix). If there is a history of prior malignancy, the patient must be disease-free for ≥5 years. Patients with other prior malignancies <5 years before study entry may be enrolled if treatment resulted in complete resolution of the cancer and currently have no clinical, radiologic, or laboratory evidence of active or recurrent disease Have participated in any other investigational study or received an experimental therapeutic procedure considered to interfere with the study in the 2 months preceding this study Human immunodeficiency virus (HIV)-positive diagnosis with a CD4 count of <100 mm3 or detectable viral load within the past 3 months, and is receiving combination anti-retroviral therapy Have had PUVA, topical nitrogen mustard, spot or total skin electron beam therapy, oral retinoids, or any, immunotherapy (e.g. interferon-α, denileukin difitox, alemtuzumab) or chemotherapy regimen within 2 weeks of this study. Patients must have recovered from all acute toxicities Evidence of CNS lymphoma Active uncontrolled infection, underlying medical condition that would impair ability to receive protocol treatment Uncontrolled medical conditions, requiring surgical or pharmacological treatment (exceptions must be approved by the Study Director)

Serious concomitant disease (e.g. significant cardiac disease) are not eligible

Primary or acquired thrombocytopenia

Inadequate bone marrow reserve: WBC <3.5×10^9/L, neutrophils <1.0×10^9/L, thrombocytes <100×10^9/L, Hb<8.5 g/dL or coagulation abnormalities Inadequate liver function: total bilirubin >1.5×upper limit of normal values (ULN), AST, ALT, or alkaline phosphatase >2.5×ULN Have inadequate renal function, defined by serum creatinine >250 μmol/L Retinopathy, history of retinal laser surgery, or an ERG <50% of normal Study Design:

Allocation: Non-Randomized

Endpoint Classification: Safety/Efficacy Study

Intervention Model: Parallel Assignment

Masking: Open Label

Primary Purpose: Treatment

Primary Outcome Measures:

The primary objective of this study is to characterize the safety, which includes the tolerability and dose-limiting toxicity (DLT), of compound (1) when administered to subjects with CTCL. Specifically, this measure will be assessed by number of subjects experiencing treatment emergent adverse events indicative of DLT [Time Frame: Assessed at the end of every even-numbered cycle (every 8 weeks) for the first 6 months, then every 4 cycles (16 weeks)]

Secondary Outcome Measures:

The assessment of patient-reported changes of pruritus during treatment [Time Frame: Monthly]

Responses in index lesions assessed by lesion measurements with photographic supporting documentation [Time Frame: Monthly]

Duration of Response (DOR) [Time Frame: Day 1 until disease progression/recurrence, or up to 12 months (Lead-in) and Day 1 until disease progression/recurrence, or up to 30 months]

Time to Response (TTR) [Time Frame: Up to 12 months (Lead-in) and up to 30 months]

Objective Response Rate (ORR) [Time Frame: Day 1 until disease progression/recurrence, up to 12 months (Lead-in) and Day 1 until disease progression/recurrence, up to 30 months]

Example 13

Synthesis and Characterization Data

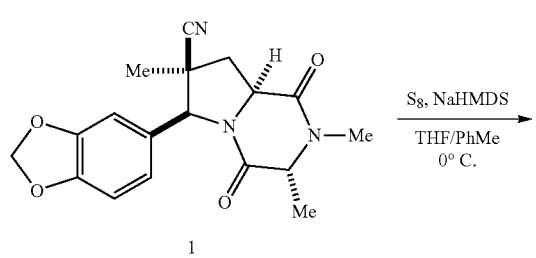

1

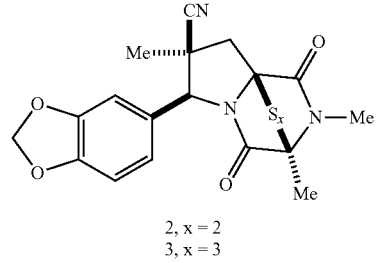

2, x = 2
3, x = 3

Scheme 2: Synthesis of racemic ETP derivatives described herein

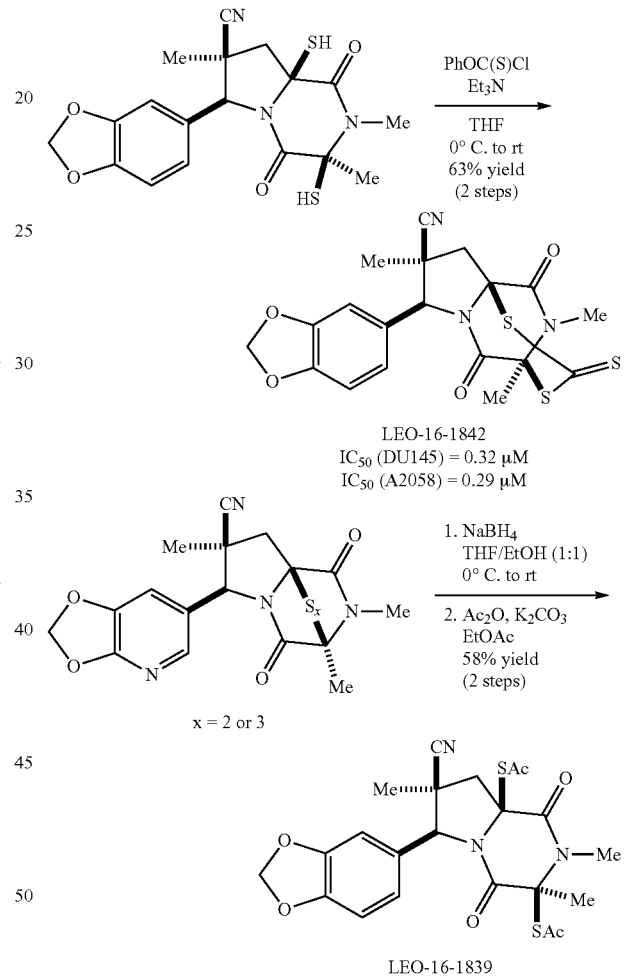

Rel-(3S,6S,7S,8aS)-6-(benzo[d][1,3]dioxol-5-yl)-2,3,7-trimethyl-1,4-dioxohexahydro-6H-3,8a-epidithiopyrrolo[1,2-a]pyrazine-7-carbonitrile (2) and Rel-(3S,6S,7S,8aS)-6-(benzo[d][1,3]dioxol-5-yl)-2,3,7-trimethyl-1,4-dioxohexahydro-6H-3,8a-epitrithiopyrrolo[1,2-a]pyrazine-7-carbonitrile (3). A three-neck 250 mL round bottom flask was fitted with an overhead mechanical stirrer with a grease-sealed glass fitting. The flask was charged with 1 (2.07 g, 6.1 mmol) and S$_8$ (1.56 g, 6.1 mmol) and fitted with two rubber septa. The flask was evacuated under vacuum and back-filled with Ar three times. The solids were suspended in anhydrous THF (60 mL) and the suspension was cooled in an ice bath. After 5 min., a solution of NaHMDS (0.6 M in PhMe, 60 mL, 36 mmol) was added over 10 min with vigorous stirring. The reaction was maintained at 0° C. for 3 h. The reaction was quenched with sat. aq. NH$_4$Cl (50 mL) and H$_2$O (50 mL). The biphasic mixture was extracted with EtOAc (3×150 mL). The combined organic extracts were dried over Na$_2$SO$_4$, filtered, and concentrated in vacuo. Flash chromatography (30×250 mm of SiO$_2$, 5 to 10% EtOAc in CH$_2$Cl$_2$ gradient elution) afforded a 2:1 mixture of 2 and 3 (880 mg, ca. 2.12 mmol, 35% yield) as an off-white solid.

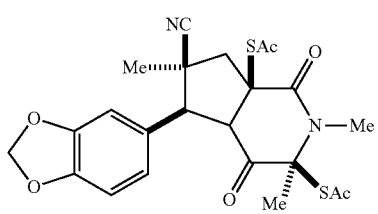

4

Rel-S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) diethanethioate (4, LEO-16-1833). A mixture of 2 and 3 (53 mg, ca. 0.13 mmol) was suspended in degassed THF/EtOH (1:1, 1.3 mL) under Ar. The suspension was cooled in an ice bath. NaBH$_4$ (17 mg, 0.44 mmol) was added in 3 portions over 3 min. After 5 min, the cold bath was removed and the reaction was maintained at room temperature for 1 h. The solvent was removed in vacuo. The crude residue was suspended in EtOAc (2.5 mL) and K$_2$CO$_3$ (35 mg, 0.25 mmol) was added. Ac$_2$O (30 μL, 0.32 mmol) was added and the reaction was maintained for 17 h. The reaction was diluted with H$_2$O (10 mL) and extracted with EtOAc (3×10 mL). The combined organic extracts were dried over Na$_2$SO$_4$, filtered, and concentrated in vacuo. Flash chromatography (12×150 mm of SiO$_2$, 10% EtOAc in CH$_2$Cl$_2$) afforded bis-thioacetate 4 (60 mg, 0.12 mmol, 92% yield) as a colorless solid. $^1$H NMR (500 MHz, CDCl$_3$): δ 6.97 (s, 1H), 6.88 (d, J=8.1 Hz, 1H), 6.84 (d, J=8.1 Hz, 1H), 6.00 (s, 2H), 4.86 (s, 1H), 4.34 (d, J 14.6 Hz, 1H), 3.18 (s, 3H), 2.41-2.37 (m, 7H), 2.10 (s, 3H), 1.70 (s, 3H); $^{13}$C NMR (125 MHz, CDCl$_3$): δ 191.9 (C), 191.8 (C), 164.9 (C), 162.8 (C), 148.3 (C), 148.2 (C), 129.2 (C), 120.9 (C), 120.0 (CH), 108.8 (CH), 106.7 (CH), 101.5 (CH$_2$), 73.6 (C), 73.2 (CH), 72.1 (C), 44.8 (CH$_2$), 42.4 (C), 31.6 (CH$_3$), 31.5 (CH$_3$), 31.1 (CH$_3$), 25.3 (CH$_3$), 23.4 (CH$_3$); IR (thin film): 3059, 2986, 2919, 1693, 1504, 1492, 1446, 1366, 1252, 1105 cm$^{-1}$; HRMS (ESI) calculated for C$_{22}$H$_{23}$N$_3$O$_6$S$_2$ (M−Na) 512.0926, observed 512.0909.

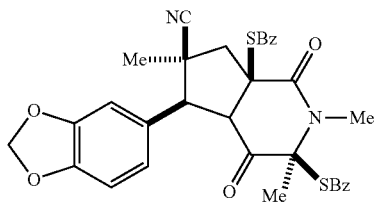

5

Rel-S,S'-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) dibenzothioate (5, LEO-16-1836). Prepared in analogous fashion to compound 4 from a mixture of 2 and 3 (51 mg, ca. 0.12 mmol) and benzoyl chloride (30 μL, 0.26 mmol). Afforded 5 (48 mg, 0.079 mmol, 66% yield) as a colorless solid. $^1$H NMR (600 MHz, CDCl$_3$): δ 7.90 (d, J=7.3 Hz, 2H), 7.87 (d, J=7.3 Hz, 2H), 7.62 (app t, J=7.4 Hz, 1H), 7.55 (app t, J=7.4 Hz, 1H), 7.46 (app t, J 7.7 Hz, 2H), 7.39 (app t, J=7.8 Hz, 2H), 7.01 (s, 1H), 6.92 (d, J=8.0 Hz, 1H), 6.79 (d, J=8.0 Hz, 1H), 5.98 (s, 2H), 4.94 (s, 1H), 4.43 (d, J=14.8 Hz, 1H), 3.29 (s, 3H), 2.59 (d, J=14.8 Hz, 1H), 2.23 (s, 3H), 1.73 (s, 3H); $^{13}$C NMR (125 MHz, CDCl$_3$): δ 188.35 (C), 188.32 (C), 165.1 (C), 163.2 (C), 148.3 (C), 148.2 (C), 137.1 (C), 136.9 (C), 134.2 (CH), 134.0 (CH), 129.2 (C), 129.0 (2CH), 128.9 (2CH), 128.0 (2CH), 127.8 (2CH), 120.8 (C), 120.0 (CH), 108.8 (CH), 107.0 (CH), 101.5 (CH$_2$), 74.0 (C), 73.4 (CH), 72.0 (C), 45.8 (CH$_2$), 42.4 (C), 31.4 (CH$_3$), 25.3 (CH$_3$), 24.2 (CH$_3$); IR (thin film): 1682, 1491, 1446, 1360, 1251, 1200, 1038 cm$^{-1}$; HRMS (ESI) calculated for C$_{32}$H$_{27}$N$_3$O$_6$S$_2$Na (M−Na) 636.1239, observed 636.1212.

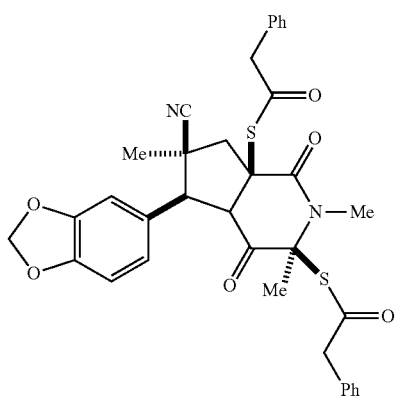

6

Rel-S,S'-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) bis(2-phenylethanethioate) (6, LEO-16-1835). Prepared in analogous fashion to compound 4 from a mixture of 2 and 3 (53 mg, ca. 0.13 mmol) and phenylacetyl chloride (40 μL, 0.30 mmol). Afforded 6 (59 mg, 0.091 mmol, 70% yield) as a colorless foam. $^1$H NMR (600 MHz, CDCl$_3$): δ 7.39 (app t, J=7.4 Hz, 2H), 7.34 (app t, J=6.7 Hz, 2H), 7.31-7.25 (m, 6H), 6.91 (s, 1H), 6.82-6.79 (m, 1H), 6.78 (d, J=8.0 Hz, 1H), 6.03 (d, J=1.3 Hz, 1H), 6.02 (d, J=1.3 Hz, 1H), 4.83 (s, 1H), 4.27 (d, J=14.6 Hz, 1H), 3.88 (d, J=16.1 Hz, 1H), 3.82 (d, J=16.1 Hz, 1H), 3.74 (app s, 2H), 3.09 (s, 3H), 2.36 (d, J=14.6 Hz, 1H), 2.04 (s, 3H), 1.66 (s, 3H); $^{13}$C NMR (125 MHz, CDCl$_3$): δ 193.3 (C), 193.2 (C), 164.9 (C), 162.5 (C), 148.3 (C), 148.2 (C), 132.6 (C), 132.3 (C), 130.3 (2CH), 129.9 (2CH), 129.1 (C), 129.0 (2CH), 128.7 (2CH), 127.9 (CH), 127.8 (CH), 120.9 (C), 120.0 (CH), 108.7 (CH), 106.8 (CH), 101.5 (CH$_2$), 73.8 (C), 73.1 (CH), 71.8 (C), 51.2 (CH$_2$), 50.9 (CH$_2$), 44.9 (CH$_2$), 42.3 (C), 30.9 (CH$_3$), 25.2 (CH$_3$), 23.3 (CH$_3$); IR (thin film): 3062, 3030, 2905, 1690, 1492, 1446, 1361, 1251, 1038 cm$^{-1}$; HRMS (ESI) calculated for C$_{34}$H$_{31}$N$_3$O$_6$S$_2$Na (M−Na), 664.1552, observed 664.1559.

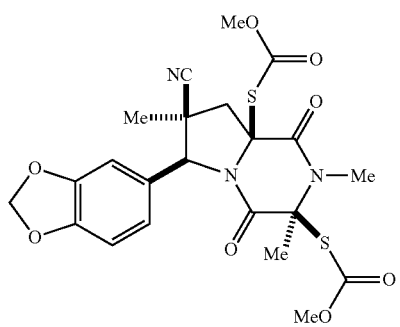

7

Rel-S,S'-((3S,6S,7S,8aS)-6-(benzo[d][1,3]dioxol-5-yl)-7-isocyano-2,3,7-trimethyl-1,4-dioxohexahydropyrrolo[1,2-a]pyrazine-3,8a(6H)-diyl) O,O'-dimethyl bis(carbonothioate) (7, LEO-16-1837). Prepared in analogous fashion to compound 4 from a mixture of 2 and 3 (48 mg, ca. 0.12 mmol) and methyl chloroformate (20 µL, 0.26 mmol). Afforded 7 (36 mg, 0.070 mmol, 57% yield) as a colorless solid. $^1$H NMR (500 MHz, CDCl$_3$): δ 6.93 (d, J=1.3 Hz, 1H), 6.89 (dd, J=8.0, 1.3 Hz, 1H), 6.82 (d, J=8.0 Hz, 1H), 5.97 (s, 2H), 4.90 (s, 1H), 4.40 (d, J=14.7 Hz, 1H), 3.85 (s, 3H), 3.79 (s, 3H), 3.16 (s, 3H), 2.42 (d, J=14.7 Hz, 1H), 2.10 (s, 3H), 1.70 (s, 3H); $^{13}$C NMR (125 MHz, CDCl$_3$) δ 166.6 (C), 166.4 (C), 165.2 (C), 1862.8 (C), 148.3 (C), 148.2 (C), 129.0 (C), 120.8 (C), 119.9 (CH), 108.7 (CH), 106.8 (CH), 101.5 (CH$_2$), 73.2 (CH), 72.9 (C), 70.9 (C), 54.9 (CH$_3$), 54.8 (CH$_3$), 45.2 (CH$_2$), 42.1 (CH), 30.6 (CH$_3$), 25.3 (CH$_3$), 23.9 (CH$_3$); IR (thin film): 2954, 1729, 1681, 1493, 1446, 1366, 1130 cm$^{-1}$; HRMS (ESI) calculated for C$_{22}$H$_{23}$N$_3$O$_8$S$_2$Na (M−Na) 544.0825, observed 544.0793.

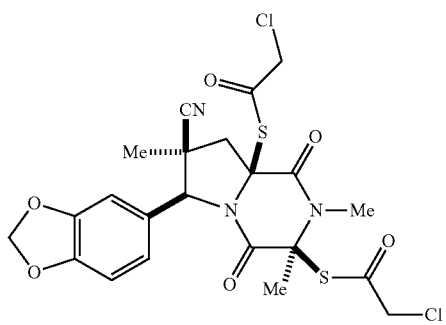

8

Rel-S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) bis(2-chloroethanethioate) (8, LEO-1840). Disulfide 2 (40 mg, 0.10 mmol) was suspended in degassed THF/EtOH (1:1, 1.0 mL) and cooled in an ice bath. Solid NaBH$_4$ (6.3 mg, 0.17 mmol) was added to the suspension. After 5 min, the cold bath was removed and the reaction was maintained for 30 min. The solvent was removed in vacuo. The residue was suspended in EtOAc (2 mL) and K$_2$CO$_3$ (32 mg, 0.23 mmol) was added. Neat chloroacetyl chloride (20 µL, 0.25 mmol) was added and the reaction was maintained for 30 min. The solution was diluted with distilled H$_2$O (5 mL) and extracted with EtOAc (3×10 mL). Combined extracts were dried over Na$_2$SO$_4$, filtered, and concentrated in vacuo. Flash chromatography (12×150 mm of SiO$_2$, 5% to 10% EtOAc in CH$_2$Cl$_2$) afforded 8 (20 mg, 0.036 mmol, 36% yield) as a colorless solid. $^1$H NMR (600 MHz, CDCl$_3$): δ 6.93 (d, J=1.2 Hz, 1H), 6.87 (dd, J=8.1, 1.2 Hz, 1H), 6.85 (d, J=8.1 Hz, 1H), 6.00 (s, 2H), 4.88 (s, 1H), 4.26 (s, 2H), 4.22 (d, J=14.6 Hz, 1H), 4.18 (s, 2H), 3.19 (s, 3H), 2.47 (d, J=14.6 Hz, 1H), 2.11 (s, 3H), 1.70 (s, 3H); $^{13}$C NMR (150 MHz, CDCl$_3$): δ 190.1 (C), 189.4 (C), 164.3 (C), 162.4 (C), 148.4 (2C), 128.7 (C), 120.7 (C), 120.0 (CH), 108.9 (CH), 106.7 (CH), 101.6 (CH$_2$), 74.5 (C), 73.4 (CH), 72.5 (C), 48.3 (CH$_2$), 48.2 (CH$_2$), 45.5 (CH$_2$), 42.4 (C), 31.3 (CH$_3$), 25.1 (CH$_3$), 23.9 (CH$_3$), missing 1C; IR (thin film): 2989, 2939, 2253, 1688, 1365, 1251, 1038, 728 cm$^{-1}$; HRMS (ESI) calculated for C$_{22}$H$_{21}$Cl$_2$N$_3$O$_6$S$_2$Na (M−Na) 580.0146, observed 580.0140.

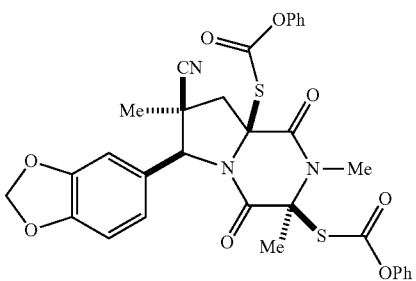

9

Rel-S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) O,O'-diphenyl bis(carbonothioate) (9, LEO-16-1841). A mixture of 2 and 3 (33 mg, ca. 0.082 mmol) was suspended in degassed THF/EtOH (1:1, 1 mL). The suspension was cooled in an ice bath and NaBH$_4$ (12.6 mg, 0.33 mmol) was added. After 5 min, the cold bath was removed and the reaction was maintained for 1 h. The solvent was removed in vacuo. The crude residue was suspended in anhydrous THF (1 mL) and cooled in an ice bath. To the cooled suspension neat Et$_3$N (50 µL, 0.36 mmol) and phenyl chloroformate (30 µL, 0.24 mmol) were added. After 1 h, the reaction was quenched with sat aq. NaHCO$_3$ (2 mL) and extracted with EtOAc (3×5 mL). Combined extracts were dried over Na$_2$SO$_4$, filtered and concentrated in vacuo. Flash chromatography ((12×150 mm of SiO$_2$, 2% to 5% EtOAc in CH$_2$Cl$_2$) afforded 9 (37 mg, 0.057 mmol, 69% yield) as a colorless solid. $^1$H NMR (500 MHz, CDCl$_3$): δ 7.40 (t, J=7.7 Hz, 4H), 7.32-7.21 (m, 4H), 7.15 (d, J=7.9 Hz, 2H), 7.07 (s, 1H), 7.00 (d, J=8.0 Hz, 1H), 6.89 (d, J=8.0 Hz, 1H), 6.04 (app s, 1H), 6.00 (app s, 1H), 5.00 (s, 1H), 4.49 (d, J=14.8 Hz, 1H), 3.27 (s, 3H), 2.48 (d, J=14.8 Hz, 1H), 2.21 (s, 3H), 1.76 (s, 3H); $^{13}$C NMR (125 MHz, CDCl$_3$): δ 165.3 (C), 165.0 (C), 164.9 (C), 162.5 (C), 150.9 (C), 150.8 (C), 148.4 (C), 148.3 (C), 129.64 (2CH), 129.63 (2CH), 128.9 (C), 126.7 (CH), 126.6 (CH), 121.5 (2CH), 121.2 (2CH), 120.8 (C), 120.1 (CH), 108.8 (CH), 106.8 (CH), 101.5 (CH$_2$), 73.4 (C), 73.3 (CH), 71.5 (C), 45.2 (CH$_2$), 42.2 (C), 30.8 (CH$_3$), 25.2 (CH$_3$), 23.9 (CH$_3$); IR (thin film): 2922, 1742, 1688, 1490, 1362, 1252, 1183, 1160, 1094, 1076 cm$^{-1}$; HRMS (ESI) calculated for C$_{32}$H$_{27}$N$_3$O$_8$S$_2$Na (M−Na) 668.1137, observed 668.1145.

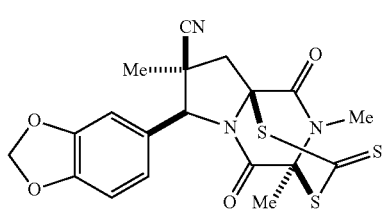

Rel-(4S,7S,8S,9aS)-7-(benzo[d][1,3]dioxol-5-yl)-4,8,11-trimethyl-5,10-dioxo-2-thioxotetrahydro-7H-4,9a-(epiminomethano)pyrrolo[2,1-d][1,3,5]dithiazepine-8-carbonitrile (10, LEO-16-1842). Prepared in analogous fashion to compound 9 from a mixture of 2 and 3 (36 mg, ca. 0.089 mmol) and phenyl chlorothionoformate (30 µL, 0.22 mmol). Afforded 10 (25 mg, 0.56 mmol, 63% yield) as a yellow solid. H NMR (600 MHz, CDCl$_3$): δ 6.83 (d, J=8.0 Hz, 1H), 6.71 (d, J=8.0 Hz, 1H), 6.69 (s, 1H), 5.98 (s, 2H), 4.91 (s, 1H), 3.12 (s, 3H), 3.10-3.06 (m, 2H), 1.89 (s, 3H), 1.70 (s, 3H); $^{13}$C NMR (125 MHz, CDCl$_3$): δ 214.0 (C), 164.6 (C), 161.4 (C), 148.7 (C), 148.5 (C), 127.6 (C), 120.3 (CH), 119.9 (C), 109.0 (CH), 106.8 (CH), 101.7 (CH$_2$), 75.0 (C), 73.6 (CH), 73.1 (C), 45.9 (CH$_2$), 43.2 (C), 28.7 (CH$_3$), 25.1 (CH$_3$), 19.9 (CH$_3$); IR (thin film): 2985, 2940, 2901, 2251, 1693, 1504, 1490, 1446, 1367, 1251, 1037 cm$^{-1}$; HRMS (ESI) calculated for C$_9$H$_{17}$N$_3$O$_4$S$_3$Na (M−Na) 470.0279, observed 470.0290.

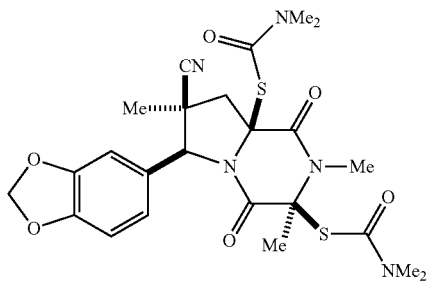

Rel-S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) bis(dimethylcarbamothioate) (11, LEO-16-1843). Prepared in analogous fashion to compound 9 from a mixture of 2 and 3 (29 mg, ca. 0.072 mmol) and phenyl chlorothionoformate (20 µL, 0.22 mmol). Afforded 11 (13 mg, 0.024 mmol, 33% yield) as a colorless solid. $^1$H NMR (500 MHz, CDCl$_3$): δ 7.05 (s, 1H), 6.90 (d, J=8.1 Hz, 1H), 6.81 (d, J=8.1 Hz, 1H), 5.97 (app s, 1H), 5.96 (app s, 1H), 4.90 (s, 1H), 4.61 (d, J=14.6 Hz, 1H), 3.21 (s, 3H), 2.08-2.94 (m, 12H), 2.37 (d, J=14.6 Hz, 1H), 2.10 (s, 3H), 1.69 (s, 3H); $^{13}$C NMR (125 MHz, CDCl$_3$): δ 165.4 (C), 163.89 (C), 163.88 (C), 163.7 (C), 148.1 (C), 148.0 (C), 129.7 (C), 121.0 (C), 120.2 (CH), 108.6 (CH), 107.0 (CH), 101.3 (CH$_2$), 73.5 (C), 73.3 (CH), 71.8 (C), 45.3 (CH$_2$), 42.2 (C), 37.2 (CH$_3$), 31.0 (2CH$_3$), 29.8 (2CH$_3$), 25.4 (CH$_3$), 24.4 (CH$_3$); IR (thin film): 2933, 2237, 1681, 1359, 1252, 1097, 1036 cm$^{-1}$; HRMS (ESI) calculated for C$_{24}$H$_{29}$N$_5$O$_6$S$_2$Na (M−Na) 570.1457, observed 570.1443.

Rel-S,S'-((3S,6S,7S,8aS)-6-(benzo[d][1,3]dioxol-5-yl)-7-cyano-2,3,7-trimethyl-1,4-dioxohexahydropyrrolo[1,2-a]pyrazine-3,8a(6H)-diyl) bis(2-methoxyethanethioate) (12, LEO-16-1844). A mixture of 2 and 3 (33 mg, ca. 0.080 mmol) was suspended in degassed THF/EtOH (1:1, 1 mL). The suspension was cooled in an ice bath and NaBH$_4$ (12.1 mg, 0.32 mmol) was added. After 5 min, the cold bath was removed and the reaction was maintained for 1.5 h. The solvent was removed in vacuo. The crude residue was suspended in anhydrous THF (1 mL) and cooled in a −78° C. bath. To the cooled suspension neat Et$_3$N (40 µL, 0.29 mmol) and 2-methoxyacetyl chloride (20 µL, 0.22 mmol) were added. After 1 h, the reaction was quenched with sat aq. NaHCO$_3$ (2 mL) and extracted with EtOAc (3×5 mL). Combined extracts were dried over Na$_2$SO$_4$, filtered and concentrated in vacuo. Flash chromatography (12×150 mm of SiO$_2$, 2% to 5% EtOAc in CH$_2$Cl$_2$) afforded 12 (26 mg, 0.047 mmol, 58% yield) as a colorless solid. $^1$H NMR (500 MHz, CDCl$_3$): δ 6.97 (s, 1H), 6.88 (d, J=8.0 Hz, 1H), 6.82 (d, J=8.0 Hz, 1H), 5.98 (S, 2H), 4.88 (S, 1H), 4.34 (d, J=14.7 Hz, 1H), 4.15 (d, J=16.3 Hz, 1H), 4.13-4.01 (m, 3H), 3.54 (s, 3H), 3.49 (s, 3H), 3.16 (s, 3H), 2.44 (d, J=14.7 Hz, 1H), 2.09 (s, 3H), 1.70 (s, 3H). $^{13}$C NMR (125 MHz, CDCl$_3$): δ 196.18 (C), 196.17 (C), 165.0 (C), 162.9 (C), 148.3 (C), 148.2 (C), 129.2 (C), 121.0 (C), 120.0 (CH), 108.7 (CH), 106.7 (CH), 101.5 (CH$_2$), 77.8 (CH$_2$), 77.7 (CH$_2$), 73.3 (C), 73.1 (CH), 71.1 (C), 60.44 (CH$_3$), 60.43 (CH$_3$), 44.9 (CH$_2$), 42.3 (C), 31.0 (CH$_2$), 25.3 (CH$_3$), 23.8 (CH$_3$); IR (thin film): 2992, 2935, 2830, 2253, 1693, 1492, 1446, 1364, 1251, 1196, 1123, 1038 cm$^{-1}$; HRMS (ESI) calculated for C$_{24}$H$_{27}$N$_3$O$_8$S$_2$Na (M−Na) 572.1137, observed 572.1130.

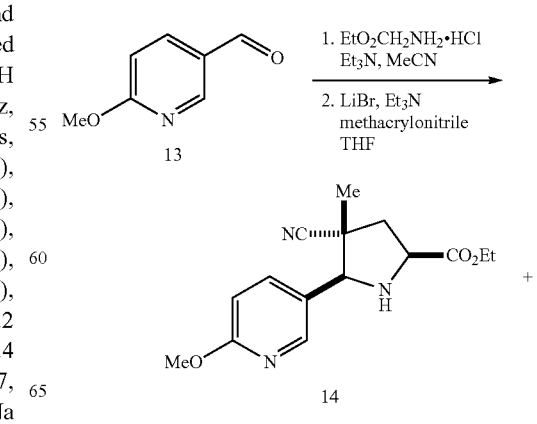

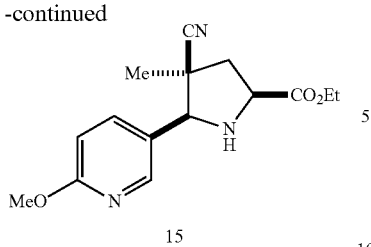

15

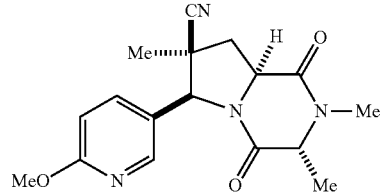

16

Ethyl Rel-(2S,4R,5S)-4-cyano-5-(6-methoxypyridin-3-yl)-4-methylpyrrolidine-2-carboxylate (14) and ethyl Rel-(2S,4S,5S)-4-cyano-5-(6-methoxypyridin-3-yl)-4-methylpyrrolidine-2-carboxylate (15). A 100 mL round-bottom flask was charged with 2-methoxypyridine-5-carbaldehyde (13, 1.33 g, 9.92 mmol) and glycine ethyl ester hydrochloride (1.66 g, 11.9 mmol) and MeCN (20 mL). To the suspension was added Et$_3$N (1.5 mL, 10.8 mmol) and the mixture was stirred vigorously for 16 h. The solvent was removed in vacuo and the crude residue was diluted with H$_2$O (20 mL) and extracted with CH$_2$Cl$_2$ (3×20 mL). Combined organic extracts were dried over Na$_2$SO$_4$, filtered through cotton, and concentrated in vacuo. The crude imine (2.11 g, 9.49 mmol, 96% yield) was dissolved in anhydrous THF (16 mL) under Ar. To the suspension was added LiBr (990 mg, 11.4 mmol) and Et$_3$N (1.6 mL, 11.5 mmol). After 2 min, methacrylonitrile (1.2 mL, 14.3 mmol) was added to the solution and the reaction was maintained for 16 h. The reaction was concentrated in vacuo. The residue was diluted with brine (20 mL) and extracted with CH$_2$Cl$_2$ (3×20 mL). The combined organic extracts were dried over Na$_2$SO$_4$, filtered through cotton, and concentrated in vacuo. Flash chromatography (28×250 mm of SiO$_2$, 20% to 50% EtOAc in hexanes) afforded pyrrolidine ester 14 (300 mg, 1.04 mmol, 11% yield) as a colorless solid and pyrrolidine ester 15 (1.74 g, 6.01 mmol, 63% yield) as a pale yellow oil. Data for 14: $^1$H NMR (600 MHz, CDCl$_3$): δ 8.24 (d, J=2.5 Hz, 1H), 7.70 (dd, J=8.6, 2.5 Hz, 1H), 6.76 (d, J=8.7 Hz, 1H), 4.54 (s, 1H), 4.25 (q, J=7.1 Hz, 2H), 4.06 (app t, J=7.3 Hz, 1H), 3.94 (s, 3H), 2.75 (dd, J=13.5, 9.7 Hz, 1H), 2.60 (br s, 1H), 2.25 (dd, J=13.5, 6.1 Hz, 1H), 1.31 (t, J=7.1 Hz, 3H), 1.03 (s, 3H); $^{13}$C NMR (125 MHz, CDCl$_3$): δ 173.0 (C), 164.5 (C), 145.9 (CH), 137.8 (CH), 125.1 (C), 123.8 (C), 110.9 (CH), 67.3 (CH), 61.7 (CH$_2$), 57.2 (CH), 53.7 (CH$_3$), 41.5 (CH$_2$), 40.2 (C), 20.5 (CH$_3$), 14.3 (CH$_3$); IR (thin film): 3344, 2983, 2947, 2904, 2850, 2235, 1737, 1608, 1495, 1285, 1202, 1028 cm$^{-1}$; HRMS (ESI) calculated for C$_{15}$H$_{19}$N$_3$O$_3$ (M−Na) 312.1324, observed 312.1316. Data for 15: $^1$H NMR (600 MHz, CDCl$_3$): δ 8.12 (d, J=2.5 Hz, 1H), 7.96 (dd, J=8.6, 2.5 Hz, 1H), 6.81 (d, J=8.7 Hz, 1H), 4.33-4.23 (m, 2H), 3.97 (dd, J=9.7, 4.1 Hz, 1H), 3.93 (s, 3H), 3.90 (s, 1H), 2.83 (dd, J=13.7, 4.1 Hz, 1H), 2.69 (br s, 1H), 2.28 (dd, J=13.7, 9.7 Hz, 1H), 1.40 (s, 3H), 1.33 (t, J=7.1 Hz, 3H); $^{13}$C NMR (125 MHz, CDCl$_3$): δ 172.9 (C), 164.9 (C), 146.5 (CH), 137.7 (CH), 125.1 (C), 121.9 (C), 111.3 (CH), 69.7 (CH), 61.8 (CH$_2$), 57.3 (CH), 53.7 (CH$_3$), 43.8 (C), 42.1 (CH$_2$), 21.9 (CH$_3$), 14.3 (CH$_3$); IR (thin film): 3346, 2981, 2948, 2904, 2878, 2850, 2235, 1736, 1609, 1495, 1285, 1205, 1028 cm$^{-1}$; HRMS (ESI) calculated for C$_{15}$H$_{19}$N$_3$O$_3$ (M−Na) 312.1324, observed 312.1329.

Rel-(3R,6S,7S,8aS)-6-(6-methoxypyridin-3-yl)-2,3,7-trimethyl-1,4-dioxooctahydropyrrolo[1,2-a]pyrazine-7-carbonitrile (16). In a 100 mL round bottom flask, pyrrolidine ester 15 (1.28 g, 4.42 mmol) was dissolved in anhydrous CH$_2$Cl$_2$ (15 mL). The solution was cooled in an ice bath. To the solution was added Et$_3$N (740 μL, 5.3 mmol) and 2-chloropropionyl chloride (470 μL, 4.9 mmol). The reaction was maintained for 1 h, by which time starting material had been consumed (by TLC). The reaction was quenched with H$_2$O (10 mL) and the biphasic mixture was stirred vigorously for 10 min. The biphasic mixture was extracted with CH$_2$Cl$_2$ (3×20 mL). The organic layer was concentrated in vacuo. The crude residue was dissolved in CH$_2$Cl$_2$ (20 mL) and a solution of MeNH$_2$ (40% in H$_2$O) and the biphasic mixture was stirred vigorously for 12 h. The mixture was extracted with CH$_2$Cl$_2$ (3×20 mL). Combined extracts were dried over Na$_2$SO$_4$, filtered through cotton, and concentrated in vacuo to afford a yellow foam. The residue was dissolved in CH$_2$Cl$_2$ (10 mL) and MeOH (10 mL). The solution was stirred under a stream of air until ca. 4 mL of solution remained. The suspension was cooled in the freezer for 18 h. Filtration afforded diketopiperazine 16 (490 mg, 1.50 mmol, 34% yield as a colorless solid. $^1$H NMR (600 MHz, CDCl$_3$): δ 7.97 (d, J=2.6 Hz, 1H), 7.37 (dd, J=8.6, 2.6 Hz, 1H), 6.76 (d, J=8.6 Hz, 1H), 4.87 (s, 1H), 4.37 (dd, J=11.3, 6.6 Hz, 1H), 3.92 (s, 3H), 3.89 (q, J=7.3 Hz, 1H), 3.03 (s, 3H), 2.77 (dd, J=13.4, 11.4 Hz, 1H), 2.50 (dd, J=13.4, 6.6 Hz, 1H), 1.69 (s, 3H), 1.48 (d, J=7.3 Hz, 3H); $^{13}$C NMR (125 MHz, CDCl$_3$): δ 166.8 (C), 165.9 (C), 164.7 (C), 144.8 (CH), 136.9 (CH), 125.4 (C), 119.9 (C), 111.5 (CH), 67.4 (CH), 60.9 (CH), 56.2 (CH), 53.7 (CH$_3$), 42.5 (C), 36.9 (CH$_2$), 32.2 (CH$_3$), 25.1 (CH$_3$), 15.5 (CH$_3$); IR (thin film): 2983, 2946, 2245, 1673, 1609, 1494, 1402, 1288, 1026 cm$^{-1}$; HRMS (ESI) calculated for C$_{17}$H$_{20}$N$_4$O$_3$Na (M−Na) 351.1433, observed 351.1430.

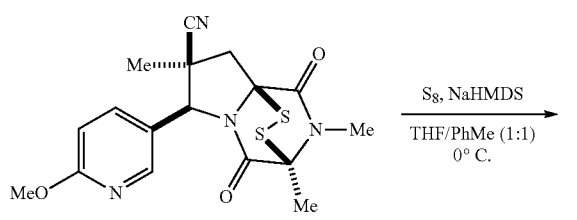

17

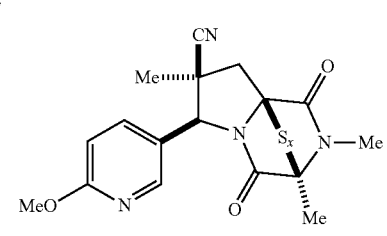

18-1, x = 2
18-2, x = 3

Rel-(3S,6S,7S,8aS)-6-(6-methoxypyridin-3-yl)-2,3,7-trimethyl-1,4-dioxohexahydro-6H-3,8a-epidithiopyrrolo[1,2-a]pyrazine-7-carbonitrile (18-1) and Rel-(3S,6S,7S,8aS)-6-(6-methoxypyridin-3-yl)-2,3,7-trimethyl-1,4-dioxohexahydro-6H-3,8a-epitrithiopyrrolo[1,2-a]pyrazine-7-carbonitrile (18-2). A 25 mL round bottom flask was charged with diketopiperazine 17 (120 mg, 0.37 mmol) and $S_8$ (100 mg, 0.39 mmol) and anhydrous TH (3.7 mL) under Ar. The suspension was cooled in an ice bath. A solution of NaHMDS (0.6 M in PhMe, 3.7 mL, 2.2 mmol) was added over 2 min. The reaction was maintained for 2 h and quenched with saturated aqueous $NH_4Cl$ (5 mL). The mixture was extracted with EtOAc (3×10 mL). The combined organic extracts were dried over $Na_2SO_4$, filtered, and concentrated in vacuo. Flash chromatography (30×250 mm of $SiO_2$, 5% to 10% acetone in $CH_2Cl_2$) afforded a mixture of 18-1 and 18-2 (68 mg, 0.17 mmol, ca. 47% yield) as a yellow solid. Data for 17: $^1$H NMR (600 MHz, $CDCl_3$): δ 8.16 (d, J=2.4 Hz, 1H), 7.64 (dd, J=8.6, 2.4 Hz, 1H), 6.84 (d, J=8.6 Hz, 1H), 4.86 (s, 1H), 3.96 (s, 3H), 3.31 (d, J=15.0 Hz, 1H), 3.08 (s, 3H), 3.00 (d, J=15.0 Hz, 1H), 1.94 (s, 3H), 1.69 (s, 3H); $^{13}$C NMR (125 MHz, $CDCl_3$): δ 165.5 (C), 165.0 (C), 162.1 (C), 145.5 (CH), 137.3 (CH), 122.5 (C), 120.2 (C), 111.7 (CH), 73.44 (C), 73.43 (C), 69.9 (CH), 53.8 ($CH_3$), 44.4 (C), 42.9 ($CH_2$), 27.9 ($CH_3$), 24.4 ($CH_3$), 18.2 ($CH_3$); IR (thin film): 2985, 2947, 2903, 2251, 1694, 1610, 1496, 1359, 1288, 1026 cm$^{-1}$; HRMS (ESI) calculated for $C_{17}H_{18}N_4O_3S_2Na$ (M−Na) 413.0718, observed 413.0716.

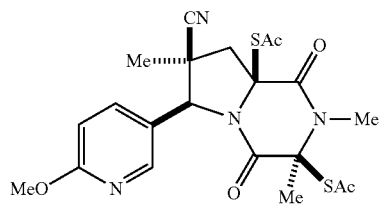

Rel-S,S'-((3S,6S,7S,8aS)-7-cyano-6-(6-methoxypyridin-3-yl)-2,3,7-trimethyl-1,4-dioxohexahydropyrrolo[1,2-a]pyrazine-3,8a(6H)-diyl) diethanethioate (19, LEO-16-1839). Prepared in analogous fashion to compound 5 from a mixture of 18-1 and 18-2 (52 mg, ca. 0.13 mmol) and acetic anhydride (40 μL, 0.42 mmol). Afforded 18 (37 mg, 0.078 mmol, 58% yield) as a colorless solid. $^1$H NMR (600 MHz, $CDCl_3$): δ 8.25 (d, J=2.5 Hz, 1H), 7.76 (dd, J=8.6, 2.5 Hz, 1H), 6.83 (d, J=8.6 Hz, 1H), 4.90 (s, 1H), 4.39 (d, J=14.6 Hz, 1H), 3.96 (s, 3H), 3.17 (s, 3H), 2.42 (d, J=14.6 Hz, 1H), 2.40 (s, 3H), 2.35 (s, 3H), 2.08 (s, 3H), 1.69 (s, 3H); $^{13}$C NMR (150 MHz, $CDCl_3$): δ 191.9 (C), 191.7 (C), 164.8 (C), 164.7 (C), 162.8 (C), 145.5 (CH), 137.0 (CH), 124.0 (C), 120.8 (C), 111.5 (CH), 73.6 (C), 72.0 (C), 71.1 (CH), 53.8 ($CH_3$), 44.7 ($CH_2$), 42.3 (C), 31.50 ($CH_3$), 31.48 ($CH_3$), 31.0 ($CH_3$), 25.1 ($CH_3$), 23.7 ($CH_3$); IR (thin film): 2980, 2923, 2850, 2361, 1686, 1610, 1496, 1365, 1288, 1109 cm$^{-1}$; HRMS (ESI) calculated for $C_{21}H_{24}N_4O_5S_2Na$ (M−Na) 499.1086, observed 499.1077.

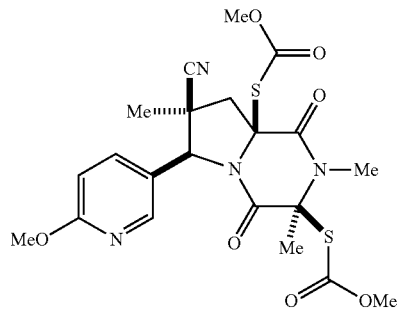

Rel-S,S'-((3S,6S,7S,8aS)-7-cyano-6-(6-methoxypyridin-3-yl)-2,3,7-trimethyl-1,4-dioxohexahydropyrrolo[1,2-a]pyrazine-3,8a(6H)-diyl) O,O'-dimethyl bis(carbonothioate) (20, LEO-16-1857). Prepared in analogous fashion to compound 7 from a mixture of 17 and 18 (55 mg, 0.14 mmol) and methyl chloroformate (30 μL, 0.39 mmol). Afforded 20 (44 mg, 0.087 mmol, 61% yield) as a colorless solid. $^1$H NMR (600 MHz, $CDCl_3$): δ 8.22 (d, J=2.5 Hz, 1H), 7.77 (dd, J=8.7, 2.5 Hz, 1H), 6.80 (d, J=8.7 Hz, 1H), 4.94 (s, 1H), 4.45 (d, J=14.8 Hz, 1H), 3.94 (s, 3H), 3.86 (s, 3H), 3.78 (s, 3H), 3.16 (s, 3H), 2.45 (d, J=14.8 Hz, 1H), 2.09 (s, 3H), 1.70 (s, 3H); $^{13}$C NMR (150 MHz, $CDCl_3$): δ 166.5 (C), 166.4 (C), 165.1 (C), 164.7 (C), 163.0 (C), 145.6 (CH), 136.9 (CH), 123.9 (C), 120.7 (C), 111.5 (CH), 72.9 (C), 71.2 (CH), 70.9 (C), 55.0 ($CH_3$), 54.8 ($CH_3$), 53.7 ($CH_3$), 45.1 ($CH_2$), 42.0 (C), 30.6 ($CH_3$), 25.0 ($CH_3$), 24.1 ($CH_3$); IR (thin film): 2984, 2954, 2255, 1731, 1688, 1496, 1366, 1289, 1190, 1129 cm$^{-1}$; HRMS (ESI) calculated for $C_{21}H_{24}N_4O_7S_2Na$ (M−Na) 531.0984, observed 531.1003.

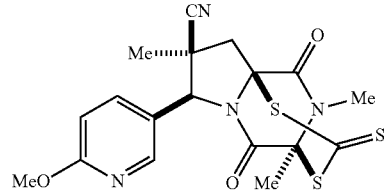

Rel-(4S,7S,8S,9aS)-7-(6-methoxypyridin-3-yl)-4,8,11-trimethyl-5,10-dioxo-2-thioxotetrahydro-7H-4,9a-(epiminomethano)pyrrolo[2,1-d][1,3,5]dithiazepine-8-carbonitrile (21, LEO-16-1858). Prepared in analogous fashion to compound 9 from a mixture of 17 and 18 (54 mg, ca. 0.14 mmol) and phenyl chlorothionoformate (30 μL, 0.22 mmol). Afforded 21 (22 mg, 0.56 mmol, 36% yield) as a yellow solid. $^1$H NMR (600 MHz, $CDCl_3$): δ 8.15 (d, J=2.5 Hz, 1H), 7.49 (dd, J=8.7, 2.5 Hz, 1H), 6.86 (d, J=8.7 Hz, 1H), 5.01 (s, 1H), 3.99 (s, 3H), 3.18-3.14 (m, 5H), 1.94 (s, 3H), 1.76 (s, 3H); $^{13}$C NMR (150 MHz, $CDCl_3$): δ 213.7 (C), 165.0 (C), 164.5 (C), 161.5 (C), 145.6 (CH), 136.7 (CH), 122.6 (C), 119.7 (C), 112.0 (CH), 75.0 (C), 73.0 (C), 71.3 (CH), 53.9 ($CH_3$), 45.8 ($CH_2$), 43.0 (C), 28.7 ($CH_3$), 24.7 ($CH_3$), 19.9 ($CH_3$); IR (thin film): 2985, 2946, 2240, 1690, 1495, 1369, 1288, 1002, 731 cm$^{-1}$; HRMS (ESI) calculated for $C_{18}H_{18}N_4O_3S_3Na$ (M−Na) 457.0439, observed 457.0425.

297

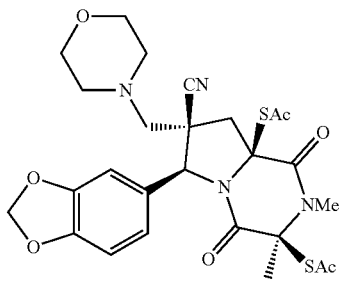

Leo-16-1862 v(R, S, S, S)-enentiomer. 1H NMR (600 MHz, CDCl₃): δ 7.11 (d, J=1.9 Hz, 1H), 7.00 (dd, J=8.1, 1.9 Hz, 1H), 6.89 (d, J=8.1 Hz, 1H), 6.06 (s, br, 1H), 5.07 (s, 1H), 4.33 (d, J=14.3 Hz, 1H), 3.77-3.73 (m, 4H), 3.25 (s, 3H), 2.96 (d, J=14.1 Hz, 1H), 2.83 (d, J=14.1 Hz, 1H), 2.76-2.72 (m, 4H), 2.56 (d, J=14.3 Hz, 1H), 2.48 (s, 3H), 2.43 (s, 3H), 2.16 (s, 3H). HRMS (ESI) calculated for C26H30N4O7S2Na (M–Na) 597.1454, observed 597.1446.

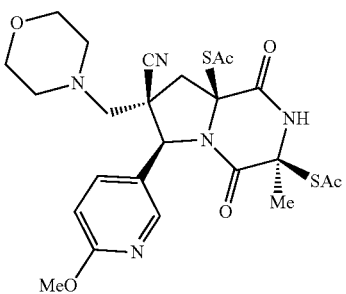

Leo-16-1866 (racemate). 1H NMR (600 MHz, CDCl₃): δ 8.36 (d, J=2.5 Hz, 1H), 7.92 (dd, J=8.7, 12.5 Hz, 1H), 6.87 (d, J=8.7 Hz, 1H), 5.15 (s, 1H), 4.36 (d, J=14.5 Hz, 1H), 4.01 (s, 3H), 3.76-3.73 (m, 4H), 3.23 (s, 3H), 2.90 (d, J=14.0 Hz, 1H), 2.86 (d, J=14.0 Hz, 1H), 2.73-2.71 (m, 4H), 2.56 (d, J=14.5 Hz, 1H), 2.47 (s, 3H), 2.41 (s, 3H), 2.14 (s, 3H). HRMS (ESI) calculated for C25H31N5O6S2Na (M–Na) 584.1614, observed 584.1619.

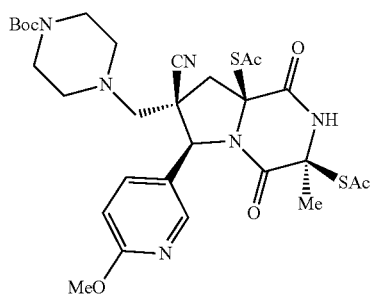

Leo-16-1867 (racemate). 1H NMR (600 MHz, CDCl₃): δ 8.36 (d, J=2.5 Hz, 1H), 7.91 (dd, J=8.8, 2.5 Hz, 1H), 6.87 (d, J=8.8 Hz, 1H), 5.15 (s, 1H), 4.35 (d, J=14.0 Hz, 1H), 4.01 (s, 3H), 3.51-3.46 (m, 4H), 3.23 (s, 3H), 2.91 (d, J=13.8 Hz, 1H), 2.88 (d, J=13.8 Hz, 1H), 2.69-2.64 (m, 4H), 2.56 (d, J=14.0 Hz, 1H), 2.47 (s, 3H), 2.40 (s, 3H), 2.13 (s, 3H), 1.51 (s, 9H). HRMS (ESI) calculated for C30H40N6O7S2Na (M–Na) 683.2297, observed 683.2299.

298

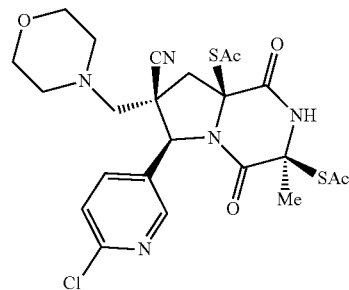

Leo-16-1868 (racemate). 1H NMR (600 MHz, CDCl₃): δ 8.66 (d, J=2.7 Hz, 1H), 8.05 (dd, J=8.3, 2.7 Hz, 1H), 7.47 (d, J=8.3 Hz, 1H), 5.25 (s, 1H), 4.40 (d, J=14.6 Hz, 1H), 3.79-3.74 (m, 4H), 3.23 (s, 3H), 2.91 (d, J=14.7 Hz, 1H), 2.88 (d, J=14.7 Hz, 1H), 2.74-2.70 (m, 4H), 2.54 (d, J=14.6 Hz, 1H), 2.46 (s, 3H), 2.42 (s, 3H), 2.13 (s, 3H). HRMS (ESI) calculated for C24H28ClN5O5S2Na (M–Na) 588.1118, observed 588.1125.

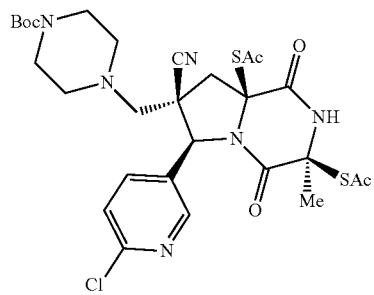

Leo-16-1869 (racemate). 1H NMR (600 MHz, CDCl₃): δ 8.28 (d, J=2.8 Hz, 1H), 8.04 (dd, J=8.5, 2.8 Hz, 1H), 7.27 (d, J=8.5 Hz, 1H), 5.25 (s, 1H), 4.39 (d, J=14.7 Hz, 1H), 3.52-3.46 (m, 4H), 3.22 (s, 3H), 2.90 (t, J=13.9 Hz, 2H), 2.68-2.64 (m, 4H), 2.53 (d, J=14.7 Hz, 1H), 2.45 (s, 3H), 2.42 (s, 3H), 2.13 (s, 3H), 2.10 (s, 9H). HRMS (ESI) calculated for C29H37ClN6O6S2Na (M–Na) 687.1802, observed 687.1811.

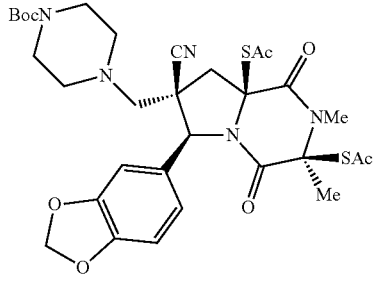

Leo-17-1876 (S, R, R, R)-enentiomer. 1H NMR (600 MHz, CDCl₃): δ 7.10 (d, J=1.9 Hz, 1H), 6.98 (dd, J=8.0, 1.9 Hz, 1H), 6.88 (d, J=8.0 Hz, 1H), 6.05 (d, J=1.6 Hz, 1H), 6.04 (d, J=1.6 Hz, 1H), 5.06 (s, 1H), 4.31 (d, J=14.8 Hz, 1H), 3.48-3.46 (m, 4H), 3.24 (s, 3H), 2.95 (d, J=13.7 Hz, 1H), 2.84 (d, J=13.7 Hz, 1H), 2.69-2.66 (m, 4H), 2.55 (d, J=14.8 Hz, 1H), 2.46 (s, 3H), 2.42 (s, 3H), 2.14 (s, 3H), 1.50 (s, 9H). HRMS (ESI) calculated for C31H39N5O8S2Na (M–Na) 696.2138, observed 696.2135.

Example 14

Cell Viability Assay of Compound (2) against CTCL

Figure 8A:
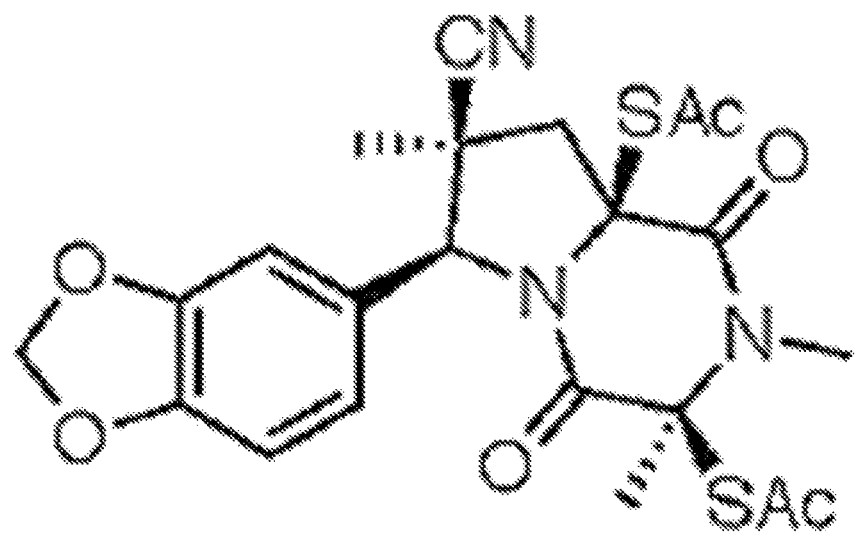
FIG. 8A illustrates a structure of compound (2).

Compound (2) (FIG. 8A) was tested in a cell viability assay using HUT78 cells in a CELLTITER-GLO® assay. To determine $IC_{50}$ value of Compound (2) against human CTCL HUT78 cells, viability assay was performed using CELLTITER-GLO® Reagent as described by the supplier (Promega, Madison, WI). Briefly, cells (7500/well) were seeded in opaque 96-well plates and exposed to Compound (1) in a dose-dependent manner for 72 h at 37° C. in 5% $CO_2$. After 72 h treatment with compound (1), CELLTITER-GLO® Reagent (50 L/well) was added to 96-well plates. Viable cells which are metabolically active are directly proportional to the ATP present. Luminescent signals correlate with the amount of ATP present in cells. After 10 min incubation with CELLTITER-GLO® Reagent, luminescence was measured at an integration time of 1 second/well using an automated BMG plate reader. Dimethyl sulfoxide (DMSO) was used as the vehicle control. Each experiment was conducted in triplicate. $IC_{50}$ values were determined using CalcuSyn software (Biosoft).

Figure 8B:
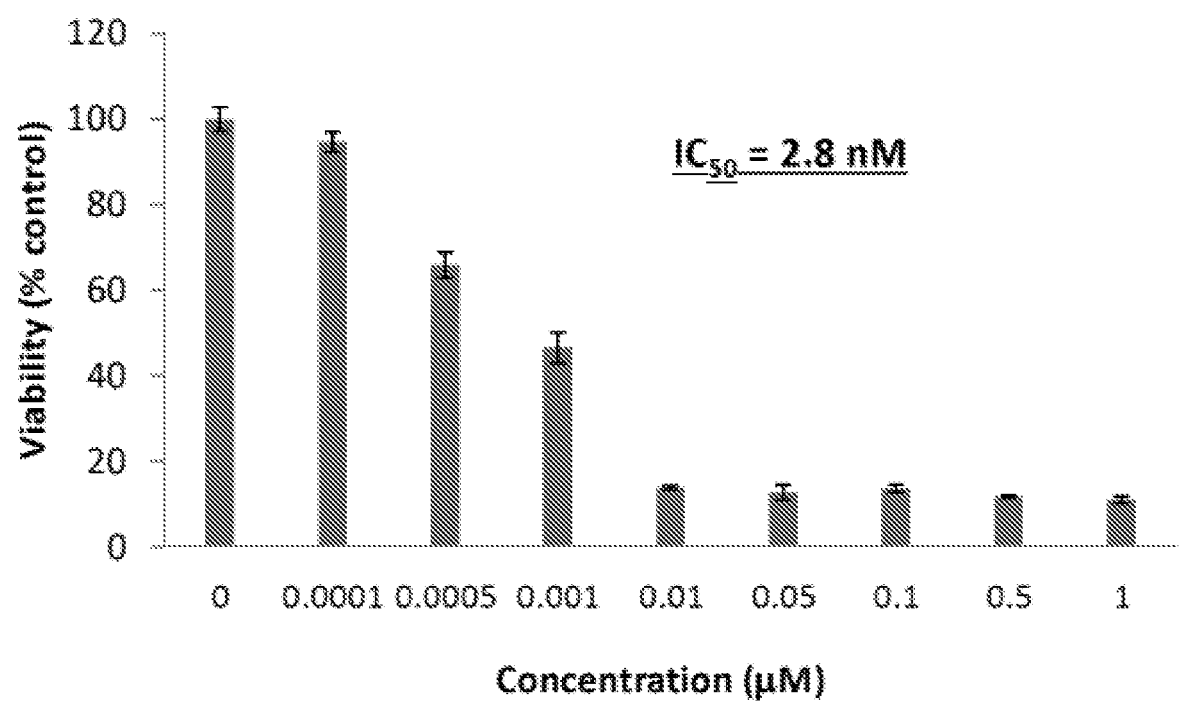
FIG. 8B shows compound (2) activity against HUT78 CTCL cell proliferation in dose-dependent manner.

An $IC_{50}$ value of 2.8 nM was determined for compound (2). See FIG. 8B. Analysis of the results demonstrates that the compound (2) exhibits in antitumor activities against CTCL.

What is claimed is:

1. A method for treating cutaneous T-cell lymphoma (CTCL) in a subject in need thereof, comprising administering to the subject a compound having the following structure:

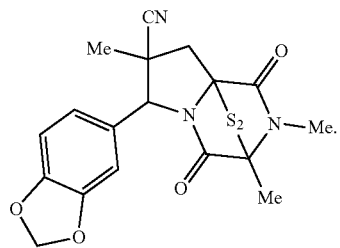

2. The method of claim 1,
    wherein the cutaneous T-cell lymphoma is Sezary syndrome, mycosis fungoides, folliculotropic mycosis fungoides, pagetoid reticulosis, granulomatous slack skin, primary cutaneous CD30+ T-cell lymphoproliferative disorders, lymphomatoid papulosis, primary cutaneous anaplastic large-cell lymphoma, primary cutaneous γδ T-cell lymphoma, primary cutaneous CD8+ aggressive epidermotropic lymphoma, primary cutaneous CD8+ aggressive epidermotropic cytotoxic T-cell lymphoma, or primary cutaneous CD4+ small/medium T-cell lymphoma.

3. The method of claim 1, wherein the cutaneous T-cell lymphoma is associated with at least one of the following conditions: smoking, obesity, infection, HIV, Epstein-Barr virus, human T-lymphotropic virus, *Helicobacter pyroli* infection, chronic *Helicobacter pyroli* infection, exposure to chemicals, exposure to insecticides, exposure to pesticides, use of immunosuppressant drugs, weakened immune system, genetic disorders, previous chemotherapy, and previous radiation therapy.

4. The method of claim 1, further comprising administering to the subject an additional therapeutic agent used in the treatment of T-cell lymphoma,
    wherein the additional therapeutic agent is alemtuzumab, bendamustine, bexarotene, bleomycin, bortezomib, brentuximab vedotin, carboplatin, carfilzomib, carmustine, cisplatin, cyclophosphamide, cytarabine, dacarbazine, dazatinib, denileukin diftitox, dexamethasone, doxorubicin, etoposide, everolimus, fludarabine, forodesine, gemcitabine, hydroxydaunorubicin, ifosfamide, imiquimod, interferons, lenalidomide, liposomal doxorubicin, mechlorethamine, methotrexate, methylprednisolone, nelfinavir, oral corticosteroids, panobinostat, pentostatin, pralatrexate, prednisone, prednisolone, psoralen, retinoids, resiquimod, rituximab, romidepsin, SGX301, temsirolimus, topical corticosteroids, vinblastine, vincristine, vinorelbine, vorinostat, or a combination thereof.

5. The method of claim 1, wherein the compound is:

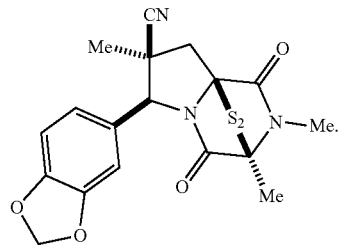

* * * * *